United States Patent
Santella et al.

(10) Patent No.: US 9,169,252 B2
(45) Date of Patent: Oct. 27, 2015

(54) HETEROARYL SUBSTITUTED NICOTINAMIDE COMPOUNDS

(71) Applicant: BRISTOL-MYERS SQUIBB COMPANY, Princeton, NJ (US)

(72) Inventors: Joseph B. Santella, Springfield, PA (US); Sreekantha Ratna Kumar, Bangalore (IN); John V. Duncia, Newtown, PA (US); Daniel S. Gardner, Furlong, PA (US); Venkatram Reddy Paidi, Bangalore (IN); Satheesh Kesavan Nair, Bangalore (IN); John Hynes, Washington Crossing, PA (US); Hong Wu, New Hope, PA (US); Natesan Murugesan, Princeton Junction, NJ (US); Kandhasamy Sarkunam, Bangalore (IN); Piramanayagam Arunachalam, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/588,470

(22) Filed: Jan. 2, 2015

(65) Prior Publication Data

US 2015/0191464 A1 Jul. 9, 2015

Related U.S. Application Data

(60) Provisional application No. 61/923,403, filed on Jan. 3, 2014.

(51) Int. Cl.
| | |
|---|---|
| C07D 213/02 | (2006.01) |
| C07D 519/00 | (2006.01) |
| C07D 401/14 | (2006.01) |
| C07D 471/04 | (2006.01) |
| C07D 401/04 | (2006.01) |
| C07D 487/04 | (2006.01) |
| C07F 9/6561 | (2006.01) |

(52) U.S. Cl.
CPC ............ *C07D 471/04* (2013.01); *C07D 401/04* (2013.01); *C07D 401/14* (2013.01); *C07D 487/04* (2013.01); *C07D 519/00* (2013.01); *C07F 9/65616* (2013.01)

(58) Field of Classification Search
CPC .. C07D 213/02; C07D 519/00; C07D 401/14; C07D 471/04; C07D 401/04
USPC ........................................................ 546/256
See application file for complete search history.

(56) References Cited

U.S. PATENT DOCUMENTS

| 7,273,868 B2 * | 9/2007 | Yamada et al. ............... 514/249 |
| 8,586,751 B2 | 11/2013 | DeLucca et al. |
| 8,987,311 B2 | 3/2015 | Dodd et al. |
| 2005/0272753 A1 | 12/2005 | Nagashima et al. |
| 2006/0148800 A1 | 7/2006 | Stadtmueller et al. |
| 2009/0082329 A1 | 3/2009 | Halley et al. |
| 2011/0237590 A1 | 9/2011 | Kitamura et al. |
| 2015/0011532 A1 | 1/2015 | Paidi et al. |
| 2015/0018344 A1 | 1/2015 | Paidi et al. |

FOREIGN PATENT DOCUMENTS

| EP | 2 532 656 A1 | 12/2012 |
| GB | 2 388 596 A | 9/2002 |
| WO | WO 02/102800 A1 | 12/2002 |
| WO | WO 03/013523 A1 | 2/2003 |
| WO | WO 2004/065378 A1 | 8/2004 |
| WO | WO 2005/007646 A1 | 1/2005 |

(Continued)

OTHER PUBLICATIONS

Buckley, George M., et al. "IRAK-4 inhibitors. Part I: A series of amides," Bioorganic & Medicinal Chemistry Letters, 18(11), 3211-3214 (2008).

Buckley, George M., et al. "IRAK-4 inhibitors. Part II: A structure-based assessment of imidazo[1,2-a]pyridine binding," Bioorganic & Medicinal Chemistry Letters, 18(11), 3291-3295 (2008).

Buckley, George M., et al. "IRAK-4 inhibitors. Part III: A series of imidazo[1,2-a]pyridines," Bioorganic & Medicinal Chemistry Letters, 18(12), 3656-3660 (2008).

(Continued)

*Primary Examiner* — Niloofar Rahmani
(74) *Attorney, Agent, or Firm* — Gary D. Greenblatt

(57) ABSTRACT

Disclosed are compounds of Formula (I)

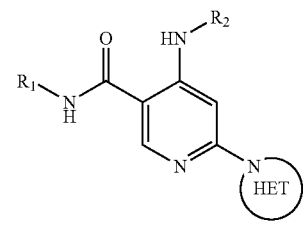

(I)

or salts thereof, wherein: HET is a heteroaryl selected from pyrazolyl, indolyl, pyrrolo[2,3-b]pyridinyl, pyrrolo[2,3-d]pyrimidinyl, pyrazolo[3,4-b]pyridinyl, pyrazolo[3,4-d]pyrimidinyl, 2,3-dihydro-1H-pyrrolo[2,3-b]pyridinyl, imidazo[4,5-b]pyridinyl, and purinyl, wherein said heteroaryl is substituted with $R_a$ and $R_b$; and $R_1$ and $R_2$ are define herein. Also disclosed are methods of using such compounds as modulators of IRAK4, and pharmaceutical compositions comprising such compounds. These compounds are useful in treating, preventing, or slowing inflammatory and autoimmune diseases.

9 Claims, 2 Drawing Sheets

(56) References Cited

FOREIGN PATENT DOCUMENTS

| WO | WO 2005/075468 A2 | 8/2005 |
|---|---|---|
| WO | WO 2008/148889 A1 | 12/2008 |
| WO | WO 2009/046416 A1 | 4/2009 |
| WO | WO 2011/053701 A1 | 5/2011 |
| WO | WO 2012/149567 A1 | 11/2012 |
| WO | WO2014/074657 A1 | 5/2014 |
| WO | WO2014/074660 A1 | 5/2014 |
| WO | WO2014/074675 A1 | 5/2014 |

OTHER PUBLICATIONS

Hynes, Jr., John, et al., "Advances in the Discovery of Small-Molecule IRAK4 Inhibitors," Annual Reports in Medicinal Chemistry, vol. 49, pp. 117-133, (2014).

Wermuth, C.G., "Molecular Variations Based on Isosteric Replacements," Practice of Medicinal Chemistry, pp. 203-237 (1996).

International Search Report issued mailed Mar. 23, 2015.

* cited by examiner

HETEROARYL SUBSTITUTED NICOTINAMIDE COMPOUNDS

CROSS-REFERENCE TO RELATED APPLICATIONS

This application claims the benefit of U.S. Application Ser. No. 61/923,403, filed Jan. 3, 2014, which is incorporated herein it its entirety.

DESCRIPTION

The present invention generally relates to heteroaryl substituted nicotinamide compounds useful as kinase inhibitors, including the modulation of IRAK-4. Provided herein are heteroaryl substituted nicotinamide compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including IRAK-4 in a mammal.

Toll/IL-1 receptor family members are important regulators of inflammation and host resistance. The Toll like receptor (TLR) family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Members of the IRAK family of serine/threonine kinases are recruited to the receptor via interactions with MyD88. The family consists of four members. Several lines of evidence indicate that IRAK4 plays a critical and non-redundant role in initiating signaling via MyD88 dependent TLRs and IL-1R family members. Structural data confirms that IRAK4 directly interacts with MyD88 and subsequently recruits either IRAK1 or IRAK2 to the receptor complex to facilitate downstream signaling (Lin, S. et al., *Nature*, 465:885-890 (2010)). IRAK4 directly phosphorylates IRAK1 to facilitate downstream signaling to the E3 ubiquitin ligase TRAF6, resulting in activation of the serine/threonine kinase TAK1 with subsequent activation of the NFκB pathway and MAPK cascade (Flannery, S. et al., *Biochem. Pharmacol.*, 80:1981-1991 (2010)). A subset of human patients was identified who lack IRAK4 expression (Picard, C. et al., *Science*, 299:2076-2079 (2003)). Cells from these patients fail to respond to all TLR agonists with the exception of TLR3 as well as to members of the IL-1 family including IL-13 and IL-18 (Ku, C. et al., *J. Exp. Med.*, 204:2407-2422 (2007)). Deletion of IRAK4 in mice results in a severe block in IL-1, IL-18 and all TLR dependent responses with the exception of TLR3 (Suzuki, N. et al., *Nature*, 416:750-754 (2002)). In contrast, deletion of either IRAK1 (Thomas, J. A. et al., *J. Immunol.*, 163:978-984 (1999); Swantek, J. L. et al., *J. Immunol.*, 164:4301-4306 (2000) or IRAK2 (Wan, Y. et al., *J. Biol. Chem.*, 284:10367-10375 (2009)) results in partial loss of signaling. Furthermore, IRAK4 is the only member of the IRAK family whose kinase activity has been shown to be required for initiation of signaling. Replacement of wild type IRAK4 in the mouse genome with a kinase inactive mutant (KDKI) impairs signaling via all MyD88 dependent receptors including IL-1, IL-18 and all TLRs with the exception of TLR3 (Koziczak-Holbro, M. et al., *J. Biol. Chem.*, 282:13552-13560 (2007); Kawagoe, T. et al., *J. Exp. Med.*, 204:1013-1024 (2007); and Fraczek, J. et al., *J. Biol. Chem.*, 283:31697-31705 (2008)).

As compared to wild type animals, IRAK4 KDKI mice show greatly reduced disease severity in mouse models of multiple sclerosis (Staschke, K. A. et al., *J. Immunol.*, 183: 568-577 (2009)), rheumatoid arthritis (Koziczak-Holbro, M. et al., *Arthritis Rheum.*, 60:1661-1671 (2009)), atherosclerosis (Kim, T. W. et al., *J. Immunol.*, 186:2871-2880 (2011) and Rekhter, M. et al., Biochem. *Biophys. Res. Comm.*, 367:642-648 (2008)), and myocardial infarction (Maekawa, Y. et al., *Circulation*, 120:1401-1414 (2009)). As described, IRAK4 inhibitors will block all MyD88 dependent signaling. MyD88 dependent TLRs have been shown to contribute to the pathogenesis of multiple sclerosis, rheumatoid arthritis, cardiovascular disease, metabolic syndrome, sepsis, systemic lupus erythematosus, inflammatory bowel diseases including Crohn's disease and ulcerative colitis, autoimmune uveitis, asthma, allergy, type I diabetes, and allograft rejection (Keogh, B. et al., *Trends Pharmacol. Sci.*, 32:435-442 (2011); Mann, D. L., *Circ. Res.*, 108:1133-1145 (2011); Horton, C. G. et al., *Mediators Inflamm.*, Article ID 498980 (2010), doi: 10.1155/2010/498980; Goldstein, D. R. et al., *J. Heart Lung Transplant.*, 24:1721-1729 (2005); and Cario, E., *Inflamm. Bowel Dis.*, 16:1583-1597 (2010)). Oncogenically active MyD88 mutations in diffuse large B cell lymphomas have been identified that are sensitive to IRAK4 inhibition (Ngo, V. N. et al., *Nature*, 470:115-121 (2011)). Whole genome sequencing also identified mutations in MyD88 associated with chronic lymphatic leukemia suggesting that IRAK4 inhibitors may also have utility in treating leukemias (Puente, X. S. et al., *Nature*, 475:101-105 (2011)).

In addition to blocking TLR signaling, IRAK4 inhibitors will also block signaling by members of the IL-1 family. Neutralization of IL-1 has been shown to be efficacious in multiple diseases including gout; gouty arthritis; type 2 diabetes; auto-inflammatory diseases including Cryopyrin-Associated Periodic Syndromes (CAPS), TNF Receptor Associated Periodic Syndrome (TRAPS), Familial Mediterranean Fever (FMF), adult onset stills; systemic onset juvenile idiopathic arthritis; stroke; Graft-versus-Host Disease (GVHD); smoldering multiple myeloma; recurrent pericarditis; osteoarthritis; emphysema (Dinarello, C. A., *Eur. J. Immunol.*, 41:1203-1217 (2011) and Couillin, I. et al., *J. Immunol.*, 183:8195-8202 (2009)). In a mouse model of Alzheimer's disease, blockade of IL-1 receptor improved cognitive defects, attenuated tau pathology and reduced oligomeric forms of amyloid-β (Kitazawa, M. et al., *J. Immunol.*, 187: 6539-6549 (2011)). IL-1 has also been shown to be a critical link to adaptive immunity, driving differentiation of the TH17 effector T cell subset (Chung, Y. et al., *Immunity*, 30:576-587 (2009)). Therefore, IRAK4 inhibitors are predicted to have efficacy in TH17 associated diseases including multiple sclerosis, psoriasis, inflammatory bowel diseases, autoimmune uveitis, and rheumatoid arthritis (Wilke, C. M. et al., *Trends Immunol.*, 32:603-661 (2011)).

WO 2013/106612, WO 2013/106614, and WO 2013/106641 disclose substituted pyridyl compounds useful as kinase inhibitors, including the modulation of IRAK4.

In view of the conditions that may benefit by treatment involving modulation of protein kinases, it is immediately apparent that new compounds capable of modulating protein kinases such as IRAK-4 and methods of using these compounds could provide substantial therapeutic benefits to a wide variety of patients.

The present invention relates to a new class of heteroaryl substituted nicotinamide compounds found to be effective inhibitors of protein kinases including IRAK-4. These compounds are provided to be useful as pharmaceuticals with desirable stability, bioavailability, therapeutic index, and toxicity values that are important to their drugability.

SUMMARY OF THE INVENTION

The present invention provides to compounds of Formula (I) that are useful as inhibitors of IRAK-4, and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of IRAK-4 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

One embodiment provides a method for treating inflammatory and autoimmune diseases wherein the treatment of inflammatory diseases is even more preferred. Particular, inflammatory and autoimmune diseases include, but are not limited to, Crohn's disease, ulcerative colitis, asthma, graft versus host disease, allograft rejection, chronic obstructive pulmonary disease, Graves' disease, rheumatoid arthritis, systemic lupus erythematosus, lupus nephritis, cutaneous lupus, psoriasis, cryopyrin-associated periodic syndromes (CAPS), TNF receptor associated periodic syndrome (TRAPS), familial Mediterranean fever (FMF), adult onset stills, systemic onset juvenile idiopathic arthritis, multiple sclerosis, neuropathic pain, gout, and gouty arthritis.

One embodiment provides a method for treating gout and gouty arthritis.

An alternate preferred embodiment is a method for treating metabolic diseases, including type 2 diabetes and atherosclerosis.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancers.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

BRIEF DESCRIPTION OF THE DRAWINGS

The invention is illustrated by reference to the accompanying drawings described below.

DETAILED DESCRIPTION

Figure 1:
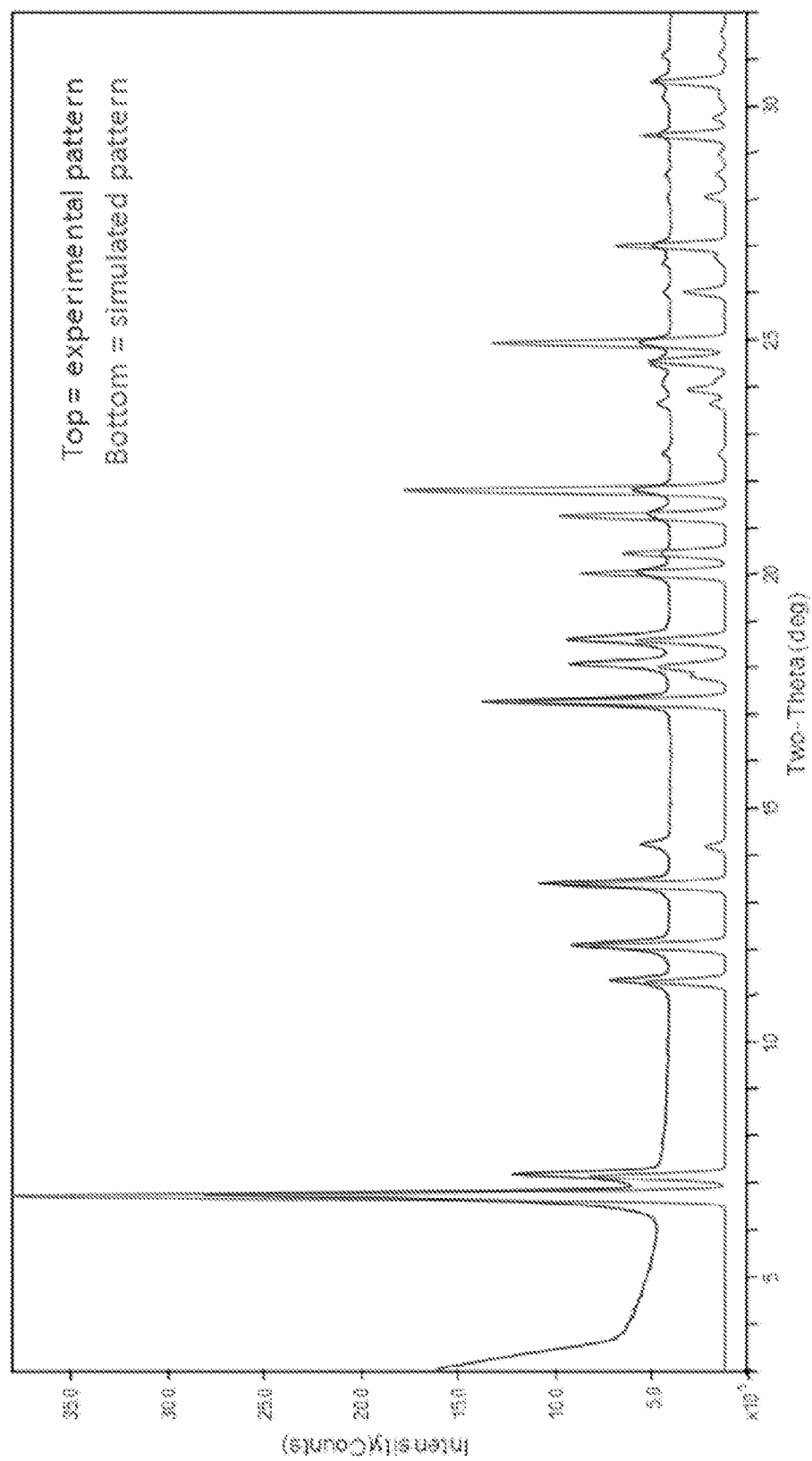
FIG. 1 shows the experimental (at approximately 25° C.) and the simulated (at 296 K) PXRD patterns (CuKα λ=1.5418 Å) of the N-1 Form of the compound of Example 133.

The first aspect of the present invention provides at least one compound of Formula (I):

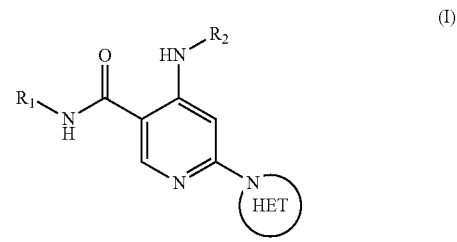

or a salt thereof, wherein:

HET is a heteroaryl selected from pyrazolyl, indolyl, pyrrolo[2,3-b]pyridinyl, pyrrolo[2,3-d]pyrimidinyl, pyrazolo[3,4-b]pyridinyl, pyrazolo[3,4-d]pyrimidinyl, 2,3-dihydro-1H-pyrrolo[2,3-b]pyridinyl, imidazo[4,5-b]pyridinyl, and purinyl, wherein said heteroaryl is substituted with $R_a$ and $R_b$;

$R_a$ is H, F, Cl, Br, —CN, —OH, $C_{1-4}$ alkyl, $C_{1-4}$ fluoroalkyl, $C_{1-4}$ hydroxyalkyl, $C_{1-4}$ alkoxy, —NH$_2$, —NH($C_{1-4}$ alkyl), —N($C_{1-4}$ alkyl)$_2$, —NH($C_{1-4}$ hydroxyalkyl), —NH($C_{1-4}$ fluoroalkyl), —NH($C_{1-6}$ hydroxy-fluoroalkyl), —C(O)NH$_2$, —CH$_2$NHC(O)($C_{1-6}$ alkyl), —CH$_2$NHC(O)($C_{1-6}$ hydroxyalkyl), —CH$_2$NHC(O)NH($C_{1-6}$ alkyl), —CH$_2$NHC(O)NHCH$_2$(phenyl), —CH$_2$NHC(O)N($C_{1-4}$ alkyl)$_2$, —CH$_2$NHC(O)O($C_{1-4}$ alkyl), —CH$_2$NHC(O)($C_{3-6}$ cycloalkyl), —CH$_2$NHC(O)(tetrahydrofuranyl), —CH$_2$NHC(O)CH$_2$($C_{3-6}$ cycloalkyl), —CH$_2$NHC(O)CH$_2$(tetrahydropyranyl), —CH$_2$NHC(O)CH$_2$(phenyl), —NHC(O)($C_{1-4}$ alkyl), pyrrolidinyl, hydroxypyrrolidinyl, or pyridazinyl;

$R_b$ is H or —NH$_2$;

$R_1$ is:
(i) $C_{1-6}$ alkyl, $C_{1-6}$ fluoroalkyl, $C_{1-6}$ hydroxyalkyl, $C_{1-8}$ hydroxy-fluoroalkyl, —($C_{1-6}$ alkylenyl)O($C_{1-4}$ alkyl), —($C_{1-6}$ alkylenyl)O($C_{1-4}$ fluoroalkyl), —($C_{1-6}$ fluoroalkylenyl)O($C_{1-4}$ alkyl), —($C_{1-6}$ fluoroalkylenyl)O($C_{1-4}$ deuteroalkyl), —($C_{1-6}$ fluoroalkylenyl)O($C_{1-4}$ fluoroalkyl), —($C_{1-4}$ fluoroalkylenyl)C($C_{3-6}$ cycloalkyl)$_2$(OH), —($C_{1-4}$ alkylenyl)NHC(O)($C_{1-4}$ alkylenyl)OC(O)($C_{1-3}$ alkyl), —($C_{1-6}$ alkylenyl)NHS(O)$_2$($C_{1-4}$ alkyl), —($C_{1-6}$ alkylenyl)P(O)($C_{1-4}$ alkoxy)$_2$, —($C_{1-6}$ fluoroalkylenyl)NH($C_{1-4}$ alkyl), —($C_{1-6}$ alkylenyl)C(O)NH($C_{1-4}$ alkyl), —($C_{1-6}$ fluoroalkylenyl)C(O)NH($C_{1-4}$ alkyl), —(C₁₋₆ fluoroalkylenyl)C(O)NH(C₁₋₄ hydroxyalkyl), or —(C₁₋₆ fluoroalkylenyl)OP(O)(OH)₂;

(ii) —(C₁₋₃ alkylenyl)Rₓ, —(C₁₋₃ fluoroalkylenyl)Rₓ, —(C₁₋₃ alkylenyl)C(O)Rₓ, —(C₁₋₃ alkylenyl)C(O)NHRₓ, —(C₁₋₃ fluoroalkylenyl)C(O)Rₓ, or —CH₂CF= (tetrahydropyranyl), wherein Rₓ is a cyclic group selected from C₃₋₆ cycloalkyl, tetrazolyl, 1,1-dioxidotetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —CH₃, —C(CH₂)₂OH, —OCH₃, —C(O)CH₂CN, —S(O)₂CH₃, —S(O)₂NH₂, —NHC(O)CH₃, —N(S(O)₂CH₃)₂, —CH₂CH₂(acetamidophenyl), —CH₂CH₂(methoxyphenyl), —CH₂CH₂(sulfamoylphenyl), oxetanyl, benzyl, and morpholinyl;

(iii) C₃₋₆ cycloalkyl or C₄₋₆ cycloalkenyl, each substituted with zero to 3 substituents independently selected from F, —OH, —CN, C₁₋₃ alkyl, C₁₋₃ alkoxy, —S(C₁₋₃ alkyl), —NO₂, —S(O)₂(C₁₋₃ alkyl), C₁₋₄ hydroxyalkyl, —C(C₁₋₃ alkyl)(OH)(C₃₋₆ cycloalkyl), —CH₂C(O)NH(C₁₋₃ alkyl), —NHC(O)(C₁₋₃ alkyl), —NHC(O)(C₁₋₄ hydroxyalkyl), —C(O)NH(C₁₋₃ alkyl), —C(O)NH(C₁₋₃ deuteroalkyl), —C(O)NH(C₃₋₆ cycloalkyl), —NHC(O)O(C₁₋₃ alkyl), —NHS(O)₂(C₁₋₃ alkyl), pyridinyl, imidazolyl, pyrazolyl, methylimidazolyl, methylpyrazolyl, and thiazolyl;

(iv) tetrahydropyranyl, piperidinyl, pyrazolyl, phenyl, pyridinyl, or pyrimidinyl, each substituted with zero to 1 substituent selected from —OH, C₁₋₃ alkyl, C₁₋₃ fluoroalkyl, C₁₋₄ hydroxyalkyl, C₁₋₃ alkoxy, —C(O)(C₁₋₄ alkyl), —S(O)₂(C₁₋₄ alkyl), —S(O)₂NH(C₁₋₄ alkyl), —NH(C₁₋₃ alkyl), —N(C₁₋₃ alkyl)₂, —O(C₁₋₃ alkylenyl)N(C₁₋₃ alkyl)₂, —CH₂(morpholinyl), azetidinyl, oxetanyl, tetrahydropyranyl, morpholinyl, piperazinyl, piperidinyl, methylpiperazinyl, methoxypiperidinyl, pyridinyl, pyrimidinyl, methylsulfonyl azetidinyl, and —C(O)(methylsulfonyl azetidinyl); or (v) pyrrolo[2,3-c]pyridinyl, bicyclo[2.2.1]heptan-1-ol, tetrahydrobenzo[d]thiazol-2-amine, or 1,3-diazaspiro[4.5]decane-2,4-dione; and R₂ is:
(i) C₁₋₇ alkyl or C₂₋₆ alkenyl, each substituted with zero to three substituents independently selected from F, —OH, and —CN; —(C₁₋₄ alkylenyl)O(C₁₋₄ alkyl), —(C₁₋₄ alkylenyl)O(C₁₋₄ fluoroalkyl), —(C₁₋₆ alkylenyl)NH₂, —(C₁₋₆ alkylenyl)S(O)₂(C₁₋₃ alkyl), —(C₁₋₆ fluoroalkylenyl)NH(C₁₋₃ alkyl), or —(C₁₋₆ alkylenyl)NHC(O)(C₁₋₄ fluoroalkyl);

(ii) —(C₁₋₄ alkylenyl)Rᵧ, wherein Rᵧ is C₃₋₆ cycloalkyl, azetidinyl, oxetanyl, oxazolyl, pyridinyl, tetrahydropyranyl, or morpholinyl, each substituted with zero to 2 substituents independently selected from F, —OH, and C₁₋₃ alkyl;

(iii) C₃₋₆ cycloalkyl, azetidinyl, oxetanyl, furanyl, tetrahydrofuranyl, pyrrolidinyl, piperidinyl, or tetrahydropyranyl, each substituted with zero to 2 substituents independently selected from F, —OH, C₁₋₃ alkyl, C₁₋₃ hydroxyalkyl, —C(O)(C₁₋₃ alkyl), —C(O)(C₁₋₃ fluoroalkyl), —C(O)(C₁₋₃ cyanoalkyl), —C(O)O(C₁₋₃ alkyl), —C(O)NH₂, —C(O)NH(C₁₋₃ alkyl), —C(O)(difluorophenyl), —NH₂, —NH(C₁₋₃ alkyl), —NH(C₁₋₃ fluoroalkyl), —NH(oxetanyl), —NHC(O)(C₁₋₃ alkyl), —NHC(O)(C₁₋₃ fluoroalkyl), —NHC(O)(C₃₋₆ cycloalkyl), —NHC(O)(fluorophenyl), —S(O)₂(C₁₋₃ alkyl), imidazolyl, phenyl, pyrimidinyl, fluoropyrimidinyl, chloropyrimidinyl, and methoxypyrimidinyl;

(iv) adamantanyl, hydroxyadamantanyl, benzo[d]imidazolyl, benzo[d]oxazolyl, benzo[d]triazolyl, benzothiazolyl, bicyclo[1.1.1]pentanyl, or hydroxy-bicyclo[2.2.1]heptanyl; or (v) phenyl, pyrazolyl, thiazolyl, thiadiazolyl, or indazolyl, each substituted with 0 to 2 substituents independently selected from F, Cl, —OH, —CN, C₁₋₄ alkyl, C₁₋₄ hydroxyalkyl, C₁₋₄ fluoroalkyl, C₁₋₄ cyanoalkyl, C₁₋₃ alkoxy, C₃₋₆ cycloalkyl, —(C₁₋₃ alkylenyl)O(C₁₋₃ alkyl), —(C₁₋₃ alkylenyl)O(C₁₋₃ fluoroalkyl), —C(O)NH₂, —C(O)NH(C₁₋₃ alkyl), —NHC(O)(C₁₋₃ alkyl), —NHC(O)S(O)₂(C₁₋₃ alkyl), —S(O)₂NH₂, —S(O)₂(C₁₋₃ alkyl), pyrazolyl, methyl pyrazolyl, imidazolyl, triazolyl, methyl tetrazolyl, ethyl tetrazolyl, phenyl, pyrimidinyl, fluoropyrimidinyl, and tetrahydropyranyl.

In the chemical structures represented by Formula (I), the HET group is a heteroaryl group having at least one nitrogen heteroatom, wherein one nitrogen heteroatom of the HET group forms a bond to a carbon atom adjacent to the nitrogen heteroatom in the pyridine ring.

One embodiment provides a compound of Formula (I) or a salt thereof, wherein HET is a heteroaryl selected from:

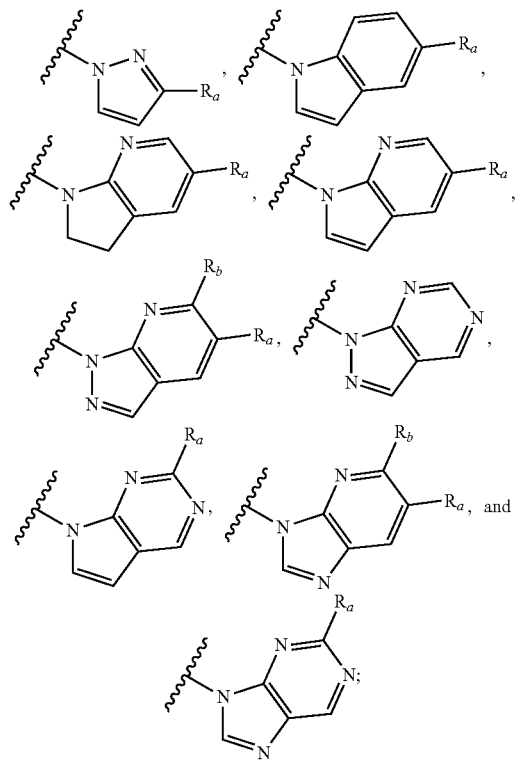

Rₐ is H, F, Cl, Br, —CN, —OH, —CH₃, —CHF₂, —OCH₃, —NH₂, —N(CH₃)₂, —NHCH₂CH₂OH, —NHCH₂C(CH₃)₂OH, —NHCH₂CHFC(CH₃)₂OH, —C(O)NH₂, —CH₂NHC(O)CH₂CH₂CH₃, —CH₂NHC(O)CH(CH₃)₂, —CH₂NHC(O)CH₂CH(CH₃)₂, —CH₂NHC(O)CH₂C(CH₃)₃, —CH₂NHC(O)CH₂CH₂CH(CH₃)₂, —CH₂NHC(O)CH₂C(CH₃)₂OH, —CH₂NHC(O)NHCH₂CH₂CH₃, —CH₂NHC(O)NHCH₂CH₂CH₂CH₃, —CH₂NHC(O)NHCH₂(phenyl), —CH₂NHC(O)N(CH₂CH₃)₂, —CH₂NHC(O)OCH₂CH₃, —CH₂NHC(O)OCH₂CH(CH₃)₂, —CH₂NHC(O)(cyclopropyl), —CH₂NHC(O)

(tetrahydrofuranyl), —CH$_2$NHC(O)CH$_2$(cyclopentyl), —CH$_2$NHC(O)CH$_2$(cyclohexyl), —CH$_2$NHC(O)CH$_2$ (tetrahydropyranyl), —CH$_2$NHC(O)CH$_2$(phenyl), —NHC(O)CH$_3$, hydroxypyrrolidinyl, or pyridazinyl;

R$_b$ is H or —NH$_2$;

R$_1$ is:

(i) —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH(CH$_3$)$_2$, —CH$_2$CHFCH$_3$, —CH$_2$CH$_2$CF$_2$CH$_3$, —CH$_2$CHFCH(CH$_3$)$_2$, —CH$_2$CH$_2$C(CH$_3$)$_2$F, —CH$_2$CHFC(CH$_3$)$_2$F, —CH$_2$CH$_2$CH(OH)CH$_3$, —CH$_2$CH$_2$C(CH$_3$)$_2$OH, —CH$_2$CHFCH(CH$_3$)OH, —CH$_2$CHFC(CH$_3$)$_2$OH, —CH$_2$CF$_2$C(CH$_3$)$_2$OH, —CH$_2$CHFC(CH$_2$CH$_3$)$_2$OH, —CH$_2$CHFC(cyclopropyl)$_2$(OH), —CH$_2$CHFCH(OH)CH(CH$_3$)$_2$, —CH$_2$CH$_2$OCH$_2$CH$_3$, —(CH$_2$)$_3$OCH(CH$_3$)$_2$, —(CH$_2$)$_3$OC(CH$_3$)$_3$, —CH$_2$CHFCH$_2$OCH$_3$, —CH$_2$CHFC(CH$_3$)$_2$OCH$_3$, —CH$_2$CHFC(CH$_3$)$_2$OCD$_3$, —CH$_2$CHFC(CH$_3$)$_2$OCHF$_2$, —CH$_2$CHFC(CH$_3$)$_2$OCH$_2$CH$_3$, —CH$_2$CH$_2$C(O)OCH$_3$, —CH$_2$CH$_2$NHC(O)C(CH$_3$)$_2$OC(O)CH$_3$, —CH$_2$CH$_2$NHS(O)$_2$CH$_3$, —CH$_2$CH$_2$CH(CH$_3$)NHS(O)$_2$CH$_3$, —CH$_2$CH$_2$C(CH$_3$)$_2$NHS(O)$_2$CH$_3$, —CH$_2$CH$_2$P(O)(OCH$_2$CH$_3$)$_2$, —CH$_2$CHFCH(CH$_3$)NHCH(CH$_3$)$_2$, —CH$_2$CHFC(O)NHCH$_3$, —CH$_2$CH$_2$C(O)NHCH$_2$CH$_3$, —CH$_2$CHFC(O)NHCH(CH$_3$)$_2$, —CH$_2$CHFC(O)NHCH(CH$_3$)CH$_2$OH, or —CH$_2$CHFC(CH$_3$)$_2$OP(O)(OH)$_2$;

(ii) —(C$_{1-3}$ alkylenyl)R$_x$, —(C$_{1-2}$ fluoroalkylenyl)R$_x$, —(C$_{1-2}$ alkylenyl)C(O)R$_x$, —CH$_2$C(O)NHR$_x$, —CH$_2$CHFC(O)R$_x$, or —CH$_2$CF=(tetrahydropyranyl), wherein R$_x$ is a cyclic group selected from cyclopropyl, cyclopentyl, cyclohexyl, tetrazolyl, 1,1-dioxidotetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —CH$_3$, —C(CH$_2$)$_2$OH, —OCH$_3$, —C(O)CH$_2$CN, —S(O)$_2$CH$_3$, —S(O)$_2$NH$_2$, —NHC(O)CH$_3$, —N(S(O)$_2$CH$_3$)$_2$, —CH$_2$CH$_2$(acetamidophenyl), —CH$_2$CH$_2$(methoxyphenyl), —CH$_2$CH$_2$(sulfamoylphenyl), oxetanyl, benzyl, and morpholinyl;

(iii) cyclopropyl, cyclopentyl, cyclopentenyl, or cyclohexyl, each substituted with zero to 2 substituents independently selected from F, —OH, —CN, —CH$_3$, —OCH$_3$, —SCH$_3$, —NO$_2$, —S(O)$_2$CH$_3$, —C(CH$_3$)$_2$OH, —C(CH$_3$)(OH)(cyclopropyl), —CH$_2$C(O)NHCH$_3$, —NHC(O)CH(OH)CH$_3$, —C(O)NHCD$_3$, —C(O)NHCH$_3$, —C(O)NHCH$_2$CH$_3$, —C(O)NH(cyclopropyl), —NHC(O)CH$_3$, —NHC(O)OCH$_3$, —NHS(O)$_2$CH$_3$, pyridinyl, methylimidazolyl, methylpyrazolyl, and thiazolyl;

(iv) tetrahydropyranyl, piperidinyl, pyrazolyl, phenyl, pyridinyl, or pyrimidinyl, each substituted with zero to 1 substituent selected from —OH, —OCH$_3$, —CH$_2$CHF$_2$, —C(CH$_3$)$_2$OH, —CH$_2$C(CH$_3$)$_2$OH, —C(O)CH(CH$_3$)$_2$, —S(O)$_2$CH$_3$, —S(O)$_2$CH$_2$CH$_3$, —S(O)$_2$CH(CH$_3$)$_2$, —S(O)$_2$NHCH$_3$, —S(O)$_2$NHCH(CH$_3$)$_2$, —N(CH$_3$)$_2$, —OCH$_2$CH$_2$N(CH$_3$)$_2$, —CH$_2$(morpholinyl), oxetanyl, tetrahydropyranyl, morpholinyl, piperazinyl, methylpiperazinyl, methoxypiperidinyl, pyrimidinyl, methylsulfonyl azetidinyl, and —C(O)(methylsulfonyl azetidinyl); or (v) pyrrolo[2,3-c]pyridinyl, bicyclo[2.2.1]heptan-1-ol, tetrahydrobenzo[d]thiazol-2-amine, or 1,3-diazaspiro[4.5]decane-2,4-dione; and R$_2$ is:

(i) —CH$_2$CH$_3$, —CH$_2$CH$_2$CH$_3$, —CH(CH$_3$)$_2$, —C(CH$_3$)$_3$, —CH$_2$C(CH$_3$)$_3$, —CH(CH$_3$)CH$_2$CH$_3$, —CH$_2$CH$_2$CH(CH$_3$)$_2$, —CH(CH$_3$)CH$_2$CH(CH$_3$)$_2$, —CH(CH$_3$)CH$_2$OH, —CH$_2$CH$_2$CH(CH$_3$)OH, —CH(CH$_3$)CH$_2$CH$_2$OH, —CH$_2$C(CH$_3$)$_2$OH, —C(CH$_3$)$_2$CH$_2$OH, —CH(CH$_3$)CH(OH)CH$_2$CH(CH$_3$)$_2$, —CH$_2$CH(OH)CH(CH$_3$)$_2$, —CH(CH$_2$OH)CH$_2$CH$_3$, —CH(CH$_2$OH)CH(CH$_3$)$_2$, —CH=CHC(CH$_3$)$_2$OH, —CH$_2$CH$_2$CN, —CH$_2$CHF$_2$, —CH$_2$CF$_3$, —CH$_2$CHFCH$_3$, —CH(CH$_3$)CF$_3$, —CH$_2$CH$_2$CF$_3$, —CH(CH$_3$)CH$_2$F, —CH$_2$CH$_2$CH$_2$F, —CH$_2$CHFCH$_2$CH$_3$, —CH$_2$CH$_2$CHFCH$_3$, —CH(CH$_3$)CHFCH$_3$, —CH(CH$_3$)CH$_2$CH$_2$F, —CH$_2$CH$_2$C(CH$_3$)$_2$F, —CH$_2$CHFC(CH$_3$)$_2$OH, —CH$_2$CF$_2$C(CH$_3$)$_2$OH, —CH$_2$C(CH$_3$)FCH$_2$OH, —CH(CH$_2$F)CH$_2$OH, —CH$_2$CH$_2$OCHF$_2$, —CH$_2$C(CH$_3$)OCHF$_2$, —CH$_2$C(CH$_3$)$_2$OCHF$_2$, —CH$_2$C(CH$_3$)$_2$OCH$_3$, —CH$_2$C(CH$_3$)$_2$CH$_2$NH$_2$, —CH$_2$CHFC(O)NHCH(CH$_3$)$_2$, —CH$_2$CH$_2$NHS(O)$_2$CH$_3$, or —CH$_2$CH$_2$NHC(O)OC(CH$_3$)$_2$CF$_3$;

(ii) —CH$_2$(azetidinyl), —CH$_2$(cyclopropyl), —CH$_2$(fluorocyclobutyl), —CH$_2$(hydroxycyclobutyl), —CH$_2$(oxetanyl), —CH$_2$(methyloxetanyl), —CH$_2$(oxazolyl), —CH$_2$(methylpyridinyl), —CH$_2$(tetrahydropyranyl), —CH$_2$CH$_2$(methylmorpholinyl) —CH(CH$_3$)(cyclopropyl), —CH$_2$CH$_2$(morpholinyl), —CH$_2$CH(CH$_3$)(morpholinyl), or —CH$_2$C(CH$_3$)$_2$(morpholinyl);

(iii) C$_{3-6}$ cycloalkyl substituted with zero to 3 substituents independently selected from F, —OH, —CH$_3$, —CH$_2$OH, —C(CH$_3$)$_2$OH, —C(O)NH$_2$, —C(O)NHCH(CH$_3$)$_2$, —NH$_2$, —NHCH$_2$CF$_3$, —NH(oxetanyl), —NHC(O)CHF$_2$, —NHC(O)(cyclopropyl), —NHC(O)(fluorophenyl), and imidazolyl; azetidinyl substituted with —C(O)CH$_3$, —C(O)OCH$_3$, —C(O)OCH$_2$CH$_3$, —C(O)OC(CH$_3$)$_3$, —S(O)$_2$CH$_3$, fluoropyrimidinyl, or chloropyrimidinyl; tetrahydrofuranyl substituted with zero to 2 substituents independently selected from F and —OH; pyrrolidinyl substituted with zero to 1 substituent selected from —C(O)CH$_3$, —C(O)CH$_2$CF$_3$, —C(O)CH$_2$CN, —C(O)OCH$_3$, —S(O)$_2$CH$_3$, —C(O)(difluorophenyl), pyrimidinyl, fluoropyrimidinyl, and methoxypyrimidinyl; piperidinyl substituted with —S(O)$_2$CH$_3$, phenyl, or fluoropyrimidinyl; tetrahydropyranyl, fluorotetrahydropyranyl, or oxetanyl;

(iv) adamantanyl, hydroxyadamantanyl, benzo[d]imidazolyl, benzo[d]oxazolyl, benzo[d]triazolyl, benzothiazolyl, bicyclo[1.1.1]pentanyl, or hydroxy-bicyclo[2.2.1]heptanyl; or (v) phenyl substituted with 1 to 2 substituents independently selected from F, —OH, —CN, —CH$_2$OH, —C(CH$_3$)$_2$OH, —OCH$_3$, —C(O)NH$_2$, —C(O)NHCH$_3$, —NHC(O)CH$_3$, —NHC(O)S(O)$_2$CH$_3$, —S(O)$_2$NH$_2$, pyrazolyl, methyl pyrazolyl, imidazolyl, triazolyl, methyl tetrazolyl, and ethyl tetrazolyl; pyrazolyl substituted with 1 to 2 substituents independently selected from —CH$_3$, —CH$_2$CH$_3$, —CH$_2$CH$_2$CH$_3$, —CH(CH$_3$)$_2$, —CHF$_2$, —CH$_2$CHF$_2$, —CH$_2$CF$_3$, —CH$_2$CHFCH$_3$, —CH$_2$CH$_2$F, —CH$_2$C(CH$_3$)$_2$F, —CH$_2$CF$_2$CH$_3$, —CH$_2$C(CH$_3$)$_2$OH, —CH$_2$CH$_2$OCH$_3$, —CH$_2$CH(CH$_3$)OCHF$_2$, —CH$_2$CH$_2$CN, —C(O)NHCH$_2$CH$_3$, —S(O)$_2$CH$_3$, cyclopropyl, oxetanyl, phenyl, pyrimidinyl, fluoropyrimidinyl, and tetrahydropyranyl; methyl thiadiazolyl, hydroxypropyl thiazolyl, or indazolyl.

One embodiment provides a compound of Formula (I) or a salt thereof, wherein HET is a heteroaryl selected from:

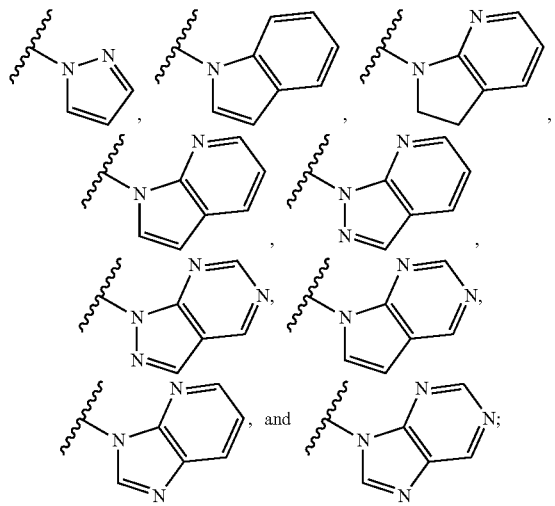

wherein each of said heteroaryl is substituted with $R_a$ and $R_b$; and $R_1$, $R_2$, $R_a$, and $R_b$ are defined in the first aspect. Included in this embodiment are compounds in which Q is selected from:

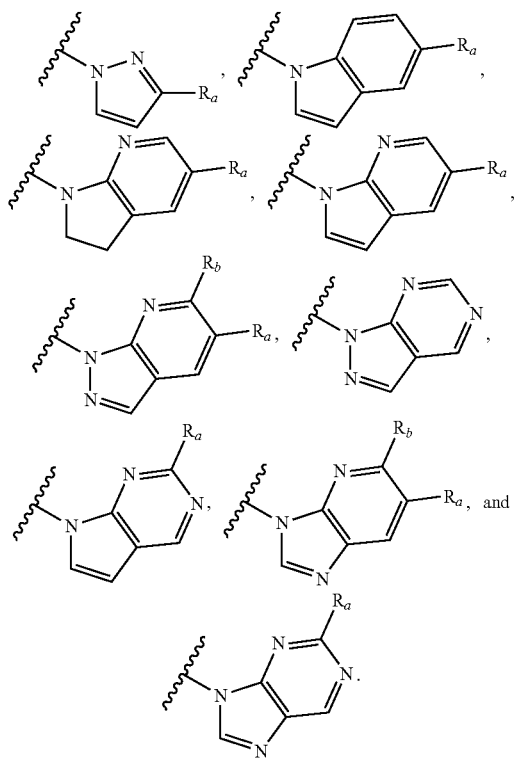

One embodiment provides a compound of Formula (I) or a salt thereof, wherein Q is pyrazolyl substituted with $R_a$ and $R_b$; and $R_1$, $R_2$, $R_a$, and $R_b$ are defined in the first aspect. Included in this embodiment are compounds in which Q is

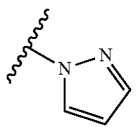 [SMILES: *n1cccn1]

substituted with $R_a$ and $R_b$; and compounds in which Q is

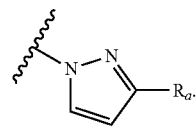

Also included in this embodiment are compounds in which $R_a$ is pyridazinyl; $R_b$ is H; $R_1$ is —$CH_2CF_2C(CH_3)_2OH$; and $R_2$ is —$CH(CH_3)_2$.

One embodiment provides a compound of Formula (I) or a salt thereof, wherein Q is indolyl substituted with $R_a$ and $R_b$; and $R_1$, $R_2$, $R_a$, and $R_b$ are defined in the first aspect. Included in this embodiment are compounds in which Q is

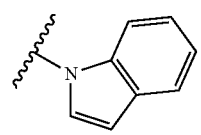 [SMILES: *n1ccc2ccccc21]

substituted with $R_a$ and $R_b$; and compounds in which Q is

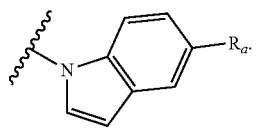

Also included in this embodiment are compounds in which $R_a$ is Cl or —CN; $R_b$ is H; $R_1$ is —$CH_2CHFC(CH_3)_2OH$ or cyclohexyl substituted with —$C(CH_3)_2OH$ or —$C(O)NHCH_3$.

One embodiment provides a compound of Formula (I) or a salt thereof, wherein Q is pyrrolo[2,3-b]pyridinyl substituted with $R_a$ and $R_b$; and $R_1$, $R_2$, $R_a$, and $R_b$ are defined in the first aspect. Included in this embodiment are compounds in which Q is

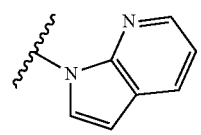 [SMILES: *n1ccc2cccnc21]

substituted with $R_a$ and $R_b$; and compounds in which Q is

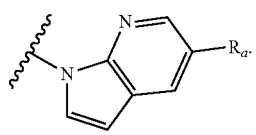

Also included in this embodiment are compounds wherein $R_a$ is H, F, Cl, —CN, —C(O)NH$_2$, —NHC(O)CH$_3$, —CH$_2$NHC(O)CH(CH$_3$)$_2$, —CH$_2$NHC(O)CH$_2$C(CH$_3$)$_2$OH, —CH$_2$NHC(O)CH$_2$C(CH$_3$)$_3$, —CH$_2$NHC(O)CH$_2$CH(CH$_3$)$_2$, —CH$_2$NHC(O)CH$_2$CH$_2$CH(CH$_3$)$_2$, —CH$_2$NHC(O)CH$_2$CH$_3$, —CH$_2$NHC(O)N(CH$_2$CH$_3$)$_2$, —CH$_2$NHC(O)NHCH$_2$(phenyl), —CH$_2$NHC(O)NHCH$_2$CH$_2$CH$_3$, —CH$_2$NHC(O)NHCH$_2$CH$_2$CH$_3$, —CH$_2$NHC(O)OCH$_2$CH(CH$_3$)$_2$, —CH$_2$NHC(O)OCH$_2$CH$_3$, —CH$_2$NHC(O)(cyclopropyl), —CH$_2$NHC(O)(tetrahydrofuranyl), —CH$_2$NHC(O)CH$_2$(tetrahydropyranyl), —CH$_2$NHC(O)CH$_2$(cyclopentyl), —CH$_2$NHC(O)CH$_2$(cyclohexyl), —CH$_2$NHC(O)CH$_2$(phenyl), or —CH$_2$NHC(O)NHCH$_2$(phenyl); $R_b$ is H;

$R_1$ is:
(i) —CH$_2$CHFC(CH$_3$)$_2$F, —CH$_2$CH$_2$C(CH$_3$)$_2$OH, —CH$_2$CHFCH(CH$_3$)OH, —CH$_2$CHFC(CH$_3$)$_2$OH, —(CH$_2$)$_3$OCH(CH$_3$)$_2$, —(CH$_2$)$_3$OC(CH$_3$)$_3$, —CH$_2$CHFCH$_2$OCH$_3$, —CH$_2$CHFC(CH$_3$)$_2$OCD$_3$, —CH$_2$CHFC(CH$_3$)$_2$OCH$_2$CH$_3$, —CH$_2$CH$_2$NHC(O)C(CH$_3$)$_2$OC(O)CH$_3$, —CH$_2$CH$_2$NHS(O)$_2$CH$_3$, —CH$_2$CHFCH(CH$_3$)NHCH(CH$_3$)$_2$, or —CH$_2$CHFC(O)NHCH$_3$;
(ii) —(C$_{1-2}$ fluoroalkylenyl)R$_x$, —CH$_2$C(O)R$_x$, or —CH$_2$C(O)NHR$_x$, wherein R$_x$ is a cyclic group selected from cyclopropyl, piperazinyl, oxetanyl, and phenyl, wherein each cyclic group is substituted with zero to 3 substituents independently selected from —OH, —CH$_3$, and —S(O)$_2$NH$_2$;
(iii) cyclopentyl or cyclohexyl, each substituted with 1 to 2 substituents independently selected from F, —OH, —CH$_3$, —SCH$_3$, —NO$_2$, —S(O)$_2$CH$_3$, —C(CH$_3$)$_2$OH, —C(CH$_3$)(OH)(cyclopropyl), —C(O)NHCD$_3$, —C(O)NHCH$_3$, —C(O)NHCH$_2$CH$_3$, —C(O)NH(cyclopropyl), —NHC(O)OCH$_3$, pyridinyl, methylimidazolyl, methylpyrazolyl, and thiazolyl;
(iv) piperidinyl substituted with —S(O)$_2$CH$_3$; or
(v) bicyclo[2.2.1]heptan-1-ol, tetrahydrobenzo[d]thiazol-2-amine, or 1,3-diazaspiro[4.5]decane-2,4-dione; and $R_2$ is:
(i) —CH$_2$CH$_3$, —CH$_2$CH$_2$CH$_3$, —CH(CH$_3$)$_2$, —CH$_2$CH$_2$CH(CH$_3$)$_2$, —CH(CH$_3$)CH$_2$CH(CH$_3$)$_2$, —CH(CH$_3$)CH$_2$OH, —CH$_2$CH$_2$CH(CH$_3$)OH, —CH(CH$_3$)CH$_2$CH$_2$OH, —CH$_2$C(CH$_3$)$_2$OH, —CH(CH$_3$)CH(OH)CH$_2$CH(CH$_3$)$_2$, —CH=CHC(CH$_3$)$_2$OH, —CH$_2$CF$_3$, —CH$_2$CHFCH$_3$, —CH$_2$CH$_2$CF$_3$, —CH(CH$_3$)CH$_2$F, —CH(CH$_3$)CHFCH$_3$, —CH(CH$_3$)CH$_2$CH$_2$F, —CH$_2$CHFC(CH$_3$)$_2$OH, —CH(CH$_2$F)CH$_2$OH, or —CH$_2$CHFC(O)NHCH(CH$_3$)$_2$;
(ii) —CH$_2$(azetidinyl), —CH$_2$(fluorocyclobutyl), —CH$_2$(hydroxycyclobutyl), —CH$_2$(oxetanyl), —CH$_2$(methyloxetanyl), —CH$_2$(methylpyridinyl), —CH$_2$(tetrahydropyranyl), —CH$_2$CH$_2$(methylmorpholinyl) —CH(CH$_3$)(cyclopropyl), or —CH$_2$CH$_2$(morpholinyl);
(iii) C$_{3-6}$ cycloalkyl substituted with zero to 3 substituents independently selected from F, —OH, —CH$_3$, —CH$_2$OH, —C(CH$_3$)$_2$OH, —C(O)NH$_2$, —NH$_2$, —NHCH$_2$CF$_3$, and imidazolyl; azetidinyl substituted with —C(O)CH$_3$, —C(O)OCH$_3$, —C(O)OC(CH$_3$)$_3$, —S(O)$_2$CH$_3$, or fluoropyrimidinyl; tetrahydrofuranyl substituted with zero to 2 substituents independently selected from F and —OH; pyrrolidinyl substituted with zero to 1 substituent selected from —C(O)CH$_3$, —C(O)CH$_2$CF$_3$, —C(O)CH$_2$CN, —C(O)OCH$_3$, —S(O)$_2$CH$_3$, and fluoropyrimidinyl; piperidinyl substituted with —S(O)$_2$CH$_3$, or phenyl; tetrahydropyranyl, fluorotetrahydropyranyl, or oxetanyl;

(iv) adamantanyl, benzo[d]imidazolyl, benzo[d]oxazolyl, benzo[d]triazolyl, benzothiazolyl, or hydroxy-bicyclo[2.2.1]heptanyl; or
(v) phenyl substituted with 1 to 2 substituents independently selected from F, —OH, —CN, —CH$_2$OH, —C(CH$_3$)$_2$OH, —OCH$_3$, —C(O)NH$_2$, —C(O)NHCH$_3$, —NHC(O)CH$_3$, —NHC(O)S(O)$_2$CH$_3$, —S(O)$_2$NH$_2$, pyrazolyl, imidazolyl, triazolyl, methyl tetrazolyl, and ethyl tetrazolyl; pyrazolyl substituted with 1 to 2 substituents independently selected from —CH$_3$, —CH$_2$CH$_3$, —CH$_2$CH$_2$CH$_3$, —CH$_2$CHF$_2$, and tetrahydropyranyl; or indazolyl.

One embodiment provides a compound of Formula (I) or a salt thereof, wherein Q is pyrrolo[2,3-d]pyrimidinyl substituted with R$_a$ and R$_b$; and R$_1$, R$_2$, R$_a$, and R$_b$ are defined in the first aspect. Included in this embodiment are compounds in which Q is

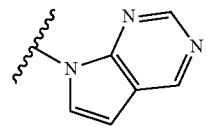 [SMILES: *n1ccc2cncnc21]

substituted with R$_a$ and R$_b$; and compounds in which Q is

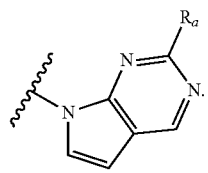

Also included in this embodiment are compounds in which R$_a$ is H, —NH$_2$, N(CH$_3$)$_2$, —NHCH$_2$CH$_2$OH, —NHCH$_2$C(CH$_3$)$_2$OH, or hydroxypyrrolidinyl; R$_b$ is H; R$_1$ is —CH$_2$CHFC(CH$_3$)$_2$OH or cyclohexyl substituted with —C(O)NHCH$_3$; and R$_2$ is —CH(CH$_3$)$_2$, —CH(CH$_3$)CH$_2$F, —CH$_2$C(CH$_3$)$_2$OH, cyclopropyl, tetrahydropyranyl, or —CH$_2$CH(CH$_3$)(morpholinyl).

One embodiment provides a compound of Formula (I) or a salt thereof, wherein Q is pyrazolo[3,4-b]pyridinyl substituted with R$_a$ and R$_b$; and R$_1$, R$_2$, R$_a$, and R$_b$ are defined in the first aspect. Included in this embodiment are compounds in which Q is

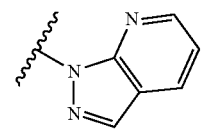

substituted with R$_a$ and R$_b$; and compounds in which Q is

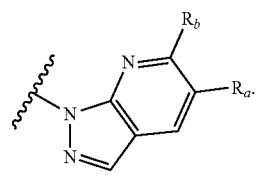

Also included in this embodiment are compounds in which $R_a$ is F, Cl, Br, —CN, —OH, —CH$_3$, —CHF$_2$, —OCH$_3$, —C(O)NH$_2$, or —CH$_2$NHC(O)CH$_2$CH(CH$_3$)$_2$; $R_b$ is H or —NH$_2$;

$R_1$ is:

(i) —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH(CH$_3$)$_2$, —CH$_2$CHFCH$_3$, —CH$_2$CH$_2$CF$_2$CH$_3$, —CH$_2$CHFCH(CH$_3$)$_2$, —CH$_2$CH$_2$C(CH$_3$)$_2$F, —CH$_2$CHFC(CH$_3$)$_2$F, —CH$_2$CH$_2$CH(OH)CH$_3$, —CH$_2$CH$_2$C(CH$_3$)$_2$OH, —CH$_2$CHFC(CH$_3$)$_2$OH, —CH$_2$CF$_2$C(CH$_3$)$_2$OH, —CH$_2$CHFC(cyclopropyl)$_2$(OH), —CH$_2$CHFCH(OH)CH(CH$_3$)$_2$, —CH$_2$CH$_2$OCH$_2$CH$_3$, —CH$_2$CHFCH$_2$OCH$_3$, —CH$_2$CHFC(CH$_3$)$_2$OCH$_3$, —CH$_2$CHFC(CH$_3$)$_2$OCD$_3$, —CH$_2$CHFC(CH$_3$)$_2$OCH$_2$CH$_3$, —CH$_2$CH$_2$C(O)OCH$_3$, —CH$_2$CH$_2$NHS(O)$_2$CH$_3$, —CH$_2$CH$_2$CH(CH$_3$)NHS(O)$_2$CH$_3$, —CH$_2$CH$_2$C(CH$_3$)$_2$NHS(O)$_2$CH$_3$, —CH$_2$CH$_2$P(O)(OCH$_3$)$_2$, —CH$_2$CHFC(O)NHCH$_3$, —CH$_2$CH$_2$C(O)NHCH$_2$CH$_3$, —CH$_2$CHFC(O)NHCH(CH$_3$)$_2$, —CH$_2$CHFC(O)NHCH(CH$_3$)CH$_2$OH, or —CH$_2$CHFC(CH$_3$)$_2$OP(O)(OH)$_2$;

(ii) —(C$_{1-3}$ alkylenyl)R$_x$, —(C$_{1-2}$ fluoroalkylenyl)R$_x$, —(C$_{1-2}$ alkylenyl)C(O)R$_x$, —CH$_2$CHFC(O)R$_x$, or —CH$_2$CF=(tetrahydropyranyl), wherein R$_x$ is a cyclic group selected from cyclopropyl, cyclopentyl, cyclohexyl, tetrazolyl, 1,1-dioxidotetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —CH$_3$, —C(CH$_2$)$_2$OH, —OCH$_3$, —C(O)CH$_2$CN, —S(O)$_2$CH$_3$, —S(O)$_2$NH$_2$, —NHC(O)CH$_3$, —N(S(O)$_2$CH$_3$)$_2$, oxetanyl, and benzyl;

(iii) cyclopropyl, cyclopentyl, cyclopentenyl, or cyclohexyl, each substituted with zero to 1 substituent independently selected from —CN, —CH$_3$, —OCH$_3$, —S(O)$_2$CH$_3$, —C(CH$_3$)$_2$OH, —CH$_2$C(O)NHCH$_3$, —NHC(O)CH(OH)CH$_3$, —C(O)NHCD$_3$, —C(O)NHCH$_3$, —NHC(O)CH$_3$, and —NHS(O)$_2$CH$_3$;

(iv) tetrahydropyranyl, piperidinyl, pyrazolyl, phenyl, pyridinyl, or pyrimidinyl, each substituted with a substituent selected from —OH, —OCH$_3$, —CH$_2$CHF$_2$, —C(CH$_3$)$_2$OH, —CH$_2$C(CH$_3$)$_2$OH, —C(O)CH(CH$_3$)$_2$, —S(O)$_2$CH$_3$, —S(O)$_2$CH$_2$CH$_3$, —S(O)$_2$CH(CH$_3$)$_2$, —S(O)$_2$NHCH$_3$, —S(O)$_2$NHCH(CH$_3$)$_2$, —N(CH$_3$)$_2$, —OCH$_2$CH$_2$N(CH$_3$)$_2$, —CH$_2$(morpholinyl), oxetanyl, tetrahydropyranyl, morpholinyl, piperazinyl, methylpiperazinyl, methoxypiperidinyl, pyrimidinyl, methylsulfonyl azetidinyl, and —C(O)(methylsulfonyl azetidinyl); or (v) pyrrolo[2,3-c]pyridinyl or tetrahydrobenzo[d]thiazol-2-amine; and $R_2$ is:

(i) —CH$_2$CH$_3$, —CH$_2$CH$_2$CH$_3$, —CH(CH$_3$)$_2$, —C(CH$_3$)$_3$, —CH$_2$C(CH$_3$)$_3$, —CH(CH$_3$)CH$_2$CH$_3$, —CH(CH$_3$)CH$_2$OH, —CH$_2$CH$_2$CH(CH$_3$)OH, —C(CH$_3$)$_2$CH$_2$OH, —CH$_2$CH(OH)CH(CH$_3$)$_2$, —CH(CH$_2$OH)CH$_2$CH$_3$, —CH(CH$_2$OH)CH(CH$_3$)$_2$, —CH$_2$CHF$_2$, —CH$_2$CF$_3$, —CH$_2$CHFCH$_3$, —CH(CH$_3$)CF$_3$, —CH$_2$CH$_2$CF$_3$, —CH(CH$_3$)CH$_2$F, —CH$_2$CH$_2$CH$_2$F, —CH$_2$CHFCH$_2$CH$_3$, —CH$_2$CH$_2$CHFCH$_3$, —CH(CH$_3$)CHFCH$_3$, —CH(CH$_3$)CH$_2$CH$_2$F, —CH$_2$CH$_2$C(CH$_3$)$_2$F, —CH$_2$CF$_2$C(CH$_3$)$_2$OH, —CH$_2$C(CH$_3$)FCH$_2$OH, —CH$_2$CH$_2$OCHF$_2$, —CH$_2$C(CH$_3$)OCHF$_2$, —CH$_2$C(CH$_3$)$_2$OCHF$_2$, —CH$_2$C(CH$_3$)$_2$OCH$_3$, —CH$_2$C(CH$_3$)$_2$CH$_2$NH$_2$, —CH$_2$CH$_2$NHS(O)$_2$CH$_3$, or —CH$_2$CH$_2$NHC(O)OC(CH$_3$)$_2$CF$_3$;

(ii) —CH$_2$(cyclopropyl), —CH$_2$(fluorocyclobutyl), —CH$_2$(oxazolyl), or —CH$_2$C(CH$_3$)$_2$(morpholinyl);

(iii) C$_{3-6}$ cycloalkyl substituted with zero to 3 substituents independently selected from F, —OH, —CH$_3$, —CH$_2$OH, —C(CH$_3$)$_2$OH, —C(O)NHCH(CH$_3$)$_2$, —NH$_2$, —NH(oxetanyl), —NHC(O)CHF$_2$, —NHC(O)(cyclopropyl), and —NHC(O)(fluorophenyl); azetidinyl substituted with —C(O)OCH$_3$, —C(O)OCH$_2$CH$_3$, fluoropyrimidinyl, or chloropyrimidinyl; tetrahydrofuranyl substituted with zero to 2 substituents selected from F; pyrrolidinyl substituted with —C(O)(difluorophenyl), pyrimidinyl, fluoropyrimidinyl, or methoxypyrimidinyl; piperidinyl substituted with phenyl or fluoropyrimidinyl; tetrahydropyranyl, or oxetanyl;

(iv) hydroxyadamantanyl, benzo[d]oxazolyl, benzothiazolyl, bicyclo[1.1.1]pentanyl, or hydroxy-bicyclo[2.2.1]heptanyl; or (v) phenyl substituted with 1 to 2 substituents independently selected from F, —CN, triazolyl, and methyl tetrazolyl; pyrazolyl substituted with 1 to 2 substituents independently selected from —CH$_3$, —CH$_2$CH$_3$, —CH$_2$CH$_2$CH$_3$, —CH(CH$_3$)$_2$, —CHF$_2$, —CH$_2$CHF$_2$, —CH$_2$CH$_2$F, —CH$_2$C(CH$_3$)$_2$F, —CH$_2$CF$_2$CH$_3$, —CH$_2$C(CH$_3$)$_2$OH, —CH$_2$CH$_2$OCH$_3$, —CH$_2$CH(CH$_3$)OCHF$_2$, —CH$_2$CH$_2$CN, —C(O)NHCH$_2$CH$_3$, —S(O)$_2$CH$_3$, cyclopropyl, oxetanyl, phenyl, pyrimidinyl, fluoropyrimidinyl, and tetrahydropyranyl; methyl thiadiazolyl, or hydroxypropyl thiazolyl.

One embodiment provides a compound of Formula (I) or a salt thereof, wherein Q is pyrazolo[3,4-d]pyrimidinyl substituted with $R_a$ and $R_b$; and $R_1$, $R_2$, $R_a$, and $R_b$ are defined in the first aspect. Included in this embodiment are compounds in which Q is

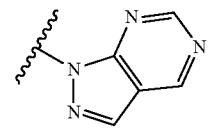 [SMILES: *n1ncc2cncnc21]

substituted with $R_a$ and $R_b$; and compounds in which Q is

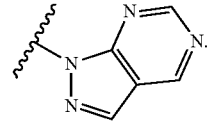 [SMILES: *n1ncc2cncnc21]

Also included in this embodiment are compounds in which $R_a$ is H or —NH$_2$; $R_b$ is H; $R_1$ is —CH$_2$CHFC(CH$_3$)$_2$OH or —CH$_2$CHFC(CH$_3$)$_2$OH; and $R_2$ is —CH$_2$CH$_3$, —CH(CH$_3$)$_2$, or cyclopropyl.

One embodiment provides a compound of Formula (I) or a salt thereof, wherein Q is 2,3-dihydro-1H-pyrrolo[2,3-b]pyridinyl substituted with $R_a$ and $R_b$; and $R_1$, $R_2$, $R_a$, and $R_b$ are defined in the first aspect. Included in this embodiment are compounds in which Q is

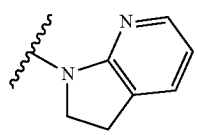 [SMILES: *N1CCc2cccnc21]

substituted with $R_a$ and $R_b$; and compounds in which Q is

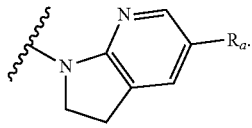

Also included in this embodiment are compounds in which $R_a$ is —CN; $R_b$ is H; $R_1$ is —CH$_2$CHFC(CH$_3$)$_2$OH; and $R_2$ is —CH(CH$_3$)$_2$, cyclopropyl, or oxetanyl.

One embodiment provides a compound of Formula (I) or a salt thereof, wherein Q is imidazo[4,5-b]pyridinyl substituted with $R_a$ and $R_b$; and $R_1$, $R_2$, $R_a$, and $R_b$ are defined in the first aspect. Included in this embodiment are compounds in which Q is

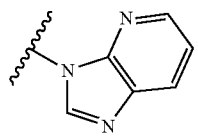

substituted with $R_a$ and $R_b$; and compounds in which Q is

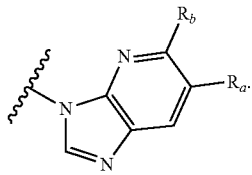

Also included in this embodiment are compounds in which $R_a$ is Cl or —CN; $R_b$ is H or —NH$_2$; $R_1$ is —CH$_2$CHFC(CH$_3$)$_2$F or —CH$_2$CHFC(CH$_3$)$_2$OH; and $R_2$ is —CH$_2$CH$_3$, —CH(CH$_3$)$_2$, —CH$_2$CH$_2$CN, cyclopropyl, methylcyclopropyl, cyclobutyl, oxetanyl, tetrahydrofuranyl, or pyrazolyl substituted with —CH$_3$, CHF$_2$, —CH$_2$CH$_3$, —CH$_2$CH$_2$CN, —CH$_2$CHF$_2$, —CH$_2$CH$_2$CH$_3$, CH$_2$CHFCH$_3$, —CH$_2$CH$_2$CH$_2$F, —CH(CH$_3$)$_2$, or —CH$_2$CH(CH$_3$)OCHF$_2$.

One embodiment provides a compound of Formula (I) or a salt thereof, wherein Q is purinyl substituted with $R_a$ and $R_b$; and $R_1$, $R_2$, $R_a$, and $R_b$ are defined in the first aspect. Included in this embodiment are compounds in which Q is

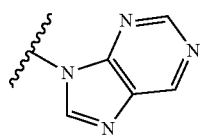 [SMILES: *n1cnc2cncnc21]

substituted with $R_a$ and $R_b$; and compounds in which Q is

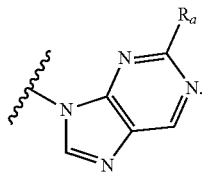

Also included in this embodiment are compounds in which $R_a$ is H, —NH$_2$, —NHCH$_2$CH$_2$OH, or —NHCH$_2$CHFC(CH$_3$)$_2$OH; $R_b$ is H; $R_1$ is —CH$_2$CHFC(CH$_3$)$_2$F or —CH$_2$CF$_2$C(CH$_3$)$_2$OH; and $R_2$ is —CH(CH$_3$)$_2$.

One embodiment provides a compound of Formula (I) or a salt thereof, wherein Q is pyrrolo[2,3-b]pyridinyl or pyrazolo [3,4-b]pyridinyl; $R_a$ is H, F, Cl, Br, —CN, —OH, —CH$_3$, —CHF$_2$, —OCH$_3$, —C(O)NH$_2$, —NHC(O)CH$_3$, —CH$_2$NHC(O)CH(CH$_3$)$_2$, —CH$_2$NHC(O)CH$_2$C(CH$_3$)$_3$, —CH$_2$NHC(O)CH$_2$CH(CH$_3$)$_2$, —CH$_2$NHC(O) CH$_2$CH$_2$CH$_3$, —CH$_2$NHC(O)N(CH$_2$CH$_3$)$_2$, —CH$_2$NHC (O)CH$_2$C(CH$_3$)$_2$OH, —CH$_2$NHC(O)CH$_2$CH$_2$CH(CH$_3$)$_2$, —CH$_2$NHC(O)NHCH$_2$CH$_2$CH$_3$, —CH$_2$NHC(O) NHCH$_2$CH$_2$CH$_3$, —CH$_2$NHC(O)OCH$_2$CH(CH$_3$)$_2$, —CH$_2$NHC(O)OCH$_2$CH$_3$, —CH$_2$NHC(O)(cyclopropyl), —CH$_2$NHC(O)CH$_2$(cyclopentyl), —CH$_2$NHC(O)CH$_2$(cyclohexyl), —CH$_2$NHC(O)(tetrahydrofuranyl), —CH$_2$NHC (O)CH$_2$(phenyl), —CH$_2$NHC(O)CH$_2$(tetrahydropyranyl), or —CH$_2$NHC(O)NHCH$_2$(phenyl); $R_b$ is H or —NH$_2$; $R_1$ is:

(i) —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH(CH$_3$)$_2$, —CH$_2$CHFCH$_3$, —CH$_2$CH$_2$CF$_2$CH$_3$, —CH$_2$CHFCH(CH$_3$)$_2$, —CH$_2$CH$_2$C(CH$_3$)$_2$F, —CH$_2$CHFC(CH$_3$)$_2$F, —CH$_2$CH$_2$CH(OH)CH$_3$, —CH$_2$CH$_2$C(CH$_3$)$_2$OH, —CH$_2$CHFCH(CH$_3$)OH, —CH$_2$CHFC(CH$_3$)$_2$OH, —CH$_2$CF$_2$C(CH$_3$)$_2$OH, —CH$_2$CHFC(cyclopropyl)$_2$ (OH), —CH$_2$CHFCH(OH)CH(CH$_3$)$_2$, —CH$_2$CH$_2$OCH$_2$CH$_3$, —(CH$_2$)$_3$OCH(CH$_3$)$_2$, —(CH$_2$)$_3$OC(CH$_3$)$_3$, —CH$_2$CHFCH$_2$OCH$_3$, —CH$_2$CHFC(CH$_3$)$_2$OCH$_3$, —CH$_2$CHFC(CH$_3$)$_2$ OCD$_3$, —CH$_2$CHFC(CH$_3$)$_2$OCHF$_2$, —CH$_2$CHFC (CH$_3$)$_2$OCH$_2$CH$_3$, —CH$_2$CH$_2$C(O)OCH$_3$, —CH$_2$CH$_2$NHC(O)C(CH$_3$)$_2$OC(O)CH$_3$, —CH$_2$CH$_2$NHS(O)$_2$CH$_3$, —CH$_2$CH$_2$CH(CH$_3$)NHS (O)$_2$CH$_3$, —CH$_2$CH$_2$C(CH$_3$)$_2$NHS(O)$_2$CH$_3$, —CH$_2$CH$_2$P(O)(OCH$_2$CH$_3$)$_2$, —CH$_2$CHFCH(CH$_3$) NHCH(CH$_3$)$_2$, —CH$_2$CHFC(O)NHCH$_3$, —CH$_2$CH$_2$C (O)NHCH$_2$CH$_3$, —CH$_2$CHFC(O)NHCH(CH$_3$)$_2$, —CH$_2$CHFC(O)NHCH(CH$_3$)CH$_2$OH, or —CH$_2$CHFC(CH$_3$)$_2$OP(O)(OH)$_2$;

(ii) —(C$_{1-3}$ alkylenyl)R$_x$, —(C$_{1-2}$ fluoroalkylenyl)R$_x$, —(C$_{1-2}$ alkylenyl)C(O)R$_x$, —CH$_2$C(O)NHR$_x$, —CH$_2$CHFC(O)R$_x$, or —CH$_2$CF=(tetrahydropyranyl), wherein R$_x$ is a cyclic group selected from cyclopropyl, cyclopentyl, cyclohexyl, tetrazolyl, 1,1-dioxidotetrahydrothiophenyl, 1,1-dioxidothiomorpholinyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —CH$_3$, —C(CH$_2$)$_2$OH, —OCH$_3$, —C(O)CH$_2$CN, —S(O)$_2$CH$_3$, —S(O)$_2$NH$_2$, —NHC(O)CH$_3$, —N(S(O)$_2$CH$_3$)$_2$, and oxetanyl, benzyl;

(iii) cyclopropyl, cyclopentyl, cyclopentenyl, or cyclohexyl, each substituted with zero to 2 substituents independently selected from F, —OH, —CN, —CH$_3$, —OCH$_3$, —SCH$_3$, —NO$_2$, —S(O)$_2$CH$_3$, —C(CH$_3$)$_2$OH, —C(CH$_3$)(OH)(cyclopropyl), —CH$_2$C(O)NHCH$_3$, —NHC(O)CH(OH)CH$_3$, —C(O)NHCD$_3$, —C(O)NHCH$_3$, —C(O)NHCH$_2$CH$_3$, —C(O)NH(cyclopropyl), —NHC(O)CH$_3$, —NHC(O)OCH$_3$, —NHS(O)$_2$CH$_3$, pyridinyl, methylimidazolyl, methylpyrazolyl, and thiazolyl;

(iv) tetrahydropyranyl, piperidinyl, pyrazolyl, phenyl, pyridinyl, or pyrimidinyl, each substituted with zero to 1 substituent selected from —OH, —OCH$_3$, —CH$_2$CHF$_2$, —C(CH$_3$)$_2$OH, —CH$_2$C(CH$_3$)$_2$OH, —C(O)CH(CH$_3$)$_2$, —S(O)$_2$CH$_3$, —S(O)$_2$CH$_2$CH$_3$, —S(O)$_2$CH(CH$_3$)$_2$, —S(O)$_2$NHCH$_3$, —S(O)$_2$NHCH(CH$_3$)$_2$, —N(CH$_3$)$_2$, —OCH$_2$CH$_2$N(CH$_3$)$_2$, —CH$_2$(morpholinyl), oxetanyl, tetrahydropyranyl, morpholinyl, piperazinyl, methylpiperazinyl, methoxypiperidinyl, pyrimidinyl, and —C(O)(methylsulfonyl azetidinyl); or (v) pyrrolo[2,3-c]pyridinyl, bicyclo[2.2.1]heptan-1-ol, tetrahydrobenzo[d]thiazol-2-amine, or 1,3-diazaspiro[4.5]decane-2,4-dione; and R$_2$ is:
(i) —CH$_2$CH$_3$, —CH$_2$CH$_2$CH$_3$, —CH(CH$_3$)$_2$, —C(CH$_3$)$_3$, —CH$_2$C(CH$_3$)$_3$, —CH(CH$_3$)CH$_2$CH$_3$, —CH$_2$CH$_2$CH(CH$_3$)$_2$, —CH(CH$_3$)CH$_2$CH(CH$_3$)$_2$, —CH(CH$_3$)CH$_2$OH, —CH$_2$CH$_2$CH(CH$_3$)OH, —CH(CH$_3$)CH$_2$CH$_2$OH, —CH$_2$C(CH$_3$)$_2$OH, —C(CH$_3$)$_2$CH$_2$OH, —CH(CH$_3$)CH(OH)CH$_2$CH(CH$_3$)$_2$, —CH$_2$CH(OH)CH(CH$_3$)$_2$, —CH(CH$_2$OH)CH(CH$_3$)$_2$, —CH=CHC(CH$_3$)$_2$OH, —CH$_2$CHF$_2$, —CH$_2$CF$_3$, —CH$_2$CHFCH$_3$, —CH(CH$_3$)CF$_3$, —CH$_2$CH$_2$CF$_3$, —CH(CH$_3$)CH$_2$F, —CH$_2$CH$_2$CH$_2$F, —CH$_2$CHFCH$_2$CH$_3$, —CH$_2$CH$_2$CHFCH$_3$, —CH(CH$_3$)CHFCH$_3$, —CH(CH$_3$)CH$_2$CH$_2$F, —CH$_2$CH$_2$C(CH$_3$)$_2$F, —CH$_2$CHFC(CH$_3$)$_2$OH, —CH$_2$CF$_2$C(CH$_3$)$_2$OH, —CH$_2$C(CH$_3$)FCH$_2$OH, —CH(CH$_2$F)CH$_2$OH, —CH$_2$CH$_2$OCHF$_2$, —CH$_2$C(CH$_3$)$_2$OCHF$_2$, —CH$_2$C(CH$_3$)$_2$OCH$_3$, —CH$_2$C(CH$_3$)$_2$CH$_2$NH$_2$, —CH$_2$CHFC(O)NHCH(CH$_3$)$_2$, —CH$_2$CH$_2$NHS(O)$_2$CH$_3$, or —CH$_2$CH$_2$NHC(O)OC(CH$_3$)$_2$CF$_3$;

(ii) —CH$_2$(azetidinyl), —CH$_2$(cyclopropyl), —CH$_2$(fluorocyclobutyl), —CH$_2$(hydroxycyclobutyl), —CH$_2$(oxetanyl), —CH$_2$(methyloxetanyl), —CH$_2$(oxazolyl), —CH$_2$(methylpyridinyl), —CH$_2$(tetrahydropyranyl), —CH$_2$CH$_2$(methylmorpholinyl) —CH(CH$_3$)(cyclopropyl), —CH$_2$CH$_2$(morpholinyl), or —CH$_2$C(CH$_3$)$_2$(morpholinyl);

(iii) C$_{3-6}$ cycloalkyl substituted with zero to 3 substituents independently selected from F, —OH, —CH$_3$, —CH$_2$OH, —C(CH$_3$)$_2$OH, —C(O)NH$_2$, —C(O)NHCH(CH$_3$)$_2$, —NH$_2$, —NHCH$_2$CF$_3$, —NH(oxetanyl), —NHC(O)CHF$_2$, —NHC(O)(cyclopropyl), —NHC(O)(fluorophenyl), and imidazolyl; azetidinyl substituted with —C(O)CH$_3$, —C(O)OCH$_3$, —C(O)OCH$_2$CH$_3$, —C(O)OC(CH$_3$)$_3$, —S(O)$_2$CH$_3$, fluoropyrimidinyl, or chloropyrimidinyl; tetrahydrofuranyl substituted with zero to 2 substituents independently selected from F and —OH; pyrrolidinyl substituted with zero to 1 substituent selected from —C(O)CH$_3$, —C(O)CH$_2$CF$_3$, —C(O)CH$_2$CN, —C(O)OCH$_3$, —S(O)$_2$CH$_3$, —C(O)(difluorophenyl), pyrimidinyl, fluoropyrimidinyl, and methoxypyrimidinyl; piperidinyl substituted with —S(O)$_2$CH$_3$, phenyl, or fluoropyrimidinyl; tetrahydropyranyl, fluorotetrahydropyranyl, or oxetanyl;

(iv) adamantanyl, hydroxyadamantanyl, benzo[d]imidazolyl, benzo[d]oxazolyl, benzo[d]triazolyl, benzothiazolyl, bicyclo[1.1.1]pentanyl, or hydroxy-bicyclo[2.2.1]heptanyl; or (v) phenyl substituted with 1 to 2 substituents independently selected from F, —OH, —CN, —CH$_2$OH, —C(CH$_3$)$_2$OH, —OCH$_3$, —C(O)NH$_2$, —C(O)NHCH$_3$, —NHC(O)CH$_3$, —NHC(O)S(O)$_2$CH$_3$, and —S(O)$_2$NH$_2$; pyrazolyl substituted with 1 to 2 substituents independently selected from —CH$_3$, —CH$_2$CH$_3$, —CH$_2$CH$_2$CH$_3$, —CH(CH$_3$)$_2$, —CHF$_2$, —CH$_2$CHF$_2$, —CH$_2$CF$_3$, —CH$_2$CH$_2$CH$_2$F, —CH$_2$C(CH$_3$)$_2$F, —CH$_2$CF$_2$CH$_3$, —CH$_2$C(CH$_3$)$_2$OH, —CH$_2$CH$_2$OCH$_3$, —CH$_2$CH$_2$CN, —C(O)NHCH$_2$CH$_3$, —S(O)$_2$CH$_3$, cyclopropyl, oxetanyl, phenyl, pyrimidinyl, fluoropyrimidinyl, and tetrahydropyranyl; methyl thiadiazolyl, hydroxypropyl thiazolyl, or indazolyl.

The second aspect of the invention provides a compound of Formula (I) or a salt thereof, within the scope of the first aspect, wherein: HET is a heteroaryl selected from pyrazole, indole, pyrrolo[2,3-b]pyridine, pyrrolo[2,3-d]pyrimidine, pyrazolo[3,4-b]pyridine, pyrazolo[3,4-d]pyrimidine, or purine, wherein said heteroaryl is substituted with zero or one substituent selected from F, Cl, Br, —OH, —CN, —NH$_2$, —N(CH$_3$)$_2$, —NHCH$_2$C(CH$_3$)$_2$OH, —NHC(O)CH$_3$, —NHCH$_2$CH$_2$OH, —C(O)NH$_2$, hydroxypyrrolidine, and pyridazine;

R$_1$ is:
(i) C$_{1-7}$ alkyl substituted with 1 to 4 substituents independently selected from F, —OH, —OCH$_3$, —OCH(CH$_3$)$_2$, —OC(CH$_3$)$_3$, —C(O)NHCH$_3$, —NH(CH(CH$_3$)$_2$), —NHS(O)$_2$CH$_3$, —NHC(O)C(CH$_3$)$_2$OC(O)CH$_3$, —C(O)NH(tetrahydrothiophene 1,1-dioxide), —OP(O)(OH)$_2$, morpholine, and phenyl substituted with —S(O)$_2$NH$_2$;

(ii) bicyclo[2.2.1]heptan-1-ol, tetrahydrobenzo[d]thiazol-2-amine, or 1,3-diazaspiro[4.5]decane-2,4-dione; or (iii) C$_{3-6}$ cycloalkyl substituted with 1 to 3 substituents independently selected from F, —OH, —NO$_2$, —CH$_3$, —C(CH$_3$)$_2$OH, —C(O)NH(CH$_3$), —C(O)NH(CD$_3$), —C(O)NH(CH$_2$CH$_3$), —C(O)NH(cyclopropyl), —NHC(O)CH$_3$, —NHC(O)OCH$_3$), —NHS(O)$_2$CH$_3$, —S(O)$_2$CH$_3$, —SCH$_3$, pyridine, methylimidazole, methylpyrazole, and thiazole; and R$_2$ is:
(i) C$_{2-6}$ alkyl substituted with zero to three substituents independently selected from F and —OH;

(ii) —(CH$_2$)$_{0-3}$—R$_x$ wherein R$_x$ is C$_{3-6}$ cycloalkyl, oxetane, tetrahydrofuran, or tetrahydropyran, each substituted with zero to 2 substituents selected from F, —OH, and —CH$_3$;

(iii) adamantane, benzothiazole, or bicyclo[2.2.1]heptan-1-ol; or (iv) phenyl substituted with —OH, —CN, —CH$_2$OH, —C(CH$_3$)$_2$OH, —OCH$_3$, —C(O)NH$_2$, —C(O)NH(CH$_3$), —NHC(O)CH$_3$, —NHS(O)$_2$CH$_3$, —S(O)$_2$NH$_2$, pyrazole, triazole, or methyl tetrazole.

One embodiment provides a compound of Formula (I) or a salt thereof wherein HET is a pyrazole substituted with zero or one substituent selected from F, Cl, Br, —OH, —CN, —CH$_3$, —NH$_2$, —N(CH$_3$)$_2$, —NHCH$_2$C(CH$_3$)$_2$OH, —NHC(O)CH$_3$, —NHCH$_2$CH$_2$OH, —C(O)NH$_2$, hydroxypyrrolidine, and pyridazine. Included in this embodiment are compounds in which HET is pyrazole substituted with pyridazine. Also included in this embodiment are compounds in which HET is

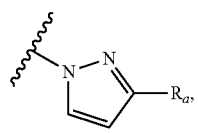

wherein $R_a$ is defined in the second aspect.

One embodiment provides a compound of Formula (I) or a salt thereof, wherein HET is a bicyclic heteroaryl selected from indole, pyrrolo[2,3-b]pyridine, pyrrolo[2,3-d]pyrimidine, pyrazolo[3,4-b]pyridine, pyrazolo[3,4-d]pyrimidine, or purine, wherein each of said bicyclic heteroaryl is substituted with zero or one substituent selected from F, Cl, Br, —OH, —CN, —CH$_3$, —NH$_2$, —N(CH$_3$)$_2$, —NHCH$_2$C(CH$_3$)$_2$OH, —NHC(O)CH$_3$, —NHCH$_2$CH$_2$OH, —C(O)NH$_2$, hydroxypyrrolidine, and pyridazine. Included in this embodiment are compounds in which HET is:

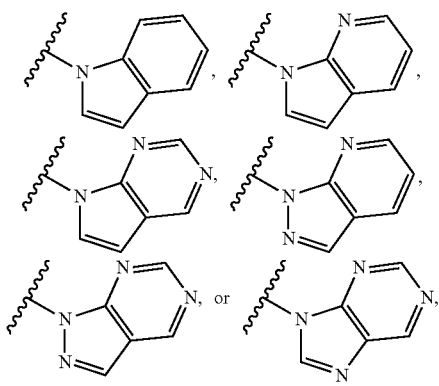

wherein each of said heteroaryl is substituted with zero or 1 substituent selected from F, Cl, Br, —OH, —CN, —CH$_3$, —NH$_2$, —N(CH$_3$)$_2$, —NHCH$_2$C(CH$_3$)$_2$OH, —NHC(O)CH$_3$, —NHCH$_2$CH$_2$OH, —C(O)NH$_2$, and hydroxypyrrolidine.

One embodiment provides a compound of Formula (I) or a salt thereof, wherein HET is a bicyclic heteroaryl selected:

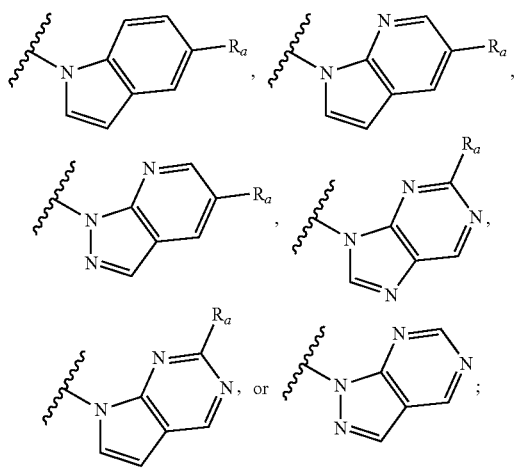

and
$R_a$ is H, F, Cl, Br, —OH, —CN, —CH$_3$, —NH$_2$, —N(CH$_3$)$_2$, —NHCH$_2$C(CH$_3$)$_2$OH, —NHC(O)CH$_3$, —NHCH$_2$CH$_2$OH, —C(O)NH$_2$, or hydroxypyrrolidine.

One embodiment provides a compound of Formula (I) or a salt thereof, wherein HET is:

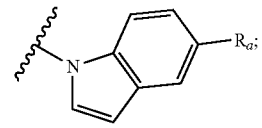

and wherein $R_a$ is Cl or —CN.

One embodiment provides a compound of Formula (I) or a salt thereof, wherein HET is:

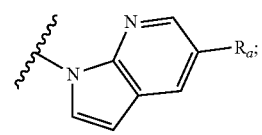

and wherein $R_a$ is H, F, Cl, —CN, —C(O)NH$_2$, or —NHC(O)CH$_3$.

One embodiment provides a compound of Formula (I) or a salt thereof, wherein HET is:

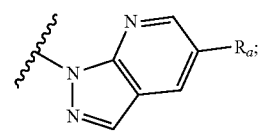

and wherein $R_a$ is F, Cl, Br, —OH, —CN, or —CH$_3$. Included in this embodiment are compounds in which $R_a$ is Cl or —CN. Also included in this embodiment are compounds in which HET is

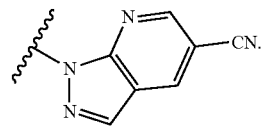 [SMILES: *n1ncc2cc(C#N)cnc21]

One embodiment provides a compound of Formula (I) or a salt thereof, wherein HET is:

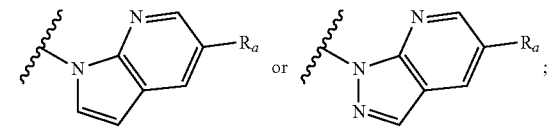

and wherein $R_a$ is H, F, Cl, Br, —CN, —OH, —CH$_3$, —C(O)NH$_2$, or —NHC(O)CH$_3$. Included in this embodiment are compounds in which $R_a$ is Cl or —CN.

One embodiment provides a compound of Formula (I) or a salt thereof, wherein HET is:

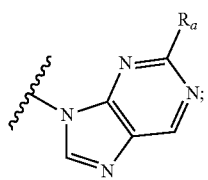

and wherein $R_a$ is H, —NH$_2$, or —NHCH$_2$CH$_2$OH.

One embodiment provides a compound of Formula (I) or a salt thereof, wherein HET is:

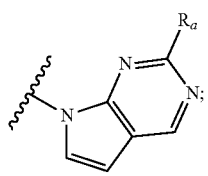

and wherein $R_a$ is H, —NH$_2$, —N(CH$_3$)$_2$, —NHCH$_2$CH$_2$OH, —NHCH$_2$C(CH$_3$)$_2$OH, or hydroxypyrrolidine.

One embodiment provides a compound of Formula (I) or a salt thereof, wherein HET is:

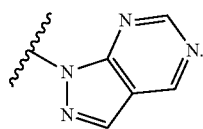

One embodiment provides a compound of Formula (I) or a salt thereof, wherein $R_a$ is H, F, Cl, or —CN. Included in this embodiment are compounds in which $R_a$ is —CN. Also included in this embodiment are compounds in which $R_a$ is Cl.

One embodiment provides a compound of Formula (I) or a salt thereof, wherein
$R_1$ is:
(i) —CH$_2$CH$_2$C(CH$_3$)$_2$OH, —CH$_2$CHFCH(CH$_3$)OH, —CH$_2$CHFC(CH$_3$)$_2$OH, —CH$_2$CF$_2$C(CH$_3$)$_2$OH, —CH$_2$CHFC(CH$_2$CH$_3$)$_2$OH, —CH$_2$CHFC(CH$_3$)$_2$OP(O)(OH)$_2$, —CH$_2$CHFC(O)NHCH$_3$, —CH$_2$CHFCH(CH$_3$)NH(CH(CH$_3$)$_2$), —CH$_2$CHFCH$_2$OCH$_3$, —(CH$_2$)$_3$—O—CH(CH$_3$)$_2$, —(CH$_2$)$_3$—O—C(CH$_3$)$_3$, —CH$_2$CH$_2$-morpholine, —CH$_2$CH$_2$(phenyl-S(O)$_2$NH$_2$), —CH$_2$CH$_2$NHC(O)C(CH$_3$)$_2$OC(O)CH$_3$, —CH$_2$CH$_2$NHS(O)$_2$CH$_3$, or —CH$_2$C(O)NH(tetrahydrothiophene 1,1-dioxide);
(ii) bicyclo[2.2.1]heptan-1-ol, tetrahydrobenzo[d]thiazol-2-amine, or 1,3-diazaspiro[4.5]decane-2,4-dione; or
(iii) cyclohexyl substituted with 1 to 2 substituents independently selected from F, —OH, —NO$_2$, —CH$_3$, —C(CH$_3$)$_2$OH, —C(O)NH(CH$_3$), —C(O)NH(CD$_3$), —C(O)NH(CH$_2$CH$_3$), —C(O)NH(cyclopropyl), —NHC(O)CH$_3$, —NHC(O)OCH$_3$, —NHS(O)$_2$CH$_3$, —S(O)$_2$CH$_3$, —SCH$_3$, pyridine, methylimidazole, methylpyrazole, and thiazole.

One embodiment provides a compound of Formula (I) or a salt thereof, wherein $R_1$ is $C_{1-7}$ alkyl substituted with 1 to 4 substituents independently selected from F, —OH, —OCH$_3$, —OCH(CH$_3$)$_2$, —OC(CH$_3$)$_3$, —C(O)NHCH$_3$, —NH(CH(CH$_3$)$_2$), —NHS(O)$_2$CH$_3$, —NHC(O)C(CH$_3$)$_2$OC(O)CH$_3$, —C(O)NH(tetrahydrothiophene 1,1-dioxide), —OP(O)(OH)$_2$, morpholine, and phenyl substituted with —S(O)$_2$NH$_2$. Included in this embodiment are compounds in which $R_1$ is —CH$_2$CH$_2$C(CH$_3$)$_2$OH, —CH$_2$CHFCH(CH$_3$)OH, —CH$_2$CHFC(CH$_3$)$_2$OH, —CH$_2$CF$_2$C(CH$_3$)$_2$OH, —CH$_2$CHFC(CH$_2$CH$_3$)$_2$OH, —CH$_2$CHFC(O)NHCH$_3$, —CH$_2$CHFCH(CH$_3$)NH(CH(CH$_3$)$_2$), —CH$_2$CHFCH$_2$OCH$_3$, —(CH$_2$)$_3$—O—CH(CH$_3$)$_2$, —(CH$_2$)$_3$—O—C(CH$_3$)$_3$, —CH$_2$CH$_2$-morpholine, —CH$_2$CH$_2$(phenyl-S(O)$_2$NH$_2$), —CH$_2$CH$_2$NHC(O)C(CH$_3$)$_2$OC(O)CH$_3$, —CH$_2$CH$_2$NHS(O)$_2$CH$_3$, or —CH$_2$C(O)NH(tetrahydrothiophene 1,1-dioxide).

One embodiment provides a compound of Formula (I) or a salt thereof, wherein $R_1$ is bicyclo[2.2.1]heptan-1-ol, tetrahydrobenzo[d]thiazol-2-amine, or 1,3-diazaspiro[4.5]decane-2,4-dione.

One embodiment provides a compound of Formula (I) or a salt thereof, wherein $R_1$ is $C_{3-6}$ cycloalkyl substituted with 1 to 3 substituents independently selected from F, —OH, —NO$_2$, —CH$_3$, —C(CH$_3$)$_2$OH, —C(O)NH(CH$_3$), —C(O)NH(CD$_3$), —C(O)NH(CH$_2$CH$_3$), —C(O)NH(cyclopropyl), —NHC(O)CH$_3$, —NHC(O)OCH$_3$, —NHS(O)$_2$CH$_3$, —S(O)$_2$CH$_3$, —SCH$_3$, pyridine, methylimidazole, methylpyrazole, and thiazole. Included in this embodiment are compounds in which $R_1$ is cyclohexyl substituted with 1 to 2 substituents independently selected from F, —OH, —NO$_2$, —CH$_3$, —C(CH$_3$)$_2$OH, —C(O)NH(CH$_3$), —C(O)NH(CD$_3$), —C(O)NH(CH$_2$CH$_3$), —C(O)NH(cyclopropyl), —NHC(O)CH$_3$, —NHC(O)OCH$_3$, —NHS(O)$_2$CH$_3$, —S(O)$_2$CH$_3$, —SCH$_3$, pyridine, methylimidazole, methylpyrazole, and thiazole.

One embodiment provides a compound of Formula (I) or a salt thereof, wherein $R_2$ is $C_{2-6}$ alkyl substituted with zero to three substituents independently selected from F and —OH. Included in this embodiment are compounds in which $R_2$ is —CH$_2$CH$_3$, —CH$_2$CH$_2$CH$_3$, —CH(CH$_3$)$_2$, —CH$_2$CH$_2$CH(CH$_3$)$_2$, —CH$_2$CF$_3$, —CH(CH$_3$)CH$_2$F, —CH(CH$_3$)CHF(CH$_3$), —CH(CH$_3$)CH$_2$CH$_2$OH, —CH(CH$_3$)CH$_2$OH, —CH(CH$_2$F)CH$_2$OH, —CH$_2$C(CH$_3$)$_2$OH, —CH$_2$CHFC(CH$_3$)$_2$OH, or —CH$_2$CF$_2$C(CH$_3$)$_2$OH.

One embodiment provides a compound of Formula (I) or a salt thereof, wherein $R_2$ is —(CH$_2$)$_{0-3}$—$R_x$ wherein $R_x$ is $C_{3-6}$ cycloalkyl, oxetane, or tetrahydropyran, each substituted with zero to 2 substituents selected from F, —OH, and —CH$_3$. Included in this embodiment are compounds of Formula (I) in which $R_2$ is tetrahydropyran, fluorotetrahydropyran, —CH$_2$(fluorocyclobutyl), —CH$_2$(hydroxycyclobutyl), —CH$_2$(oxetane), —CH$_2$(methyloxetane), or $C_{3-6}$ cycloalkyl substituted with zero to 3 substituents independently selected from F, —OH, and —CH$_3$.

One embodiment provides a compound of Formula (I) or a salt thereof, wherein $R_2$ is adamantane, benzothiazole, or bicyclo[2.2.1]heptan-1-ol.

One embodiment provides a compound of Formula (I) or a salt thereof, wherein $R_2$ is phenyl substituted with —OH, —CN, —CH$_2$OH, —C(CH$_3$)$_2$OH, —OCH$_3$, —C(O)NH$_2$, —C(O)NH(CH$_3$), —NHC(O)CH$_3$, —NHS(O)$_2$CH$_3$, —S(O)$_2$NH$_2$, pyrazole, triazole, or methyl tetrazole.

The third aspect of the invention provides a compound of Formula (I) or a salt thereof, within the scope of the first aspect, wherein:

HET is a heteroaryl selected from:

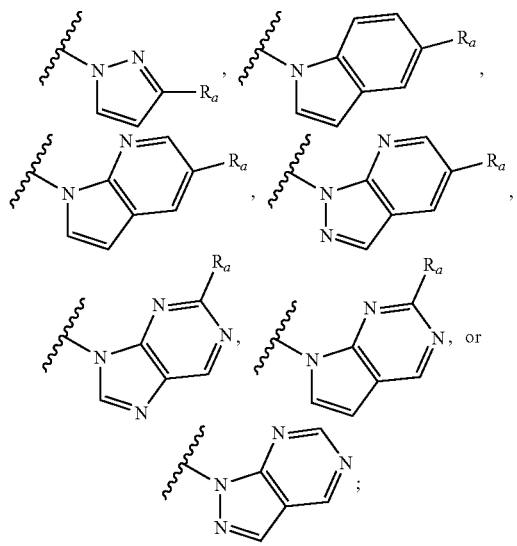

$R_a$ is H, F, Cl, Br, —OH, —CN, —CH$_3$, —NH$_2$, —N(CH$_3$)$_2$, —NHCH$_2$C(CH$_3$)$_2$OH, —NHC(O)CH$_3$, —NHCH$_2$CH$_2$OH, —C(O)NH$_2$, hydroxypyrrolidine, or pyridazine;

R$_1$ is:
(i) —CH$_2$CH$_2$C(CH$_3$)$_2$OH, —CH$_2$CHFCH(CH$_3$)OH, —CH$_2$CHFC(CH$_3$)$_2$OH, —CH$_2$CF$_2$C(CH$_3$)$_2$OH, —CH$_2$CHFC(CH$_2$CH$_3$)$_2$OH, —CH$_2$CHFC(CH$_3$)$_2$OP(O)(OH)$_2$, —CH$_2$CHFC(O)NHCH$_3$, —CH$_2$CHFCH(CH$_3$)NH(CH(CH$_3$)$_2$), —CH$_2$CHFCH$_2$OCH$_3$, —(CH$_2$)$_3$—O—CH(CH$_3$)$_2$, —(CH$_2$)$_3$—O—C(CH$_3$)$_3$, —CH$_2$CH$_2$-morpholine, —CH$_2$CH$_2$(phenyl-S(O)$_2$NH$_2$), —CH$_2$CH$_2$NHC(O)C(CH$_3$)$_2$OC(O)CH$_3$, —CH$_2$CH$_2$NHS(O)$_2$CH$_3$, or —CH$_2$C(O)NH(tetrahydrothiophene 1,1-dioxide);
(ii) bicyclo[2.2.1]heptan-1-ol, tetrahydrobenzo[d]thiazol-2-amine, or 1,3-diazaspiro[4.5]decane-2,4-dione; or
(iii) cyclohexyl substituted with 1 to 2 substituents independently selected from F, —OH, —NO$_2$, —CH$_3$, —C(CH$_3$)$_2$OH, —C(O)NH(CH$_3$), —C(O)NH(CD$_3$), —C(O)NH(CH$_2$CH$_3$), —C(O)NH(cyclopropyl), —NHC(O)CH$_3$, —NHC(O)OCH$_3$, —NHS(O)$_2$CH$_3$, —S(O)$_2$CH$_3$, —SCH$_3$, pyridine, methylimidazole, methylpyrazole, and thiazole; and R$_2$ is
(i) —CH$_2$CH$_3$, —CH$_2$CH$_2$CH$_3$, —CH(CH$_3$)$_2$, —CH$_2$CH$_2$CH(CH$_3$)$_2$, —CH$_2$CF$_3$, —CH(CH$_3$)CH$_2$F, —CH(CH$_3$)CHF(CH$_3$), —CH(CH$_3$)CH$_2$CH$_2$OH, —CH(CH$_3$)CH$_2$OH, —CH(CH$_2$F)CH$_2$OH, —CH$_2$C(CH$_3$)$_2$OH, —CH$_2$CHFC(CH$_3$)$_2$OH, —CH$_2$CF$_2$C(CH$_3$)$_2$OH;
(ii) tetrahydropyran, fluorotetrahydropyran, —CH$_2$(fluorocyclobutyl), —CH$_2$(hydroxycyclobutyl), —CH$_2$(oxetane), —CH$_2$(methyloxetane), or C$_{3-6}$ cycloalkyl substituted with zero to 3 substituents independently selected from F, —OH, and —CH$_3$;
(iii) adamantane, benzothiazole, or bicyclo[2.2.1]heptan-1-ol; or
(iv) phenyl substituted with one substituent selected from —OH, —CN, —CH$_2$OH, —C(CH$_3$)$_2$OH, —OCH$_3$, —C(O)NH$_2$, —C(O)NH(CH$_3$), —NHC(O)CH$_3$, —NHS(O)$_2$CH$_3$, —S(O)$_2$NH$_2$, pyrazole, triazole, and methyl tetrazole.

One embodiment provides a compound of Formula (I) or a salt thereof, wherein HET is

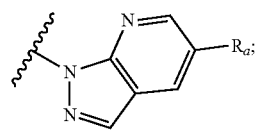

$R_a$ is F, Cl, Br, —OH, —CN, or —CH$_3$;
R$_1$ is —CH$_2$CHFCH(CH$_3$)OH, —CH$_2$CHFC(CH$_3$)$_2$OH, —CH$_2$CF$_2$C(CH$_3$)$_2$OH, —CH$_2$CHFC(CH$_2$CH$_3$)$_2$OH, or —CH$_2$CHFC(CH$_3$)$_2$OP(O)(OH)$_2$; and
R$_2$ is —CH$_2$CH$_3$, —CH$_2$CH$_2$CH$_3$, —CH(CH$_3$)$_2$, or —CH$_2$CH$_2$CH(CH$_3$)$_2$.

One embodiment provides a compound of Formula (I) or a salt thereof, wherein:
HET is

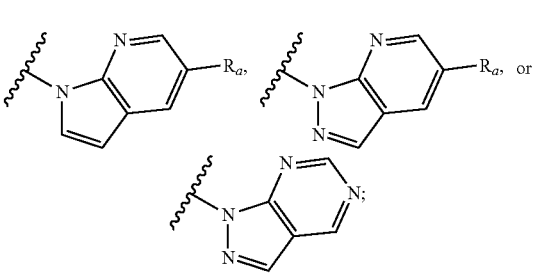

$R_a$ is H, F, Cl, —CN, —CH$_3$, or —C(O)NH$_2$;
R$_1$ is —CH$_2$CHFC(CH$_3$)$_2$OH, —CH$_2$CHFC(CH$_3$)$_2$OP(O)(OH)$_2$, —CH$_2$CHFC(O)NHCH$_3$, or cyclohexyl substituted with —C(O)NHCH$_3$, —NHC(O)CH$_3$, or —S(O)$_2$CH$_3$; and
R$_2$ is C$_{3-6}$ cycloalkyl substituted with zero to 3 substituents independently selected from F, —OH, and —CH$_3$.

One embodiment provides a compound of Formula (I) or a salt thereof, wherein:
HET is a heteroaryl selected from:
HET is

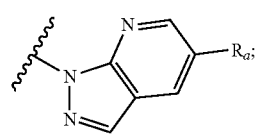

$R_a$ is F, Cl, Br, —OH, —CN, or —CH$_3$;
R$_1$ is —CH$_2$CHFCH(CH$_3$)OH, —CH$_2$CHFC(CH$_3$)$_2$OH, —CH$_2$CF$_2$C(CH$_3$)$_2$OH, —CH$_2$CHFC(CH$_2$CH$_3$)$_2$OH, or —CH$_2$CHFC(CH$_3$)$_2$OP(O)(OH)$_2$; and
R$_2$ is —CH(CH$_3$)$_2$.

One embodiment provides a compound of Formula (I) or a salt thereof, wherein HET is

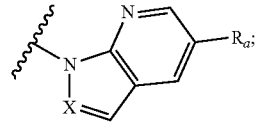

X is CH or N;
$R_a$ is Cl or —CN;

R₁ is —CH₂CH₂C(CH₃)₂OH, —CH₂CHFC(CH₃)₂OH, or —CH₂CHFC(CH₃)₂OP(O)(OH)₂; and R₂ is —CH(CH₃)₂.

One embodiment provides a compound of Formula (I) or a salt thereof, wherein said compound is selected from: (R)-6-(5-cyano-1H-indol-1-yl)-N-(2-fluoro-3-hydroxy-3-methylbutyl)-4-(isopropylamino)nicotinamide (1); (R)-6-(5-cyano-1H-pyrrolo[2,3-b]pyridin-1-yl)-4-(cyclopropylamino)-N-(2-fluoro-3-hydroxy-3-methylbutyl)nicotinamide (2); (R)-6-(5-cyano-1H-pyrrolo[2,3-b]pyridin-1-yl)-N-(2-fluoro-3-hydroxy-3-methylbutyl)-4-((tetrahydro-2H-pyran-4-yl)amino)nicotinamide (3); (R)-6-(5-cyano-1H-pyrrolo[2,3-b]pyridin-1-yl)-4-(ethylamino)-N-(2-fluoro-3-hydroxy-3-methylbutyl) nicotinamide (4); (R)-6-(5-cyano-1H-pyrrolo[2,3-b]pyridin-1-yl)-N-(2-fluoro-3-hydroxy-3-methylbutyl)-4-((2,2,2-trifluoroethyl)amino)nicotinamide (5); (R)-6-(5-cyano-1H-pyrrolo[2,3-b]pyridin-1-yl)-4-(cyclobutylamino)-N-(2-fluoro-3-hydroxy-3-methylbutyl) nicotinamide (6); 6-(5-cyano-1H-pyrrolo[2,3-b]pyridin-1-yl)-N—((R)-2-fluoro-3-hydroxy-3-methylbutyl)-4-((tetrahydro-2H-pyran-3-yl)amino)nicotinamide (7); 6-(5-cyano-1H-pyrrolo[2,3-b]pyridin-1-yl)-N—((S)-2-fluoro-3-hydroxy-3-methylbutyl)-4-((tetrahydro-2H-pyran-3-yl)amino)nicotinamide (8); 6-(5-cyano-1H-pyrrolo[2,3-b]pyridin-1-yl)-N—((R)-2-fluoro-3-hydroxy-3-methylbutyl)-4-(((S)-1-hydroxypropan-2-yl)amino) nicotinamide (9); (R)-6-(5-cyano-1H-pyrrolo[2,3-b]pyridin-1-yl)-4-(cyclopentylamino)-N-(2-fluoro-3-hydroxy-3-methylbutyl) nicotinamide (10); 6-(5-cyano-1H-pyrrolo[2,3-b]pyridin-1-yl)-N-(3-hydroxy-3-methylbutyl)-4-(isopropylamino) nicotinamide (11); 6-(5-cyano-1H-pyrrolo[2,3-b]pyridin-1-yl)-N-(3-hydroxy-3-methylbutyl)-4-((tetrahydro-2H-pyran-4-yl)amino)nicotinamide (12); 4-((1s,3S)-adamantan-1-ylamino)-6-(5-cyano-1H-pyrrolo[2,3-b]pyridin-1-yl)-N—((R)-2-fluoro-3-hydroxy-3-methylbutyl)nicotinamide (13); 6-(5-cyano-1H-pyrrolo[2,3-b]pyridin-1-yl)-N-(4-hydroxybicyclo[2.2.1]heptan-1-yl)-4-(isopropylamino)nicotinamide (14); N-(3-(tert-butoxy)propyl)-6-(5-cyano-1H-pyrrolo[2,3-b]pyridin-1-yl)-4-(isopropylamino)nicotinamide (15); (R)-6-(5-cyano-1H-pyrrolo[2,3-b]pyridin-1-yl)-N-(2-fluoro-3-hydroxy-3-methylbutyl)-4-((4-hydroxybicyclo[2.2.1]heptan-1-yl)amino)nicotinamide (16); (R)-6-(5-cyano-1H-pyrrolo[2,3-b]pyridin-1-yl)-N-(2-fluoro-3-hydroxy-3-methylbutyl)-4-((1-methylcyclopropyl)amino)nicotinamide (17); (R)-6-(5-cyano-1H-pyrrolo[2,3-b]pyridin-1-yl)-N-(2-fluoro-3-hydroxy-3-methylbutyl)-4-((1-methylcyclopropyl)amino)nicotinamide (18); (R)-6-(5-cyano-1H-pyrrolo[2,3-b]pyridin-1-yl)-N-(2-fluoro-3-hydroxy-3-methylbutyl)-4-(isopentylamino) nicotinamide (19); (R)-6-(5-cyano-1H-pyrrolo[2,3-b]pyridin-1-yl)-N-(2-fluoro-3-hydroxy-3-methylbutyl)-4-(((3-methyloxetan-3-yl)methyl)amino) nicotinamide (20); 6-(5-cyano-1H-pyrrolo[2,3-b]pyridin-1-yl)-N—((R)-2-fluoro-3-hydroxy-3-methylbutyl)-4-((4-hydroxybutan-2-yl)amino)nicotinamide (21); 6-(5-cyano-1H-pyrrolo[2,3-b]pyridin-1-yl)-N—((S)-2-fluoro-3-hydroxy-3-methylbutyl)-4-((4-hydroxybutan-2-yl)amino) nicotinamide (22); (S)-6-(5-cyano-1H-pyrrolo[2,3-b]pyridin-1-yl)-N-(2-fluoro-3-hydroxy-3-methylbutyl)-4-(isopropylamino)nicotinamide (23); 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (24); diastereomer 1; 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (25); diastereomer 2; 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (26); diastereomer 3; 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (27); diastereomer 4; (R)-6-(5-cyano-1H-pyrrolo[2,3-b]pyridin-1-yl)-N-(2-fluoro-3-hydroxy-3-methylbutyl)-4-(((1-hydroxycyclobutyl)methyl)amino) nicotinamide (28); (R)-6-(5-cyano-1H-pyrrolo[2,3-b]pyridin-1-yl)-N-(2-fluoro-3-hydroxy-3-methylbutyl)-4-((oxetan-3-ylmethyl)amino) nicotinamide (29); 6-(5-cyano-1H-pyrrolo[2,3-b]pyridin-1-yl)-N—((R)-2-fluoro-3-hydroxy-3-methylbutyl)-4-(((1R,2R)-2-hydroxycyclopentyl)amino)nicotinamide (30); (R)-6-(5-chloro-1H-pyrrolo[2,3-b]pyridin-1-yl)-4-(cyclobutylamino)-N-(2-fluoro-3-hydroxy-3-methylbutyl) nicotinamide (31); (R)-6-(5-chloro-1H-pyrrolo[2,3-b]pyridin-1-yl)-N-(2-fluoro-3-hydroxy-3-methylbutyl)-4-((tetrahydro-2H-pyran-4-yl)amino) nicotinamide (32); (R)-6-(5-chloro-1H-pyrrolo[2,3-b]pyridin-1-yl)-4-(ethylamino)-N-(2-fluoro-3-hydroxy-3-methylbutyl)nicotinamide (33); (R)-6-(5-chloro-1H-pyrrolo[2,3-b]pyridin-1-yl)-4-(cyclopropylamino)-N-(2-fluoro-3-hydroxy-3-methylbutyl)nicotinamide (34); (R)-6-(5-chloro-1H-pyrrolo[2,3-b]pyridin-1-yl)-N-(2-fluoro-3-hydroxy-3-methylbutyl)-4-((2-hydroxy-2-methylpropyl)amino)nicotinamide (35); 6-(5-chloro-1H-pyrrolo[2,3-b]pyridin-1-yl)-N-(3-hydroxy-3-methylbutyl)-4-((tetrahydro-2H-pyran-4-yl)amino)nicotinamide (36); (R)-6-(5-chloro-1H-indol-1-yl)-N-(2-fluoro-3-hydroxy-3-methylbutyl)-4-(isopropylamino)nicotinamide (37); (R)-6-(5-fluoro-1H-pyrrolo[2,3-b]pyridin-1-yl)-N-(2-fluoro-3-hydroxy-3-methylbutyl)-4-(isopropylamino)nicotinamide (38); (R)—N-(2-fluoro-3-hydroxy-3-methylbutyl)-4-(isopropylamino)-6-(7H-pyrrolo[2,3-d]pyrimidin-7-yl)nicotinamide (39); (R)—N-(2-fluoro-3-hydroxy-3-methylbutyl)-6-(7H-pyrrolo[2,3-d]pyrimidin-7-yl)-4-((tetrahydro-2H-pyran-4-yl)amino)nicotinamide (40); (R)-4-(cyclopropylamino)-N-(2-fluoro-3-hydroxy-3-methylbutyl)-6-(7H-pyrrolo[2,3-d]pyrimidin-7-yl) nicotinamide (41); (R)—N-(2-fluoro-3-hydroxy-3-methylbutyl)-4-((2-hydroxy-2-methylpropyl)amino)-6-(7H-pyrrolo[2,3-d]pyrimidin-7-yl)nicotinamide (42); N-(3-hydroxy-3-methylbutyl)-6-(7H-pyrrolo[2,3-d]pyrimidin-7-yl)-4-((tetrahydro-2H-pyran-4-yl)amino)nicotinamide (43); N-(3-hydroxy-3-methylbutyl)-4-(isopropylamino)-6-(7H-pyrrolo[2,3-d]pyrimidin-7-yl)nicotinamide (44); (R)-6-(5-acetamido-1H-pyrrolo[2,3-b]pyridin-1-yl)-N-(2-fluoro-3-hydroxy-3-methylbutyl)-4-(isopropylamino)nicotinamide (45); (R)-6-(5-cyano-1H-pyrrolo[2,3-b]pyridin-1-yl)-N-(2-fluoro-3-hydroxy-3-methylbutyl)-4-((3-hydroxyphenyl)amino)nicotinamide (46); 6-(5-cyano-1H-pyrrolo[2,3-b]pyridin-1-yl)-N-(3-isopropoxypropyl)-4-(isopropylamino) nicotinamide (47); 6-(5-cyano-1H-pyrrolo[2,3-b]pyridin-1-yl)-N-((2R)-2-fluoro-3-hydroxybutyl)-4-(isopropylamino) nicotinamide (48); 6-(5-cyano-1H-pyrrolo[2,3-b]pyridin-1-yl)-N-((2S)-2-fluoro-3-hydroxybutyl)-4-(isopropylamino) nicotinamide (49); (R)-6-(5-cyano-1H-pyrrolo[2,3-b]pyridin-1-yl)-N-(2-fluoro-3-hydroxy-3-methylbutyl)-4-((3-sulfamoylphenyl)amino)nicotinamide (50); (R)-6-(5-cyano-1H-pyrrolo[2,3-b]pyridin-1-yl)-N-(2-fluoro-3-hydroxy-3-methylbutyl)-4-((3-methoxyphenyl)amino)nicotinamide (51); 6-(5-cyano-1H-pyrrolo[2,3-b]pyridin-1-yl)-N—((R)-2-fluoro-3-hydroxy-3-methylbutyl)-4-(((R)-2-fluoro-3-hydroxy-3-methylbutyl)amino)nicotinamide (52); (R)-6-(5-cyano-1H-pyrrolo[2,3-b]pyridin-1-yl)-4-((3,3-difluorocyclobutyl)amino)-N-(2-fluoro-3-hydroxy-3-methylbutyl)nicotinamide (53); (R)-4-((3-acetamidophenyl)amino)-6-(5-cyano-1H-pyrrolo[2,3-b]pyridin-1-yl)-N-(2-fluoro-3-hydroxy-3-methylbutyl) nicotinamide (54); (R)-6-

(5-cyano-1H-pyrrolo[2,3-b]pyridin-1-yl)-N-(2-fluoro-3-hydroxy-3-methylbutyl)-4-((3-(methylcarbamoyl)phenyl) amino)nicotinamide (55); (R)-4-((3-carbamoylphenyl) amino)-6-(5-cyano-1H-pyrrolo[2,3-b]pyridin-1-yl)-N-(2-fluoro-3-hydroxy-3-methylbutyl)nicotinamide (56); (R)-6-(5-cyano-1H-pyrrolo[2,3-b]pyridin-1-yl)-N-(2-fluoro-3-hydroxy-3-methylbutyl)-4-((3-(methylsulfonamido)phenyl) amino) nicotinamide (57); 6-(5-cyano-1H-pyrrolo[2,3-b]pyridin-1-yl)-4-(isopropylamino)-N-(4-sulfamoylphenethyl)nicotinamide (58); (R)-6-(5-cyano-1H-pyrrolo[2,3-b]pyridin-1-yl)-N-(2-fluoro-3-hydroxy-3-methylbutyl)-4-((3-(2-hydroxypropan-2-yl)phenyl)amino) nicotinamide (59); (R)-4-((4-carbamoylphenyl)amino)-6-(5-cyano-1H-pyrrolo[2,3-b]pyridin-1-yl)-N-(2-fluoro-3-hydroxy-3-methylbutyl)nicotinamide (60); 6-(5-cyano-1H-pyrrolo[2,3-b]pyridin-1-yl)-N—((R)-2-fluoro-3-hydroxy-3-methylbutyl)-4-(((1s,4S)-4-hydroxy-4-methylcyclohexyl) amino)nicotinamide (61); 6-(5-cyano-1H-pyrrolo[2,3-b]pyridin-1-yl)-N—((R)-2-fluoro-3-hydroxy-3-methylbutyl)-4-(((trans)-4-hydroxy-4-methylcyclohexyl)amino) nicotinamide (62); 6-(5-cyano-1H-pyrrolo[2,3-b]pyridin-1-yl)-4-(isopropylamino)-N-(2-(methylsulfonamido)ethyl) nicotinamide (63); (R)-4-(benzo[d]thiazol-6-ylamino)-6-(5-cyano-1H-pyrrolo[2,3-b]pyridin-1-yl)-N-(2-fluoro-3-hydroxy-3-methylbutyl)nicotinamide (64); (R)-6-(5-cyano-1H-pyrrolo[2,3-b]pyridin-1-yl)-N-(2-fluoro-3-hydroxy-3-methylbutyl)-4-(((1-fluorocyclobutyl)methyl)amino) nicotinamide (65); (R)-6-(5-cyano-1H-pyrrolo[2,3-b]pyridin-1-yl)-4-((3-cyanophenyl)amino)-N-(2-fluoro-3-hydroxy-3-methylbutyl)nicotinamide (66); (R)-4-((4-(1H-1,2,4-triazol-1-yl)phenyl)amino)-6-(5-cyano-1H-pyrrolo[2,3-b]pyridin-1-yl)-N-(2-fluoro-3-hydroxy-3-methylbutyl) nicotinamide (67); (R)-6-(5-cyano-1H-pyrrolo[2,3-b]pyridin-1-yl)-N-(2-fluoro-3-hydroxy-3-methylbutyl)-4-((4-(1-methyl-1H-tetrazol-5-yl)phenyl)amino)nicotinamide (68); (R)-6-(5-cyano-1H-pyrrolo[2,3-b]pyridin-1-yl)-N-(2-fluoro-3-hydroxy-3-methylbutyl)-4-((4-(1-methyl-1H-tetrazol-5-yl)phenyl)amino)nicotinamide (69); 6-(5-cyano-1H-pyrrolo[2,3-b]pyridin-1-yl)-N-(2-((1,1-dioxidotetrahydrothiophen-3-yl)amino)-2-oxoethyl)-4-(isopropylamino)nicotinamide (70); (R)-6-(5-cyano-1H-pyrrolo[2,3-b]pyridin-1-yl)-N-(2-fluoro-3-hydroxy-3-methylbutyl)-4-((3-(hydroxymethyl)phenyl)amino) nicotinamide (71); 6-(5-cyano-1H-pyrrolo[2,3-b]pyridin-1-yl)-N—((R)-2-fluoro-3-hydroxy-3-methylbutyl)-4-(((2S)-3-fluorobutan-2-yl)amino) nicotinamide (72); N-(2-amino-4,5,6,7-tetrahydrobenzo[d]thiazol-6-yl)-6-(5-cyano-1H-pyrrolo[2,3-b]pyridin-1-yl)-4-(isopropylamino)nicotinamide (73); (R)—N-(2-fluoro-3-hydroxy-3-methylbutyl)-4-(isopropylamino)-6-(1H-pyrrolo[2,3-b]pyridin-1-yl)nicotinamide (74); (R)-6-(5-cyano-1H-pyrrolo[2,3-b]pyridin-1-yl)-N-(2-fluoro-3-hydroxy-3-methylbutyl)-4-(isopropylamino)nicotinamide (75); (R)-6-(5-chloro-1H-pyrrolo[2,3-b]pyridin-1-yl)-N-(2-fluoro-3-hydroxy-3-methylbutyl)-4-(isopropylamino) nicotinamide (76); (R)-6-(5-cyano-1H-pyrrolo[2,3-b]pyridin-1-yl)-N-(2-fluoro-3-hydroxy-3-methylbutyl)-4-((2-hydroxy-2-methylpropyl)amino) nicotinamide (77); 6-(5-cyano-1H-pyrrolo[2,3-b]pyridin-1-yl)-N—((R)-2-fluoro-3-hydroxy-3-methylbutyl)-4-((1-fluoropropan-2-yl)amino)nicotinamide (78); 6-(5-cyano-1H-indol-1-yl)-4-(isopropylamino)-N-((trans)-4-(methylcarbamoyl)cyclohexyl)nicotinamide (79); 6-(5-cyano-1H-pyrrolo[2,3-b]pyridin-1-yl)-4-(isopropylamino)-N-((trans)-4-(methylcarbamoyl)cyclohexyl)nicotinamide (80); 4-(isopropylamino)-N-((trans)-4-(methylcarbamoyl) cyclohexyl)-6-(7H-pyrrolo[2,3-d]pyrimidin-7-yl)nicotinamide (81); N-((trans)-4-(methylcarbamoyl)cyclohexyl)-6-(7H-pyrrolo[2,3-d]pyrimidin-7-yl)-4-((tetrahydro-2H-pyran-4-yl)amino)nicotinamide (82); N-((trans)-4-acetamidocyclohexyl)-6-(7H-pyrrolo[2,3-d]pyrimidin-7-yl)-4-((tetrahydro-2H-pyran-4-yl)amino)nicotinamide (83); N-((trans)-4-acetamidocyclohexyl)-4-(isopropylamino)-6-(7H-pyrrolo[2,3-d]pyrimidin-7-yl)nicotinamide (84); 6-(5-cyano-1H-pyrrolo[2,3-b]pyridin-1-yl)-4-(cyclopropylamino)-N-((trans)-4-(methylcarbamoyl)cyclohexyl) nicotinamide (85); 6-(5-cyano-1H-pyrrolo[2,3-b]pyridin-1-yl)-N-((trans)-4-(methylcarbamoyl)cyclohexyl)-4-((tetrahydro-2H-pyran-4-yl)amino)nicotinamide (86); N-((trans)-4-acetamidocyclohexyl)-6-(5-cyano-1H-pyrrolo[2,3-b]pyridin-1-yl)-4-(cyclopropylamino)nicotinamide (87); N-((trans)-4-acetamidocyclohexyl)-6-(5-cyano-1H-pyrrolo[2,3-b]pyridin-1-yl)-4-((tetrahydro-2H-pyran-4-yl)amino) nicotinamide (88); 6-(5-cyano-1H-pyrrolo[2,3-b]pyridin-1-yl)-4-(((S)-1-hydroxypropan-2-yl)amino)-N-((1r,4S)-4-(methylcarbamoyl)cyclohexyl)nicotinamide (89); 6-(5-cyano-1H-pyrrolo[2,3-b]pyridin-1-yl)-4-(isopropylamino)-N-((trans)-4-(isopropylcarbamoyl)cyclohexyl) nicotinamide (90); 6-(5-cyano-1H-pyrrolo[2,3-b]pyridin-1-yl)-N-((trans)-4-(cyclopropylcarbamoyl)cyclohexyl)-4-(isopropylamino) nicotinamide (91); 6-(5-cyano-1H-pyrrolo[2,3-b]pyridin-1-yl)-N-((trans)-4-(ethylcarbamoyl)cyclohexyl)-4-(isopropylamino)nicotinamide (92); 6-(5-cyano-1H-pyrrolo[2,3-b]pyridin-1-yl)-4-((2-hydroxy-2-methylpropyl)amino)-N-((trans)-4-(methylcarbamoyl)cyclohexyl) nicotinamide (93); 6-(5-cyano-1H-pyrrolo[2,3-b]pyridin-1-yl)-4-((2-hydroxy-2-methylpropyl)amino)-N-((trans)-4-($^{2}H_{3}$)methylcarbamoyl)cyclohexyl)nicotinamide (94); 6-(5-cyano-1H-pyrrolo[2,3-b]pyridin-1-yl)-4-(isopropylamino)-N-((trans)-4-nitrocyclohexyl)nicotinamide (95); 6-(5-cyano-1H-pyrrolo[2,3-b]pyridin-1-yl)-N-((trans)-4-(2-hydroxypropan-2-yl)cyclohexyl)-4-(isopropylamino)nicotinamide (96); methyl((trans)-4-(6-(5-cyano-1H-pyrrolo[2,3-b]pyridin-1-yl)-4-(isopropylamino) nicotinamido)cyclohexyl)carbamate (97); 6-(5-cyano-1H-pyrrolo[2,3-b]pyridin-1-yl)-N-((trans)-4-hydroxycyclohexyl)-4-(isopropylamino)nicotinamide (98); 6-(5-cyano-1H-pyrrolo[2,3-b]pyridin-1-yl)-N-((trans)-4-hydroxy-4-methylcyclohexyl)-4-(isopropylamino)nicotinamide (99); 6-(5-cyano-1H-pyrrolo[2,3-b]pyridin-1-yl)-4-(ethylamino)-N-((trans)-4-(2-hydroxypropan-2-yl) cyclohexyl)nicotinamide (100); 6-(5-cyano-1H-pyrrolo[2,3-b]pyridin-1-yl)-4-(isopropylamino)-N-((trans)-4-(methylthio)cyclohexyl)nicotinamide (101); 6-(5-cyano-1H-pyrrolo[2,3-b]pyridin-1-yl)-4-(isopropylamino)-N-((trans)-4-(methylsulfonyl)cyclohexyl)nicotinamide (102); 6-(5-cyano-1H-pyrrolo[2,3-b]pyridin-1-yl)-N-((trans)-4-(methylsulfonyl)cyclohexyl)-4-((tetrahydro-2H-pyran-4-yl) amino)nicotinamide (103); 6-(5-cyano-1H-pyrrolo[2,3-b]pyridin-1-yl)-4-(cyclopropylamino)-N-((trans)-4-(methylsulfonyl)cyclohexyl) nicotinamide (104); 4-((3-carbamoylphenyl)amino)-6-(5-cyano-1H-pyrrolo[2,3-b]pyridin-1-yl)-N-((trans)-4-(methylsulfonyl)cyclohexyl) nicotinamide (105); 6-(5-cyano-1H-pyrrolo[2,3-b]pyridin-1-yl)-N—((R)-2-fluoro-3-hydroxy-3-methylbutyl)-4-((3-fluorotetrahydro-2H-pyran-4-yl)amino)nicotinamide (106); 6-(5-cyano-1H-pyrrolo[2,3-b]pyridin-1-yl)-N—((R)-2-fluoro-3-hydroxy-3-methylbutyl)-4-((3-fluorotetrahydro-2H-pyran-4-yl)amino)nicotinamide (107); 6-(5-cyano-1H-pyrrolo[2,3-b]pyridin-1-yl)-N—((S)-2-fluoro-3-hydroxy-3-methylbutyl)-4-((3-fluorotetrahydro-2H-pyran-4-yl)amino) nicotinamide (108); 6-(5-cyano-1H-pyrrolo[2,3-b]pyridin-1-yl)-N—((R)-2-fluoro-3-hydroxy-3-methylbutyl)-4-((3-fluorocyclopentyl)amino)nicotinamide (109); 6-(5-cyano-1H-pyrrolo[2,3-b]pyridin-1-yl)-N—((S)-2-fluoro-3-hydroxy-3-methylbutyl)-4-((3-fluorocyclopentyl)amino)nicotinamide (110); 6-(5-cyano-1H-pyrrolo[2,3-b]pyridin-1-yl)-4-((3,3-difluoro-2-hydroxycyclohexyl)amino)-N—((R)-2-fluoro-3-hydroxy-3-methylbutyl) nicotinamide (111); 6-(5-cyano-1H-pyrrolo[2,3-b]pyridin-1-yl)-4-((3,3-difluoro-2-hydroxycyclohexyl)amino)-N—((R)-2-fluoro-3-hydroxy-3-methylbutyl)nicotinamide (112); N—((R)-2-fluoro-3-hydroxy-3-methylbutyl)-4-((1-fluoropropan-2-yl)amino)-6-(7H-pyrrolo[2,3-d]pyrimidin-7-yl)nicotinamide (113); 6-(5-cyano-1H-pyrazolo[3,4-b]pyridin-1-yl)-N—((R)-2-fluoro-3-hydroxy-3-methylbutyl)-4-(((R)-1-fluoropropan-2-yl) amino) nicotinamide (114); N—((R)-2-fluoro-3-hydroxy-3-methylbutyl)-4-(((R)-1-fluoropropan-2-yl)amino)-6-(7H-pyrrolo[2,3-d]pyrimidin-7-yl)nicotinamide (115); N—((R)-2-fluoro-3-hydroxy-3-methylbutyl)-4-(((S)-1-fluoropropan-2-yl)amino)-6-(7H-pyrrolo[2,3-d]pyrimidin-7-yl) nicotinamide (116); 6-(5-cyano-1H-pyrrolo[2,3-b]pyridin-1-yl)-N—((R)-2-fluoro-3-hydroxy-3-methylbutyl)-4-(((S)-1-fluoropropan-2-yl)amino)nicotinamide (117); 6-(5-cyano-1H-pyrrolo[2,3-b]pyridin-1-yl)-N—((R)-2-fluoro-3-hydroxy-3-methylbutyl)-4-(((R)-1-fluoropropan-2-yl) amino)nicotinamide (118); (S)-6-(5-cyano-1H-pyrrolo[2,3-b]pyridin-1-yl)-4-((1-fluoropropan-2-yl)amino)-N-(3-hydroxy-3-methylbutyl)nicotinamide (119); (R)-6-(5-cyano-1H-pyrrolo[2,3-b]pyridin-1-yl)-4-((1-fluoropropan-2-yl)amino)-N-(3-hydroxy-3-methylbutyl)nicotinamide (120); 6-(5-cyano-1H-pyrazolo[3,4-b]pyridin-1-yl)-N—((R)-2-fluoro-3-hydroxy-3-methylbutyl)-4-(((S)-1-fluoropropan-2-yl)amino) nicotinamide (121); 6-(5-cyano-1H-pyrazolo[3,4-b]pyridin-1-yl)-4-(((S)-1-fluoropropan-2-yl)amino)-N-((1r,4S)-4-(methylcarbamoyl)cyclohexyl)nicotinamide (122); (R)-1-(4-(ethylamino)-5-((2-fluoro-3-hydroxy-3-methylbutyl)carbamoyl)pyridin-2-yl)-1H-pyrrolo[2,3-b]pyridine-5-carboxamide (123); (R)-1-(4-(cyclobutylamino)-5-((2-fluoro-3-hydroxy-3-methylbutyl)carbamoyl)pyridin-2-yl)-1H-pyrrolo[2,3-b]pyridine-5-carboxamide (124); 1-((2-(6-(5-cyano-1H-pyrrolo[2,3-b]pyridin-1-yl)-4-(isopropylamino) nicotinamido)ethyl)amino)-2-methyl-1-oxopropan-2-yl acetate (125); 6-(5-cyano-1H-pyrrolo[2,3-b]pyridin-1-yl)-N-(2-(2-hydroxy-2-methylpropanamido)ethyl)-4-(isopropylamino)nicotinamide (126); (R)-6-(5-cyano-1H-pyrrolo[2,3-b]pyridin-1-yl)-N-(2-fluoro-3-methoxypropyl)-4-(isopropylamino)nicotinamide (127); (R)-6-(5-cyano-1H-pyrazolo[3,4-b]pyridin-1-yl)-N-(2-fluoro-3-methoxypropyl)-4-(isopropylamino) nicotinamide (128); 6-(5-cyano-1H-pyrrolo[2,3-b]pyridin-1-yl)-N-((2R)-2-fluoro-3-(isopropylamino)butyl)-4-(isopropylamino)nicotinamide (129); 6-(5-cyano-1H-pyrrolo[2,3-b]pyridin-1-yl)-N-((2R)-2-fluoro-3-(isopropylamino)butyl)-4-(isopropylamino) nicotinamide (130); 6-(5-cyano-1H-pyrrolo[2,3-b]pyridin-1-yl)-N—((R)-2-fluoro-3-hydroxy-3-methylbutyl)-4-((1-fluoro-3-hydroxypropan-2-yl)amino) nicotinamide (131); (R)-6-(5-cyano-1H-pyrrolo[2,3-b]pyridin-1-yl)-4-(cyclopropylamino)-N-(2-fluoro-3-(methylamino)-3-oxopropyl)nicotinamide (132); (R)-6-(5-cyano-1H-pyrrolo[2,3-b]pyridin-1-yl)-N-(2-fluoro-3-hydroxy-3-methylbutyl)-4-(isopropylamino)nicotinamide (133); (R)-4-(cyclopropylamino)-N-(2-fluoro-3-hydroxy-3-methylbutyl)-6-(1H-pyrazolo[3,4-d]pyrimidin-1-yl)nicotinamide (134); (R)-6-(5-chloro-1H-pyrazolo[3,4-b]pyridin-1-yl)-N-(2-fluoro-3-hydroxy-3-methylbutyl)-4-((tetrahydro-2H-pyran-4-yl)amino) nicotinamide (135); (R)-6-(5-chloro-1H-pyrazolo[3,4-b]pyridin-1-yl)-4-(cyclopropylamino)-N-(2-fluoro-3-hydroxy-3-methylbutyl) nicotinamide (136); (R)-6-(5-chloro-1H-pyrazolo[3,4-b]pyridin-1-yl)-N-(2-fluoro-3-hydroxy-3-methylbutyl)-4-(isopropylamino)nicotinamide (137); (R)-6-(5-cyano-1H-pyrazolo[3,4-b]pyridin-1-yl)-4-(ethylamino)-N-(2-fluoro-3-hydroxy-3-methylbutyl)nicotinamide (138); (R)-6-(5-cyano-1H-pyrazolo[3,4-b]pyridin-1-yl)-4-(cyclopropylamino)-N-(2-fluoro-3-hydroxy-3-methylbutyl)nicotinamide (139); 6-(5-cyano-1H-pyrazolo[3,4-b]pyridin-1-yl)-4-(cyclopropylamino)-N-((trans)-4-(methylcarbamoyl)cyclohexyl)nicotinamide (140); (R)-6-(5-cyano-1H-pyrazolo[3,4-b]pyridin-1-yl)-N-(2-fluoro-3-hydroxy-3-methylbutyl)-4-((tetrahydro-2H-pyran-4-yl)amino)nicotinamide (141); 6-(5-cyano-1H-pyrazolo[3,4-b]pyridin-1-yl)-N—((R)-2-fluoro-3-hydroxy-3-methylbutyl)-4-((tetrahydro-2H-pyran-3-yl)amino) nicotinamide, diastereomer 1 (142); 6-(5-cyano-1H-pyrazolo[3,4-b]pyridin-1-yl)-N—((S)-2-fluoro-3-hydroxy-3-methylbutyl)-4-((tetrahydro-2H-pyran-3-yl)amino) nicotinamide, diastereomer 2 (143); (R)—N-(2-fluoro-3-hydroxy-3-methylbutyl)-4-(isopropylamino)-6-(1H-pyrazolo[3,4-d]pyrimidin-1-yl)nicotinamide (144); (R)-6-(5-cyano-1H-pyrazolo[3,4-b]pyridin-1-yl)-4-(cyclobutylamino)-N-(2-fluoro-3-hydroxy-3-methylbutyl)nicotinamide (145); 6-(5-cyano-1H-pyrazolo[3,4-b]pyridin-1-yl)-N-(3-hydroxy-3-methylbutyl)-4-(isopropylamino)nicotinamide (146); (R)-6-(5-cyano-1H-pyrazolo[3,4-b]pyridin-1-yl)-N-(2-fluoro-3-hydroxy-3-methylbutyl)-4-((2,2,2-trifluoroethyl)amino) nicotinamide (147); 6-(5-cyano-1H-pyrazolo[3,4-b]pyridin-1-yl)-N-((trans)-4-(2-hydroxypropan-2-yl)cyclohexyl)-4-(isopropylamino)nicotinamide (148); (R)—N-(3-ethyl-2-fluoro-3-hydroxypentyl)-4-(isopropylamino)-6-(1H-pyrazolo[3,4-d]pyrimidin-1-yl)nicotinamide (149); 6-(5-chloro-1H-pyrazolo[3,4-b]pyridin-1-yl)-N-((trans)-4-(2-hydroxypropan-2-yl)cyclohexyl)-4-(isopropylamino) nicotinamide (150); 6-(5-cyano-1H-pyrazolo[3,4-b]pyridin-1-yl)-N-(3-hydroxy-3-methylbutyl)-4-((tetrahydro-2H-pyran-4-yl)amino)nicotinamide (151); 6-(5-chloro-1H-pyrazolo[3,4-b]pyridin-1-yl)-4-(isopropylamino)-N-((trans)-4-(methylcarbamoyl)cyclohexyl)nicotinamide (152); (R)—N-(2-fluoro-3-hydroxy-3-methylbutyl)-6-(5-hydroxy-1H-pyrazolo[3,4-b]pyridin-1-yl)-4-(isopropylamino)nicotinamide (153); 6-(5-chloro-1H-pyrazolo[3,4-b]pyridin-1-yl)-4-(isopropylamino)-N-(2-morpholinoethyl)nicotinamide (154); (R)—N-(2-fluoro-3-hydroxy-3-methylbutyl)-4-(isopropylamino)-6-(5-methyl-1H-pyrazolo[3,4-b]pyridin-1-yl)nicotinamide (155); (R)-4-(cyclopropylamino)-6-(5-fluoro-1H-pyrazolo[3,4-b]pyridin-1-yl)-N-(2-fluoro-3-hydroxy-3-methylbutyl) nicotinamide (156); (R)-6-(5-fluoro-1H-pyrazolo[3,4-b]pyridin-1-yl)-N-(2-fluoro-3-hydroxy-3-methylbutyl)-4-(isopropylamino) nicotinamide (157); (R)-6-(5-bromo-1H-pyrazolo[3,4-b]pyridin-1-yl)-N-(2-fluoro-3-hydroxy-3-methylbutyl)-4-(isopropylamino)nicotinamide (158); 6-(5-cyano-1H-pyrazolo[3,4-b]pyridin-1-yl)-N—((R)-2-fluoro-3-hydroxy-3-methylbutyl)-4-(((trans)-4-hydroxycyclohexyl)amino)nicotinamide (159); 6-(5-cyano-1H-pyrazolo[3,4-b]pyridin-1-yl)-4-(isopropylamino)-N-((trans)-4-(methylcarbamoyl)cyclohexyl)nicotinamide (160); 6-(5-cyano-1H-pyrazolo[3,4-b]pyridin-1-yl)-4-(isopropylamino)-N-((trans)-4-(methylsulfonyl)cyclohexyl) nicotinamide (161); (R)-6-(5-cyano-1H-pyrazolo[3,4-b]pyridin-1-yl)-4-(isopropylamino)-N-((trans)-4-(($^2$H$_3$)methylcarbamoyl)cyclohexyl)nicotinamide (162); (R)-6-(5-cyano-1H-pyrazolo[3,4-b]pyridin-1-yl)-N-(2-fluoro-3-hydroxy-3-methylbutyl)-4-((4-fluorocyclohexyl)amino) nicotinamide (163); N-((trans)-4-acetamidocyclohexyl)-6-(5-cyano-1H-pyrazolo[3,4-b]pyridin-1-yl)-4-(isopropylamino) nicotinamide (164); N-(2-amino-4,5,6,7-tetrahydrobenzo[d]thiazol-6-yl)-6-(5-cyano-1H-pyrazolo[3,4-b]pyridin-1-yl)-4-(isopropylamino)nicotinamide (165); 6-(5-cyano-1H-pyrazolo[3,4-b]pyridin-1-yl)-4-(isopropylamino)-N-((trans)-4-(methylsulfonamido)cyclohexyl)nicotinamide (166); 6-(5-cyano-1H-pyrazolo[3,4-b]pyridin-1-yl)-N-(2,2-difluoro-3-hydroxy-3-methylbutyl)-4-(isopropylamino)nicotinamide (167); (R)—N-(2-fluoro-3-hydroxy-3-methylbutyl)-4-(isopropylamino)-6-(3-(pyridazin-4-yl)-1H-pyrazol-1-yl)nicotinamide (168); (R)-6-(5-cyano-1H-pyrazolo[3,4-b]pyridin-1-yl)-4-((2,2-difluoro-3-hydroxy-3-methylbutyl)amino)-N-(2-fluoro-3-hydroxy-3-methylbutyl) nicotinamide (169); (R)—N-(2-fluoro-3-hydroxy-3-methylbutyl)-4-(isopropylamino)-6-(9H-purin-9-yl)nicotinamide (170); (R)-6-(2-amino-9H-purin-9-yl)-N-(2-fluoro-3-hydroxy-3-methylbutyl)-4-(isopropylamino) nicotinamide (171); (R)—N-(2-fluoro-3-hydroxy-3-methylbutyl)-6-(2-((2-hydroxyethyl)amino)-9H-purin-9-yl)-4-(isopropylamino)nicotinamide (172); 6-(5-cyano-1H-pyrrolo[2,3-b]pyridin-1-yl)-N-((1 s,4s)-4-hydroxy-4-(1-methyl-1H-pyrazol-5-yl)cyclohexyl)-4-(isopropylamino) nicotinamide (173); 6-(5-cyano-1H-pyrrolo[2,3-b]pyridin-1-yl)-N-((1s,4s)-4-fluoro-4-(1-methyl-1H-pyrazol-5-yl)cyclohexyl)-4-(isopropylamino)nicotinamide (174); 6-(5-cyano-1H-pyrrolo[2,3-b]pyridin-1-yl)-N-((1s,4s)-4-hydroxy-4-(thiazol-2-yl)cyclohexyl)-4-(isopropylamino)nicotinamide (175); 6-(5-cyano-1H-pyrrolo[2,3-b]pyridin-1-yl)-N-((1 s,4s)-4-hydroxy-4-(1-methyl-1H-imidazol-2-yl)cyclohexyl)-4-(isopropylamino) nicotinamide (176); 6-(5-cyano-1H-pyrrolo[2,3-b]pyridin-1-yl)-N-((1s,4s)-4-hydroxy-4-(pyridin-3-yl)cyclohexyl)-4-(isopropylamino)nicotinamide (177); 6-(5-cyano-1H-pyrrolo[2,3-b]pyridin-1-yl)-N-((1s,4s)-4-hydroxy-4-(pyridin-2-yl)cyclohexyl)-4-(isopropylamino)nicotinamide (178); 6-(5-cyano-1H-pyrrolo[2,3-b]pyridin-1-yl)-N-((1 s,4s)-4-hydroxy-4-(pyridin-4-yl)cyclohexyl)-4-(isopropylamino)nicotinamide (179); 6-(5-cyano-1H-pyrrolo[2,3-b]pyridin-1-yl)-N-((1s,4s)-4-fluoro-4-(thiazol-2-yl)cyclohexyl)-4-(isopropylamino) nicotinamide (180); 6-(5-cyano-1H-pyrrolo[2,3-b]pyridin-1-yl)-N-((1 s,4s)-4-fluoro-4-(1-methyl-1H-imidazol-2-yl) cyclohexyl)-4-(isopropylamino) nicotinamide (181); 6-(5-cyano-1H-pyrrolo[2,3-b]pyridin-1-yl)-N-((trans)-4-fluoro-4-(1-methyl-1H-imidazol-2-yl)cyclohexyl)-4-(isopropylamino)nicotinamide (182); 6-(5-cyano-1H-pyrrolo[2,3-b]pyridin-1-yl)-N-(2,4-dioxo-1,3-diazaspiro[4.5]decan-8-yl)-4-(isopropylamino)nicotinamide (183); (S)-6-(5-cyano-1H-pyrrolo[2,3-b]pyridin-1-yl)-4-(isopropylamino)-N-(4-(pyridin-4-yl)cyclohex-3-en-1-yl)nicotinamide (184); (R)-6-(2-(dimethylamino)-7H-pyrrolo[2,3-d]pyrimidin-7-yl)-N-(2-fluoro-3-hydroxy-3-methylbutyl)-4-(isopropylamino)nicotinamide (185); (R)-6-(2-amino-7H-pyrrolo[2,3-d]pyrimidin-7-yl)-N-(2-fluoro-3-hydroxy-3-methylbutyl)-4-(isopropylamino) nicotinamide (186); (R)—N-(2-fluoro-3-hydroxy-3-methylbutyl)-6-(2-((2-hydroxy-2-methylpropyl)amino)-7H-pyrrolo[2,3-d]pyrimidin-7-yl)-4-(isopropylamino)nicotinamide (187); (R)—N-(2-fluoro-3-hydroxy-3-methylbutyl)-6-(2-((2-hydroxyethyl)amino)-7H-pyrrolo[2,3-d]pyrimidin-7-yl)-4-(isopropylamino) nicotinamide (188); N—((R)-2-fluoro-3-hydroxy-3-methylbutyl)-6-(2-((S)-3-hydroxypyrrolidin-1-yl)-7H-pyrrolo[2,3-d]pyrimidin-7-yl)-4-(isopropylamino) nicotinamide (189); N—((R)-2-fluoro-3-hydroxy-3-methylbutyl)-6-(2-((R)-3-hydroxypyrrolidin-1-yl)-7H-pyrrolo[2,3-d]pyrimidin-7-yl)-4-(isopropylamino) nicotinamide (190); and (R)-4-(6-(5-cyano-1H-pyrazolo[3,4-b]pyridin-1-yl)-4-(isopropylamino)nicotinamido)-3-fluoro-2-methylbutan-2-yl dihydrogen phosphate.

One embodiment provides a compound of Formula (I) or a salt thereof, wherein said compound is:

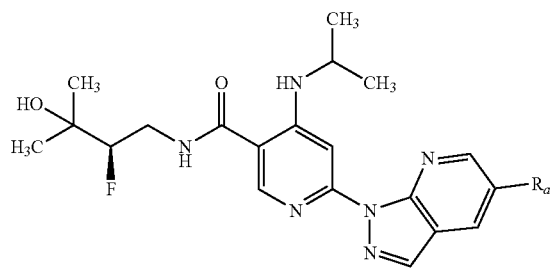

wherein $R_a$ is defined in the second aspect. Included in this embodiment are compounds in which $R_a$ is —Cl and —CN.

One embodiment provides a compound of Formula (I) or a salt thereof, wherein said compound is:

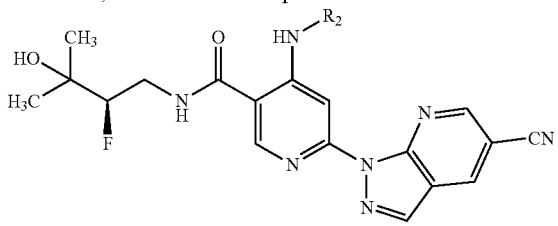

wherein $R_2$ is defined in the second aspect. Included in this embodiment are compounds in which $R_2$ is $C_{2-6}$ alkyl substituted with zero to three substituents independently selected from F and —OH. Also included in this embodiment are compounds in which $R_2$ is an unsubstituted $C_{2-5}$ alkyl.

One embodiment provides a compound of Formula (I) or a salt thereof, wherein said compound is:

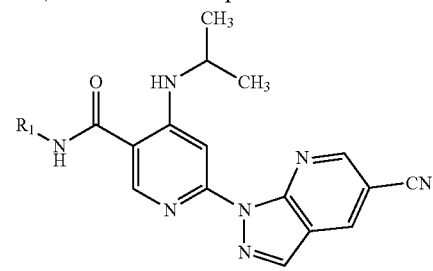

wherein $R_1$ is defined in the second aspect. Included in this embodiment are compounds in which $R_1$ is $C_{1-7}$ alkyl substituted with 1 to 3 substituents independently selected from F and —OH. Also included in this embodiment are compounds in which $R_1$ is $C_{2-6}$ alkyl substituted with one hydroxy group and zero to 2 fluorine substituents.

One embodiment provides a compound of Formula (I) or a salt thereof, wherein said compound is:

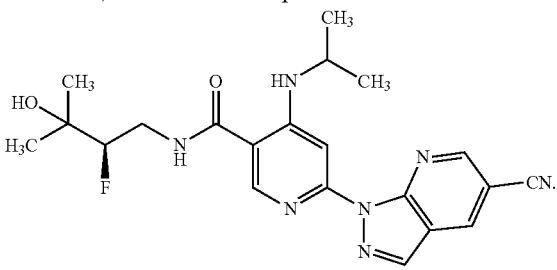

One embodiment provides a compound of Formula (I) wherein said compound is:

One embodiment provides a compound of Formula (I) or a salt thereof, wherein said compound is:

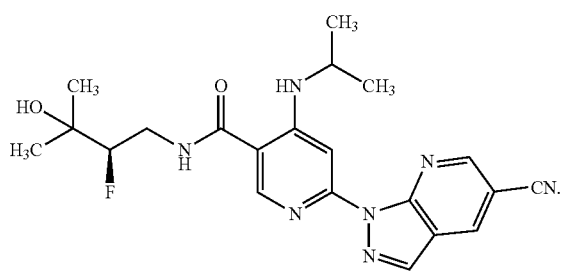 [SMILES: CC(C)Nc1cc(-n2ncc3cc(C#N)cnc32)ncc1C(=O)NC[C@@H](F)C(C)(C)O]

The compound of this embodiment is a prodrug of the compound of Example 133.

One embodiment provides a compound of Formula (I) wherein said compound is:

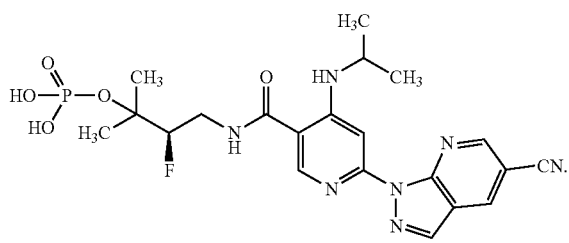 [SMILES: CC(C)Nc1cc(-n2ncc3cc(C#N)cnc32)ncc1C(=O)NC[C@@H](F)C(C)(C)OP(=O)(O)O]

or

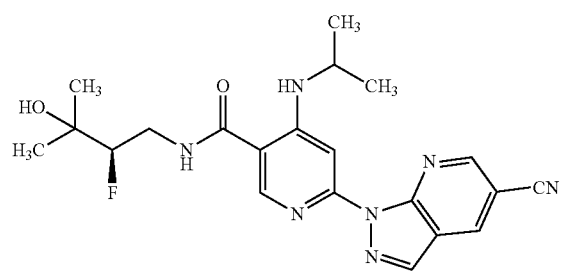

or salts thereof.

One embodiment provides compounds of the Formula (I) having IRAK4 $IC_{50}$ values of ≤0.05 µM.

One embodiment provides compounds of the Formula (I) having IRAK4 $IC_{50}$ values of ≤0.025 µM.

One embodiment provides compounds of the Formula (I) having IRAK4 $IC_{50}$ values of ≤0.015 µM.

One embodiment provides compounds of the Formula (I) having IRAK4 $IC_{50}$ values of ≤0.01 µM.

Crystal Forms

TABLE 1

| Example | Form |
|---|---|
| 133 | N-1 |
| 133 | N-2 |

In one embodiment, the compound of Example 133 is provided as a crystalline material comprising Form N-1. This crystalline form of the compound of Example 133 comprises a neat crystalline form referred to herein as "Form N-1" or "N-1 Form" of Example 133.

In one embodiment, the N-1 Form of the compound of Example 133 is characterized by unit cell parameters approximately equal to the following:
Cell dimensions:
a=14.86 Å
b=5.41 Å
c=14.93 Å
α=90.0°
β=115.7°
γ=90.0°
Space group: $P2_1$
Molecules of Example 133/asymmetric unit: 2
Volume/Number of molecules in the unit cell=540 Å$^3$
Density (calculated)=1.308 g/cm$^3$,
wherein the unit cell parameters of Form N-1 are measured at a temperature of about 296 K.

In another embodiment, N-1 form of Example 133 is characterized by a simulated powder x-ray diffraction (PXRD) pattern substantially in accordance with the pattern shown in FIG. 1.

In yet an even further embodiment, the N-1 Form of Example 133 is characterized by fractional atomic coordinates substantially as listed in Table 2.

TABLE 2

Fractional Atomic Coordinates of Example 133, Form N-1 Calculated at 296 K; Atomic Coordinates (x10$^4$)

| Atom | X | Y | Z |
|---|---|---|---|
| N(3) | 6597 | 7363 | 4376 |
| N(6) | 6232 | −333 | 7366 |
| N(2) | 5802 | 7040 | 3471 |
| C(11) | 6956 | 2759 | 6693 |
| C(13) | 7028 | 975 | 7491 |
| N(5) | 6021 | 4153 | 5003 |
| O(1) | 7820 | 784 | 8258 |
| C(10) | 7679 | 4544 | 6849 |
| N(4) | 8011 | 10167 | 5020 |
| C(8) | 6729 | 5878 | 5195 |
| C(12) | 6156 | 2629 | 5767 |
| C(9) | 7546 | 6178 | 6076 |
| C(6) | 7187 | 9285 | 4316 |
| N(7) | 8529 | 4793 | 7744 |
| C(2) | 8019 | 13081 | 3808 |
| C(19) | 9330 | 6603 | 7943 |
| C(4) | 6728 | 10155 | 3329 |
| C(5) | 5892 | 8650 | 2862 |
| C(3) | 7161 | 12160 | 3061 |
| C(7) | 8420 | 12042 | 4753 |
| C(14) | 6305 | −2293 | 8061 |
| C(20) | 10014 | 5800 | 7486 |
| C(21) | 9902 | 6780 | 9070 |
| N(1) | 8941 | 16780 | 3491 |
| F(1) | 5226 | −970 | 8689 |
| C(1) | 8501 | 15170 | 3595 |
| C(15) | 6201 | −1500 | 8950 |

TABLE 2-continued

Fractional Atomic Coordinates of
Example 133, Form N-1 Calculated at
296 K; Atomic Coordinates (x10⁴)

| Atom | X | Y | Z |
|---|---|---|---|
| O(2) | 7673 | −3690 | 10174 |
| C(16) | 6696 | −2680 | 9880 |
| C(18) | 5988 | −4970 | 9417 |
| C(17) | 6401 | −1500 | 10677 |

In one embodiment, the compound of Example 133 is provided as a crystalline material comprising Form N-2. This crystalline form of the compound of Example 133 comprises a neat crystalline form referred to herein as "Form N-2" or "N-1 Form" of Example 133.

In one embodiment, the N-1 Form of the compound of Example 133 is characterized by unit cell parameters approximately equal to the following:
Cell dimensions:
a=36.08 Å
b=6.72 Å
c=22.77 Å
α=90.0°
β=125.3°
γ=90.0°
Space group: C2
Molecules of Example 133/asymmetric unit: 1
Volume/Number of molecules in the unit cell=564 Å³
Density (calculated)=1.253 g/cm³,
wherein the unit cell parameters of Form N-1 are measured at a temperature of 296 K.

Figure 2:
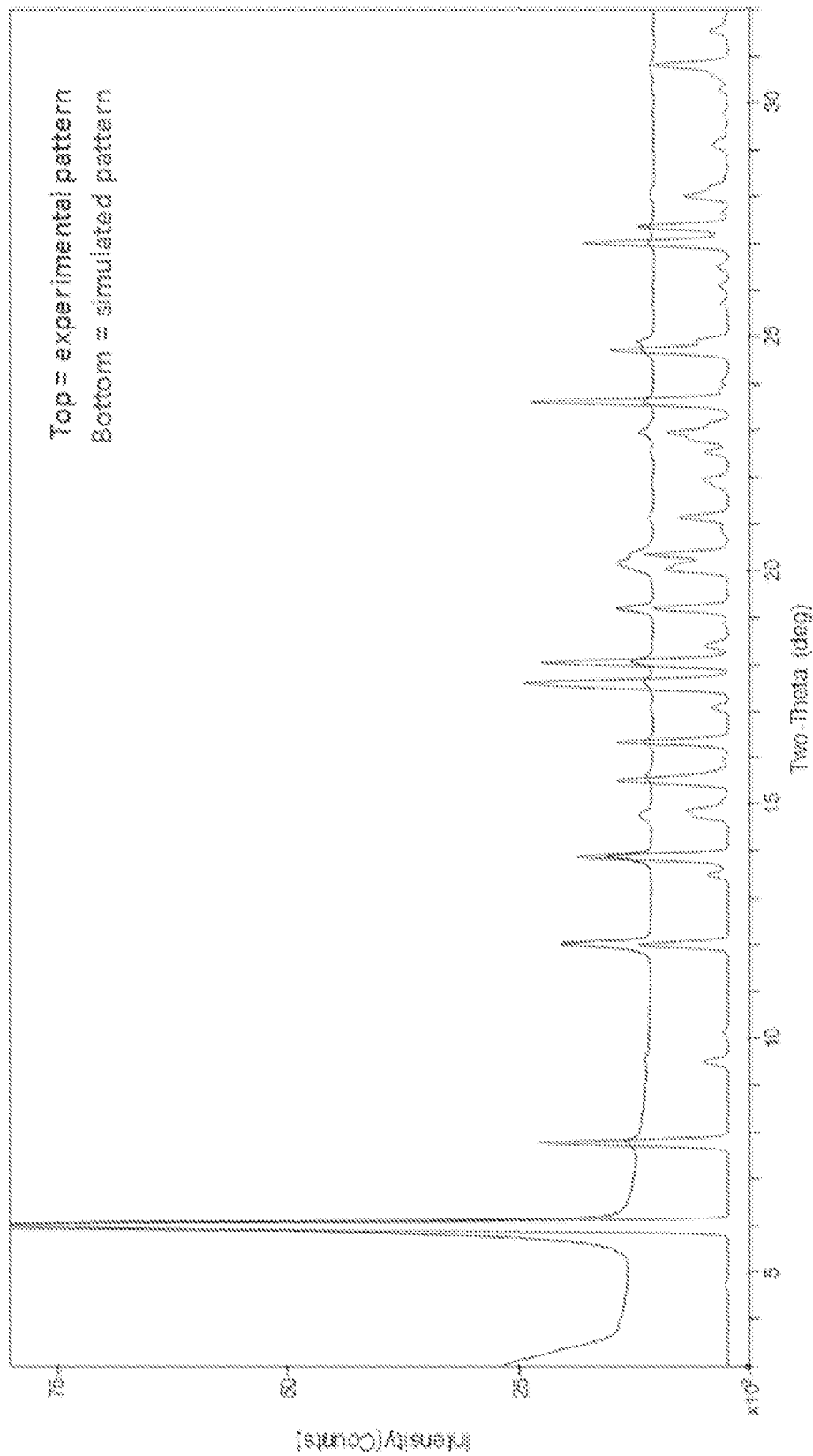
FIG. 2 shows the experimental (at approximately 25° C.) and the simulated (at 296 K) PXRD patterns (CuKα λ=1.5418 Å) of the N-1 Form of the compound of Example 133.

In another embodiment, N-1 form of Example 133 is characterized by a simulated powder x-ray diffraction (PXRD) pattern substantially in accordance with the pattern shown in FIG. 2.

In yet an even further embodiment, the N-1 Form of Example 133 is characterized by fractional atomic coordinates substantially as listed in Table 3.

TABLE 3

Fractional Atomic Coordinates of
Example 133, Form N-2 Calculated at
296 K; Atomic Coordinates (x10⁴)

| Atom | X | Y | Z |
|---|---|---|---|
| O(4) | 1351 | 14181 | 10840 |
| O(2) | 1361 | 1591 | 5869 |
| O(3) | 1001 | 10687 | 8462 |
| O(1) | 992 | 5294 | 3359 |
| F(1) | 756 | 5049 | 4426 |
| N(2) | 2255 | 12355 | 3682 |
| N(9) | 2247 | 3548 | 8676 |
| N(10) | 2708 | 3621 | 9093 |
| N(1) | 2283 | 9430 | 4238 |
| N(3) | 2726 | 12386 | 4140 |
| N(14) | 1623 | 11062 | 9555 |
| N(8) | 2267 | 6482 | 9220 |
| N(7) | 1597 | 4993 | 4532 |
| N(4) | 1692 | 14440 | 2734 |
| N(11) | 1661 | 1392 | 7750 |
| N(6) | 862 | 8714 | 2813 |
| N(5) | 1824 | 20680 | 1906 |
| N(12) | 1788 | −4902 | 6863 |
| C(5) | 2021 | 10760 | 3742 |
| C(26) | 2003 | 5158 | 8719 |
| C(2) | 1619 | 7670 | 3846 |
| C(23) | 1572 | 8313 | 8831 |
| C(10) | 2127 | 14036 | 3267 |

TABLE 3-continued

Fractional Atomic Coordinates of
Example 133, Form N-2 Calculated at
296 K; Atomic Coordinates (x10⁴)

| Atom | X | Y | Z |
|---|---|---|---|
| C(37) | 1380 | 10080 | 8937 |
| C(22) | 2046 | 8038 | 9257 |
| C(4) | 1549 | 10770 | 3270 |
| C(31) | 2073 | 1935 | 8208 |
| C(25) | 1542 | 5270 | 8276 |
| C(16) | 1367 | 5835 | 3877 |
| C(1) | 2059 | 7938 | 4272 |
| C(19) | 972 | 2360 | 5230 |
| C(11) | 2510 | 15084 | 3450 |
| C(12) | 1893 | 19220 | 2200 |
| C(7) | 2430 | 16959 | 3074 |
| C(3) | 1311 | 9100 | 3294 |
| C(18) | 1143 | 4030 | 4966 |
| C(33) | 1868 | −3360 | 7144 |
| C(8) | 1980 | 17450 | 2563 |
| C(29) | 1978 | −1416 | 7536 |
| C(24) | 1335 | 6873 | 8311 |
| C(32) | 2454 | 902 | 8377 |
| C(28) | 2416 | −800 | 8050 |
| C(38) | 1429 | 12742 | 9725 |
| C(17) | 1423 | 3320 | 4676 |
| C(6) | 2855 | 14024 | 3953 |
| C(40) | 947 | 13730 | 10136 |
| C(30) | 1613 | −320 | 7396 |
| C(13) | 571 | 10240 | 2252 |
| C(27) | 2844 | 2060 | 8946 |
| C(9) | 1623 | 16123 | 2405 |
| C(20) | 744 | 500 | 4695 |
| C(41) | 587 | 13000 | 10248 |
| C(14) | 111 | 10170 | 2215 |
| C(15) | 406 | 8980 | 1582 |
| C(35) | 150 | 5160 | 7282 |
| C(42) | 801 | 15490 | 9711 |
| C(34) | 520 | 5000 | 7392 |
| C(21) | 675 | 3310 | 5418 |
| C(36) | 559 | 5670 | 6860 |
| C(39) | 1052 | 12159 | 9792 |
| F(2) | 1227 | 10440 | 10251 |
| N(13) | 880 | 6907 | 7894 |

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "cycloalkyl", as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", *A Textbook of Drug Design and Development*, pp. 113-191, Krogsgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to IRAK4, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The compounds of the invention modulate kinase activity, including the modulation of IRAK-4. Other types of kinase activity that may be modulated by the compounds of the instant invention include, but are not limited to, the Pelle/IRAK family and mutants thereof.

Accordingly, compounds of Formula (I) have utility in treating conditions associated with the modulation of kinase activity, and particularly the selective inhibition of IRAK-4 activity or the inhibition of IRAK and other Pelle family kinases. Such conditions include TLR/IL-1 family receptor associated diseases in which cytokine levels are modulated as a consequence of intracellular signaling. Moreover, the compounds of Formula (I) have advantageous selectivity for IRAK-4 activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors IRAK-4, compounds of Formula (I) are useful in treating TLR/IL-1 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic (3-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the kinase inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional IRAK-4-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

In view of their activity as selective inhibitors of IRAK-4, the compounds of Formula (I) are useful in treating cancers associated with the MyD88 L265P mutation, including but not limited to, activated B cell-like subset of diffuse large B cell lymphoma (ABC-DLBCL); ref: Ngo, V. N. et al., *Nature*, 470:115-119 (2011); Waldenström's macroglobulinemia (WM); ref: Treon, S. P. et al., *N. Engl. J. Med.*, 367:826-833 (2012); chronic lymphocytic leukemia (CLL); cutaneous diffuse large B cell lymphoma; and primary central nervous system lymphoma; ref: Wang, J. Q. et al., *Frontiers Immunol.*, 5:367-377 (2014).

The compounds of Formula (I) are useful in treating cancers associated the overexpression of TLR2/activated IRAK1 including myelodysplastic syndrome (MDS); ref: Rhyasen, G. W. et al., *Cancer Cell*, 24:90-104 (2013).

When the terms "IRAK-4-associated condition" or "IRAK-4-associated disease or disorder" are used herein, each is intended to encompass all of the conditions identified above as if repeated at length, as well as any other condition that is affected by IRAK-4 kinase activity.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit IRAK-4 and/or treat diseases.

The methods of treating IRAK-4 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit IRAK-4 and/or treat diseases associated with IRAK-4.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IRAK-4 kinase-associated conditions, including TLR and IL-1 family receptor mediated diseases as described above.

METHODS OF PREPARATION

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of the general Formula (I) can be prepared according to the method outlined in Scheme 1. Hydrolysis of ester (1) to the acid 1.1 followed by reaction with an amine using standard amide bond forming conditions can afford the dichloro amide 1.2. Selective displacement of the C4 chloride by reacting with an amine can afford the mono-chloro product 1.3. Reaction of 1.3 with an appropriate heterocyclic nucleophile, in the presence of a catalyst, such as palladium, can afford compounds of the general formula I.

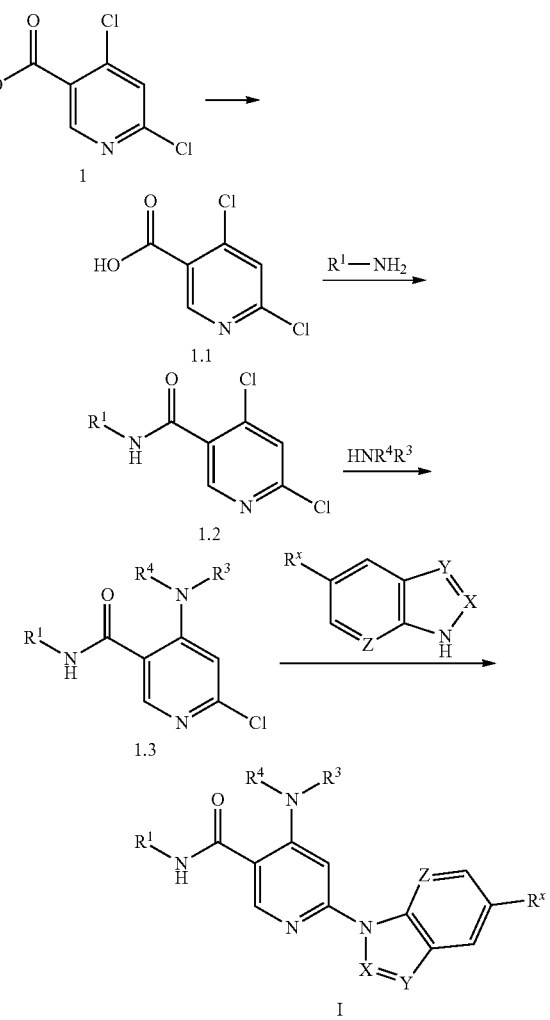

Scheme 1

Alternatively, the order of reactions can be modified to change the overall synthesis to allow for variations at different positions of the molecule at different stages of the preparation. For example, in Scheme 2, the chloride 1 may be reacted with an amine first to form the mono-chlorinated ester 2.1. Subsequent reaction with a heterocyclic nucleophile, may form the disubstituted intermediate 2.2. Hydrolysis of the ester to acid 2.3 followed by amide bond formation can afford the final analog 2.4.

pling in the presence of a metal catalyst such as palladium, may afford the final compound 3.4.

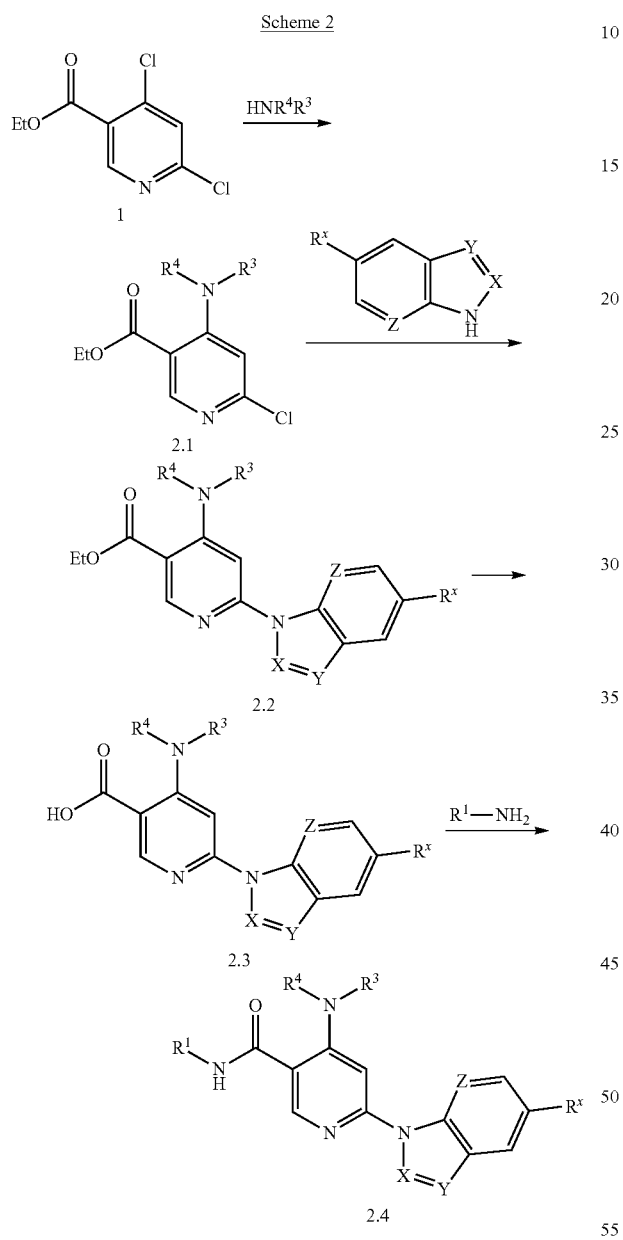

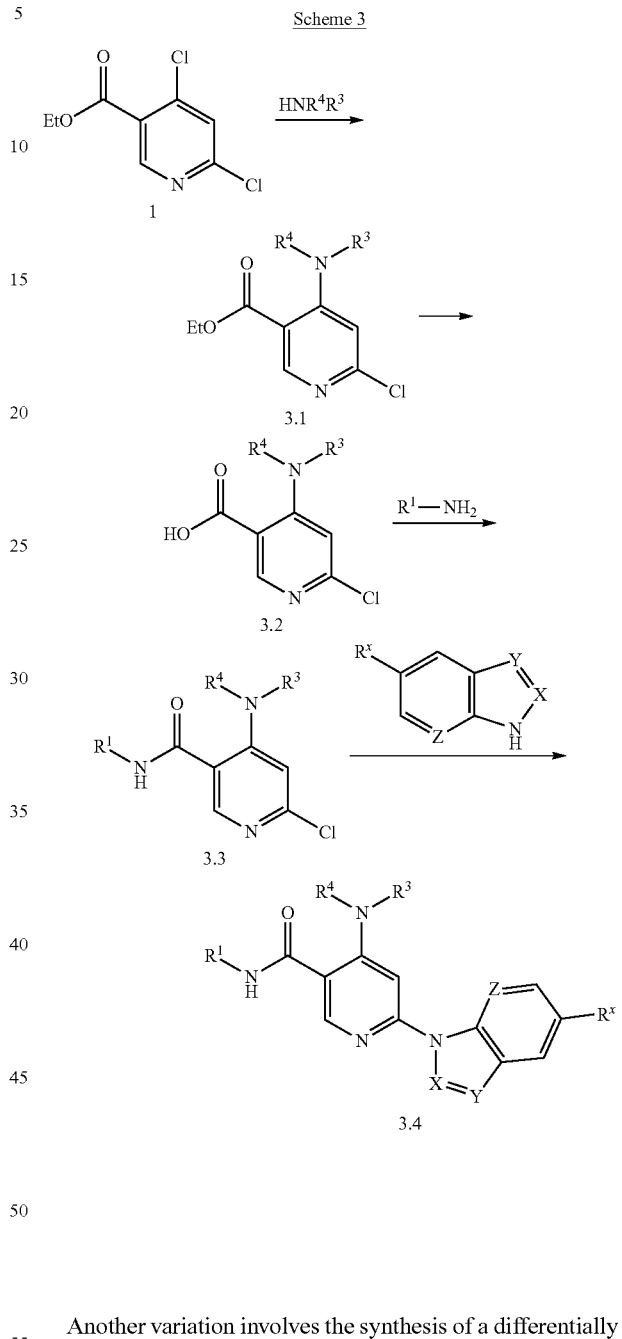

An additional variation on the order of substitution is shown in Scheme 3. First, reacting the dichloride with an amine may afford compound 3.1. Hydrolysis of the ester with a base, such as NaOH or KOH, may afford the acid 3.2. This acid may be reacted with an amine using standard amide bond forming reaction conditions, such as HOBt, EDC and DIPEA, in an appropriate solvent to form the amide 3.3, similar to amide 1.3 in Scheme 1. Subsequent heterocyclic amine cou- Another variation involves the synthesis of a differentially halogenated pyridine core to allow for variation of the $HNR^3R^4$ substituent at the last stage of the synthesis. 6-Bromo-4-chloronicotinic acid may be reacted with a halogenating reagent, such as oxalyl chloride, to afford the acid chloride 4.1. This may be further reacted with an amine in the presence of a base, such as DIPEA or TEA, in an appropriate solvent, such as DCM, to afford the amide 4.2. Amide 4.2 may be reacted with a heterocyclic amine in the presence of a metal catalyst, such as Pd, in a solvent to afford compound 4.3. Finally, compound 4.3 may be reacted with an amine in the presence of a base at elevated temperature to afford compound 4.4.

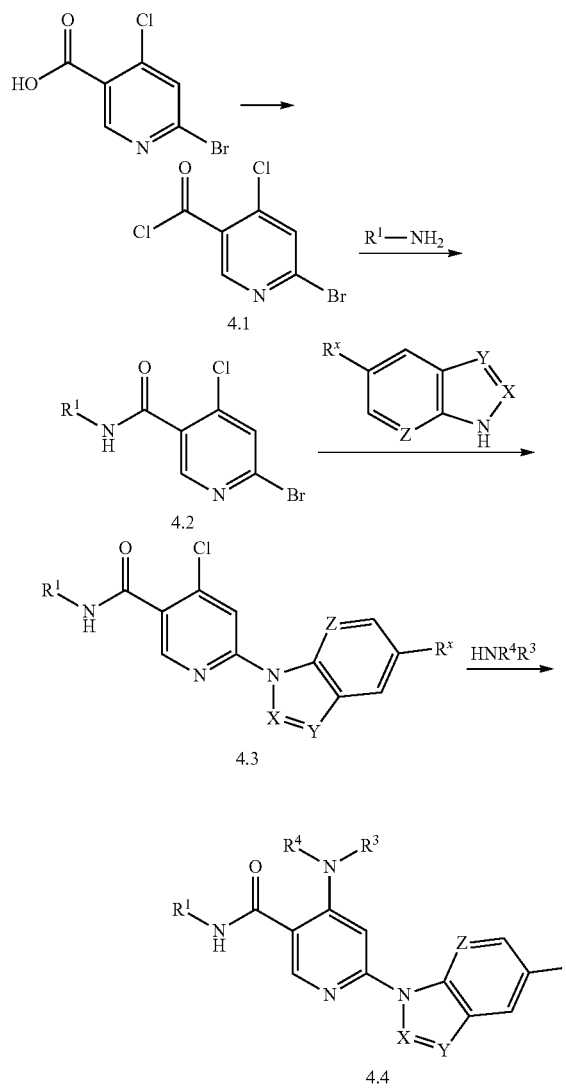

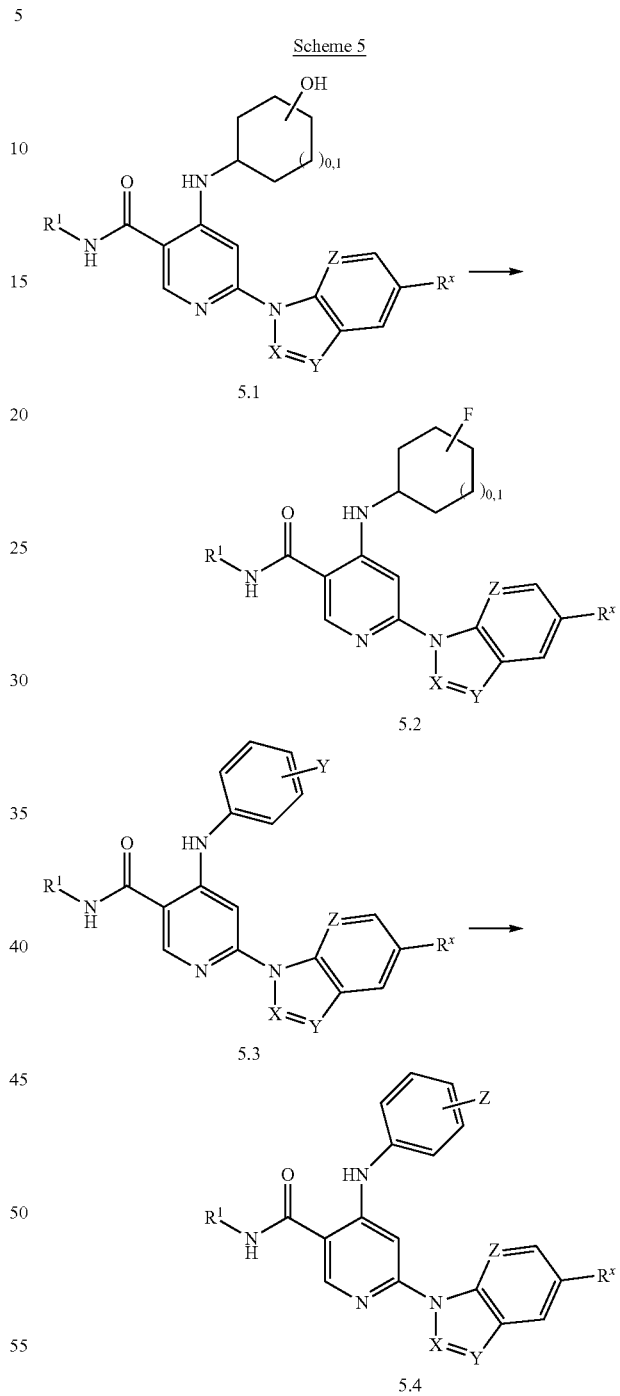

It should be also noted, and obvious to those skilled in the art, that synthetic manipulations of the incorporated $R^1$, $R^2$, and $R^3$ groups is possible. An illustrative example is shown in Scheme 5. The secondary alcohol incorporated in compound 5.1 may be converted to the fluoro analog 5.2 upon treatment with a fluorinating reagent, such as DAST, in an appropriate solvent, such as DCM. Other functionalities than an alcohol may be present for subsequent functionalization. For example, nitro groups can be converted readily to amines and subsequently functionalized, and esters can be readily converted to acids, amides or heterocycles. Additionally, aryl or heteroaryl groups incorporated into compound 5.3 may be converted, through standard chemical manipulations, to analogs of varying degrees of substitution. For example, when Y is nitro, the functionality may be converted to an amine under standard reducing conditions and further functionalized as an amide (Z is $NHCOCH_3$) or sulfonamide (Z is $NHSO_2CH_3$). The order of synthetic manipulations, of course, may be carried out in a fashion that is consistent with the methods outlined in Schemes 1-3 and should not be limited to the final step of the example preparation.

Additionally, variations to the $R^1$ group can be made via functionalization after incorporating onto the pyridine scaffold. For example, in Scheme 6, an appropriately protected amine, sulfide or ester may be coupled to the pyridine acid 6.1 via standard amide bond forming conditions to form 6.2. Compound 6.2 may be further manipulated (amine deprotection/functionalization; sulfide oxidation; ester hydrolysis/amide or heterocycle formation) to form compounds of the general formula 6.3.

Scheme 6

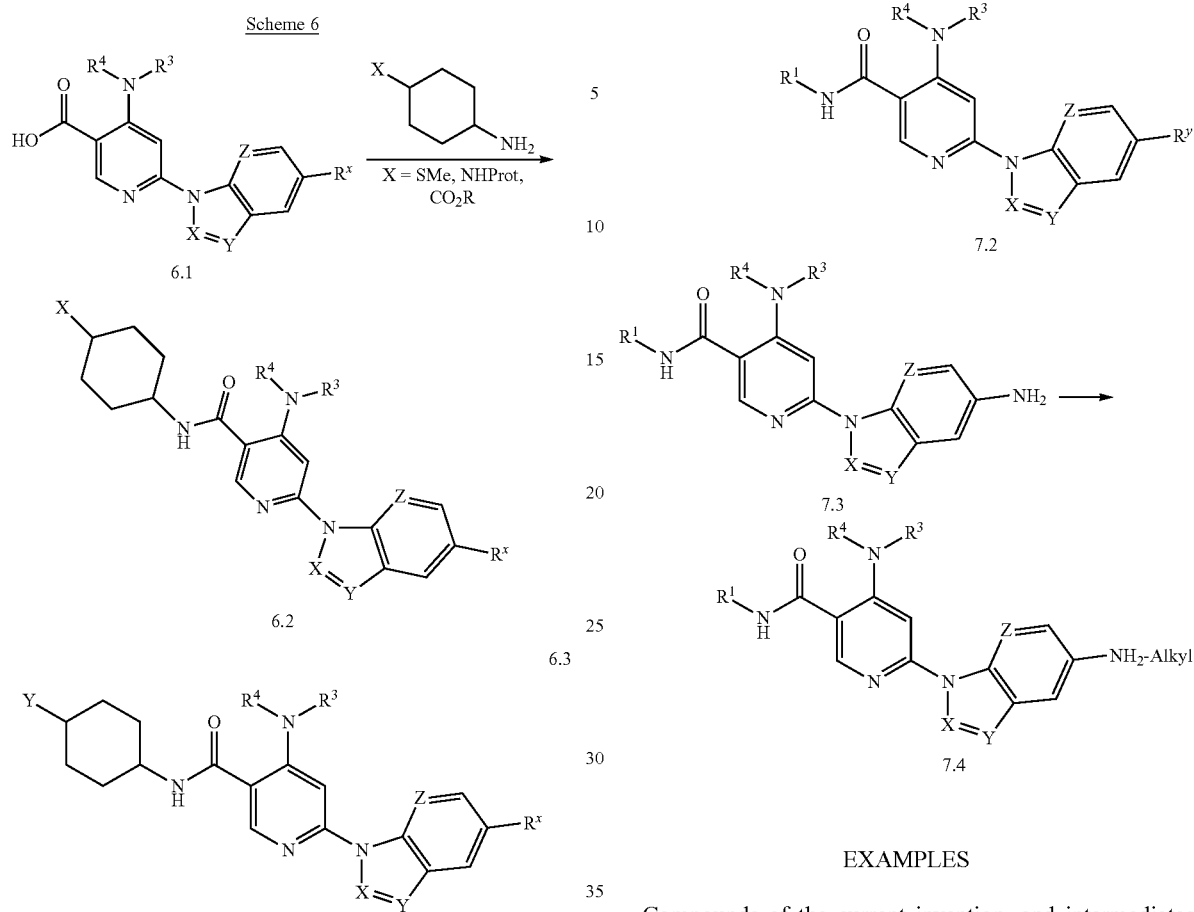

Substitution on the heterocyclic substituent may be accomplished via the methods outlined in Scheme 7. Preparation of an appropriately functionalized precursor, such as compound 7.1 ($R^x$ is a functional group such as an amine, ester or halogen), and reaction with a variety of reagents, such as amines, aryl cross coupling partners, cyanide may form compounds of the formula 9.2 ($R^x$). For example, compound 7.3 may be converted to compound 7.4 via reaction with an aldehyde in the presence of a reducing agent.

Scheme 7

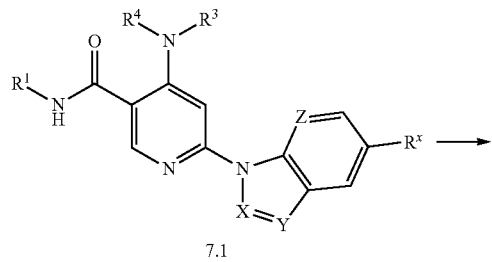

EXAMPLES

Compounds of the current invention, and intermediates used in the preparation of compounds of the current invention, can be prepared using procedures shown in the following examples and related procedures. The methods and conditions used in these examples, and the actual compounds prepared in these examples, are not meant to be limiting, but are meant to demonstrate how the compounds of the current invention can be prepared. Starting materials and reagents used in these examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared).

Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters SunFire $C_{18}$, Waters XBridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using CHEMDRAW® Ultra, version 9.0.5 (CambridgeSoft). The following abbreviations are used:

BrettPhos=2-(dicyclohexylphosphino)3,6-dimethoxy-2',4',6'-triisopropyl-1,1'-biphenyl
BrettPhos precatalyst=[2-(2-aminoethyl)phenyl](chloro)palladium; dicyclohexyl({3,6-dimethoxy-2-[2,4,6-tris(propan-2-yl)phenyl]phenyl})phosphane
Bn=benzyl
$(BOC)_2O$=di(tert-butoxycarbonyl) ether
BOP=benzotriazol-1-yloxytris-(dimethylamino)-phosphonium hexafluorophosphate
brine=saturated aqueous sodium chloride
DAST=(diethylamino)sulfur trifluoride
DCM=dichloromethane
DIPEA=N,N-diisopropylethylamine
DMA=N,N-dimethylacetamide
DMF=N,N-dimethylformamide
DMSO=dimethyl sulfoxide
Et=ethyl
EtOAc=ethyl acetate
EtOH=ethanol
g=gram(s)
h=hour(s)
HATU=O-(7-azabenzotriazol-1-yl)-N,N,N',N'-tetramethyluronium hexafluorophosphate
LCMS=Liquid Chromatography-Mass Spectroscopy
MeCN=acetonitrile
MeOH=methanol
MTBE=methyl t-butyl ether
$NaHCO_3$ (aq)=saturated aqueous sodium bicarbonate
n-BuLi=n-butyl lithium
$NH_4OAc$=ammonium acetate
$Pd_2(dba)_3$=tris-(dibenzylideneacetone)dipalladium
PyBOP=bromotripyrrolidinophosphonium hexafluorophosphate
t-BuOH=tert-butanol
TEA=triethylamine
TFA=trifluoroacetic acid
THF=tetrahydrofuran
Xantphos=4,5-Bis(diphenylphosphino)-9,9-dimethylxanthene HPLC Conditions:

Method A: SunFire C18 (4.6×150 mm), 3.5µ, Mobile Phase A: 95:5 water/MeCN, 0.05% TFA; Mobile Phase B: 95:5 MeCN/water, 0.05% TFA; 1 mL/min, 12 min gradient.

Method B: XBridge Phenyl (4.6×150 mm), 3.5µ, Mobile Phase A: 95:5 water/MeCN, 0.05% TFA; Mobile Phase B: 95:5 MeCN/water, 0.05% TFA; 1 mL/min, 12 min gradient.

Method C: Ascentis Express C18 (2.1×50 mm), 2.7µ, Mobile Phase A: 95:5 water/MeCN, 10 mM $NH_4OAc$; Mobile Phase B: 5:95 water/MeCN, 10 mM $NH_4OAc$; 1.1 mL/min, 3 min gradient, 50° C.

Method D: Ascentis Express C18 (2.1×50 mm), 2.7µ, Mobile Phase A: 95:5 water/MeCN, 0.01% TFA; Mobile Phase B: 5:95 water/MeCN, 0.01% TFA; 1.1 mL/min, 3 min gradient, 50° C.

Method E: Waters Acquity UPLC BEH C18, 2.1×50 mm, 1.7µ; Mobile Phase A: 5:95 MeCN:water with 10 mM ammonium acetate; Mobile Phase B: 95:5 MeCN:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.

Method F: Column: Waters Acquity UPLC BEH C18, 2.1×50 mm, 1.7µ; Mobile Phase A: 5:95 MeCN:water with 0.1% trifluoroacetic acid; Mobile Phase B: 95:5 MeCN:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

Method G: Ascentis Express C18 (4.6×50 mm), 2.7µ, Mobile Phase A: 95:5 water/MeCN, 10 mM $NH_4OAc$; Mobile Phase B: 5:95 water/MeCN, 10 mM $NH_4OAc$; 4 mL/min, 4 min gradient, 50° C.

Method H: Ascentis Express C18 (2.1×50 mm), 2.7µ, Mobile Phase A: 95:5 water/MeCN, 0.1% TFA; Mobile Phase B: 5:95 water/MeCN, 0.1% TFA; 1.1 mL/min, 3 min gradient, 50° C.

Method I: Column: Waters Acquity UPLC BEH C18, 2.0×50 mm, 1.7µ; Mobile Phase A: 10:90 MeCN:water with 0.1% trifluoroacetic acid; Mobile Phase B: 90:10 MeCN:water with 0.1% trifluoroacetic acid; Temperature: 40° C.; Gradient: 0-100% B over 1.5 minutes, then a 0.75-minute hold at 100% B; Flow: 1.0 mL/min; Detection: UV at 220 nm.

Method J: Column: Waters Acquity UPLC BEH C18, 2.1×50 mm, 1.7µ; Mobile Phase A: 100% water with 0.05% trifluoroacetic acid; Mobile Phase B: 100% MeCN with 0.05% trifluoroacetic acid; Temperature: 40° C.; Gradient: 20-100% B over 1.8 minutes, then a 0.2-minute hold at 100% B; Flow: 0.8 mL/min; Detection: UV at 220 nm.

Intermediate 1

Ethyl 6-chloro-4-(cyclopropylamino)nicotinate

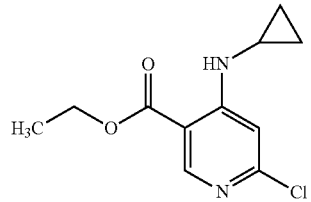

(I-1)

To a solution of ethyl 4,6-dichloronicotinate (50 g, 227 mmol) in DMA (500 mL) were added DIPEA (39.7 mL, 227 mmol) and cyclopropyl amine (17.6 mL, 250 mmol). The mixture was heated at 90° C. for 5 h. The reaction mixture was quenched into crushed ice with stirring. The resulting slurry was stirred and filtered to afford the crude product (42 g, 91% yield) which was used without further purification. LCMS m/z 241.1 (M+H)+. $^1$H NMR (400 MHz, DMSO-$d_6$) δ 8.54 (s, 1H), 8.09 (s, 1H), 7.03 (s, 1H), 4.29 (q, J=7.2 Hz, 2H), 2.61 (m, 1H), 1.31 (t, J=7.2 Hz, 3H), 0.86 (m, 2H), 0.58 (m, 2H).

Intermediate 2

6-Chloro-4-(cyclopropylamino)nicotinic acid

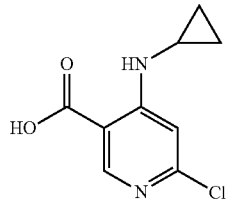

(I-2)

To a solution of ethyl 6-chloro-4-(cyclopropylamino)nicotinate (2 g, 8.31 mmol) in EtOH (14 mL), was added LiOH.H$_2$O (1.02 g, 25 mmol) and water (6 mL, 8.31 mmol). The reaction mixture was stirred at room temperature for 1 h. The solvents were removed in vacuo and the pH adjusted to 3-4 with 1.5 N HCl. The resulting solid was filtered and dried to afford 6-chloro-4-(cyclopropylamino)nicotinic acid (1.5 g, 82% yield) as a white solid. LCMS m/z 213.2 (M+H)$^+$.

Intermediate 3

Ethyl 6-chloro-4-(((1S)-3-hydroxycyclohexyl)amino)nicotinate

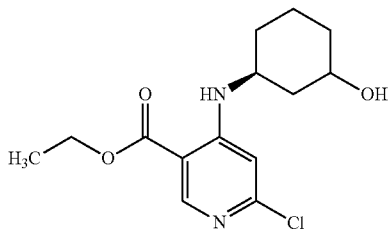

(I-3)

Intermediate I-3 was prepared according to the general procedure for Example 5, Step 1 using ethyl 4,6-dichloronicotinate and (3S)-3-aminocyclohexanol. LC/MS: ZORBAX® SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.65 min; LCMS (ES-API), m/z 299.0 (M+H).

Intermediate 4

6-Chloro-4-((1S)-3-hydroxycyclohexylamino)nicotinic acid

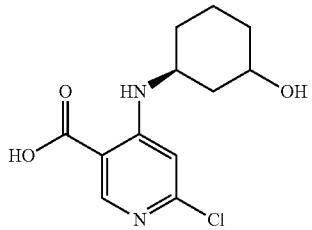

(I-4)

Intermediate I-4 was prepared according to the general procedure for Example 5, Step 3 using 6-chloro-4-(3-hydroxycyclohexylamino)nicotinate. LC/MS: ZORBAX® SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.095 min; LCMS (ES-API), m/z 271.0 (M+H).

Intermediate 5

6-Chloro-N-(2-fluoro-3-hydroxy-3-methylbutyl)-4-((1S)-3-hydroxycyclohexylamino)nicotinamide

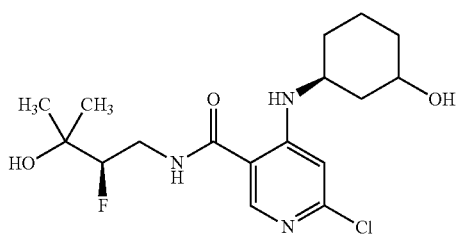

(I-5)

Intermediate I-5 was prepared according to the general procedure for Example 5, Step 4, using (R)-4-amino-3-fluoro-2-methylbutan-2-ol and 6-chloro-4-((1S)-3-hydroxycyclohexylamino)nicotinic acid.

Intermediate 6

Ethyl 6-chloro-4-((1S)-3-fluorocyclohexylamino)nicotinate

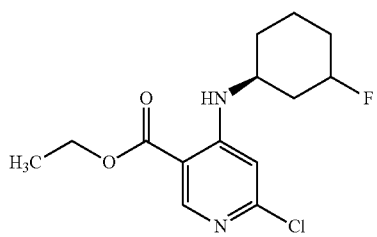

(I-6)

A solution of ethyl 6-chloro-4-((3-hydroxycyclohexyl)amino)nicotinate (0.3 g, 1 equiv.) in DCM (10 mL) was cooled to −78° C. and the mixture was stirred for 5 min. XtalFluor-E (1.2 equiv.) was added to the reaction mixture. After completion of addition the reaction mixture was stirred for 5 min. The reaction mixture was quenched with saturated solution of NH$_4$Cl at −78° C. and extracted with DCM (twice). The organic layers were collected together, dried over anhydrous sodium sulfate and concentrated. The crude material obtained was purified via column chromatography (EtOAc: pet ether) to afford ethyl 6-chloro-4-((1S)-3-fluorocyclohexylamino)nicotinate. LC/MS: ZORBAX® SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.981 min; LCMS (ES-API), m/z 301 (M+H).

Intermediate 7

6-Chloro-4-((1S)-3-fluorocyclohexylamino)nicotinic acid

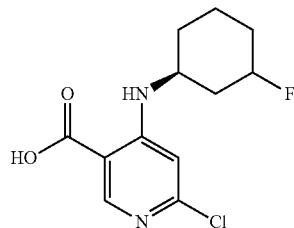

(I-7)

Intermediate I-7 was prepared according to the general procedure for Example 5, Step 3 using 6-chloro-4-((1S)-3-fluorocyclohexylamino)nicotinate. LC/MS: ZORBAX® SB C18, 4.6×50 mm, 5 μm; Solvent A=10% MeOH: 90% H$_2$O: 0.1% TFA; Solvent B=90% MeOH: 10% H$_2$O: 0.1% TFA; gradient 0-100% B over 2 min (3 min run time); retention time: 1.393 min; LCMS (ES-API), m/z 273.0 (M+H).

Intermediate 8

6-Chloro-N-(2-fluoro-3-hydroxy-3-methylbutyl)-4-((1S)-3-fluorocyclohexylamino)nicotinamide

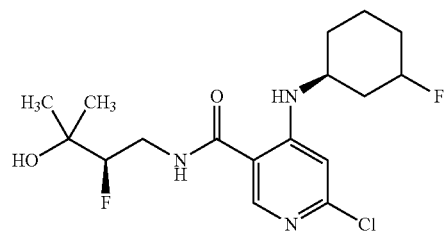

(I-8)

Intermediate 8 was prepared according to the general procedure for Example 5, Step 4, using (R)-4-amino-3-fluoro-2-methylbutan-2-ol and 6-chloro-4-((1S)-3-fluorocyclohexylamino)nicotinic acid.

Intermediate 9

Ethyl 6-chloro-4-((1R,2R)-2-hydroxycyclopentylamino)nicotinate

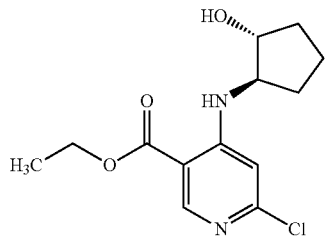

(I-9)

Intermediate 9 was prepared according to the general procedure for Example 5, Step 1 using ethyl 4,6-dichloronicotinate and (1R,2R)-2-aminocyclopentenol. LC/MS: Ascentis Express C18, 5×2.1 mm, 2.7 μm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.786 min; LCMS (ES-API), m/z 285.2 (M+H).

Intermediate 10

6-Chloro-4-(((1R,2R)-2-hydroxycyclopentyl)amino)nicotinic acid

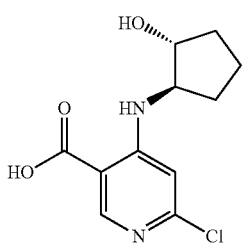

(I-10)

Ethyl 6-chloro-4-(((1R,2R)-2-hydroxycyclopentyl)amino)nicotinate (1.3 g, 4.57 mmol) in THF (10 mL), MeOH (4 mL) and water (2 mL) was added LiOH (0.328 g, 13.7 mmol) and the mixture was stirred at room temperature for 18 h. The organic layer was evaporated and the pH of the crude mixture was adjusted to 6 with 1.5N HCl to precipitate the crude acid. The solids were filtered and dried under vacuum to afford 6-chloro-4-(((1R,2R)-2-hydroxycyclopentyl)amino) nicotinic acid (0.95 mg, 81% yield). LCMS (ES-API), m/z 257.4 (M+H).

Intermediate 11

6-Chloro-N—((R)-2-fluoro-3-hydroxy-3-methylbutyl)-4-(((1R,2R)-2-hydroxycyclopentyl)amino)nicotinamide

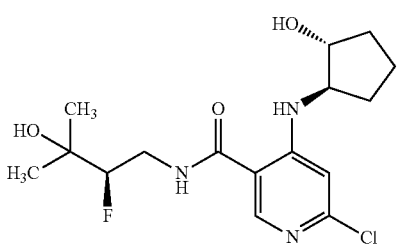

(I-11)

To a solution of 6-chloro-4-(((1R,2R)-2-hydroxycyclopentyl)amino)nicotinic acid (900 mg, 3.51 mmol) in DMF (10 mL) and (R)-4-amino-3-fluoro-2-methylbutan-2-ol (425 mg, 3.51 mmol) were added HATU (1333 mg, 3.51 mmol) and DIPEA (0.612 mL, 3.51 mmol). The reaction mixture was allowed to stir for 18 h at room temperature. The DMF was removed under vacuum and the crude mass was diluted with water and extracted with ethyl acetate. The ethyl acetate layer was washed with NaHCO$_3$, then dried and concentrated to give 1.4 g crude mass which was purified by column chromatography (CHCl$_3$:MeOH:9.5/0.5) to provide the product. LCMS m/z 360.5 (M+H).

Intermediate 12

Ethyl 6-chloro-4-((1R)-2-fluorocyclopentylamino)nicotinate

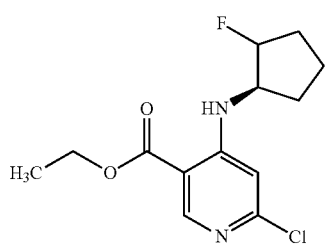

(I-12)

A solution of ethyl 6-chloro-4-(((2S)-2-hydroxycyclopentyl)amino)nicotinate (1.0 g, 1 equiv.) in DCM (15 mL) was cooled to 0° C. DAST (0.7 mL, 1.5 equiv.) was added dropwise. The reaction mixture was stirred overnight at room temperature. The reaction mixture was again cooled to 0° C. and quenched with 10% NaHCO$_3$ solution. The product was extracted in DCM. The aqueous layer was washed with DCM (twice). The organic extracts were combined, dried over anhydrous sodium sulfate, filtered and concentrated. The crude product was purified by flash column chromatography using silica gel and EtOAc: pet ether to obtain the desired product. LC/MS: Ascentis Express C18, 5×2.1 mm, 2.7 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 2.013 min; LCMS (ES-API), m/z 287.2 (M+H).

Intermediate 13

(R)-Ethyl 6-chloro-4-(2-oxocyclopentylamino)nicotinate

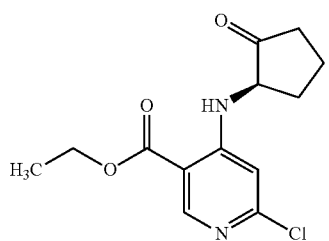

(I-13)

To a solution of ethyl 6-chloro-4-(((2S)-2-hydroxycyclopentyl)amino)nicotinate (0.5 g, 1 equiv.) in DCM (20 mL) was added Dess-Martin Periodinane (2.98 g, 4 equiv.). The reaction mixture was stirred at room temperature for 10 min. The reaction mixture was concentrated and the residue was dissolved in ethyl acetate and filtered through a bed of CELITE®. The filtrate was concentrated. The crude product was purified by flash column chromatography using silica gel and EtOAc: pet ether to obtain the desired product. LC/MS: Ascentis Express C18, 5×2.1 mm, 2.7 µm; Solvent A=2% ACN: 98% H$_2$O: 10 mM NH$_4$COOH; Solvent B=98% ACN: 2% H$_2$O: 10 mM NH$_4$COOH; gradient 0-100% B over 1.5 min; retention time: 1.863 min; LCMS (ES-API), m/z 283.2 (M+H).

Intermediate 14

(R)-Ethyl 6-chloro-4-(2,2-difluorocyclopentylamino)nicotinate

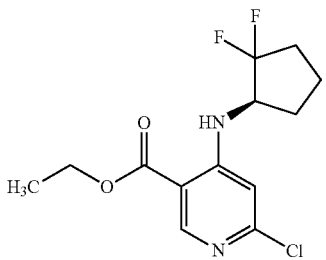

(I-14)

Ethyl 6-chloro-4-((2-oxocyclopentyl)amino)nicotinate (0.57 g, 1 equiv.) in DCM (10 mL) was cooled to 0° C. DAST (0.67 mL, 2.5 equiv.) was added dropwise to the reaction mixture and allowed to stir overnight at room temperature. The reaction mixture was diluted with DCM, quenched with 10% NaHCO$_3$ at 0° C. The organic layer was collected, dried over anhydrous sodium sulfate, filtered and concentrated. The crude product was purified by flash column chromatography using silica gel and EtOAc: pet ether to obtain the desired product. LC/MS: PUROSPHER® Star RP-18, 4×55 mm, 3 µm; Solvent A=10% ACN: 90% H$_2$O: 20 mM NH$_4$OAc; Solvent B=90% ACN: 10% H$_2$O: 20 mM NH$_4$COOAc; gradient 0-100% B over 1.5 min (3.2 min run time); retention time: 2.017 min; LCMS (ES-API), m/z 305 (M+H).

Intermediate 15

Ethyl 6-chloro-4-((1S)-3-hydroxycyclopentylamino)nicotinate

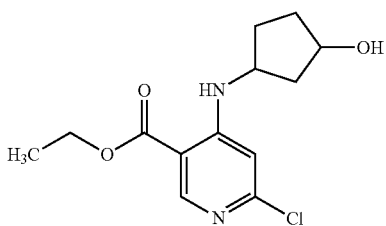

(I-15)

Intermediate 15 was prepared from 3-aminocyclopentenol and ethyl 4,6-dichloronicotinate following the standard procedures outlined in Example 5. LC/MS:

Acquity BEH C18 2.1×50 mm, 1.8µ; Solvent A=0.1% TFA in water; Solvent B=0.1% TFA in ACN; gradient 0-100% B over 2 min; retention time: 0.70 min; LCMS (ES-API), m/z 285.1 (M+H).

Intermediate 16

Ethyl 6-chloro-4-((1S)-3-fluorocyclopentylamino)nicotinate

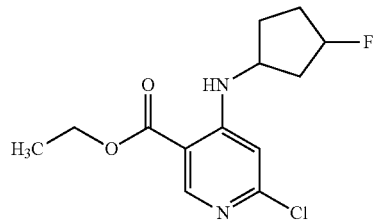
(I-16)

Intermediate 16 was prepared from the reaction of ethyl 6-chloro-4-(3-hydroxycyclopentylamino)nicotinate and DAST according to the methods outlined for the preparation of ethyl 6-chloro-4-((1R)-2-fluorocyclopentylamino)nicotinate. LC/MS: XBridge Phenyl, 4.6×30 mm, 3.5 μm; Solvent A=2% ACN: 98% $H_2O$: 10 mM $NH_4COOH$; Solvent B=98% ACN: 2% $H_2O$: 10 mM $NH_4COOH$; gradient 0-100% B over 1.5 min (3.2 min run time); retention time: 1.165 min; LCMS (ES-API), m/z 287.0 (M+H).

Intermediate 17

(S)-Ethyl 6-chloro-4-((1-hydroxypropan-2-yl)amino)nicotinate

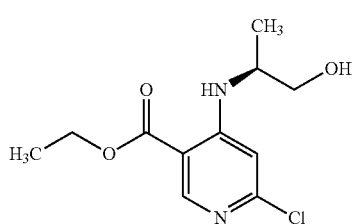
(I-17)

To a stirred solution of ethyl 4,6-dichloronicotinate (1.0 g, 4.54 mmol) in DMA (5 mL) were added DIPEA (2.381 mL, 13.63 mmol) and (S)-2-aminopropan-1-ol (0.424 mL, 5.45 mmol). The reaction mixture was stirred for 3 h at 100° C., cooled to room temperature and the solvents removed in vacuo. The residue was added to water and extracted with ethyl acetate. The organic solution was dried over anhydrous $Na_2SO_4$, filtered, and concentrated. The product was purified via column chromatography to afford (S)-ethyl 6-chloro-4-((1-hydroxypropan-2-yl)amino)nicotinate (1.1 g, 93% yield). $^1H$ NMR (400 MHz, DMSO-$d_6$) δ ppm 8.53 (s, 1H) 8.22 (d, J=8.03 Hz, 1H) 8.20-8.24 (m, 1H) 6.87 (s, 1H) 6.85-6.88 (m, 1H) 4.97-4.97 (m, 1H) 4.99 (t, J=5.27 Hz, 1H) 4.30 (q, J=7.03 Hz, 1H) 4.26-4.33 (m, 2H) 3.73-3.82 (m, 1H) 3.39-3.52 (m, 2H) 1.29-1.34 (m, 3H) 1.16 (m, 3H); LCMS 259.3 (M+H)$^+$.

Intermediate 18

(S)-Ethyl 6-chloro-4-((1-fluoropropan-2-yl)amino)nicotinate

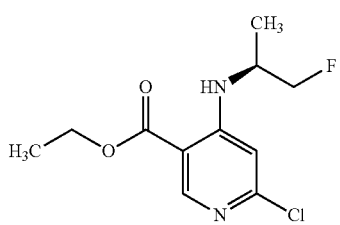
(I-18)

To a stirred solution of (S)-ethyl-6-chloro-4-((1-hydroxypropan-2-yl)amino) nicotinate (2 g, 7.73 mmol) in THF (15 mL) at −78° C. was added DAST (2.55 mL, 19.33 mmol). The reaction mixture was then allowed to warm to room temperature and stirred overnight. The reaction was quenched with 10% aq $NaHCO_3$ and extracted with EtOAc. The organic layer was dried over anhydrous $Na_2SO_4$, filtered, and concentrated to afford the crude material which was purified via column chromatography to afford the product (1.2 g, 60% yield). LCMS 261.0 (M+H)$^+$.

Intermediate 19

(S)-6-Chloro-4-((1-fluoropropan-2-yl)amino)nicotinic acid

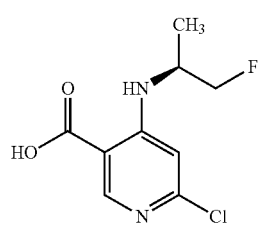
(I-19)

To a solution of (S)-ethyl 6-chloro-4-((1-fluoropropan-2-yl)amino)nicotinate (1.3 g, 4.99 mmol) in ethanol (10 mL), was added LiOH (0.615 g, 14.96 mmol) and water (3 mL, 4.99 mmol). The reaction mixture was stirred at room temperature for 1 h. TLC showed absence of starting material. The mixture was concentrated and acidified to a pH of 3-4 using 1.5 N HCl. The resulting solid was filtered to afford (S)-6-chloro-4-((1-fluoropropan-2-yl)amino)nicotinic acid (1.0 g, 41% yield) as an off-white solid. LCMS 233.2 (M+H)$^+$.

Intermediate 20

6-Chloro-N—((R)-2-fluoro-3-hydroxy-3-methylbutyl)-4-(((S)-1-fluoropropan-2-yl)amino)nicotinamide

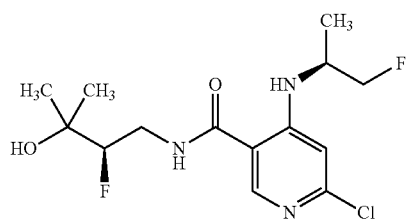

(I-20)

To as solution of (S)-6-chloro-4-((1-fluoropropan-2-yl)amino)nicotinic acid (0.650 g, 2.79 mmol) in DMF (6 mL) were added DIPEA (1.952 mL, 11.18 mmol), (R)-4-amino-3-fluoro-2-methylbutan-2-ol (0.406 g, 3.35 mmol) and HATU (1.062 g, 2.79 mmol). The reaction mixture was stirred at room temperature for 1 h. The reaction mixture was diluted with water (50 mL) and extracted with ethyl acetate. The combined organic extracts was washed with 10% sodium bicarbonate, dried over sodium sulfate and concentrated. The crude material was purified via column chromatography to afford 6-chloro-N—((R)-2-fluoro-3-hydroxy-3-methylbutyl)-4-(((S)-1-fluoropropan-2-yl)amino) nicotinamide (0.4 g, 42% yield) as a pale yellow oil. LCMS 336.2 (M+H)+.

Intermediate 21

(R)-6-Chloro-N-(2,3-difluoro-3-methylbutyl)-4-(isopropylamino)nicotinamide

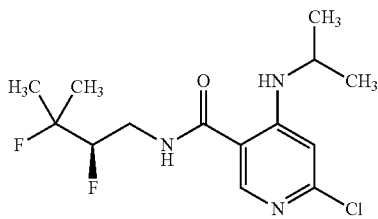

(I-21)

To a solution of (R)-6-chloro-N-(2-fluoro-3-hydroxyl-3-methylbutyl)-4-(isopropylamino)nicotinamide (250 mg, 0.79 mmol) in DCM (10 mL) at −40° C. were added DAST (0.21 mL, 1.57 mmol). The reaction was allowed to warm to room temperature slowly. The reaction was stirred at room temperature for 30 min then quenched with MeOH and concentrated. The crude product was purified by column chromatography using 0-40% EtOAc in hexane to afford (R)-6-chloro-N-(2,3-difluoro-3-methylbutyl)-4-(isopropylamino) nicotinamide (80 mg, 29% yield) as a white solid. $^1$H NMR (400 MHz, DMSO-$d_6$) δ 8.86 (d, J=5.5 Hz, 1H), 8.41 (m, 1H), 6.73 (s, 1H), 4.60 (m, 1H), 3.70 (m, 2H), 3.39 (m, 1H), 1.44 (s, 3H), 1.38 (S, 3H), 1.19 (s, 3H), 1.17 (s, 3H).

Intermediate 22

3-Vinyloxetan-3-ol

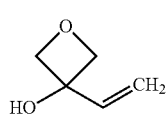

(I-22)

In a dry flask, under a nitrogen atmosphere, a stirring solution of oxetan-3-one (2.1 g, 29.1 mmol) in anhydrous THF (100 mL) was cooled to 0° C., and treated dropwise with vinylmagnesium bromide (1M in THF) (50 mL, 50.0 mmol) at a rate which maintained an internal temperature below 10° C. The reaction mixture was stirred for 10 minutes, then allowed to warm to room temperature and stirred for 2 hours. The reaction mixture was poured into saturated ammonium chloride (200 mL). The mixture was stirred for 5 minutes, the layers were separated, and the aqueous phase was extracted 4× with diethyl ether (75 mL). The combined organic phases were dried over sodium sulfate, and concentrated in vacuo to yield 3-vinyloxetan-3-ol (2.66 g, 26.6 mmol, 91% yield) as a pale yellow oil, which was used as-is in the next step. $^1$H NMR (400 MHz, chloroform-d) δ 6.31 (dd, J=17.4, 10.8 Hz, 1H), 5.44 (dd, J=17.4, 0.7 Hz, 1H), 5.29 (dd, J=10.8, 0.7 Hz, 1H), 4.70 (q, J=7.0 Hz, 4H), 2.31 (s, 1H).

Intermediate 23

3-(Benzyloxy)-3-vinyloxetane

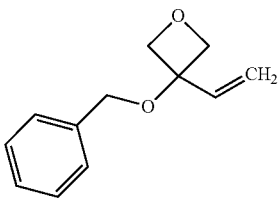

(I-23)

A stirring solution of 3-vinyloxetan-3-ol (1.0 g, 9.99 mmol) in anhydrous THF (50 mL) was cooled to 5° C. and treated with sodium hydroxide (60% in mineral oil) (0.799 g, 19.98 mmol). The mixture was stirred at 5° C. for 1 hour, then treated with benzyl bromide (2.495 mL, 20.98 mmol) and tetrabutyl ammonium iodide (0.369 g, 0.999 mmol). The reaction mixture was allowed to slowly come to room temperature, and was stirred for 18 hours, at which point it was judged to be complete by TLC (3:1 hexanes/ethyl acetate; UV/KMnO$_4$). About half of the THF was evaporated via rotary evaporator, and the remaining solution was poured into saturated ammonium chloride. The turbid mixture was extracted three times with diethyl ether, then the combined ether phases were washed with brine, dried over sodium sulfate, and concentrated in vacuo.

The residue was chromatographed via MPLC over an 80 g silica gel column, eluting at 60 mL/min with 5% to 25% acetone/hexanes over 10 column volumes. Fractions containing the desired product were pooled and concentrated in vacuo to yield 3-(benzyloxy)-3-vinyloxetane (1.58 g, 8.31 mmol, 83% yield. $^1$H NMR (400 MHz, chloroform-d) δ 7.45-

7.29 (m, 5H), 6.14 (dd, J=17.6, 10.8 Hz, 1H), 5.54 (dd, J=17.6, 0.7 Hz, 1H), 5.49 (dd, J=10.9, 0.8 Hz, 1H), 4.81 (d, J=7.0 Hz, 2H), 4.65 (d, J=7.3 Hz, 2H), 4.42 (s, 2H).

Intermediate 24

3-(Benzyloxy)-3-(oxiran-2-yl)oxetane

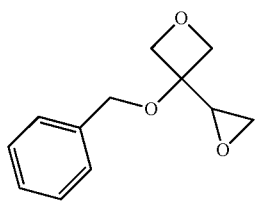

(I-24)

A stirring solution of 3-(benzyloxy)-3-vinyloxetane (3.13 g, 16.45 mmol) in dichloromethane (50 mL) was cooled to 5° C. and treated with m-CPBA (8.11 g, 36.2 mmol). The reaction mixture was allowed to slowly come to room temperature, heated at reflux for 1 hour, then cooled to room temperature and stirred for 42 hours, at which point it was judged to be complete by LCMS. The mixture was cooled to 5° C. and treated with half-saturated sodium bisulfite (150 mL). The mixture was allowed to come to room temperature and stirred for 30 minutes, then most of the DCM was evaporated via rotary evaporator. The resulting heterogeneous mixture was extracted 3× with ethyl acetate (30 mL), then the combined organic phases were washed 3× with saturated sodium bicarbonate and once with brine, then dried over sodium sulfate and concentrated in vacuo to yield 3-(benzyloxy)-3-(oxiran-2-yl)oxetane (3.32 g, 16.10 mmol, 98% yield). $^1$H NMR (400 MHz, chloroform-d) δ 7.45-7.30 (m, 5H), 4.75 (d, J=6.6 Hz, 1H), 4.68 (d, J=6.6 Hz, 1H), 4.66 (d, J=2.4 Hz, 1H), 4.60-4.54 (m, 1H), 4.48 (d, J=6.6 Hz, 1H), 4.40 (d, J=7.3 Hz, 1H), 3.35 (dd, J=3.6, 2.8 Hz, 1H), 3.00-2.95 (m, 1H), 2.94-2.90 (m, 1H).

Intermediate 25

2-Azido-1-(3-(benzyloxy)oxetan-3-yl)ethanol

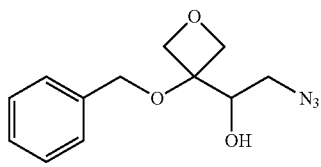

(I-25)

A mixture of 3-(benzyloxy)-3-(oxiran-2-yl)oxetane (3.7 g, 17.94 mmol) and sodium azide (1.749 g, 26.9 mmol) in acetone/water (1:1) (40 mL) was stirred at room temperature for 60 hours. Most of the acetone was evaporated, and the remainder of the reaction mixture was treated with saturated ammonium chloride (20 mL). The turbid solution was extracted 3× with dichloromethane (30 mL), and the combined aqueous phases were washed once with water and once with brine, then dried over sodium sulfate and concentrated in vacuo. The residue was chromatographed via MPLC over a 40 g silica gel column, eluting at 40 mL/min with a 5% to 50% methylene chloride/hexanes gradient over 12 column volumes. Fractions containing the desired product were pooled and concentrated in vacuo to yield 2-azido-1-(3-(benzyloxy)oxetan-3-yl)ethanol (2.31 g, 9.27 mmol, 51.7% yield) as an amber oil. $^1$H NMR (400 MHz, chloroform-d) δ 7.45-7.31 (m, 5H), 4.94-4.81 (m, 4H), 4.79 (d, J=7.7 Hz, 1H), 4.68-4.63 (m, 1H), 4.22-4.09 (m, 1H), 3.55-3.50 (m, 2H), 2.38 (d, J=6.6 Hz, 1H).

Intermediate 26

3-(2-Azido-1-fluoroethyl)-3-(benzyloxy)oxetane

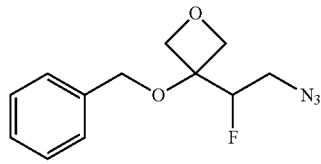

(I-26-isomers 1 and 2)

A stirring solution of 2-azido-1-(3-(benzyloxy)oxetan-3-yl)ethanol (1.2 g, 4.81 mmol) in anhydrous dichloromethane (30 mL) was cooled to −78° C. and treated with diethylaminosulfur trifluoride (1.209 mL, 9.15 mmol). The mixture was stirred at −78° C. for 2 hours, then allowed to come to room temperature and stirred for 42 hours. The reaction mixture was poured into stirring, ice-cold saturated sodium carbonate solution (200 mL), and the mixture was stirred for 30 minutes. The layers were separated, the aqueous phase was extracted twice with dichloromethane (50 mL), and the combined organic phases were dried over sodium sulfate and concentrated in vacuo. The residue was chromatographed via MPLC over a 80 g silica gel column, eluting at 60 mL/min with a 5% to 30% acetone/hexanes gradient over 10 column volumes. Fractions containing the product were pooled and concentrated in vacuo to yield 3-(2-azido-1-fluoroethyl)-3-(benzyloxy)oxetane (0.65 g, 2.59 mmol, 53.7% yield) as a colorless oil. $^1$H NMR (400 MHz, chloroform-d) δ 7.46-7.31 (m, 5H), 5.04-4.82 (m, 5H), 4.81-4.74 (m, 1H), 4.63 (d, J=7.5 Hz, 1H), 3.70 (ddd, J=19.6, 13.6, 7.0 Hz, 1H), 3.58-3.43 (m, 1H). The enantiomers were resolved by supercritical fluid chromatography using the following conditions: Instrument: Thar Preparative SFC-350; Column: CHIRALPAK® AD (5×25 cm, 5 μm); BPR pressure: 100 bars; Temperature: 30° C.; Flow rate: 270 mL/min; Mobile Phase: $CO_2$/MeOH (87/13); Detector Wavelength: 212 nm; Separation Program: Sequence injection; Injection: 0.90 mL with cycle time 3.25 min. The separation yielded: First-eluting isomer: 3-(2-azido-1-fluoroethyl)-3-(benzyloxy)oxetane, Isomer 1 (0.25 g, 1.00 mmol, 77% yield); Second-eluting isomer: 3-(2-azido-1-fluoroethyl)-3-(benzyloxy)oxetane, Isomer 2 (0.19 g, 0.73 mmol, 53% yield).

Intermediate 27 tert-Butyl (2-fluoro-2-(3-hydroxyoxetan-3-yl)ethyl)carbamate

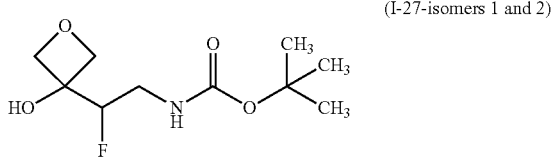 [SMILES: CC(C)(C)OC(=O)NCC(F)C1(O)COC1]

(I-27-isomers 1 and 2)

A Parr bottle was charged with 20% palladium hydroxide on carbon (100 mg, 0.142 mmol) under nitrogen, and the catalyst was wetted with methanol. The vessel was charged with a solution of 3-(2-azido-1-fluoroethyl)-3-(benzyloxy)oxetane, Isomer 2 (122 mg, 0.486 mmol) in methanol (5 mL) and BOC-anhydride (0.135 mL, 0.583 mmol), and the mixture was degassed by thrice evacuating the vessel under vacuum and repressurizing with nitrogen. The mixture was hydrogenated at 50 psi for 9 hours, at which point the reaction was judged to be complete by LCMS. The catalyst was removed by filtration and thoroughly rinsed with methanol. The combined filtrate and rinsings were concentrated in vacuo to yield tert-butyl (2-fluoro-2-(3-hydroxyoxetan-3-yl)ethyl) carbamate, Isomer 2 (135 mg, 0.574 mmol, 118% yield) as a slightly yellow oil, which was used as-is in the next step. $^1$H NMR (400 MHz, chloroform-d) δ 4.96 (bd, J=7.3 Hz, 1H), 4.89 (d, J=5.7 Hz, 1H), 4.76-4.67 (m, 2H), 4.66-4.48 (m, 3H), 3.77-3.58 (m, 1H), 3.45 (tdd, J=15.8, 6.2, 4.2 Hz, 1H), 1.47 (s, 9H).

Intermediate 28

3-(2-Amino-1-fluoroethyl)oxetan-3-ol, TFA salt

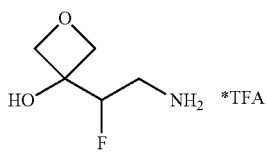

(I-28-isomers 1 and 2)

A solution of tert-butyl (2-fluoro-2-(3-hydroxyoxetan-3-yl)ethyl)carbamate, Intermediate 27, isomer 2 (0.6 g, 2.55 mmol) in anhydrous methylene chloride (3 mL) was cooled to 5° C. and treated with TFA (3 mL, 38.9 mmol). The reaction mixture was stirred at 5° C. for 1 hour, at which point it was judged to be complete by TLC. The mixture was concentrated in a vacuum, and the residue was concentrated once from 1:1 DCM/toluene (10 mL), then twice from DCM (10 mL) to remove residual TFA. The residue was dried under vacuum for 3 hours to yield 3-(2-amino-1-fluoroethyl)oxetan-3-ol, isomer 2, TFA (0.66 g, 2.65 mmol, 104% yield) as a colorless oil. $^1$H NMR (400 MHz, methanol-$d_4$) δ 5.11-4.94 (m, 1H), 4.75 (d, J=7.0 Hz, 1H), 4.66-4.58 (m, 3H), 3.30-3.23 (m, 1H).

Intermediate 29

1,6-Dioxaspiro[2.5]octane-2-carbonitrile

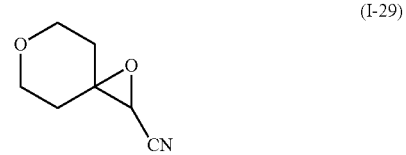

(I-29)

To a mixture of dihydro-2H-pyran-4(3H)-one (2.5 g, 25 mmol) and 2-chloroacetonitrile (1.89 g, 25 mmol) was added a solution of potassium tert-butoxide in tert-butanol (1.0 M, 25 mL) dropwise. The reaction mixture was stirred overnight and quenched with water (50 mL). The mixture was extracted with ethyl acetate (100 mL). The organic layer was washed with water and brine, then dried over magnesium sulfate, filtered and concentrated. The crude product was purified via column chromatography (10-60% ethyl acetate/pet ether) to afford 1,6-dioxaspiro[2.5]octane-2-carbonitrile (2.9 g, 83% yield) as a yellow oil. $^1$H NMR (400 MHz, CDCl$_3$) δ 3.95-3.80 (m, 4H), 3.35 (s, 1H), 2.18-2.01 (m, 1H), 1.96-1.76 (m, 2H), 1.67-1.50 (m, 1H).

Intermediate 30

4-(2-Aminoethyl)tetrahydro-2H-pyran-4-ol

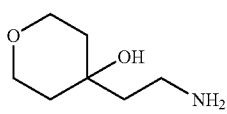

(I-30)

A mixture of 1,6-dioxaspiro[2.5]octane-2-carbonitrile (3.0 g, 22 mmol) and 10% Pd on carbon (0.3 g) in methanol (40 mL) was stirred for 2 h under a hydrogen balloon. The mixture was filtered through a pad of CELITER and the filtrate was concentrated. The residue was dissolved in THF (50 mL). The solution was added dropwise to a mixture of lithium aluminum hydride (1.6 g, 43 mmol) and THF (100 mL), and the mixture was stirred for 2 hours at reflux temperature. After cooling to 0° C., Na$_2$SO$_4$-10H$_2$O (16 g) and KF (2.5 g) were added and the mixture was stirred overnight. After filtration, the filtrate was concentrated, and the residue was acidified with 4N HCl in 1,4-dioxane. The mixture was concentrated and the residue was crystallized from ethanol-ether. The precipitate was filtered to afford 4-(2-aminoethyl)tetrahydro-2H-pyran-4-ol (2.1 g, 67% yield) as a HCl salt. $^1$H NMR (400 MHz, CDCl$_3$) δ 3.94-3.65 (m, 6H), 2.57 (s, 2H), 1.95-1.51 (m, 6H).

Intermediate 31

6-Chloro-N-(2-(4-hydroxytetrahydro-2H-pyran-4-yl)ethyl)-4-(isopropylamino)nicotinamide

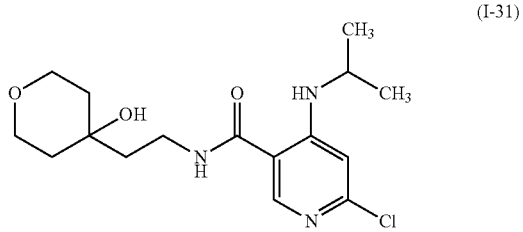 [SMILES: CC(C)Nc1cc(Cl)ncc1C(=O)NCCC1(O)CCOCC1]
(I-31)

To a solution of 6-chloro-4-(isopropylamino)nicotinic acid (0.1 g, 0.47 mmol) in DMF (1 mL), were added HOBt (0.7 g, 0.51 mmol) and EDC (0.1 g, 0.51 mmol). The mixture was stirred at room temperature for 0.5 h and then 4-(2-aminoethyl)tetrahydro-2H-pyran-4-ol hydrochloride (0.09 g, 0.49 mmol) and DIPEA (0.17 mL, 0.978 mmol) were added. The mixture was stirred for 2 h, quenched with water, stirred, and filtered to give 6-chloro-N-(2-(4-hydroxytetrahydro-2H-pyran-4-yl)ethyl)-4-(isopropylamino) nicotinamide (67 mg, 42% yield) as a off-white solid.

Intermediate 32

4-Nitro-1-(oxetan-3-yl)-1H-pyrazole

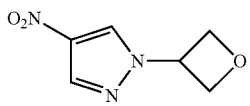
(I-32)

To a stirred solution of 4-nitro-1H-pyrazole (4 g, 35 mmol) in THF (80 mL) were added oxetan-3-ol (2.9 g, 39 mmol), triphenylphosphine (11.1 g, 42 mmol), and di-tert-butyl azodicarboxylate (10.6 g, 46 mmol) at 0° C. The mixture was stirred at room temperature for 16 h. The reaction mixture was then concentrated to give crude product. The product was purified via column chromatography to afford 4-nitro-1-(oxetan-3-yl)-1H-pyrazole (4.4 g, 74% yield). $^1$H NMR (400 MHz, DMSO-$d_6$) δ 9.03 (s, 1H), 8.41 (s, 1H), 5.65 (m, 1H), 4.91 (m, 4H).

Intermediate 33

1-(Oxetan-3-yl)-1H-pyrazol-4-amine

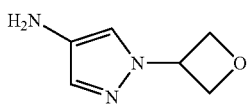
(I-33)

To a solution of 4-nitro-1-(oxetan-3-yl)-1H-pyrazole (4.4 g, 26 mmol) in MeOH (80 mL) was added Pc/C (2.77 g, 2.6 mmol) and the mixture was degassed by evacuating the vessel under vacuum and repressurizing with hydrogen. The mixture was hydrogenated under balloon pressure. After TLC indicated completion of the reaction, the mixture was degassed, and the reaction mixture was filtered under nitrogen through fiberglass filter paper. The filter cake was thoroughly rinsed with methanol (300 mL total rinse volume), and the combined filtrate and rinsings were concentrated in vacuo to obtain 1-(oxetan-3-yl-1H-pyrazole-4-amine (3.4 g, 94% yield). $^1$H NMR (400 MHz, DMSO-$d_6$) δ 7.16 (s, 1H), 7.04 (s, 1H), 5.35 (m, 1H), 4.81 (m, 4H), 3.88 (br s, 2H).

Intermediate 34

(R)-4-Amino-3-fluoro-2-methylbutan-2-ol

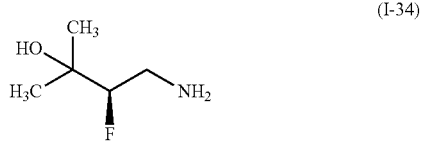
(I-34)

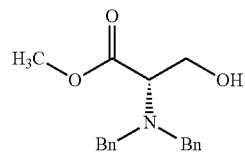 [SMILES: COC(=O)[C@H](CO)N(Cc1ccccc1)Cc1ccccc1]

Step 1: To a solution of $K_2CO_3$ (34.8 g, 2 equiv.) in DMF (280 mL), L-serine methyl ester hydrochloride (1 equiv.), potassium iodide (10.8 g, 0.5 equiv.) and benzyl bromide (38 mL, 2.5 equiv.) were added. The mixture was stirred for 16 h at room temperature. The reaction mixture was concentrated under reduced pressure to remove excess of DMF and then diluted with EtOAc. The organic layer was washed with brine and water. The organic layer was separated, dried over anhydrous sodium sulfate, filtered and concentrated. The crude material was purified by column chromatography through silica gel (EtOAC: pet ether as eluent) to afford methyl 2-(dibenzylamino)-3-hydroxypropanoate. $^1$H NMR: 400 MHz, DMSO-$d_6$: δ 2.49 (s, 1H), 3.58-3.59 (m, 1H), 3.67-3.70 (m, 2H), 3.73-3.75 (m, 2H), 3.77-3.80 (m, 3H), 3.90-3.94 (m, 2H), 7.24-7.38 (m, 10H).

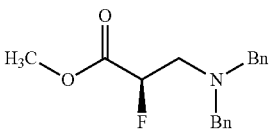 [SMILES: COC(=O)[C@H](F)CN(Cc1ccccc1)Cc1ccccc1]

Step 2: To an ice cool solution of methyl 2-(dibenzylamino)-3-hydroxypropanoate (15 g, 1 equiv.) in THF (95 mL), DAST (13.1 mL, 1.23 equiv.) was added dropwise under $N_2$-atmosphere and the reaction mixture was stirred for 14 h at room temperature. The reaction mixture was quenched with aqueous 10% $NaHCO_3$ solution at 0° C. and extracted into ethyl acetate (twice). The organic layers were collected, dried over anhydrous sodium sulfate, filtered and concentrated. The crude product was purified by flash column chromatography using silica gel and EtOAc: pet ether to afford (R)-methyl 3-(dibenzylamino)-2-fluoropropanoate. $^1$H NMR: 400 MHz, CDCl$_3$: δ 2.93-3.11 (m, 2H), 3.51-3.55 (m, 2H), 3.70 (s, 3H), 3.82-3.85 (m, 2H), 4.98-5.13 (m, 1H), 7.22-7.34 (m, 10H).

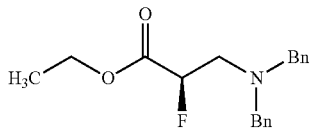 [SMILES: CCOC(=O)[C@H](F)CN(Cc1ccccc1)Cc1ccccc1]

Step 3: (R)-Ethyl 3-(dibenzylamino)-2-fluoropropanoate was prepared according to the method as described for the synthesis of (R)-methyl 3-(dibenzylamino)-2-fluoropropanoate.

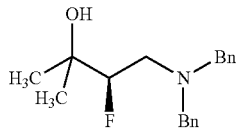 [SMILES: CC(C)(O)[C@H](F)CN(Cc1ccccc1)Cc1ccccc1]

Step 4: To a solution of (R)-ethyl 3-(dibenzylamino)-2-fluoropropanoate (15 g, 1 equiv.) in THF (150 mL), methyl magnesium bromide (3M in diethyl ether) (15 mL, 2.5 equiv.) was added dropwise at 0° C. under N$_2$ atm. The reaction mixture was slowly allowed to attain room temperature and stirred for 1 h. The reaction mixture was quenched with saturated aqueous ammonium chloride at 0° C. and extracted into ethyl acetate (twice). The organic layers were collected, dried over anhydrous sodium sulfate, filtered and concentrated. The crude product was purified by flash column chromatography using silica gel and EtOAc: pet ether to afford (R)-4-(dibenzylamino)-3-fluoro-2-methylbutan-2-ol. $^1$H NMR: 400 MHz, DMSO-d$_6$: δ 0.92-0.92 (m, 3H), 0.98-0.98 (m, 3H), 2.53-2.94 (m, 2H), 3.51-3.81 (m, 4H), 4.34-4.46 (m, 1H), 4.80 (s, 1H), 7.22-7.40 (m, 10H).

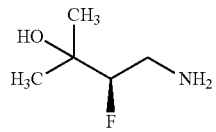

Step 5: To a solution of (R)-4-(dibenzylamino)-3-fluoro-2-methylbutan-2-ol (44 g, 146 mmol) in MeOH (400 mL) was added Pd/C (3.11 g, 29.2 mmol) and PdOH$_2$ (2.05 g, 14.6 mmol) and the mixture was evacuated and backfilled with H$_2$ gas and stirred for 18 h. The reaction mixture was filtered through CELITE® using 500 mL of methanol and the filterate was concentrated to afford (R)-4-amino-3-fluoro-2-methylbutan-2-ol (16.8 g, 95% yield). $^1$H NMR: 400 MHz, DMSO-d$_6$: δ 1.06 (s, 3H), 1.10 (s, 3H), 2.64-2.91 (m, 2H), 3.96-4.16 (m, 1H).

Example 1

(R)-6-(5-Cyano-1H-indol-1-yl)-N-(2-fluoro-3-hydroxy-3-methylbutyl)-4-(isopropylamino)nicotinamide

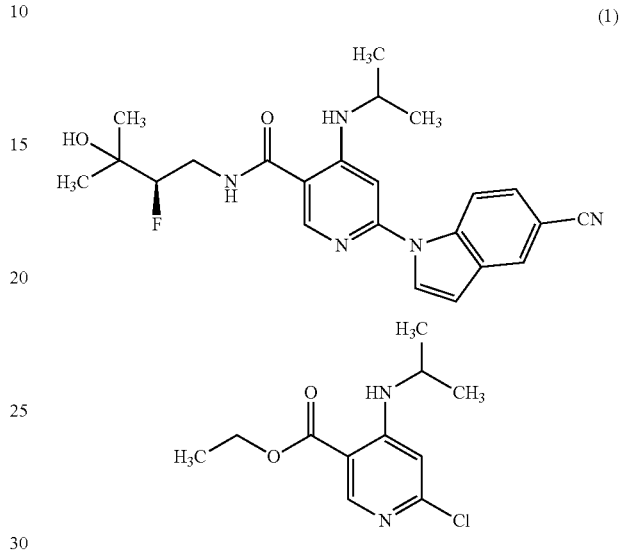

(1)

Step 1: To a solution of ethyl 4,6-dichloronicotinate (10 g, 45 mmol) in DMA (40 mL) was added propan-2-amine (5.3 g, 91 mmol) and DIPEA (31.7 mL, 182 mmol). The reaction mixture was stirred at room temperature for 48 h. The reaction mixture was diluted with MTBE and washed water (3×). The organic layer was dried over Na$_2$SO$_4$, filtered and concentrated to afford the crude product. The product was purified by flash chromatography through silica gel (10% EtOAc:pet ether as eluent) to afford ethyl 6-chloro-4-(isopropylamino) nicotinate (8.3 g, 75% yield) as a crystalline solid. LCMS m/z 243.7 (M+H); $^1$H NMR (400 MHz, DMSO-d$_6$) δ 8.54 (s, 1H), 7.98 (d, J=7.6 Hz, 1H), 6.85 (s, 1H), 4.29 (q, J=7.2 Hz, 2H), 3.86 (m, 1H), 1.32 (d, J=6.8 Hz, 3H), 1.20 (s, 3H), 1.19 (s, 3H).

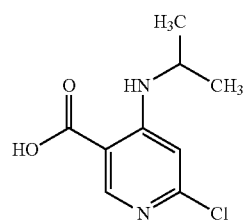

Step 2: To a solution of ethyl 6-chloro-4-(isopropylamino) nicotinate (7 g, 28.8 mmol) in EtOH (70 mL) was added water (30 mL) and LiOH (2.1 g, 87 mmol). The mixture was stirred for 3 h, concentrated and acidified with 1.5 N HCl. The resultant solids were collected and dried to afford 6-chloro-4-(isopropylamino)nicotic acid (5.3 g, 85% yield) as a white solid. LCMS 215.3 (M+H)$^+$; $^1$H NMR (400 MHz, DMSO-d$_6$) δ 13.32 (br s, 1H), 8.51 (s, 1H), 8.19 (d, J=7.6 Hz, 1H), 6.79 (s, 1H), 2.50 (m, 1H), 1.20 (s, 3H), 1.18 (s, 3H).

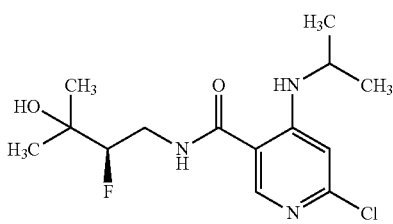 [SMILES: CC(C)Nc1cc(Cl)ncc1C(=O)NC[C@@H](F)C(C)(C)O]

Step 3: To a stirred solution of 6-chloro-4-(isopropylamino)nicotinic acid (2.9 g, 13.51 mmol) in DMF was added (R)-4-amino-3-fluoro-2-methylbutan-2-ol (1.637 g, 13.51 mmol), HATU (6.16 g, 16.21 mmol), and DIPEA (9.44 mL, 54.0 mmol). The reaction mixture was stirred for 18 h. The reaction mixture was diluted with ethyl acetate and washed with water (3×). The organic layer was dried over $Na_2SO_4$ and concentrated to provide the crude compound which was purified via column chromatography (10-40% ethyl acetate/pet ether) to afford (R)-6-chloro-N-(2-fluoro-3-hydroxy-3-methylbutyl)-4-(isopropylamino)nicotinamide (2.8 g, 65% yield) as an off-white solid. LCMS 318.1 (M+H): $^1$H NMR (400 MHz, DMSO-$d_6$) δ 8.75 (t, J=7.6 Hz, 1H), 8.44 (br d, J=10.4 Hz, 1H), 8.38 (s, 1H), 6.71 (s, 1H), 4.24 (m, 1H), 3.64 (m, 2H), 3.42 (m, 1H), 1.16 (m, 12H).

Example 1

To a solution of (R)-6-chloro-N-(2-fluoro-3-hydroxy-3-methylbutyl)-4-(isopropylamino)nicotinamide (100 mg, 0.315 mmol) and 1H-indole-5-carbonitrile (44.7 mg, 0.315 mmol) in 1,4-dioxane (5 mL) was added $Cs_2CO_3$ (308 mg, 0.944 mmol) and Xantphos (72.8 mg, 0.126 mmol). The reaction vessel was purged with $N_2$ for 20 mins then added $Pd_2(dba)_3$ (115 mg, 0.126 mmol) and again purged for 5 mins. The vessel was heated in a sealed tube at 110° C. for 18 h. The reaction mixture was cooled to room temperature, filtered through CELITER, and diluted with EtOAc (50 mL). The crude mixture was washed with water (10 mL) and brine (10 mL) then dried over $Na_2SO_4$. The filtered solution was concentrated to give the crude compound which was purified via silica gel chromatography (50% EtOAc in hexane) to afford (R)-6-(5-cyano-1H-indol-1-yl)-N-(2-fluoro-3-hydroxy-3-methylbutyl)-4-(isopropylamino)nicotinamide (20 mg, 15% yield). LCMS 424.2 (M+H)$^+$; $^1$H-NMR (400 MHz, DMSO-$d_6$) δ 8.75 (t, J=5.60 Hz, 1H), 8.62 (s, 1H), 8.57 (d, J=8.00 Hz, 1H), 8.52 (d, J=8.80 Hz, 1H), 8.26 (d, J=3.60 Hz, 1H), 8.19 (d, J=1.20 Hz, 1H), 7.62 (dd, J=1.60, 8.80 Hz, 1H), 6.87-6.89 (m, 2H), 4.84 (s, 1H), 4.37 (ddd, J=2.00, 9.20, 49.20 Hz, 1H), 3.95-4.00 (m, 1H), 3.62-3.78 (m, 1H), 3.40-3.45 (m, 1H), 1.23 (d, J=6.00 Hz, 6H), 1.18 (d, J=6.80 Hz, 6H); LC/MS: 424.2 (M+H); HPLC rt 9.47 min, Conditions A.

The Examples in Table 4 were prepared using the methods outlined for Example 1 using the appropriate starting material and amine. The absolute stereochemistry of the diastereomers was undetermined.

TABLE 4

| Ex. No. | Structure | HPLC rt (min) | HPLC cond. | LCMS |
|---|---|---|---|---|
| 2 | 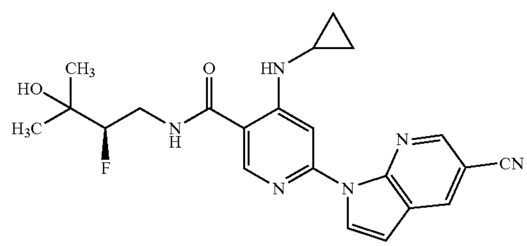 | 8.60 | A | 423.2 |
| 3 | 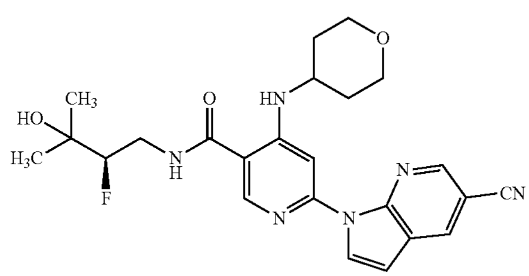 [SMILES: CC(C)(O)[C@H](F)CNC(=O)c1cnc(-n2ccc3cc(C#N)cnc32)cc1NC1CCOCC1] | 7.62 | A | 467.2 |
| 4 | 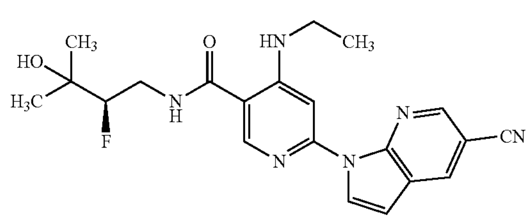 [SMILES: CCNc1cc(-n2ccc3cc(C#N)cnc32)ncc1C(=O)NC[C@@H](F)C(C)(C)O] | 7.35 | A | 411.2 |

TABLE 4-continued

| Ex. No. | Structure | HPLC rt (min) | HPLC cond. | LCMS |
|---|---|---|---|---|
| 5 | 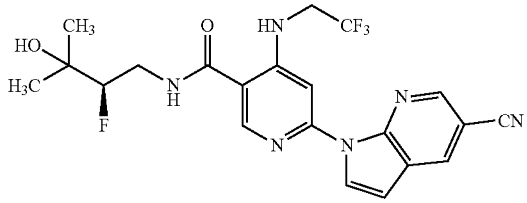 | 9.12 | B | 465.5 |
| 6 | 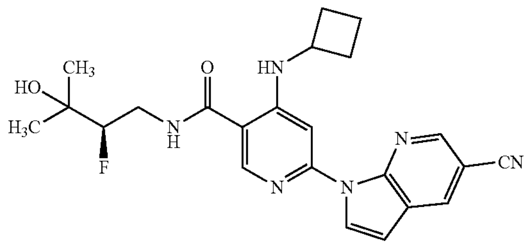 [SMILES: CC(C)(O)[C@H](F)CNC(=O)c1cnc(-n2ccc3cc(C#N)cnc32)cc1NC1CCC1] | 14.2 | A, 25 min grad. | 437.2 |
| 7 Diastereomer 1 | 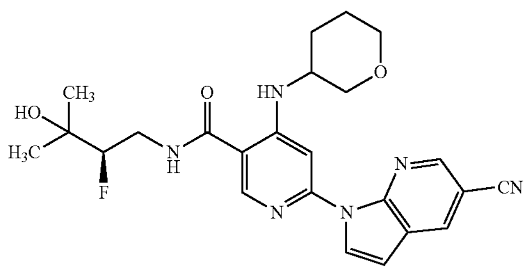 [SMILES: CC(C)(O)[C@H](F)CNC(=O)c1cnc(-n2ccc3cc(C#N)cnc32)cc1NC1CCCOC1] | 7.92 | A | 467.2 |
| 8 Diastereomer 2 | 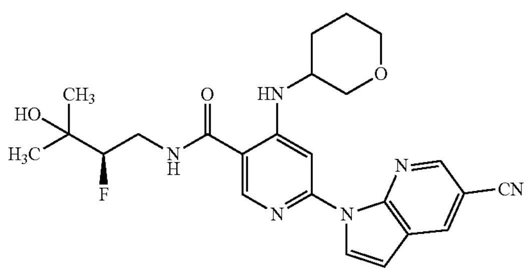 [SMILES: CC(C)(O)[C@H](F)CNC(=O)c1cnc(-n2ccc3cc(C#N)cnc32)cc1NC1CCCOC1] | 7.91 | A | 467.1 |
| 9 | 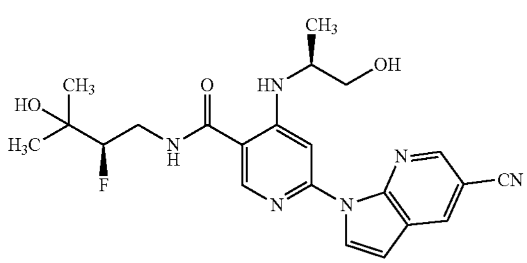 [SMILES: C[C@@H](CO)Nc1cc(-n2ccc3cc(C#N)cnc32)ncc1C(=O)NC[C@@H](F)C(C)(C)O] | 6.22 | A | 441.4 |
| 10 | 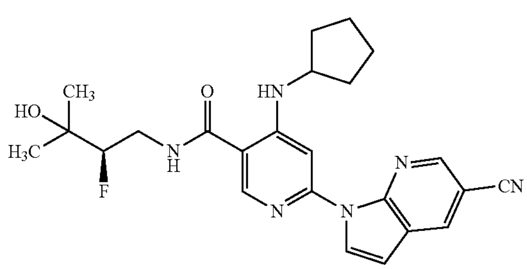 [SMILES: CC(C)(O)[C@H](F)CNC(=O)c1cnc(-n2ccc3cc(C#N)cnc32)cc1NC1CCCC1] | 9.37 | A | 451.6 |

TABLE 4-continued

| Ex. No. | Structure | HPLC rt (min) | HPLC cond. | LCMS |
|---|---|---|---|---|
| 11 | 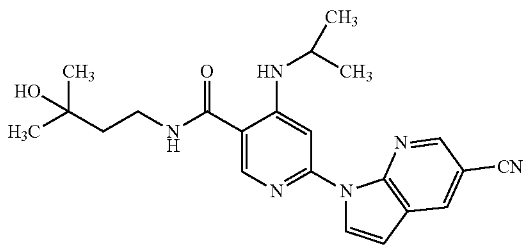 [SMILES: CC(C)Nc1cc(-n2ccc3cc(C#N)cnc32)ncc1C(=O)NCCC(C)(C)O] | 1.70 | E | 406.9 |
| 12 | 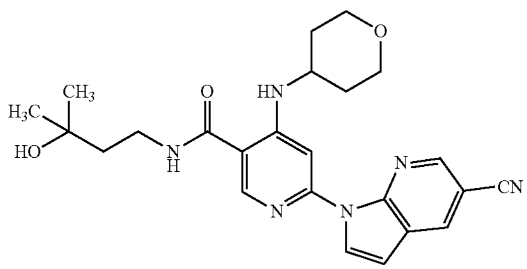 [SMILES: CC(C)(O)CCNC(=O)c1cnc(-n2ccc3cc(C#N)cnc32)cc1NC1CCOCC1] | 1.56 | E | 449.2 |
| 13 | 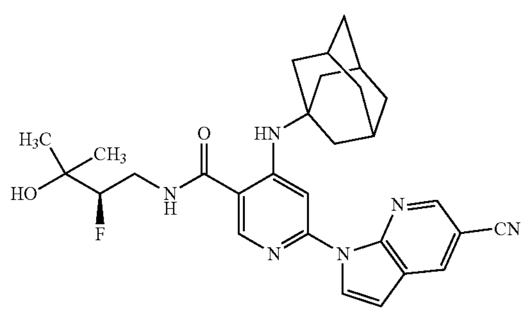 [SMILES: CC(C)(O)[C@H](F)CNC(=O)c1cnc(-n2ccc3cc(C#N)cnc32)cc1NC12CC3CC(CC(C3)C1)C2] | 2.40 | E | 517.2 |
| 14 | 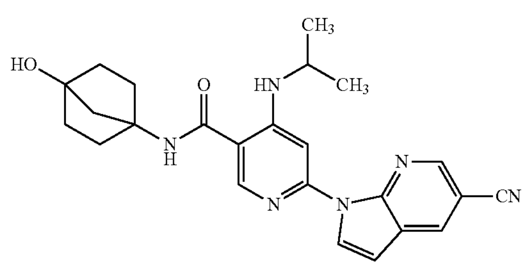 [SMILES: CC(C)Nc1cc(-n2ccc3cc(C#N)cnc32)ncc1C(=O)NC12CCC(O)(CC1)C2] | 1.78 | E | 431.2 |
| 15 | 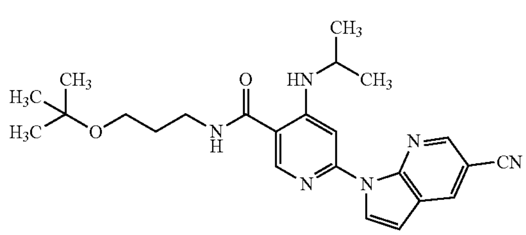 [SMILES: CC(C)Nc1cc(-n2ccc3cc(C#N)cnc32)ncc1C(=O)NCCCOC(C)(C)C] | 2.29 | E | 435.2 |

TABLE 4-continued

| Ex. No. | Structure | HPLC rt (min) | HPLC cond. | LCMS |
|---|---|---|---|---|
| 16 | 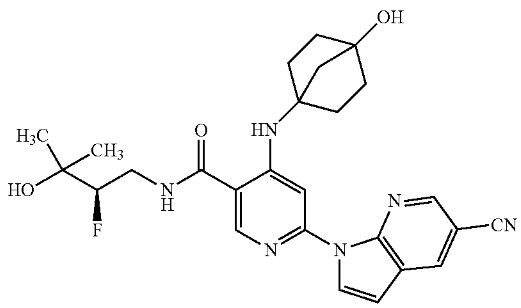 [SMILES: CC(C)(O)[C@H](F)CNC(=O)c1cnc(-n2ccc3cc(C#N)cnc32)cc1NC12CCC(O)(CC1)C2] | 1.52 | E | 493.3 |
| 17 | 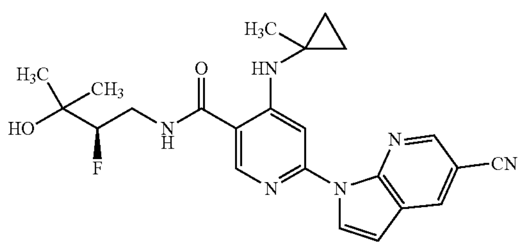 [SMILES: CC1(Nc2cc(-n3ccc4cc(C#N)cnc43)ncc2C(=O)NC[C@@H](F)C(C)(C)O)CC1] | 8.56 | B | 437.0 |
| 18 | 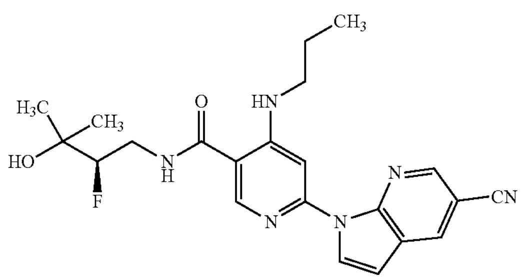 [SMILES: CCCNc1cc(-n2ccc3cc(C#N)cnc32)ncc1C(=O)NC[C@@H](F)C(C)(C)O] | 1.89 | E | 425.4 |
| 19 | 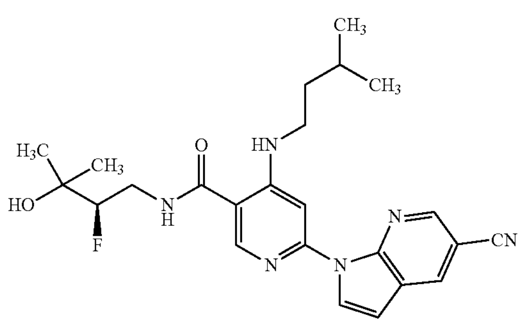 [SMILES: CC(C)CCNc1cc(-n2ccc3cc(C#N)cnc32)ncc1C(=O)NC[C@@H](F)C(C)(C)O] | 2.07 | E | 453.3 |
| 20 | 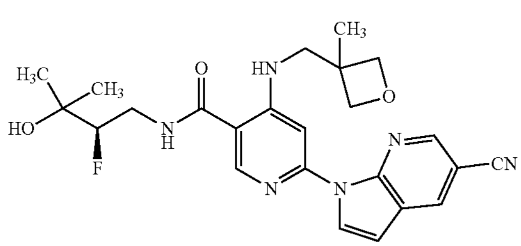 [SMILES: CC1(CNc2cc(-n3ccc4cc(C#N)cnc43)ncc2C(=O)NC[C@@H](F)C(C)(C)O)COC1] | 1.55 | E | 467.4 |

TABLE 4-continued

| Ex. No. | Structure | HPLC rt (min) | HPLC cond. | LCMS |
|---|---|---|---|---|
| 21 Diastereomer 1 | 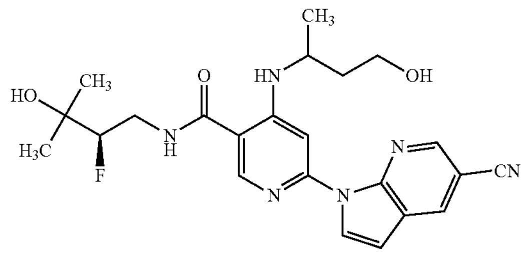 [SMILES: CC(CCO)Nc1cc(-n2ccc3cc(C#N)cnc32)ncc1C(=O)NC[C@@H](F)C(C)(C)O] | 6.34 | A | 453.2 (M-H) |
| 22 Diastereomer 2 | 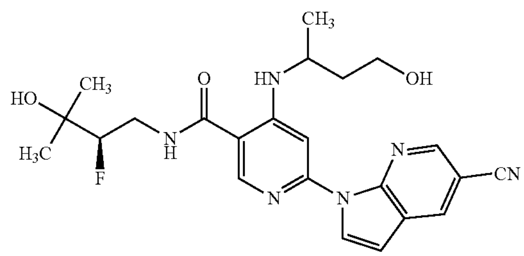 [SMILES: CC(CCO)Nc1cc(-n2ccc3cc(C#N)cnc32)ncc1C(=O)NC[C@@H](F)C(C)(C)O] | 6.35 | A | 453.2 (M-H) |
| 23 | 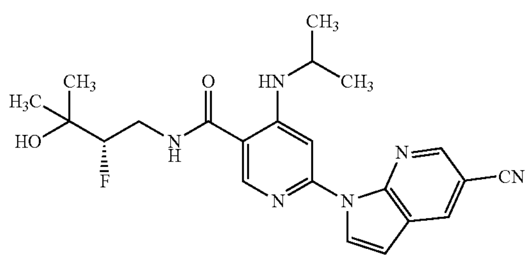 [SMILES: CC(C)Nc1cc(-n2ccc3cc(C#N)cnc32)ncc1C(=O)NC[C@H](F)C(C)(C)O] | 8.21 | B | 425.0 |
| 24 Diastereomer 1 | 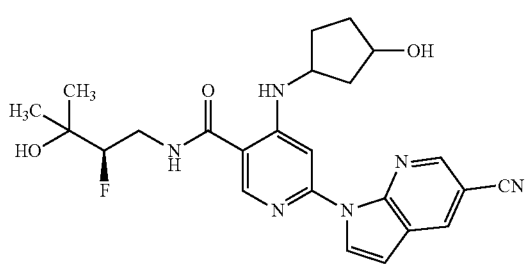 [SMILES: CC(C)(O)[C@H](F)CNC(=O)c1cnc(-n2ccc3cc(C#N)cnc32)cc1NC1CCC(O)C1] | 6.15 | A | 467.0 |
| 25 Diastereomer 2 | 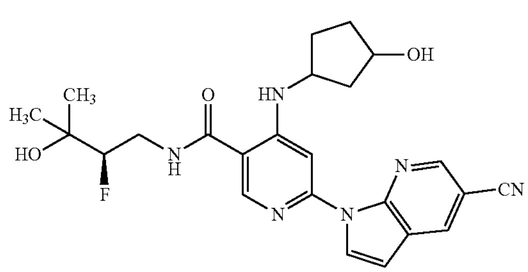 [SMILES: CC(C)(O)[C@H](F)CNC(=O)c1cnc(-n2ccc3cc(C#N)cnc32)cc1NC1CCC(O)C1] | 6.15 | A | 467.0 |
| 26 Diastereomer 3 | 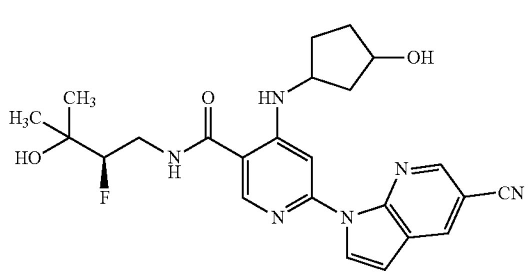 [SMILES: CC(C)(O)[C@H](F)CNC(=O)c1cnc(-n2ccc3cc(C#N)cnc32)cc1NC1CCC(O)C1] | 6.35 | A | 467.0 |

TABLE 4-continued
| Ex. No. | Structure | HPLC rt (min) | HPLC cond. | LCMS |
|---|---|---|---|---|
| 27 Diastereomer 4 | 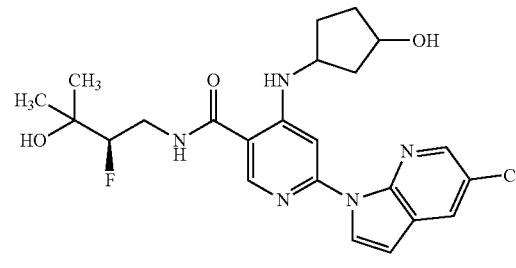 | 6.35 | A | 467.0 |
| 28 | 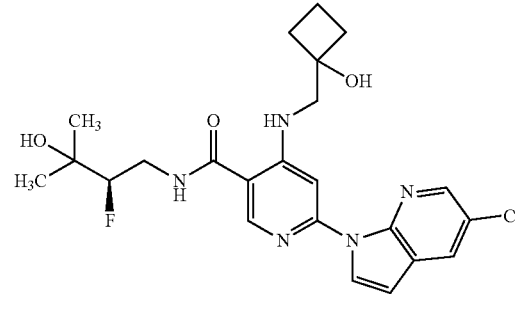 | 7.13 | A | 467.2 |
| 29 | 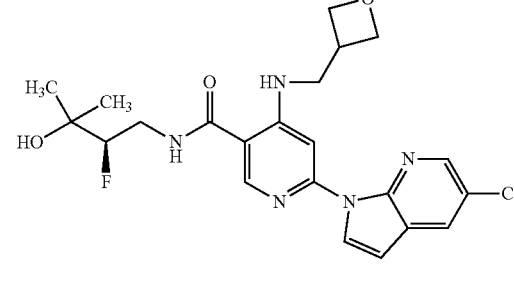 | 1.35 | E | 453.3 |
| 30 | 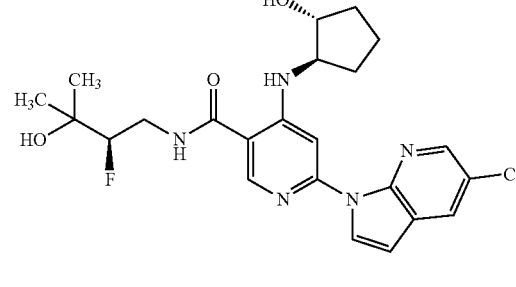 | 6.89 | A | 467.5 |
| 31 | 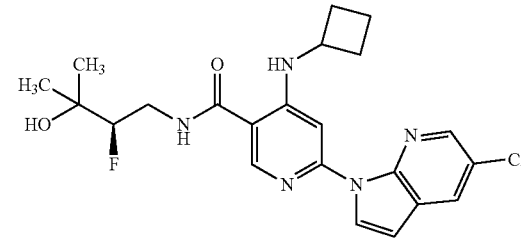 [SMILES: CC(C)(O)[C@H](F)CNC(=O)c1cnc(-n2ccc3cc(Cl)cnc32)cc1NC1CCC1] | 1.99 | E | 446.0 |

TABLE 4-continued
| Ex. No. | Structure | HPLC rt (min) | HPLC cond. | LCMS |
|---|---|---|---|---|
| 32 | 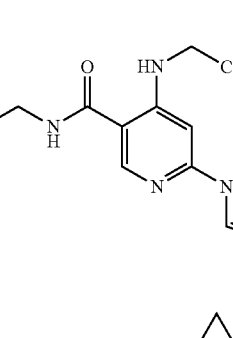 | 1.72 | E | 476.1 |
| 33 | 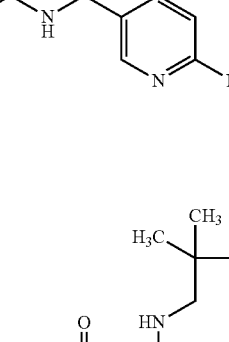 | 2.06 | E | 420.2 |
| 34 | 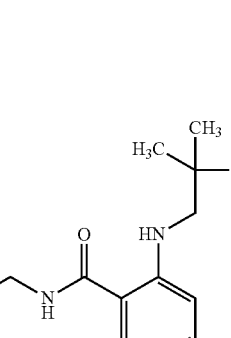 | 2.06 | E | 432.2 |
| 35 | 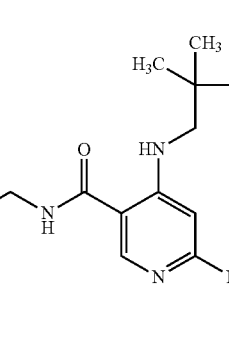 | 1.80 | E | 464.0 |
| 36 | 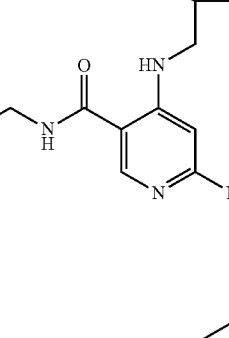 | 2.02 | E | 458.1 |

TABLE 4-continued
| Ex. No. | Structure | HPLC rt (min) | HPLC cond. | LCMS |
|---|---|---|---|---|
| 37 | 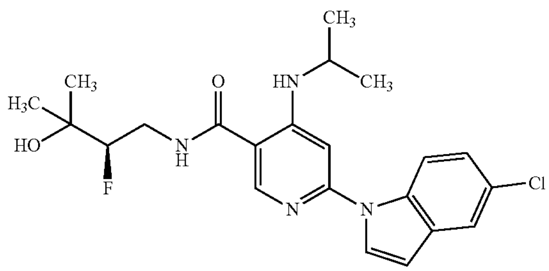 [SMILES: CC(C)Nc1cc(-n2ccc3cc(Cl)ccc32)ncc1C(=O)NC[C@@H](F)C(C)(C)O] | 2.14 | E | 433.2 |
| 38 | 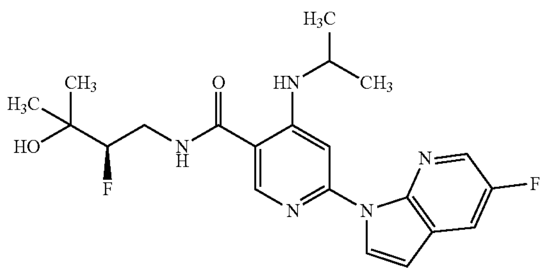 [SMILES: CC(C)Nc1cc(-n2ccc3cc(F)cnc32)ncc1C(=O)NC[C@@H](F)C(C)(C)O] | 7.55 | B | 418.2 |
| 39 | 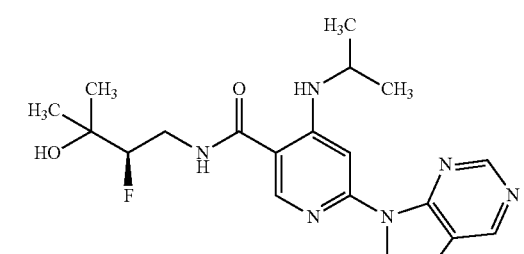 | 1.39 | E | 401.2 |
| 40 | 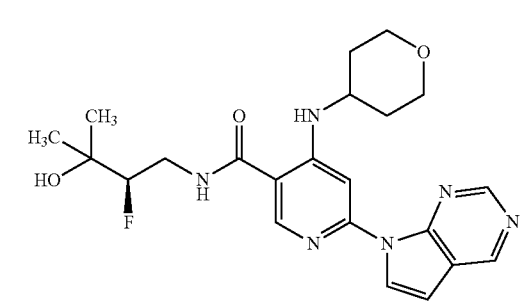 [SMILES: CC(C)(O)[C@H](F)CNC(=O)c1cnc(-n2ccc3cncnc32)cc1NC1CCOCC1] | 1.19 | E | 443.2 |
| 41 | 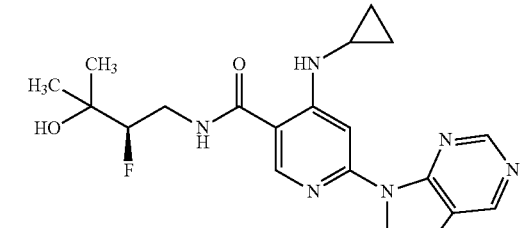 | 1.28 | E | 399.1 |

TABLE 4-continued

| Ex. No. | Structure | HPLC rt (min) | HPLC cond. | LCMS |
|---|---|---|---|---|
| 42 | 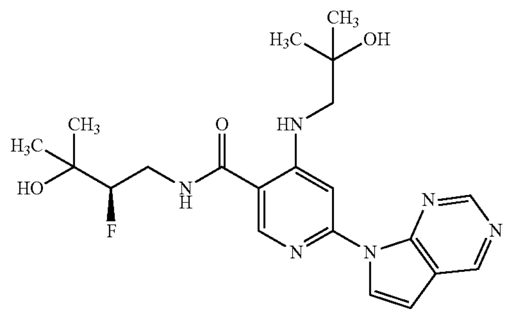 [SMILES: CC(C)(O)CNc1cc(-n2ccc3cncnc32)ncc1C(=O)NC[C@@H](F)C(C)(C)O] | 1.06 | E | 431.1 |
| 43 | 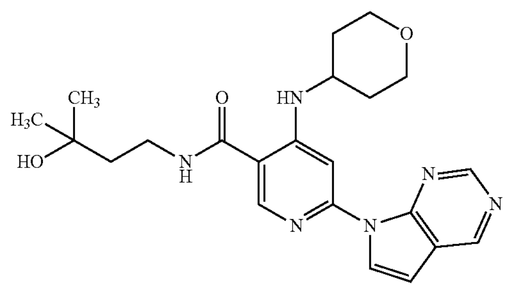 [SMILES: CC(C)(O)CCNC(=O)c1cnc(-n2ccc3cncnc32)cc1NC1CCOCC1] | 1.30 | E | 425.2 |
| 44 | 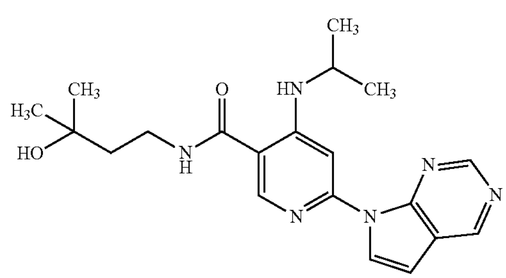 [SMILES: CC(C)Nc1cc(-n2ccc3cncnc32)ncc1C(=O)NCCC(C)(C)O] | 1.36 | E | 383.2 |
| 45 | 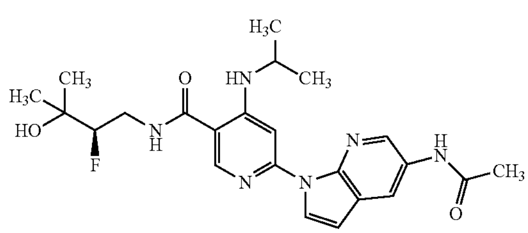 [SMILES: CC(=O)Nc1cnc2c(ccn2-c2cc(NC(C)C)c(C(=O)NC[C@@H](F)C(C)(C)O)cn2)c1] | 12.28 | B, 15 min grad. | 457.0 |
| 46 | 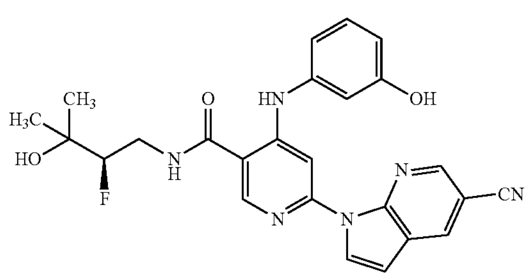 | 1.61 | E | 475.1 |

TABLE 4-continued

| Ex. No. | Structure | HPLC rt (min) | HPLC cond. | LCMS |
|---|---|---|---|---|
| 47 | 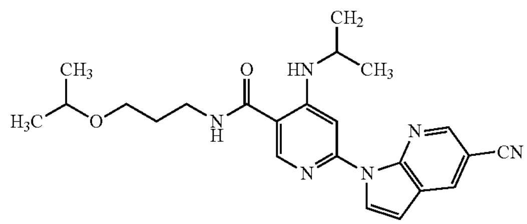 [SMILES: CC(C)Nc1cc(-n2ccc3cc(C#N)cnc32)ncc1C(=O)NCCCOC(C)C] | 2.17 | E | 421.2 |
| 48 Diastereomer 1 | 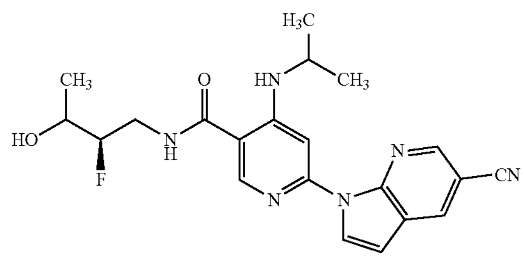 [SMILES: CC(C)Nc1cc(-n2ccc3cc(C#N)cnc32)ncc1C(=O)NC[C@@H](F)C(C)O] | 7.78 | B | 411.2 |
| 49 Diastereomer 2 | 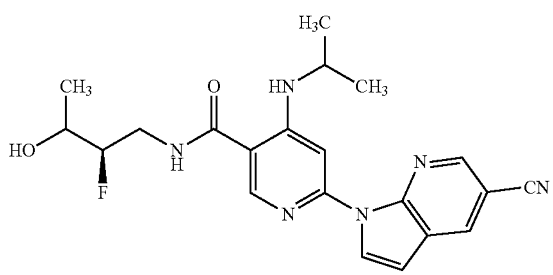 [SMILES: CC(C)Nc1cc(-n2ccc3cc(C#N)cnc32)ncc1C(=O)NC[C@@H](F)C(C)O] | 8.00 | B | 411.2 |
| 50 | 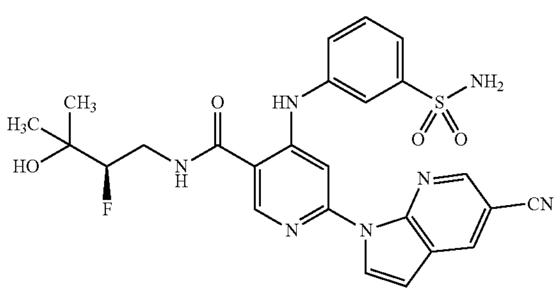 [SMILES: CC(C)(O)[C@H](F)CNC(=O)c1cnc(-n2ccc3cc(C#N)cnc32)cc1Nc1cccc(S(N)(=O)=O)c1] | 1.48 | E | 538.1 |
| 51 | 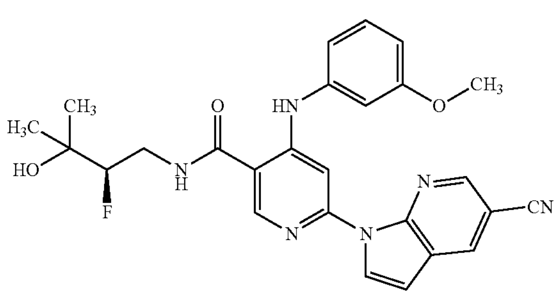 [SMILES: COc1cccc(Nc2cc(-n3ccc4cc(C#N)cnc43)ncc2C(=O)NC[C@@H](F)C(C)(C)O)c1] | 1.92 | E | 490.2 |

TABLE 4-continued
| Ex. No. | Structure | HPLC rt (min) | HPLC cond. | LCMS |
|---|---|---|---|---|
| 52 | 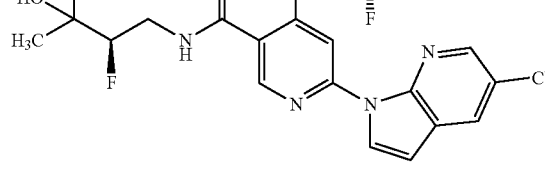 | 1.39 | C | 487.0 |
| 53 | 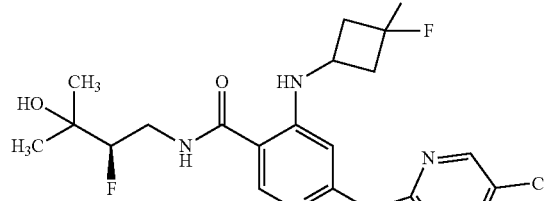 | 1.80 | E | 473.1 |
| 54 | 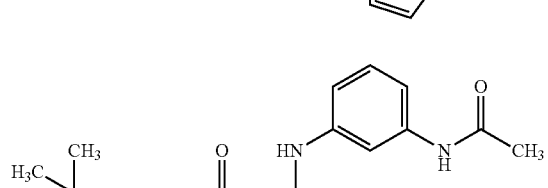 | 1.54 | E | 516.2 |
| 55 | 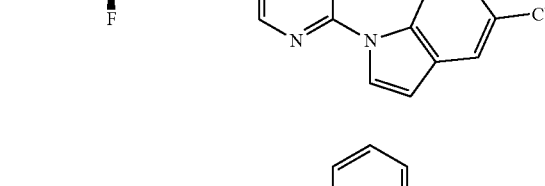 | 1.51 | E | 516.2 |
| 56 | 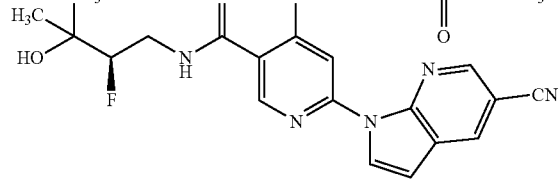 | 1.42 | E | 502.2 |

TABLE 4-continued

| Ex. No. | Structure | HPLC rt (min) | HPLC cond. | LCMS |
|---|---|---|---|---|
| 57 | 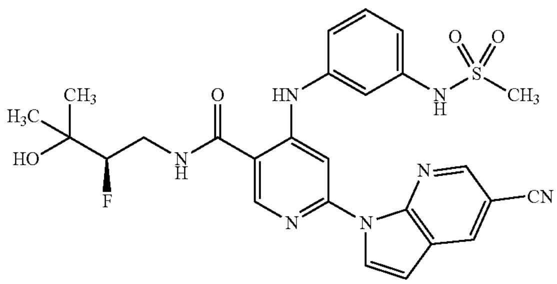 [SMILES: CC(C)(O)[C@H](F)CNC(=O)c1cnc(-n2ccc3cc(C#N)cnc32)cc1Nc1cccc(NS(C)(=O)=O)c1] | 1.59 | E | 552.2 |
| 58 | 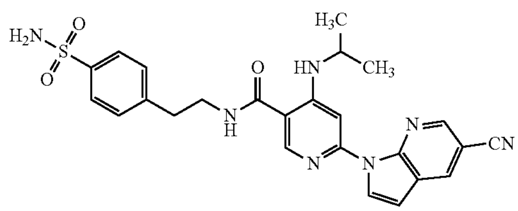 [SMILES: CC(C)Nc1cc(-n2ccc3cc(C#N)cnc32)ncc1C(=O)NCCc1ccc(S(N)(=O)=O)cc1] | 8.65 | B | 504.0 |
| 59 | 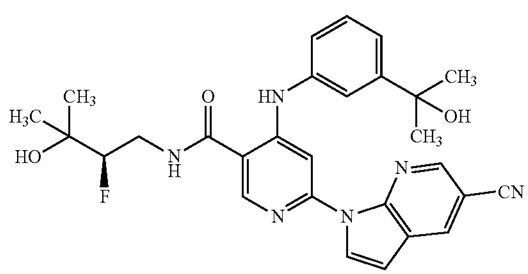 [SMILES: CC(C)(O)c1cccc(Nc2cc(-n3ccc4cc(C#N)cnc43)ncc2C(=O)NC[C@@H](F)C(C)(C)O)c1] | 1.74 | E | 517.3 |
| 60 | 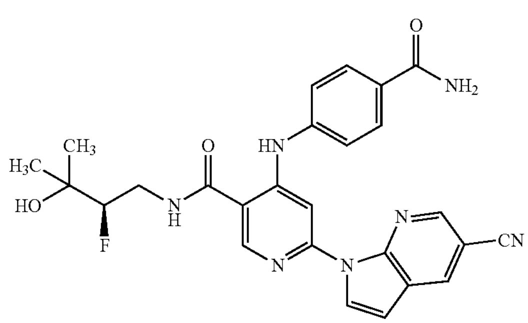 [SMILES: CC(C)(O)[C@H](F)CNC(=O)c1cnc(-n2ccc3cc(C#N)cnc32)cc1Nc1ccc(C(N)=O)cc1] | 1.37 | E | 502.2 |
| 61 | 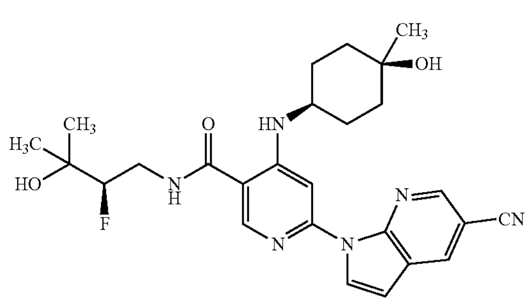 [SMILES: CC(C)(O)[C@H](F)CNC(=O)c1cnc(-n2ccc3cc(C#N)cnc32)cc1N[C@H]1CC[C@@](C)(O)CC1] | 1.66 | E | 495.3 |

TABLE 4-continued

| Ex. No. | Structure | HPLC rt (min) | HPLC cond. | LCMS |
|---|---|---|---|---|
| 62 | 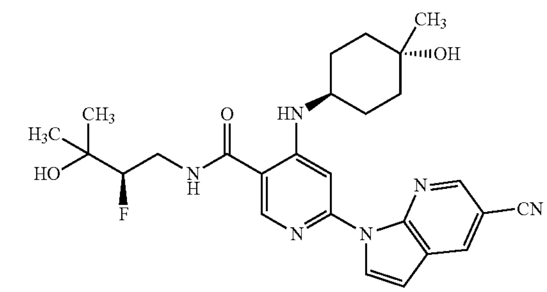 [SMILES: CC(C)(O)[C@H](F)CNC(=O)c1cnc(-n2ccc3cc(C#N)cnc32)cc1N[C@H]1CC[C@](C)(O)CC1] | 1.52 | E | 495.2 |
| 63 | 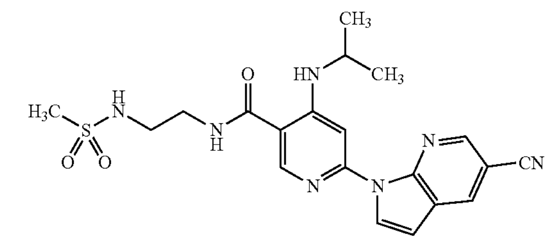 [SMILES: CC(C)Nc1cc(-n2ccc3cc(C#N)cnc32)ncc1C(=O)NCCNS(C)(=O)=O] | 7.43 | A | 442.2 |
| 64 | 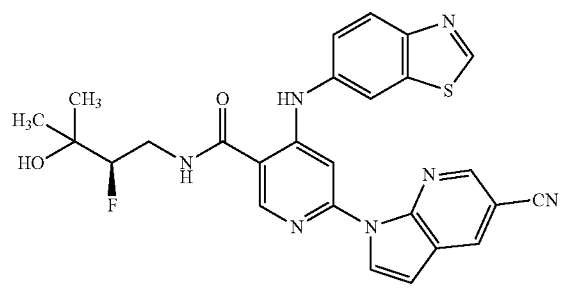 [SMILES: CC(C)(O)[C@H](F)CNC(=O)c1cnc(-n2ccc3cc(C#N)cnc32)cc1Nc1ccc2ncsc2c1] | 1.76 | E | 516.1 |
| 65 | 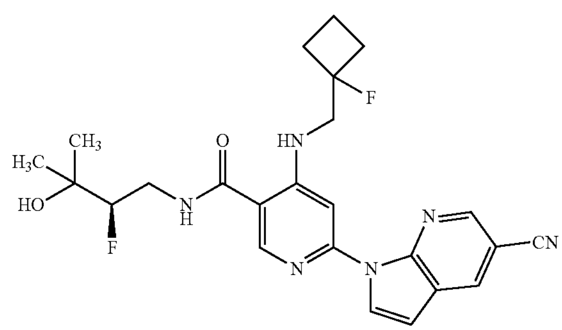 [SMILES: CC(C)(O)[C@H](F)CNC(=O)c1cnc(-n2ccc3cc(C#N)cnc32)cc1NCC1(F)CCC1] | 9.04 | A | 469.0 |
| 66 | 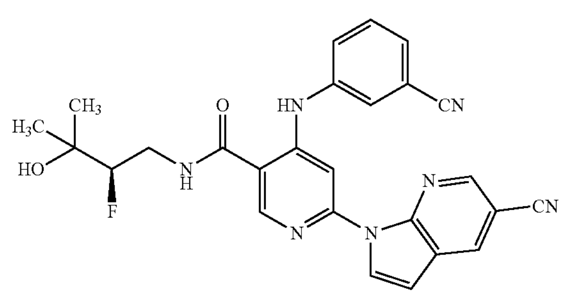 [SMILES: CC(C)(O)[C@H](F)CNC(=O)c1cnc(-n2ccc3cc(C#N)cnc32)cc1Nc1cccc(C#N)c1] | 1.78 | E | 484.2 |

TABLE 4-continued

| Ex. No. | Structure | HPLC rt (min) | HPLC cond. | LCMS |
|---|---|---|---|---|
| 67 | 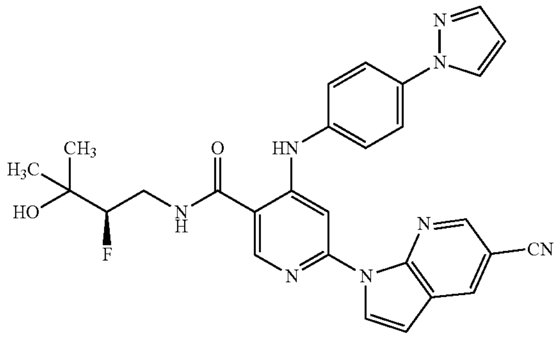 [SMILES: CC(C)(O)[C@H](F)CNC(=O)c1cnc(-n2ccc3cc(C#N)cnc32)cc1Nc1ccc(-n2cccn2)cc1] | 1.90 | E | 525.3 |
| 68 | 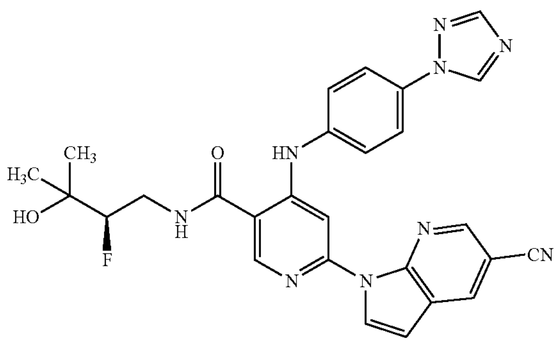 [SMILES: CC(C)(O)[C@H](F)CNC(=O)c1cnc(-n2ccc3cc(C#N)cnc32)cc1Nc1ccc(-n2cncn2)cc1] | 1.65 | E | 526.3 |
| 69 | 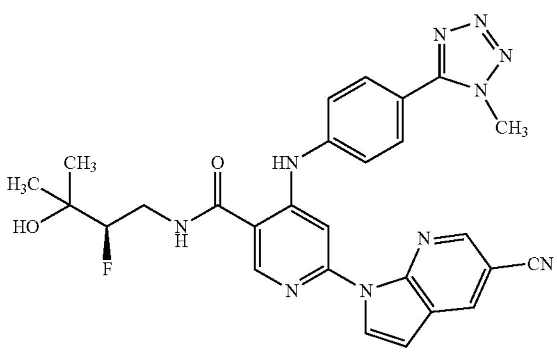 [SMILES: Cn1nnnc1-c1ccc(Nc2cc(-n3ccc4cc(C#N)cnc43)ncc2C(=O)NC[C@@H](F)C(C)(C)O)cc1] | 1.58 | E | 541.1 |
| 70 | 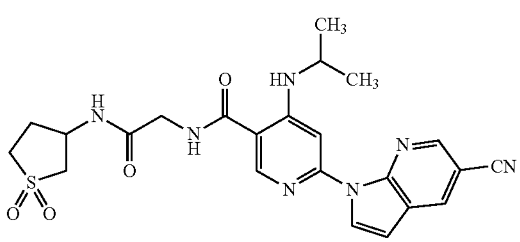 [SMILES: CC(C)Nc1cc(-n2ccc3cc(C#N)cnc32)ncc1C(=O)NCC(=O)NC1CCS(=O)(=O)C1] | 7.14 | B | 495.8 (M+) |
| 71 | 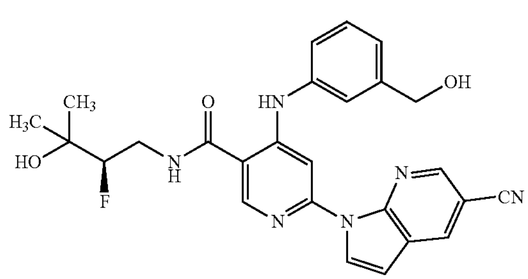 | 1.51 | E | 489.3 |

TABLE 4-continued

| Ex. No. | Structure | HPLC rt (min) | HPLC cond. | LCMS |
|---|---|---|---|---|
| 72 | 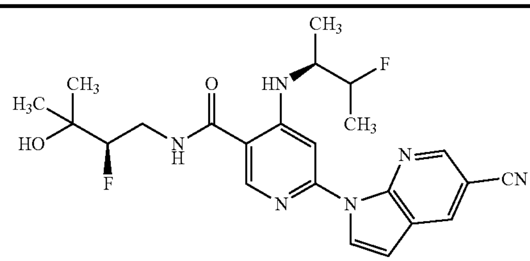 | 1.35 | C | 457.0 |
| 73 | 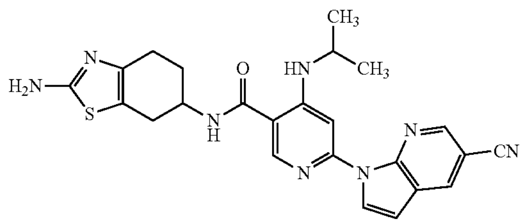 [SMILES: CC(C)Nc1cc(-n2ccc3cc(C#N)cnc32)ncc1C(=O)NC1CCc2nc(N)sc2C1] | 1.73 | E | 473.2 |
| 74 | 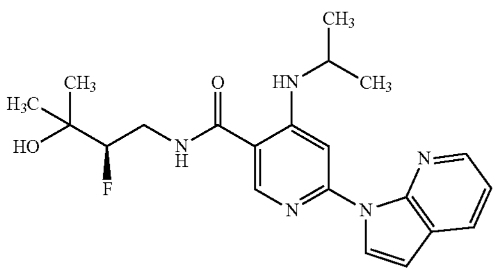 [SMILES: CC(C)Nc1cc(-n2ccc3cccnc32)ncc1C(=O)NC[C@@H](F)C(C)(C)O] | 1.85 | E | 400.1 |
| 75 | 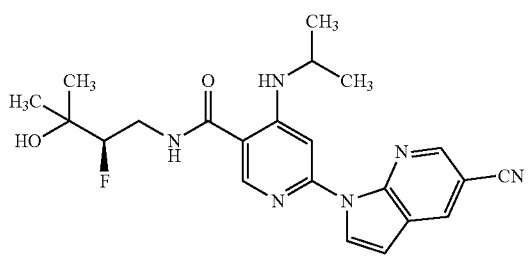 [SMILES: CC(C)Nc1cc(-n2ccc3cc(C#N)cnc32)ncc1C(=O)NC[C@@H](F)C(C)(C)O] | 7.59 | B | 425.6 |
| 76 | 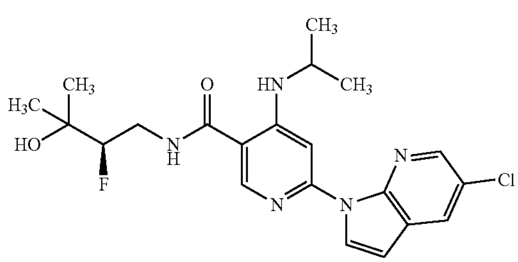 [SMILES: CC(C)Nc1cc(-n2ccc3cc(Cl)cnc32)ncc1C(=O)NC[C@@H](F)C(C)(C)O] | 1.90 | E | 433.6 (M+) |
| 77 | 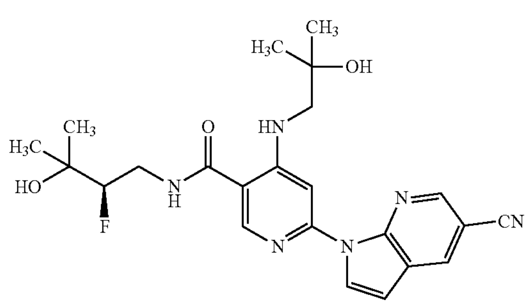 [SMILES: CC(C)(O)CNc1cc(-n2ccc3cc(C#N)cnc32)ncc1C(=O)NC[C@@H](F)C(C)(C)O] | 6.71 | B | 455.5 |

TABLE 4-continued

| Ex. No. | Structure | HPLC rt (min) | HPLC cond. | LCMS |
|---|---|---|---|---|
| 78 | 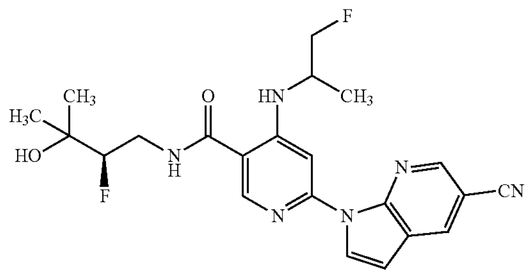 [SMILES: CC(CF)Nc1cc(-n2ccc3cc(C#N)cnc32)ncc1C(=O)NC[C@@H](F)C(C)(C)O] | 1.72 | E | 443.2 |

Example 79

6-(5-Cyano-1H-indol-1-yl)-4-(isopropylamino)-N-((trans)-4-(methylcarbamoyl)cyclohexyl)nicotinamide (79)

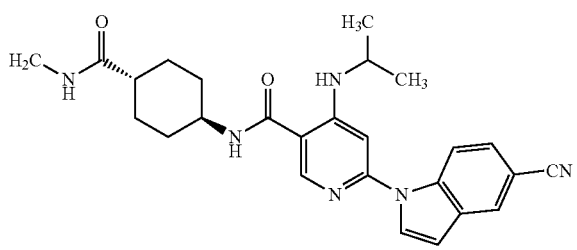

Step 1: To a stirred solution of (trans)-4-((tert-butoxycarbonyl)amino)cyclohexanecarboxylic acid (250 mg, 1.03 mmol), PyBOP (535 mg, 1.03 mmol) and Hunig's Base (0.538 mL, 3.08 mmol) in DMF (5 mL) at 25° C. was added methanamine, HCl (104 mg, 1.541 mmol). After 2 hours, the reaction mixture was diluted with ethyl acetate and rinsed with 10% LiCl (3×). The organic layer was dried over $Na_2SO_4$ and concentrated to provide tert-butyl ((trans)-4-(methylcarbamoyl)cyclohexyl)carbamate (250 mg, 85% yield) of white solids as product. LCMS (TFA) 201.1 (M+H-t-butyl)$^+$.

Step 2: To a stirred solution of tert-butyl ((trans)-4-(methylcarbamoyl)cyclohexyl)carbamate (250 mg, 0.975 mmol) in dioxane (5 mL) at 25° C. was added 4N HCl in dioxane (2.438 mL, 9.75 mmol). The reaction mixture was stirred for 3 hours then was concentrated from methylene chloride (5×) to provide (trans)-4-amino-N-methylcyclohexanecarboxamide, HCl (150 mg, 71.8% yield) as a tan solid.

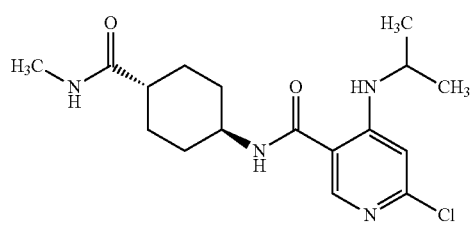 [SMILES: CNC(=O)[C@H]1CC[C@H](NC(=O)c2cnc(Cl)cc2NC(C)C)CC1]

Step 3: To a stirred solution of 6-chloro-4-(isopropylamino)nicotinic acid (100 mg, 0.466 mmol), PyBOP (242 mg, 0.466 mmol) and Hunig's Base (0.244 mL, 1.398 mmol) in DMF (3 mL) at 25° C. was added (trans)-4-amino-N-methylcyclohexanecarboxamide, HCl (90 mg, 0.466 mmol). After 1 hour, the reaction mixture was diluted with ethyl acetate and rinsed with 10% LiCl (3×). The organic layer was dried over $Na_2SO_4$ and concentrated to provide 6-chloro-4-(isopropylamino)-N-((trans)-4-(methylcarbamoyl)cyclohexyl)nicotinamide (130 mg, 71.2% yield) of off-white solids.

Step 4: To a stirred solution of 6-chloro-4-(isopropylamino)-N-((trans)-4-(methylcarbamoyl)cyclohexyl)nicotinamide (20 mg, 0.057 mmol) in 6:1 tert-butanol/DMA (1 mL) at room temperature was added 1H-indole-5-carbonitrile (8.06 mg, 0.057 mmol), and $K_2CO_3$ (23.50 mg, 0.170 mmol). The reaction vessel was purged with $N_2$ for 5 mins then added BrettPhos precatalyst (2.264 mg, 2.83 μmol) and again purged for 5 mins. The vessel was heated in a microwave tube at 150° C. for 40 min. The reaction mixture was cooled to room temperature. The reaction mixture was filtered, then the filtrate was concentrated and purified via preparative HPLC to provide 6-(5-cyano-1H-indol-1-yl)-4-(isopropylamino)-N-((trans)-4-(methylcarbamoyl)cyclohexyl)nicotinamide, 2 TFA (11 mg, 28%) of white solids. $^1$H NMR (400 MHz, DMSO-$d_6$) δ $^1$H NMR (500 MHz, methanol-$d_4$) δ 8.25 (s, 1H), 7.84-7.79 (m, 2H), 7.54 (d, J=3.5 Hz, 1H), 7.38 (s, 1H), 7.30 (d, J=9.9 Hz, 1H), 6.61 (d, J=3.5 Hz, 1H), 6.47 (s, 1H), 3.70-3.55 (m, 2H), 3.09 (dt, J=3.3, 1.5 Hz, 3H), 1.98-1.89 (m, 1H), 1.89-1.82 (m, 2H), 1.71 (d, J=12.4 Hz, 2H), 1.40 (qd, J=13.0, 3.0 Hz, 2H), 1.18 (qd, J=12.6, 3.2 Hz, 2H), 1.10 (d, J=6.4 Hz, 6H). LCMS 458.55 (M+H)$^+$. HPLC rt 1.72 min, Conditions E.

The Examples in Table 5 were prepared using the general method outlined for Example 79 using the appropriate starting material and amine.

TABLE 5

| Ex. No. | Structure | HPLC rt (min) | HPLC cond. | LCMS |
|---|---|---|---|---|
| 80 | 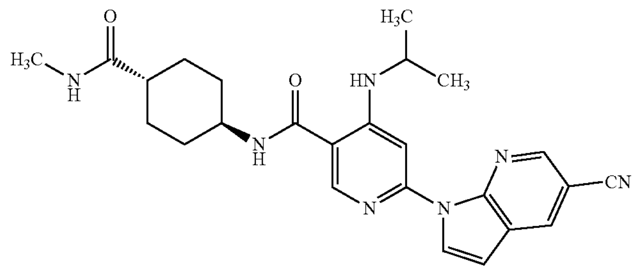 | 1.58 | E | 460.2 |
| 81 | 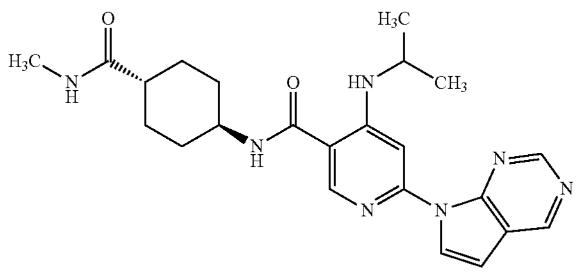 [SMILES: CNC(=O)[C@H]1CC[C@H](NC(=O)c2cnc(-n3ccc4cncnc43)cc2NC(C)C)CC1] | 1.27 | E | 436.2 |
| 82 | 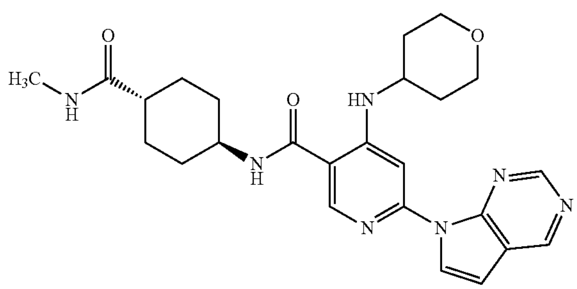 [SMILES: CNC(=O)[C@H]1CC[C@H](NC(=O)c2cnc(-n3ccc4cncnc43)cc2NC2CCOCC2)CC1] | 1.10 | E | 478.2 |
| 83 | 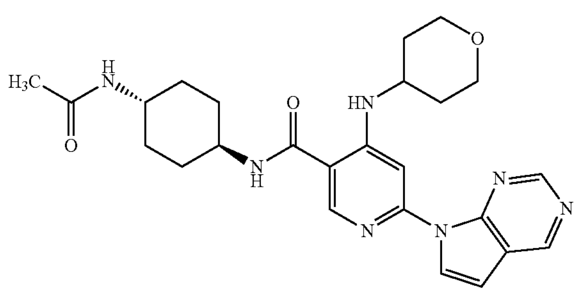 [SMILES: CC(=O)N[C@H]1CC[C@H](NC(=O)c2cnc(-n3ccc4cncnc43)cc2NC2CCOCC2)CC1] | 1.11 | E | 478.2 |
| 84 | 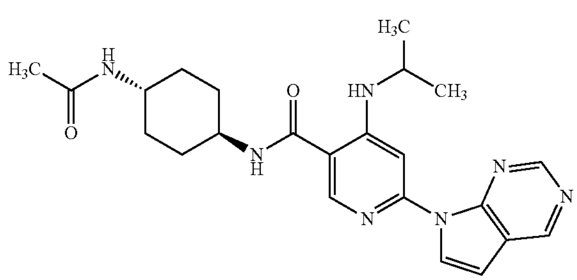 [SMILES: CC(=O)N[C@H]1CC[C@H](NC(=O)c2cnc(-n3ccc4cncnc43)cc2NC(C)C)CC1] | 1.29 | E | 436.2 |

TABLE 5-continued

| Ex. No. | Structure | HPLC rt (min) | HPLC cond. | LCMS |
|---|---|---|---|---|
| 85 | 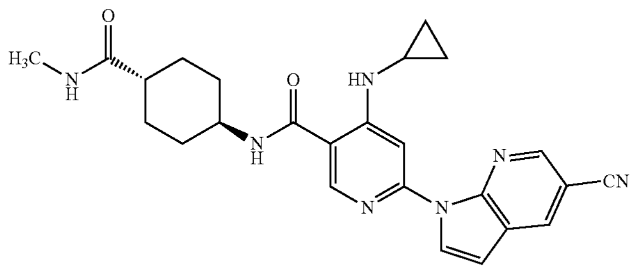 [SMILES: CNC(=O)[C@H]1CC[C@H](NC(=O)c2cnc(-n3ccc4cc(C#N)cnc43)cc2NC2CC2)CC1] | 7.25 | B | 458.8 |
| 86 | 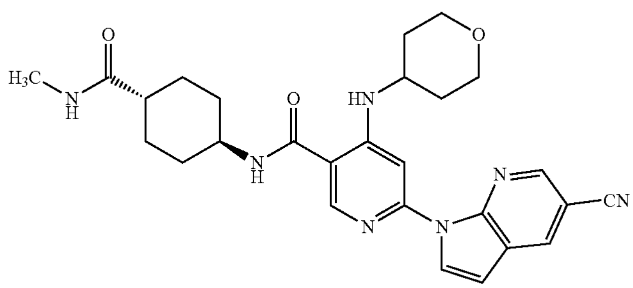 [SMILES: CNC(=O)[C@H]1CC[C@H](NC(=O)c2cnc(-n3ccc4cc(C#N)cnc43)cc2NC2CCOCC2)CC1] | 1.40 | E | 501.8 (M+) |
| 87 | 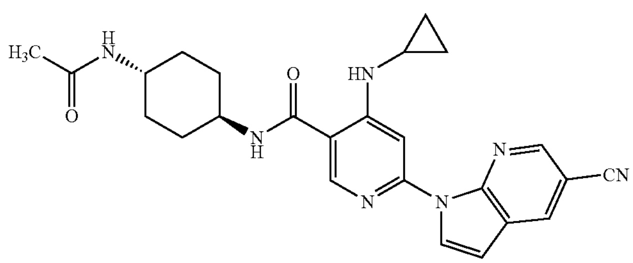 [SMILES: CC(=O)N[C@H]1CC[C@H](NC(=O)c2cnc(-n3ccc4cc(C#N)cnc43)cc2NC2CC2)CC1] | 1.63 | E | 458.2 |
| 88 | 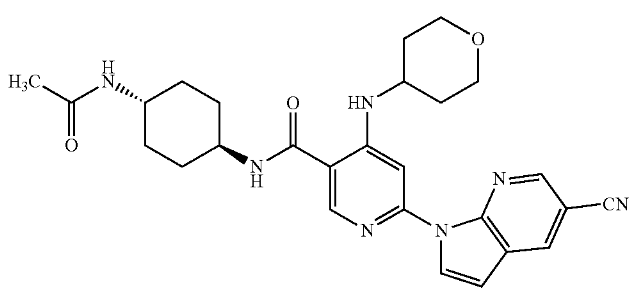 [SMILES: CC(=O)N[C@H]1CC[C@H](NC(=O)c2cnc(-n3ccc4cc(C#N)cnc43)cc2NC2CCOCC2)CC1] | 1.55 | E | 502.2 |
| 89 | 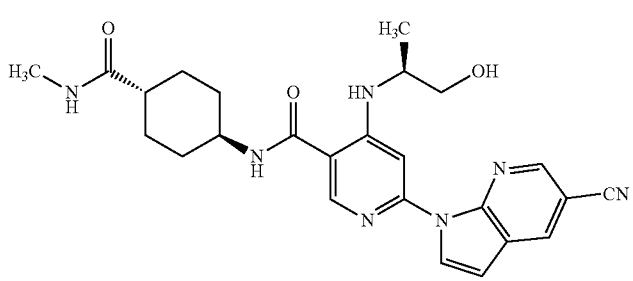 [SMILES: CNC(=O)[C@H]1CC[C@H](NC(=O)c2cnc(-n3ccc4cc(C#N)cnc43)cc2N[C@@H](C)CO)CC1] | 11.20 | B, 18 min grad. | 476.0 |

TABLE 5-continued

| Ex. No. | Structure | HPLC rt (min) | HPLC cond. | LCMS |
|---|---|---|---|---|
| 90 | 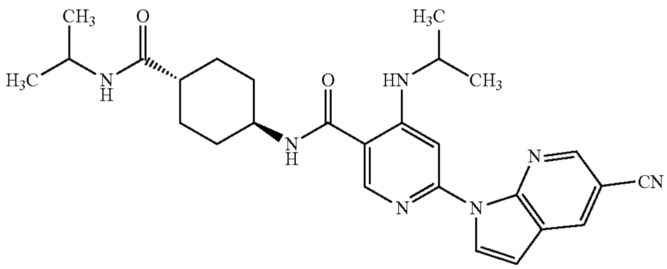 [SMILES: CC(C)Nc1cc(-n2ccc3cc(C#N)cnc32)ncc1C(=O)N[C@H]1CC[C@H](C(=O)NC(C)C)CC1] | 1.82 | E | 488.3 |
| 91 | 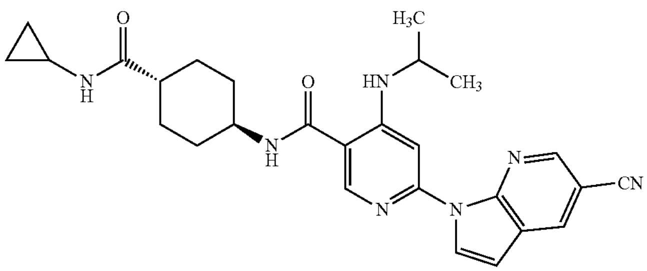 [SMILES: CC(C)Nc1cc(-n2ccc3cc(C#N)cnc32)ncc1C(=O)N[C@H]1CC[C@H](C(=O)NC2CC2)CC1] | 1.73 | E | 486.3 |
| 92 | 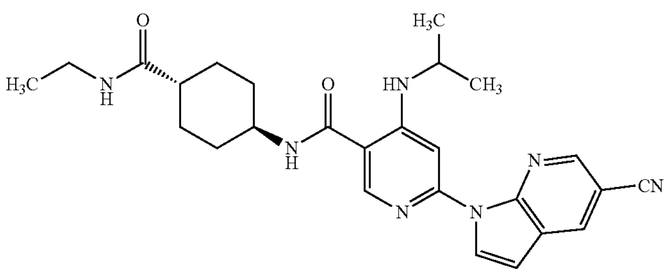 [SMILES: CCNC(=O)[C@H]1CC[C@H](NC(=O)c2cnc(-n3ccc4cc(C#N)cnc43)cc2NC(C)C)CC1] | 1.71 | E | 474.3 |
| 93 | 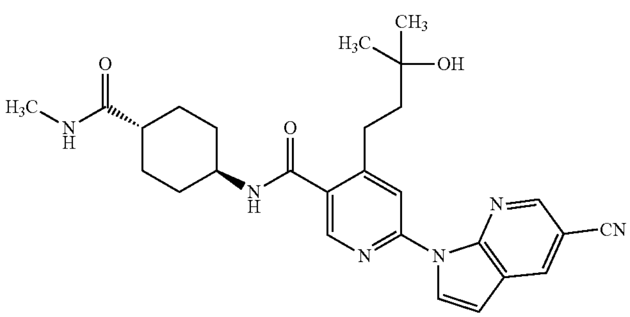 [SMILES: CNC(=O)[C@H]1CC[C@H](NC(=O)c2cnc(-n3ccc4cc(C#N)cnc43)cc2CCC(C)(C)O)CC1] | 11.74 | A, 18 min grad. | 490.0 |
| 94 | 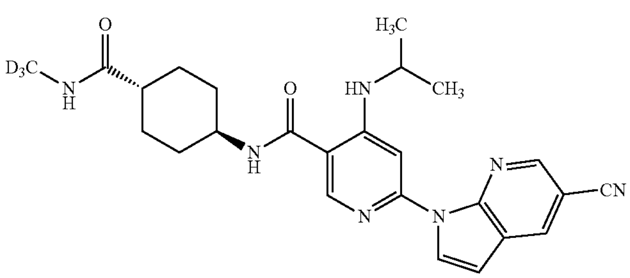 [SMILES: [2H]C([2H])([2H])NC(=O)[C@H]1CC[C@H](NC(=O)c2cnc(-n3ccc4cc(C#N)cnc43)cc2NC(C)C)CC1] | 1.69 | E | 463.0 |

TABLE 5-continued

| Ex. No. | Structure | HPLC rt (min) | HPLC cond. | LCMS |
|---|---|---|---|---|
| 95 | 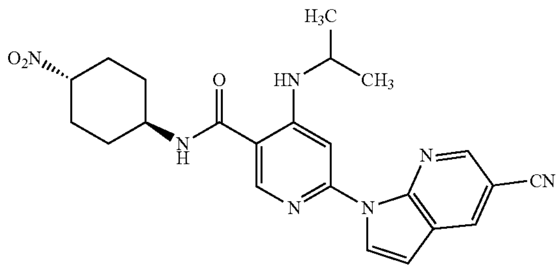 [SMILES: CC(C)Nc1cc(-n2ccc3cc(C#N)cnc32)ncc1C(=O)N[C@H]1CC[C@H]([N+](=O)[O-])CC1] | 2.13 | E | 448.2 |
| 96 | 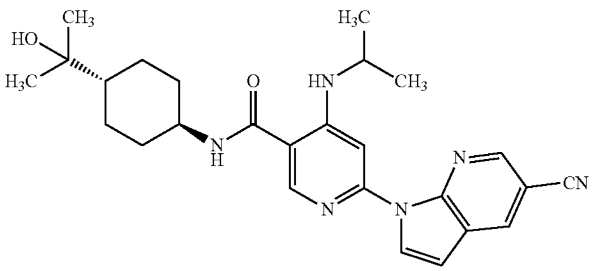 [SMILES: CC(C)Nc1cc(-n2ccc3cc(C#N)cnc32)ncc1C(=O)N[C@H]1CC[C@H](C(C)(C)O)CC1] | 8.35 | B | 461.0 |
| 97 | 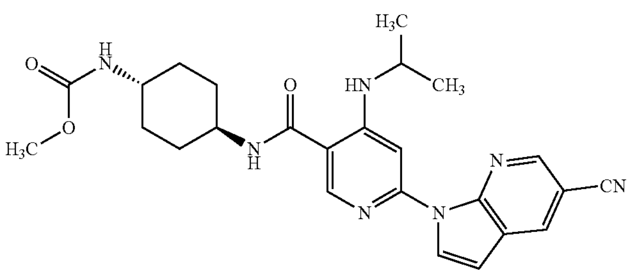 [SMILES: COC(=O)N[C@H]1CC[C@H](NC(=O)c2cnc(-n3ccc4cc(C#N)cnc43)cc2NC(C)C)CC1] | 1.90 | E | 476.2 |
| 98 | 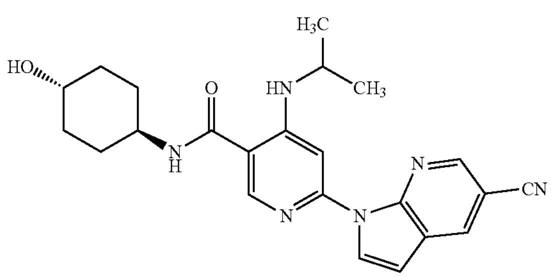 [SMILES: CC(C)Nc1cc(-n2ccc3cc(C#N)cnc32)ncc1C(=O)N[C@H]1CC[C@H](O)CC1] | 7.19 | B | 419.2 |
| 99 | 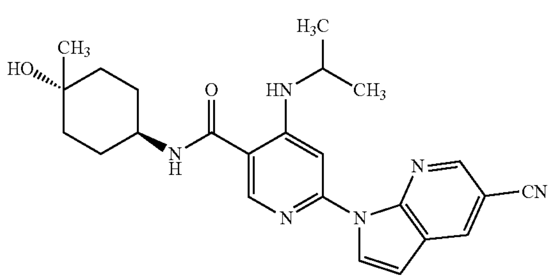 [SMILES: CC(C)Nc1cc(-n2ccc3cc(C#N)cnc32)ncc1C(=O)N[C@H]1CC[C@](C)(O)CC1] | 1.91 | E | 433.3 |

TABLE 5-continued

| Ex. No. | Structure | HPLC rt (min) | HPLC cond. | LCMS |
|---|---|---|---|---|
| 100 | 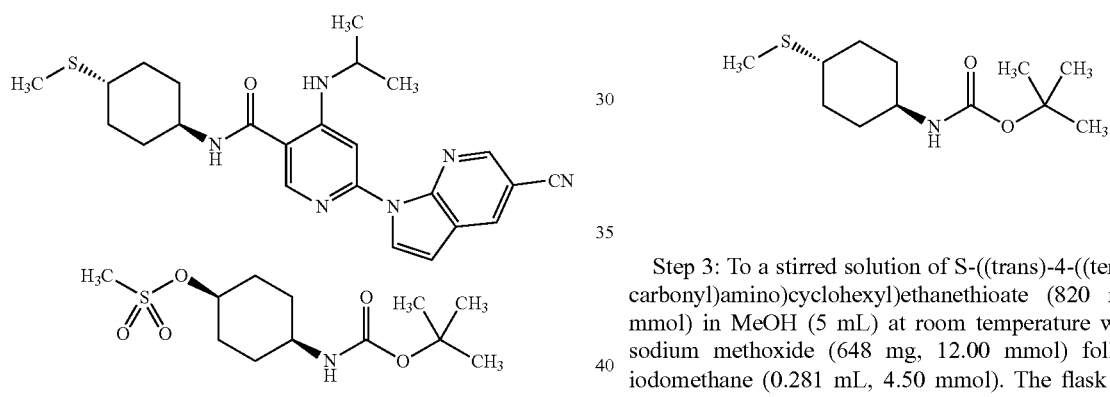 | 8.21 | A | 447.0 |

Example 101

6-(5-Cyano-1H-pyrrolo[2,3-b]pyridin-1-yl)-4-(isopropylamino)-N-((trans)-4-(methylthio)cyclohexyl)nicotinamide (101)

Step 1: To a stirred solution of tert-butyl ((1s,4s)-4-hydroxycyclohexyl) carbamate (1.00 g, 4.64 mmol) and triethylamine (3.24 mL, 23.22 mmol) in $CH_2Cl_2$ (10 mL) at 0° C. were added methanesulfonyl chloride (0.543 mL, 6.97 mmol) dropwise. The mixture was stirred at 0° C. for 15 min then diluted with water. The layers were separated and the organic layer was rinsed with saturated sodium bicarbonate (1×) followed by brine (1×). The organic layer was dried over $Na_2SO_4$ and concentrated to provide (1s,4s)-4-((tert-butoxycarbonyl)amino)cyclohexyl methanesulfonate (3.20 g, 89% yield) as a light amber solid. LCMS (TFA) 238.0 (M+H-t-butyl)$^+$.

Step 2: To a stirred solution of (1s,4s)-4-((tert-butoxycarbonyl)amino)cyclohexyl methanesulfonate (3.20 g, 10.91 mmol) in DMF (40 mL) at room temperature was added potassium thioacetate (1.869 g, 16.36 mmol). The reaction mixture was heated at 80° C. behind a safety shield for 7 hours, then at room temperature for 48 hours. The reaction mixture was diluted with ethyl acetate and rinsed with 10% LiCl (2×), saturated ammonium chloride (1×), saturated sodium bicarbonate (1×), and brine (2×). The organic layer was dried over $Na_2SO_4$ and concentrated to provide a dark oil as crude product. Purification via column chromatography provided S-((trans)-4-((tert-butoxycarbonyl) amino)cyclohexyl)ethanethioate (820 mg, 27.5% yield). LCMS (TFA) 218.0 (M+H-t-butyl)$^+$.

Step 3: To a stirred solution of S-((trans)-4-((tert-butoxycarbonyl)amino)cyclohexyl)ethanethioate (820 mg, 3.00 mmol) in MeOH (5 mL) at room temperature was added sodium methoxide (648 mg, 12.00 mmol) followed by iodomethane (0.281 mL, 4.50 mmol). The flask was then stoppered and stirred for 16 hours. The reaction mixture was diluted with water then extracted with ethyl acetate (3×). The combined organic layer was rinsed with saturated ammonium chloride (1×), saturated sodium bicarbonate (1×), and brine (1×). The organic layer was dried over $Na_2SO_4$ and concentrated to provide tert-butyl ((trans)-4-(methylthio)cyclohexyl)carbamate (650 mg, 79% yield) of amber solids. LCMS (TFA) 190.0 (M+H)$^+$.

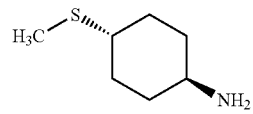

Step 4: To a stirred solution of tert-butyl ((trans)-4-(methylthio)cyclohexyl) carbamate (650 mg, 2.65 mmol) in dioxane (5 mL) and methanol (1 mL) at room temperature was added 4N HCl in dioxane (3.31 mL, 13.24 mmol). After 20 hours, the reaction mixture was concentrated from methylene chloride (5×) to provide (trans)-4-(methylthio)cyclohexanamine, HCl (490 mg, 92% yield) of tan solids as product.

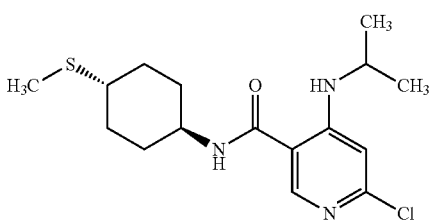 [SMILES: CS[C@H]1CC[C@H](NC(=O)c2cnc(Cl)cc2NC(C)C)CC1]

Step 5: To a stirred solution of 6-chloro-4-(isopropylamino)nicotinic acid (236 mg, 1.101 mmol), BOP (487 mg, 1.101 mmol) and TEA (0.307 mL, 2.201 mmol) in DMF (0.5 mL) at 25° C. was added (trans)-4-(methylthio)cyclohexanamine, HCl (200 mg, 1.101 mmol). After 2 hours, the reaction mixture was diluted with ethyl acetate and rinsed with 10% LiCl (2×), saturated sodium bicarbonate (1×) and finally 10% LiCl (1×). The organic layer was dried over Na$_2$SO$_4$ and concentrated to provide tert-butyl ((trans)-4-(methylcarbamoyl)cyclohexyl)carbamate (320 mg, 77% yield) of an amber oil as product. LCMS 342.2 (M+H)$^+$.

Step 6: A mixture of 6-chloro-4-(isopropylamino)-N-((trans)-4-(methylthio)cyclohexyl) nicotinamide (100 mg, 0.292 mmol), 1H-pyrrolo[2,3-b]pyridine-5-carbonitrile (41.9 mg, 0.292 mmol), potassium carbonate (29.4 mg, 0.213 mmol), and 6:1 t-BuOH/DMA (2 mL) were mixed in a 5 mL microwave vial containing a magnetic stir bar and degassed with bubbling nitrogen for 5 minutes. The mixture was treated with BrettPhos precatalyst (23.36 mg, 0.029 mmol) and degassed for another 5 minutes. The vial was sealed and the reaction heated in the microwave with stirring at 145° C. for 15 minutes. The reaction mixture was evaporated, diluted with DMF, filtered, purified via preparative HPLC to afford the product (16.8 mg, 12% yield). $^1$H NMR (500 MHz, DMSO-d$_6$) δ 8.80 (d, J=1.8 Hz, 1H), 8.66 (d, J=1.8 Hz, 1H), 8.60-8.53 (m, 2H), 8.51 (d, J=3.7 Hz, 1H), 8.34 (d, J=7.9 Hz, 1H), 8.07 (s, 1H), 6.87 (d, J=4.3 Hz, 1H), 3.82-3.71 (m, 2H), 2.06 (s, 3H), 2.02 (d, J=12.2 Hz, 2H), 1.90 (d, J=13.4 Hz, 2H), 1.47-1.30 (m, 5H), 1.28 (d, J=6.7 Hz, 6H). LCMS 449.20 (M+H)$^+$; HPLC rt 2.31 min, Conditions E.

Example 102

6-(5-Cyano-1H-pyrrolo[2,3-b]pyridin-1-yl)-4-(isopropylamino)-N-((trans)-4-(methylsulfonyl)cyclohexyl)nicotinamide

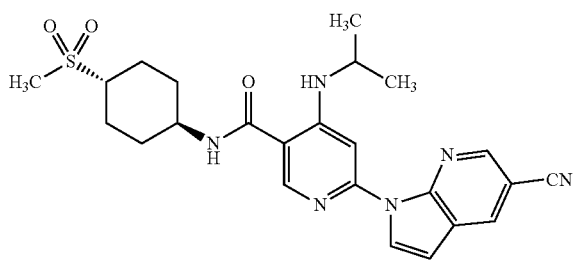

(102)

To a stirred solution of 6-(5-cyano-1H-pyrrolo[2,3-b]pyridin-1-yl)-4-(isopropylamino)-N-((trans)-4-(methylthio)cyclohexyl)nicotinamide (40 mg, 0.089 mmol) in methanol (3.5 mL) at 0° C. was added a solution of OXONE® (110 mg, 0.178 mmol) in water (1.5 mL). The reaction mixture was stirred for 1 h at 0° C. then allowed to stir at room temperature overnight. Solids present were filtered off and rinsed well with methanol. The filtrate was concentrated to remove the methanol, then extracted with methylene chloride (2×). The organic layer was dried over Na$_2$SO$_4$ and concentrated to provide an amber oil as crude product. Purified via preparative HPLC to afford the product (29 mg, 65% yield). $^1$H NMR (500 MHz, DMSO-d$_6$) δ 8.80 (d, J=1.8 Hz, 1H), 8.66 (d, J=1.8 Hz, 1H), 8.59-8.54 (m, 2H), 8.51 (d, J=3.7 Hz, 1H), 8.40 (d, J=7.9 Hz, 1H), 8.07 (s, 1H), 6.88 (d, J=3.7 Hz, 1H), 3.76 (dq, J=13.1, 6.6 Hz, 2H), 3.13-3.01 (m, 1H), 2.94 (s, 3H), 2.15 (d, J=12.2 Hz, 2H), 2.01 (d, J=9.8 Hz, 2H), 1.58-1.46 (m, 2H), 1.46-1.36 (m, 2H), 1.28 (d, J=6.1 Hz, 6H). LCMS 481.3 (M+H)$^+$. HPLC rt 1.70 min, Conditions E.

Example 103

6-(5-Cyano-1H-pyrrolo[2,3-b]pyridin-1-yl)-N-((trans)-4-(methylsulfonyl)cyclohexyl)-4-((tetrahydro-2H-pyran-4-yl)amino)nicotinamide

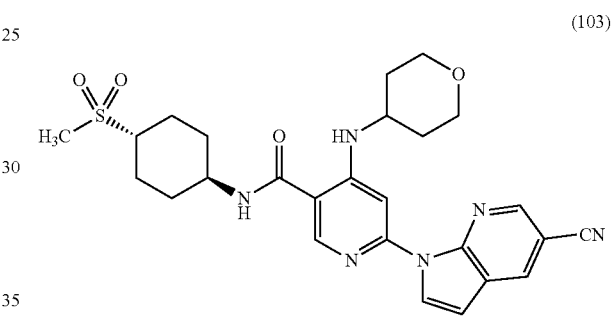

(103)

Example 103 was prepared according to the general procedure described for Example 102 substituting, where appropriate the requisite amines in the synthesis. LCMS 523.4 (M+H)$^+$. HPLC rt 1.51 min, Conditions E.

Example 104

6-(5-Cyano-1H-pyrrolo[2,3-b]pyridin-1-yl)-4-(cyclopropylamino)-N-((trans)-4-(methylsulfonyl)cyclohexyl)nicotinamide

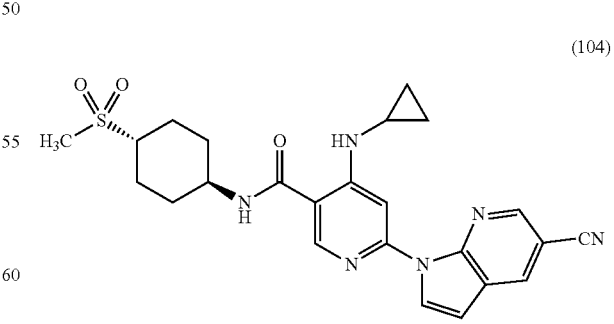

(104)

Example 104 was prepared according to the general procedure described for Example 102 substituting, where appropriate the requisite amines in the synthesis. LCMS 479.2 (M+H)$^+$. HPLC rt 1.72 min, Conditions E.

Example 105

4-((3-Carbamoylphenyl)amino)-6-(5-cyano-1H-pyrrolo[2,3-b]pyridin-1-yl)-N-((trans)-4-(methylsulfonyl)cyclohexyl)nicotinamide

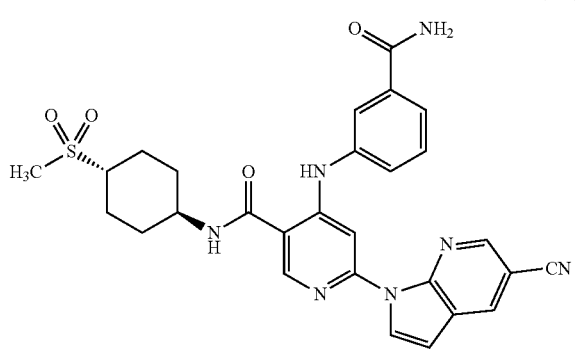
(105)

Example 106 was prepared in according to the general procedure described for Example 102 substituting, where appropriate the requisite amines in the synthesis. LCMS 558.2 (M+H)$^+$. HPLC rt 1.36 min, Conditions E.

Example 106

6-(5-Cyano-1H-pyrrolo[2,3-b]pyridin-1-yl)-N—((R)-2-fluoro-3-hydroxy-3-methylbutyl)-4-((3-fluorotetrahydro-2H-pyran-4-yl)amino)nicotinamide

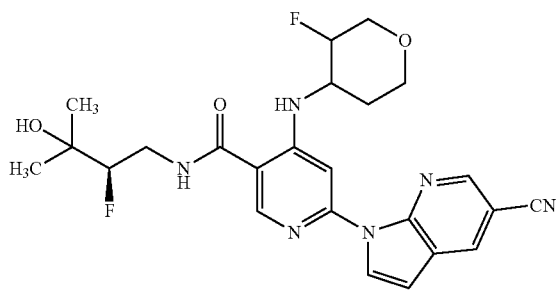
(106)

To solution of 6-chloro-N—((R)-2-fluoro-3-hydroxy-3-methylbutyl)-4-((3-fluorotetrahydro-2H-pyran-4-yl)amino) nicotinamide (0.1 g, 0.265 mmol) in dioxane (5 mL):water (1 mL), 1H-pyrrolo[2,3-b]pyridine-5-carbonitrile (0.049 g, 0.344 mmol), Cs$_2$CO$_3$ (0.259 g, 0.794 mmol) and Xantphos (0.077 g, 0.132 mmol) were added and degassed for 10 min. The reaction mixture was added Pd$_2$(dba)$_3$ (0.121 g, 0.132 mmol) and degassed again for 10 min. It was then heated for 18 h at 110° C. The reaction mass was cooled and filtered through small pad of CELITE®. The filtrate obtained was concentrated to provide crude material. The crude material was purified by flash column chromatography through silica gel and MeOH: CHCl$_3$ as eluent. Further purification via chiral HPLC afforded two isomers, the latter being the desired product 6-(5-cyano-1H-pyrrolo[2,3-b]pyridin-1-yl)-N—((R)-2-fluoro-3-hydroxy-3-methylbutyl)-4-((3-fluorotetrahydro-2H-pyran-4-yl)amino)nicotinamide (2.5 mg, 4.85 µmol, 1.8% yield). LCMS 483.2 (M–H)$^+$. HPLC rt 7.68 min, Conditions B.

Examples 107 and 108

Diastereomers 1 and 2

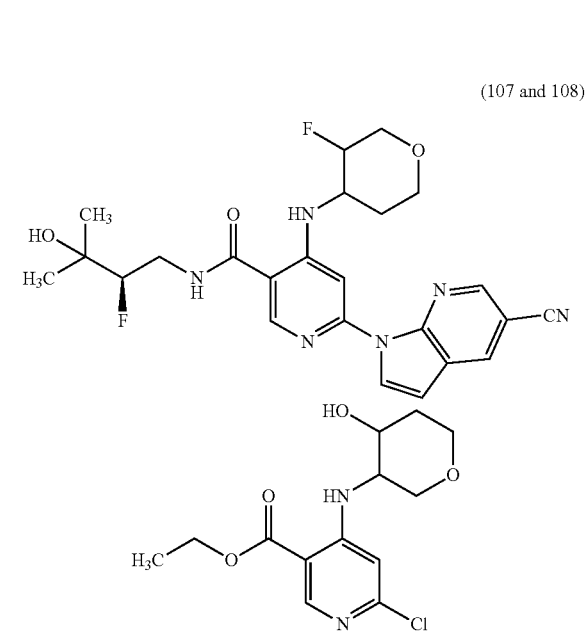
(107 and 108)

Step 1: To a solution of 3-aminotetrahydro-2H-pyran-4-ol hydrochloride (1.26 g, 8.20 mmol) and ethyl 4,6-dichloronicotinate (1.805 g, 8.20 mmol) in DMA (20 mL) was added DIPEA (7.16 mL, 41.0 mmol) and the reaction mixture was heated at 100° C. for 4 h. Water (20 mL) was added and the product was extracted with ethyl acetate (2×50 mL). The extracts were washed with cold water (30 mL) and brine (20 mL) then dried over Na$_2$SO$_4$. The concentrated extracts were purified over silica gel eluting 50% EtOAc in hexane to afford ethyl 6-chloro-4-((4-hydroxytetrahydro-2H-pyran-3-yl)amino) nicotinate (1.67 g, 5.55 mmol, 68% yield). $^1$H NMR (400 MHz, DMSO-d$_6$) δ 8.54-8.57 (m, 1H) 8.29 (d, J=8.53 Hz, 1H) 6.94-7.00 (m, 1H) 5.19-5.24 (m, 1H) 4.28-4.36 (m, 2H) 3.87-3.97 (m, 1H) 3.72-3.82 (m, 1H) 3.45-3.69 (m, 4H) 1.72-1.92 (m, 1H) 1.47-1.58 (m, 1H) 1.30-1.36 (m, 3H) LCMS (M+H) 301.0.

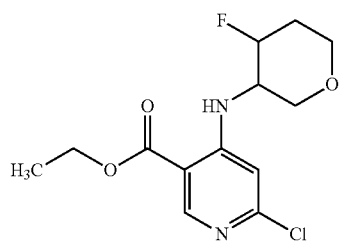 [SMILES: CCOC(=O)c1cnc(Cl)cc1NC1COCCC1F]

Step 2: To a solution of ethyl 6-chloro-4-((4-hydroxytetrahydro-2H-pyran-3-yl)amino) nicotinate (1.0 g, 3.33 mmol) in DCM (20 mL) was added DAST (0.879 mL, 6.65 mmol) at –20° C. and stirred for 1 h at the same temp. The reaction was quenched with aqueous NaHCO$_3$ and extracted with DCM (50 mL). The extracts were washed with water (30 mL) and brine (20 mL) then dried over Na$_2$SO$_4$ and concentrated. The compound was purified over silica gel eluting 1:9 EtOAc and hexane to give ethyl 6-chloro-4-((4-fluorotetrahydro-2H-pyran-3-yl)amino) nicotinate (0.38 g, 1.25 mmol, 38% yield) as colorless syrup, which was taken for the next step without chiral separation. $^1$H NMR (400 MHz, chloroform-d) δ 8.69-8.72 (m, 1H) 8.57 (d, J=8.28 Hz, 1H) 6.66 (s, 1H) 4.59-4.77 (m, 1H) 4.36 (q, J=7.03 Hz, 2H) 4.07 (dt, J=11.92, 3.83 Hz, 1H) 3.89-3.96 (m, 1H) 3.62-3.71 (m, 2H) 3.51 (dd, J=11.92, 5.90 Hz, 1H) 2.10-2.25 (m, 1H) 1.92 (dddd, J=14.30, 10.79, 7.15, 3.89 Hz, 1H) 1.72 (d, J=0.50 Hz, 1H) 1.36-1.42 (m, 3H) 1.06-1.17 (m, 2H) LCMS (M+H) 303.0.

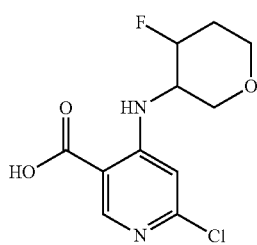 [SMILES: O=C(O)c1cnc(Cl)cc1NC1COCCC1F]

Step 3: To a solution of ethyl 6-chloro-4-((4-fluorotetrahydro-2H-pyran-3-yl)amino)nicotinate (0.38 g, 1.25 mmol) in MeOH (5 mL) was added LiOH (0.090 g, 3.77 mmol) as 2N aq solution at 0° C., then stirred for 1 h at 60° C. After cooling the MeOH was removed and water (2 mL) was added and acidified to pH 4 with 1.5N HCl. The precipitated solids (0.26 g, 75% yield) were collected and used directly in the next step. $^1$H NMR (300 MHz, DMSO-d$_6$) δ 13.48 (br s., 1H) 8.44-8.56 (m, 2H) 7.03 (s, 1H) 4.67-4.94 (m, 1H) 3.76-4.04 (m, 3H) 3.39-3.60 (m, 2H) 2.04 (d, J=15.30 Hz, 1H) 1.81 (d, J=9.82 Hz, 1H) LCMS (M+H) 275.0.

Step 4: To a solution of 6-chloro-4-((4-fluorotetrahydro-2H-pyran-3-yl)amino) nicotinic acid (0.26 g, 0.947 mmol) and 4-amino-3-fluoro-2-methylbutan-2-ol (0.115 g, 0.947 mmol) in DMF (10 mL) was added DIPEA (0.496 mL, 2.84 mmol) and HATU (0.720 g, 1.893 mmol) at 0° C. The reaction mixture was warmed to room temperature and stirred for 2 h. EtOAc (50 mL) was added and the organic layer was washed with cold water (3×20 mL), brine (15 mL) then dried over Na$_2$SO$_4$ and concentrated. The crude product was purified over silica gel eluting 50% EtOAc in hexane to afford 6-chloro-N-(2-fluoro-3-hydroxy-3-methylbutyl)-4-((4-fluorotetrahydro-2H-pyran-3-yl)amino)nicotinamide (0.21 g, 59% yield) which was taken for the next step without chiral separation. $^1$H NMR (300 MHz, chloroform-d) δ 8.74 (d, J=8.31 Hz, 1H) 8.25-8.28 (m, 1H) 6.85 (br. s., 1H) 6.67 (s, 1H) 4.73-4.81 (m, 1H) 4.50-4.65 (m, 2H) 3.89-4.19 (m, 3H) 3.41-3.71 (m, 4H) 2.11-2.31 (m, 1H) 2.05 (d, J=6.52 Hz, 1H) 1.84-1.98 (m, 1H) 1.31-1.39 (m, 6H); LCMS (M+H) 378.2.

Step 5: To a solution of 6-chloro-N—((R)-2-fluoro-3-hydroxy-3-methylbutyl)-4-((4-fluorotetrahydro-2H-pyran-3-yl)amino)nicotinamide (300 mg, 0.794 mmol) and 1H-pyrrolo[2,3-b]pyridine-5-carbonitrile (114 mg, 0.794 mmol) in 1,4-dioxane (6 mL) was added Cs$_2$CO$_3$ (776 mg, 2.382 mmol) and Xantphos (184 mg, 0.318 mmol). The mixture was degassed with nitrogen for 15 mins, then Pd$_2$dba$_3$ (291 mg, 0.318 mmol) was added to the reaction mixture and again degassed for 5 mins. The reaction vessel was sealed and heated at 110° C. for 16 h. The reaction mixture was cooled and filtered through small pad of CELITE®. The filtrate was concentrated and purified by column chromatography through silica gel eluting 10% MeOH in DCM to afford diastereomeric mixture of 6-(5-cyano-1H-pyrrolo[2,3-b]pyridin-1-yl)-N—((R)-2-fluoro-3-hydroxy-3-methylbutyl)-4-((4-fluorotetrahydro-2H-pyran-3-yl)amino)nicotinamide. The two diastereomers were separated by SFC.

Diastereomer 1: $^1$H NMR (400 MHz, DMSO-d$_6$) δ 8.99 (d, J=8.53 Hz, 1H) 8.81-8.85 (m, 2H) 8.64-8.70 (m, 2H) 8.53 (d, J=3.51 Hz, 1H) 8.21 (s, 1H) 6.90 (d, J=4.02 Hz, 1H) 4.85 (s, 2H) 4.29-4.46 (m, 1H) 4.00-4.07 (m, 1H) 3.66-3.90 (m, 3H) 3.58 (br. s., 1H) 3.35-3.49 (m, 2H) 2.07-2.20 (m, 1H) 1.77-1.89 (m, 1H) 1.18 (dd, J=5.77, 1.25 Hz, 6H); LC/MS 485.0 (M+H); 15 mg, 5% yield.

Diastereomer 2: $^1$H NMR (400 MHz, DMSO-d$_6$) δ 9.01 (d, J=8.03 Hz, 1H) 8.89 (t, J=5.52 Hz, 1H) 8.81 (d, J=2.01 Hz, 1H) 8.65-8.69 (m, 2H) 8.53 (d, J=4.02 Hz, 1H) 8.20 (s, 1H) 6.90 (s, 1H) 4.80-4.99 (m, 2H) 4.30-4.47 (m, 1H) 4.04 (dt, J=11.55, 4.52 Hz, 1H) 3.66-3.89 (m, 3H) 3.55-3.62 (m, 1H) 3.40-3.50 (m, 2H) 2.06-2.18 (m, 1H) 1.78-1.90 (m, 1H) 1.18 (dd, J=6.02, 1.51 Hz, 6H); LC/MS 485.0 (M+H); 25 mg, 6.5% yield.

Examples 109 and 110

Diastereomers 1 and 2

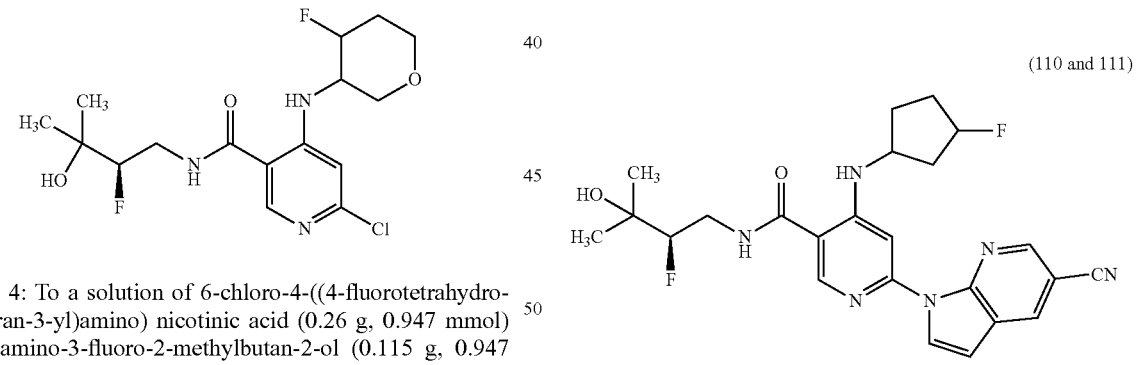

(110 and 111)

Step 1: To a solution of 3-aminocyclopentenol hydrochloride (1.05 g, 7.63 mmol) and ethyl 4,6-dichloronicotinate (1.679 g, 7.63 mmol) in DMA (10 mL) was added DIPEA (6.66 mL, 38.2 mmol), then reaction mixture was heated at 100° C. for 4 h. Water (50 mL) was added and the mixture was extracted with ethyl acetate (2×150 mL). The combined organic layers were washed with cold water (2×50 mL) and brine solution (40 mL) then dried over Na$_2$SO$_4$. The filtrate was concentrated and the product was purified using silica gel eluting 40% ethyl acetate in hexane to afford ethyl 6-chloro-4-((3-hydroxycyclopentyl)amino)nicotinate (1.5 g, 5.27 mmol, 69% yield), which was taken for the next step without chiral separation. $^1$H NMR (400 MHz, DMSO-d$_6$) δ ppm 8.54 (br. s., 1H) 8.03-8.42 (m, 1H) 6.78 (d, J=9.54 Hz, 1H) 4.62-

4.77 (m, 1H) 3.99-4.33 (m, 4H) 1.86-2.29 (m, 3H) 1.38-1.78 (m, 3H) 1.31 (td, J=7.03, 1.00 Hz, 3H); LCMS (M+H) 285.0.

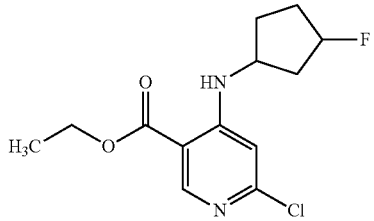 [SMILES: CCOC(=O)c1cnc(Cl)cc1NC1CCC(F)C1]

Step 2: To a solution of ethyl 6-chloro-4-((3-hydroxycyclopentyl)amino) nicotinate (1.5 g, 5.27 mmol) in DCM (20 mL) was added DAST (1.392 mL, 10.54 mmol) slowly at −20° C. The reaction mixture was stirred at room temperature for 2 h.

After the reaction was complete, the mixture was quenched with aqueous NaHCO$_3$ solution and extracted with DCM (50 mL). The organic layer was washed with water (30 mL) and brine (20 mL) then dried over Na$_2$SO$_4$. The crude compound was purified over silica gel eluting 1:9 EtOAc and hexane to get two diastereomers of desired product separately. Yield: Diastereomer 1: 540 mg, Diastereomer 2: 320 mg.

Diastereomer 1: $^1$H NMR (400 MHz, chloroform-d) δ ppm 8.67 (s, 1H) 8.22 (br. s., 1H) 6.58 (s, 1H) 5.16-5.34 (m, 1H) 4.33 (q, J=7.03 Hz, 2H) 4.06-4.15 (m, 1H) 2.47-2.60 (m, 1H) 2.35 (dq, J=13.18, 7.99 Hz, 1H) 2.00-2.16 (m, 2H) 1.59-1.84 (m, 2H) 1.36-1.41 (m, 3H) LC/MS 287.0 (M+H).

Diastereomer 2: $^1$H NMR (400 MHz, chloroform-d) δ ppm 8.67 (s, 1H) 8.42 (br. s., 1H) 6.52 (s, 1H) 5.16-5.33 (m, 1H) 4.30-4.38 (m, 2H) 3.93-4.00 (m, 1H) 1.81-2.35 (m, 6H) 1.37 (t, J=7.03 Hz, 3H) LC/MS 287.0 (M+H).

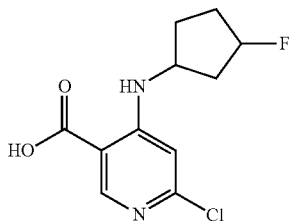 [SMILES: O=C(O)c1cnc(Cl)cc1NC1CCC(F)C1]

Step 3: To a solution of ethyl 6-chloro-4-((3-fluorocyclopentyl)amino)nicotinate (1.0 g, 3.49 mmol) in EtOH (10 mL) was added LiOH (0.167 g, 6.98 mmol) as 2N aq solution at 0° C., then stirred for 3 h at room temperature. When the reaction was complete, the EtOH was removed and water (1 mL) was added and acidified to pH 4 with 1.5N HCl. The precipitated solid was collected on a filter and used in the next step without chiral separation. Yield: 88% (0.79 g). $^1$H NMR (400 MHz, DMSO-d$_6$) δ ppm 13.37 (br. s., 1H) 8.52 (d, J=9.04 Hz, 1H) 8.32 (d, J=7.03 Hz, 1H) 6.83 (s, 1H) 5.17-5.35 (m, 1H) 4.19 (dq, J=13.68, 6.99 Hz, 1H) 2.21-2.47 (m, 2H) 1.73-2.17 (m, 3H) 1.47-1.57 (m, 1H) LCMS (M+H) 259.0.

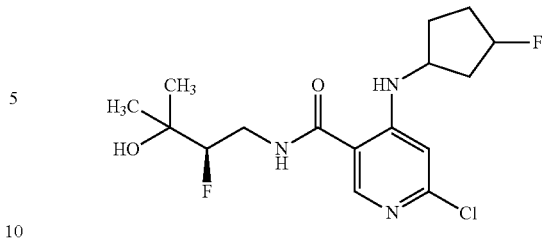

Step 4: To a solution of 6-chloro-4-((3-fluorocyclopentyl)amino)nicotinic acid (0.91 g, 3.52 mmol) and (R)-4-amino-3-fluoro-2-methylbutan-2-ol (0.511 g, 4.22 mmol) in DMF (10 mL) was added DIPEA (1.843 mL, 10.55 mmol) and HATU (2.68 g, 7.04 mmol). The reaction mixture was stirred for 2 hrs at room temperature. Then reaction mixture was diluted with EtOAc (50 mL) and the organic layer was washed with cold water (3×20 mL) and brine (15 mL). The extracts were dried over Na$_2$SO$_4$ and concentrated to give the crude compound which was purified over silica gel eluting 60% EtOAc in hexane to afford 6-chloro-N—((R)-2-fluoro-3-hydroxy-3-methylbutyl)-4-((3-fluorocyclopentyl)amino) nicotinamide (0.98 g, 2.71 mmol, 77% yield) as off-white solid, which was taken for the next step without chiral separation. $^1$H NMR 400 MHz, DMSO-d$_6$: δ 8.71 (t, J=7.20 Hz, 2H), 8.38 (s, 1H), 6.71 (s, 1H), 5.14-5.27 (m, 1H), 4.83 (s, 1H), 4.24-4.39 (m, 1H), 4.03 (d, J=2.80 Hz, 1H), 3.60-3.69 (m, 1H), 3.31-3.37 (m, 1H), 2.25-2.42 (m, 1H), 2.14-2.18 (m, 1H), 1.59-1.97 (m, 4H), 1.15 (dd, J=0.80, 6.00 Hz, 6H), LCMS (M+H) 362.2

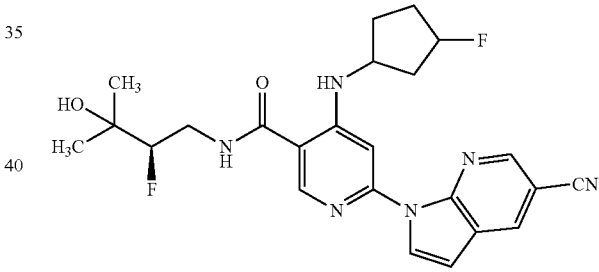

Step 5: To a solution of 6-chloro-N—((R)-2-fluoro-3-hydroxy-3-methylbutyl)-4-((3-fluorocyclopentyl)amino)nicotinamide (120 mg, 0.332 mmol) and 1H-pyrrolo[2,3-b]pyridine-5-carbonitrile (47.5 mg, 0.332 mmol) in 1,4-dioxane (6 mL) was added Cs$_2$CO$_3$ (324 mg, 0.995 mmol) and Xantphos (77 mg, 0.133 mmol). The mixture was degassed with nitrogen for 15 mins, then Pd$_2$(dba)$_3$ (121 mg, 0.133 mmol) was added and again degassed for 5 mins. The vessel was sealed and the reaction mixture was heated at 110° C. for 16 h. The reaction mixture was cooled and filtered through small pad of CELITE®. The filtrate was concentrated and the crude material was purified by column chromatography through silica gel eluting 10% MeOH in DCM to afford a diastereomeric mixture of 6-(5-cyano-1H-pyrrolo[2,3-b]pyridin-1-yl)-N—((R)-2-fluoro-3-hydroxy-3-methylbutyl)-4-((4-fluorotetrahydro-2H-pyran-3-yl)amino)nicotinamide. The two diastereomers were separated by SFC.

Diastereomer 1: $^1$H NMR (400 MHz, DMSO-d$_6$) δ 8.82-8.87 (m, 2H) 8.74 (t, J=5.52 Hz, 1H) 8.68 (s, 1H) 8.61 (s, 1H) 8.56 (d, J=4.02 Hz, 1H) 8.16 (s, 1H) 6.90 (d, J=4.02 Hz, 1H) 5.18-5.37 (m, 1H) 4.28-4.45 (m, 1H) 4.06 (br. s., 1H) 3.63-3.80 (m, 1H) 3.35-3.48 (m, 1H) 2.43 (dd, J=8.03, 5.02 Hz, 1H) 2.28-2.37 (m, 1H) 1.72-2.11 (m, 4H) 1.17 (dd, J=5.77, 1.25 Hz, 6H); LC/MS 469.2 (M+H); HPLC Condition A, RT 8.015 min; 20 mg, 13% yield.

Diastereomer 2: $^1$H NMR (400 MHz, DMSO-d$_6$) δ 8.82-8.87 (m, 2H) 8.74 (t, J=5.52 Hz, 1H) 8.68 (d, J=2.01 Hz, 1H) 8.62 (s, 1H) 8.56 (d, J=4.02 Hz, 1H) 8.16 (s, 1H) 6.90 (d, J=3.51 Hz, 1H) 5.19-5.37 (m, 1H) 4.83 (s, 1H) 4.28-4.45 (m, 1H) 4.02-4.11 (m, 1H) 3.64-3.81 (m, 1H) 3.34-3.46 (m, 1H) 2.53-2.59 (m, 1H) 2.28-2.37 (m, 1H) 1.72-2.10 (m, 4H) 1.17 (dd, J=6.27, 1.25 Hz, 6H); LC/MS 469.2 (M+H); HPLC Condition A, RT 7.993 min; 20 mg, 14% yield.

Examples 111 and 112

Diastereomers 1 and 2

(111 and 112)

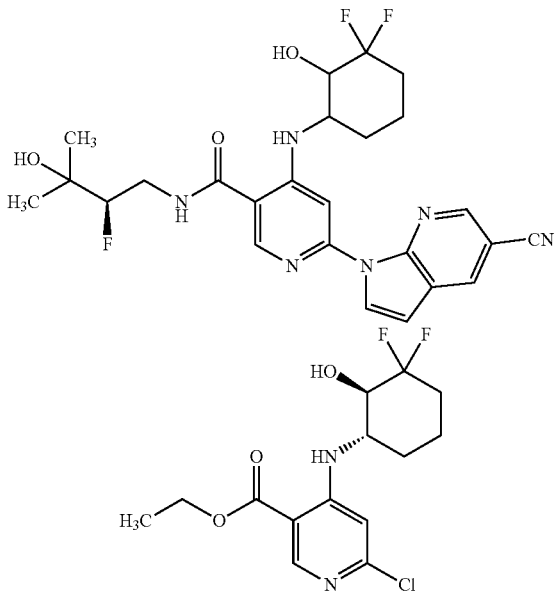

Step 1: To a stirred solution of ethyl 4,6-dichloronicotinate (650 mg, 2.95 mmol) in DMA (10 mL) was added (1S,6R)-6-amino-2,2-difluorocyclohexanol (491 mg, 3.25 mmol) and DIPEA (2.064 mL, 11.82 mmol). The reaction mixture was heated at 130° C. for 2 hours and cooled to room temperature. DMA was removed in vacuo and the residue was partitioned between ethyl acetate and water. The layers were separated and the organic layer was dried over Na$_2$SO$_4$, filtered, and evaporated. The product was purified by silica gel column using 10% ethyl acetate/pet ether to provide the desired product. LCMS m/z 335.3 (M+H).

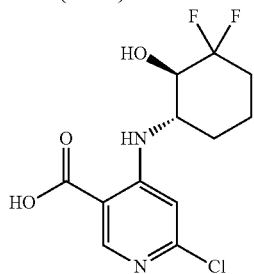

Step 2: To a stirred solution of ethyl 6-chloro-4-(((1S,2R)-3,3-difluoro-2-hydroxycyclohexyl)amino)nicotinate (700 mg, 2.091 mmol) in ethanol (5 mL), THF (10 mL) and water (5 mL), was added lithium hydroxide monohydrate (263 mg, 6.27 mmol) and stirred at 25° C. for 2 h. The reaction mixture was evaporated to dryness, and neutralized with 1.5 N HCl to obtain a white solid which was filtered and dried to afford the desired compound. LCMS m/z 307.3 (M+H).

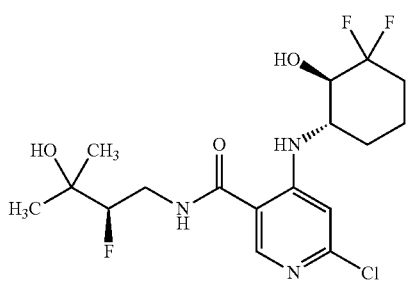 [SMILES: CC(C)(O)[C@H](F)CNC(=O)c1cnc(Cl)cc1N[C@H]1CCCC(F)(F)[C@@H]1O]

Step 3: To a stirred solution of 6-chloro-4-(((1S,2R)-3,3-difluoro-2-hydroxycyclohexyl)amino)nicotinic acid (500 mg, 1.630 mmol) in DMF (10 mL) was added (R)-4-amino-3-fluoro-2-methylbutan-2-ol (198 mg, 1.630 mmol), DIPEA (0.712 mL, 4.08 mmol) and HATU (620 mg, 1.630 mmol). The mixture was stirred at 25° C. for 14 h. The reaction mixture was concentrated to dryness, and extracted with ethyl acetate (3 times). The combined organic layers were dried over Na$_2$SO$_4$, filtered, and concentrated. The residue was purified by column chromatography using 2% MeOH:DCM to isolate desired product (550 mg, 82% yield); LCMS m/z 410.4 (M+H).

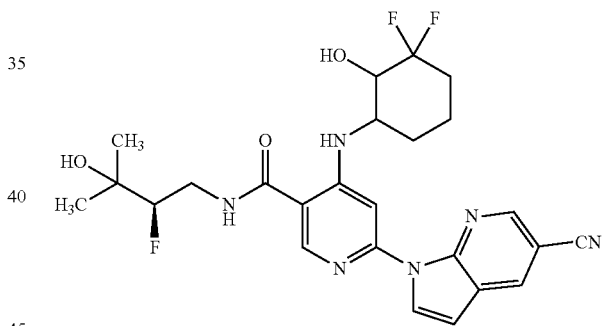

Step 4: A stirred solution of 6-chloro-4-((3,3-difluoro-2-hydroxycyclohexyl)amino)-N—((R)-2-fluoro-3-hydroxy-3-methylbutyl)nicotinamide (100 mg, 0.244 mmol), 1H-pyrrolo[2,3-b]pyridine-5-carbonitrile (34.9 mg, 0.244 mmol), Xantphos (85 mg, 0.146 mmol) and Cs$_2$CO$_3$ (159 mg, 0.488 mmol) in 1,4-dioxane (10 mL) was degassed for 5 min. Pd$_2$(dba)$_3$ (67.0 mg, 0.073 mmol) was added and the mixture was degassed for additional 5 mins then heated at 110° C. for 12 hours. The reaction mixture was filtered, evaporated, and the residue was purified by silica gel chromatography using 3% MeOH:DCM to isolate expected diastereomeric mixture product (55 mg), which was subjected chiral separation to give the desired chiral compounds.

Diastereomer 1: $^1$H NMR (400 MHz, methanol-d$_4$) δ 8.71 (d, J=2.01 Hz, 1H), 8.52 (s, 1H), 8.47-8.50 (m, 2H), 8.28 (s, 1H), 6.86 (d, J=4.02 Hz, 1H), 4.36-4.54 (m, 1H), 3.79-3.99 (m, 3H), 3.43-3.57 (m, 2H), 2.15-2.40 (m, 2H), 1.67-1.99 (m, 3H), 1.48-1.63 (m, 1H), 1.32 (d, J=1.51 Hz, 6H); LCMS m/z 517.4 (M+H), 26 mg (20% yield).

Diastereomer 2: $^1$H NMR (400 MHz, methanol-d$_4$) δ 8.71 (d, J=2.00 Hz, 1H), 8.52 (s, 1H), 8.48-8.49 (m, 2H), 8.28 (s, 1H), 6.86 (d, J=4.00 Hz, 1H), 4.45 (ddd, J=2.40, 9.20, 48.80 Hz, 1H), 3.82-3.98 (m, 3H), 3.45-3.55 (m, 1H), 2.18-2.39 (m, 2H), 1.82-1.99 (m, 2H), 1.74-1.81 (m, 1H), 1.54-1.69 (m, 1H), 1.31-1.32 (m, 6H); LCMS m/z 517.4 (M+H); 25 mg (19% yield).

Example 113

N—((R)-2-Fluoro-3-hydroxy-3-methylbutyl)-4-((1-fluoropropan-2-yl)amino)-6-(7H-pyrrolo[2,3-d]pyrimidin-7-yl)nicotinamide

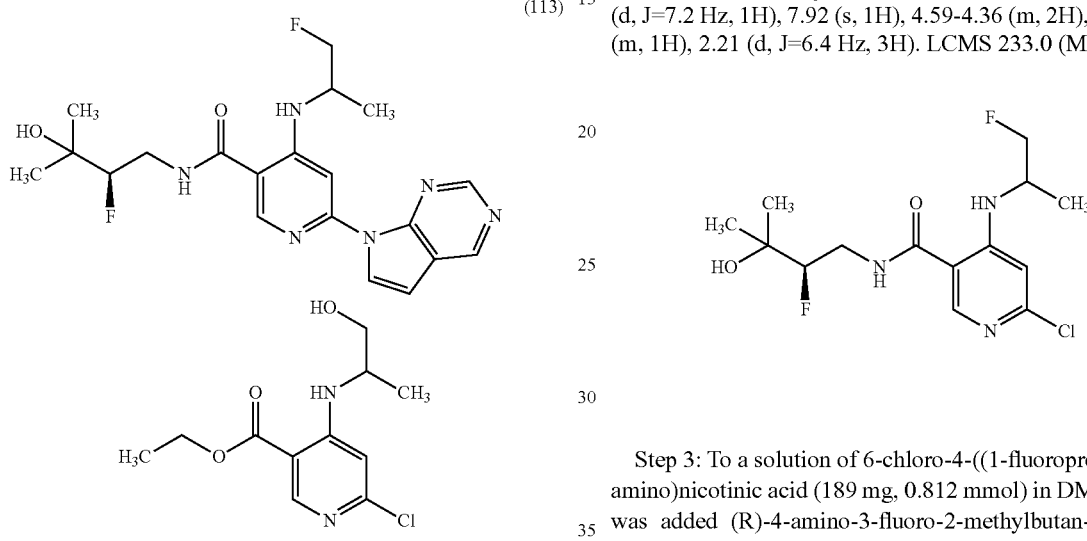

(113)

Step 1: To a sealed vial, ethyl 4,6-dichloronicotinate (270 mg, 1.227 mmol), 1-aminopropan-2-ol (111 mg, 1.472 mmol) and DIPEA (0.262 mL, 1.472 mmol) in 2-propanol (1 mL) were stirred and heated at 100° C. for 3 h. The mixture was cooled to room temperature, concentrated and purified by a flash column, using 20-40% EtOAc in hexanes as an eluent. Ethyl 6-chloro-4-((2-hydroxypropyl)amino)nicotinate (269 mg, 1.040 mmol, 85% yield) was obtained as a white solid. $^1$H NMR (400 MHz, chloroform-d) δ 9.34 (s, 1H), 9.14 (br. s., 1H), 7.97 (s, 1H), 5.04 (q, J=7.2 Hz, 2H), 4.81 (dt, J=6.5, 3.4 Hz, 1H), 4.04-3.94 (m, 1H), 3.91-3.82 (m, 1H), 3.11 (d, J=4.2 Hz, 1H), 2.57 (s, 1H), 2.08 (t, J=7.2 Hz, 3H), 2.02 (d, J=6.4 Hz, 3H). LCMS 259.0 (M+H)$^+$.

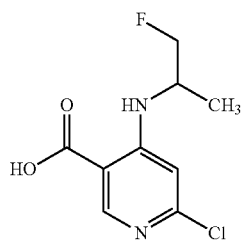

Step 2: To a solution of ethyl 6-chloro-4-((1-hydroxypropan-2-yl)amino) nicotinate (270 mg, 1.044 mmol) in DCM (10 mL) at −40° C., was added DAST (0.276 mL, 2.087 mmol), the mixture was stirred at room temperature for 1 h, warmed to room temperature and stirred overnight. The reaction was quenched with aqueous sodium bicarbonate (aq). The mixture was extracted with DCM (50 mL), concentrated to give a yellow solid. The ester was hydrolyzed in sodium hydroxide (1N, 4.17 mL, 4.17 mmol) in a mixed solvent of THF (2 mL) and MeOH (2 mL) at room temperature overnight, the reaction mixture was neutralized with 1N HCl. The product precipitated from the mixture. The solid was collected by filtration, washed with water and ether, dried under vacuum to give 6-chloro-4-((1-fluoropropan-2-yl)amino) nicotinic acid (189 mg, 0.812 mmol, 78% yield). $^1$H NMR (400 MHz, DMSO-d$_6$) δ 13.40 (br. s, 1H), 8.52 (s, 1H), 8.40 (d, J=7.2 Hz, 1H), 7.92 (s, 1H), 4.59-4.36 (m, 2H), 4.19-4.11 (m, 1H), 2.21 (d, J=6.4 Hz, 3H). LCMS 233.0 (M+H)$^+$.

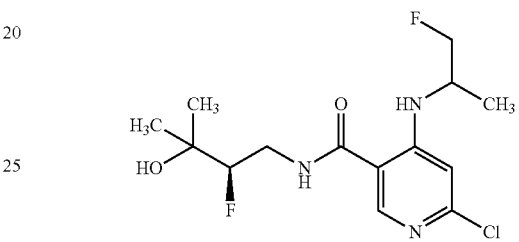

Step 3: To a solution of 6-chloro-4-((1-fluoropropan-2-yl) amino)nicotinic acid (189 mg, 0.812 mmol) in DMF (1 mL), was added (R)-4-amino-3-fluoro-2-methylbutan-2-ol (103 mg, 0.853 mmol), BOP (396 mg, 0.894 mmol) and DIPEA (0.301 mL, 1.706 mmol). The mixture was stirred at room temperature for 1 h, then added water, extracted by EtOAc, washed with aqueous NaHCO$_3$ and brine, concentrated. The product was purified by flash chromatography through silica gel (30% EtOAc in hexanes as eluent) to afford 6-chloro-N—((R)-2-fluoro-3-hydroxy-3-methylbutyl)-4-((1-fluoropropan-2-yl)amino) nicotinamide (221 mg, 0.658 mmol, 81% yield). LCMS 336.1 (M+H)$^+$.

Step 4: To a solution of 6-chloro-N—((R)-2-fluoro-3-hydroxy-3-methylbutyl)-4-((1-fluoropropan-2-yl)amino)nicotinamide (20 mg, 0.060 mmol) in t-BuOH (0.6 mL) and DMA (0.1 mL), was added 7H-pyrrolo[2,3-d]pyrimidine (7.80 mg, 0.066 mmol), BrettPhos (0.960 mg, 1.787 mol), BrettPhos precatalyst (1.428 mg, 1.787 mol) and K$_2$CO$_3$ (24.66 mg, 0.179 mmol). The mixture vial was purged with N$_2$, sealed and heated at 135° C. for one hour, cooled to room temperature. The residue was purified via preparative HPLC to afford residue was purified via preparative HPLC to afford the diastereomeric mixture of N—((R)-2-fluoro-3-hydroxy-3-methylbutyl)-4-((1-fluoropropan-2-yl)amino)-6-(7H-pyrrolo[2,3-d]pyrimidin-7-yl)nicotinamide (7.3 mg, 0.016 mmol, 27.5% yield). $^1$H NMR (500 MHz, DMSO-d$_6$) δ 9.17 (s, 1H), 9.01 (s, 1H), 8.90 (br. s., 1H), 8.81 (t, J=5.4 Hz, 1H), 8.61 (s, 1H), 8.44 (d, J=4.0 Hz, 1H), 8.13 (s, 1H), 6.91 (s, 1H), 5.10-4.91 (m, 1H), 4.45-4.28 (m, 1H), 3.83-3.49 (m, 2H), 2.88 (s, 1H), 2.73 (s, 1H), 1.47-1.36 (m, 3H), 1.18 (d, J=6.4 Hz, 6H). LCMS 419.2 (M+H)$^+$. HPLC rt 1.39 min, Conditions E.

Example 114

6-(5-Cyano-1H-pyrazolo[3,4-b]pyridin-1-yl)-N—((R)-2-fluoro-3-hydroxy-3-methylbutyl)-4-(((R)-1-fluoropropan-2-yl)amino)nicotinamide (114)

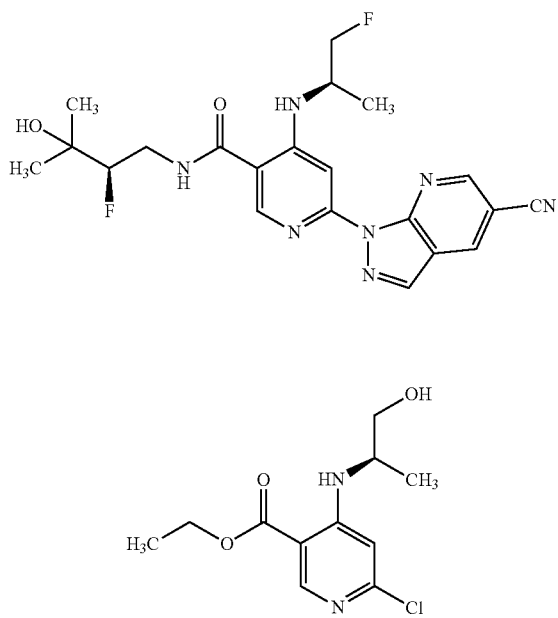

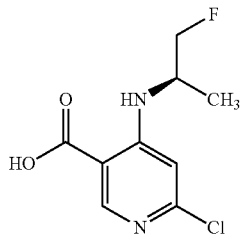

Step 1: In a sealed vial, a stirring mixture of ethyl 4,6-dichloronicotinate (400 mg, 1.818 mmol), (R)-2-aminopropan-1-ol (150 mg, 2.000 mmol) and DIPEA (0.678 mL, 3.82 mmol) in isopropanol (2 mL) was heated at 100° C. over night. The mixture was concentrated. The residue was purified by a flash column using 30-60% EtOAc in hexanes to give (R)-ethyl 6-chloro-4-((1-hydroxypropan-2-yl)amino)nicotinate (418 mg, 1.616 mmol, 89% yield). $^1$H NMR (400 MHz, chloroform-d) δ 9.34 (s, 1H), 9.14 (br. s., 1H), 7.97 (s, 1H), 5.04 (q, J=7.2 Hz, 2H), 4.81 (dt, J=6.5, 3.4 Hz, 1H), 4.04-3.94 (m, 1H), 3.91-3.82 (m, 1H), 3.11 (d, J=4.2 Hz, 1H), 2.57 (s, 1H), 2.08 (t, J=7.2 Hz, 3H), 2.02 (d, J=6.4 Hz, 3H). LCMS 259.0 (M+H)$^+$.

Step 2: To a solution of (R)-ethyl 6-chloro-4-((1-hydroxypropan-2-yl)amino) nicotinate (0.39 g, 1.508 mmol) in DCM (10 mL) at −78° C., was added DAST (0.398 mL, 3.02 mmol). The mixture was stirred and warmed to room temperature over night. The reaction was quenched with NaHCO$_3$, extracted by DCM (30 mL), washed with aqueous NaHCO$_3$ and brine, concentrated. The residue was added THF (2 mL), MeOH (2 mL) and 1N NaOH (6.03 mL, 6.03 mmol). The mixture was stirred at room temperature for 3 h, then neutralized with 1N HCl. The precipitated solid was filtered and dried to afford (R)-6-chloro-4-((1-fluoropropan-2-yl)amino)nicotinic acid (200 mg, 0.860 mmol, 57.0% yield) as a yellow solid. $^1$H NMR (400 MHz, DMSO-d$_6$) δ 13.40 (br. s, 1H), 8.52 (s, 1H), 8.40 (d, J=7.2 Hz, 1H), 7.92 (s, 1H), 4.59-4.36 (m, 2H), 4.19-4.11 (m, 1H), 2.21 (d, J=6.4 Hz, 3H). LCMS (ESI)=233.2 (M+H).

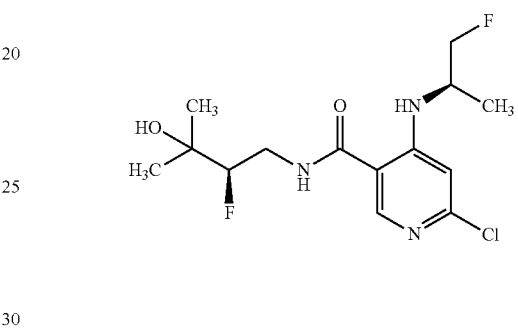

Step 3: To a solution of (R)-6-chloro-4-((1-fluoropropan-2-yl)amino)nicotinic acid (40 mg, 0.172 mmol) in THF (2 mL), was added (R)-4-amino-3-fluoro-2-methylbutan-2-ol (20.83 mg, 0.172 mmol), BOP (84 mg, 0.189 mmol), DIPEA (0.063 mL, 0.361 mmol), the mixture was stirred at room temperature for 2 hours and concentrated. The residue was purified by a flash column using 30-60% EtOAc in hexanes to give 6-chloro-N—((R)-2-fluoro-3-hydroxy-3-methylbutyl)-4-(((R)-1-fluoropropan-2-yl)amino)nicotinamide (43 mg, 0.128 mmol, 74.5% yield). LCMS (ESI)=416.2 (M+H); HPLC rt 1.25 min, Conditions E.

Step 4: In a sealed vial, a mixture of 6-chloro-N—((R)-2-fluoro-3-hydroxy-3-methylbutyl)-4-(((R)-1-fluoropropan-2-yl)amino)nicotinamide (20 mg, 0.060 mmol), 1H-pyrazolo[3,4-b]pyridine-5-carbonitrile (9.01 mg, 0.063 mmol), di-tert-butyl(2',4',6'-triisopropyl-3,4,5,6-tetramethyl-[1,1'-biphenyl]-2-yl)phosphine oxide (8.88 mg, 0.018 mmol), Pd$_2$(dba)$_3$ (8.18 mg, 8.93 μmol), K$_2$CO$_3$ (24.70 mg, 0.179 mmol) in dioxane (1 mL) was purged with nitrogen, stirred and heated at 100° C. over night. The mixture was cooled and concentrated. The residue was purified via preparative HPLC to afford 6-(5-cyano-1H-pyrazolo[3,4-b]pyridin-1-yl)-N—((R)-2-fluoro-3-hydroxy-3-methylbutyl)-4-(((R)-1-fluoropropan-2-yl)amino)nicotinamide (5.1 mg, 10.93 mol, 18.34% yield). $^1$H NMR (500 MHz, DMSO-d$_6$) δ 9.03 (s, 1H), 8.99 (s, 1H), 8.86 (br. s., 1H), 8.83-8.78 (m, 1H), 8.63 (m, 2H), 7.40-7.34 (m, 1H), 5.02-4.85 (m, 2H), 4.47-4.27 (m, 1H), 3.83-3.63 (m, 1H), 1.38 (d, J=6.1 Hz, 1H), 1.33 (d, J=6.4 Hz, 1H), 1.25 (d, J=6.1 Hz, 1H), 1.17 (d, J=5.7 Hz, 9H). LCMS (ESI)=443.2 (M+H); HPLC rt 1.27 min, Conditions E.

The Examples in Table 6 were prepared using the general methods for Examples 115-122 using the appropriate starting material and amine.

TABLE 6

| Ex. No. | Structure | HPLC rt (min) | HPLC cond. | LCMS |
|---|---|---|---|---|
| 115 | 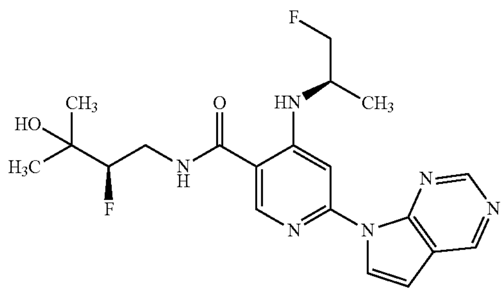 [SMILES: C[C@H](CF)Nc1cc(-n2ccc3cncnc32)ncc1C(=O)NC[C@@H](F)C(C)(C)O] | 1.24 | E | 419.2 |
| 116 | 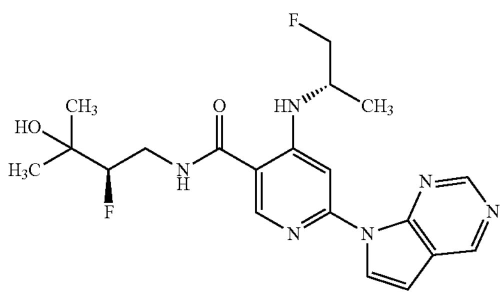 [SMILES: C[C@@H](CF)Nc1cc(-n2ccc3cncnc32)ncc1C(=O)NC[C@@H](F)C(C)(C)O] | 1.29 | E | 419.2 |
| 117 | 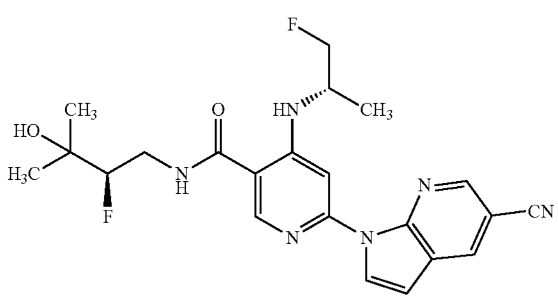 [SMILES: C[C@@H](CF)Nc1cc(-n2ccc3cc(C#N)cnc32)ncc1C(=O)NC[C@@H](F)C(C)(C)O] | 1.56 | E | 443.3 |
| 118 | 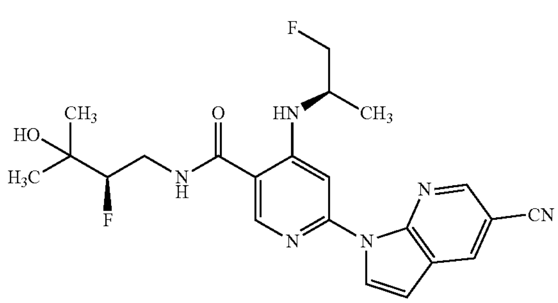 [SMILES: C[C@H](CF)Nc1cc(-n2ccc3cc(C#N)cnc32)ncc1C(=O)NC[C@@H](F)C(C)(C)O] | 1.56 | E | 443.3 |
| 119 | 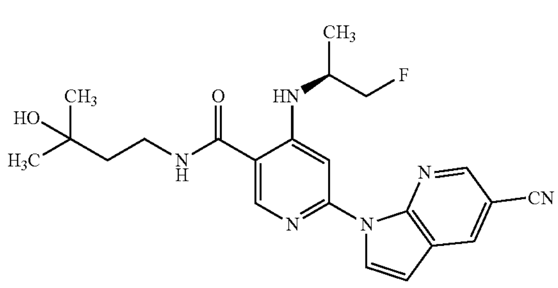 [SMILES: C[C@@H](CF)Nc1cc(-n2ccc3cc(C#N)cnc32)ncc1C(=O)NCCC(C)(C)O] | 1.65 | E | 425.2 |

TABLE 6-continued

| Ex. No. | Structure | HPLC rt (min) | HPLC cond. | LCMS |
|---|---|---|---|---|
| 120 | 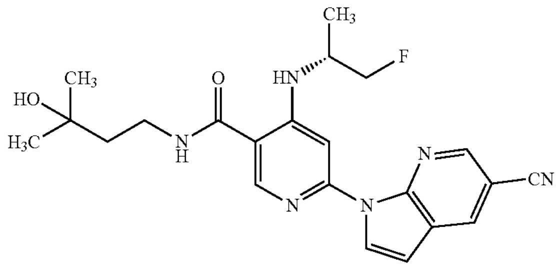 [SMILES: C[C@H](CF)Nc1cc(-n2ccc3cc(C#N)cnc32)ncc1C(=O)NCCC(C)(C)O] | 1.57 | E | 425.3 |
| 121 | 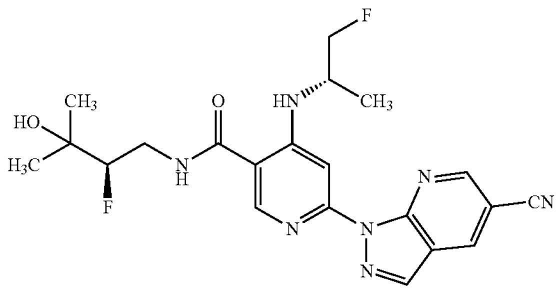 [SMILES: C[C@@H](CF)Nc1cc(-n2ncc3cc(C#N)cnc32)ncc1C(=O)NC[C@@H](F)C(C)(C)O] | 1.32 | E | 444.1 |
| 122 | 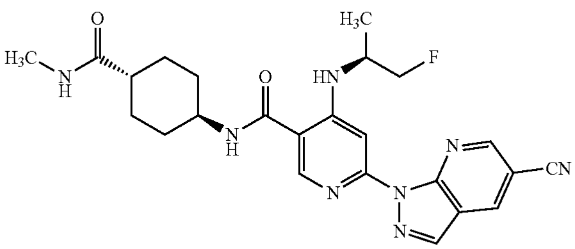 [SMILES: CNC(=O)[C@H]1CC[C@H](NC(=O)c2cnc(-n3ncc4cc(C#N)cnc43)cc2N[C@@H](C)CF)CC1] | 6.45 | B | 479.4 |

Example 123

(R)-1-(4-(Ethylamino)-5-((2-fluoro-3-hydroxy-3-methylbutyl)carbamoyl)pyridin-2-yl)-1H-pyrrolo[2,3-b]pyridine-5-carboxamide (123)

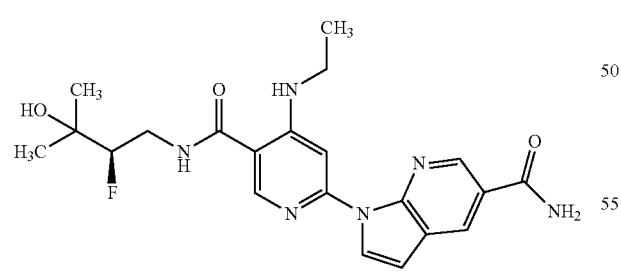

To a stirred solution of (R)-6-(5-cyano-1H-pyrrolo[2,3-b]pyridin-1-yl)-4-(ethylamino)-N-(2-fluoro-3-hydroxy-3-methylbutyl)nicotinamide (25 mg, 0.061 mmol) in DMSO (1 mL) at room temperature was added 5M KOH (0.061 mL, 0.305 mmol), then 35% hydrogen peroxide (69.1 mg, 0.609 mmol). After 1 hour, the reaction mixture was filtered, then the filtrate was concentrated and purified via preparative HPLC to afford the product (R)-1-(4-(ethylamino)-5-((2-fluoro-3-hydroxy-3-methylbutyl)carbamoyl)pyridin-2-yl)-1H-pyrrolo[2,3-b]pyridine-5-carboxamide (3.3 mg, 12% yield). $^1$H NMR (500 MHz, DMSO-$d_6$) δ 8.94 (d, J=1.8 Hz, 1H), 8.73 (t, J=5.8 Hz, 1H), 8.60-8.51 (m, 3H), 8.47 (d, J=4.3 Hz, 1H), 8.29 (s, 1H), 8.14 (br. s., 1H), 7.95 (s, 1H), 7.48 (br. s., 1H), 6.84 (d, J=3.7 Hz, 1H), 6.60-6.58 (m, 1H), 4.85 (s, 1H), 4.44-4.28 (m, 1H), 3.81-3.63 (m, 1H), 3.45-3.36 (m, 1H), 1.30 (t, J=7.0 Hz, 3H), 1.17 (d, J=6.1 Hz, 6H). LCMS (M+H)$^+$=429.1. HPLC rt 1.22 min, Conditions E.

Example 124

(R)-1-(4-(Cyclobutylamino)-5-((2-fluoro-3-hydroxy-3-methylbutyl)carbamoyl)pyridin-2-yl)-1H-pyrrolo[2,3-b]pyridine-5-carboxamide (124)

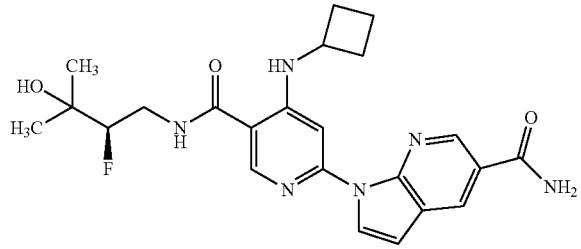

Example 124 was prepared according to the general procedure for Example 123 substituting, where appropriate, the requisite amines in the synthesis. LCMS 455.1 (M+H)+. HPLC rt 1.41 min, Conditions E.

Example 125

1-((2-(6-(5-Cyano-1H-pyrrolo[2,3-b]pyridin-1-yl)-4-(isopropylamino)nicotinamido)ethyl)amino)-2-methyl-1-oxopropan-2-yl acetate (125)

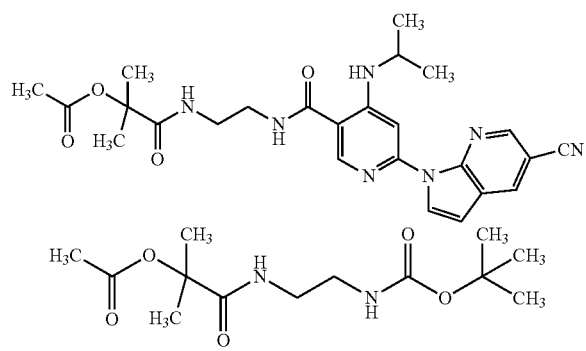

Step 1: A mixture of 1-chloro-2-methyl-1-oxopropan-2-yl acetate (2.0 g, 12.15 mmol) in DCM (20 mL) and TEA (3.39 mL, 24.30 mmol) was added tert-butyl(2-aminoethyl)carbamate (1.95 g, 12.15 mmol) at 0° C. The reaction mixture was stirred at room temperature for 2 h then diluted with DCM and washed with water. The organic layer was dried (Na$_2$SO$_4$), filtered and concentrated to afford 1-((2-((tert-butoxycarbonyl)amino)ethyl)amino)-2-methyl-1-oxopropan-2-yl acetate (2.7 g, 9.36 mmol, 77% yield) as a brown oil. $^1$H NMR (400 MHz, CDCl$_3$) δ 6.85 (br s, 1H), 4.91 (br s, 1H), 3.36 (m, 4H), 2.10 (s, 3H), 1.60 (s, 6H), 1.44 (s, 9H); LCMS 289.4 (M+H)+.

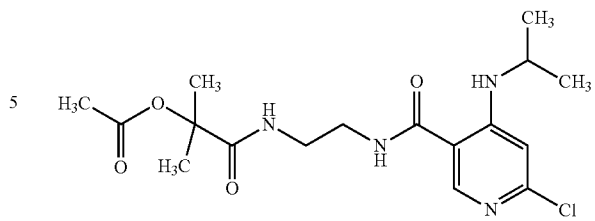

Step 2: 1-((2-((tert-Butoxycarbonyl)amino)ethyl)amino)-2-methyl-1-oxopropan-2-yl acetate (2.5 g, 8.67 mmol) was dissolved in 1,4-dioxane (10 mL), cooled to −10° C. and HCl (0.132 mL, 4.34 mmol, 4N in dioxane) was added dropwise. The reaction mixture was then allowed to stir at room temperature for 1 h. The reaction mixture was concentrated and dried to afford ((2-aminoethyl)amino)-2-methyl-1-oxopropan-2-yl acetate (1.5 g, 7.97 mmol, 92% yield) which was used without further purification.

Step 3: 6-Chloro-4-(isopropylamino)nicotinic acid (0.5 g, 2.329 mmol) and 1-((2-aminoethyl)amino)-2-methyl-1-oxopropan-2-yl acetate (0.438 g, 2.329 mmol) were dissolved in DMF (10 mL), added DIPEA (2.034 mL, 11.65 mmol) and HATU (0.886 g, 2.329 mmol) and the reaction mixture was stirred at room temperature overnight. From the reaction mixture, all solvent was removed and the crude product was purified by ISCO (24 g silica column, MeOH/CHCl$_3$) to obtain 1-((2-(6-chloro-4-(isopropylamino) nicotinamido) ethyl)amino)-2-methyl-1-oxopropan-2-yl acetate (0.73 g, 81% yield) as a colorless gel. $^1$H NMR (400 MHz, CDCl$_3$) δ 8.29 (s, 1H), 6.71 (s, 1H), 3.77-3.71 (m, 1H), 3.49-3.32 (m, 4H), 2.02 (s, 3H), 1.55 (s, 6H), 1.41 (d, 6H, J=8 Hz); LCMS 385.4 (M+H)+.

Step 4: 1-((2-(6-Chloro-4-(isopropylamino)nicotinamido) ethyl)amino)-2-methyl-1-oxopropan-2-yl acetate (0.07 g, 0.182 mmol) and 1H-pyrrolo[2,3-b]pyridine-5-carbonitrile (0.026 g, 0.182 mmol) was dissolved in 1,4-dioxane (10 mL). To this mixture was added Na$_2$CO$_3$ (0.019 g, 0.182 mmol) and water (1 mL). The vessel was purged with N$_2$ and added Xantphos (0.105 g, 0.182 mmol) followed by Pd$_2$(dba)$_3$ (0.167 g, 0.182 mmol). The reaction mixture was heated at 110° C. for 18 h then cooled to room temperature. The product was isolated via column chromatography and repurified via preparative HPLC to afford the product (27 mg, 30% yield) as a white solid. $^1$H NMR (400 MHz, MeOD$_4$) δ 8.7 (s, 1H), 8.49-8.47 (m, 3H), 8.18 (s, 1H), 6.85 (6, 1H, J=4 Hz), 3.91-3.88 (m, 1H), 3.54-3.50 (m, 2H), 3.46-3.43 (m, 2H), 2.08 (s, 3H), 1.57 (s, 6H), 1.38 (d, 6H, J=8 Hz); LCMS 490.2 (M+H)+.

Example 126

6-(5-Cyano-1H-pyrrolo[2,3-b]pyridin-1-yl)-N-(2-(2-hydroxy-2-methylpropanamido)ethyl)-4-(isopropylamino)nicotinamide (126)

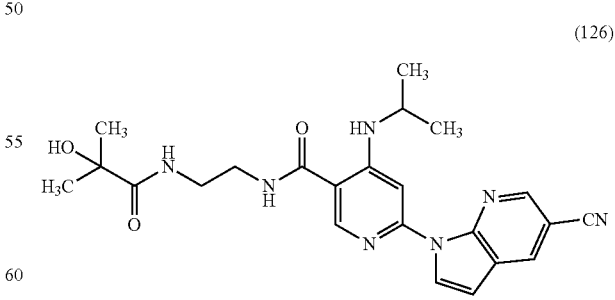

To a solution of 1-((2-(6-(5-cyano-1H-pyrrolo[2,3-b]pyridin-1-yl)-4-(isopropylamino)nicotinamido)ethyl)amino)-2-methyl-1-oxopropan-2-yl acetate (0.1 g, 0.203 mmol) in MeCN (10 mL) was added K$_2$CO$_3$ (0.056 g, 0.407 mmol). The mixture was stirred at room temperature for 30 mins. The mixture was filtered and the concentrated residue was purified via preparative TLC to afford the product (11 mg, 12% yield) as a white solid. ¹H NMR (400 MHz, MeOD₄) δ ¹H NMR (400 MHz, CD₃OD) δ 8.7 (s, 1H), 8.47-8.44 (m, 3H), 8.15 (s, 1H), 6.83 (d, 1H, J=4 Hz), 3.90-3.85 (m, 1H), 3.52-3.44 (m, 4H), 1.37-1.35 (m, 12H); LCMS 450.2 (M+H)⁺.

Example 127

(R)-6-(5-Cyano-1H-pyrrolo[2,3-b]pyridin-1-yl)-N-(2-fluoro-3-methoxypropyl)-4-(isopropylamino) nicotinamide (127)

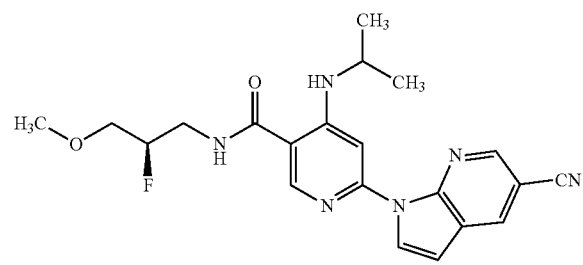

Step 1: To a stirred solution of (R)-methyl 3-(dibenzylamino)-2-fluoropropanoate (1.00 g, 3.32 mmol) in anhydrous THF (15 mL) at 0° C. was added 2N lithium tetrahydroborate in THF (1.659 mL, 3.32 mmol). The reaction mixture was stirred at room temperature for 48 hours and was then added saturated aqueous NH₄Cl solution to quench. The product was extracted with ethyl acetate and the organic layer was dried over Na₂SO₄ and concentrated to provide (R)-3-(dibenzylamino)-2-fluoropropan-1-ol (800 mg, 79% yield) of a colorless oil. LCMS (M+H)⁺=274.3.

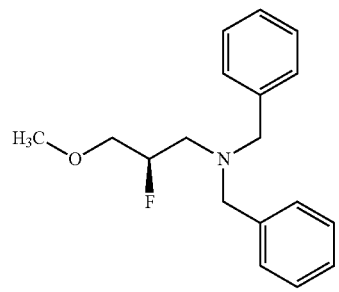 [SMILES: COC[C@H](F)CN(Cc1ccccc1)Cc1ccccc1]

Step 2: To a stirred solution of (R)-3-(dibenzylamino)-2-fluoropropan-1-ol (400 mg, 1.463 mmol) in THF (10 mL) and DMF (10 mL) at 0° C. under nitrogen was added NaH (70.2 mg, 1.756 mmol). After 10 min iodomethane (0.092 mL, 1.463 mmol) was added. After an additional 30 min additional NaH (70.2 mg, 1.756 mmol) was added. After an additional 10 min iodomethane (0.092 mL, 1.463 mmol) was added again. The mixture was carefully quenched with the dropwise addition of water. The mixture was diluted with ethyl acetate and rinsed with 10% LiCl (2×), saturated sodium bicarbonate (1×), and finally 10% LiCl (1×). The organic layer was dried over Na₂SO₄ and concentrated to provide (R)—N,N-dibenzyl-2-fluoro-3-methoxypropan-1-amine (400 mg, 86%) as a colorless oil. LCMS (M+H)⁺=287.7.

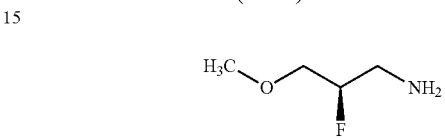

Step 3: Under a nitrogen atmosphere, a Parr bottle was carefully charged with 10% Pd/C (74.1 mg, 0.070 mmol), and the catalyst was carefully wetted with methanol (10 mL). The vessel was charged with a methanol (10 mL) solution of (R)—N,N-dibenzyl-2-fluoro-3-methoxypropan-1-amine (400 mg, 1.392 mmol) and the mixture was degassed by evacuating the vessel under vacuum and depressurizing with nitrogen. The mixture was shaken under 50 psi hydrogen for 4 hours. The mixture was degassed as previously described, and the reaction mixture was filtered under nitrogen through fiberglass filter paper. The filter cake was thoroughly rinsed with methanol (25 mL), and the filtrate was concentrated in vacuo to provide (R)-2-fluoro-3-methoxypropan-1-amine (125 mg, 75% yield) as a colorless oil as product.

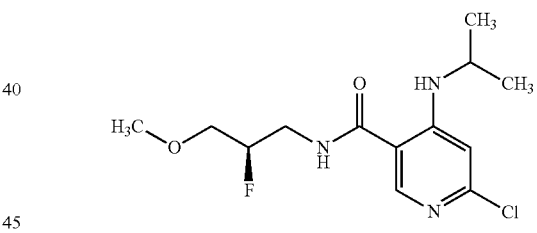

Step 4: To a stirred solution of 6-chloro-4-(isopropylamino)nicotinic acid (250 mg, 1.167 mmol), BOP (516 mg, 1.167 mmol) and TEA (0.325 mL, 2.334 mmol) in DMF (5 mL) at 25° C. was added (R)-2-fluoro-3-methoxypropan-1-amine (125 mg, 1.167 mmol). After 20 hours, the reaction mixture was diluted with ethyl acetate and rinsed with 10% LiCl (2×), saturated sodium bicarbonate (1×) and finally 10% LiCl (1×). The organic layer was dried over Na₂SO₄ and concentrated to provide (R)-6-chloro-N-(2-fluoro-3-methoxypropyl)-4-(isopropylamino)nicotinamide (300 mg, 71% yield) as tan solid. LCMS (M+H)⁺=304.2.

Step 5: A mixture of (R)-6-chloro-N-(2-fluoro-3-methoxypropyl)-4-(isopropylamino)nicotinamide (35 mg, 0.115 mmol), 1H-pyrrolo[2,3-b]pyridine-5-carbonitrile (16.49 mg, 0.115 mmol), potassium carbonate (31.8 mg, 0.230 mmol), and 6:1 t-BuOH/DMA (2 mL) in a 5 mL microwave vial containing a magnetic stir bar was degassed with bubbling nitrogen for 5 minutes. The mixture was treated with BrettPhos precatalyst (4.6 mg, 0.115 mmol), and degassed for another 5 minutes. The vial was sealed and the reaction mixture was heated in the microwave with stirring at 145° C. for 15 minutes. The reaction mixture was evaporated, diluted with DMF, filtered, and purified via preparative HPLC to afford the product (12 mg, 24% yield). $^1$H NMR (500 MHz, DMSO-$d_6$) δ 8.80 (d, J=1.8 Hz, 2H), 8.66 (d, J=1.8 Hz, 1H), 8.58 (s, 1H), 8.52 (d, J=3.7 Hz, 2H), 8.09 (s, 1H), 6.88 (d, J=3.7 Hz, 1H), 4.87-4.69 (m, 1H), 3.77 (dq, J=13.0, 6.4 Hz, 1H), 3.65-3.45 (m, 4H), 3.31 (s, 3H), 1.29 (d, J=6.1 Hz, 6H). LCMS (M+H)$^+$=411.3 for product. HPLC rt 1.88 min, Conditions E.

Example 128

(R)-6-(5-Cyano-1H-pyrazolo[3,4-b]pyridin-1-yl)-N-(2-fluoro-3-methoxypropyl)-4-(isopropylamino)nicotinamide

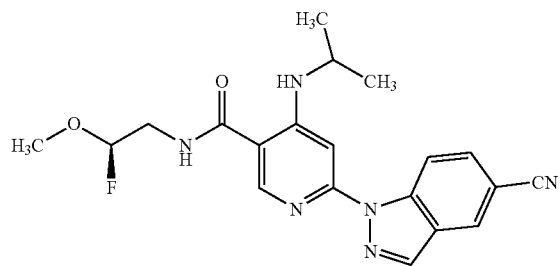

(128)

Example 128 was prepared according to the general procedure for Example 127 utilizing 1H-pyrazolo[3,4-b]pyridine-5-carbonitrile in the final step. LCMS 412.2 (M+)$^+$, HPLC rt 1.47 min, Conditions E.

Example 129

6-(5-cyano-1H-pyrrolo[2,3-b]pyridin-1-yl)-N-((2R)-2-fluoro-3-(isopropylamino)butyl)-4-(isopropylamino)nicotinamide

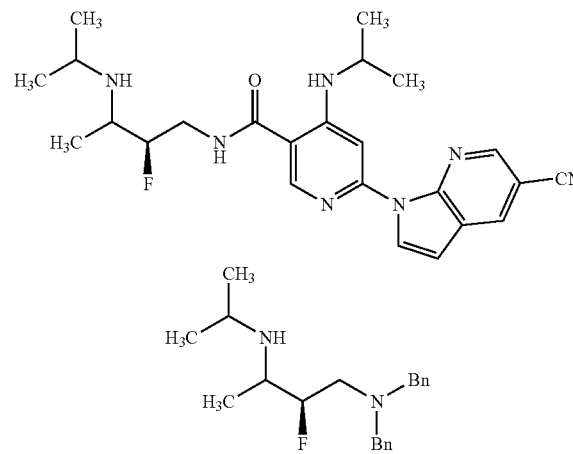

(129)

Step 1: To a solution of 4-(dibenzylamino)-3-fluorobutan-2-one (1.0 g, 3.50 mmol) in DCM (4 mL) at 0° C. was added TEA (2.442 mL, 17.52 mmol). After 5 minutes, propan-2-amine (1.036 g, 17.52 mmol) and TiCl$_4$ (1.159 mL, 10.51 mmol) were added and stirred continued at room temperature overnight. NaCNBH$_4$ (1.10 g, 17.52 mmol) was added to the reaction mixture at 0° C. and again stirred at room temperature for 1 hr. The reaction mixture was filtered through CELITE® using 1:1 methanol and dichloromethane and was concentrated to obtain brown solid. Sodium bicarbonate was added to the mixture and extracted with ethylacetate (3 times). The combined organic extracts were washed with water and brine then dried over anhydrous Na$_2$SO$_4$, filtered and concentrated to obtain brown color liquid. This crude product was purified via column chromatography to afford N1,N1-dibenzyl-2-fluoro-N3-isopropylbutane-1,3-diamine (1.06 g, 92% yield). LCMS 329.0 (M+H)$^+$.

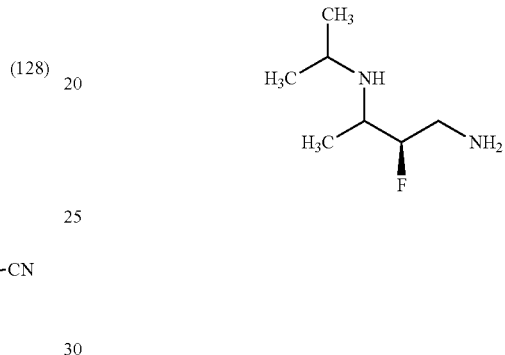

Step 2: A solution of (2S)—N1,N1-dibenzyl-2-fluoro-N3-isopropylbutane-1,3-diamine (1.0 g, 3.04 mmol) in MeOH (30 mL) was added Pd/C (0.2 g, 1.879 mmol) and PdOH$_2$ (0.2 g, 1.424 mmol). The vessel was charged with H$_2$ gas and stirred overnight. The reaction mixture was filtered through CELITE® using 500 mL of methanol and the filtrate was concentrated to afford the product (0.42 g, 93% yield) as a brown solid. $^1$H NMR (400 MHz, DMSO-$d_6$) δ 5.40-5.20 (m, 1H), 3.72-3.40 (m, 1H), 3.55-3.45 (m, 3H), 1.31-1.21 (m, 9H).

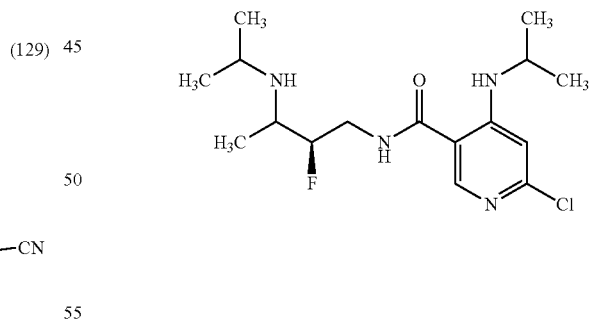

Step 3: 6-Chloro-4-(isopropylamino)nicotinic acid (0.22 g, 1.025 mmol) in DMF (5 mL), was added HATU (0.585 g, 1.537 mmol), DIPEA (0.895 mL, 5.12 mmol) and (2S)-2-fluoro-N3-isopropylbutane-1,3-diamine (0.182 g, 1.230 mmol). The reaction mixture was stirred at room temperature for 4 hrs. Sodium bicarbonate was added to the reaction mixture and it was extracted with ethylacetate (3 times). The combined organic extracts were washed with water, brine, then dried over anhydrous Na$_2$SO$_4$. The organic layer was filtered and concentrated to afford the crude product which was purified via column chromatography to afford 6-chloro-N-((2R)-2-fluoro-3-(isopropylamino)butyl)-4-(isopropylamino)nicotinamide (0.34 g, 96% yield). $^1$H NMR (400 MHz, DMSO-$d_6$) δ 8.79-8.76 (m, 1H), 8.41-8.32 (m, 2H), 6.70 (s, 1H), 4.65-4.40 (m, 1H), 3.78-3.73 (m, 1H), 3.55-3.45 (m, 2H), 2.92-2.85 (m, 3H), 1.16 (d, 6H, J=8.0 Hz), 1.07-0.93 (m, 9H); LCMS 345.4 (M+H)$^+$.

Step 4: A solution of 6-chloro-N-((2R)-2-fluoro-3-(isopropylamino)butyl)-4-(isopropylamino)nicotinamide (0.2 g, 0.580 mmol) and 1H-pyrrolo[2,3-b]pyridine-5-carbonitrile (0.125 g, 0.870 mmol) in 1,4 dioxane (5 mL) was added Xantphos (0.168 g, 0.290 mmol) and 3 eq of $K_2CO_3$ (0.240 g, 1.740 mmol). The mixture was purged with $N_2$ and then added $Pd_2dba_3$ (0.266 g, 0.290 mmol) and again purged for 10 minutes. The vessel was then heated at 110° C. for 18 h. The mixture was cooled and filtered through CELITE® using 1:1 methanol and dichloromethane and extracted using 1.5N HCl and ethyl acetate. The water layer was neutralized with sodium carbonate and extracted with ethylacetate (3 times). The combined organic extracts were washed with water, brine then dried over anhydrous $Na_2SO_4$. The organics were filtered and concentrated to obtain a brown solid which was purified via column chromatography and then preparative HPLC to afford 12 mg of the diastereomeric mixture. This material was separated via SFC chiral chromatography to furnish Example 129 (5 mg) as an off-white solid. $^1$H NMR (400 MHz, DMSO-$d_6$) δ 8.81-8.77 (m, 3H), 8.67 (d, 1H; J=2.0 Hz), 8.58-8.52 (m, 3H), 8.31 (s, 1H), 8.10 (s, 1H), 6.87 (d, 1H, J=4 Hz), 4.55-4.39 (m, 1H), 3.79-3.76 (m, 1H), 3.70-3.40 (m, 3H), 2.90-2.85 (m, 2H), 1.27 (d, 6H), J=8.0 Hz), 1.08-0.94 (m, 9H); LCMS 452.0 (M+H)$^+$.

The second diastereomer (3 mg) was isolated as Example 130.

Example 130

6-(5-Cyano-1H-pyrrolo[2,3-b]pyridin-1-yl)-N-((2R)-2-fluoro-3-(isopropylamino)butyl)-4-(isopropylamino)nicotinamide (130)

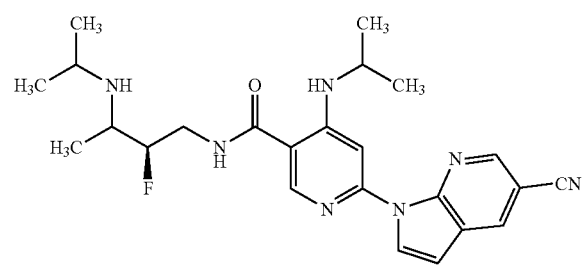

$^1$H NMR (400 MHz, DMSO-$d_6$) δ 8.81-8.80 (m, 2H), 8.67 (d, 1H, J=2.0 Hz), 8.59-8.57 (m, 2H), 8.53-8.52 (m, 1H), 8.31 (s, 1H), 8.10 (s, 1H), 6.87 (d, 1H, J=4 Hz), 4.61-4.46 (m, 1H), 3.80-3.76 (m, 1H), 3.55-3.45 (m, 2H), 2.95-2.80 (m, 3H), 1.29 (d, 6H, J=8.0 Hz), 1.07 (d, 3H, J=8.0 Hz), 1.01 (d, 3H, J=8.0 Hz), 0.95 (d, 3H, J=8.0 Hz); LCMS 452.0 (M+H)$^+$.

Example 131

6-(5-Cyano-1H-pyrrolo[2,3-b]pyridin-1-yl)-N—((R)-2-fluoro-3-hydroxy-3-methylbutyl)-4-((1-fluoro-3-hydroxypropan-2-yl)amino)nicotinamide (131)

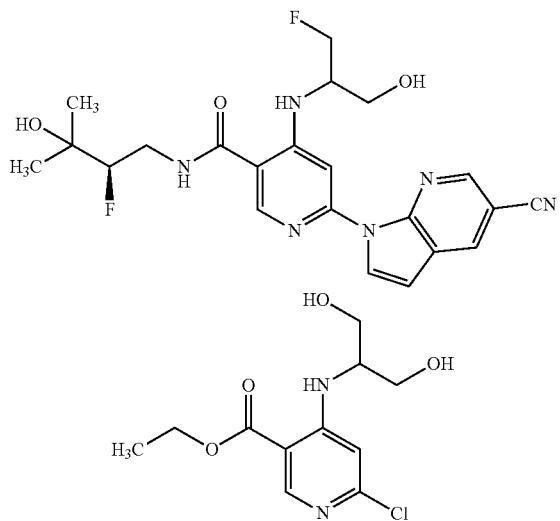

Step 1: To a stirred solution of ethyl 4,6-dichloronicotinate (6.0 g, 27.3 mmol) in DMA (100 mL), DIPEA (23.81 mL, 136 mmol) and 2-aminopropane-1,3-diol (2.98 g, 32.7 mmol) were added and heated at 60° C. in a round bottom flask for 4 h. Reaction mixture was cooled to room temperature, added water and extracted with ethyl acetate (3 times). The organic extracts were combined together, dried over $Na_2SO_4$, filtered and concentrated to get the brown color liquid as the required crude product. The crude material obtained was purified by column chromatography through silica gel and EtOAC: pet. Ether (70%) as eluent to obtain the ethyl 6-chloro-4-((1,3-dihydroxypropan-2-yl)amino)nicotinate (7.1 g, 95% yield). LC/MS: 275.4 (M+H)$^+$.

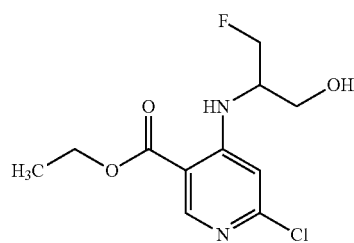 [SMILES: CCOC(=O)c1cnc(Cl)cc1NC(CO)CF]

Step 2: Ethyl 6-chloro-4-((1,3-dihydroxypropan-2-yl)amino)nicotinate (0.1 g, 0.364 mmol) in DCM (3 mL) at −78° C. was added DAST (0.096 mL, 0.728 mmol) and then allowed to stir at room temperature for 10 min. Sodium bicarbonate in ice water was added the reaction mixture slowly and then extracted 3 times with DCM. The combined organic extracts were dried $Na_2SO_4$, filtered, and concentrated to obtain the crude product which was purified via column chromatography to afford ethyl 6-chloro-4-((1-fluoro-3-hydroxypropan-2-yl)amino)nicotinate (0.090 g, 89% yield). LCMS 277.0 (M+H)$^+$.

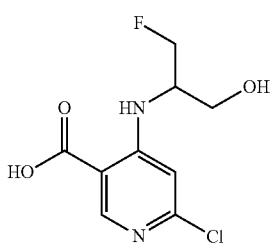 [SMILES: O=C(O)c1cnc(Cl)cc1NC(CO)CF]

Step 3: To a solution of ethyl 6-chloro-4-((1-fluoro-3-hydroxypropan-2-yl)amino) nicotinate (0.12 g, 0.434 mmol) in EtOH (4 mL) and water (1 mL) was added LiOH (0.052 g, 2.168 mmol) and the reaction mixture was stirred at room temperature for 2 h. The reaction mixture was concentrated and the residue was acidified with 1.5N HCl to precipitate the product. The white solids were filtered and washed to afford 6-chloro-4-((1-fluoro-3-hydroxypropan-2-yl)amino)nicotinic acid (0.1 g, 93% yield) as a white solid. LCMS 249.4 (M+H)$^+$.

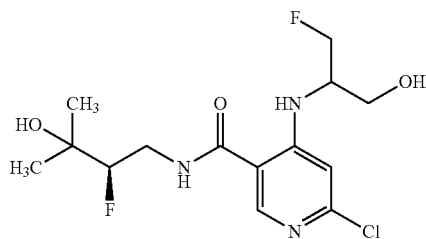 [SMILES: CC(C)(O)[C@H](F)CNC(=O)c1cnc(Cl)cc1NC(CO)CF]

Step 4: A solution of 6-chloro-4-((1-fluoro-3-hydroxypropan-2-yl)amino) nicotinic acid (0.1 g, 0.40 mmol) in DMF (3 mL) was added HATU (0.23 g, 0.60 mmol), DIPEA (0.35 mL, 2.01 mmol) and (R)-4-amino-3-fluoro-2-methylbutan-2-ol (0.058 g, 0.48 mmol). The reaction mixture was stirred at room temperature overnight. Sodium bicarbonate was added and the reaction mixture was extracted with ethylacetate (3 times). The combined organic extracts were washed with water and brine then dried over Na$_2$SO$_4$. The solution was filtered and concentrated to obtain brown liquid which was purified via column chromatography to afford 6-chloro-N—((R)-2-fluoro-3-hydroxy-3-methylbutyl)-4-((1-fluoro-3-hydroxypropan-2-yl)amino)nicotinamide (0.13 g, 92% yield). LCMS 352.3 (M+H).

Step 5: A solution of 6-chloro-N—((R)-2-fluoro-3-hydroxy-3-methylbutyl)-4-((1-fluoro-3-hydroxypropan-2-yl) amino)nicotinamide (0.15 g, 0.426 mmol) and 1H-pyrrolo[2,3-b]pyridine-5-carbonitrile (0.092 g, 0.640 mmol) in 1,4 dioxane (3 mL) was added Xantphos (0.123 g, 0.213 mmol) and K$_2$CO$_3$ (0.177 g, 1.279 mmol). The mixture was evacuated and backfilled with N$_2$ then added Pd$_2$(dba)$_3$ (0.195 g, 0.213 mmol). The mixture was evacuated and backfilled with N$_2$ again and then heated at 110° C. for 18 h. The mixture was cooled to room temperature and filtered through CELITE® using 1:1 methanol and dichloromethane. The crude product was purified via column chromatography and preparative HPLC to afford 6-(5-cyano-1H-pyrrolo[2,3-b]pyridin-1-yl)-N—((R)-2-fluoro-3-hydroxy-3-methylbutyl)-4-((1-fluoro-3-hydroxypropan-2-yl)amino)nicotinamide (3 mg, 1.5% yield). LCMS 459.2 (M+H)$^+$; $^1$H NMR (400 MHz, DMSO-d$_6$) δ 8.82-8.80 (m, 1H), 8.70-8.64 (m, 2H), 8.54-8.53 (m, 1H), 8.33-8.32 (m, 1H), 8.18-8.16 (m, 1H), 6.91-6.90 (m, 1H), 5.23-5.19 (m, 1H), 4.74-4.58 (m, 3H), 3.45-3.37 (m, 4H), 1.20-1.17 (m, 6H).

Example 132

(R)-6-(5-Cyano-1H-pyrrolo[2,3-b]pyridin-1-yl)-4-(cyclopropylamino)-N-(2-fluoro-3-(methylamino)-3-oxopropyl)nicotinamide (132)

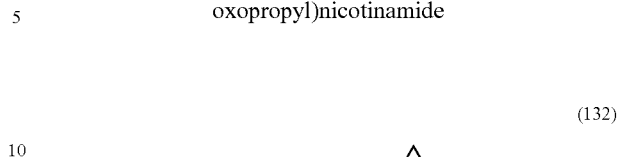

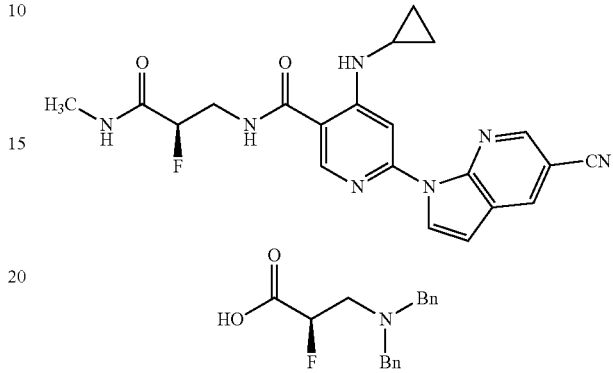

Step 1: (R)-Ethyl 3-(dibenzylamino)-2-fluoropropanoate (5 g, 15.85 mmol) was taken in ethanol (15 mL), water (3 mL) and to this LiOH (1.139 g, 47.6 mmol) was added and allowed to stir overnight. Ethanol and water were removed under vacuum and the crude reaction mixture was acidified using 1.5N HCl. The aqueous layer was extracted with ethylacetate and the ethylacetate layer was washed with water, dried and evaporated. The crude material was purified by combiflash using 5% MeOH in CHCl$_3$ to afford a brown oily product (3.5 g, 77% yield). LCMS 288.1 (M+H)$^+$.

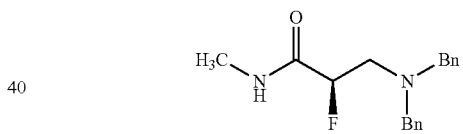

Step 2: (R)-3-(Dibenzylamino)-2-fluoropropanoic acid (0.5 g, 1.740 mmol) was taken in DMF (2 mL) and to this solution, methanamine (0.054 g, 1.740 mmol) was added along with HATU (0.662 g, 1.740 mmol) and DIPEA (1.216 mL, 6.96 mmol). The reaction mixture was allowed to stir for 4 hrs. DMF removed under vacuum and the crude was diluted with water and extracted with ethylacetate. The ethyl acetate layer was washed with 10% NaHCO$_3$, dried and evaporated. The crude brown solid was purified by combiflash (12 g column) using 5% MeOH in CHCl$_3$ and used directly in the next reaction (some starting material remained in the product).

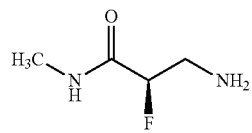

Step 3: To a solution of (R)-3-(dibenzylamino)-2-fluoro-N-methylpropanamide (800 mg, 2.66 mmol) in MeOH (5 mL) was added Pd/C (142 mg, 1.332 mmol) and Pd(OH)₂ (187 mg, 1.332 mmol). The solution was hydrogenated at 1 atm pressure for 6 hrs. The reaction mixture was diluted with ethyl acetate and passed through a small plug of CELITE®. The filtrate was concentrated and the crude product (150 mg, 47% yield) was used without further purification.

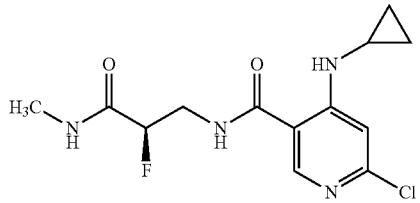 [SMILES: CNC(=O)[C@H](F)CNC(=O)c1cnc(Cl)cc1NC1CC1]

Step 4: 6-Chloro-4-(cyclopropylamino)nicotinic acid (500 mg, 2.351 mmol) was taken in DMF (3 mL) and to this solution, (R)-3-amino-2-fluoro-N-methylpropanamide (282 mg, 2.351 mmol) was added along with HATU (894 mg, 2.351 mmol) and DIPEA (0.411 mL, 2.351 mmol). The reaction mixture was stirred at room temperature for 4 hrs. TLC indicated the absence of starting material. The reaction mixture was diluted with 10% NaHCO₃ and extracted with ethyl acetate. The ethyl acetate layer was washed with water, dried and evaporated to afford the crude product which was purified by column chromatography (12 g, 5% MeOH in CHCl₃). The compound (340 mg, 46% yield) was used without further purification.

Step 5: To solution of 1H-pyrrolo[2,3-b]pyridine-5-carbonitrile (54.6 mg, 0.381 mmol) in dioxane (5 mL):water (1 mL), 1H-pyrrolo[2,3-b]pyridine-5-carbonitrile (54.6 mg, 0.381 mmol), K₂CO₃ (132 mg, 0.953 mmol) and Xantphos (92 mg, 0.159 mmol) were added and degassed for 10 min. To the reaction mixture Pd₂(dba)₃ (116 mg, 0.127 mmol) was added and degassed again for 10 min and then heated at 110° C. overnight in a pressure tube. The reaction mixture was cooled and filtered through small pad of CELITE®. The filtrate obtained was concentrated to provide crude material. The crude product was purified via preparative HPLC to afford (R)-6-(5-cyano-1H-pyrrolo[2,3-b]pyridin-1-yl)-4-(cyclopropylamino)-N-(2-fluoro-3-(methylamino)-3-oxopropyl)nicotinamide (8 mg, 0.018 mmol, 5.56% yield). ¹H NMR (400 MHz, DMSO-d₆) δ 8.86-8.81 (m, 1H), 8.69 (d, J=2.0 Hz, 1H), 8.61-8.56 (m, 4H), 8.24 (br. s., 1H), 6.91 (d, J=4.0 Hz, 1H), 5.11-4.93 (m, 1H), 3.88-3.72 (m, 1H), 3.61-3.48 (m, 1H), 2.69-2.59 (m, 4H), 0.98-0.92 (m, 2H), 0.63-0.58 (m, 2H); LCMS (M+H)⁺=422.2; HPLC rt 7.49 min, Conditions B.

Example 133

(R)-6-(5-Cyano-1H-pyrazolo[3,4-b]pyridin-1-yl)-N-(2-fluoro-3-hydroxy-3-methylbutyl)-4-(isopropylamino)nicotinamide (133)

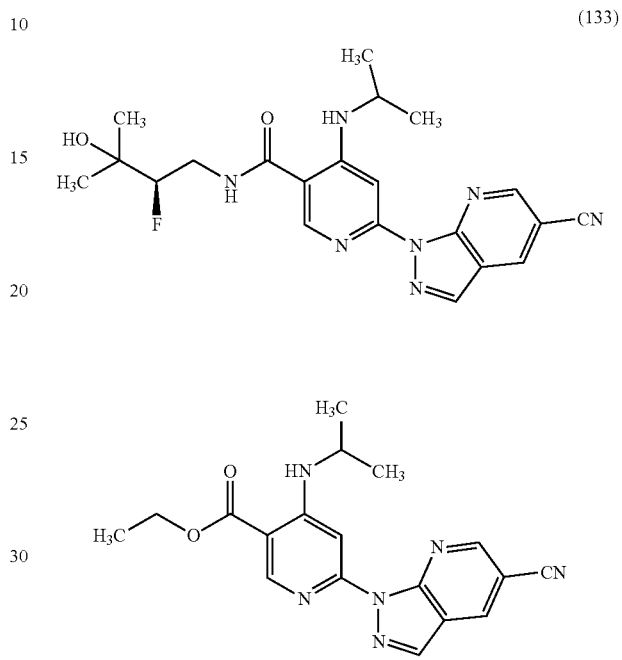

Step 1: Ethyl 6-chloro-4-(isopropylamino)nicotinate (1 g, 4.12 mmol) and 1H-pyrazolo[3,4-b]pyridine-5-carbonitrile (0.594 g, 4.12 mmol) was dissolved in 1,4-dioxane (10 mL) in a pressure tube at room temperature. The reaction mixture was degassed by bubbling nitrogen into the reaction mixture. 2-Di-tert-butylphosphino-2',4',6'-triisopropylbiphenyl (0.525 g, 1.236 mmol) and potassium phosphate dibasic (2.153 g, 12.36 mmol) was added and the mixture was degassed for another 20 min. Pd₂(dba)₃ (0.755 g, 0.824 mmol) was added and the nitrogen purging continued for 5 min. The reaction mixture was then heated at 110° C. for 18 h. Reaction mixture was cooled to room temperature and diluted with EtOAc (150 mL), filtered through CELITER, and washed with 100 mL of EtOAc. The filtrate was concentrated and the crude material was purified by flash column chromatography using silica gel as stationary phase and EtOAc: pet ether (1:1) as eluent to afford the compound. The material was further purified by reverse phase HPLC to get ethyl 6-(5-cyano-1H-pyrazolo[3,4-b]pyridin-1-yl)-4-(isopropylamino)nicotinate (100 mg, 6.44% Yield). ¹H NMR (400 MHz, DMSO-d₆) δ 9.08 (d, J=1.5 Hz, 2H), 9.03 (d, J=2.0 Hz, 2H), 8.82 (s, 2H), 8.68 (s, 1H), 8.10 (d, J=7.5 Hz, 1H), 7.48 (s, 1H), 4.36 (q, J=7.0 Hz, 2H), 4.12-4.07 (m, 1H), 3.92-3.83 (m, 2H), 1.36 (t, J=7.0 Hz, 3H), 1.32-1.29 (m, 6H).

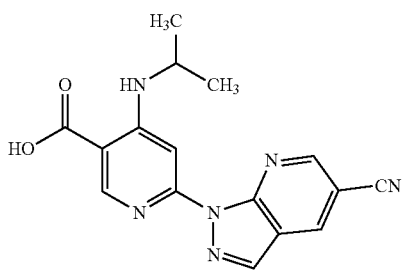 [SMILES: CC(C)Nc1cc(-n2ncc3cc(C#N)cnc32)ncc1C(=O)O]

Step 2: To the solution of ethyl 6-(5-cyano-1H-pyrazolo[3,4-b]pyridin-1-yl)-4-(isopropylamino)nicotinate (0.7 g, 1.998 mmol) in ethanol (2 mL) and THF (10 mL) was added lithium hydroxide (0.5 g) in water (0.500 mL) at room temperature in 2 portions (at an interval of 4 h). The reaction mixture was stirred at room temperature for 1 h. Temperature of the reaction mixture was raised to 65° C. and stirred for 18 hrs. Excess solvent was removed under reduced pressure, diluted with water 10 mL, cooled to 0° C. The pH of the reaction mixture was adjusted using a saturated solution of citric acid (dropwise addition) at 0° C. to pH 7. The product precipitated from solution to afford 6-(5-cyano-1H-pyrazolo[3,4-b]pyridin-1-yl)-4-(isopropylamino)nicotinic acid (0.6 g, 1.861 mmol, 93% yield) after filtration. LC/MS 321 (M−H).

Step 3: To a stirred solution of 6-(5-cyano-1H-pyrazolo[3,4-b]pyridin-1-yl)-4-(isopropylamino)nicotinic acid (0.6 g, 1.861 mmol) in DMF (2 mL) was added DIPEA (0.975 mL, 5.58 mmol) and HATU (1.416 g, 3.72 mmol) and stirred for 20 min at room temperature. (R)-4-Amino-3-fluoro-2-methylbutan-2-ol (0.226 g, 1.861 mmol) in DMF (2 mL) was added to the reaction mixture and stirred at room temperature for 1 h. Excess DMF was removed under reduced pressure. The residue was diluted with ethyl acetate (100 mL), washed with 10% NaHCO$_3$ solution (20 mL) followed by brine (20 mL). The organic layer was collected, dried over Na$_2$SO$_4$, filtered and concentrated to get the crude material which was purified by RP-HPLC to obtain (R)-6-(5-cyano-1H-pyrazolo[3,4-b]pyridin-1-yl)-N-(2-fluoro-3-hydroxy-3-methylbutyl)-4-(isopropylamino)nicotinamide (0.3015 g, 37.7% yield). HPLC: 99%, Condition A. LC/MS: 426 (M+H). $^1$H NMR (400 MHz, DMSO-d$_6$) δ=9.05 (dd, J=2.0, 13.6 Hz, 1H), 8.85-8.79 (m, 1H), 8.66-8.64 (m, 1H), 8.60-8.55 (m, 1H), 7.34 (s, 1H), 4.85 (s, 1H), 4.47-4.29 (m, 1H), 3.82-3.74 (m, 1H), 1.29-1.17 (m, 6H).

Alternatively, the penultimate carboxylic acid was prepared according to the following procedures:

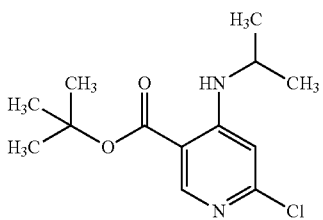 [SMILES: CC(C)Nc1cc(Cl)ncc1C(=O)OC(C)(C)C]

Step 1: A suspension of 6-chloro-4-(isopropylamino)nicotinic acid (240 g, 1118 mmol) in toluene (1800 mL) in a 1 L round bottom flask was heated to 90° C. N,N-dimethylformamide di-tert-butyl acetal (1609 mL, 6709 mmol) in toluene (1800 mL) was added slowly over 8-9 hrs. The reaction mixture was heated at 90° C. for 12 hrs. After completion of 12 hrs, the reaction mixture was cooled and concentrated under reduced pressure to remove excess of solvent and obtain the crude material. The crude material was purified by flash column chromatography using silica gel as stationary phase and EtOAc: pet ether (2:8) as eluent to afford the title compound, tert-butyl 6-chloro-4-(isopropylamino)nicotinate (275 g, 91% yield). LC/MS 271.0 (M+H). $^1$H NMR (400 MHz, CDCl$_3$) δ=8.59 (s, 1H), 8.14-8.08 (m, 1H), 6.51 (s, 1H), 3.71-3.61 (m, 1H), 1.57 (s, 9H), 1.28 (d, J=6.5 Hz, 6H).

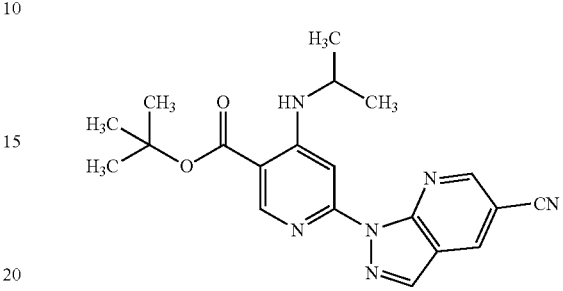

Step 2: A solution of 1H-pyrazolo[3,4-b]pyridine-5-carbonitrile (69.2 g, 480 mmol) and tert-butyl 6-chloro-4-(isopropylamino)nicotinate (130 g, 480 mmol) in 1,4-dioxane (4200 mL) in 10 L autoclave was degassed by purging nitrogen gas into the reaction mixture for 10 min. Xantphos (111 g, 192 mmol) and potassium carbonate (199 g, 1440 mmol) were added to the autoclave and degassing was continued for another 10 min. Bis(dibenzylidineacetone)palladium (110 g, 192 mmol) was added to the reaction mixture. The reaction mixture was purged with nitrogen gas for additional 10 min. The autoclave was then heated under 10 kg pressure at 120° C. for 12 hrs. After the completion of 12 hrs, the autoclave was cooled to room temperature and reaction mass was unloaded. The solvent was removed under vacuum. Ethyl acetate (2.5 L) and water (2.5 L) was added to the residue and the resulting mixture was filtered through a CELITE® bed. The CELITE® was washed with 1×1000 mL ethyl acetate. The organic layer was separated, washed with water (1 L) followed by brine (0.5 L). The organic layer was collected, dried over sodium sulfate, filtered and concentrated to get a dark green crude material. The crude material was purified by column chromatography using silica gel as stationary phase and EtOAc: pet ether (2:8) as eluent to get the desired compound. The material obtained after purification was treated with MTBE to precipitate the product tert-butyl 6-(5-cyano-1H-pyrazolo[3,4-b]pyridin-1-yl)-4-(isopropylamino)nicotinate (50 g, 27.5%). LC/MS 379.2 (M+H). $^1$H NMR (400 MHz, CDCl$_3$) δ=8.97-8.93 (m, 2H), 8.48 (d, J=2.0 Hz, 1H), 8.36 (s, 1H), 8.27-8.22 (m, 1H), 7.49 (s, 1H), 3.91-3.82 (m, 1H), 1.61-1.52 (m, 9H), 1.37 (d, J=6.5 Hz, 6H).

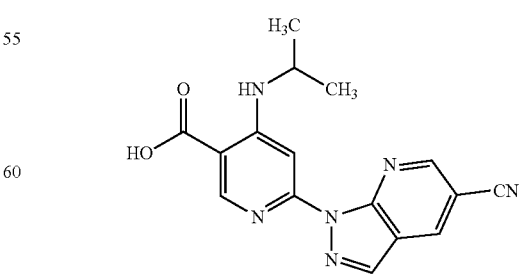

Step 3: A solution of tert-butyl 6-(5-cyano-1H-pyrazolo[3,4-b]pyridin-1-yl)-4-(isopropylamino)nicotinate (42 g, 111 mmol) in DCE (277 mL) in a 1 L pressure tube at room temperature was added TFA (86 mL, 1110 mmol). The reaction mixture was heated at 80° C. for 2 hrs. After completion of 2 hrs, the reaction mixture was cooled to room temperature and concentrated under reduced pressure to remove excess solvent. The residue obtained was diluted with 350 mL of water and the pH of the reaction mixture was adjusted to 5 with saturated $Na_2CO_3$ solution (21 mL). The solids were stirred for 10 min at room temperature, filtered, and washed with 200 mL of water and air dried. The crude material was purified by flash column chromatography using silica gel (230-400 mesh) as stationary phase and MeOH: DCM (1:9) as eluent to afford 6-(5-cyano-1H-pyrazolo[3,4-b]pyridin-1-yl)-4-(isopropylamino)nicotinic acid (31.05 g, 81% yield). LC/MS 323.4 (M+H). $^1$H NMR (400 MHz, DMSO-$d_6$) δ=13.39-13.19 (bs, 1H), 9.05 (d, J=19.1 Hz, 2H), 8.80-8.64 (m, 2H), 8.32 (d, J=7.5 Hz, 1H), 7.44 (s, 1H), 3.86-3.81 (m, 1H), 1.30 (d, J=6.0 Hz, 6H).

Step 4: To a solution of (R)-4-amino-3-fluoro-2-methylbutan-2-ol (27.8 g, 229 mmol) in DMF (579 mL) was added 6-(5-cyano-1H-pyrazolo[3,4-b]pyridin-1-yl)-4-(isopropylamino)nicotinic acid (61.63 g, 191 mmol) followed by DIPEA (100 mL, 574 mmol) and HATU (109 g, 287 mmol). The reaction mixture was stirred for a total of 60 min then added water (20 mL) slowly via dropping funnel. After the addition, the mixture slowly became cloudy and was allowed to stir for ~1 h and then another 20 mL of water was added and stirred for 0.5 h then filtered. The solids were washed with water (2×20 mL) and dried on the filter to give (R)-6-(5-cyano-1H-pyrazolo[3,4-b]pyridin-1-yl)-N-(2-fluoro-3-hydroxy-3-methylbutyl)-4-(isopropylamino)nicotinamide (76 g, 172 mmol, 90% yield).

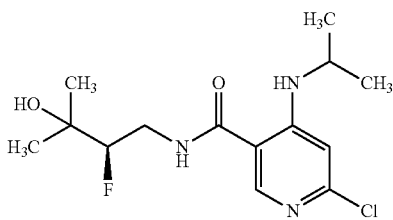 [SMILES: CC(C)Nc1cc(Cl)ncc1C(=O)NC[C@@H](F)C(C)(C)O]

In a 5 mL microwave vial, a mixture of (R)-6-chloro-N-(2-fluoro-3-hydroxy-3-methylbutyl)-4-(isopropylamino)nicotinamide (33 mg, 0.104 mmol), 1H-pyrazolo[3,4-b]pyridine-5-carbonitrile (17.96 mg, 0.125 mmol), and potassium phosphate, tribasic (66.1 mg, 0.312 mmol) in dioxane (1 mL) was degassed with bubbling nitrogen for 5 minutes. In a separate sealed vial, a degassed, stirring mixture of $Pd_2(dba)_3$ (4.75 mg, 5.19 mol) and tetramethyl t-Bu XPhos (5.99 mg, 0.012 mmol) in 5:1 toluene/dioxane (0.1 mL) was heated at 120° C. for 5 minutes. After cooling to room temperature, this solution was transferred to the vial containing the reaction mixture. The vial was sealed, and the reaction mixture was heated at 80° C. for 3 hours, then cooled to room temperature and stirred for 18 hours. LCMS detects a 3.5:1 ratio of the desired product and starting material chloropyridine. The reaction mixture was heated at 80° C. for an additional 4 hours, at which point it was judged to be essentially complete by LCMS. The solvent was evaporated, and the residue was taken up in DMF (5 mL). Solids were removed by filtration and rinsed 3 times with DMF (1 mL), and the combined filtrate and rinses were concentrated in vacuo. The residue was chromatographed via MPLC over a 12 g silica gel column, eluting at 30 mL/min with 0-5% methanol/methylene chloride. Fractions containing the desired product were pooled and concentrated in vacuo to yield (R)-6-(5-cyano-1H-pyrazolo[3,4-b]pyridin-1-yl)-N-(2-fluoro-3-hydroxy-3-methylbutyl)-4-(isopropylamino) nicotinamide (27 mg, 0.063 mmol, 61.1% yield) as a slightly yellow film. LCMS 426.3 (M+H)$^+$. $^1$H NMR (400 MHz, MeOH-$d_4$) δ 8.98 (d, J=2.0 Hz, 1H), 8.83 (d, J=2.0 Hz, 1H), 8.53 (s, 1H), 8.52 (s, 1H), 7.75 (s, 1H), 4.45 (ddd, J=49.1, 9.3, 2.4 Hz, 1H), 3.99-3.83 (m, 2H), 3.51 (ddd, J=16.4, 14.5, 9.1 Hz, 1H), 1.37 (d, J=6.4 Hz, 6H), 1.32 (d, J=1.5 Hz, 6H).

Preparations of Crystalline Form N-1

To a slurry of 1.15 grams of (R)-6-(5-cyano-1H-pyrazolo [3,4-b]pyridin-1-yl)-N-(2-fluoro-3-hydroxy-3-methylbutyl)-4-(isopropylamino)nicotinamide in water (18 mL) was added acetone (2 mL). The mixture was stirred at room temperature for 18 h. A fine white solid was collected by filtration and rinsed with water. After drying, 1.10 g (96% recovery) of Example 133 was obtained as a white crystalline solid.

A solution of Example 133 (50 mg) was prepared in DMF (1 ml) at room temperature (~22 to 25° C.). The solution was evaporated to dryness at room temperature to afford needle-like crystals.

Preparation of Crystalline Form N-2

Example 133 (25 mg) was dissolved in 2-propanol (2.5 ml) at 60-70° C. The saturated solution was allowed to cool to afford needle shaped crystals.

The Examples in Table 7 were prepared according to the general procedure for Example 133 using the appropriate starting material and amine.

TABLE 7

| Ex. No. | Structure | HPLC rt (min) | HPLC cond. | LCMS |
|---|---|---|---|---|
| 134 | 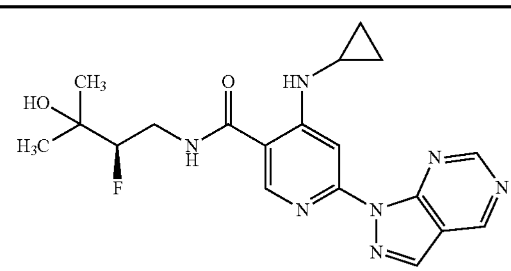 | 10.84 | B, 18 min grad. | 400.2 |

TABLE 7-continued
| Ex. No. | Structure | HPLC rt (min) | HPLC cond. | LCMS |
|---|---|---|---|---|
| 135 | 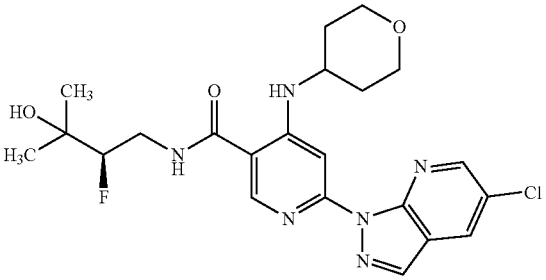 [SMILES: CC(C)(O)[C@H](F)CNC(=O)c1cnc(-n2ncc3cc(Cl)cnc32)cc1NC1CCOCC1] | 6.32 | A | 477.9 |
| 136 | 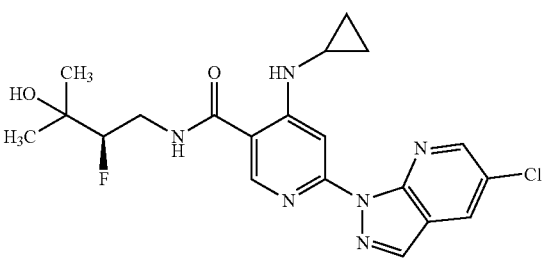 [SMILES: CC(C)(O)[C@H](F)CNC(=O)c1cnc(-n2ncc3cc(Cl)cnc32)cc1NC1CC1] | 6.81 | A | 433.9 |
| 137 | 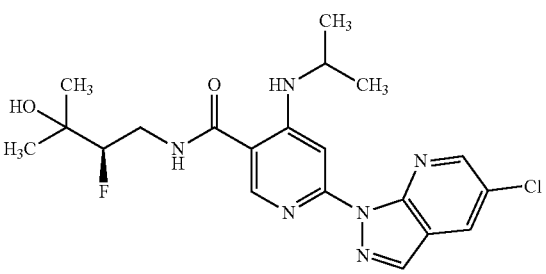 [SMILES: CC(C)Nc1cc(-n2ncc3cc(Cl)cnc32)ncc1C(=O)NC[C@@H](F)C(C)(C)O] | 6.97 | A | 435.9 |
| 138 | 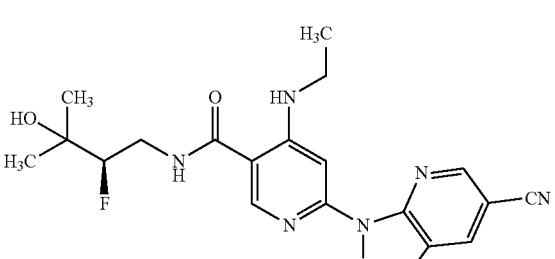 | 6.67 | A | 412.0 |
| 139 | 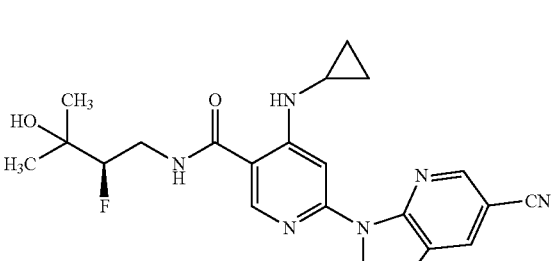 | 6.29 | A | 424.4 |

TABLE 7-continued

| Ex. No. | Structure | HPLC rt (min) | HPLC cond. | LCMS |
|---|---|---|---|---|
| 140 | 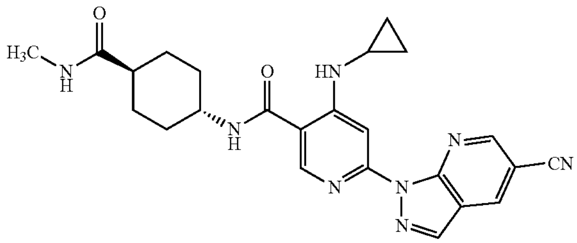 [SMILES: CNC(=O)[C@H]1CC[C@H](NC(=O)c2cnc(-n3ncc4cc(C#N)cnc43)cc2NC2CC2)CC1] | 6.53 | B | 459.6 |
| 141 | 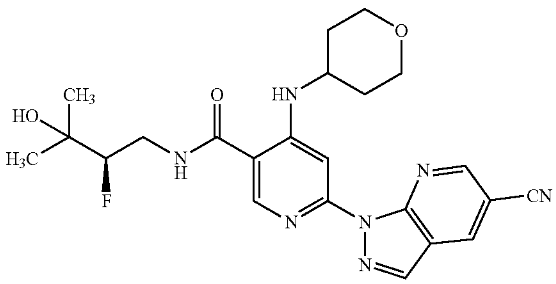 [SMILES: CC(C)(O)[C@H](F)CNC(=O)c1cnc(-n2ncc3cc(C#N)cnc32)cc1NC1CCOCC1] | 9.13 | A | 466.5 (M − H) |
| 142 Diastereomer 1 | 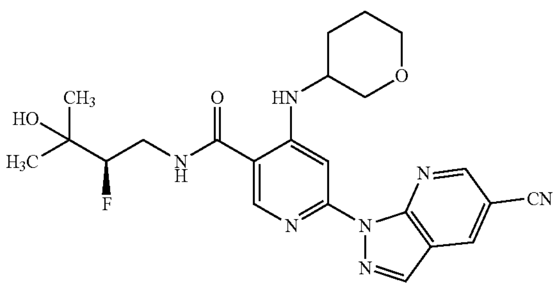 [SMILES: CC(C)(O)[C@H](F)CNC(=O)c1cnc(-n2ncc3cc(C#N)cnc32)cc1NC1CCCOC1] | 9.47 | A | 468.5 |
| 143 Diastereomer 2 | 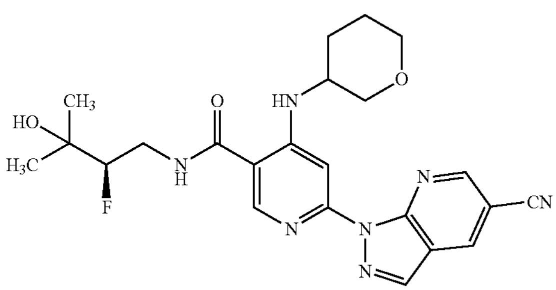 [SMILES: CC(C)(O)[C@H](F)CNC(=O)c1cnc(-n2ncc3cc(C#N)cnc32)cc1NC1CCCOC1] | 9.50 | A | 468.5 |
| 144 | 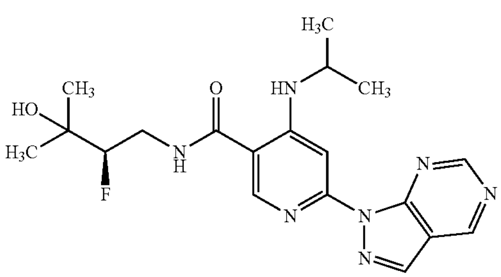 [SMILES: CC(C)Nc1cc(-n2ncc3cncnc32)ncc1C(=O)NC[C@@H](F)C(C)(C)O] | 10.68 | A, 18 min grad. | 402.0 |

TABLE 7-continued

| Ex. No. | Structure | HPLC rt (min) | HPLC cond. | LCMS |
|---|---|---|---|---|
| 145 | 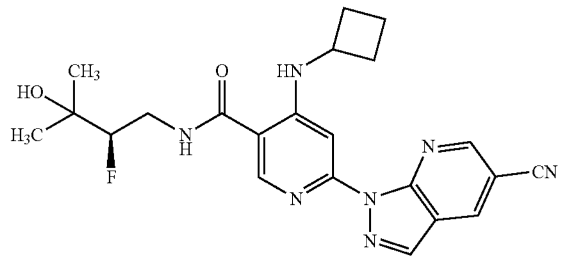 [SMILES: CC(C)(O)[C@H](F)CNC(=O)c1cnc(-n2ncc3cc(C#N)cnc32)cc1NC1CCC1] | 13.42 | A, 18 min grad. | 438.0 |
| 146 | 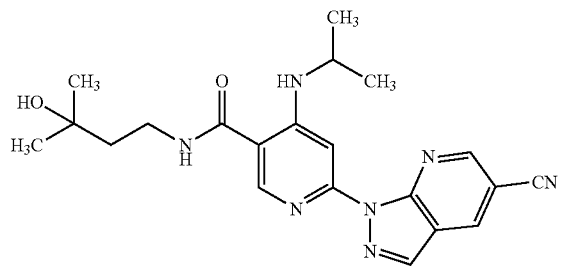 [SMILES: CC(C)Nc1cc(-n2ncc3cc(C#N)cnc32)ncc1C(=O)NCCC(C)(C)O] | 1.44 | E | 408.2 |
| 147 | 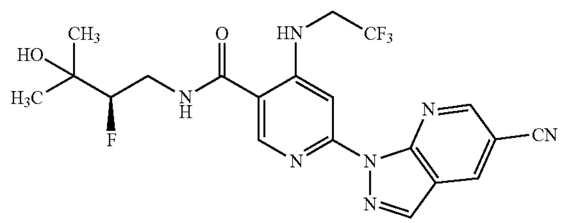 [SMILES: CC(C)(O)[C@H](F)CNC(=O)c1cnc(-n2ncc3cc(C#N)cnc32)cc1NCC(F)(F)F] | 7.50 | B | 465.8 (M+) |
| 148 | 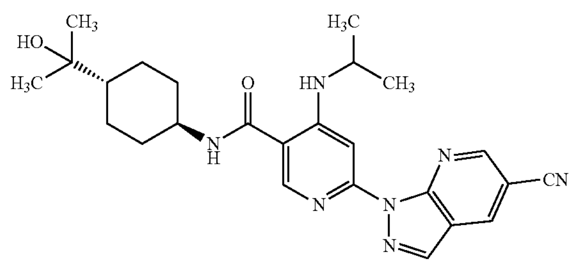 | 7.83 | B | 462.0 |
| 149 | 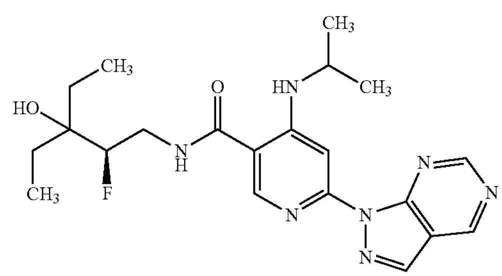 [SMILES: CCC(O)(CC)[C@H](F)CNC(=O)c1cnc(-n2ncc3cncnc32)cc1NC(C)C] | 6.63 | A | 430.0 |
| 150 | 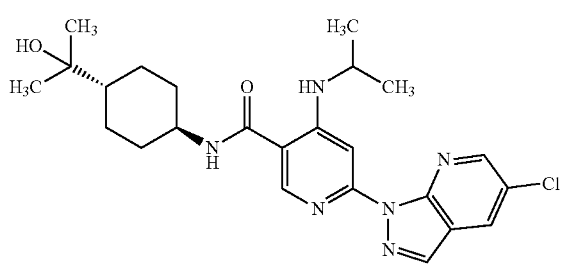 [SMILES: CC(C)Nc1cc(-n2ncc3cc(Cl)cnc32)ncc1C(=O)N[C@H]1CC[C@H](C(C)(C)O)CC1] | 7.09 | A | 471.2 (M+) |

TABLE 7-continued
| Ex. No. | Structure | HPLC rt (min) | HPLC cond. | LCMS |
|---|---|---|---|---|
| 151 | 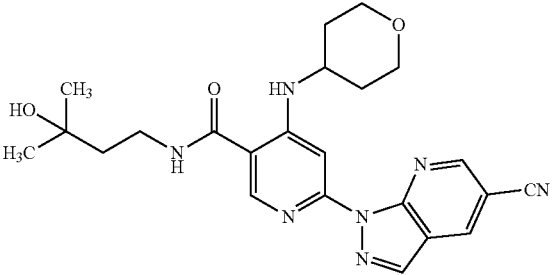 [SMILES: CC(C)(O)CCNC(=O)c1cnc(-n2ncc3cc(C#N)cnc32)cc1NC1CCOCC1] | 1.21 | E | 450.2 |
| 152 | 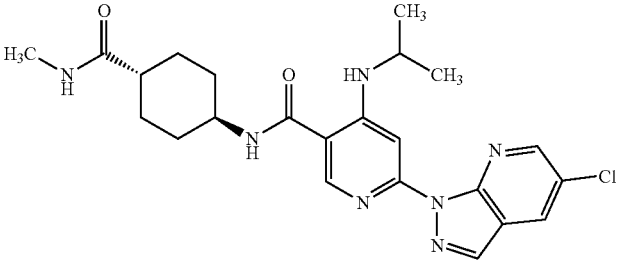 [SMILES: CNC(=O)[C@H]1CC[C@H](NC(=O)c2cnc(-n3ncc4cc(Cl)cnc43)cc2NC(C)C)CC1] | 6.11 | A | 470.2 (M+) |
| 153 | 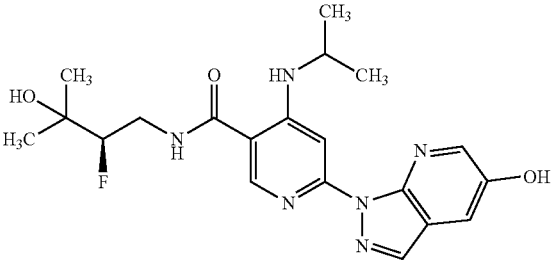 | 1.05 | D | 418.0 |
| 154 | 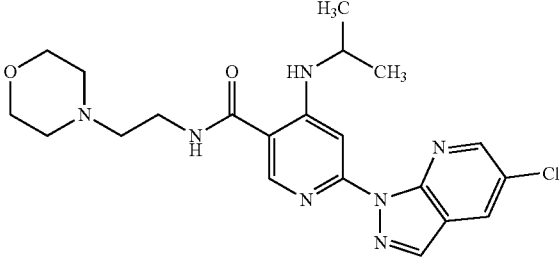 [SMILES: CC(C)Nc1cc(-n2ncc3cc(Cl)cnc32)ncc1C(=O)NCCN1CCOCC1] | 1.52 | C | 444.0 |

TABLE 7-continued

| Ex. No. | Structure | HPLC rt (min) | HPLC cond. | LCMS |
|---|---|---|---|---|
| 155 | 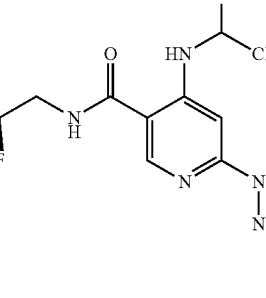 | 1.49 | C | 415.0 |
| 156 | 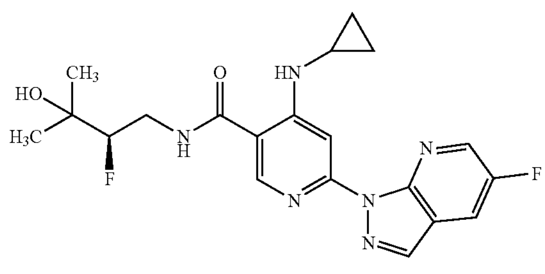 [SMILES: CC(C)(O)[C@H](F)CNC(=O)c1cnc(-n2ncc3cc(F)cnc32)cc1NC1CC1] | 1.09 | D | 417.0 |
| 157 | 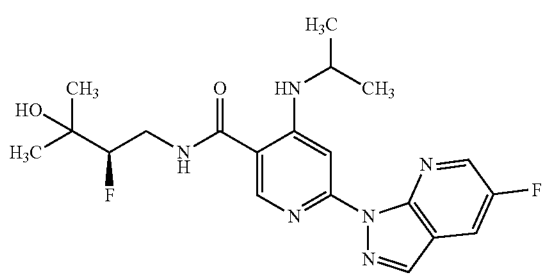 [SMILES: CC(C)Nc1cc(-n2ncc3cc(F)cnc32)ncc1C(=O)NC[C@@H](F)C(C)(C)O] | 1.16 | D | 419.0 |

Example 158

(R)-6-(5-Bromo-1H-pyrazolo[3,4-b]pyridin-1-yl)-N-(2-fluoro-3-hydroxy-3-methylbutyl)-4-(isopropylamino)nicotinamide (158)

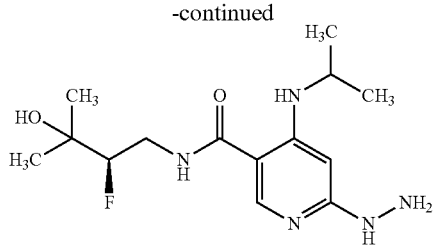

Step 1: (R)-6-Chloro-N-(2-fluoro-3-hydroxy-3-methylbutyl)-4-(isopropylamino) nicotinamide (100 mg, 0.315 mmol) and hydrazine hydrate (3 mL, 0.315 mmol) were heated at 120° C. for 2 hours in a round bottom flask. TLC indicated complete consumption of the starting material and the mixture was concentrated with toluene (2×). The crude material was used directly in the next step.

Step 2: To a stirred solution of (R)—N-(2-fluoro-3-hydroxy-3-methylbutyl)-6-hydrazinyl-4-(isopropylamino)

nicotinamide (50 mg, 0.160 mmol) in 1,4-dioxane (1 mL) was added 5-bromo-2-fluoronicotinaldehyde (32.5 mg, 0.160 mmol), K₂CO₃ (44.1 mg, 0.319 mmol) and CuI (3.04 mg, 0.016 mmol). The mixture was heated at 110° C. for 13 hours in a sealed tube, cooled to room temperature and filtered. The filtrate was concentrated and the product purified via preparative HPLC to afford the desired product (10 mg, 13% yield). LCMS 479.0 (M⁺).

The Examples in Table 8 were prepared according to the general procedure for Example 133 using the appropriate starting material and amine.

TABLE 8

| Ex. No. | Structure | HPLC rt (min) | HPLC cond. | LCMS |
|---|---|---|---|---|
| 159 | 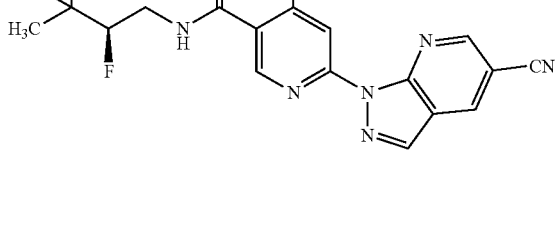 | 1.00 | C | 482.0 |
| 160 | 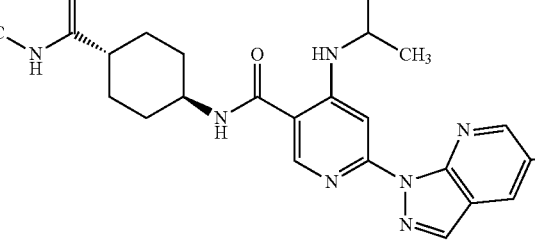 | 1.31 | E | 461.3 |
| 161 | 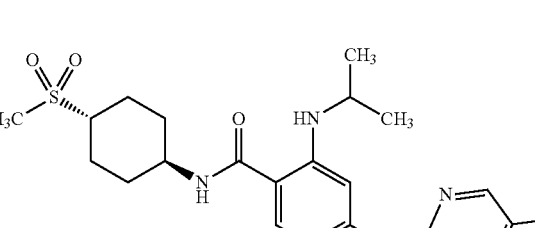 | 1.48 | E | 482.1 |
| 162 | 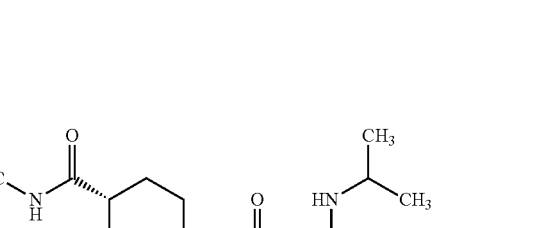 | 1.31 | E | 464.3 |

TABLE 8-continued
| Ex. No. | Structure | HPLC rt (min) | HPLC cond. | LCMS |
|---|---|---|---|---|
| 163 | 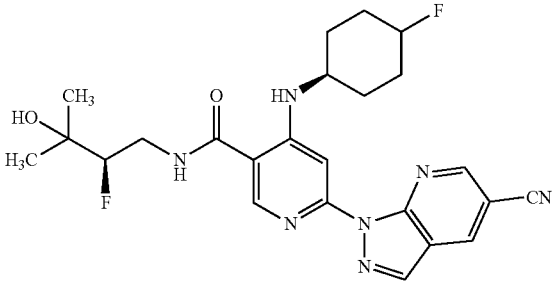 | 1.41 | C | 484.2 |
| 164 | 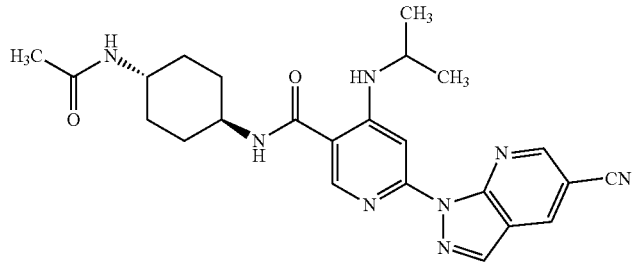 [SMILES: CC(=O)N[C@H]1CC[C@H](NC(=O)c2cnc(-n3ncc4cc(C#N)cnc43)cc2NC(C)C)CC1] | 1.35 | E | 461.3 |
| 165 | 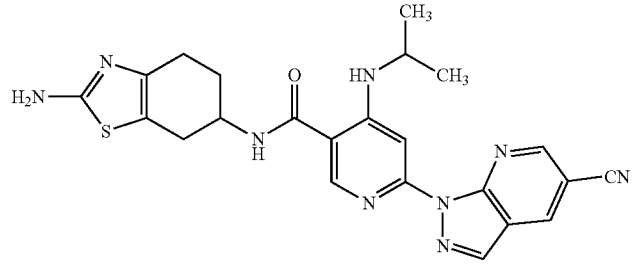 [SMILES: CC(C)Nc1cc(-n2ncc3cc(C#N)cnc32)ncc1C(=O)NC1CCc2nc(N)sc2C1] | 1.41 | E | 474.2 |
| 166 | 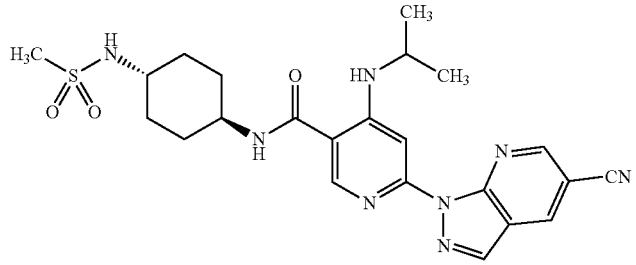 [SMILES: CC(C)Nc1cc(-n2ncc3cc(C#N)cnc32)ncc1C(=O)N[C@H]1CC[C@H](NS(C)(=O)=O)CC1] | 1.51 | E | 497.3 |

Example 167

6-(5-Cyano-1H-pyrazolo[3,4-b]pyridin-1-yl)-N-(2,2-difluoro-3-hydroxy-3-methylbutyl)-4-(isopropylamino)nicotinamide (167)

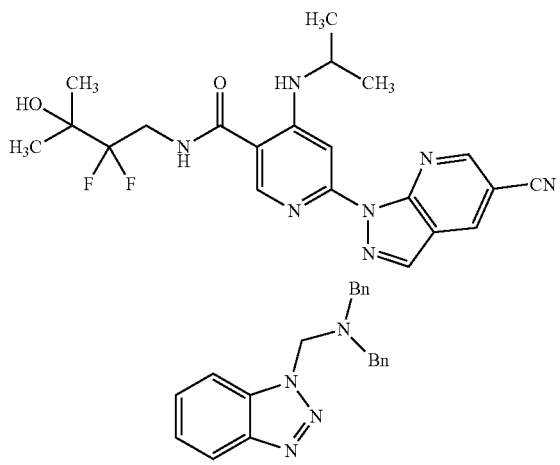

Step 1: To a stirred solution of 1H-benzo[d][1,2,3]triazole (2 g, 16.79 mmol) in MeOH (28 mL) was added dibenzylamine (17.6 mL, 16.79 mmol) and formaldehyde (8.1 mL, 16.79 mmol). The reaction mixture was made homogenous by adding $Et_2O$ (10 mL) to the reaction mixture and refluxed for 18 h. After cooling, the reaction mixture was diluted with $H_2O$ (100 mL) followed by brine solution. A white solid was formed during the wash with brine which was filtered. The residue was washed with $Et_2O$ and dried under high vacuum to obtain the desired product, N-((1H benzo[d][1,2,3]triazol-1-yl)methyl)-N-benzyl-1-phenylmethanamine (4.9 g, 90% yield). $^1$H NMR (400 MHz, $CDCl_3$-d) δ=8.11 (td, J=1.1, 8.1 Hz, 1H), 7.46-7.36 (m, 10H), 7.34-7.25 (m, 2H), 7.24-7.20 (m, 1H), 5.49 (s, 2H), 3.82 (s, 4H).

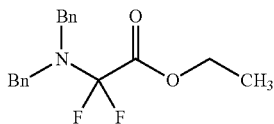 [SMILES: CCOC(=O)C(F)(F)N(Cc1ccccc1)Cc1ccccc1]

Step 2: To a stirred suspension of zinc dust (0.795 g, 12.18 mmol) in THF (20 mL) was added TMSCl (0.662 g, 6.09 mmol), followed by ethyl 2-bromo-2,2-difluoroacetate (1.360 g, 6.70 mmol). The reaction mixture was stirred for 15 min and a solution of N-((1H-benzo[d][1,2,3]triazol-1-yl)methyl)-N-benzyl-1-phenylmethanamine (2 g, 6.09 mmol) in THF (20 mL) was added dropwise. The reaction mixture was allowed to stir for 2 h at room temperature. The reaction mixture was diluted with aqueous $NaHCO_3$ and EtOAC. The aqueous layer was extracted with EtOAc (twice). The organic extracts were combined, dried over $Na_2SO_4$ and concentrated. The crude material was purified by flash column chromatography using silica gel as stationary phase and EtOAc: pet ether (0-10%) as eluent to get ethyl 3-(dibenzylamino)-2,2-difluoropropanoate (1.8 g, 94.6% yield). LC/MS: 334.6 (M+H).

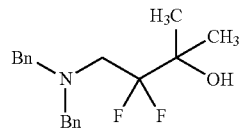

Step 3: To a solution of ethyl 3-(dibenzylamino)-2,2-difluoropropanoate (5.5 g, 16.50 mmol) in THF (50 mL) at 0° C. was added methyl magnesium bromide (3M in diethyl ether) (16.50 mL, 49.5 mmol) dropwise. After completion of the addition the reaction mixture was allowed to stir at room temperature for 2 h. The mixture was cooled to 0° C. and quenched with saturated ammonium chloride solution. The aqueous layer was extracted with ethyl acetate, dried over $Na_2SO_4$ and concentrated to afford 4-(dibenzylamino)-3,3-difluoro-2-methylbutan-2-ol (5 g, 90% yield). LC/MS: 320.2 (M+H).

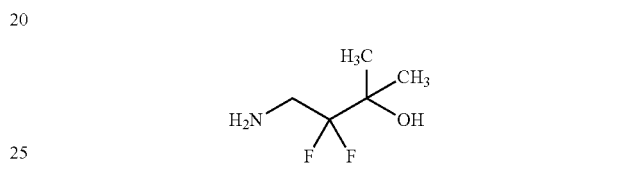

Step 4: A solution of 4-(dibenzylamino)-3,3-difluoro-2-methylbutan-2-ol (5 g, 15.65 mmol) in MeOH (50 mL) was added Pd/C ((2.5 g, 23.49 mmol) and $PdOH_2$ (2.5 g, 15.65 mmol) and then hydrogenated at 1 atm pressure for 4 hrs. The reaction mixture was diluted with ethyl acetate and passed through a small plug of CELITE®. The filtrate was concentrated to afford 4-amino-3,3-difluoro-2-methylbutan-2-ol (2 g, 91% yield). The product was used without further purification. $^1$H NMR (400 MHz, methanol-$d_4$) δ=3.14 (t, J=16.3 Hz, 2H), 1.30 (t, J=1.1 Hz, 6H).

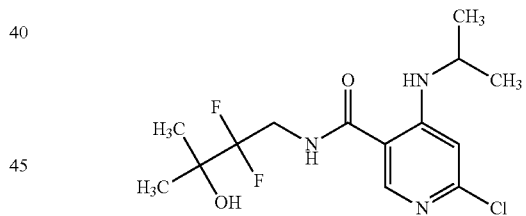

Step 5: To a solution of 6-chloro-4-(isopropylamino)nicotinic acid (1 g, 4.66 mmol) in DMF (10 mL), DIPEA (2.441 mL, 13.98 mmol), was added HATU (1.771 g, 4.66 mmol) and 4-amino-3,3-difluoro-2-methylbutan-2-ol (0.778 g, 5.59 mmol). The reaction mixture was stirred for 2 h, diluted with water and extracted with EtOAc (3×75 mL). The organic layers were combined, washed with 10% $NaHCO_3$ and dried over $Na_2SO_4$. The filtrate was concentrated to afford 6-chloro-N-(2,2-difluoro-3-hydroxy-3-ethylbutyl)-4-(isopropylamino)nicotinamide (1 g, 60% yield). LC/MS 336.2 (M+H).

Step 6: 6-Chloro-N-(2,2-difluoro-3-hydroxy-3-methylbutyl)-4-(isopropylamino) nicotinamide (0.15 g, 0.447 mmol) and 1H-pyrazolo[3,4-b]pyridine-5-carbonitrile (0.064 g, 0.447 mmol) were dissolved in 1,4-dioxane (10 mL) in a pressure tube at room temperature. Xantphos (0.258 g, 0.447 mmol) and $Na_2CO_3$ (0.142 g, 1.340 mmol) were added and the mixture was purged with nitrogen for 20 min. $Pd_2(dba)_3$ (0.205 g, 0.223 mmol) was added to the reaction mixture and purging was continued for another 5 min. The reaction vessel was sealed and heated at 100° C. for 18 h. The reaction mixture was cooled to room temperature and diluted with 15% MeOH:DCM (150 mL) and filtered through CELITE®. The CELITE® was washed with 15% MeOH:DCM (50 mL) and the filtrate was concentrated to get the crude material. The crude material was purified by flash column chromatography using silica gel as stationary phase and 5-6% MeOH/CHCl$_3$ as eluent to afford the compound. The material obtained was further purified by reverse phase HPLC. LC/MS 444.4 (M+H)$^+$. HPLC 7.322 min, Condition A. $^1$H NMR (400 MHz DMSO-d$_6$) δ 9.09-9.03 (m, 2H), 8.89-8.85 (m, 1H), 8.67 (d, J=10.5 Hz, 2H), 8.58-8.53 (m, 1H), 7.42 (s, 1H), 5.41 (bs, 1H), 3.92 (d, J=6.5 Hz, 3H), 1.29-1.22 (m, 12H)

Example 168

(R)—N-(2-Fluoro-3-hydroxy-3-methylbutyl)-4-(isopropylamino)-6-(3-(pyridazin-4-yl)-1H-pyrazol-1-yl)nicotinamide (168)

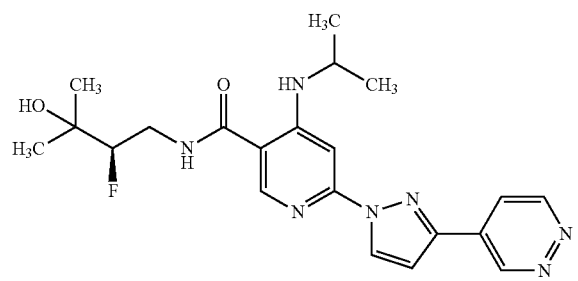

Step 1: In a heavy-walled glass vial, a mixture of 4-bromopyridazine hydrobromide (156 mg, 0.650 mmol), 5-(4,4,5,5-tetramethyl-1,3,2-dioxaborolan-2-yl)-1-((2-(trimethylsilyl)ethoxy)methyl)-1H-pyrazole (422 mg, 1.301 mmol) (prepared via the method of Rault et al., *Tetrahedron Letters*, 47:4665-4669 (2006)), degassed 0.5 M potassium phosphate (aq) (5.20 mL, 2.60 mmol), and THF (5 mL) was degassed with bubbling nitrogen for 5 minutes. XPhos precatalyst, second generation (CAS #[1310584-14-5]) (51.2 mg, 0.065 mmol) was added, and the mixture was degassed for another 5 minutes. The vial was sealed, and the reaction mixture was stirred at room temperature for 96 hours, at which point it was judged to be complete by LCMS. The THF was evaporated with a stream of nitrogen, and the remaining aqueous mixture was extracted three times with diethyl ether (5 mL). The combined ether phases were washed once with saturated sodium carbonate and once with brine, then dried over sodium sulfate and concentrated in vacuo. The residue was chromatographed via MPLC over a 24 g silica gel column, eluting at 40 mL/min with 15-95% ethyl acetate/hexanes. Fractions containing the product were pooled and concentrated in vacuum to yield 4-(1-((2-(trimethylsilyl)ethoxy)methyl)-1H-pyrazol-5-yl)pyridazine (123 mg, 0.445 mmol, 68.4% yield) as a colorless oil. LCMS=276.5 (M+H)$^+$.

Step 2: A solution of 4-(1-((2-(trimethylsilyl)ethoxy)methyl)-1H-pyrazol-5-yl)pyridazine (123 mg, 0.445 mmol) in dichloromethane (1 mL) was stirred at room temperature for 2 hours, at which point the reaction mixture was judged to be complete by LCMS based on the complete consumption of starting material, and a single product peak with m/z=177. The mixture was concentrated in vacuo, and the residue was concentrated twice from dichloromethane to remove residual TFA. The residue was stirred in saturated sodium bicarbonate (1.5 mL) for 5 minutes, then the turbid mixture was extracted 4× with ethyl acetate (3 mL). The combined organic phases were dried over sodium sulfate and concentrated in vacuo. The residue was triturated with diethyl ether (3 mL), and the resulting amber powder was collected by filtration, rinsed twice with diethyl ether (0.5 mL), and dried under vacuum to yield 42 mg of amber powder. LCMS of this material detects m/z=177.0, which was consistent with (3-(pyridazin-4-yl)-1H-pyrazol-1-yl)methanol, resulting from partial decomposition of the SEM protecting group. In a 2-dram vial, the powder was suspended in ethanol (1 mL), and the mixture was treated with 5 M HCl in water (0.445 mL, 2.225 mmol) (5 eq). The vial was capped, and the reaction mixture was stirred at 60° C. for 18 hours. The mixture was concentrated in vacuo, and the residue was treated carefully with saturated sodium bicarbonate (1 mL). The turbid mixture was stirred for 10 minutes, then extracted 4× with ethyl acetate (2 mL). The combined organic phases were dried over sodium sulfate and concentrated in vacuo to yield 4-(1H-pyrazol-3-yl)pyridazine (29 mg, 0.198 mmol, 44.6% yield). LCMS=147.3 (M+H)$^+$.

Step 3: In a 2 mL microwave vial, a mixture of ethyl 6-chloro-4-(isopropylamino) nicotinate (46.8 mg, 0.193 mmol), 4-(1H-pyrazol-3-yl)pyridazine (31 mg, 0.212 mmol), and NaOtBu (37.1 mg, 0.386 mmol) in toluene (1 mL) was degassed with bubbling nitrogen for 5 minutes. The mixture was treated with tBu XPhos precatalyst, first generation (CAS #[1142811-12-8]) (13.24 mg, 0.019 mmol) and degassed for another 5 minutes. The vial was sealed, and the reaction mixture was heated with stirring at 150° C. for 20 minutes, at which point it was judged to be complete by LCMS. The toluene was evaporated, and the residue was taken up in 1:1 methanol/water (2 mL). The mixture was treated with LiOH (6.93 mg, 0.289 mmol), and the reaction mixture was stirred for 2 hours, with occasional gentle heating via heat gun. LCMS shows that the reaction was essentially complete. The mixture was concentrated in vacuo, and the residue was concentrated twice from isopropanol and dried under vacuum to yield lithium 4-(isopropylamino)-6-(3-(pyridazin-4-yl)-1H-pyrazol-1-yl)nicotinate as a brown solid which was used as-is in the next step. LCMS=325.2 (M+H)$^+$ of the protonated carboxylic acid.

Step 4: A stirring mixture of (R)-4-amino-3-fluoro-2-methylbutan-2-ol (46.0 mg, 0.380 mmol), sodium 4-(isopropylamino)-6-(3-(pyridazin-4-yl)-1H-pyrazol-1-yl)nicotinate (65.8 mg, 0.19 mmol), and TEA (0.053 mL, 0.380 mmol) was treated with BOP (126 mg, 0.285 mmol). The reaction mixture was stirred at room temperature for 2 hours, at which point it was judged to be complete by LCMS based on the complete consumption of the starting nicotinate. The reaction mixture was concentrated in vacuo. The crude material was purified via preparative LC/MS with the following conditions: Column: 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 0-100% B over 20 minutes, then a 0-minute hold at 100% B; Flow: 20 mL/min. Fractions containing the desired product were combined and dried via centrifugal evaporation to yield (R)—N-(2-fluoro-3-hydroxy-3-methylbutyl)-4-(isopropylamino)-6-(3-(pyridazin-4-yl)-1H-pyrazol-1-yl)nicotinamide (21 mg, 0.045 mmol, 23.53% yield), 98264-072-01. LCMS=428.2 (M+H)$^+$. HPLC rt=1.32 min, Conditions E. $^1$H NMR (500 MHz, DMSO-d$_6$) δ 9.88 (s, 1H), 9.35 (d, J=4.9 Hz, 1H), 8.85-8.76 (m, 2H), 8.69 (d, J=7.9 Hz, 1H), 8.56 (s, 1H), 8.23 (dd, J=5.5, 1.8 Hz, 1H), 7.40 (d, J=2.4 Hz, 1H), 7.30 (s, 1H), 4.45-4.28 (m, 1H), 3.99-3.88 (m, 1H), 3.81-3.66 (m, 1H), 1.27 (d, J=6.1 Hz, 6H), 1.18 (d, J=6.7 Hz, 6H). Note that one proton from the fluoroalkyl side-chain and the isopropyl methyl proton are obscured by the water signal at 3.7-3.3 ppm in this spectrum.

Example 169

(R)-6-(5-Cyano-1H-pyrazolo[3,4-b]pyridin-1-yl)-4-((2,2-difluoro-3-hydroxy-3-methylbutyl)amino)-N-(2-fluoro-3-hydroxy-3-methylbutyl)nicotinamide (169)

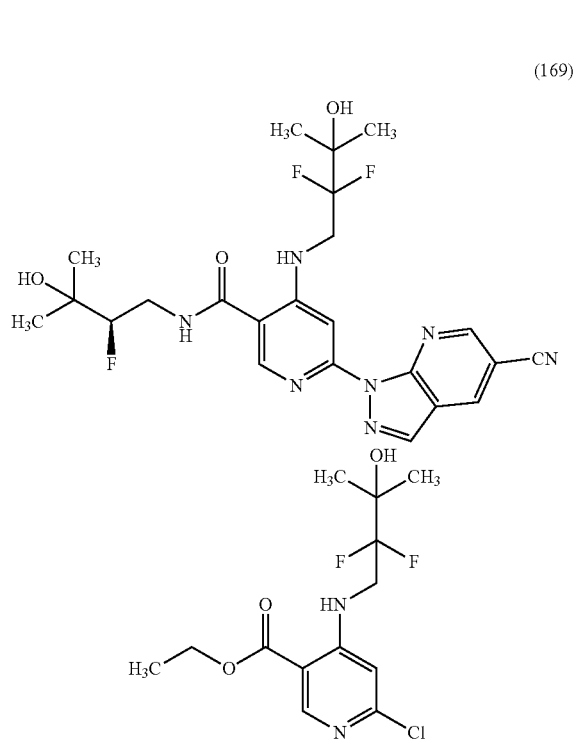

Step 1: To a stirred solution of ethyl 4,6-dichloronicotinate (0.5 g, 2.272 mmol) and 4-amino-3,3-difluoro-2-methylbutan-2-ol (0.379 g, 2.73 mmol) in DMA (2 mL) was added DIPEA (1.191 mL, 6.82 mmol). The reaction mixture was stirred for 18 h then diluted with water and extracted with ethyl acetate (3×75 mL). The extracts were dried over $Na_2SO_4$, filtered and concentrated to get the crude material which was purified by column chromatography (12 g, 40% EtOAc: pet ether). Ethyl 6-chloro-4-((2,2-difluoro-3-hydroxy-3-methylbutyl)amino)nicotinate (0.7 g, 95% yield) was obtained. LC/MS 323.2 (M+H).

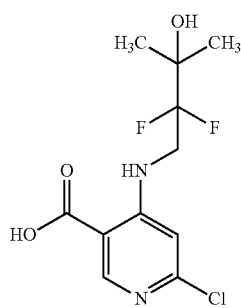 [SMILES: CC(C)(O)C(F)(F)CNc1cc(Cl)ncc1C(=O)O]

Step 2: To a solution of ethyl 6-chloro-4-((2,2-difluoro-3-hydroxy-3-methylbutyl)amino)nicotinate (0.3 g, 0.930 mmol) in ethanol (5 mL) and water (2 mL) was added lithium hydroxide (0.067 g, 2.79 mmol) and the reaction mixture was stirred at room temperature for 2 h. The reaction mixture was concentrated completely to dryness and the residue was acidified with 1.5N HCl solution to pH 4-5. The resulting solid was filtered to afford 6-chloro-4-((2,2-difluoro-3-hydroxy-3-methylbutyl)amino)nicotinic acid (0.25 g, 90% yield) as off-white solid. LC/MS 295 (M+H).

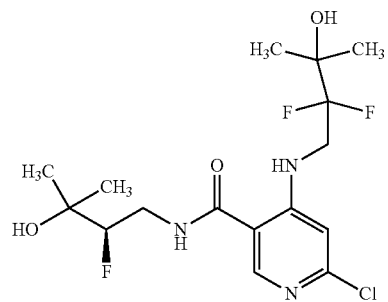 [SMILES: CC(C)(O)[C@H](F)CNC(=O)c1cnc(Cl)cc1NCC(F)(F)C(C)(C)O]

Step 3: To a solution of 6-chloro-4-((2,2-difluoro-3-hydroxy-3-methylbutyl)amino)nicotinic acid (0.4 g, 1.357 mmol) in DMF (5 mL) was added DIPEA (0.711 mL, 4.07 mmol), HATU (0.516 g, 1.357 mmol) and (R)-4-amino-3-fluoro-2-methylbutan-2-ol (0.197 g, 1.629 mmol) and the reaction mixture was stirred at room temperature for 2 h. The reaction mixture was diluted with water (80 mL) and extracted with ethyl acetate (3×80 mL). The extracts were dried over $Na_2SO_4$, filtered and concentrated to afford the crude material which was purified by column chromatography (24 g, 80% EtOAc: pet ether). The compound, (R)-6-chloro-4-((2,2-difluoro-3-hydroxy-3-methylbutyl)amino)-N-(2-fluoro-3-hydroxy-3-methylbutyl)nicotinamide (180 mg, 32.7% yield) was isolated as a light brown oil. LC/MS 398.2 (M+H).

Step 4: A mixture of 1H-pyrazolo[3,4-b]pyridine-5-carbonitrile (36.2 mg, 0.251 mmol) in dioxane (10 mL) in a pressure tube at room temperature was degassed by bubbling nitrogen gas into the reaction mixture for 5 min. Xantphos (29.1 mg, 0.050 mmol) and $K_2CO_3$ (104 mg, 0.754 mmol) was added into the reaction mixture and degassed for another 5 min. (R)-6-Chloro-4-((2,2-difluoro-3-hydroxy-3-methylbutyl)amino)-N-(2-fluoro-3-hydroxy-3-methylbutyl)nicotinamide (100 mg, 0.251 mmol) was added into the reaction mixture and degassed for another 5 min. $Pd_2(dba)_3$ (46.0 mg, 0.050 mmol) was added to the reaction mixture and purging was continued for another 5 min. The reaction mixture temperature was raised to 100° C. and stirred for 18 h in a closed condition. The reaction mixture was cooled to room temperature, diluted with 15% MeOH:DCM (150 mL) and filtered through CELITE®. The CELITE® was washed with 15% MeOH: DCM (50 mL) and the filtrate was concentrated to afford the crude material. The crude material was purified by reverse phase HPLC. LC/MS 506.2 (M+H)$^+$. HPLC 7.322 min, Condition F. $^1$H NMR (400 MHz, MeOH-d$_4$) δ=8.98 (d, J=2.0 Hz, 1H), 8.84 (d, J=2.0 Hz, 1H), 8.61-8.54 (m, 2H), 7.92 (s, 1H), 4.55-4.38 (m, 1H), 4.03 (t, J=16.1 Hz, 4H), 3.51 (d, J=1.5 Hz, 2H), 1.42-1.38 (m, 6H), 1.32 (d, J=2.0 Hz, 6H).

Example 170

(R)—N-(2-Fluoro-3-hydroxy-3-methylbutyl)-4-(isopropylamino)-6-(9H-purin-9-yl) nicotinamide

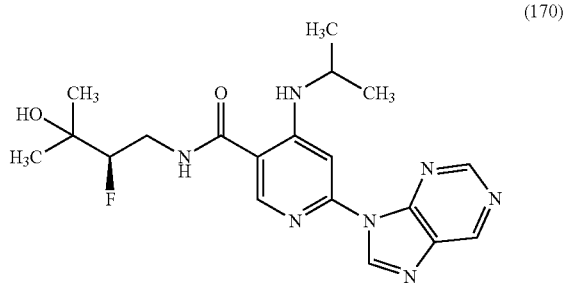 [SMILES: CC(C)Nc1cc(-n2cnc3cncnc32)ncc1C(=O)NC[C@@H](F)C(C)(C)O]

(170)

The title compound was prepared from (R)-6-chloro-N-(2-fluoro-3-hydroxy-3-methylbutyl)-4-(isopropylamino)nicotinamide and purine via the conditions used in Example 1. LCMS detects m/z=401.6 (M+). HPLC rt=1.17, method F. $^1$H NMR (500 MHz, DMSO-$d_6$) δ 9.32 (s, 1H), 9.30 (s, 1H), 9.12 (s, 1H), 8.85 (t, J=5.4 Hz, 1H), 8.72 (d, J=6.4 Hz, 1H), 8.63 (s, 1H), 7.92 (s, 1H), 4.89 (br. s., 1H), 4.50-4.27 (ddd, J=1.5, 9.9, 49.4 Hz, 1H), 3.89-3.64 (m, 2H), 1.31 (d, J=5.9 Hz, 6H), 1.18 (d, J=6.4 Hz, 6H).

Example 171

(R)-6-(2-Amino-9H-purin-9-yl)-N-(2-fluoro-3-hydroxy-3-methylbutyl)-4-(isopropylamino)nicotinamide

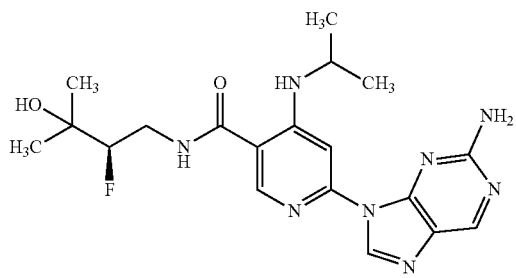

(171)

In a 5 mL microwave vial, a mixture of (R)-6-chloro-N-(2-fluoro-3-hydroxy-3-methylbutyl)-4-(isopropylamino)nicotinamide (35 mg, 0.110 mmol), 7H-purin-2-amine (22.32 mg, 0.165 mmol), and powdered phosphoric acid, potassium salt (58.4 mg, 0.275 mmol) in toluene (1 mL) was degassed with bubbling nitrogen for 5 minutes. The mixture was treated with di-tert-butyl(2',4',6'-triisopropyl-3,4,5,6-tetramethyl-[1,1'-biphenyl]-2-yl)phosphine (21.18 mg, 0.044 mmol) and Pd$_2$(dba)$_3$ (10.09 mg, 0.011 mmol), and degassed for another 5 minutes. The vial was sealed, and the reaction mixture was heated with stirring at 100° C. for 18 hours, at which point the reaction mixture was judged to be complete by LCMS. The toluene was evaporated, and the residue was taken up in DMF (2 mL). The solution was filtered and purified via preparative LC/MS with the following conditions: Column: Waters XBridge C18, 19×100 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 10 minutes, then a 5-minute hold at 100% B; Flow: 20 mL/min. Fractions containing the desired product were combined and dried via centrifugal evaporation to yield (R)-6-(2-amino-9H-purin-9-yl)-N-(2-fluoro-3-hydroxy-3-methylbutyl)-4-(isopropylamino)nicotinamide (14 mg, 29% yield). LCMS=417.2 (M+H)$^+$. HPLC rt=1.13 min, Conditions E. $^1$H NMR (500 MHz, DMSO-$d_6$) δ 8.82-8.75 (m, 2H), 8.71 (s, 1H), 8.64 (d, J=7.4 Hz, 1H), 8.57 (s, 1H), 7.97 (s, 1H), 6.79 (br. s., 2H), 4.87 (s, 1H), 4.44-4.29 (m, 1H), 3.90 (dq, J=12.9, 6.4 Hz, 1H), 3.79-3.65 (m, 2H), 1.28 (d, J=6.4 Hz, 6H), 1.18 (d, J=6.9 Hz, 6H).

Example 172

(R)—N-(2-Fluoro-3-hydroxy-3-methylbutyl)-6-(2-((2-hydroxyethyl)amino)-9H-purin-9-yl)-4-(isopropylamino)nicotinamide

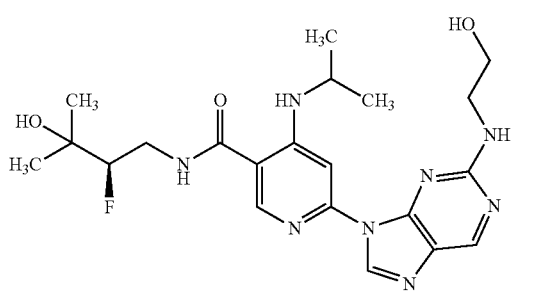

(172)

Step 1: In a sealed vial, a stirring mixture of 2-chloro-9H-purine (69 mg, 0.446 mmol) and 2-aminoethanol (0.243 mL, 4.02 mmol) in ethanol (0.75 mL) was heated at 160° C. for 1 hour, at which point the reaction mixture was judged to be complete by LCMS. The ethanol was evaporated, and the residue was chromatographed via MPLC over a 12 g silica gel column, eluting at 30 mL/min with a 5% to 15% methanol/methylene chloride gradient over 12 column volumes, then with 15% methanol/methylene chloride to complete the elution of the major product. Fractions containing the product were pooled and concentrated in vacuo to yield 2-((9H-purin-2-yl)amino)ethanol (43 mg, 0.240 mmol, 53.8% yield). LCMS m/z=180 (M+H)$^+$.

Step 2: In a 5 mL microwave vial, a mixture of (R)-6-chloro-N-(2-fluoro-3-hydroxy-3-methylbutyl)-4-(isopropylamino)nicotinamide (30 mg, 0.094 mmol), 2-((9H-purin-2-yl)amino)ethanol (20.30 mg, 0.113 mmol), and powdered phosphoric acid, potassium salt (40.1 mg, 0.189 mmol) in toluene (0.5 mL) was degassed with bubbling nitrogen for 5 minutes. The mixture was treated with di-tert-butyl(2',4',6'-triisopropyl-3,4,5,6-tetramethyl-[1,1'-biphenyl]-2-yl)phosphine (9.08 mg, 0.019 mmol) and Pd$_2$(dba)$_3$ (4.32 mg, 4.72 µmol), and degassed for another 5 minutes. The vial was sealed, and the reaction mixture was heated with stirring at 110° C. for 6 hours, at which point it was judged to be complete by LCMS. The solvents were evaporated, and the residue was taken up in DMF (2 mL). The product was isolated from the solution via preparative LC/MS with the following conditions: Column: Waters XBridge C18, 19×200 mm, 5-m particles; Mobile Phase A: 5:95 acetonitrile:water with 10-mM ammonium acetate; Mobile Phase B: 95:5 acetonitrile:water with 10-mM ammonium acetate; Gradient: 5-50% B over 25 minutes, then a 10-minute hold at 50% B; Flow: 25 mL/min. Fractions containing the desired product were combined and dried via centrifugal evaporation to yield (R)—N-(2-fluoro-3-hydroxy-3-methylbutyl)-6-(2-((2-hydroxyethyl)amino)-9H-purin-9-yl)-4-(isopropylamino)nicotinamide (24 mg, 0.052 mmol, 55.2% yield). LCMS m/z=461.2 (M+H)$^+$. HPLC rt=1.18 min, Conditions E. $^1$H NMR (500 MHz, DMSO-d$_6$) δ 8.82 (s, 1H), 8.78 (t, J=5.5 Hz, 1H), 8.74 (s, 1H), 8.66 (d, J=7.3 Hz, 1H), 8.57 (s, 1H), 8.04 (br. s., 1H), 7.33 (br. s., 1H), 4.89 (s, 1H), 4.77 (t, J=5.2 Hz, 1H), 4.44-4.28 (m, 1H), 3.84 (d, J=7.3 Hz, 1H), 3.78-3.64 (m, 1H), 3.61 (q, J=5.7 Hz, 2H), 3.51-3.45 (m, 3H, peaks partially obscured by water peak), 1.28 (d, J=6.1 Hz, 6H), 1.17 (d, J=6.7 Hz, 6H).

Example 173

6-(5-Cyano-1H-pyrrolo[2,3-b]pyridin-1-yl)-N-((1s,4s)-4-hydroxy-4-(1-methyl-1H-pyrazol-5-yl)cyclohexyl)-4-(isopropylamino)nicotinamide (173)

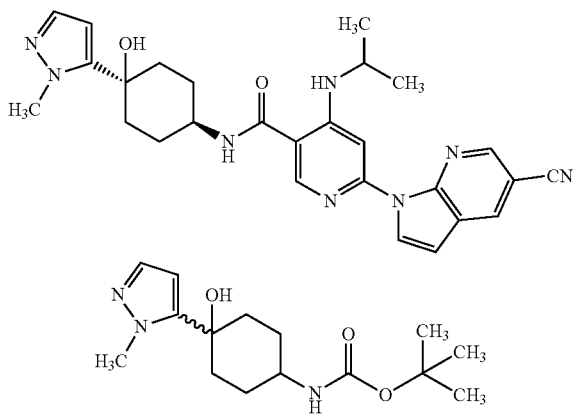

Step 1: A solution of 1-methyl-1H-pyrazole (1.012 mL, 12.18 mmol) in THF (50 mL) was cooled to −78° C. and n-BuLi (4.87 mL, 12.18 mmol) was added. The mixture was allowed to stir at room temperature for 1 hr. Next, a solution of tert-butyl(4-oxocyclohexyl)carbamate (1.299 g, 6.09 mmol) in THF (10 mL) was added and the mixture stirred at room temperature overnight. The reaction mixture was worked up by quenching with water, evaporating the THF, adding EtOAc, and washing the product with water (2×). The organic layer was dried (sodium sulfate) and the solvent removed in vacuo to yield 1.061 g of a viscous yellow oil which was purified via column chromatography to afford a mixture of cis and trans isomers (0.85 g, 46% yield). $^1$H NMR (400 MHz, CDCl$_3$-d) δ 7.40-7.33 (m, 1H), 6.24-6.00 (m, 1H), 5.31 (s, 1H), 4.48 (br. s., 1H), 4.12-4.00 (m, 3H), 2.23-1.80 (m, 6H), 1.73-1.59 (m, 2H), 1.50-1.43 (m, 9H). Note that there are two sets of vinyl peaks in a ration of 3:1 designating the ratio of trans/cis products.

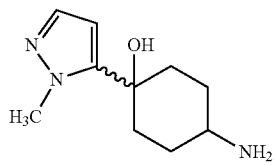

Step 2: tert-Butyl (4-hydroxy-4-(1-methyl-1H-pyrazol-5-yl)cyclohexyl) carbamate (0.85 g, 2.88 mmol) was dissolved in DCM (20 mL) and to this solution was added HCl (4N in dioxane) (7.19 mL, 28.8 mmol). The contents were stirred at room temperature. The reaction appeared to be precipitating and additional MeOH was added to help make the product more soluble. The reaction mixture was evaporated and the residue evaporated from methylene chloride 3× to remove traces of HCl. The solid thus obtained was dried under house vacuum to afford 0.75 g of a light yellow solid which was used without further purification: $^1$H NMR (400 MHz, DMSO-d$_6$) δ 8.31-8.14 (m, 3H), 7.39 (d, J=2.0 Hz, 1H), 6.14 (d, J=2.0 Hz, 1H), 3.98 (s, 3H), 3.08-2.95 (m, 1H), 2.08-1.96 (m, 2H), 1.82 (br. s., 5H).

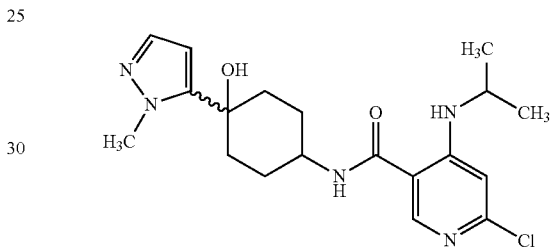

Step 3: A 4-amino-1-(1-methyl-1H-pyrazol-5-yl)cyclohexanol, HCl (200 mg, 0.863 mmol), 6-chloro-4-(isopropylamino)nicotinic acid (185 mg, 0.863 mmol), Hunig's Base (0.754 mL, 4.32 mmol), and PyBOP (898 mg, 1.726 mmol) were mixed and stirred in DMF (3 mL) at room temperature. The reaction mixture was quenched with 1N NaOH, and EtOAc was added. The layers were separated and the organic layer rinsed with 1N NaOH (2×), brine (1×), dried (sodium sulfate) and the solvent removed in vacuo to yield 1.25 g of a brown oily solid. The residue was purified via column chromatography to afford 245 mg (69% yield) of a mixture of 4-5:1 ratio of trans to cis isomers. $^1$H NMR (400 MHz, DMSO-d$_6$) δ 8.46 (d, J=7.7 Hz, 1H), 8.42-8.25 (m, 2H), 7.33-7.19 (m, 1H), 6.74-6.61 (m, 1H), 6.25-6.02 (m, 1H), 5.22-5.08 (m, 1H), 4.01-3.91 (m, 3H), 3.88-3.69 (m, 2H), 2.11-1.60 (m, 7H), 1.20 (d, J=6.6 Hz, 1H), 1.16 (d, J=6.4 Hz, 5H), 1.09-1.09 (m, 1H).

Step 4: A mixture of 6-chloro-N-(4-hydroxy-4-(1-methyl-1H-pyrazol-5-yl)cyclohexyl)-4-(isopropylamino)nicotinamide (40 mg, 0.102 mmol), 1H-pyrrolo[2,3-b]pyridine-5-carbonitrile (29.2 mg, 0.204 mmol), potassium carbonate (56.4 mg, 0.408 mmol), and 6:1 t-BuOH/DMA (1.5 mL) were mixed in a 5 mL microwave vial containing a magnetic stir bar and degassed with bubbling nitrogen for 5 minutes. The mixture was treated with BrettPhos precatalyst (4.08 mg, 5.10 mol) and degassed for another 5 minutes. The vial was sealed and the reaction heated in the microwave with stirring at 145° C. for 15 minutes. The reaction mixture was evaporated, diluted with DMF, filtered, purified via preparative HPLC to afford the trans isomer product (17.5 mg, 33% yield). $^1$H NMR (500 MHz, DMSO-d$_6$) δ 8.81 (d, J=1.7 Hz, 1H), 8.68 (d, J=1.7 Hz, 1H), 8.65-8.59 (m, 2H), 8.53 (d, J=4.0 Hz, 1H), 8.42 (d, J=7.7 Hz, 1H), 8.08 (s, 1H), 7.26 (s, 1H), 6.89 (d, J=4.0 Hz, 1H), 6.11 (d, J=1.3 Hz, 1H), 3.97 (s, 3H), 3.88-3.71 (m, 2H), 2.05 (d, J=12.1 Hz, 2H), 1.95-1.82 (m, 2H), 1.78-1.65 (m, 4H), 1.29 (d, J=6.4 Hz, 7H); LCMS 499.3 (M+H)+; HPLC rt 2.10 min, Conditions E. The minor cis isomer product was obtained in 8% yield.

Example 174

6-(5-Cyano-1H-pyrrolo[2,3-b]pyridin-1-yl)-N-((1s,4s)-4-fluoro-4-(1-methyl-1H-pyrazol-5-yl)cyclohexyl)-4-(isopropylamino)nicotinamide (174)

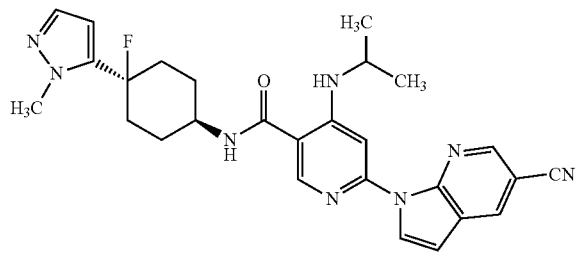

To a suspension of 6-(5-cyano-1H-pyrrolo[2,3-b]pyridin-1-yl)-N-((1s,4s)-4-hydroxy-4-(1-methyl-1H-pyrazol-5-yl)cyclohexyl)-4-(isopropylamino)nicotinamide (8.3 mg, 0.017 mmol) in dry DCM (0.5 mL) at −0° C. under N₂ was added DAST (4.40 μl, 0.033 mmol). The mixture was kept at 0° C. for 0.5 h. Additional DAST (4.40 μl, 0.033 mmol) was added and stirred for 30 min. The reaction mixture was quenched by adding 1M aqueous NaOH. The mixture was diluted with EtOAc, the layers separated and the organic layer washed with brine, dried over Na₂SO₄, and concentrated to yield 10.6 mg of a light yellow solid. The crude material was purified via preparative HPLC to afford 2.1 mg (23% yield) of the desired product. ¹H NMR (500 MHz, DMSO-d₆) δ 8.80 (s, 1H), 8.66 (s, 1H), 8.60-8.55 (m, 2H), 8.52 (d, J=3.7 Hz, 1H), 8.47 (d, J=7.7 Hz, 1H), 8.08 (s, 1H), 7.35 (s, 1H), 6.89 (d, J=4.0 Hz, 1H), 6.27 (s, 1H), 3.99-3.87 (m, 4H), 3.83-3.72 (m, 1H), 2.30 (br. s., 2H), 2.08-1.71 (m, 6H), 1.28 (d, J=6.1 Hz, 6H); LCMS 501.4 (M+H)+; HPLC rt 1.71 min, Conditions E.

Separate HPLC fractions contained the cis isomer which was also isolated in 20% yield.

The Examples in Table 9 were prepared using the methods outlined for Examples 173 and 174 using the appropriate starting material and amine.

TABLE 9

| Ex. No. | Structure | HPLC rt (min) | HPLC cond. | LCMS |
|---|---|---|---|---|
| 175 | 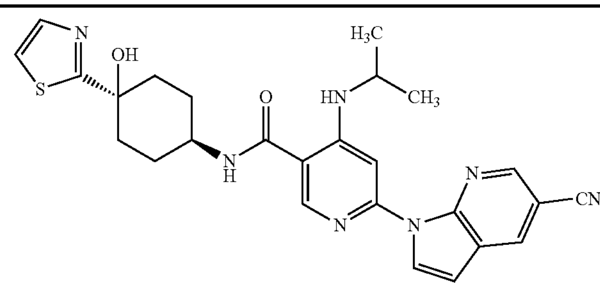 | 1.90 | E | 502.1 |
| 176 | 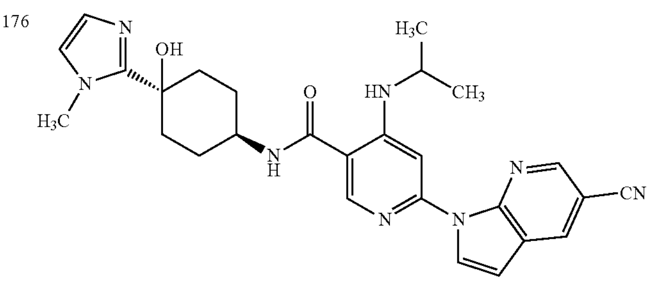 | 1.55 | E | 499.3 |
| 177 | 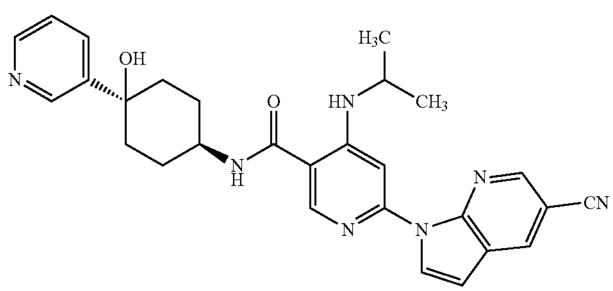 [SMILES: CC(C)Nc1cc(-n2ccc3cc(C#N)cnc32)ncc1C(=O)N[C@H]1CC[C@](O)(c2cccnc2)CC1] | 1.74 | E | 496.3 |

TABLE 9-continued

| Ex. No. | Structure | HPLC rt (min) | HPLC cond. | LCMS |
|---|---|---|---|---|
| 178 | 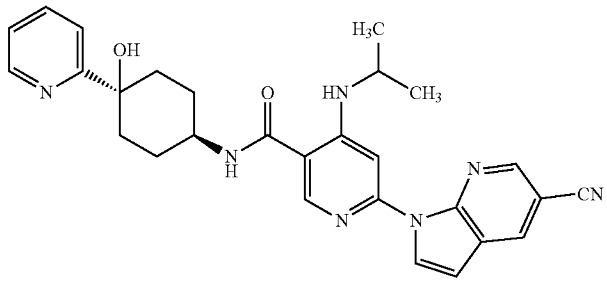 [SMILES: CC(C)Nc1cc(-n2ccc3cc(C#N)cnc32)ncc1C(=O)N[C@H]1CC[C@](O)(c2ccccn2)CC1] | 1.92 | E | 496.3 |
| 179 | 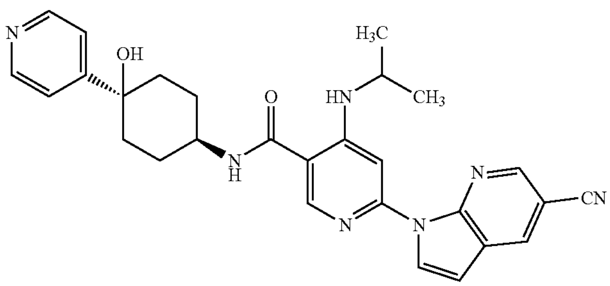 [SMILES: CC(C)Nc1cc(-n2ccc3cc(C#N)cnc32)ncc1C(=O)N[C@H]1CC[C@](O)(c2ccncc2)CC1] | 1.75 | E | 496.4 |
| 180 | 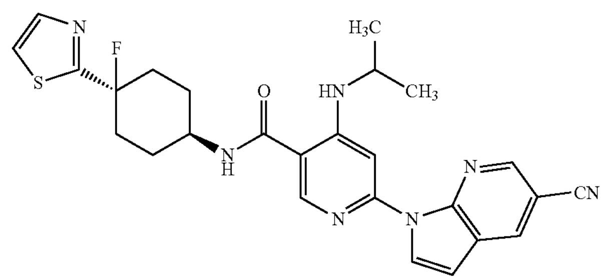 [SMILES: CC(C)Nc1cc(-n2ccc3cc(C#N)cnc32)ncc1C(=O)N[C@H]1CC[C@](F)(c2nccs2)CC1] | 2.22 | E | 504.4 |
| 181 | 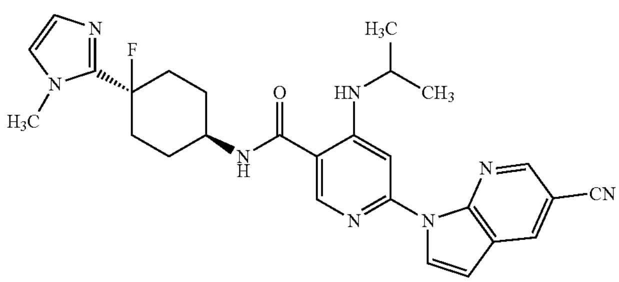 [SMILES: CC(C)Nc1cc(-n2ccc3cc(C#N)cnc32)ncc1C(=O)N[C@H]1CC[C@](F)(c2nccn2C)CC1] | 1.92 | E | 501.3 |
| 182 | 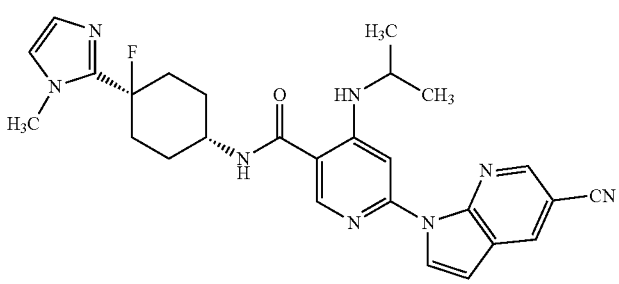 [SMILES: CC(C)Nc1cc(-n2ccc3cc(C#N)cnc32)ncc1C(=O)N[C@H]1CC[C@@](F)(c2nccn2C)CC1] | 2.04 | E | 501.3 |

Example 183

6-(5-Cyano-1H-pyrrolo[2,3-b]pyridin-1-yl)-N-(2,4-dioxo-1,3-diazaspiro[4.5]decan-8-yl)-4-(isopropylamino)nicotinamide (183)

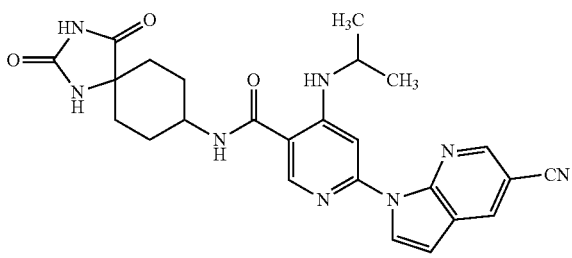

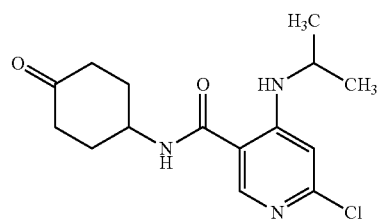 [SMILES: CC(C)Nc1cc(Cl)ncc1C(=O)NC1CCC(=O)CC1]

Step 1: 4-Aminocyclohexanone, HCl (200 mg, 1.337 mmol), 6-chloro-4-(isopropylamino)nicotinic acid (287 mg, 1.337 mmol), Hunig's Base (2.335 mL, 13.37 mmol), and PyBOP (1391 mg, 2.67 mmol) were added to DMF (5 mL). The mixture was stirred at room temperature overnight. The reaction mixture was quenched with 1N NaOH, and EtOAc was added. The layers were separated and the organic layer rinsed with 1N NaOH (2×), brine (1×), dried (sodium sulfate) and the solvent removed in vacuo to yield 1.10 g of an amber oil which was purified via column chromatography to afford the desired product (0.314 g, 76% yield) as an off-white solid. $^1$H NMR (400 MHz, DMSO-$d_6$) δ 8.47-8.41 (m, 1H), 8.37 (s, 2H), 6.69 (s, 1H), 4.40-4.12 (m, 1H), 3.76 (dd, J=13.8, 6.5 Hz, 1H), 2.49-2.42 (m, 2H), 2.36-2.23 (m, 2H), 2.13-1.97 (m, 2H), 1.86-1.70 (m, 2H), 1.17 (d, J=6.4 Hz, 6H); LCMS 310.1 (M+H)$^+$.

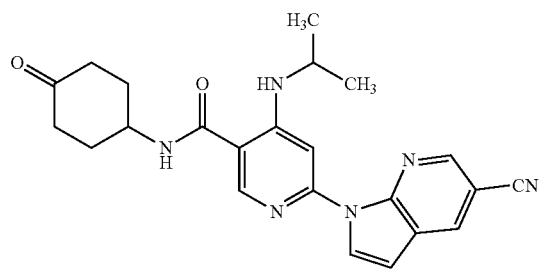 [SMILES: CC(C)Nc1cc(-n2ccc3cc(C#N)cnc32)ncc1C(=O)NC1CCC(=O)CC1]

Step 2: A mixture of 6-chloro-4-(isopropylamino)-N-(4-oxocyclohexyl) nicotinamide (40 mg, 0.129 mmol), 1H-pyrrolo[2,3-b]pyridine-5-carbonitrile (37.0 mg, 0.258 mmol), potassium carbonate (71.4 mg, 0.516 mmol), and 6:1 t-BuOH/DMA (1.5 mL) were mixed in a 5 mL microwave vial containing a magnetic stir bar and degassed with bubbling nitrogen for 5 minutes. The mixture was treated with BrettPhos precatalyst (5.16 mg, 6.46 mol) and degassed for another 5 minutes. The vial was sealed and the reaction heated in the microwave with stirring for 145° C. for 15 minutes. The reaction mixture was worked up by adding water and EtOAc, filtering off the solids, separating the layers, and washing the organic layer with water (2×), brine (1×), drying (sodium sulfate) and removing the solvent in vacuo to yield 0.0800 g of a brown glass. The product was used without further purification. LCMS 417.3 (M+H)$^+$.

Step 3: 6-(5-Cyano-1H-pyrrolo[2,3-b]pyridin-1-yl)-4-(isopropylamino)-N-(4-oxocyclohexyl)nicotinamide (0.080 g, 0.192 mmol) was dissolved in EtOH (0.4 mL). Ammonium carbonate (0.240 g, 2.497 mmol) and KCN (0.031 g, 0.480 mmol) were dissolved in water (0.4 mL). The two mixtures were mixed and stirred in a 20 mL septum capped vial equipped with a magnetic stir bar at 80° C. for 3 hours. Water and EtOAc were added to the mixture. The layers were separated and the organic layer washed with water (2×), brine (1×), dried (sodium sulfate), and the solvent removed in vacuo to yield a tan glass. The residue was dissolved in DMF and purified via preparative HPLC to afford the desired product (12.7 mg, 13% yield). $^1$H NMR (500 MHz, DMSO-$d_6$) δ 10.66 (br. s., 1H), 8.81 (s, 1H), 8.67 (s, 1H), 8.63-8.55 (m, 1H), 8.54-8.46 (m, 3H), 8.38 (d, J=6.4 Hz, 1H), 8.08 (s, 1H), 6.89 (d, J=4.0 Hz, 1H), 3.83-3.65 (m, 2H), 3.36-3.32 (m, 1H), 2.07-1.49 (m, 7H), 1.29 (d, J=6.4 Hz, 6H). LCMS 487.1 (M+H)$^+$; HPLC rt 1.23 min, Conditions F.

Example 184

(S)-6-(5-Cyano-1H-pyrrolo[2,3-b]pyridin-1-yl)-4-(isopropylamino)-N-(4-(pyridin-4-yl)cyclohex-3-en-1-yl)nicotinamide (184)

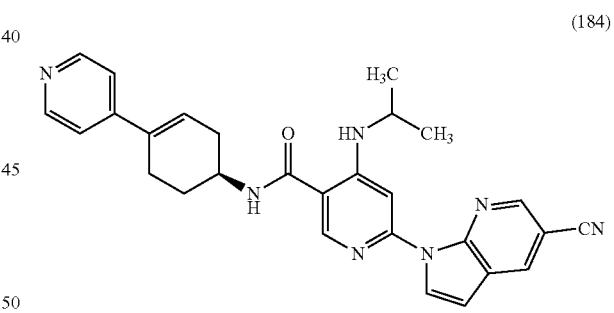

To a solution of 6-(5-cyano-1H-pyrrolo[2,3-b]pyridin-1-yl)-N-((1s,4s)-4-hydroxy-4-(pyridin-4-yl)cyclohexyl)-4-(isopropylamino)nicotinamide (7.77 mg, 0.016 mmol) in dry DCM (0.5 mL) at 0° C. under N$_2$ was added DAST (4.14 µL, 0.031 mmol). The mixture was kept at 0° C. for 1.5 h. The reaction mixture was then quenched by adding 1M aqueous NaOH. The mixture was diluted with EtOAc, the layers separated and the organic layer washed with brine, dried over Na$_2$SO$_4$, and concentrated to yield 8.6 mg of a pink solid. The crude solid was purified via preparative HPLC to afford the desired product (6.2 mg, 79% yield). $^1$H NMR (500 MHz, DMSO-$d_6$) δ 8.81 (s, 1H), 8.76 (d, J=5.7 Hz, 2H), 8.68 (s, 1H), 8.60 (s, 1H), 8.52 (d, J=4.0 Hz, 2H), 8.10 (s, 1H), 7.96 (d, J=5.7 Hz, 2H), 6.94-6.81 (m, 2H), 4.12 (br. s., 1H), 3.84-3.73 (m, 1H), 3.51 (br. s., 1H), 2.72-2.58 (m, 3H), 2.43 (d, J=11.1

Hz, 1H), 2.07 (br. s., 1H), 1.81 (d, J=11.1 Hz, 1H), 1.30 (d, J=6.1 Hz, 6H). LCMS 478.3 (M+H)+; HPLC rt 2.05 min, Conditions E.

Example 185

(R)-6-(2-(Dimethylamino)-7H-pyrrolo[2,3-d]pyrimidin-7-yl)-N-(2-fluoro-3-hydroxy-3-methylbutyl)-4-(isopropylamino)nicotinamide (185)

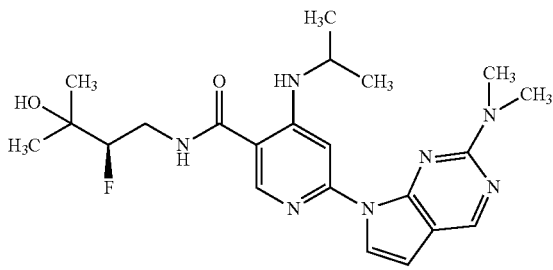

In a 5 mL microwave vial, a mixture of (R)-6-chloro-N-(2-fluoro-3-hydroxy-3-methylbutyl)-4-(isopropylamino)nicotinamide (24 mg, 0.076 mmol), N,N-dimethyl-7H-pyrrolo[2,3-d]pyrimidin-2-amine (14.70 mg, 0.091 mmol), and K$_2$CO$_3$ (41.8 mg, 0.302 mmol) in 3:1 tert-butanol/dioxane (0.6 mL) was degassed with bubbling nitrogen for 5 minutes. The mixture was treated with BrettPhos precatalyst (3.02 mg, 3.78 µmol), degassed for another 5 minutes, and the vial was sealed. The reaction mixture was heated with stirring at 120° C. for 18 hours, at which point the reaction mixture was judged to be complete by LCMS. The solvent was evaporated, and the residue was taken up in DMF (2 mL). The solution was filtered, and purified via preparative HPLC to afford (R)-6-(2-(dimethylamino)-7H-pyrrolo[2,3-d]pyrimidin-7-yl)-N-(2-fluoro-3-hydroxy-3-methylbutyl)-4-(isopropylamino)nicotinamide (20 mg, 0.044 mmol, 57.9% yield). LCMS (ESI)=444.3 (M+H). $^1$H NMR (500 MHz, DMSO-d$_6$) δ 8.74-8.68 (m, 2H), 8.63 (d, J=7.3 Hz, 1H), 8.56 (s, 1H), 8.28 (s, 1H), 8.06 (d, J=3.7 Hz, 1H), 6.60 (d, J=3.7 Hz, 1H), 4.85 (br. s., 1H), 4.46-4.27 (m, 1H), 3.87-3.79 (m, 1H), 3.78-3.64 (m, 1H), 3.23 (s, 6H), 1.28 (d, J=6.1 Hz, 6H), 1.18 (d, J=6.7 Hz, 6H). LCMS (ESI)=444.3 (M+H); HPLC rt 1.82 min, Conditions E.

Example 186

(R)-6-(2-Amino-7H-pyrrolo[2,3-d]pyrimidin-7-yl)-N-(2-fluoro-3-hydroxy-3-methylbutyl)-4-(isopropylamino)nicotinamide (186)

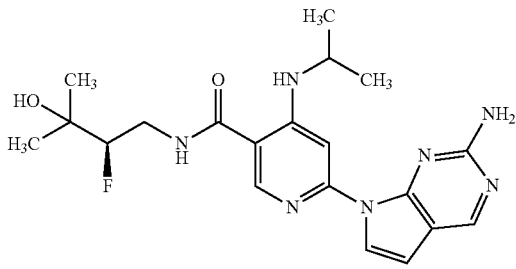

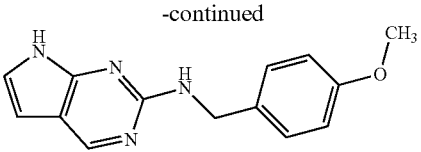

Step 1: In a sealed vial, a stirring mixture of 2-chloro-7H-pyrrolo[2,3-d]pyrimidine (167 mg, 1.087 mmol), and (4-methoxyphenyl)methanamine (0.563 mL, 4.35 mmol) in ethanol (2 mL) was heated at 120° C. for 38 hours. LCMS of the mixture detects both starting materials and a new peak with m/z=255, consistent with the expected product. Upon cooling, the product precipitated from the mixture. The solids were collected by filtration, washed twice with ethanol (0.5 mL), and dried under vacuum to yield N-(4-methoxybenzyl)-7H-pyrrolo[2,3-d]pyrimidin-2-amine (87 mg, 0.342 mmol, 31.5% yield) as an off-white powder. The combined filtrate and rinses were returned to the reaction vial, which was then capped. The contents of the vial were stirred at 130° C. for 7 hours, then allowed to cool to room temperature. The volume of the solution was reduced to ~1 mL. The resulting precipitate was collected by filtration, rinsed twice with ethanol, and dried under vacuum to yield a second crop of 55 mg as a colorless powder. The two crops were combined to yield N-(4-methoxybenzyl)-7H-pyrrolo[2,3-d]pyrimidin-2-amine (142 mg, 0.558 mmol, 51.4% yield). LCMS 255.0 (M+H)+.

Step 2: In a 5 mL microwave vial, a mixture of (R)-6-chloro-N-(2-fluoro-3-hydroxy-3-methylbutyl)-4-(isopropylamino)nicotinamide (35 mg, 0.110 mmol), N-(4-methoxybenzyl)-7H-pyrrolo[2,3-d]pyrimidin-2-amine (33.6 mg, 0.132 mmol), and K$_2$CO$_3$ (60.9 mg, 0.441 mmol) in 3:1 tert-butanol/dioxane (0.6 mL) was degassed with bubbling nitrogen for 5 minutes. The mixture was treated with BrettPhos precatalyst (4.40 mg, 5.51 mol), degassed for another 5 minutes, and the vial was sealed. The reaction mixture was heated with stirring at 120° C. for 3 hours, at which point it was judged to be complete by LCMS. The mixture was cooled to room temperature, diluted with DMF (5 mL), and filtered, and the filtrate was concentrated in vacuo. The residue was chromatographed via MPLC over a 12 g silica gel column, eluting at 30 mL/min with 3% methanol/methylene chloride. Fractions containing the desired product were pooled and concentrated in vacuo to yield (R)—N-(2-fluoro-3-hydroxy-3-methylbutyl)-4-(isopropylamino)-6-(2-((4-methoxybenzyl)amino)-7H-pyrrolo[2,3-d]pyrimidin-7-yl) nicotinamide (34 mg, 0.063 mmol, 57.6% yield). 24 mg was suspended in methylene chloride and treated with TFA (0.2 mL, 2.60 mmol), and the reaction mixture was stirred at room temperature for 3 hours. LCMS detects no conversion to the deprotected compound. A 50 µL aliquot was withdrawn and the DCM was evaporated with a stream of nitrogen. The residue was taken up in TFA (100 µL), and the mixture was stirred at 80° C. in a sealed vial for 20 minutes. LCMS shows clean conversion to the deprotected material. The DCM was evaporated from the bulk reaction mixture, and the residue was treated with TFA (1 mL). The reaction mixture was stirred at reflux for 20 minutes, at which point it was judged to be complete by LCMS. The reaction mixture was concentrated in vacuo, and the residue was concentrated twice from DCM and once from IPA to remove residual TFA. The residue was purified via preparative HPLC to afford (R)-6-(2-amino-7H-pyrrolo[2,3-d]pyrimidin-7-yl)-N-(2-fluoro-3-hydroxy-3-methylbutyl)-4-(isopropylamino) nicotinamide (11 mg, 0.026 mmol, 24% yield). $^1$H NMR (500 MHz, DMSO-d$_6$) δ 8.69 (t, J=5.5 Hz, 1H), 8.59 (s, 1H), 8.56-8.49 (m, 2H), 8.23 (s, 1H), 7.97 (d, J=3.7 Hz, 1H), 6.56 (d, J=3.7 Hz, 1H), 6.51 (br. s., 2H), 4.86 (s, 1H), 4.45-4.27 (m, 1H), 3.99-3.87 (m, 1H), 3.81-3.61 (m, 1H), 1.28 (d, J=6.1 Hz, 6H), 1.17 (d, J=6.7 Hz, 6H). LCMS (ESI)=416.2 (M+H); HPLC rt 1.25 min, Conditions E.

Example 187

(R)—N-(2-Fluoro-3-hydroxy-3-methylbutyl)-6-(2-((2-hydroxy-2-methylpropyl)amino)-7H-pyrrolo[2,3-d]pyrimidin-7-yl)-4-(isopropylamino)nicotinamide (187)

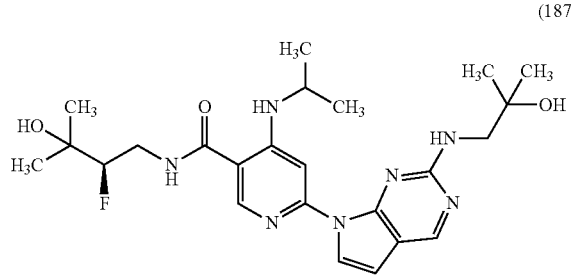

In a 5 mL microwave vial, a mixture of (R)-6-chloro-N-(2-fluoro-3-hydroxy-3-methylbutyl)-4-(isopropylamino)nicotinamide (25 mg, 0.079 mmol), 1-((7H-pyrrolo[2,3-d]pyrimidin-2-yl)amino)-2-methylpropan-2-ol (19.5 mg, 0.094 mmol), and $K_2CO_3$ (43.5 mg, 0.315 mmol) in 3:1 tert-butanol/dioxane (0.6 mL) was degassed with bubbling nitrogen for 5 minutes. The mixture was treated with BrettPhos pre-catalyst (3.14 mg, 3.93 μmol), degassed for another 5 minutes, and the vial was sealed. The reaction mixture was heated with stirring at 130° C. for 2 hours, at which point it was judged to be complete by LCMS. The solvents were evaporated, and the residue was taken up in DMF (2 mL). The solution was filtered, and purified via preparative HPLC to afford (R)—N-(2-fluoro-3-hydroxy-3-methylbutyl)-6-(2-((2-hydroxy-2-methylpropyl)amino)-7H-pyrrolo[2,3-d]pyrimidin-7-yl)-4-(isopropylamino)nicotinamide (25 mg, 0.050 mmol, 63.9% yield). H NMR (500 MHz, DMSO-$d_6$) δ 8.71 (t, J=5.2 Hz, 1H), 8.65-8.58 (m, 2H), 8.55 (s, 1H), 8.26 (s, 1H), 8.01 (d, J=4.3 Hz, 1H), 6.67-6.54 (m, 2H), 4.87 (s, 1H), 4.67 (s, 1H), 4.48-4.28 (m, 1H), 3.98-3.85 (m, 1H), 3.79-3.61 (m, 1H), 1.29 (d, J=6.1 Hz, 6H), 1.22-1.10 (m, 12H). LCMS (ESI)=488.2 (M+H); HPLC rt 1.50 min, Conditions E.

The Examples in Table 10 were prepared using the methods outlined for Examples 186 and 187 using the appropriate starting material and amine.

TABLE 10

| Ex. No. | Structure | HPLC rt (min) | HPLC cond. | LCMS |
|---|---|---|---|---|
| 188 | 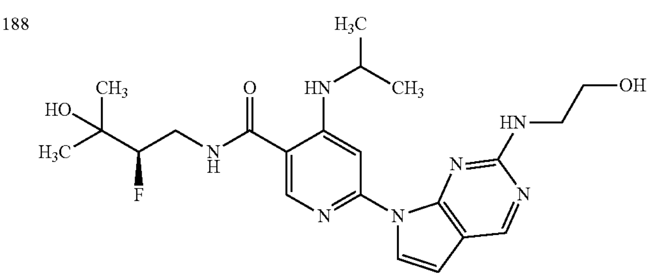 | 1.34 | E | 460.2 |
| 189 | 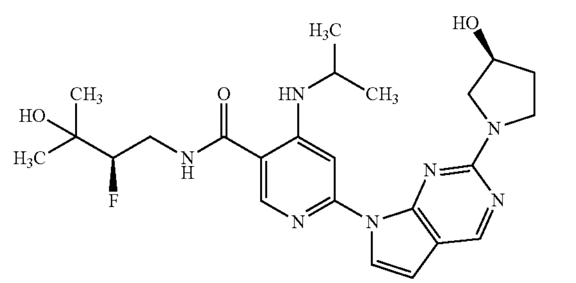 [SMILES: CC(C)Nc1cc(-n2ccc3cnc(N4CC[C@H](O)C4)nc32)ncc1C(=O)NC[C@@H](F)C(C)(C)O] | 1.43 | E | 486.3 |
| 190 | 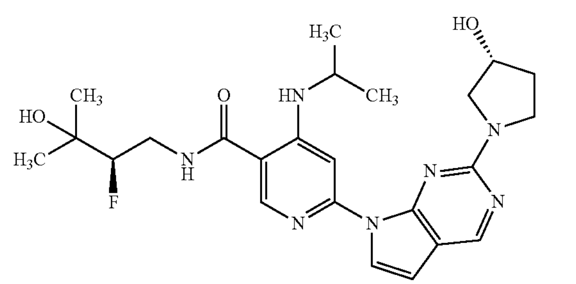 [SMILES: CC(C)Nc1cc(-n2ccc3cnc(N4CC[C@@H](O)C4)nc32)ncc1C(=O)NC[C@@H](F)C(C)(C)O] | 1.42 | E | 486.2 |

Example 191

(R)-4-(6-(5-Cyano-1H-pyrazolo[3,4-b]pyridin-1-yl)-4-(isopropylamino)nicotinamido)-3-fluoro-2-methylbutan-2-yl dihydrogen phosphate

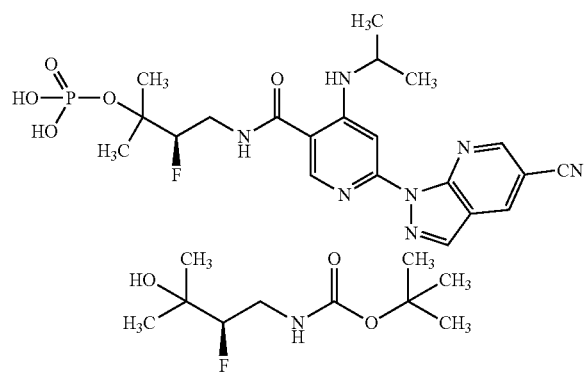

(191)

Step 1: To a solution of (R)-4-amino-3-fluoro-2-methylbutan-2-ol (10 g, 83 mmol) in DCM (100 mL) was added TEA (23.01 mL, 165 mmol) and (BOC)₂O (21.08 mL, 91 mmol). The reaction mixture was allowed to stir at room temperature overnight. The mixture was partitioned between water and DCM and the organic layer was washed consecutively with water, 1.5N HCl and brine. The organic layer was dried over Na₂SO₄ and concentrated to afford (R)-tert-butyl (2-fluoro-3-hydroxy-3-methylbutyl)carbamate (16.2 g, 73.2 mmol, 89% yield). $^1$H NMR (DMSO-d₆, 400 MHz) δ 6.93 (m, 1H), 4.71 (m, 1H), 4.14 (m, 1H), 3.26 (m, 1H), 3.05 (M, 1H), 1.38 (s, 9H), 1.10 (m, 6H).

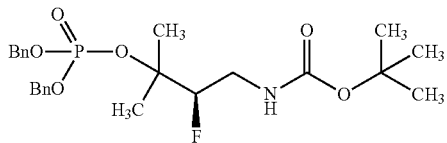 [SMILES: CC(C)(C)OC(=O)NC[C@@H](F)C(C)(C)OP(=O)(OCc1ccccc1)OCc1ccccc1]

Step 2: To a solution of (R)-tert-butyl (2-fluoro-3-hydroxy-3-methylbutyl) carbamate (13.0 g, 58.8 mmol) in DCM (130 mL) was added dibenzyl diisopropylphosphoramidite (29.6 mL, 88 mmol) and 1H-tetrazole (261 mL, 118 mmol). The resulting mixture was stirred at room temperature for 1 h. The mixture was cooled to 0° C. and H₂O₂ (4.87 mL, 58.8 mmol) was added. The mixture was stirred for 1 h. The mixture was then diluted with DCM (100 mL) and washed with brine. The organic layer was dried over Na₂SO₄, filtered and concentrated. The residue was purified via column chromatography on silica gel (10% EtOAc in DCM) to afford (R)-tert-butyl (3-((bis(benzyloxy)phosphoryl)oxy)-2-fluoro-3-methylbutyl)carbamate (18 g, 37.4 mmol, 64% yield) as colorless oil. $^1$H NMR (DMSO-d₆, 400 MHz) δ 7.35 (m, 10H), 7.08 (m, 1H), 5.00 dd, J=3.2, 8.0 Hz, 4H), 4.42 (m, 1H), 3.07 (m, 1H), 1.46 (s, 3H), 1.43 (s, 3H), 1.38 (s, 9H); LCMS 482.5 (M+H)⁺.

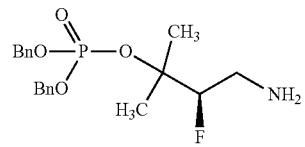 [SMILES: CC(C)(OP(=O)(OCc1ccccc1)OCc1ccccc1)[C@H](F)CN]

Step 3: To a solution of (R)-tert-butyl (3-((bis(benzyloxy)phosphoryl)oxy)-2-fluoro-3-methylbutyl)carbamate (3.2 g, 6.65 mmol) in DCM (5 mL) was added HCl (20 mL, 80 mmol) as 4M solution in dioxane and then stirred for 30 min at 0° C. The mixture was concentrated and the residue was dissolved in DCM and basified with aqueous ammonia solution. The layers were separated and the organic layer was dried over Na₂SO₄, filtered and concentrated to afford (R)-4-amino-3-fluoro-2-methylbutan-2-yl dibenzyl phosphate (2.2 g, 5.77 mmol, 87% yield). LCMS 382.1 (M+H)⁺.

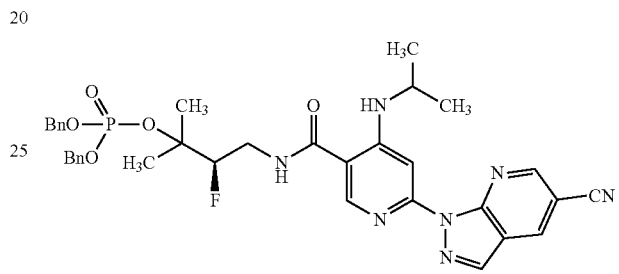

Step 4: To a solution of 6-(5-cyano-1H-pyrazolo[3,4-b]pyridin-1-yl)-4-(isopropylamino)nicotinic acid (1.1 g, 3.41 mmol) in DCM (20 mL) was added DIPEA (2.98 mL, 17.06 mmol) and HATU (2.60 g, 6.83 mmol). The mixture was stirred for 10 mins and (R)-4-amino-3-fluoro-2-methylbutan-2-yl dibenzyl phosphate (1.665 g, 3.75 mmol) was added. The reaction mixture was stirred for 3 h at room temperature. The mixture was then partitioned between water and DCM and the organic layer was washed with water and brine. The organic extracts were dried over Na₂SO₄, filtered and concentrated. The product was isolated via column chromatography (5% MeOH in DCM) to afford (R)-dibenzyl (4-(6-(5-cyano-1H-pyrazolo[3,4-b]pyridin-1-yl)-4-(isopropylamino)nicotinamido)-3-fluoro-2-methylbutan-2-yl)phosphate (1.65 g, 2.406 mmol, 70.5% yield). $^1$H NMR (400 MHz, DMSO-d₆) δ 9.06 (d, J=2.01 Hz, 1H) 9.02 (d, J=2.01 Hz, 1H) 8.92 (t, J=5.52 Hz, 1H) 8.65-8.66 (m, 2H) 8.57 (d, J=7.53 Hz, 1H) 7.34-7.41 (m, 11H) 5.05 (dd, J=7.53, 5.02 Hz, 4H) 4.58-4.74 (m, 1H) 3.69-3.84 (m, 2H) 3.36-3.52 (m, 1H) 1.54 (d, J=9.04 Hz, 6H) 1.23-1.26 (m, 6H); LCMS 686.2 (M+H).

Step 5: To a solution of (R)-dibenzyl (4-(6-(5-cyano-1H-pyrazolo[3,4-b]pyridin-1-yl)-4-(isopropylamino)nicotinamido)-3-fluoro-2-methylbutan-2-yl)phosphate (2.55 g, 3.72 mmol) in 1,2-dichloroethane was added a solution of TFA (57.3 mL, 744 mmol) in 15 mL of 1,2-dichloroethane and the resulting mixture was stirred at 35° C. for 18 h. The mixture was concentrated under vacuum at 35° C., and co-distilled with toluene (two times) and with CHCl₃ (two times). The product was isolated via prep HPLC to afford (R)-4-(6-(5-cyano-1H-pyrazolo[3,4-b]pyridin-1-yl)-4-(isopropylamino)nicotinamido)-3-fluoro-2-methylbutan-2-yl dihydrogen phosphate (1.36 g, 72% yield). $^1$H NMR (DMSO-d₆/D₂O, 400 MHz) δ 9.02 (d, J=2.0 Hz, 1H), 8.95 (d, J=2.0 Hz, 1H), 8.62 (m, 2H), 7.36 (s, 1H), 4.57 (m, 1H), 3.78 (m, 3H), 1.46 (s, 3H), 1.40 (s, 3H), 1.29 (s, 3H), 1.26 (s, 3H); LCMS 504.0 (M−H)⁺.

Example 192

(R)-6-(5-Cyano-1H-pyrazolo[3,4-b]pyridin-1-yl)-N-(2-fluoro-3-hydroxy-3-methylbutyl)-4-(isopropylamino)nicotinamide, hydrochloride A solution of Example 133, (R)-6-(5-cyano-1H-pyrazolo[3,4-b]pyridin-1-yl)-N-(2-fluoro-3-hydroxy-3-methylbutyl)-4-(isopropylamino)nicotinamide, (45 mg, 0.106 mmol) in acetonitrile (5 mL) was cooled to −20° C. HCl in diethyl ether (0.106 mL, 0.106 mmol) was added. The mixture was stirred for 2 mins and then cooled to −50° C. Water (5 mL) was added and the mixture was frozen. The solvents were removed on a lyophilizer to provide (R)-6-(5-cyano-1H-pyrazolo[3,4-b]pyridin-1-yl)-N-(2-fluoro-3-hydroxy-3-methylbutyl)-4-(isopropylamino)nicotinamide hydrochloride (40 mg, 81% yield) as an off-white powder.

Example 193

(R)-4-(sec-Butylamino)-6-(5-cyano-1H-pyrazolo[3,4-b]pyridin-1-yl)-N-(3-hydroxy-3-methylbutyl)nicotinamide

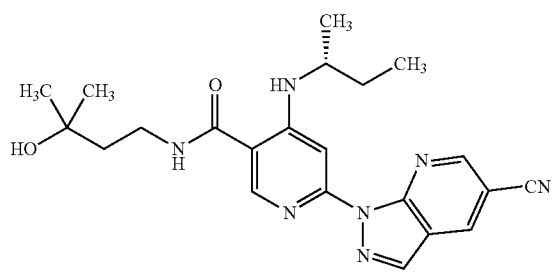
(193)

Intermediate 193A (R)-4-(sec-Butylamino)-6-chloronicotinic acid

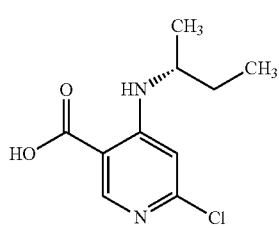
(193A)

A mixture of ethyl 4,6-dichloronicotinate (0.6 g, 2.73 mmol), (R)-butan-2-amine (0.219 g, 3 mmol) and DIPEA (0.521 mL, 3 mmol) in i-PrOH (2 mL) was heated at 85° C. for 18 h. The mixture was cooled and the solvents were removed in vacuo. MeOH (2 mL), THF (2 mL) and 1 N NaOH (5.45 mL, 5.45 mmol) was added and the mixture was stirred at room temperature for 3 h. The reaction mixture was neutralized with 1N HCl and the precipitated solids were collected via filtration. LCMS 229.2 (M+H); $^1$H NMR (500 MHz, DMSO-$d_6$) δ 8.16 (m, 2H), 7.69 (s, 1H), 5.09 (s, 1H), 4.32 (s, 1H), 3.36 (br. s., 1H), 3.25-3.16 (m, 2H), 1.61-1.53 (m, 2H), 1.52-1.41 (m, 2H), 1.13-1.05 (m, 9H), 0.88 (t, J=7.2 Hz, 3H).

Intermediate 193B (R)-4-(sec-Butylamino)-6-chloro-N-(3-hydroxy-3-methylbutyl) nicotinamide

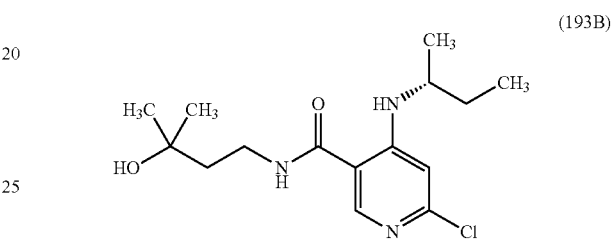
(193B)

To as solution of (R)-4-(sec-butylamino)-6-chloronicotinic acid (98 mg, 0.43 mmol) in DMF (0.5 mL) were added DIPEA (0.16 mL, 0.9 mmol), 4-amino-2-methylbutan-2-ol (49 mg, 0.47 mmol) and BOP (209 mg, 0.47 mmol). The reaction mixture was stirred at room temperature for 2 h. The reaction mixture was diluted with water and extracted with ethyl acetate. The combined organic extracts were dried over sodium sulfate and concentrated. The crude material was purified via column chromatography to afford (R)-4-(sec-butylamino)-6-chloro-N-(3-hydroxy-3-methylbutyl) nicotinamide (105 mg, 78% yield) as a pale yellow oil.

Example 193

A mixture of di-tert-butyl(2',4',6'-triisopropyl-3,4,5,6-tetramethyl-[1,1'-biphenyl]-2-yl)phosphine (9.2 mg) and Pd$_2$(dba)$_3$ (7.3 mg) in toluene/dioxane (5:1, 0.5 mL) was purged with N$_2$, sealed and heated at 120° C. for 5 mins and then cooled to room temperature. A separate mixture of (R)-4-(sec-butylamino)-6-chloro-N-(3-hydroxy-3-methylbutyl) nicotinamide, 1H-pyrazolo[3,4-b]pyridine-5-carbonitrile and K$_3$PO$_4$ in 1,4-dioxane (0.5 mL) was purged with N$_2$. The preformed catalyst was added and the mixture was purged with N$_2$ and heated at 110° C. for 4 h. The reaction mixture was cooled and the product was purified directly by preparative HPLC to afford (R)-4-(sec-butylamino)-6-(5-cyano-1H-pyrazolo[3,4-b]pyridin-1-yl)-N-(3-hydroxy-3-methylbutyl) nicotinamide (7.6 mg, 11% yield). LCMS 422.22, Rt 1.56 min, Conditions E; $^1$H NMR (500 MHz, DMSO-$d_6$) δ 9.02 (d, J=14.8 Hz, 2H), 8.68-8.48 (m, 4H), 7.31 (s, 1H), 4.39 (s, 1H), 3.64-3.50 (m, 2H), 3.36 (m, 1H), 1.74-1.50 (m, 4H), 1.20 (d, J=6.4 Hz, 3H), 1.15 (s, 6H), 0.93 (t, J=7.4 Hz, 3H).

The Examples in Table 11 were prepared using the general methods for Example 193 using the appropriate starting material and amine.

TABLE 11
| Ex. No. | Structure | HPLC Rt (min) | HPLC cond. | LCMS |
|---|---|---|---|---|
| 194 | 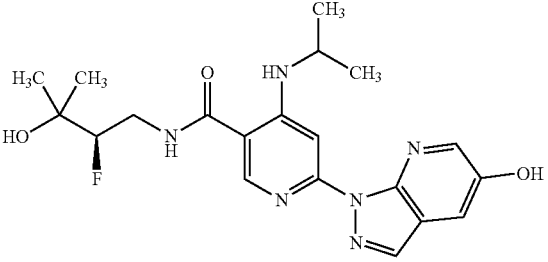 | 1.05 | H | 418.0 |
| 195 | 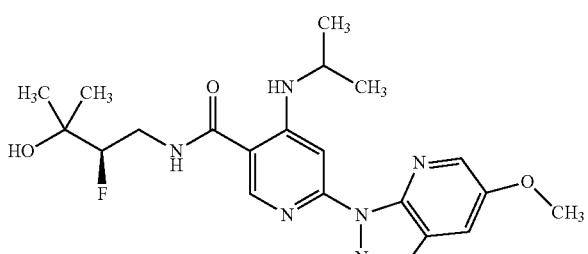 | 1.44 | C | 431.0 |
| 196 | 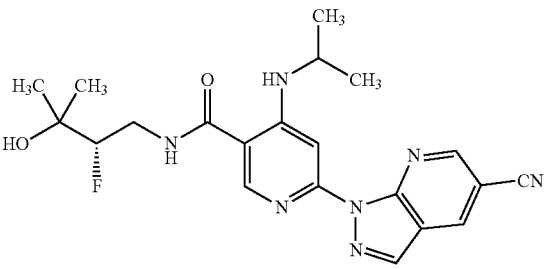 [SMILES: CC(C)Nc1cc(-n2ncc3cc(C#N)cnc32)ncc1C(=O)NC[C@H](F)C(C)(C)O] | 7.21 | B | 426.0 |
| 197 | 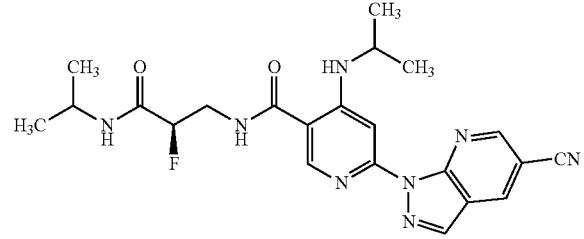 [SMILES: CC(C)NC(=O)[C@H](F)CNC(=O)c1cnc(-n2ncc3cc(C#N)cnc32)cc1NC(C)C] | 7.4 | B | 453.2 |
| 198 | 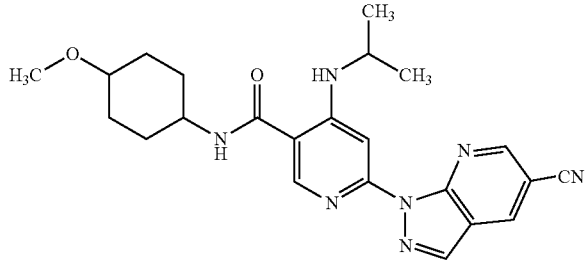 [SMILES: COC1CCC(NC(=O)c2cnc(-n3ncc4cc(C#N)cnc43)cc2NC(C)C)CC1] | 7.11 | B | 434.2 |

TABLE 11-continued

| Ex. No. | Structure | HPLC Rt (min) | HPLC cond. | LCMS |
|---|---|---|---|---|
| 199 | 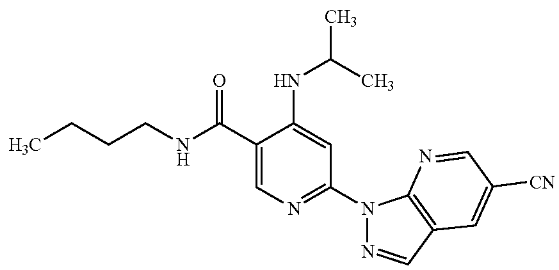 [SMILES: CCCCNC(=O)c1cnc(-n2ncc3cc(C#N)cnc32)cc1NC(C)C] | 1.71 | H | 378.0 |
| 200 | 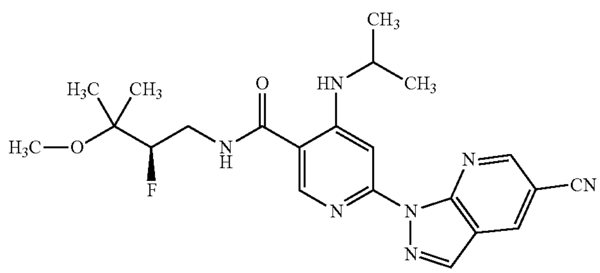 [SMILES: COC(C)(C)[C@H](F)CNC(=O)c1cnc(-n2ncc3cc(C#N)cnc32)cc1NC(C)C] | 1.74 | E | 440.4 |
| 201 | 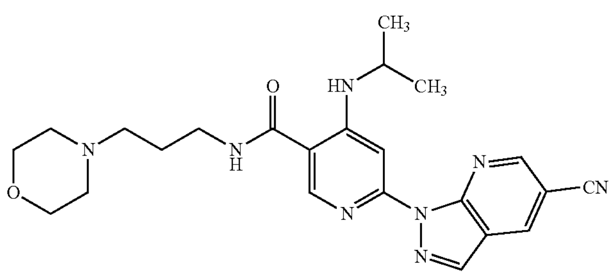 [SMILES: CC(C)Nc1cc(-n2ncc3cc(C#N)cnc32)ncc1C(=O)NCCCN1CCOCC1] | 1.36 | F | 449.23 |
| 202 | Diastereomer 1 | 6.66 | A | 458.2 |
| 203 | Diastereomer 2 | 6.65 | A | 458.2 |

TABLE 11-continued
| Ex. No. | Structure | HPLC Rt (min) | HPLC cond. | LCMS |
|---|---|---|---|---|
| 204 | 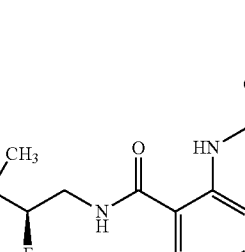 | 5.31 | A | 435.4 |
| 205 | 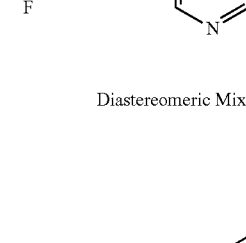<br>Diastereomeric Mixture | 6.45 | A | 458.2 |
| 206 | 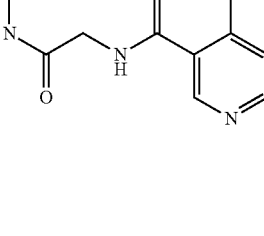 | 1.3 | E | 449.2 |
| 207 | 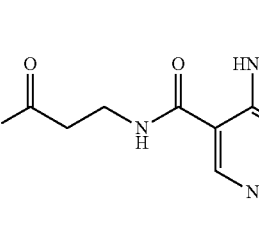 | 1.41 | E | 408.17 |
| 208 | 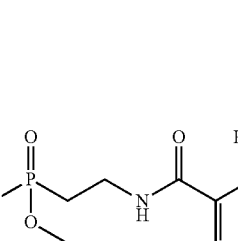 | 1.46 | E | 486.19 |

TABLE 11-continued
| Ex. No. | Structure | HPLC Rt (min) | HPLC cond. | LCMS |
|---|---|---|---|---|
| 209 | 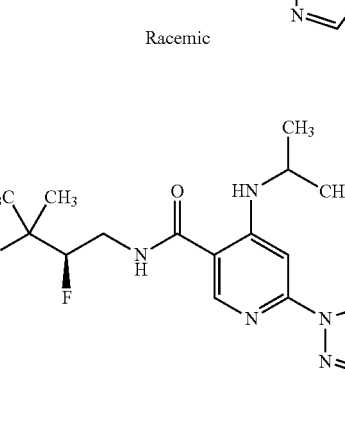 Racemic | 1.29 | E | 454.16 |
| 210 | 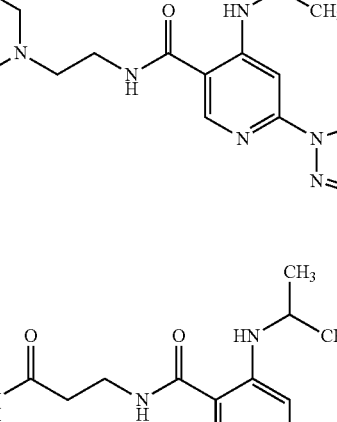 | 1.64 | E | 443.3 |
| 211 | 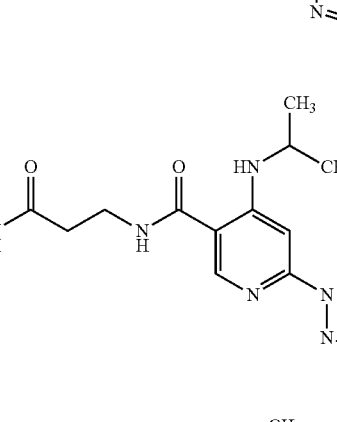 | 1.34 | E | 483.19 |
| 212 | 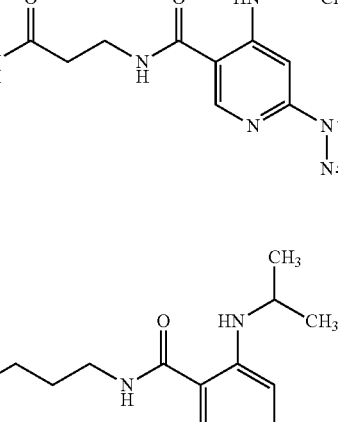 | 1.34 | E | 421.2 |
| 213 | 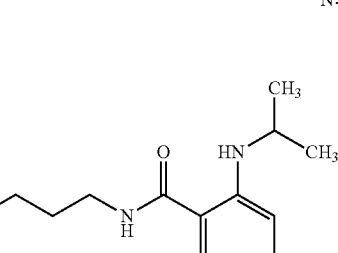 | 1.3 | E | 431.2 |

TABLE 11-continued
| Ex. No. | Structure | HPLC Rt (min) | HPLC cond. | LCMS |
|---|---|---|---|---|
| 214 | 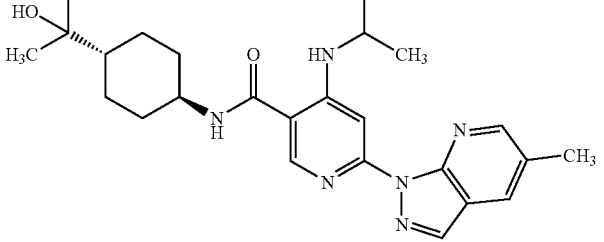 | 1.71 | C | 451.2 |
| 215 | 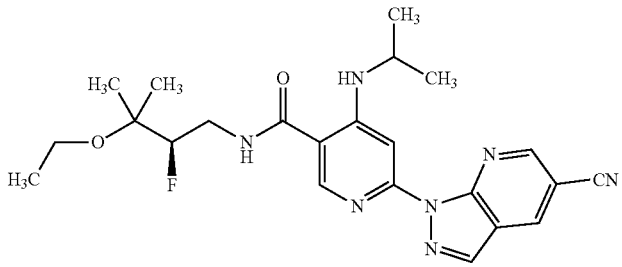 [SMILES: CCOC(C)(C)[C@H](F)CNC(=O)c1cnc(-n2ncc3cc(C#N)cnc32)cc1NC(C)C] | 1.85 | E | 454.3 |
| 216 | 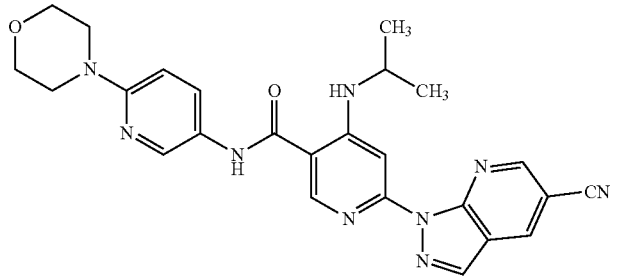 [SMILES: CC(C)Nc1cc(-n2ncc3cc(C#N)cnc32)ncc1C(=O)Nc1ccc(N2CCOCC2)nc1] | 1.6 | E | 484.21 |
| 217 | 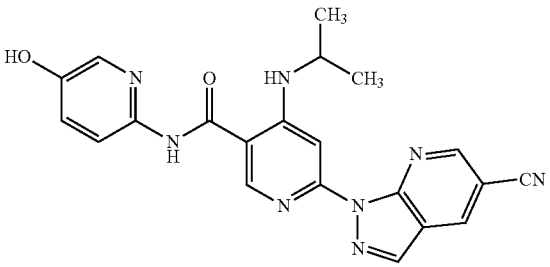 [SMILES: CC(C)Nc1cc(-n2ncc3cc(C#N)cnc32)ncc1C(=O)Nc1ccc(O)cn1] | 1.44 | E | 415.16 |
| 218 | 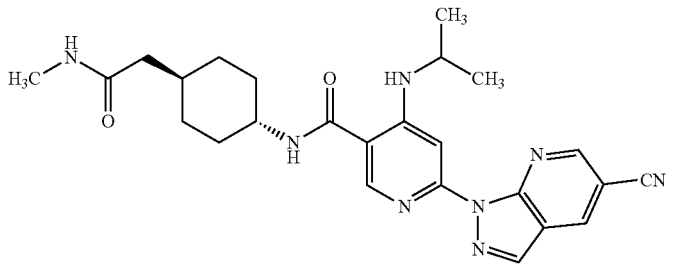 [SMILES: CNC(=O)C[C@H]1CC[C@H](NC(=O)c2cnc(-n3ncc4cc(C#N)cnc43)cc2NC(C)C)CC1] | 1.39 | E | 475.4 |

TABLE 11-continued

| Ex. No. | Structure | HPLC Rt (min) | HPLC cond. | LCMS |
|---|---|---|---|---|
| 219 | 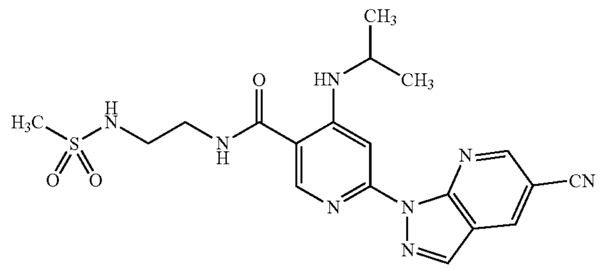 [SMILES: CC(C)Nc1cc(-n2ncc3cc(C#N)cnc32)ncc1C(=O)NCCNS(C)(=O)=O] | 6.04 | A | 441.0 (M − H) |
| 220 | Racemic | 8.3 | B | 434.2 |
| 221 | 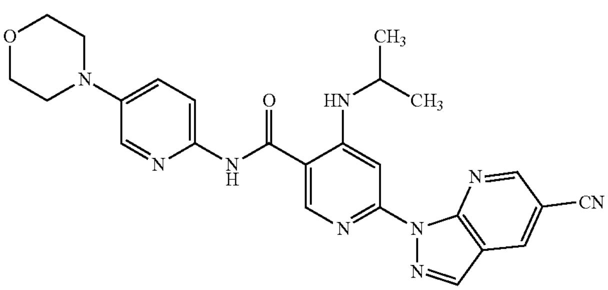 [SMILES: CC(C)Nc1cc(-n2ncc3cc(C#N)cnc32)ncc1C(=O)Nc1ccc(N2CCOCC2)cn1] | 1.67 | E | 484.21 |
| 222 | 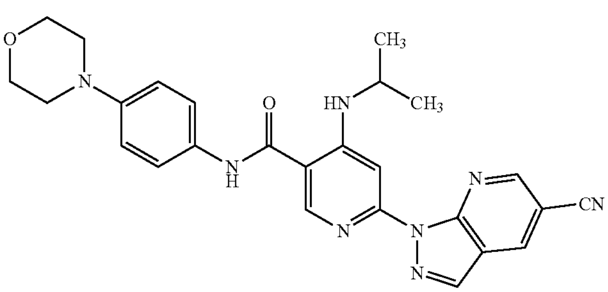 [SMILES: CC(C)Nc1cc(-n2ncc3cc(C#N)cnc32)ncc1C(=O)Nc1ccc(N2CCOCC2)cc1] | 1.75 | E | 483.22 |
| 223 | 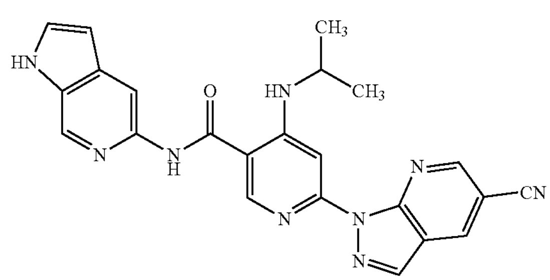 [SMILES: CC(C)Nc1cc(-n2ncc3cc(C#N)cnc32)ncc1C(=O)Nc1cc2cc[nH]c2cn1] | 1.67 | E | 438.17 |

TABLE 11-continued

| Ex. No. | Structure | HPLC Rt (min) | HPLC cond. | LCMS |
|---|---|---|---|---|
| 224 | 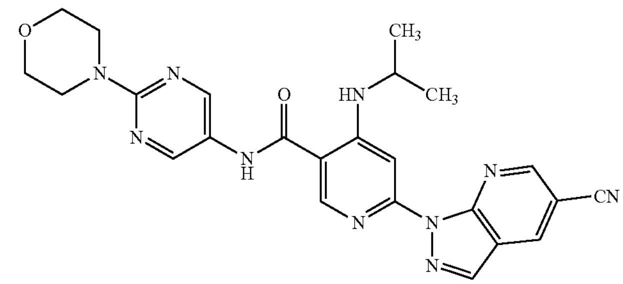 [SMILES: CC(C)Nc1cc(-n2ncc3cc(C#N)cnc32)ncc1C(=O)Nc1cnc(N2CCOCC2)nc1] | 1.67 | E | 485.21 |
| 225 | 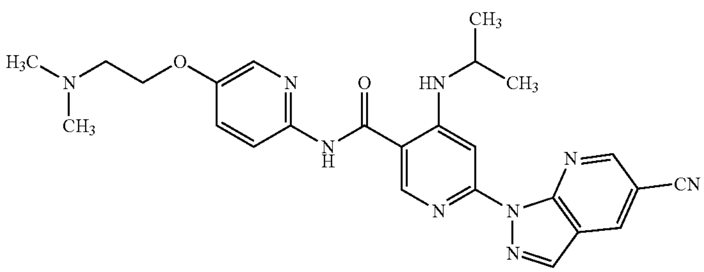 [SMILES: CC(C)Nc1cc(-n2ncc3cc(C#N)cnc32)ncc1C(=O)Nc1ccc(OCCN(C)C)cn1] | 1.29 | E | 486.23 |
| 226 | 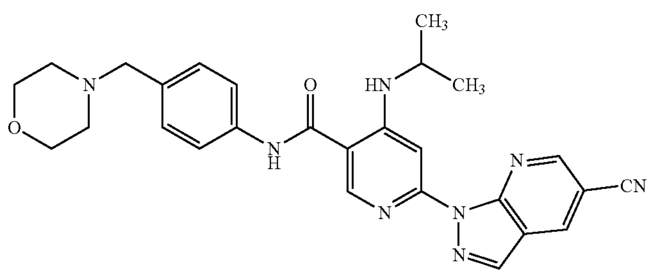 [SMILES: CC(C)Nc1cc(-n2ncc3cc(C#N)cnc32)ncc1C(=O)Nc1ccc(CN2CCOCC2)cc1] | 1.7 | E | 497.23 |
| 227 | 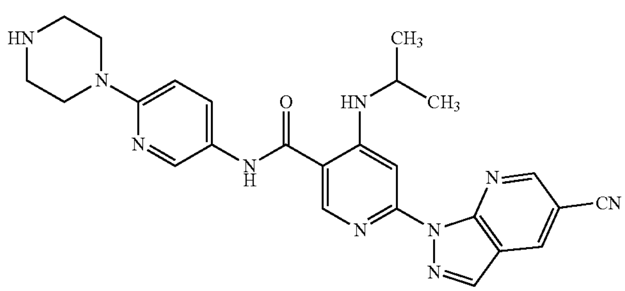 [SMILES: CC(C)Nc1cc(-n2ncc3cc(C#N)cnc32)ncc1C(=O)Nc1ccc(N2CCNCC2)nc1] | 1.21 | E | 483.23 |
| 228 | 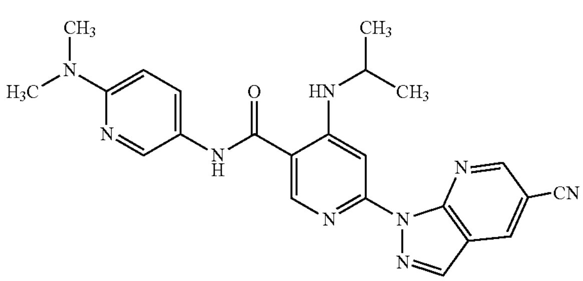 [SMILES: CC(C)Nc1cc(-n2ncc3cc(C#N)cnc32)ncc1C(=O)Nc1ccc(N(C)C)nc1] | 1.71 | E | 442.2 |

TABLE 11-continued
| Ex. No. | Structure | HPLC Rt (min) | HPLC cond. | LCMS |
|---|---|---|---|---|
| 229 | 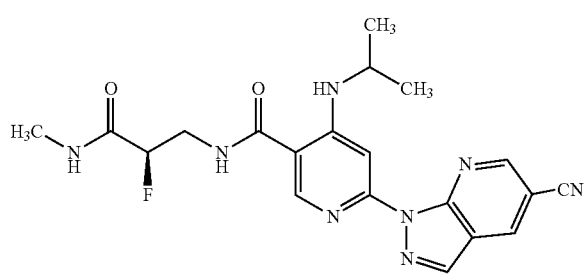 [SMILES: CNC(=O)[C@H](F)CNC(=O)c1cnc(-n2ncc3cc(C#N)cnc32)cc1NC(C)C] | 11.82 | B | 425.2 |
| 230 | 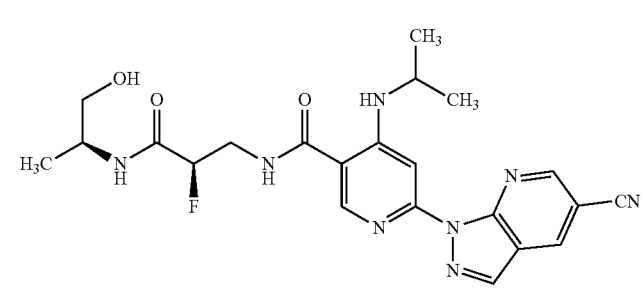 [SMILES: CC(C)Nc1cc(-n2ncc3cc(C#N)cnc32)ncc1C(=O)NC[C@@H](F)C(=O)N[C@@H](C)CO] | 5.71 | A | 46.2 |
| 231 | 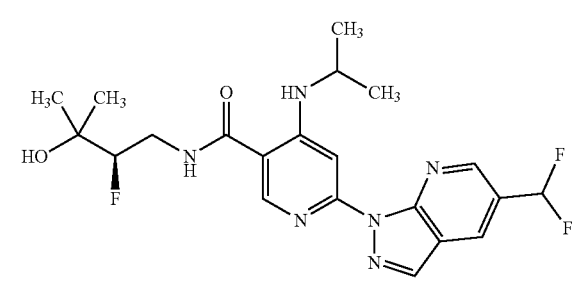 [SMILES: CC(C)Nc1cc(-n2ncc3cc(C(F)F)cnc32)ncc1C(=O)NC[C@@H](F)C(C)(C)O] | 6.89 | A | 451.2 |
| 232 | 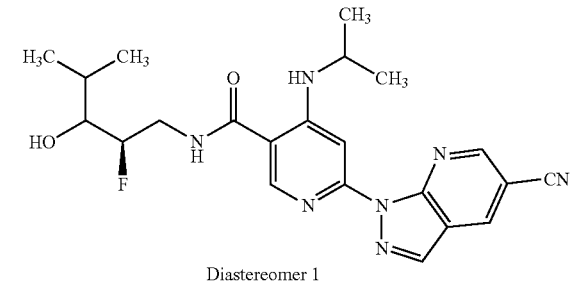 [SMILES: CC(C)Nc1cc(-n2ncc3cc(C#N)cnc32)ncc1C(=O)NC[C@@H](F)C(O)C(C)C] Diastereomer 1 | 7.16 | A | 440.2 |
| 233 | 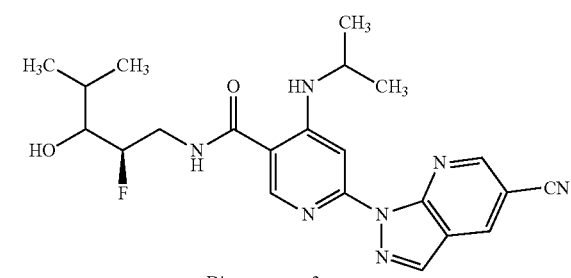 Diastereomer 2 | 7.37 | A | 440.2 |

TABLE 11-continued

| Ex. No. | Structure | HPLC Rt (min) | HPLC cond. | LCMS |
|---|---|---|---|---|
| 234 | 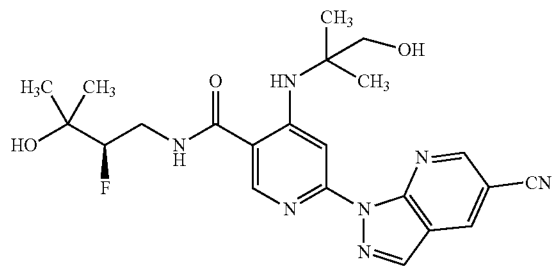 [SMILES: CC(C)(CO)Nc1cc(-n2ncc3cc(C#N)cnc32)ncc1C(=O)NC[C@@H](F)C(C)(C)O] | 1.04 | G | 456.0 |
| 235 | 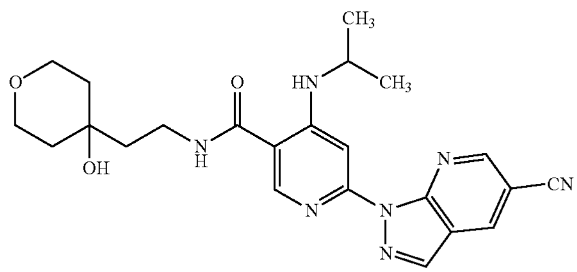 [SMILES: CC(C)Nc1cc(-n2ncc3cc(C#N)cnc32)ncc1C(=O)NCCC1(O)CCOCC1] | 1.24 | E | 450.22 |
| 236 | 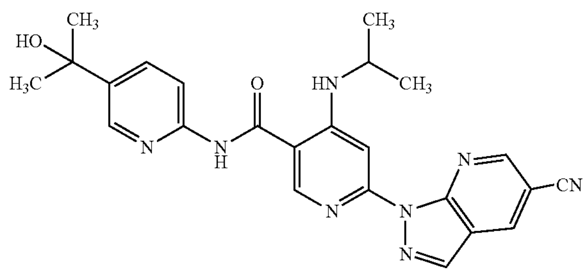 [SMILES: CC(C)Nc1cc(-n2ncc3cc(C#N)cnc32)ncc1C(=O)Nc1ccc(C(C)(C)O)cn1] | 1.62 | E | 457.2 |
| 237 | Racemic | 1.29 | E | 436.2 |
| 238 | Enantiomer 1 | 11.82 | A | 394.2 |

TABLE 11-continued
| Ex. No. | Structure | HPLC Rt (min) | HPLC cond. | LCMS |
|---|---|---|---|---|
| 239 | 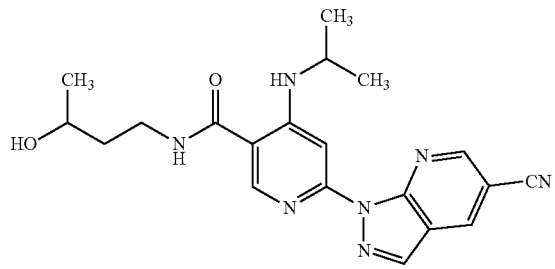 Enantiomer 2 | 11.82 | A | 394.2 |
| 240 | 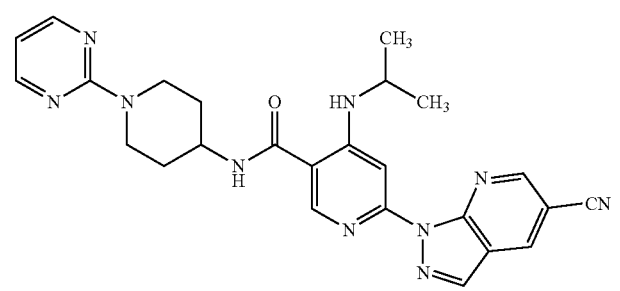 [SMILES: CC(C)Nc1cc(-n2ncc3cc(C#N)cnc32)ncc1C(=O)NC1CCN(c2ncccn2)CC1] | 6.61 | A | 483.2 |
| 241 | 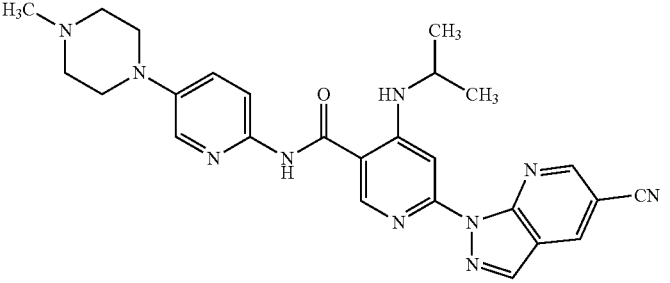 [SMILES: CC(C)Nc1cc(-n2ncc3cc(C#N)cnc32)ncc1C(=O)Nc1ccc(N2CCN(C)CC2)cn1] | 1.45 | E | 497.25 |
| 242 | 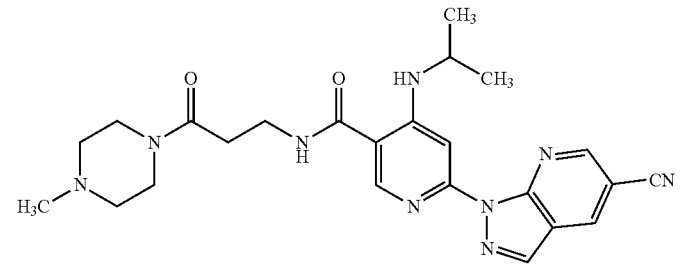 [SMILES: CC(C)Nc1cc(-n2ncc3cc(C#N)cnc32)ncc1C(=O)NCCC(=O)N1CCN(C)CC1] | 1.16 | G | 462.2 |
| 243 | 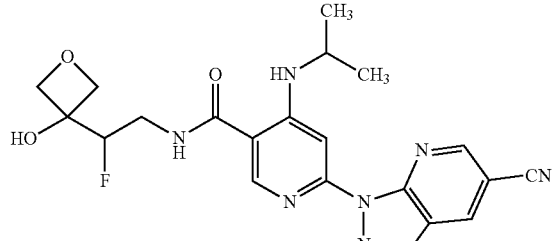 | 0.94 | I | 440.3 |

TABLE 11-continued

| Ex. No. | Structure | HPLC Rt (min) | HPLC cond. | LCMS |
|---|---|---|---|---|
| 244 | 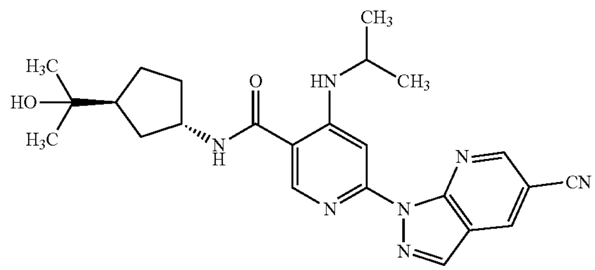 [SMILES: CC(C)Nc1cc(-n2ncc3cc(C#N)cnc32)ncc1C(=O)N[C@H]1CC[C@H](C(C)(C)O)C1] | 1.51 | E | 448.2 |
| 245 | 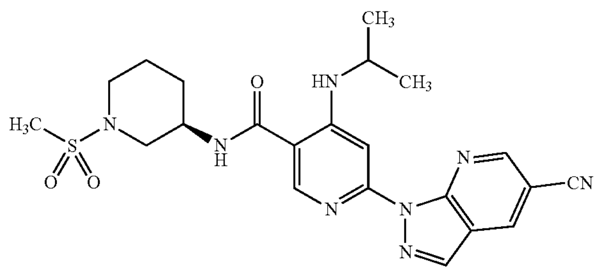 [SMILES: CC(C)Nc1cc(-n2ncc3cc(C#N)cnc32)ncc1C(=O)N[C@@H]1CCCN(S(C)(=O)=O)C1] | 1.44 | E | 483.1 |
| 246 | 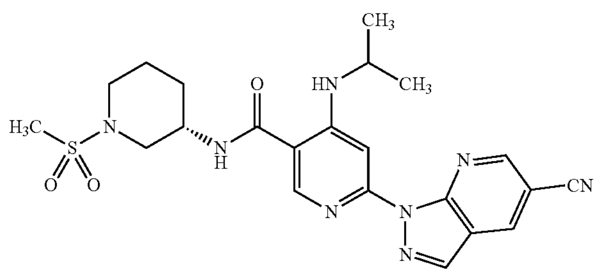 [SMILES: CC(C)Nc1cc(-n2ncc3cc(C#N)cnc32)ncc1C(=O)N[C@H]1CCCN(S(C)(=O)=O)C1] | 1.44 | E | 483.1 |
| 247 | 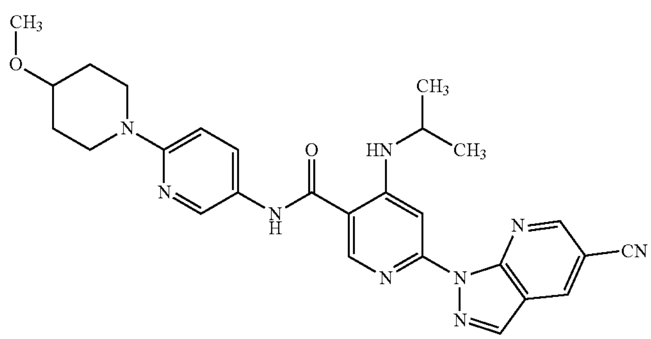 [SMILES: COC1CCN(c2ccc(NC(=O)c3cnc(-n4ncc5cc(C#N)cnc54)cc3NC(C)C)cn2)CC1] | 1.72 | E | 512.24 |
| 248 | Enantiomer 1 | 0.92 | I | 440.3 |

TABLE 11-continued

| Ex. No. | Structure | HPLC Rt (min) | HPLC cond. | LCMS |
|---|---|---|---|---|
| 249 | Enantiomer 2 | 0.93 | I | 440.3 |
| 250 | 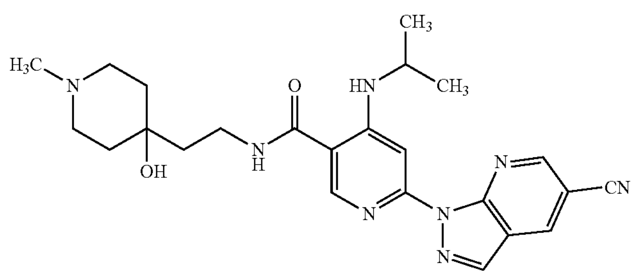 [SMILES: CC(C)Nc1cc(-n2ncc3cc(C#N)cnc32)ncc1C(=O)NCCC1(O)CCN(C)CC1] | 1.01 | E | 463.25 |
| 251 | 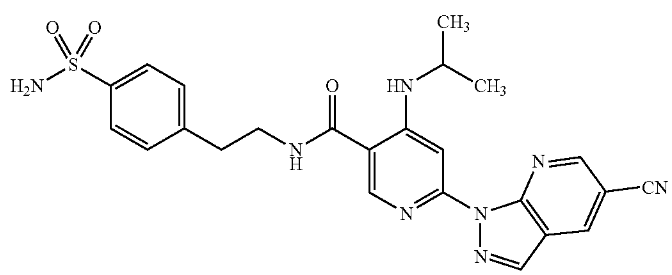 [SMILES: CC(C)Nc1cc(-n2ncc3cc(C#N)cnc32)ncc1C(=O)NCCc1ccc(S(N)(=O)=O)cc1] | 6.75 | A | 505.4 |
| 252 | 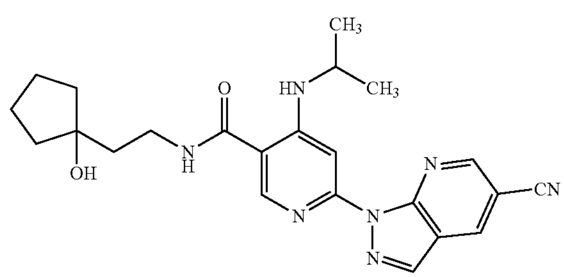 [SMILES: CC(C)Nc1cc(-n2ncc3cc(C#N)cnc32)ncc1C(=O)NCCC1(O)CCCC1] | 1.65 | E | 434.3 |
| 253 | 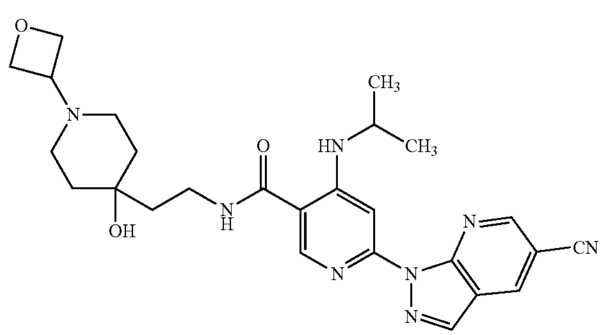 [SMILES: CC(C)Nc1cc(-n2ncc3cc(C#N)cnc32)ncc1C(=O)NCCC1(O)CCN(C2COC2)CC1] | 1.14 | E | 505.25 |

TABLE 11-continued

| Ex. No. | Structure | HPLC Rt (min) | HPLC cond. | LCMS |
|---|---|---|---|---|
| 254 | 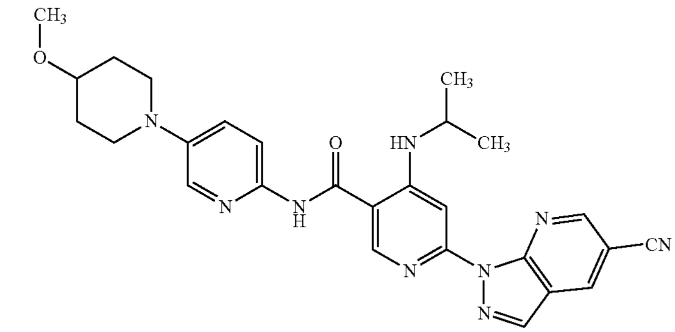 [SMILES: COC1CCN(c2ccc(NC(=O)c3cnc(-n4ncc5cc(C#N)cnc54)cc3NC(C)C)nc2)CC1] | 1.87 | E | 512.24 |
| 255 | 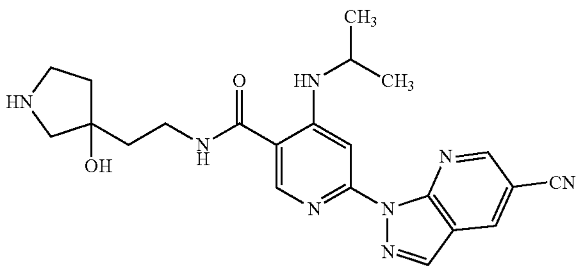 [SMILES: CC(C)Nc1cc(-n2ncc3cc(C#N)cnc32)ncc1C(=O)NCCC1(O)CCNC1] | 0.97 | E | 435.22 |
| 256 | 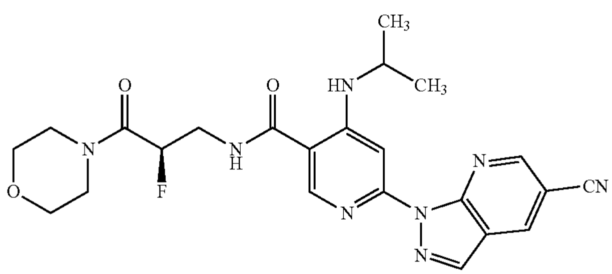 [SMILES: CC(C)Nc1cc(-n2ncc3cc(C#N)cnc32)ncc1C(=O)NC[C@@H](F)C(=O)N1CCOCC1] | 6.8 | B | 481.3 |
| 257 | 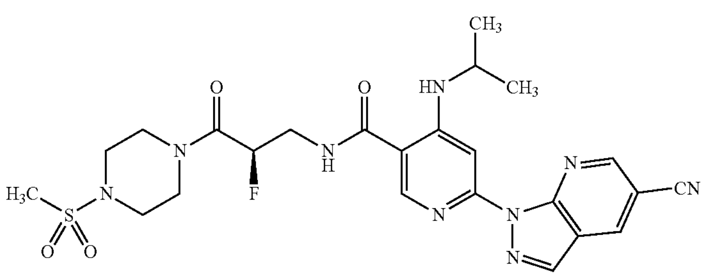 [SMILES: CC(C)Nc1cc(-n2ncc3cc(C#N)cnc32)ncc1C(=O)NC[C@@H](F)C(=O)N1CCN(S(C)(=O)=O)CC1] | 7.17 | B | 558.4 |
| 258 | Enantiomer 2 | 1.55 | E | 449.2 |

TABLE 11-continued

| Ex. No. | Structure | HPLC Rt (min) | HPLC cond. | LCMS |
|---|---|---|---|---|
| 259 | 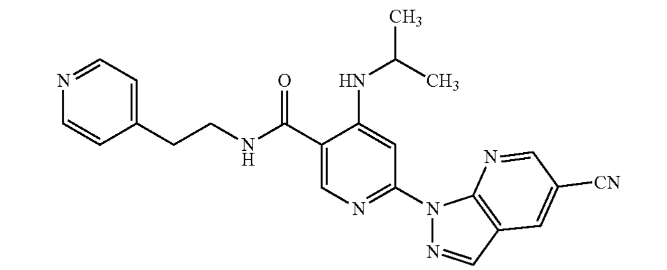 [SMILES: CC(C)Nc1cc(-n2ncc3cc(C#N)cnc32)ncc1C(=O)NCCc1ccncc1] | 0.87 | H | 427.0 |
| 260 | 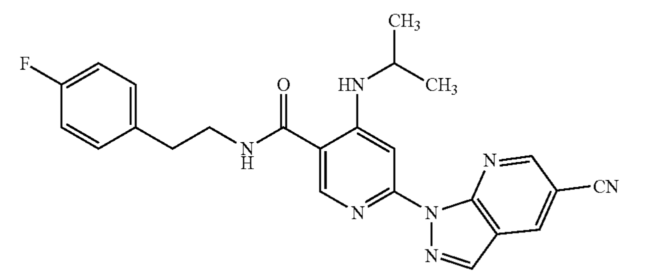 [SMILES: CC(C)Nc1cc(-n2ncc3cc(C#N)cnc32)ncc1C(=O)NCCc1ccc(F)cc1] | 1.5 | H | 444.0 |
| 261 | 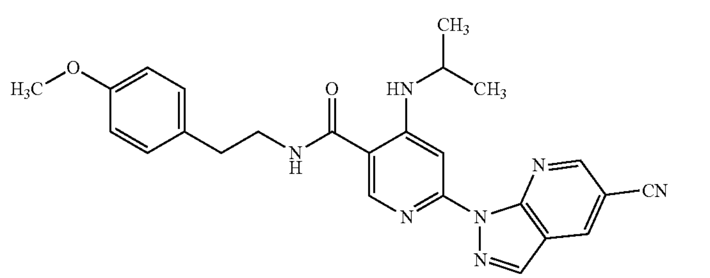 [SMILES: COc1ccc(CCNC(=O)c2cnc(-n3ncc4cc(C#N)cnc43)cc2NC(C)C)cc1] | 1.46 | H | 456.0 |
| 262 | 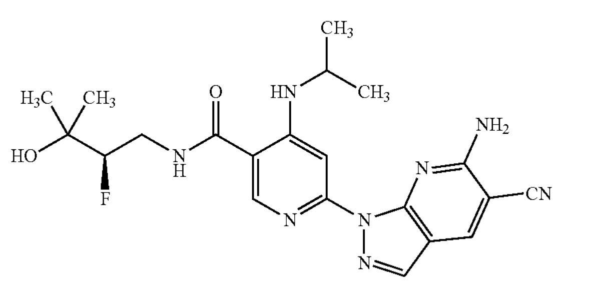 [SMILES: CC(C)Nc1cc(-n2ncc3cc(C#N)c(N)nc32)ncc1C(=O)NC[C@@H](F)C(C)(C)O] | 1.34 | E | 441.2 |
| 263 | Enantiomer 2 | 6.77 | A | 434.4 |

TABLE 11-continued

| Ex. No. | Structure | HPLC Rt (min) | HPLC cond. | LCMS |
|---|---|---|---|---|
| 264 | Enantiomer 1 | 6.48 | A | 471.4 |
| 265 | Enantiomer 2 | 6.47 | A | 471.4 |
| 266 | 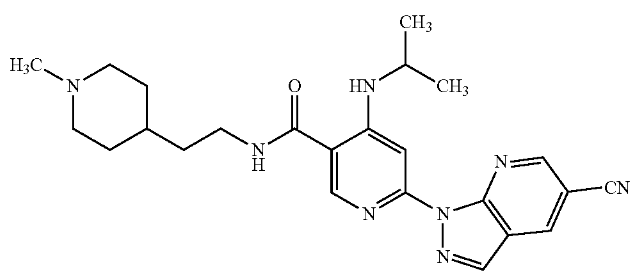 [SMILES: CC(C)Nc1cc(-n2ncc3cc(C#N)cnc32)ncc1C(=O)NCCC1CCN(C)CC1] | 0.84 | H | 447.3 |
| 267 | 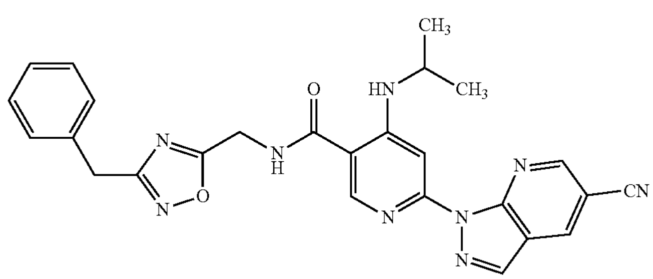 [SMILES: CC(C)Nc1cc(-n2ncc3cc(C#N)cnc32)ncc1C(=O)NCc1nc(Cc2ccccc2)no1] | 1.46 | H | 494.3 |
| 268 | 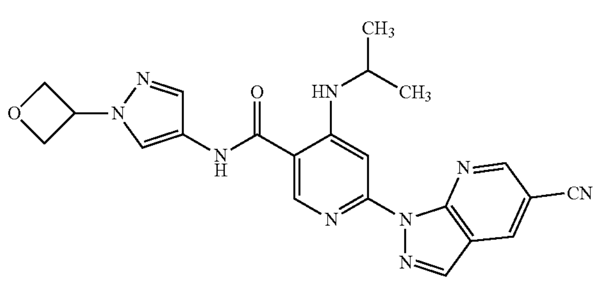 [SMILES: CC(C)Nc1cc(-n2ncc3cc(C#N)cnc32)ncc1C(=O)Nc1cnn(C2COC2)c1] | 1.36 | C | 444.3 |

TABLE 11-continued
| Ex. No. | Structure | HPLC Rt (min) | HPLC cond. | LCMS |
|---|---|---|---|---|
| 269 | 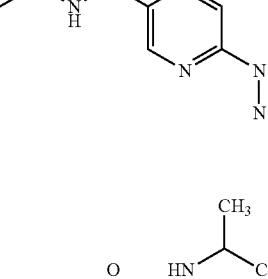 | 1.65 | C | 597.2 |
| 270 | 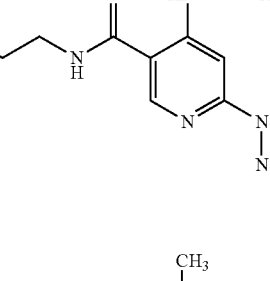 | 1.15 | H | 483.3 |
| 271 | 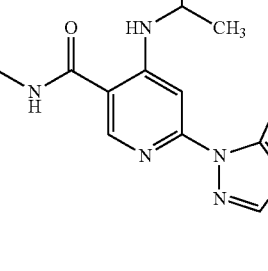 | 1.47 | C | 472.3 |
| 272 | 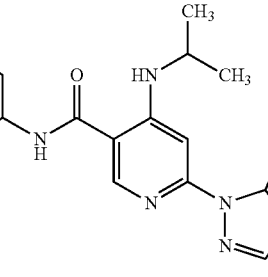 | 2.4 | G | 511.2 |
| 273 | 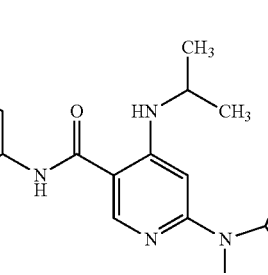 | 2.27 | G | 475.2 |

TABLE 11-continued

| Ex. No. | Structure | HPLC Rt (min) | HPLC cond. | LCMS |
|---|---|---|---|---|
| 274 | 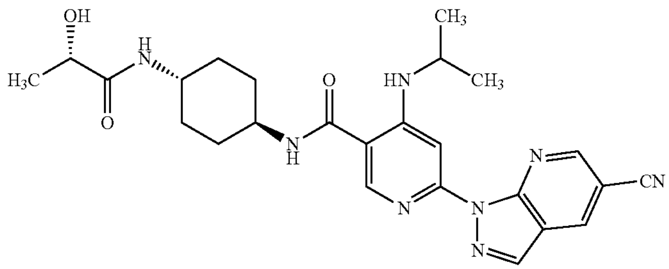 [SMILES: CC(C)Nc1cc(-n2ncc3cc(C#N)cnc32)ncc1C(=O)N[C@H]1CC[C@H](NC(=O)[C@H](C)O)CC1] | 6.11 | A | 491.2 |
| 275 | 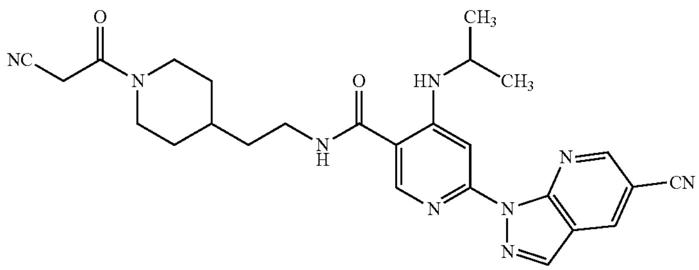 [SMILES: CC(C)Nc1cc(-n2ncc3cc(C#N)cnc32)ncc1C(=O)NCCC1CCN(C(=O)CC#N)CC1] | 2.12 | G | 500.2 |
| 276 | 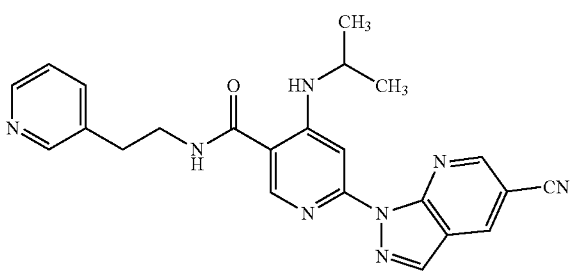 [SMILES: CC(C)Nc1cc(-n2ncc3cc(C#N)cnc32)ncc1C(=O)NCCc1cccnc1] | 2.07 | G | 427.2 |
| 277 | 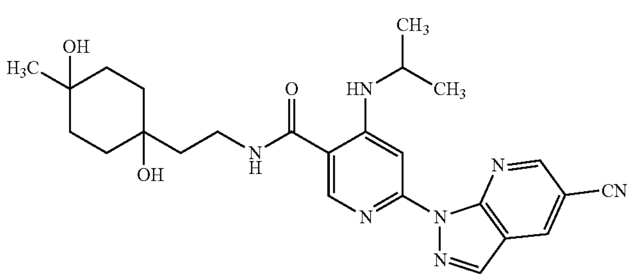 [SMILES: CC(C)Nc1cc(-n2ncc3cc(C#N)cnc32)ncc1C(=O)NCCC1(O)CCC(C)(O)CC1] | 1.69 | E | 478.2 |
| 278 | 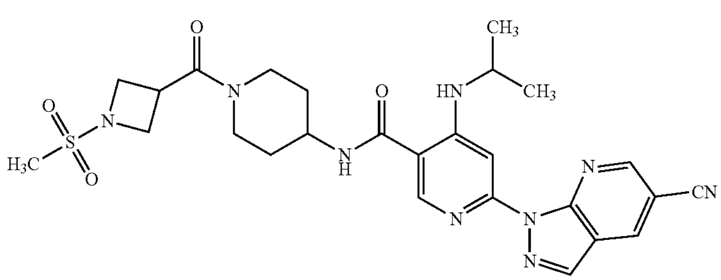 [SMILES: CC(C)Nc1cc(-n2ncc3cc(C#N)cnc32)ncc1C(=O)NC1CCN(C(=O)C2CN(S(C)(=O)=O)C2)CC1] | 2.01 | G | 599.2 |

TABLE 11-continued

| Ex. No. | Structure | HPLC Rt (min) | HPLC cond. | LCMS |
|---|---|---|---|---|
| 279 | 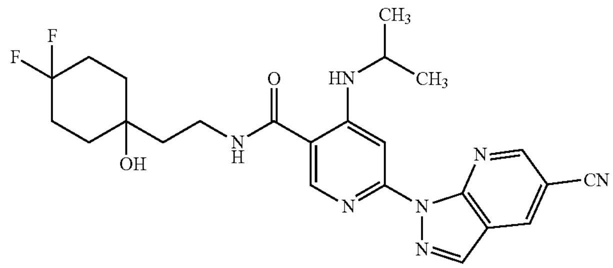 [SMILES: CC(C)Nc1cc(-n2ncc3cc(C#N)cnc32)ncc1C(=O)NCCC1(O)CCC(F)(F)CC1] | 1.52 | E | 484.3 |
| 280 | 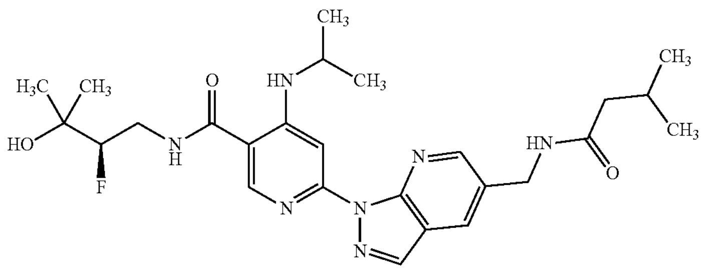 [SMILES: CC(C)CC(=O)NCc1cnc2c(cnn2-c2cc(NC(C)C)c(C(=O)NC[C@@H](F)C(C)(C)O)cn2)c1] | 1.50 | E | 514.2 |
| 281 | 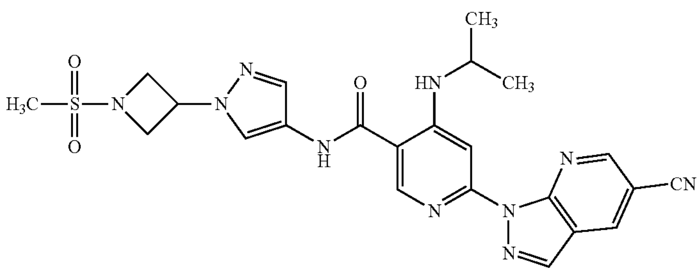 [SMILES: CC(C)Nc1cc(-n2ncc3cc(C#N)cnc32)ncc1C(=O)Nc1cnn(C2CN(S(C)(=O)=O)C2)c1] | 2.11 | C | 521.2 |
| 282 | 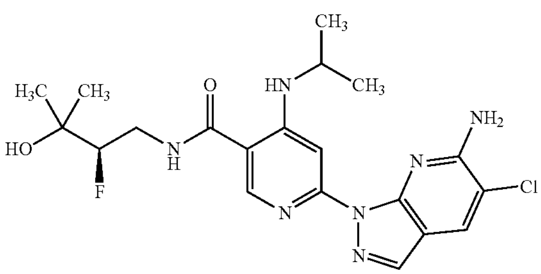 [SMILES: CC(C)Nc1cc(-n2ncc3cc(Cl)c(N)nc32)ncc1C(=O)NC[C@@H](F)C(C)(C)O] | 1.44 | E | 450.2 |
| 283 | 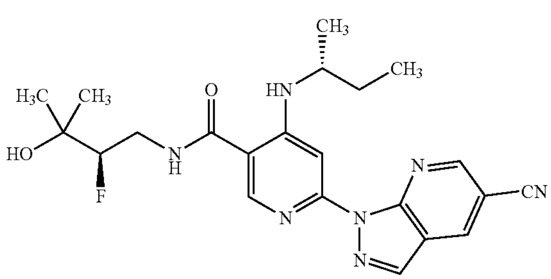 [SMILES: CC[C@@H](C)Nc1cc(-n2ncc3cc(C#N)cnc32)ncc1C(=O)NC[C@@H](F)C(C)(C)O] | 1.58 | E | 440.21 |

TABLE 11-continued

| Ex. No. | Structure | HPLC Rt (min) | HPLC cond. | LCMS |
|---|---|---|---|---|
| 284 | 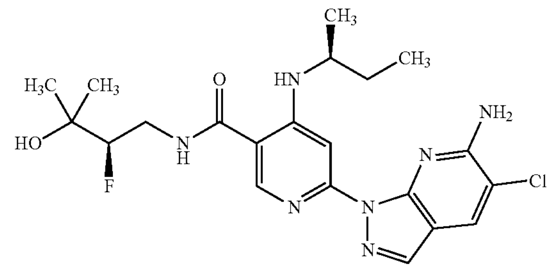 [SMILES: CC[C@H](C)Nc1cc(-n2ncc3cc(Cl)c(N)nc32)ncc1C(=O)NC[C@@H](F)C(C)(C)O] | 1.43 | E | 455.22 |
| 285 | 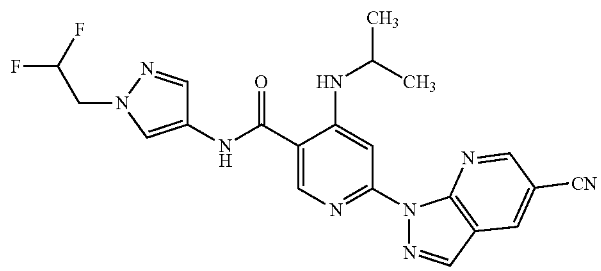 [SMILES: CC(C)Nc1cc(-n2ncc3cc(C#N)cnc32)ncc1C(=O)Nc1cnn(CC(F)F)c1] | 2.46 | G | 452.2 |
| 286 | 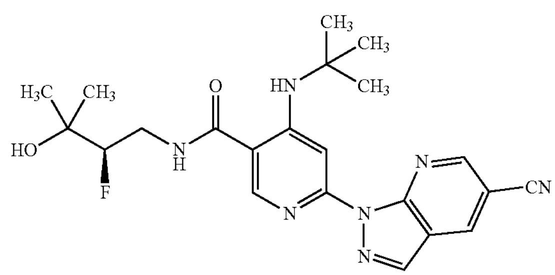 [SMILES: CC(C)(C)Nc1cc(-n2ncc3cc(C#N)cnc32)ncc1C(=O)NC[C@@H](F)C(C)(C)O] | 1.62 | E | 440.2 |
| 287 | 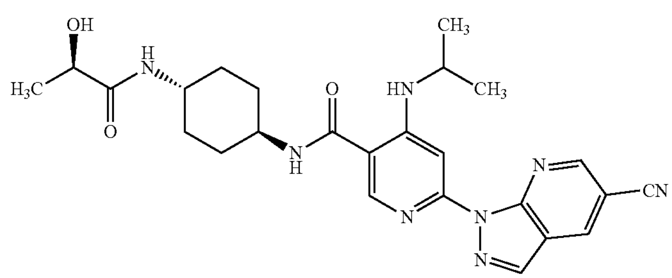 [SMILES: CC(C)Nc1cc(-n2ncc3cc(C#N)cnc32)ncc1C(=O)N[C@H]1CC[C@H](NC(=O)[C@@H](C)O)CC1] | 2.2 | C | 491.2 |
| 288 | 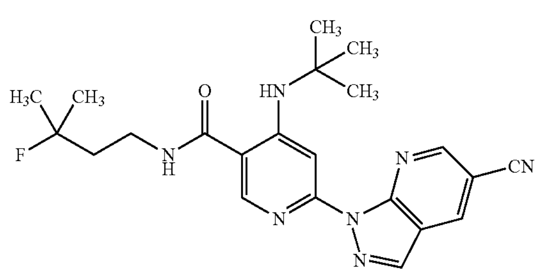 [SMILES: CC(C)(F)CCNC(=O)c1cnc(-n2ncc3cc(C#N)cnc32)cc1NC(C)(C)C] | 1.67 | E | 410.2 |

TABLE 11-continued

| Ex. No. | Structure | HPLC Rt (min) | HPLC cond. | LCMS |
|---|---|---|---|---|
| 289 | 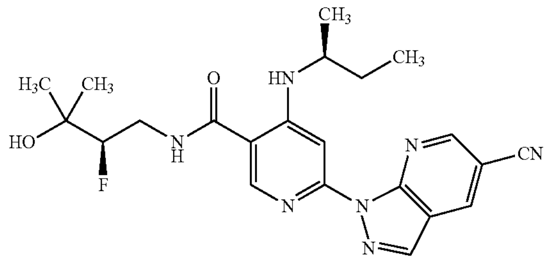 [SMILES: CC[C@H](C)Nc1cc(-n2ncc3cc(C#N)cnc32)ncc1C(=O)NC[C@@H](F)C(C)(C)O] | 1.25 | E | 440.21 |
| 290 | 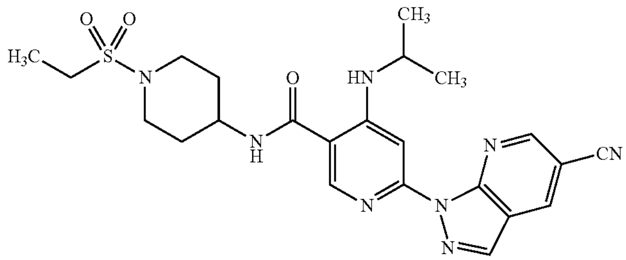 [SMILES: CCS(=O)(=O)N1CCC(NC(=O)c2cnc(-n3ncc4cc(C#N)cnc43)cc2NC(C)C)CC1] | 2.43 | G | 497.2 |
| 291 | 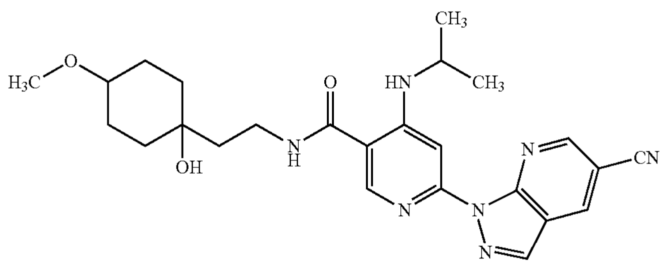 [SMILES: COC1CCC(O)(CCNC(=O)c2cnc(-n3ncc4cc(C#N)cnc43)cc2NC(C)C)CC1] | 1.48 | E | 478.25 |
| 292 | 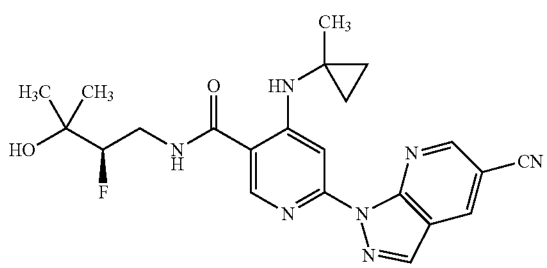 [SMILES: CC1(Nc2cc(-n3ncc4cc(C#N)cnc43)ncc2C(=O)NC[C@@H](F)C(C)(C)O)CC1] | 1.45 | E | 438.2 |
| 293 | 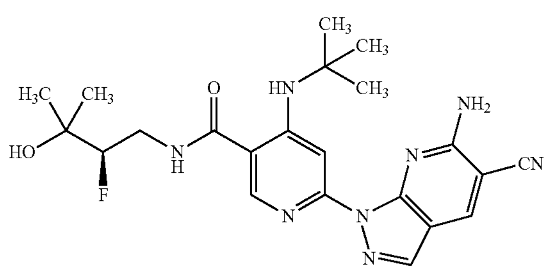 [SMILES: CC(C)(C)Nc1cc(-n2ncc3cc(C#N)c(N)nc32)ncc1C(=O)NC[C@@H](F)C(C)(C)O] | 1.39 | E | 455.2 |
| 294 | 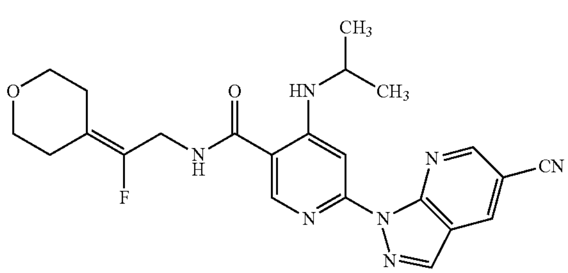 [SMILES: CC(C)Nc1cc(-n2ncc3cc(C#N)cnc32)ncc1C(=O)NCC(F)=C1CCOCC1] | 6.60 | A | 450.2 |

TABLE 11-continued

| Ex. No. | Structure | HPLC Rt (min) | HPLC cond. | LCMS |
|---|---|---|---|---|
| 295 | 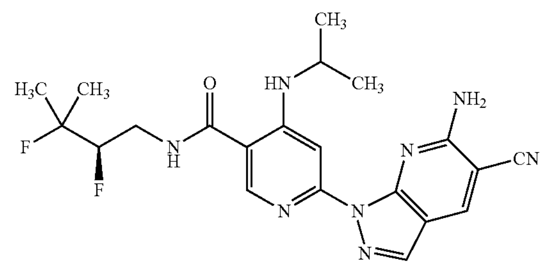 [SMILES: CC(C)Nc1cc(-n2ncc3cc(C#N)c(N)nc32)ncc1C(=O)NC[C@@H](F)C(C)(C)F] | 1.60 | E | 443.2 |
| 296 | 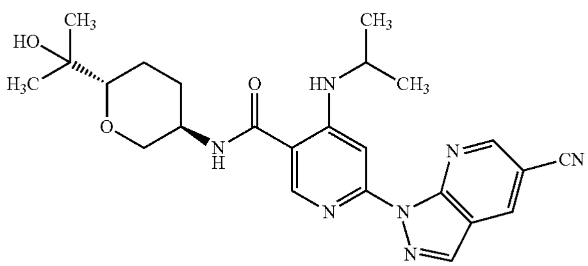 [SMILES: CC(C)Nc1cc(-n2ncc3cc(C#N)cnc32)ncc1C(=O)N[C@@H]1CC[C@@H](C(C)(C)O)OC1] | 1.23 | D | 464.3 |
| 297 | 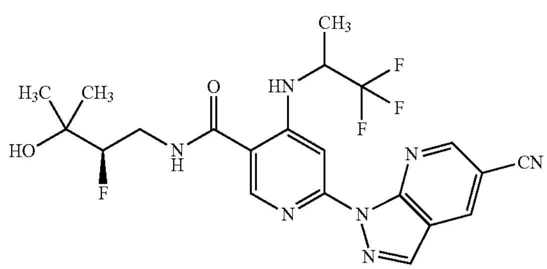 [SMILES: CC(Nc1cc(-n2ncc3cc(C#N)cnc32)ncc1C(=O)NC[C@@H](F)C(C)(C)O)C(F)(F)F] | 1.5 | E | 480.17 |
| 298 | 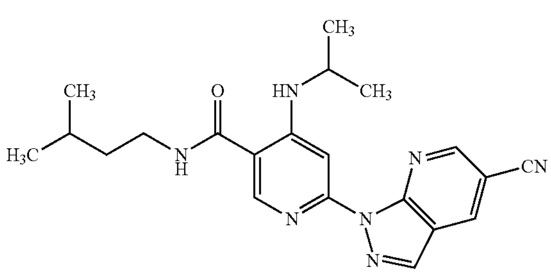 [SMILES: CC(C)CCNC(=O)c1cnc(-n2ncc3cc(C#N)cnc32)cc1NC(C)C] | 1.93 | E | 392.3 |
| 299 | 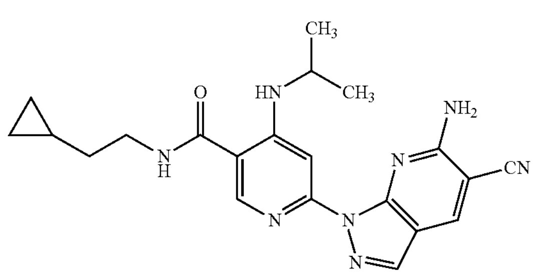 [SMILES: CC(C)Nc1cc(-n2ncc3cc(C#N)c(N)nc32)ncc1C(=O)NCCC1CC1] | 1.66 | E | 405.3 |

TABLE 11-continued

| Ex. No. | Structure | HPLC Rt (min) | HPLC cond. | LCMS |
|---|---|---|---|---|
| 300 | 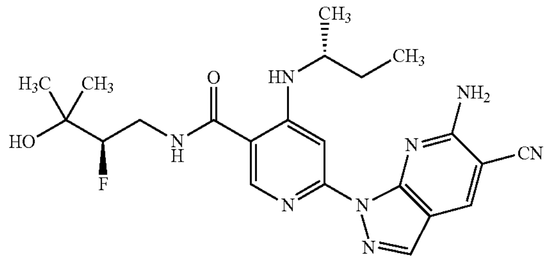 [SMILES: CC[C@@H](C)Nc1cc(-n2ncc3cc(C#N)c(N)nc32)ncc1C(=O)NC[C@@H](F)C(C)(C)O] | 1.21 | E | 455.22 |
| 301 | 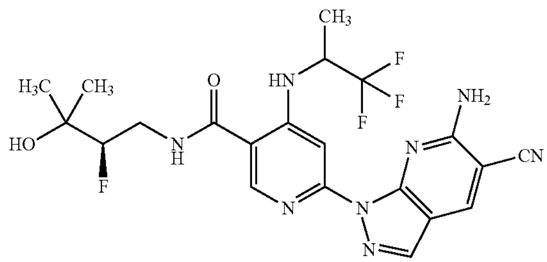 [SMILES: CC(Nc1cc(-n2ncc3cc(C#N)c(N)nc32)ncc1C(=O)NC[C@@H](F)C(C)(C)O)C(F)(F)F] | 1.44 | E | 495.18 |
| 302 | 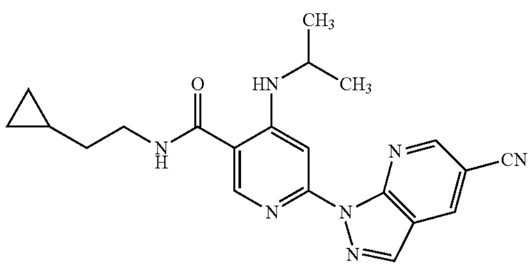 [SMILES: CC(C)Nc1cc(-n2ncc3cc(C#N)cnc32)ncc1C(=O)NCCC1CC1] | 1.77 | E | 390.2 |
| 303 | 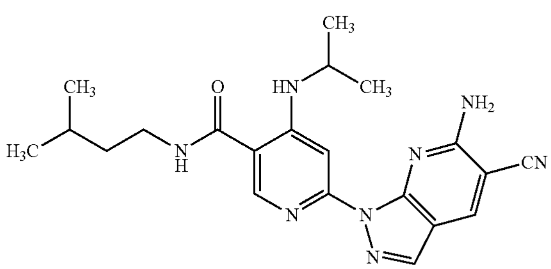 [SMILES: CC(C)CCNC(=O)c1cnc(-n2ncc3cc(C#N)c(N)nc32)cc1NC(C)C] | 1.77 | E | 407.3 |
| 304 | 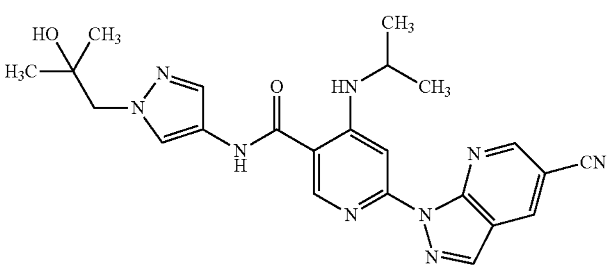 [SMILES: CC(C)Nc1cc(-n2ncc3cc(C#N)cnc32)ncc1C(=O)Nc1cnn(CC(C)(C)O)c1] | 6.99 | B | 460.2 |
| 305 | 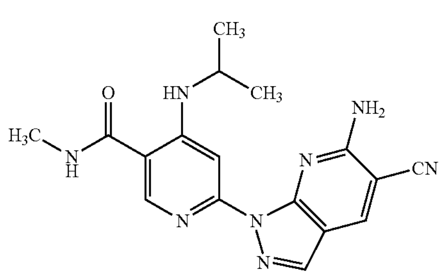 [SMILES: CNC(=O)c1cnc(-n2ncc3cc(C#N)c(N)nc32)cc1NC(C)C] | 1.21 | E | 351.2 |

TABLE 11-continued
| Ex. No. | Structure | HPLC Rt (min) | HPLC cond. | LCMS |
|---|---|---|---|---|
| 306 | 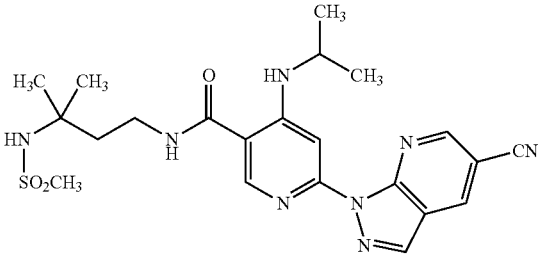 [SMILES: CC(C)Nc1cc(-n2ncc3cc(C#N)cnc32)ncc1C(=O)NCCC(C)(C)NS(C)(=O)=O] | 1.46 | C | 485.3 |
| 307 | 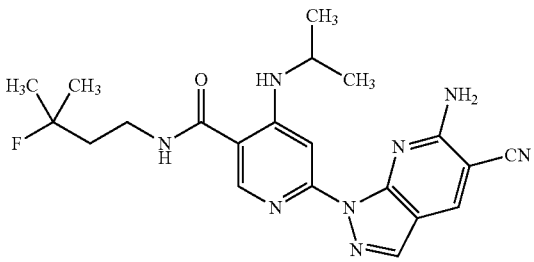 [SMILES: CC(C)Nc1cc(-n2ncc3cc(C#N)c(N)nc32)ncc1C(=O)NCCC(C)(C)F] | 1.62 | E | 425.21 |
| 308 | 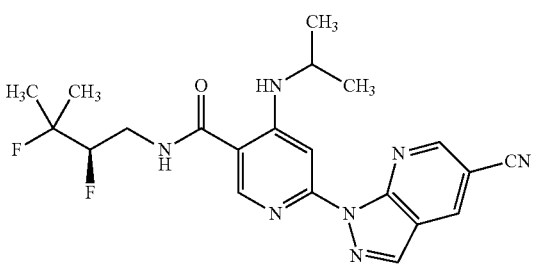 [SMILES: CC(C)Nc1cc(-n2ncc3cc(C#N)cnc32)ncc1C(=O)NC[C@@H](F)C(C)(C)F] | 1.83 | E | 428.3 |
| 309 | 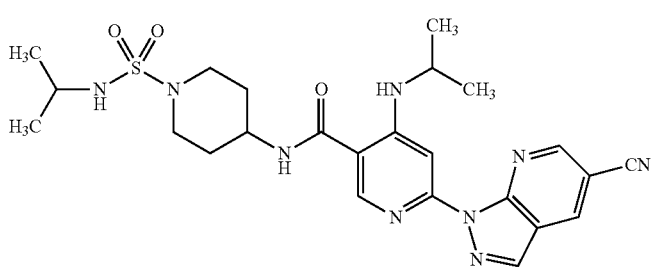 [SMILES: CC(C)Nc1cc(-n2ncc3cc(C#N)cnc32)ncc1C(=O)NC1CCN(S(=O)(=O)NC(C)C)CC1] | 1.66 | C | 526.3 |
| 310 | 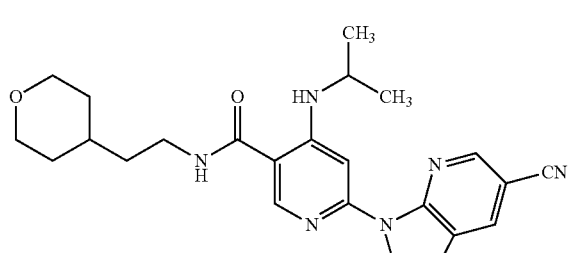 | 1.26 | D | 434.3 |

TABLE 11-continued
| Ex. No. | Structure | HPLC Rt (min) | HPLC cond. | LCMS |
|---|---|---|---|---|
| 311 | 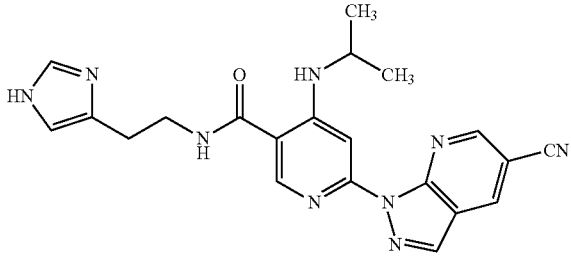 [SMILES: CC(C)Nc1cc(-n2ncc3cc(C#N)cnc32)ncc1C(=O)NCCc1c[nH]cn1] | 0.87 | D | 416.3 |
| 312 | 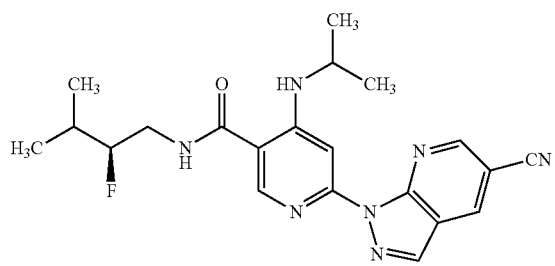 [SMILES: CC(C)Nc1cc(-n2ncc3cc(C#N)cnc32)ncc1C(=O)NC[C@@H](F)C(C)C] | 0.83 | J | 410.1 |
| 313 | 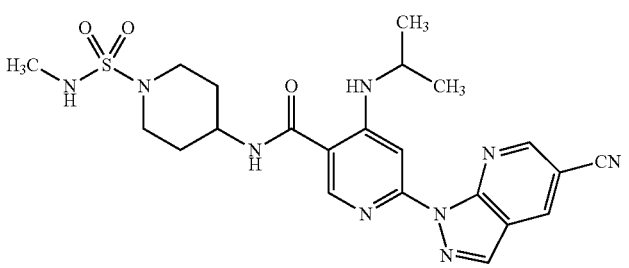 | 1.45 | C | 498.3 |
| 314 | 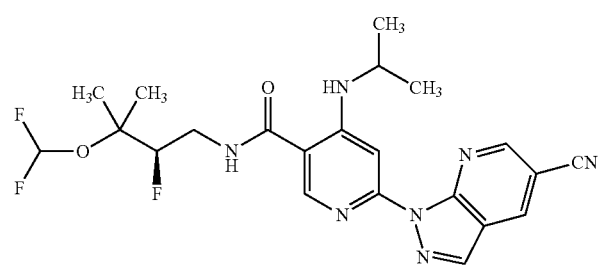 [SMILES: CC(C)Nc1cc(-n2ncc3cc(C#N)cnc32)ncc1C(=O)NC[C@@H](F)C(C)(C)OC(F)F] | 1.84 | C | 476.3 |
| 315 | 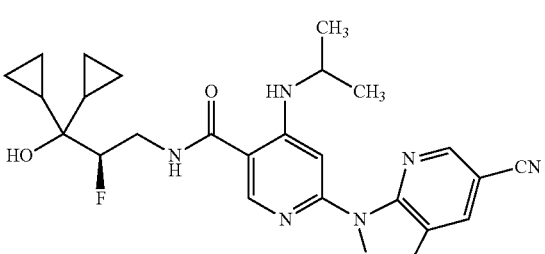 | 1.78 | C | 478.3 |
| 316 | 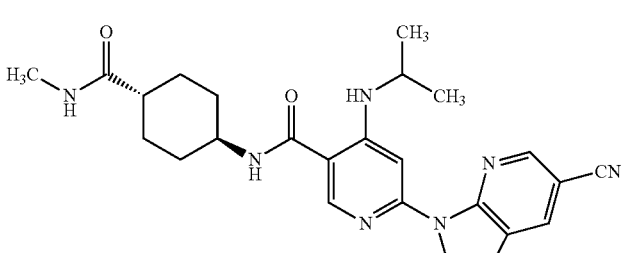 | 1.30 | E | 476.3 |

TABLE 11-continued

| Ex. No. | Structure | HPLC Rt (min) | HPLC cond. | LCMS |
|---|---|---|---|---|
| 317 | 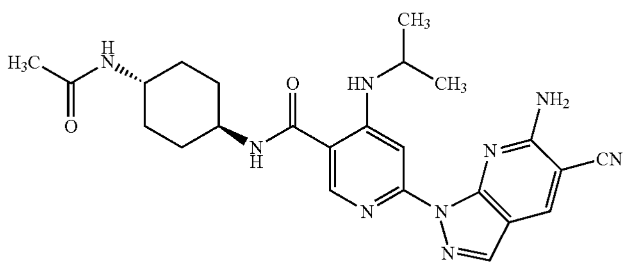 [SMILES: CC(=O)N[C@H]1CC[C@H](NC(=O)c2cnc(-n3ncc4cc(C#N)c(N)nc43)cc2NC(C)C)CC1] | 1.30 | E | 476.3 |
| 318 | 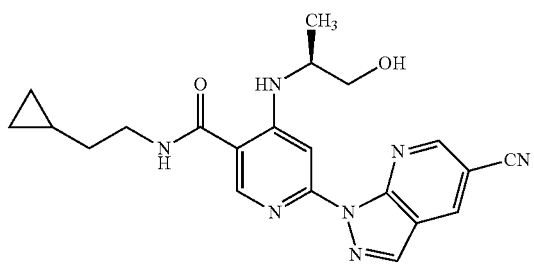 [SMILES: C[C@@H](CO)Nc1cc(-n2ncc3cc(C#N)cnc32)ncc1C(=O)NCCC1CC1] | 1.32 | E | 406.3 |
| 319 | 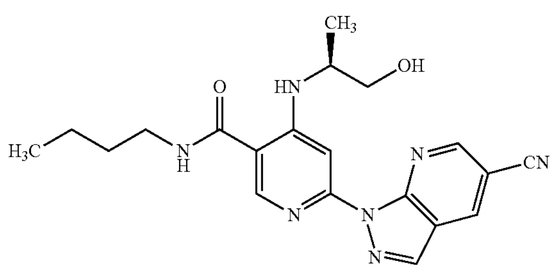 [SMILES: CCCCNC(=O)c1cnc(-n2ncc3cc(C#N)cnc32)cc1N[C@@H](C)CO] | 1.3 | E | 394.3 |
| 320 | 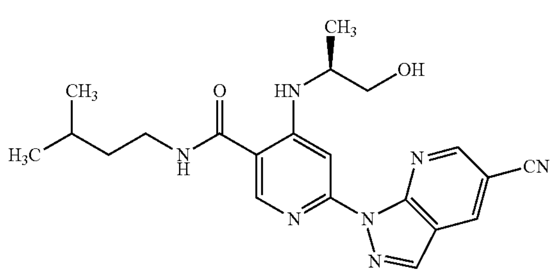 [SMILES: CC(C)CCNC(=O)c1cnc(-n2ncc3cc(C#N)cnc32)cc1N[C@@H](C)CO] | 1.44 | E | 408.3 |
| 321 | 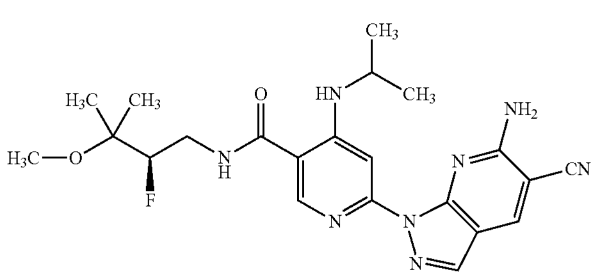 [SMILES: COC(C)(C)[C@H](F)CNC(=O)c1cnc(-n2ncc3cc(C#N)c(N)nc32)cc1NC(C)C] | 1.59 | E | 455.4 |

TABLE 11-continued

| Ex. No. | Structure | HPLC Rt (min) | HPLC cond. | LCMS |
|---|---|---|---|---|
| 322 | 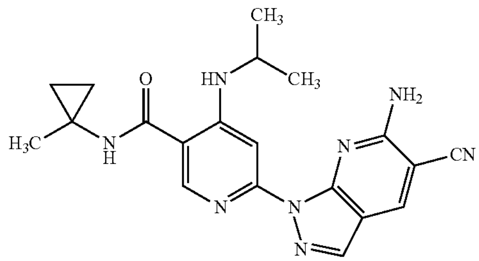 [SMILES: CC(C)Nc1cc(-n2ncc3cc(C#N)c(N)nc32)ncc1C(=O)NC1(C)CC1] | 1.51 | E | 391.3 |
| 323 | 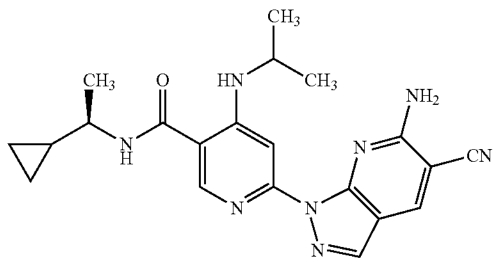 [SMILES: CC(C)Nc1cc(-n2ncc3cc(C#N)c(N)nc32)ncc1C(=O)N[C@H](C)C1CC1] | 1.66 | E | 405.3 |
| 324 | 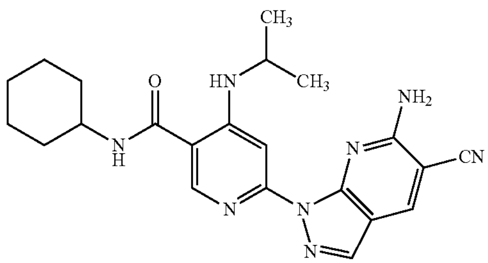 [SMILES: CC(C)Nc1cc(-n2ncc3cc(C#N)c(N)nc32)ncc1C(=O)NC1CCCCC1] | 1.8 | E | 419.3 |
| 325 | 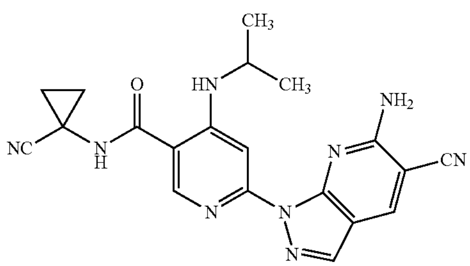 [SMILES: CC(C)Nc1cc(-n2ncc3cc(C#N)c(N)nc32)ncc1C(=O)NC1(C#N)CC1] | 1.42 | E | 402.3 |
| 326 | 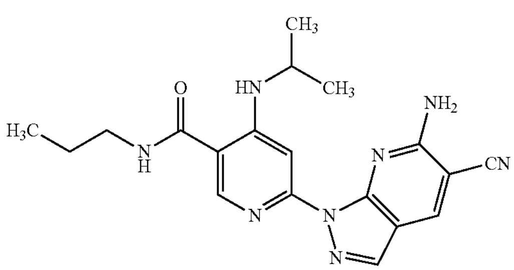 [SMILES: CCCNC(=O)c1cnc(-n2ncc3cc(C#N)c(N)nc32)cc1NC(C)C] | 1.51 | E | 379.3 |
| 327 | 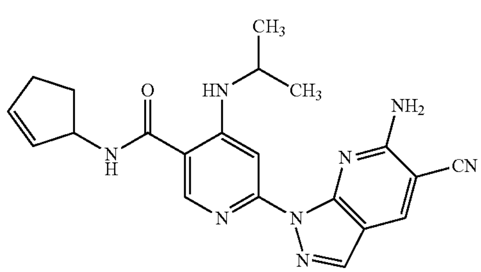 [SMILES: CC(C)Nc1cc(-n2ncc3cc(C#N)c(N)nc32)ncc1C(=O)NC1C=CCC1] | 1.95 | E | 403.3 |

TABLE 11-continued

| Ex. No. | Structure | HPLC Rt (min) | HPLC cond. | LCMS |
|---|---|---|---|---|
| 328 | 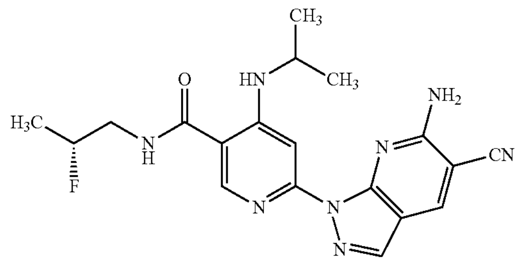 [SMILES: CC(C)Nc1cc(-n2ncc3cc(C#N)c(N)nc32)ncc1C(=O)NC[C@@H](C)F] | 1.48 | E | 397.3 |
| 329 | Enantiomer 2 | 7.06 | A | 452.2 |
| 330 | 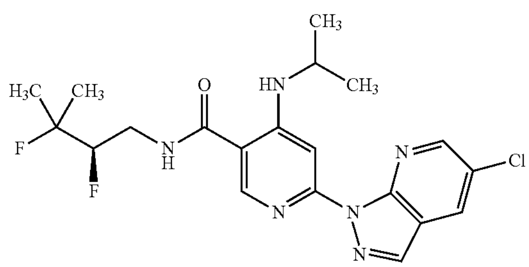 [SMILES: CC(C)Nc1cc(-n2ncc3cc(Cl)cnc32)ncc1C(=O)NC[C@@H](F)C(C)(C)F] | 1.96 | C | 437.2 |
| 331 | 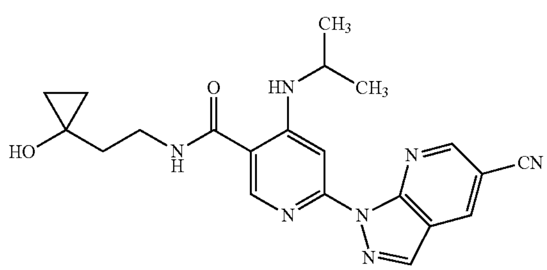 [SMILES: CC(C)Nc1cc(-n2ncc3cc(C#N)cnc32)ncc1C(=O)NCCC1(O)CC1] | 1.41 | E | 406.19 |
| 332 | 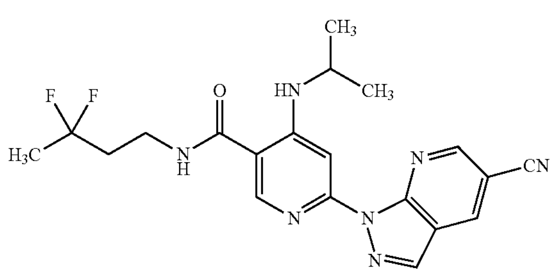 [SMILES: CC(C)Nc1cc(-n2ncc3cc(C#N)cnc32)ncc1C(=O)NCCC(C)(F)F] | 1.73 | E | 414.18 |

Example 333

(R)-6-(6-Cyano-3H-imidazo[4,5-b]pyridin-3-yl)-N-(2-fluoro-3-hydroxy-3-methylbutyl)-4-(oxetan-3-ylamino)nicotinamide

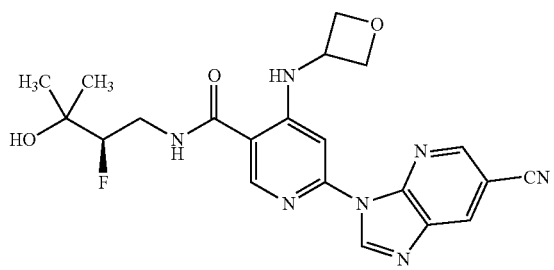

(333)

Intermediate 333A

Ethyl 6-chloro-4-(oxetan-3-ylamino)nicotinate

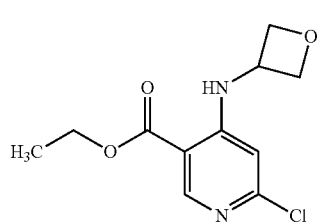

(333A)

Ethyl 4,6-dichloronicotinate (3.91 g, 17.79 mmol) was taken in a seal tube in DMA (10 mL) and oxetan-3-amine (1.3 g, 17.79 mmol) and DIPEA (12.43 mL, 71.1 mmol) were added. The reaction mixture was stirred for 16 hrs at 25° C. and then diluted with ethyl acetate, washed with water (100 ml). The organic layer was dried over anhydrous $Na_2SO_4$, filtered, and concentrated. The residue was dissolved in minimum volume of DCM (20 ml), charged with silica gel 60-120, purified through ISCO, eluting at 15% EtOAc/Pet.ether. Ethyl 6-chloro-4-(oxetan-3-ylamino)nicotinate (2.4 g, 7.74 mmol, 43.5% yield) was isolated as a colorless liquid. $^1$H NMR (400 MHz, DMSO-$d_6$) δ ppm 8.56-8.60 (m, 1H) 8.45 (d, J=5.52 Hz, 1H) 6.63 (s, 1H) 4.87-4.93 (m, 2H) 4.77-4.87 (m, 1H) 4.46-4.52 (m, 2H) 4.34 (q, J=7.03 Hz, 2H) 1.30-1.37 (m, 3H).

Intermediate 333B

6-Chloro-4-(oxetan-3-ylamino)nicotinic acid

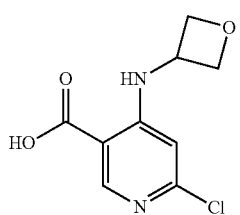

(333B)

To a stirred solution of ethyl 6-chloro-4-(oxetan-3-ylamino)nicotinate (2.35 g, 9.16 mmol) in a mixture of THF (10 mL), ethanol (4 mL) and water (4 mL), LiOH (0.658 g, 27.5 mmol) was added. The reaction mixture was stirred for 2 hrs and concentrated completely. The resulting residue was dissolved in water (5 ml) and acidified to pH 4 using saturated aqueous citric acid solution. The solids were filtered, washed with water (2×30 ml) and dried to afford 6-chloro-4-(oxetan-3-ylamino)nicotinic acid (1.9 g, 79% yield) as off-white solid. $^1$H NMR (400 MHz, DMSO-$d_6$) δ ppm 8.92 (br. s., 1H) 8.53 (s, 1H) 6.56 (s, 1H) 4.87-4.93 (m, 2H) 4.75-4.84 (m, 1H) 4.43-4.49 (m, 2H).

Intermediate 333C (R)-6-Chloro-N-(2-fluoro-3-hydroxy-3-methylbutyl)-4-(oxetan-3-ylamino)nicotinamide

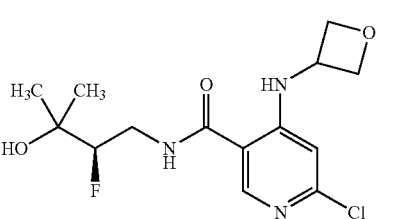

(333C)

To a stirred solution of 6-chloro-4-(oxetan-3-ylamino)nicotinic acid (0.6 g, 2.62 mmol) in DMF (10 mL) at 0° C. were added DIPEA (2.292 mL, 13.12 mmol) and HATU (1.996 g, 5.25 mmol) followed by the addition of (R)-4-amino-3-fluoro-2-methylbutan-2-ol (0.318 g, 2.62 mmol). The reaction mixture was stirred for 16 hrs at 25° C. The mixture was diluted with ethyl acetate and washed with water and brine. The organic solution was dried over anhydrous $Na_2SO_4$, filtered, concentrated and then purified on silica gel using 3.5% MeOH/chloroform to afford (R)-6-chloro-N-(2-fluoro-3-hydroxy-3-methylbutyl)-4-(oxetan-3-ylamino)nicotinamide (0.6 g, 65.3% yield) as an off-white solid. $^1$H NMR (400 MHz, DMSO-$d_6$) δ ppm 8.91 (d, J=6.53 Hz, 1H) 8.83 (t, J=5.52 Hz, 1H) 8.43 (s, 1H) 6.52 (s, 1H) 4.86-4.92 (m, 2H) 4.83 (s, 1H) 4.71-4.77 (m, 1H) 4.27-4.46 (m, 3H) 3.63-3.79 (m, 1H) 3.34-3.45 (m, 1H) 1.17 (dd, J=5.52, 1.51 Hz, 6H). LCMS m/z 332 (M+H).

Example 333

In a vial suitable for heating, a mixture of a mixture of (R)-6-chloro-N-(2-fluoro-3-hydroxy-3-methylbutyl)-4-(oxetan-3-ylamino)nicotinamide (34.5 mg, 0.104 mmol), 3H-imidazo[4,5-b]pyridine-6-carbonitrile (15 mg, 0.104 mmol) and powdered phosphoric acid, potassium salt, tribasic (66.3 mg, 0.312 mmol) in dioxane (2 mL) was degassed with bubbling nitrogen for 5 minutes. In a separate sealed vial, a degassed, stirring mixture of $Pd_2(dba)_3$ (4.76 mg, 5.20 mol) and tetramethyl t-Bu XPhos (6.00 mg, 0.012 mmol) in 5:1 toluene/dioxane (0.2 mL) was heated at 120° C. for 5 minutes. After cooling to room temperature, this solution was transferred to the vial containing the reaction mixture. The vial was sealed, and the reaction mixture was heated at 80° C. for 4 hours, at which point it was judged to be complete by LCMS. The reaction mixture was diluted with ethyl acetate (2 mL), filtered, and concentrated in vacuo. The product was purified by HPLC to afford (R)-6-(6-cyano-3H-imidazo[4,5- b]pyridin-3-yl)-N-(2-fluoro-3-hydroxy-3-methylbutyl)-4-(oxetan-3-ylamino)nicotinamide (13 mg, 26% yield). LCMS 440.3 (M+H)+. HPLC Rt 1.24 min, Conditions E. ¹H NMR (500 MHz, DMSO-d₆) δ 9.38 (s, 1H), 9.07 (d, J=4.7 Hz, 1H), 9.00 (d, J=1.7 Hz, 1H), 8.91 (t, J=5.2 Hz, 1H), 8.87 (d, J=1.3 Hz, 1H), 8.66 (s, 1H), 7.64 (s, 1H), 5.00 (t, J=6.7 Hz, 2H), 4.81-4.73 (m, 1H), 4.57 (t, J=6.2 Hz, 2H), 4.44 (d, J=8.1 Hz, 1H), 4.35 (d, J=7.7 Hz, 1H), 3.84-3.66 (m, 1H), 1.19 (d, J=6.4 Hz, 7H).

The Examples in Table 12 were prepared using the general methods for Example 333 using the appropriate starting material and amine.

TABLE 12

| Ex. No. | Structure | HPLC Rt (min) | HPLC cond. | LCMS |
|---|---|---|---|---|
| 334 | 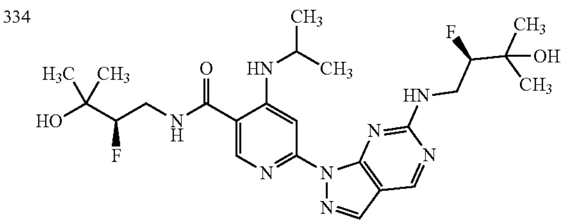 | 1.42 | E | 521.3 |
| 335 | 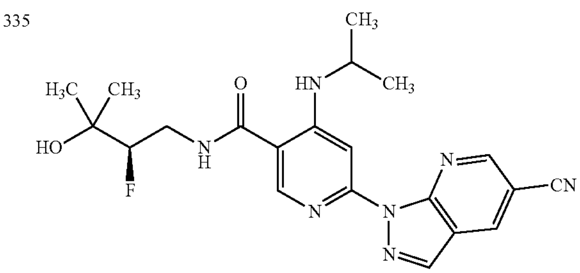 | 1.52 | E | 426.4 |
| 336 | 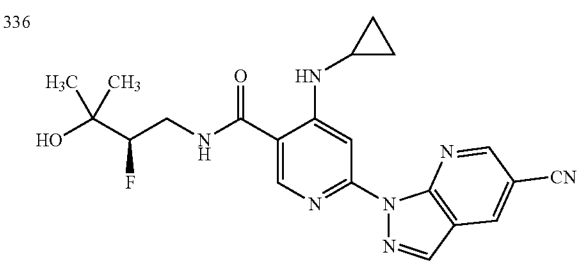 | 1.54 | E | 424.3 |
| 337 | 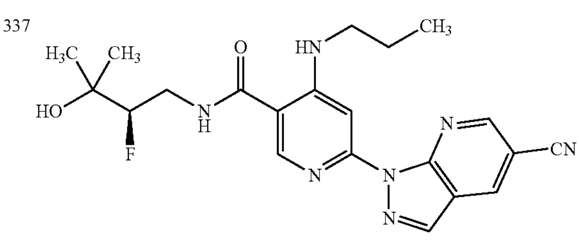 | 1.48 | E | 426.2 |
| 338 | 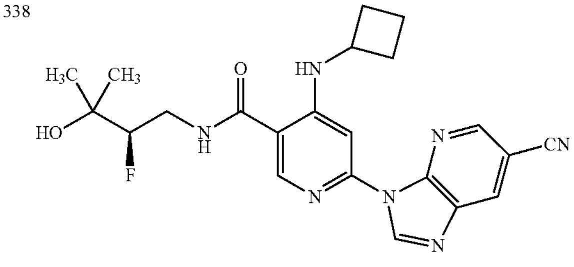 | 1.55 | E | 438.3 |

TABLE 12-continued
| Ex. No. | Structure | HPLC Rt (min) | HPLC cond. | LCMS |
|---|---|---|---|---|
| 339 | 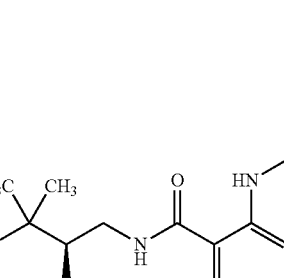 | 1.9 | E | 435.2 |
| 340 | 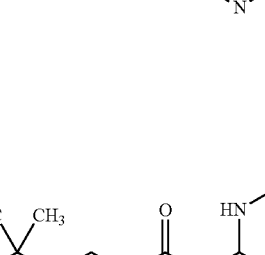 | 1.45 | E | 449.2 |
| 341 | 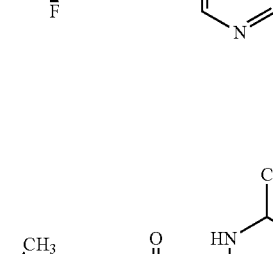 | 1.28 | E | 441.2 |
| 342 | 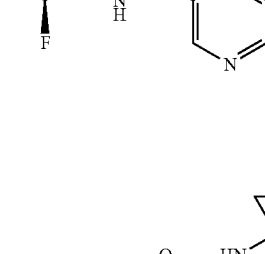 | 1.79 | E | 428.2 |
| 343 | 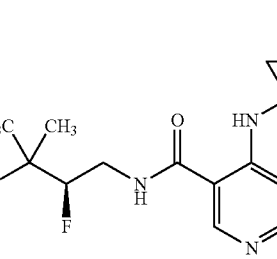 | 1.6 | E | 438.1 |

TABLE 12-continued

| Ex. No. | Structure | HPLC Rt (min) | HPLC cond. | LCMS |
|---|---|---|---|---|
| 344 | 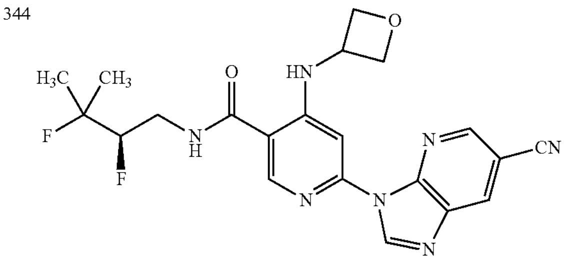 | 1.49 | E | 442.1 |
| 345 | 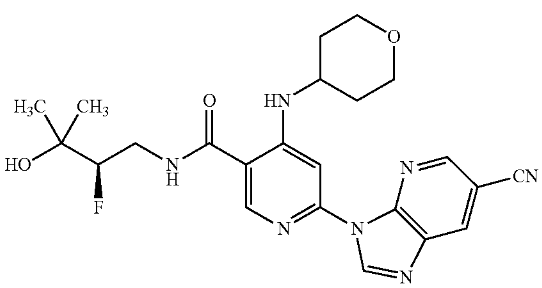 [SMILES: CC(C)(O)[C@H](F)CNC(=O)c1cnc(-n2cnc3cc(C#N)cnc32)cc1NC1CCOCC1] | 1.29 | E | 468.2 |
| 346 | 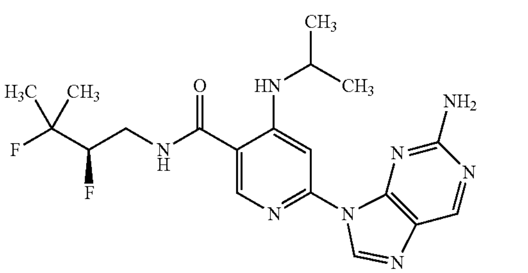 [SMILES: CC(C)Nc1cc(-n2cnc3cnc(N)nc32)ncc1C(=O)NC[C@@H](F)C(C)(C)F] | 1.52 | E | 419.1 |

Example 347

(R)-6-(5-Cyano-1H-pyrazolo[3,4-b]pyridin-1-yl)-4-((1-(2,2-difluoroethyl)-1H-pyrazol-4-yl)amino)-N-(2-fluoro-3-hydroxy-3-methylbutyl)nicotinamide

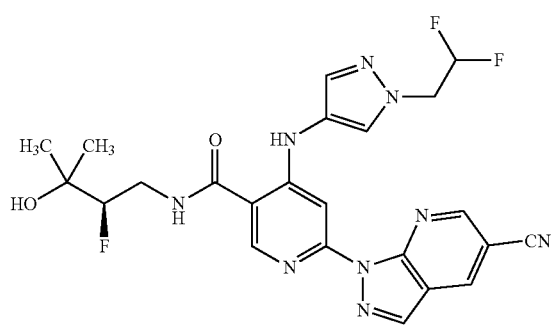

(347)

Intermediate 347A 1-(2,2-Difluoroethyl)-4-nitro-1H-pyrazole

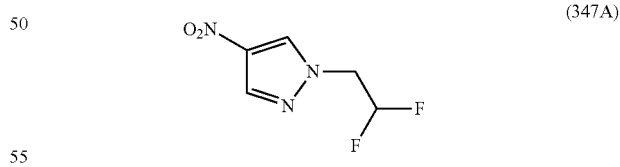

(347A)

To a stirred solution of 4-nitro-1H-pyrazole (5 g, 44.2 mmol) in DMF (60 mL) was added $K_2CO_3$ (12.22 g, 88 mmol) over a period of 5 minutes. The reaction mixture was stirred at ambient temperature for 10 minutes. Next, 1,1-difluoro-2-iodoethane (11.03 g, 57.5 mmol) was added and the reaction mixture was stirred for 12 h at 90° C. The reaction mixture was then partitioned between water (150 mL) and EtOAc (150 mL) and the aqueous layer was extracted with EtOAc (2×100 mL). The combined EtOAc layer was washed with water (2×100 mL) and brine (100 mL), dried over sodium sulfate, filtered and concentrated to give crude product. The product was purified via column chromatography to afford 1-(2,2-difluoroethyl)-4-nitro-1H-pyrazole (5.2 g, 60% yield) as a tan solid. $^1$H NMR (400 MHz, DMSO-$d_6$) δ 8.95 (s, 1H), 8.35 (s, 1H), 6.45 (m, 1H), 4.75 (td, J=15, 3.5 Hz, 2H).

Intermediate 347B 1-(2,2-Difluoroethyl)-4-amino-1H-pyrazole

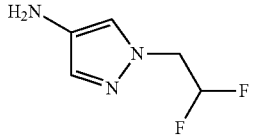

(347B)

Under a nitrogen atmosphere, a Parr bottle was carefully charged with 10% Pd on carbon (1.56 g, 1.47 mmol) and the catalyst was carefully wetted with MeOH (50 mL). The vessel was charged with a solution of 1-(2,2-difluoroethyl)-4-nitro-1H-pyrazole (5.2 g, 29.4 mmol) and the mixture was degassed by evacuating the vessel under vacuum and repressurizing with hydrogen. The mixture was hydrogenated at 15 psi for 6 hours. The mixture was degassed, and the reaction mixture was filtered under nitrogen through fiberglass filter paper. The filter cake was thoroughly rinsed with methanol (200 mL total rinse volume), and the combined filtrate and rinsings were concentrated in vacuo to obtain 1-(2,2-difluoroethyl)-4-amino-1H-pyrazole (5.2 g, 62% yield). $^1$H NMR (400 MHz, DMSO-$d_6$) δ 7.07 (s, 1H), 6.99 (d, J=0.9 Hz, 1H), 6.38-6.10 (m, 1H), 4.40 (td, J=15.1, 4.0 Hz, 2H), 3.18 (m, 2H).

Intermediate 347C

Ethyl 6-chloro-4-((1-(2,2-difluoroethyl)-1H-pyrazol-4-yl)amino) nicotinate

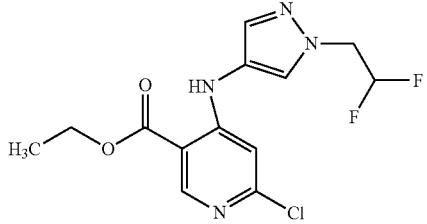

(347C)

A solution of ethyl 4,6-dichloronicotinate (0.6 g, 2.73 mmol), 1-(2,2-difluoroethyl)-1H-pyrazol-4-amine (0.401 g, 2.73 mmol), and DIPEA (2.381 mL, 13.63 mmol) in DMA (12 mL) was heated at 100° C. overnight. The reaction mixture was concentrated to remove DMA and water was added. The product was extracted with ethylacetate (3 times) and the combined extracts were washed with water and brine. The extracts were dried over anhydrous Na$_2$SO$_4$, filtered, and concentrated to obtain a brown liquid. This crude product was purified via column chromatography to afford ethyl 6-chloro-4-((1-(2,2-difluoroethyl)-1H-pyrazol-4-yl)amino)nicotinate (0.78 g, 86% yield). $^1$H NMR (300 MHz, DMSO-$d_6$) δ 9.29 (s, 1H), 8.63 (s, 1H), 8.02 (s, 1H), 7.66 (s, 1H), 6.67 (s, 1H), 6.61-6.19 (m, 1H), 4.64 (td, J=15.2, 3.6 Hz, 2H), 4.36 (q, J=7.2 Hz, 2H), 1.41-1.29 (m, 3H); LCMS m/z 331.0 (M+H).

Intermediate 347D

6-Chloro-4-((1-(2,2-difluoroethyl)-1H-pyrazol-4-yl)amino)nicotinic acid

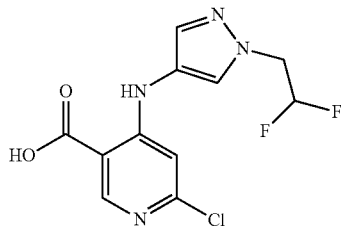

(347D)

To a solution of ethyl 6-chloro-4-((1-(2,2-difluoroethyl)-1H-pyrazol-4-yl)amino) nicotinate (0.4 g, 1.21 mmol) in ethanol (10 mL) and water (4 mL) was added LiOH (0.09 g, 3.6 mmol). The reaction mixture was stirred at room temperature overnight. The reaction mixture was concentrated to remove ethanol and the residue was acidified with 1.5N HCl. The white solid formed was collected and used without further purification (0.35 g, 96% yield). LCMS m/z 303.0 (M+H).

Intermediate 347E (R)-6-Chloro-4-((1-(2,2-difluoroethyl)-1H-pyrazol-4-yl)amino)-N-(2-fluoro-3-hydroxy-3-methylbutyl)nicotinamide

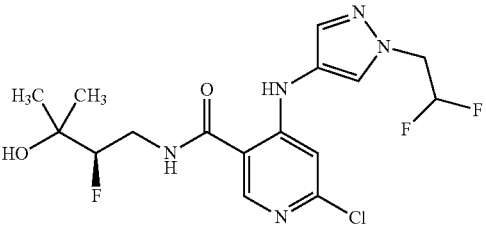

(347E)

To a solution of 6-chloro-4-((1-(2,2-difluoroethyl)-1H-pyrazol-4-yl)amino) nicotinic acid (0.4 g, 1.322 mmol) in DMF (8 mL), were added HATU (0.75 g, 2 mmol), DIPEA (1.15 mL, 6.6 mmol), and (R)-4-amino-3-fluoro-2-methylbutan-2-ol (0.19 g, 1.6 mmol). The reaction mixture was stirred at room temperature overnight. Sodium bicarbonate was added and the reaction mixture was extracted with ethyl acetate (3 times). The combined organic extracts were washed with water and brine then dried over anhydrous Na$_2$SO$_4$. The filtrate was concentrated to a brown liquid which was purified via column chromatography to afford (R)-6-chloro-4-((1-(2,2-difluoroethyl)-1H-pyrazol-4-yl)amino)-N-(2-fluoro-3-hydroxy-3-methylbutyl)nicotinamide (0.51 g, 95% yield). $^1$H NMR (300 MHz, DMSO-$d_6$) δ 9.83 (s, 1H), 8.95 (t, J=5.5 Hz, 1H), 8.49 (s, 1H), 8.00 (s, 1H), 7.63 (d, J=0.8 Hz, 1H), 6.66 (s, 1H), 6.60-6.18 (m, 1H), 4.85 (s, 1H), 4.62 (td, J=15.1, 3.8 Hz, 2H), 4.48-4.25 (m, 1H), 3.85-3.61 (m, 1H), 3.50-3.36 (m, 1H), 1.20-1.12 (m, 6H); LCMS m/z 406.0 (M+H).

Example 347

To a solution of (R)-6-chloro-4-((1-(2,2-difluoroethyl)-1H-pyrazol-4-yl)amino)-N-(2-fluoro-3-hydroxy-3-methylbutyl)nicotinamide (0.1 g, 0.25 mmol) and 1H-pyrazolo[3,4-b]pyridine-5-carbonitrile (0.043 g, 0.3 mmol) in 1,4 dioxane were added Xantphos (0.057 g, 0.1 mmol), $K_2CO_3$ (0.102 g, 0.74 mmol), LiCl (10.45 mg, 0.246 mmol), and $ZnCl_2$ (6.72 mg, 0.05 mmol). The reaction mixture was purged with nitrogen and tris(dibenzylidene)dipalladium (0.090 g, 0.1 mmol) was added. The reaction mixture was purged again with nitrogen for 10 minutes. The reaction vessel was sealed and heated at 110° C. The reaction mixture was filtered through CELITE® using 1:1 methanol and dichloromethane and extracted with 1.5N HCl and ethyl acetate. The water layer was neutralized with sodium carbonate and extracted with ethyl acetate (3 times). The combined organic extracts were washed with water and brine then dried over anhydrous $Na_2SO_4$, filtered, and concentrated to obtain a brown solid. The product was purified via column chromatography to afford (R)-6-(5-cyano-1H-pyrazolo[3,4-b]pyridin-1-yl)-4-((1-(2,2-difluoroethyl)-1H-pyrazol-4-yl)amino)-N-(2-fluoro-3-hydroxy-3-methylbutyl) nicotinamide (10 mg, 8% yield). $^1$H NMR (400 MHz, DMSO-$d_6$) δ=10.04 (s, 1H), 9.09-8.95 (m, 3H), 8.75 (s, 1H), 8.64 (s, 1H), 8.02 (s, 1H), 7.69 (s, 1H), 7.65 (s, 1H), 6.55-6.13 (m, 1H), 4.87 (s, 1H), 4.67 (td, J=15.2, 3.8 Hz, 2H), 4.52-4.30 (m, 1H), 3.89-3.66 (m, 1H), 3.51-3.39 (m, 1H), 1.19 (dd, J=5.3, 1.3 Hz, 6H). LCMS m/z 514.2 (M+H).

The Examples in Table 13 were prepared using the general methods for Example 347 using the appropriate starting material and amine.

TABLE 13

| Ex. No. | Structure | HPLC Rt (min) | HPLC cond. | LCMS |
|---|---|---|---|---|
| 348 | 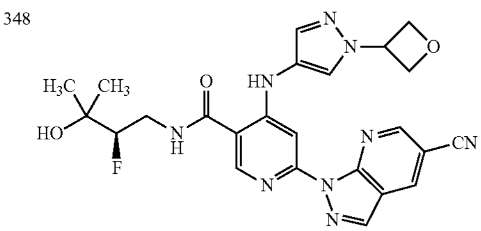 | 5.92 | A | 506.2 |
| 349 | 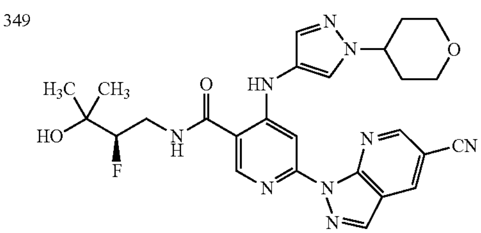 | 1.85 | C | 534.2 |
| 350 | 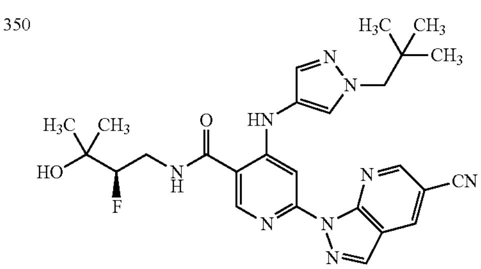 | 11.24 | B | 522.2 |
| 351 | 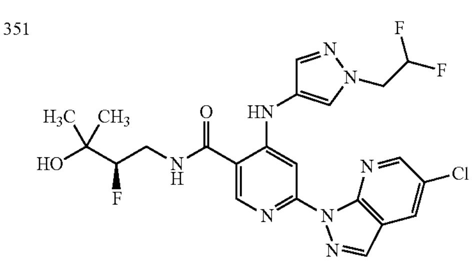 | 1.38 | C | 523.3 |

TABLE 13-continued

| Ex. No. | Structure | HPLC Rt (min) | HPLC cond. | LCMS |
|---|---|---|---|---|
| 352 | 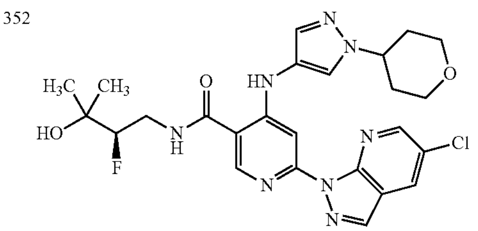 | 1.30 | C | 543.3 |
| 353 | 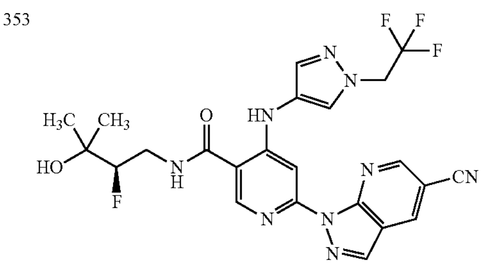 | 1.35 | C | 532.3 |
| 354 | 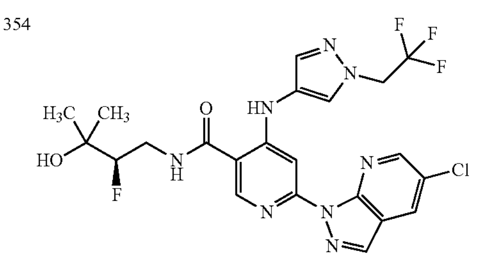 | 1.53 | C | 541.3 |
| 355 | 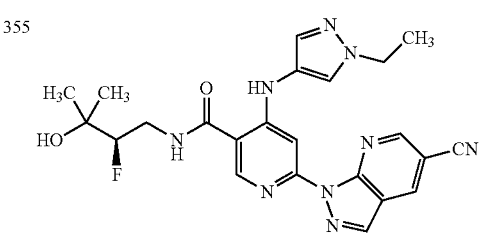 | 1.18 | C | 478.3 |
| 356 | 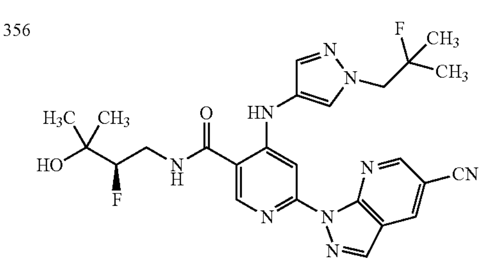 | 1.32 | C | 524.3 |
| 357 | 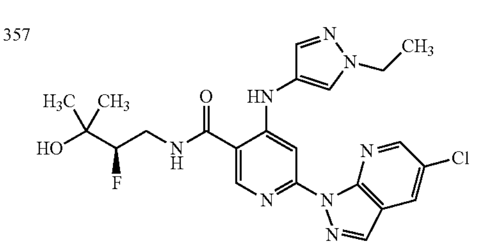 | 1.37 | C | 487.3 |

TABLE 13-continued

| Ex. No. | Structure | HPLC Rt (min) | HPLC cond. | LCMS |
|---|---|---|---|---|
| 358 | 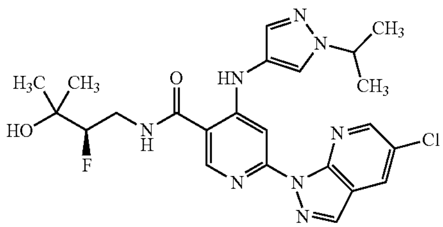 [SMILES: CC(C)n1cc(Nc2cc(-n3ncc4cc(Cl)cnc43)ncc2C(=O)NC[C@@H](F)C(C)(C)O)cn1] | 1.50 | C | 501.3 |
| 359 | 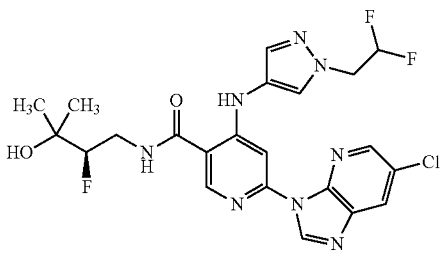 [SMILES: CC(C)(O)[C@H](F)CNC(=O)c1cnc(-n2cnc3cc(Cl)cnc32)cc1Nc1cnn(CC(F)F)c1] | 1.43 | C | 523.3 |
| 360 | 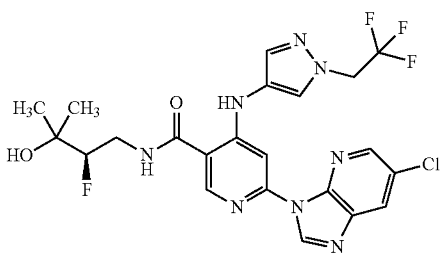 [SMILES: CC(C)(O)[C@H](F)CNC(=O)c1cnc(-n2cnc3cc(Cl)cnc32)cc1Nc1cnn(CC(F)(F)F)c1] | 1.57 | C | 541.3 |
| 361 | 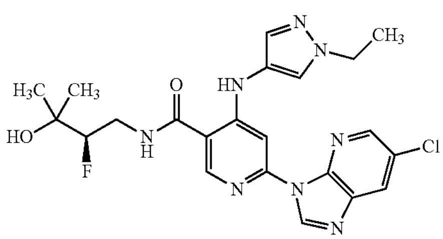 [SMILES: CCn1cc(Nc2cc(-n3cnc4cc(Cl)cnc43)ncc2C(=O)NC[C@@H](F)C(C)(C)O)cn1] | 1.43 | C | 487.3 |
| 362 | 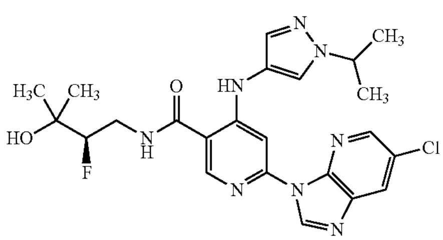 [SMILES: CC(C)n1cc(Nc2cc(-n3cnc4cc(Cl)cnc43)ncc2C(=O)NC[C@@H](F)C(C)(C)O)cn1] | 1.58 | C | 501.3 |
| 363 | 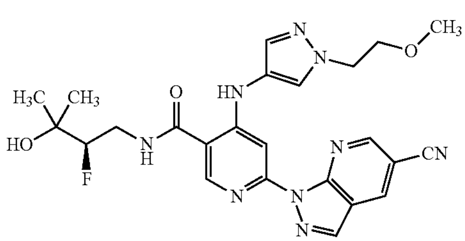 [SMILES: COCCn1cc(Nc2cc(-n3ncc4cc(C#N)cnc43)ncc2C(=O)NC[C@@H](F)C(C)(C)O)cn1] | 1.08 | C | 508.3 |

TABLE 13-continued
| Ex. No. | Structure | HPLC Rt (min) | HPLC cond. | LCMS |
|---|---|---|---|---|
| 364 | 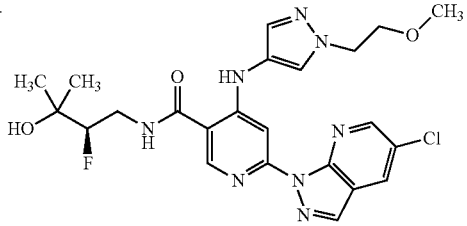 | 1.26 | C | 517.3 |
| 365 | 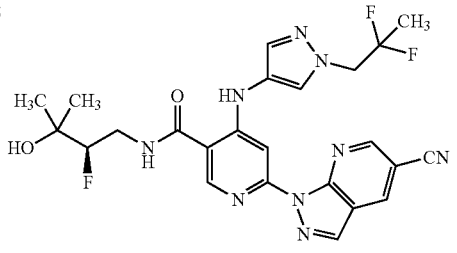 [SMILES: CC(F)(F)Cn1cc(Nc2cc(-n3ncc4cc(C#N)cnc43)ncc2C(=O)NC[C@@H](F)C(C)(C)O)cn1] | 1.28 | C | 528.3 |
| 366 | 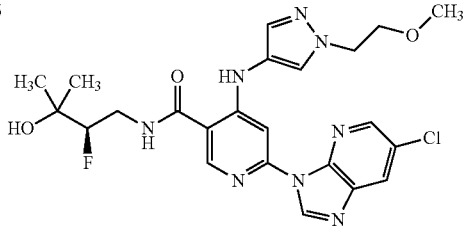 | 1.35 | C | 517.3 |
| 367 | 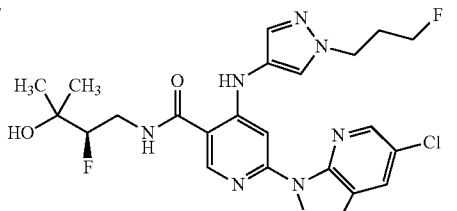 | 1.37 | C | 519.3 |
| 368 | 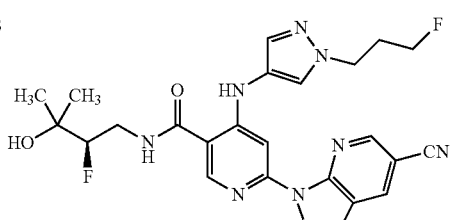 | 1.18 | C | 510.3 |
| 369 | 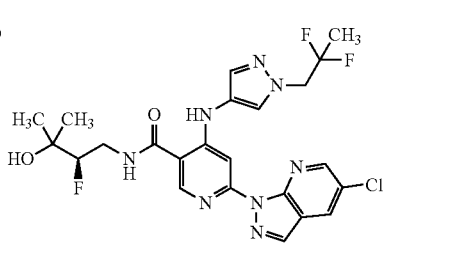 | 2.15 | G | 537.3 |

TABLE 13-continued
| Ex. No. | Structure | HPLC Rt (min) | HPLC cond. | LCMS |
|---|---|---|---|---|
| 370 | 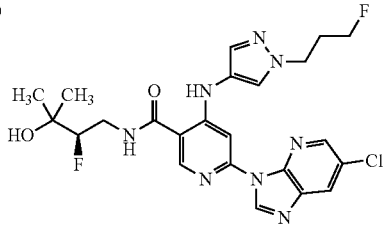 | 1.55 | C | 519.3 |
| 371 | 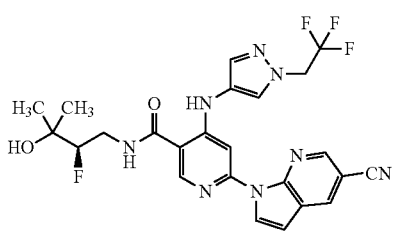 [SMILES: CC(C)(O)[C@H](F)CNC(=O)c1cnc(-n2ccc3cc(C#N)cnc32)cc1Nc1cnn(CC(F)(F)F)c1] | 1.62 | C | 531.3 |
| 372 | 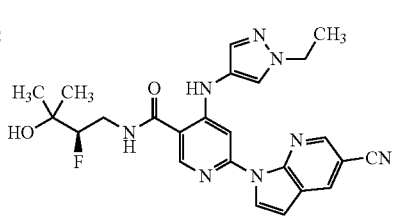 [SMILES: CCn1cc(Nc2cc(-n3ccc4cc(C#N)cnc43)ncc2C(=O)NC[C@@H](F)C(C)(C)O)cn1] | 1.63 | C | 477.3 |
| 373 | 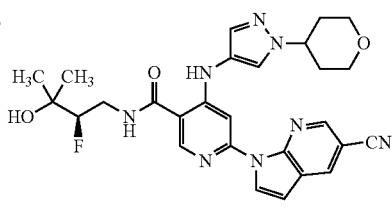 [SMILES: CC(C)(O)[C@H](F)CNC(=O)c1cnc(-n2ccc3cc(C#N)cnc32)cc1Nc1cnn(C2CCOCC2)c1] | 1.44 | C | 533.3 |
| 374 | 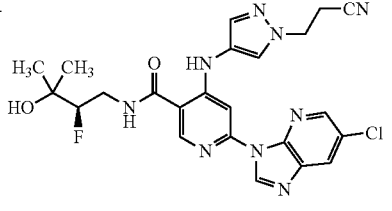 | 1.33 | C | 512.3 |
| 375 | 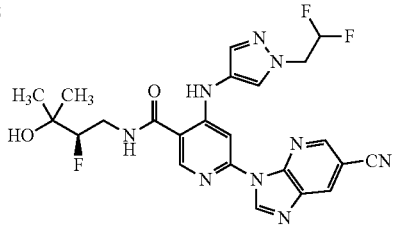 [SMILES: CC(C)(O)[C@H](F)CNC(=O)c1cnc(-n2cnc3cc(C#N)cnc32)cc1Nc1cnn(CC(F)F)c1] | 1.34 | C | 514.3 |
| 376 | 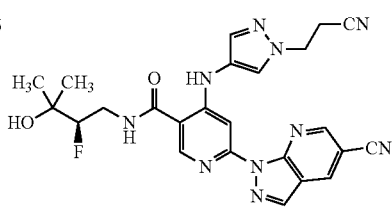 | 1.00 | C | 503.3 |

TABLE 13-continued

| Ex. No. | Structure | HPLC Rt (min) | HPLC cond. | LCMS |
|---|---|---|---|---|
| 377 | (structure) | 1.26 | C | 512.3 |
| 378 | (structure) Diastereomeric Mixture | 1.35 | C | 510.3 |
| 379 | (structure) Diastereomeric Mixture | 1.48 | C | 588.3 |
| 380 | (structure) | 1.36 | C | 492.3 |
| 381 | (structure) | 1.55 | C | 501.3 |
| 382 | (structure) | 1.64 | C | 501.3 |
| 383 | (structure) | 1.67 | C | 491.3 |

TABLE 13-continued

| Ex. No. | Structure | HPLC Rt (min) | HPLC cond. | LCMS |
|---|---|---|---|---|
| 384 | 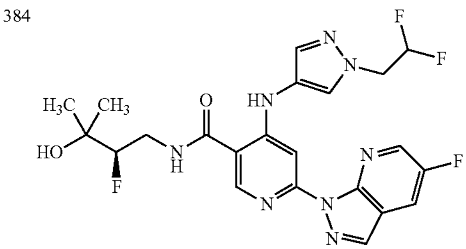 | 1.31 | C | 507.3 |
| 385 | 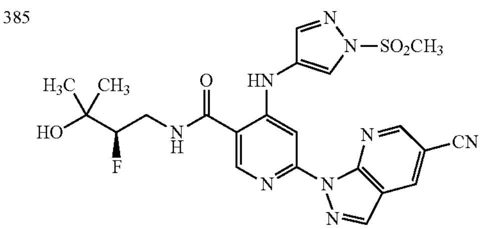 | 6.39 | A | 526.3 (M −H) |
| 386 | 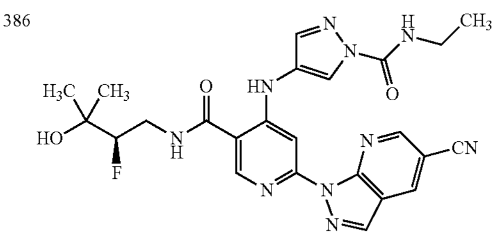 | 7.22 | A | 519.2 (M −H) |
| 387 | 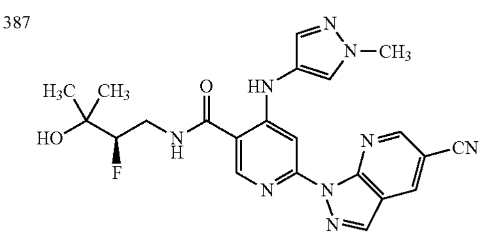 | 1.06 | C | 463.3 |
| 388 | 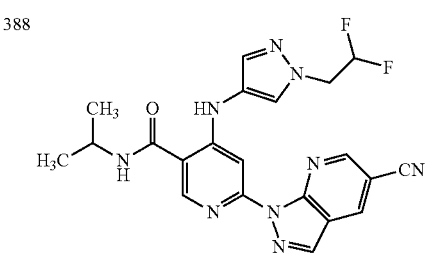 [SMILES: CCCNC(=O)c1cnc(-n2ncc3cc(C#N)cnc32)cc1Nc1cnn(CC(F)F)c1] | 1.33 | C | 452.3 |
| 389 | 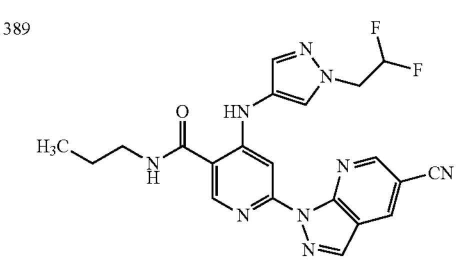 | 1.13 | C | 452.3 |

TABLE 13-continued
| Ex. No. | Structure | HPLC Rt (min) | HPLC cond. | LCMS |
|---|---|---|---|---|
| 390 | 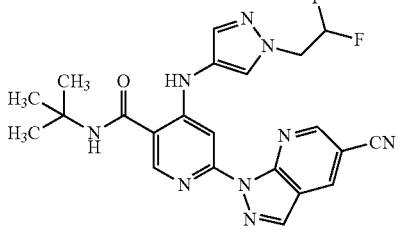 | 1.26 | C | 466.3 |
| 391 | 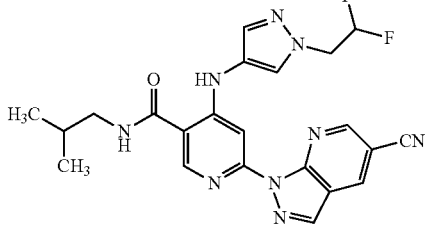 | 1.48 | C | 466.3 |
| 392 | 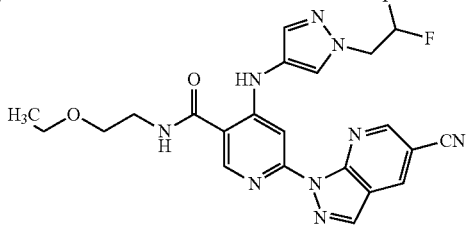 | 1.27 | C | 482.3 |
| 393 | 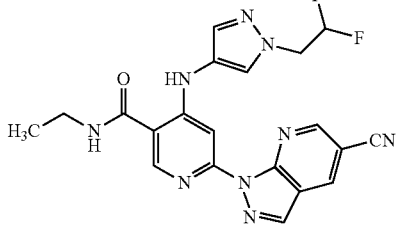 | 1.00 | H | 438.2 |
| 394 | 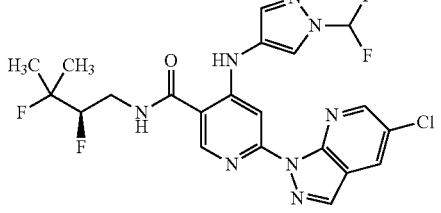 | 7.75 | B | 507.0 (M −H) |
| 395 | 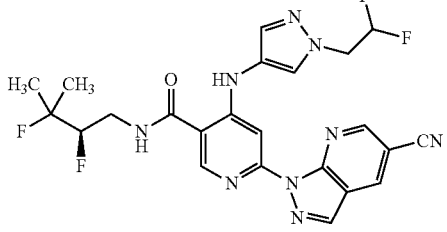 | 1.26 | C | 516.3 |

TABLE 13-continued

| Ex. No. | Structure | HPLC Rt (min) | HPLC cond. | LCMS |
|---|---|---|---|---|
| 396 | 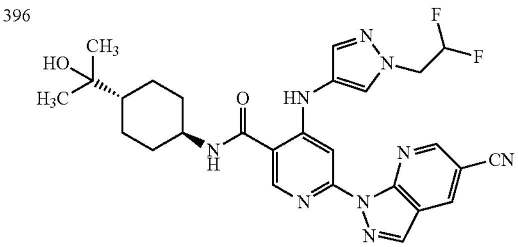 | 1.36 | C | 550.3 |
| 397 | 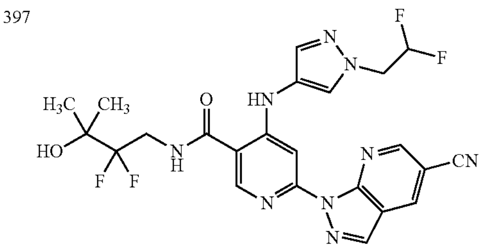 | 1.23 | C | 532.3 |
| 398 | 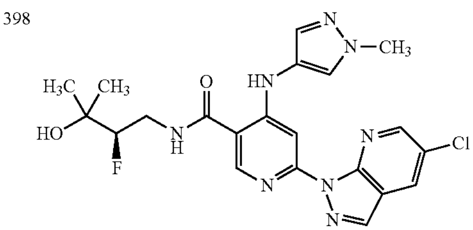 | 1.29 | C | 473.3 |
| 399 | 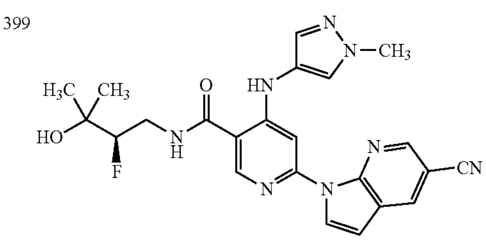 | 1.32 | C | 463.3 |
| 400 | 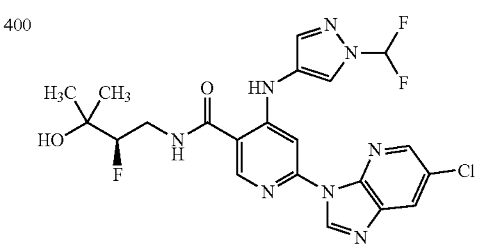 | 1.66 | C | 509.3 |
| 401 | 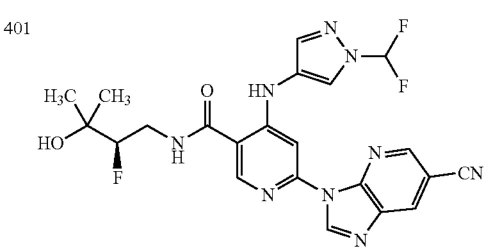 | 1.43 | C | 500.3 |

TABLE 13-continued

| Ex. No. | Structure | HPLC Rt (min) | HPLC cond. | LCMS |
|---|---|---|---|---|
| 402 | 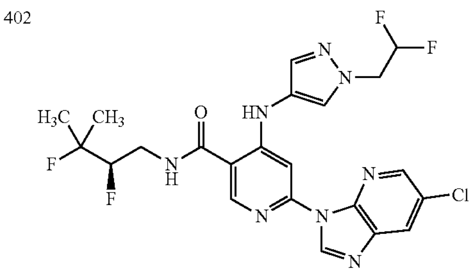 | 1.80 | C | 525.3 |
| 403 | 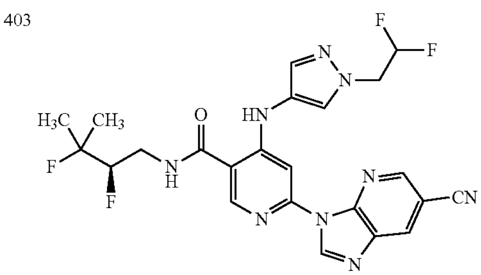 | 1.63 | C | 516.3 |
| 404 | 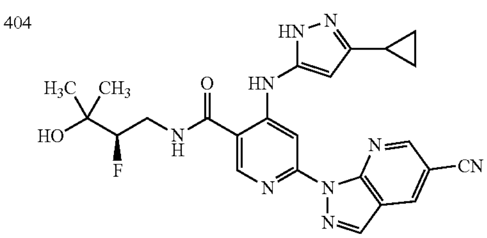 | 7.10 | B | 490.2 |
| 405 | 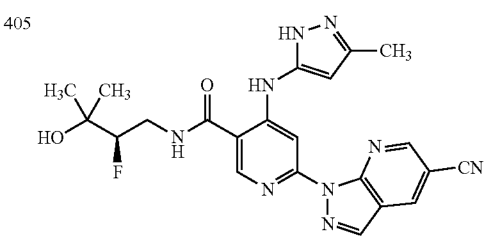 | 6.37 | B | 464.2 |
| 406 | 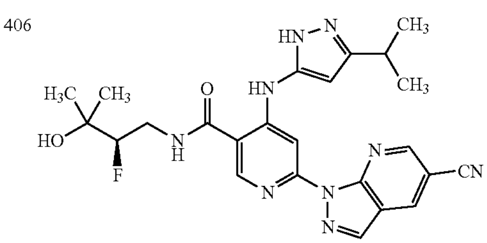 | 7.43 | B | 490.2 (M −H) |
| 407 | 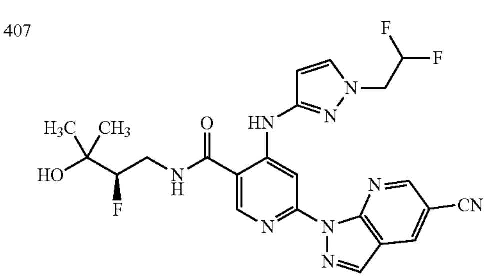 | 1.32 | C | 514.3 |

TABLE 13-continued

| Ex. No. | Structure | HPLC Rt (min) | HPLC cond. | LCMS |
|---|---|---|---|---|
| 408 | 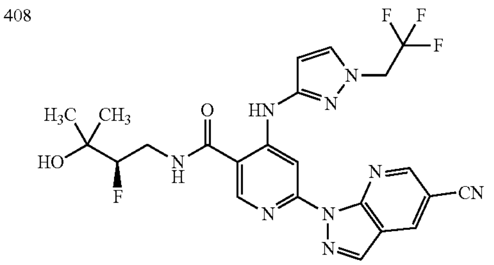 | 1.38 | H | 532.3 |
| 409 | 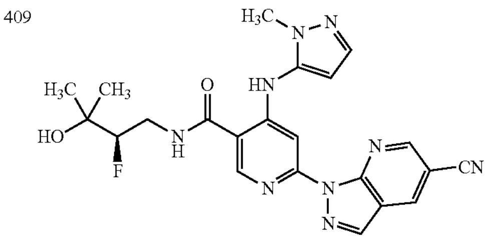 | 6.52 | B | 464.2 |
| 410 | 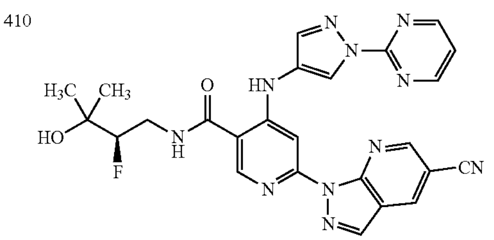 | 6.65 | A | 528.2 |
| 411 | 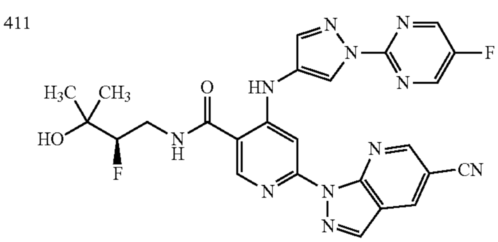 | 7.11 | A | 546.2 |
| 412 | 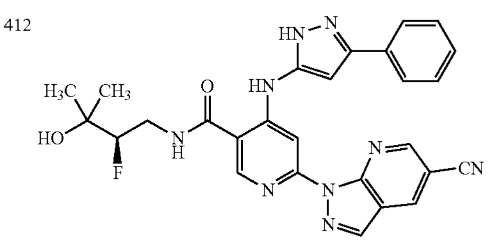 | 8.23 | A | 526.4 |
| 413 | 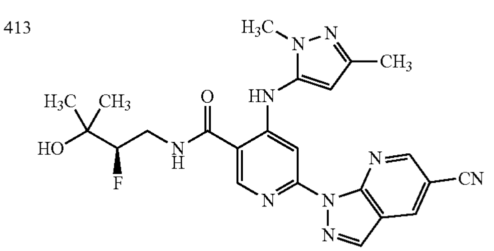 | 6.65 | B | 478.2 |

Example 414

6-(5-Cyano-1H-indol-1-yl)-N-((1R,4R)-4-(2-hydroxypropan-2-yl)cyclohexyl)-4-(isopropylamino)nicotinamide

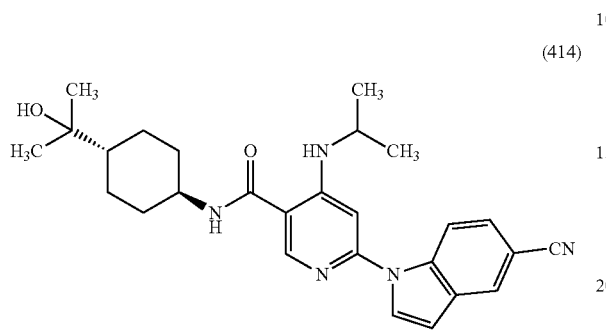

(414)

Intermediate 414A (1R,4R)-Ethyl 4-(6-chloro-4-(isopropylamino)nicotinamido)cyclohexanecarboxylate

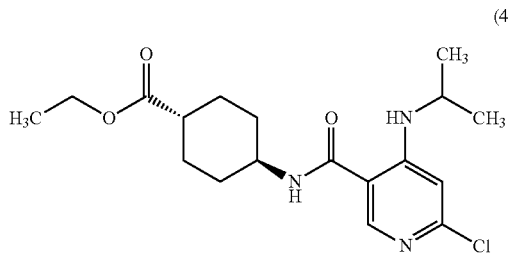

(414A)

To a solution of 6-chloro-4-(isopropylamino)nicotinic acid (0.4 g, 1.86 mmol) in DMF (10 mL), were added HATU (1.06 g, 2.8 mmol), DIPEA (1.63 mL, 9.3 mmol) and (1R,4R)-ethyl 4-aminocyclohexanecarboxylate (0.38 g, 2.24 mmol). The reaction mixture was stirred at room temperature overnight. Sodium bicarbonate was added and the reaction mixture was extracted with ethyl acetate (3 times). The combined organic extracts were washed with water and brine then dried over anhydrous $Na_2SO_4$. The extracts were filtered and concentrated to afford the crude product which was purified via column chromatography to afford (1R,4R)-ethyl 4-(6-chloro-4-(isopropylamino) nicotinamido)cyclohexanecarboxylate (0.6 g, 88% yield). This product was used directly in the next step.

Intermediate 414B

6-Chloro-N-((1R,4R)-4-(2-hydroxypropan-2-yl)cyclohexyl)-4-(isopropylamino)nicotinamide

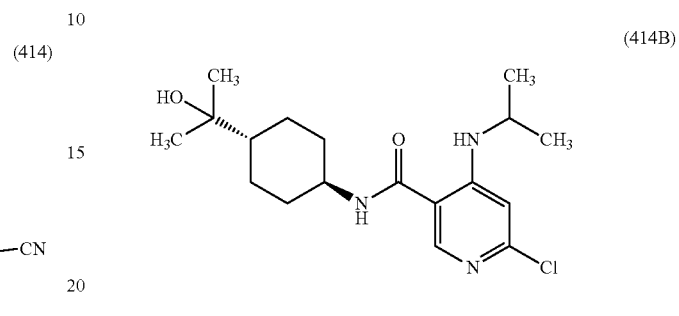

(414B)

To a solution of (1R,4R)-ethyl 4-(6-chloro-4-(isopropylamino)nicotinamido)cyclohexane carboxylate (0.3 g, 0.816 mmol) in THF (8 mL) was added MeMgBr (0.816 mL, 2.45 mmol) at −78° C. The reaction mixture was allowed to stir at room temperature overnight. The mixture was cooled in an ice bath and sodium bicarbonate was added. The mixture was extracted with ethyl acetate (3 times). The combined organic extracts were washed with water and brine then dried over anhydrous $Na_2SO_4$. The extracts were filtered and concentrated to afford the crude product which was purified via column chromatography to afford 6-chloro-N-((1R,4R)-4-(2-hydroxypropan-2-yl)cyclohexyl)-4-(isopropylamino) nicotinamide (0.26 g, 90% yield). LCMS m/z/ 354.4 (M+H).

Example 414

A solution of 6-chloro-N-((1R,4R)-4-(2-hydroxypropan-2-yl)cyclohexyl)-4-(isopropylamino)nicotinamide (100 mg, 0.283 mmol), 1H-indole-5-carbonitrile (60.3 mg, 0.424 mmol) in dioxane (10 mL) and water (1 mL) was purged with nitrogen for 2 min. Xantphos (65.4 mg, 0.113 mmol), $Cs_2CO_3$ (368 mg, 1.130 mmol) and $Pd_2(dba)_3$ (104 mg, 0.113 mmol) was added and the vessel was purged with nitrogen for 5 min. The reaction was sealed and heated at 110° C. for 16 h. The mixture was cooled, concentrated and dissolved in 10% MeOH/$CHCl_3$. The material was filtered through CELITE® and concentrated. The product was purified by preparative tlc (50% EtOAc:PE) to obtain the desired product (20 mg, 14% yield). HPLC Rt 9.33 min, Conditions B; LCMS m/z 458.2 (M+H); $^1$H NMR (400 MHz, DMSO-$d_6$) δ 8.64-8.47 (m, 3H), 8.29 (d, J=7.5 Hz, 1H), 8.25 (d, J=3.5 Hz, 1H), 8.19 (d, J=1.0 Hz, 1H), 7.61 (dd, J=8.8, 1.8 Hz, 1H), 6.91-6.81 (m, 2H), 4.03 (s, 1H), 3.96 (d, J=7.5 Hz, 1H), 3.76-3.62 (m, 1H), 1.96-1.79 (m, 4H), 1.40-1.01 (m, 17H).

The Examples in Table 14 were prepared using the general methods for Example 414 using the appropriate starting material and amine.

TABLE 14

| Ex. No. | Structure | HPLC Rt (min) | HPLC cond. | LCMS |
|---|---|---|---|---|
| 415 | 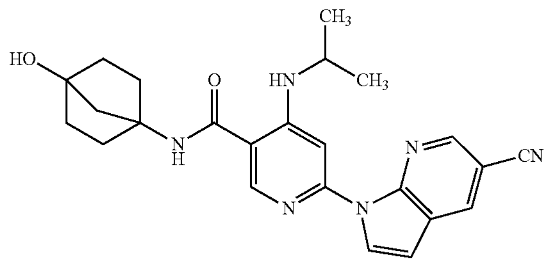 [SMILES: CC(C)Nc1cc(-n2ccc3cc(C#N)cnc32)ncc1C(=O)NC12CCC(O)(CC1)C2] | 1.78 | E | 431.2 |
| 416 | 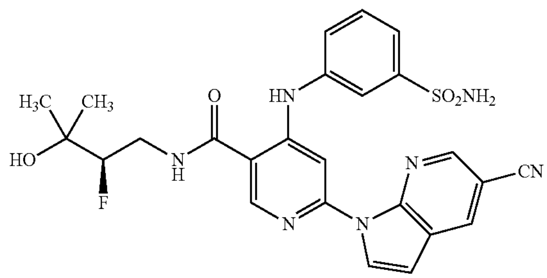 [SMILES: CC(C)(O)[C@H](F)CNC(=O)c1cnc(-n2ccc3cc(C#N)cnc32)cc1Nc1cccc(S(N)(=O)=O)c1] | 1.51 | E | 538.1 |
| 417 | 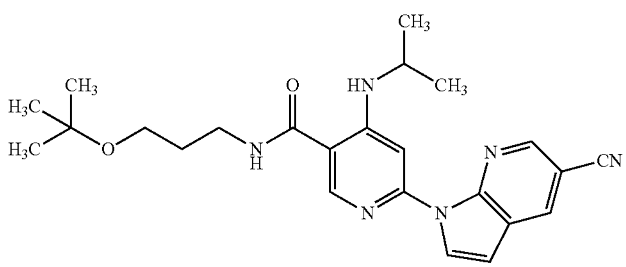 [SMILES: CC(C)Nc1cc(-n2ccc3cc(C#N)cnc32)ncc1C(=O)NCCCOC(C)(C)C] | 2.29 | E | 435.4 |
| 418 | 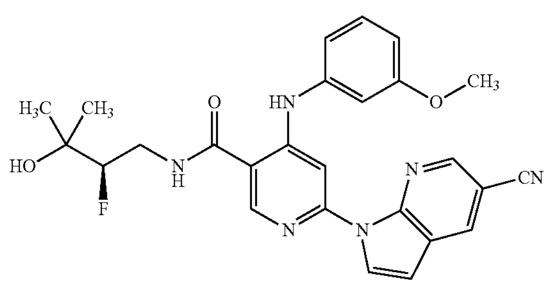 [SMILES: COc1cccc(Nc2cc(-n3ccc4cc(C#N)cnc43)ncc2C(=O)NC[C@@H](F)C(C)(C)O)c1] | 1.85 | E | 489.3 |
| 419 | 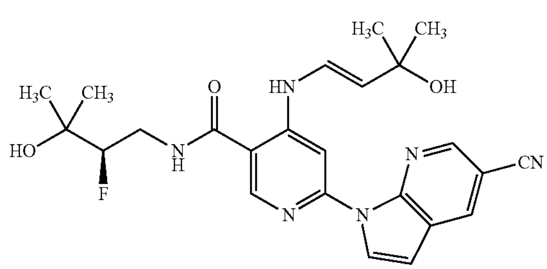 [SMILES: CC(C)(O)/C=C/Nc1cc(-n2ccc3cc(C#N)cnc32)ncc1C(=O)NC[C@@H](F)C(C)(C)O] | 1.59 | C | 467.0 |

TABLE 14-continued

| Ex. No. | Structure | HPLC Rt (min) | HPLC cond. | LCMS |
|---|---|---|---|---|
| 420 | 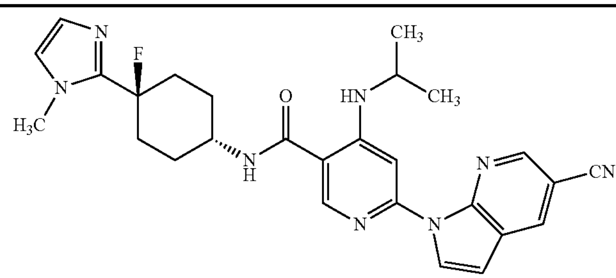 | 1.29 | F | 501.3 |
| 421 | 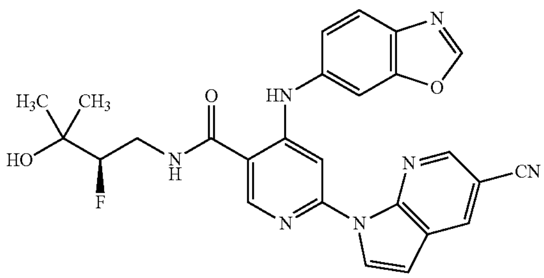 [SMILES: CC(C)(O)[C@H](F)CNC(=O)c1cnc(-n2ccc3cc(C#N)cnc32)cc1Nc1ccc2ncoc2c1] | 1.69 | E | 500.2 |
| 422 | 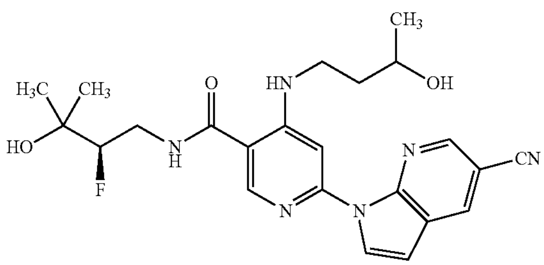 [SMILES: CC(O)CCNc1cc(-n2ccc3cc(C#N)cnc32)ncc1C(=O)NC[C@@H](F)C(C)(C)O] | 1.30 | C | 455.0 |
| 423 | 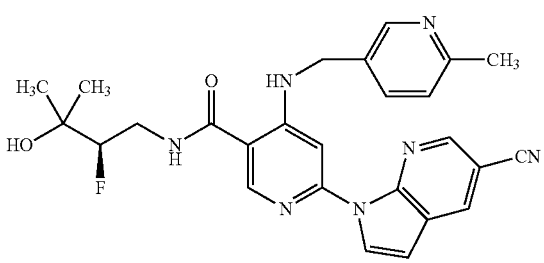 [SMILES: Cc1ccc(CNc2cc(-n3ccc4cc(C#N)cnc43)ncc2C(=O)NC[C@@H](F)C(C)(C)O)cn1] | 1.35 | C | 489.0 |
| 424 | 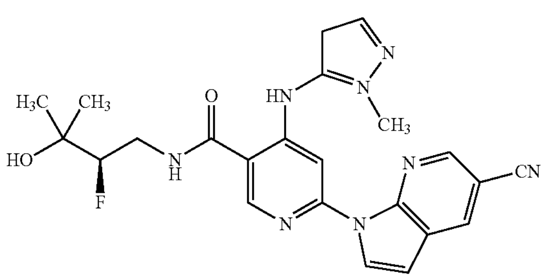 | 1.39 | C | 463.0 |
| 425 | 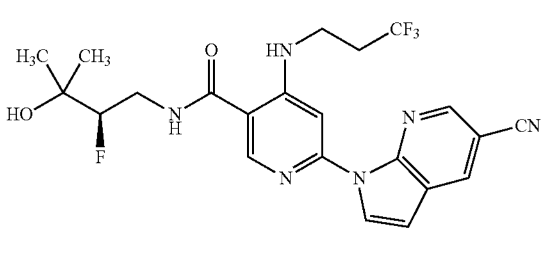 [SMILES: CC(C)(O)[C@H](F)CNC(=O)c1cnc(-n2ccc3cc(C#N)cnc32)cc1NCCC(F)(F)F] | 1.45 | D | 479.0 |

TABLE 14-continued
| Ex. No. | Structure | HPLC Rt (min) | HPLC cond. | LCMS |
|---|---|---|---|---|
| 426 | 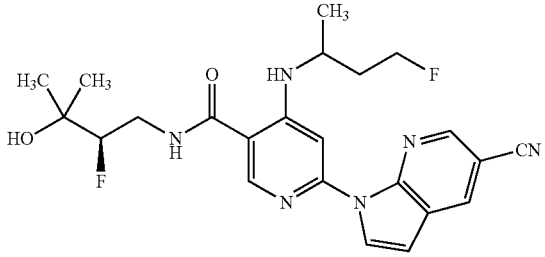 Diastereomer 1 | 8.29 | A | 457.2 |
| 427 | 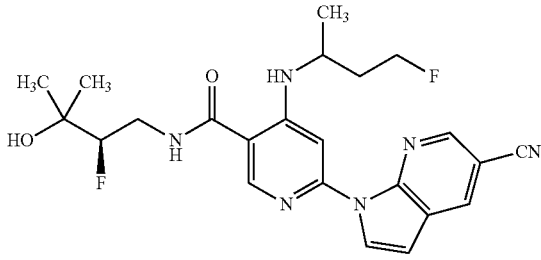 Diastereomer 2 | 8.30 | A | 457.2 |
| 428 | 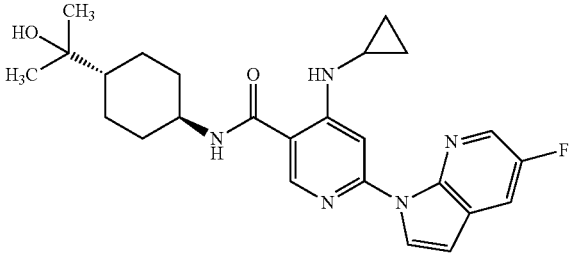 [SMILES: CC(C)(O)[C@H]1CC[C@H](NC(=O)c2cnc(-n3ccc4cc(F)cnc43)cc2NC2CC2)CC1] | 2.06 | C | 452.2 |
| 429 | 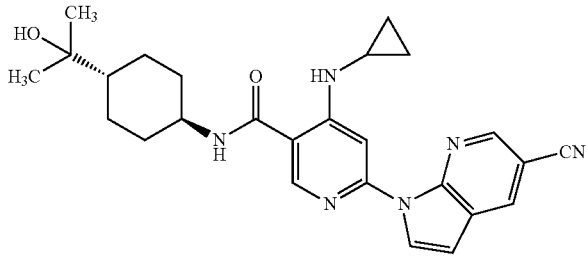 [SMILES: CC(C)(O)[C@H]1CC[C@H](NC(=O)c2cnc(-n3ccc4cc(C#N)cnc43)cc2NC2CC2)CC1] | 1.87 | C | 459.2 |
| 430 | 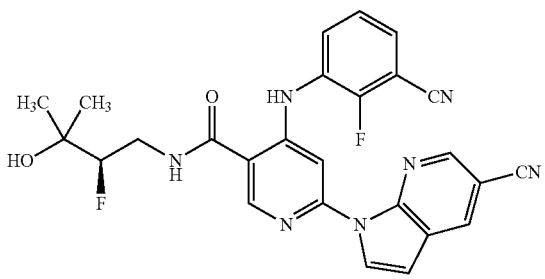 [SMILES: CC(C)(O)[C@H](F)CNC(=O)c1cnc(-n2ccc3cc(C#N)cnc32)cc1Nc1cccc(C#N)c1F] | 10.11 | B | 502.2 |

TABLE 14-continued

| Ex. No. | Structure | HPLC Rt (min) | HPLC cond. | LCMS |
|---|---|---|---|---|
| 431 | 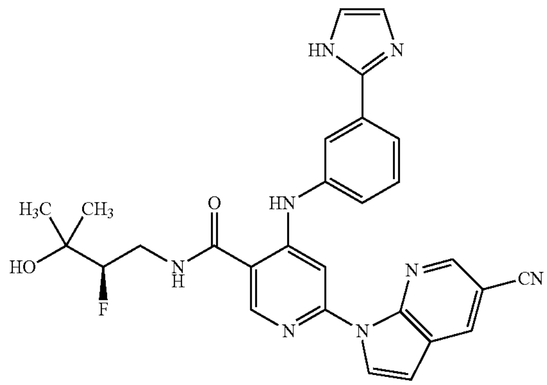 [SMILES: CC(C)(O)[C@H](F)CNC(=O)c1cnc(-n2ccc3cc(C#N)cnc32)cc1Nc1cccc(-c2ncc[nH]2)c1] | 1.16 | F | 525.3 |
| 432 | 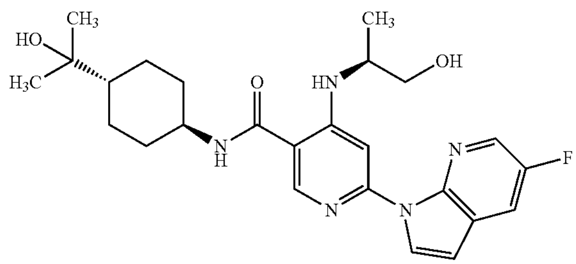 [SMILES: C[C@@H](CO)Nc1cc(-n2ccc3cc(F)cnc32)ncc1C(=O)N[C@H]1CC[C@H](C(C)(C)O)CC1] | 1.11 | D | 470.2 |
| 433 | 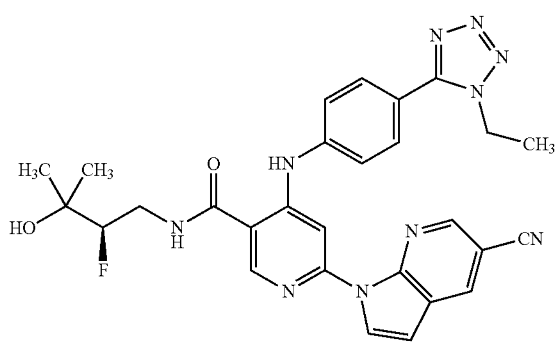 [SMILES: CCn1nnnc1-c1ccc(Nc2cc(-n3ccc4cc(C#N)cnc43)ncc2C(=O)NC[C@@H](F)C(C)(C)O)cc1] | 1.95 | E | 555.4 |
| 434 | 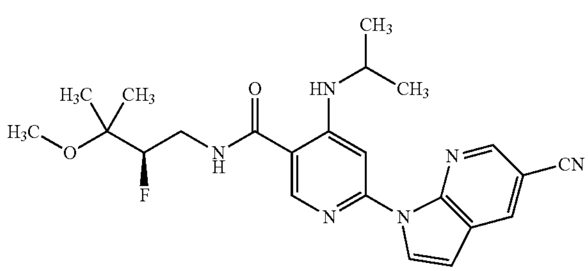 [SMILES: COC(C)(C)[C@H](F)CNC(=O)c1cnc(-n2ccc3cc(C#N)cnc32)cc1NC(C)C] | 2.01 | E | 439.3 |
| 435 | 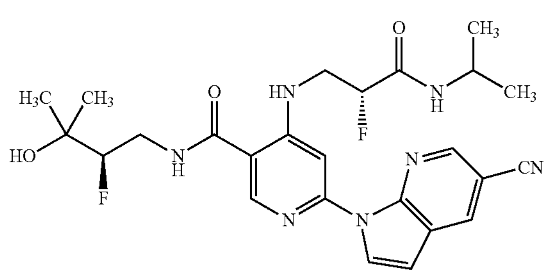 [SMILES: CC(C)NC(=O)[C@H](F)CNc1cc(-n2ccc3cc(C#N)cnc32)ncc1C(=O)NC[C@@H](F)C(C)(C)O] | 7.51 | A | 514.2 |

TABLE 14-continued
| Ex. No. | Structure | HPLC Rt (min) | HPLC cond. | LCMS |
|---|---|---|---|---|
| 436 | 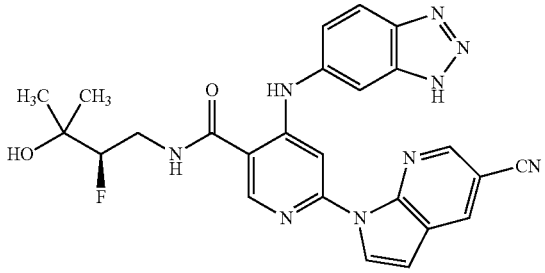 [SMILES: CC(C)(O)[C@H](F)CNC(=O)c1cnc(-n2ccc3cc(C#N)cnc32)cc1Nc1ccc2nc[nH]c2c1] | 1.27 | F | 500.2 |
| 437 | 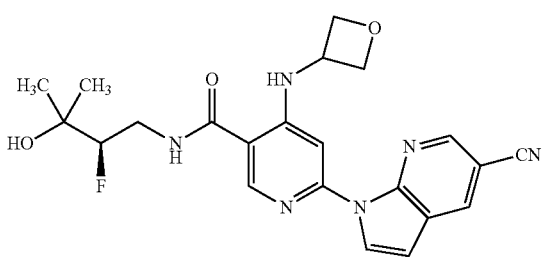 | 1.4 | E | 439.3 |
| 438 | 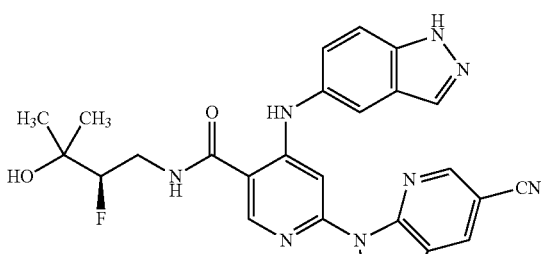 | 1.37 | F | 499.3 |
| 439 | 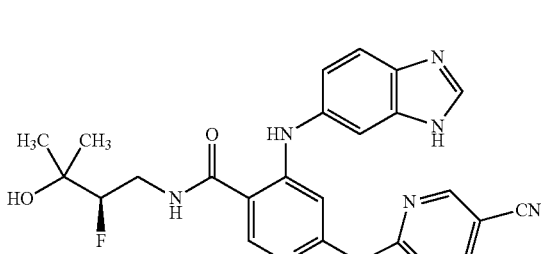 | 1.22 | F | 499.3 |
| 440 | 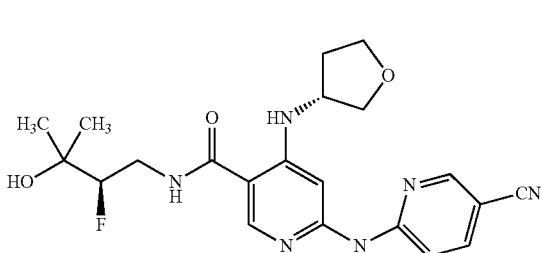 | 1.42 | E | 453.3 |

TABLE 14-continued

| Ex. No. | Structure | HPLC Rt (min) | HPLC cond. | LCMS |
|---|---|---|---|---|
| 441 | 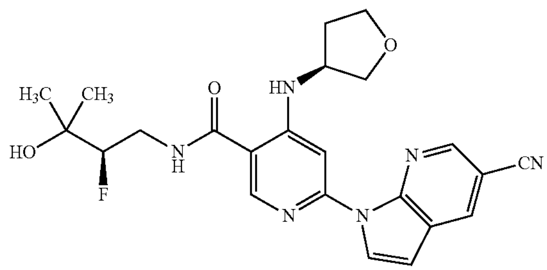 [SMILES: CC(C)(O)[C@H](F)CNC(=O)c1cnc(-n2ccc3cc(C#N)cnc32)cc1N[C@H]1CCOC1] | 1.42 | E | 453.3 |
| 442 | 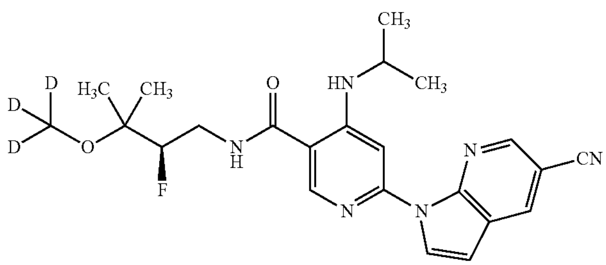 [SMILES: [2H]C([2H])([2H])OC(C)(C)[C@H](F)CNC(=O)c1cnc(-n2ccc3cc(C#N)cnc32)cc1NC(C)C] | 1.99 | E | 442.3 |
| 443 | Diastereomer 2 | 1.51 | C | 495.2 |
| 444 | Enantiomer 1 | 2.07 | C | 487.2 |
| 445 | Diastereomer 1 | 1.51 | C | 495.2 |

TABLE 14-continued
| Ex. No. | Structure | HPLC Rt (min) | HPLC cond. | LCMS |
|---|---|---|---|---|
| 446 | 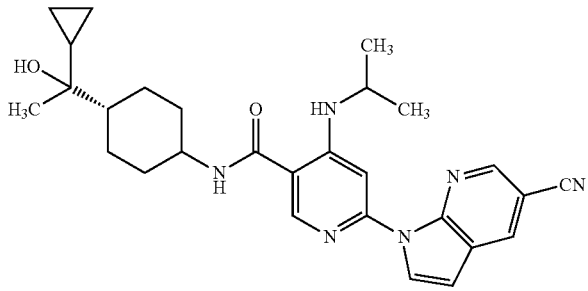 Enantiomer 2 | 2.13 | C | 487.2 |
| 447 | 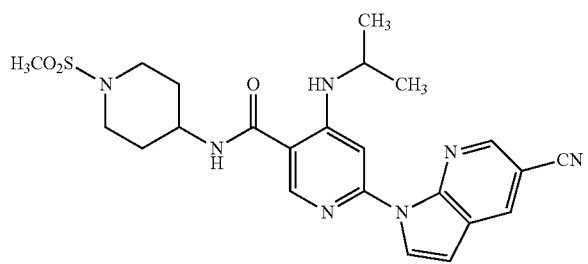 | 1.78 | E | 482.3 |
| 448 | 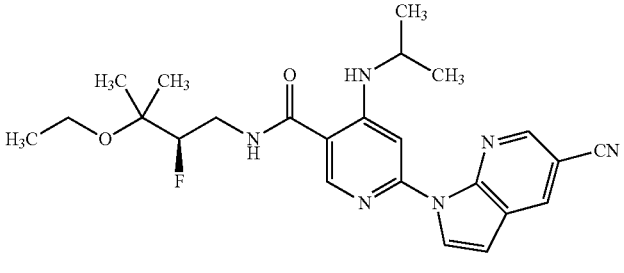 [SMILES: CCOC(C)(C)[C@H](F)CNC(=O)c1cnc(-n2ccc3cc(C#N)cnc32)cc1NC(C)C] | 2.22 | E | 453.4 |
| 449 | 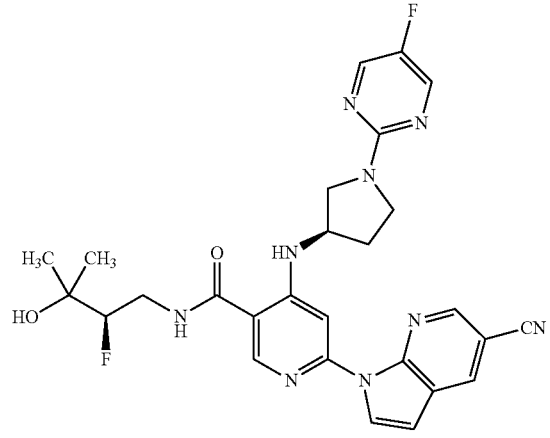 [SMILES: CC(C)(O)[C@H](F)CNC(=O)c1cnc(-n2ccc3cc(C#N)cnc32)cc1N[C@@H]1CCN(c2ncc(F)cn2)C1] | 1.55 | D | 548.2 |
| 450 | 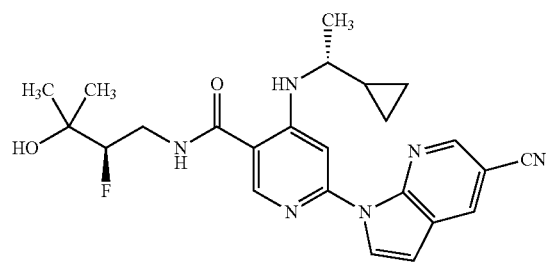 [SMILES: C[C@@H](Nc1cc(-n2ccc3cc(C#N)cnc32)ncc1C(=O)NC[C@@H](F)C(C)(C)O)C1CC1] | 1.93 | E | 451.3 |

TABLE 14-continued

| Ex. No. | Structure | HPLC Rt (min) | HPLC cond. | LCMS |
|---|---|---|---|---|
| 451 | 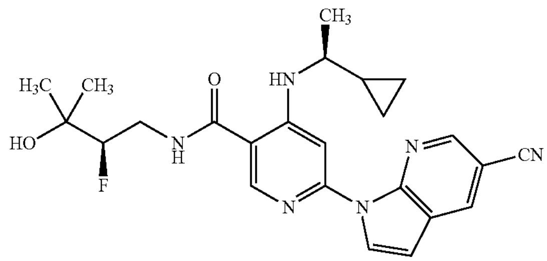 [SMILES: C[C@H](Nc1cc(-n2ccc3cc(C#N)cnc32)ncc1C(=O)NC[C@@H](F)C(C)(C)O)C1CC1] | 1.87 | E | 451.3 |
| 452 | 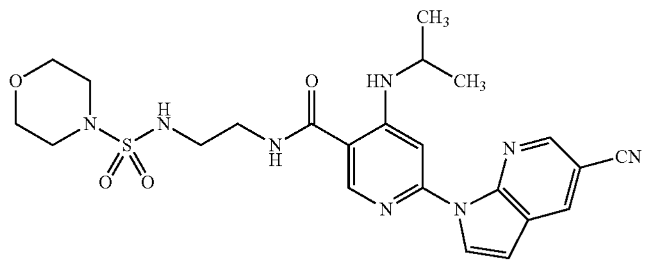 [SMILES: CC(C)Nc1cc(-n2ccc3cc(C#N)cnc32)ncc1C(=O)NCCNS(=O)(=O)N1CCOCC1] | 7.91 | A | 513.2 |
| 453 | 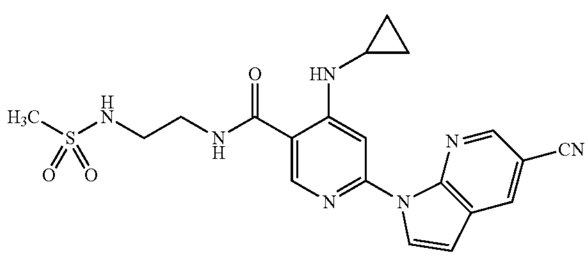 [SMILES: CS(=O)(=O)NCCNC(=O)c1cnc(-n2ccc3cc(C#N)cnc32)cc1NC1CC1] | 7.57 | A | 440.2 |
| 454 | Diastereomer 1 | 10.47 | A | 467.2 |
| 455 | 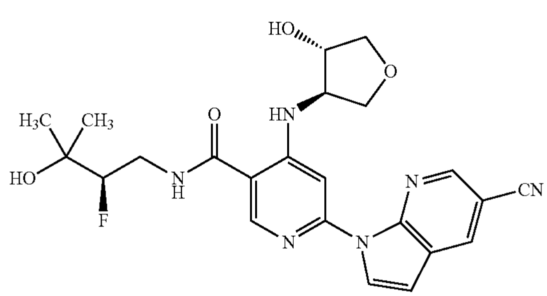 [SMILES: CC(C)(O)[C@H](F)CNC(=O)c1cnc(-n2ccc3cc(C#N)cnc32)cc1N[C@@H]1COC[C@H]1O] | 11.45 | B | 469.2 |

TABLE 14-continued

| Ex. No. | Structure | HPLC Rt (min) | HPLC cond. | LCMS |
|---|---|---|---|---|
| 456 | 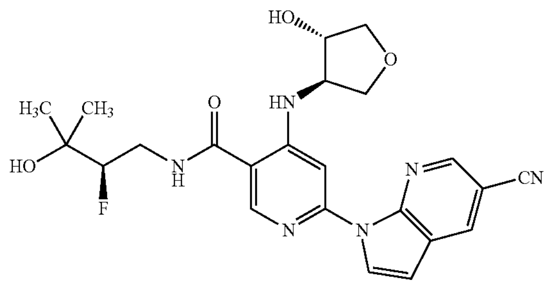 [SMILES: CC(C)(O)[C@H](F)CNC(=O)c1cnc(-n2ccc3cc(C#N)cnc32)cc1N[C@@H]1COC[C@H]1O] | 11.44 | B | 469.2 |
| 457 | 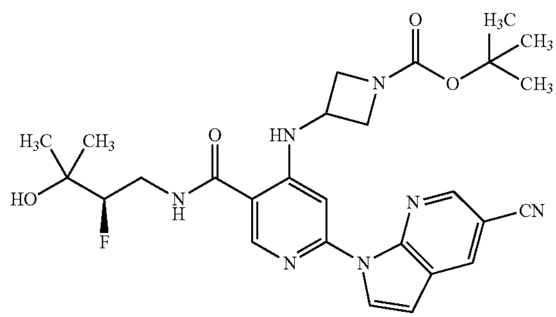 [SMILES: CC(C)(C)OC(=O)N1CC(Nc2cc(-n3ccc4cc(C#N)cnc43)ncc2C(=O)NC[C@@H](F)C(C)(C)O)C1] | 1.63 | D | 538.2 |
| 458 | Diastereomer 1 | 8.26 | B | 471.2 |
| 459 | Diastereomer 2 | 8.25 | B | 471.2 |

TABLE 14-continued
| Ex. No. | Structure | HPLC Rt (min) | HPLC cond. | LCMS |
|---|---|---|---|---|
| 460 | 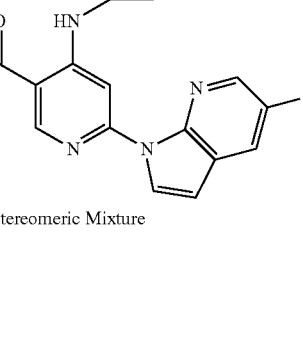 Diastereomeric Mixture | 10.84 | A | 489.2 |
| 461 | 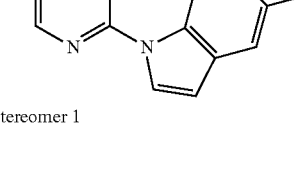 Diastereomer 1 | 6.47 | B | 455.2 |
| 462 | 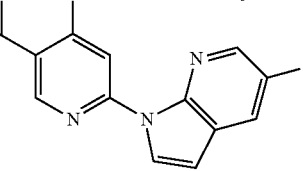 Diastereomer 2 | 6.47 | B | 455.2 |
| 463 | 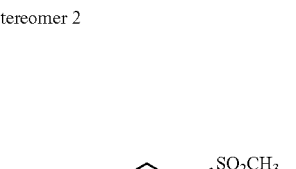 | 1.43 | F | 544.3 |

TABLE 14-continued
| Ex. No. | Structure | HPLC Rt (min) | HPLC cond. | LCMS |
|---|---|---|---|---|
| 464 | 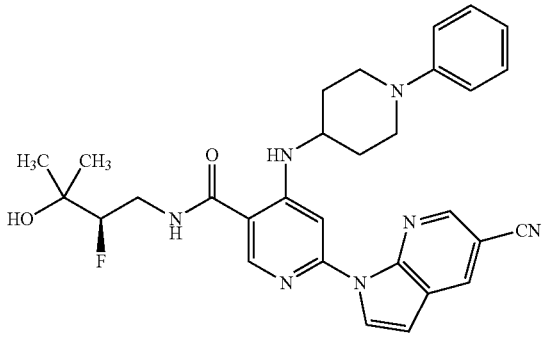 [SMILES: CC(C)(O)[C@H](F)CNC(=O)c1cnc(-n2ccc3cc(C#N)cnc32)cc1NC1CCN(c2ccccc2)CC1] | 2.14 | E | 542.3 |
| 465 | 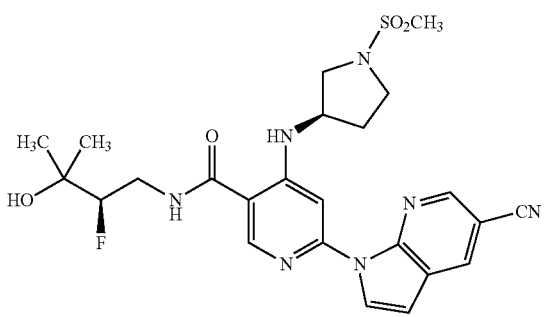 [SMILES: CC(C)(O)[C@H](F)CNC(=O)c1cnc(-n2ccc3cc(C#N)cnc32)cc1N[C@@H]1CCN(S(C)(=O)=O)C1] | 1.15 | D | 530.0 |
| 466 | 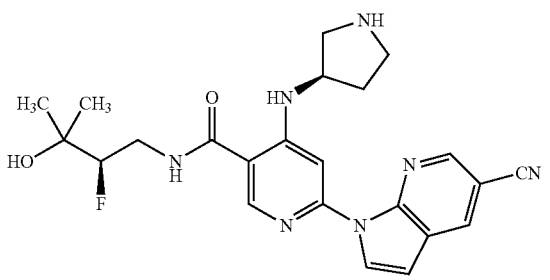 [SMILES: CC(C)(O)[C@H](F)CNC(=O)c1cnc(-n2ccc3cc(C#N)cnc32)cc1N[C@@H]1CCNC1] | 0.83 | D | 452.0 |
| 467 | 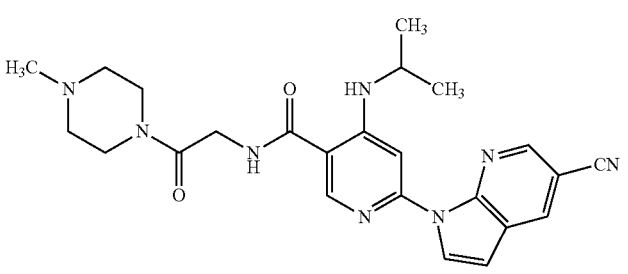 [SMILES: CC(C)Nc1cc(-n2ccc3cc(C#N)cnc32)ncc1C(=O)NCC(=O)N1CCN(C)CC1] | 1.49 | C | 461.2 |
| 468 | 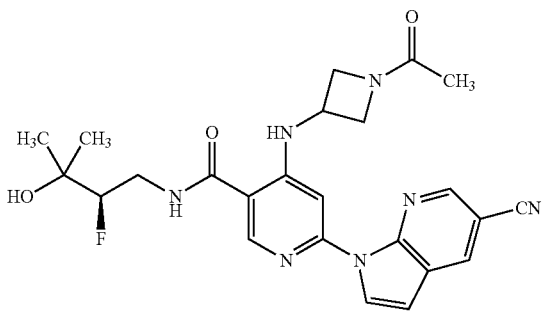 [SMILES: CC(=O)N1CC(Nc2cc(-n3ccc4cc(C#N)cnc43)ncc2C(=O)NC[C@@H](F)C(C)(C)O)C1] | 1.03 | D | 480.0 |

TABLE 14-continued
| Ex. No. | Structure | HPLC Rt (min) | HPLC cond. | LCMS |
|---|---|---|---|---|
| 469 | 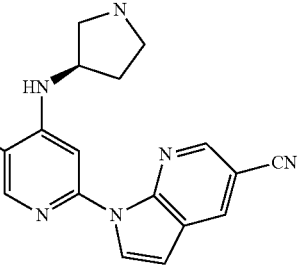 | 1.00 | D | 494.2 |
| 470 | 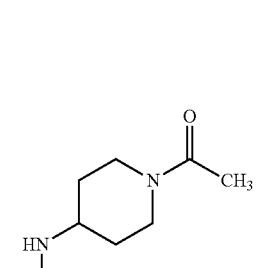 | 1.31 | E | 508.3 |
| 471 | 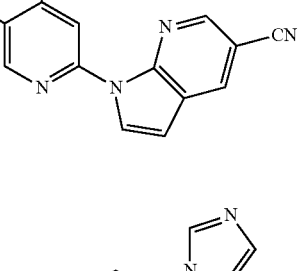 | 1.49 | E | 525.3 |
| 472 | 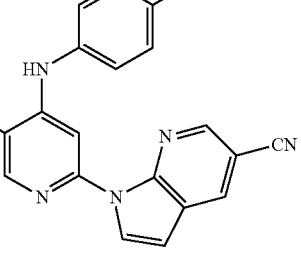 | 1.38 | D | 534.2 |

TABLE 14-continued

| Ex. No. | Structure | HPLC Rt (min) | HPLC cond. | LCMS |
|---|---|---|---|---|
| 473 | 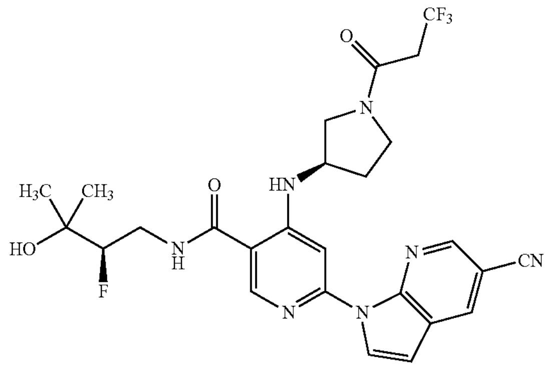 | 1.23 | D | 562.0 |
| 474 | 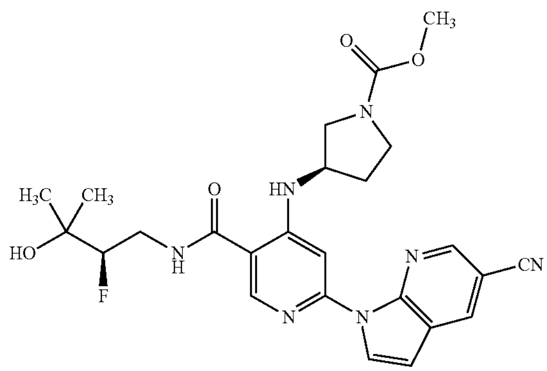 | 1.18 | D | 510.0 |
| 475 | 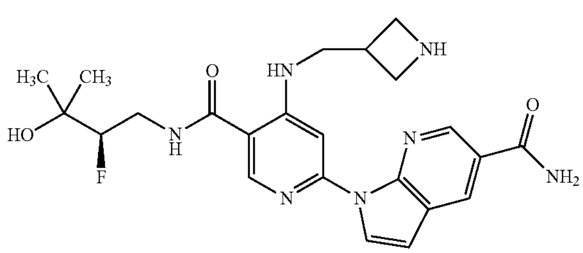 | 0.92 | D | 488.2 (M + H₂O) |
| 476 | 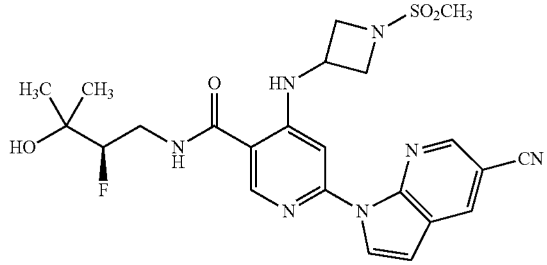 [SMILES: CC(C)(O)[C@H](F)CNC(=O)c1cnc(-n2ccc3cc(C#N)cnc32)cc1NC1CN(S(C)(=O)=O)C1] | 1.28 | C | 516.0 |

TABLE 14-continued
| Ex. No. | Structure | HPLC Rt (min) | HPLC cond. | LCMS |
|---|---|---|---|---|
| 477 | 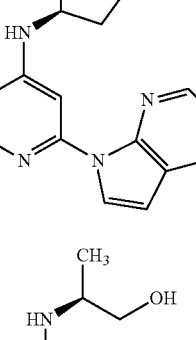 | 1.21 | C | 519.0 |
| 478 | 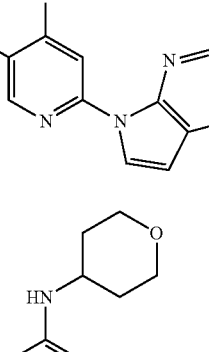 | 10.77 | A | 458.2 |
| 479 | 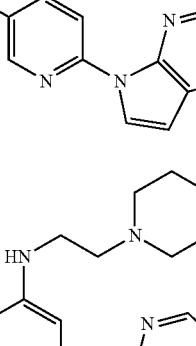 | 6.84 | A | 484.2 |
| 480 | 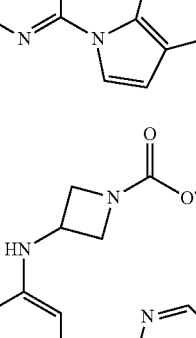 | 1.35 | E | 496.3 |
| 481 | 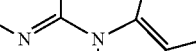 | 1.21 | D | 496.0 |

TABLE 14-continued
| Ex. No. | Structure | HPLC Rt (min) | HPLC cond. | LCMS |
|---|---|---|---|---|
| 482 | 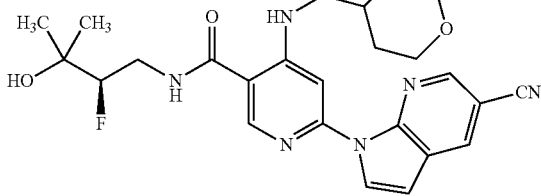 | 1.61 | E | 481.3 |
| 483 | 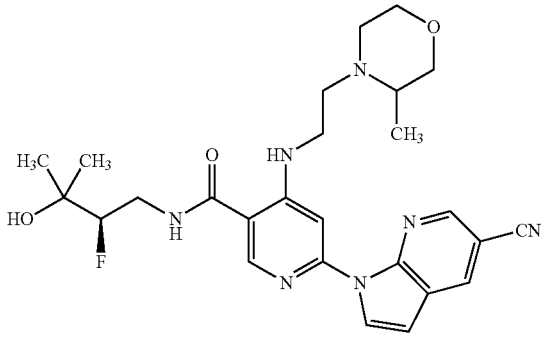  Diastereomeric Mixture | 1.61 | E | 510.3 |
| 484 | 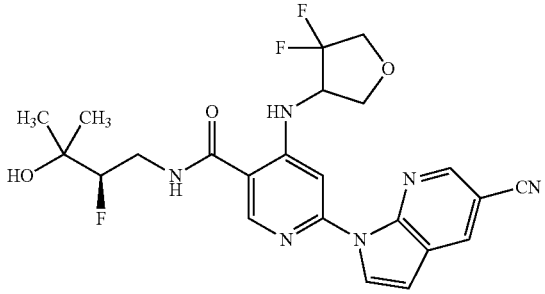  Diastereomer 1 | 9.55 | A | 489.2 |
| 485 | 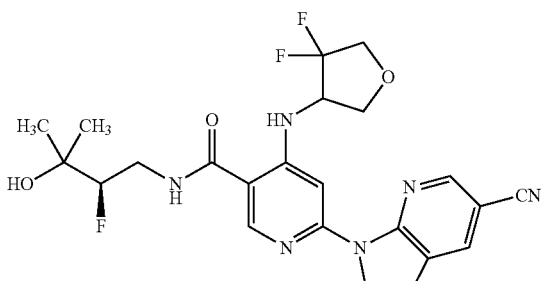  Diastereomer 2 | 9.55 | A | 489.2 |

TABLE 14-continued
| Ex. No. | Structure | HPLC Rt (min) | HPLC cond. | LCMS |
|---|---|---|---|---|
| 486 | 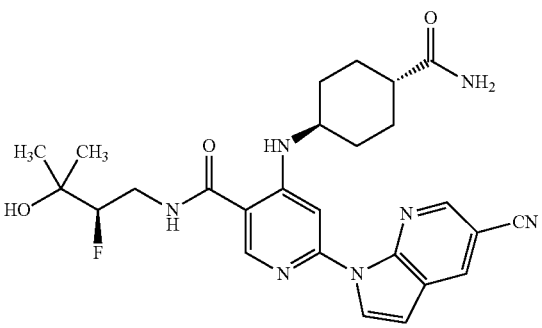 [SMILES: CC(C)(O)[C@H](F)CNC(=O)c1cnc(-n2ccc3cc(C#N)cnc32)cc1N[C@H]1CC[C@H](C(N)=O)CC1] | 1.17 | C | 508.2 |
| 487 | 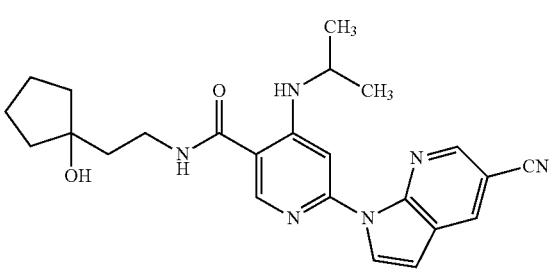 [SMILES: CC(C)Nc1cc(-n2ccc3cc(C#N)cnc32)ncc1C(=O)NCCC1(O)CCCC1] | 2.00 | E | 433.3 |
| 488 | 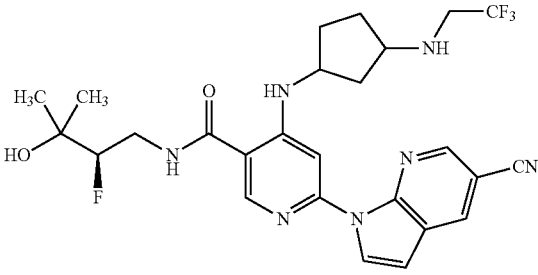  Diastereomer 3 | 5.84 | A | 548.2 |
| 489 | 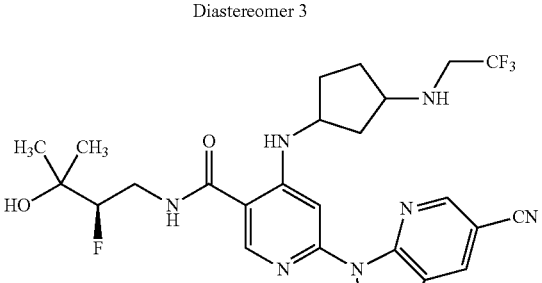  Diastereomer 4 | 5.84 | A | 548.2 |
| 490 | 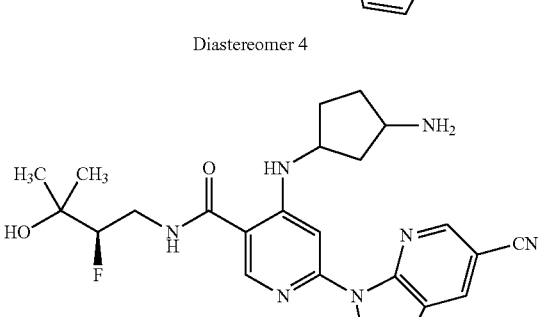  Diastereomer 1 | 6.28 | B | 467.2 |

TABLE 14-continued
| Ex. No. | Structure | HPLC Rt (min) | HPLC cond. | LCMS |
|---|---|---|---|---|
| 491 | 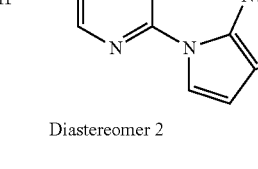<br>Diastereomer 2 | 6.28 | B | 467.2 |
| 492 | 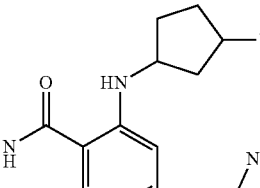<br>Diastereomer 3 | 6.55 | B | 467.2 |
| 493 | 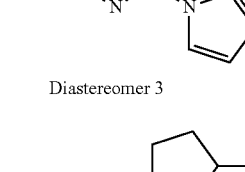<br>Diastereomer 4 | 6.53 | B | 467.2 |
| 494 | 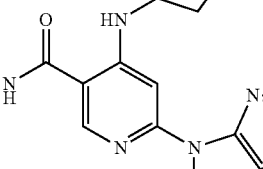<br>Enantiomer 1 | 1.65 | E | 439.2 |
| 495 | 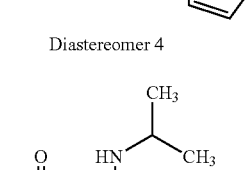<br>Enantiomer 2 | 1.65 | E | 439.2 |

TABLE 14-continued
| Ex. No. | Structure | HPLC Rt (min) | HPLC cond. | LCMS |
|---|---|---|---|---|
| 496 | 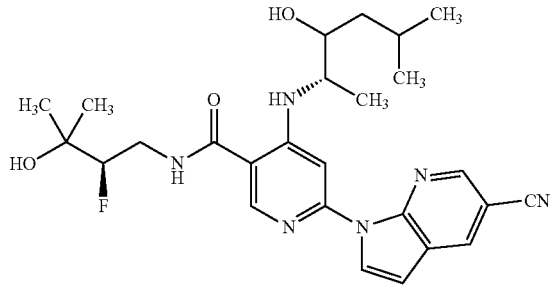 Diastereomer 2 | 8.41 | A | 497.4 |
| 497 | 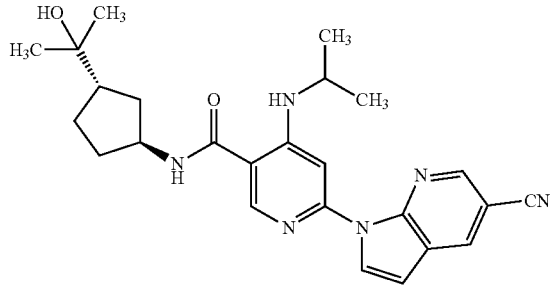 [SMILES: CC(C)Nc1cc(-n2ccc3cc(C#N)cnc32)ncc1C(=O)N[C@H]1CC[C@H](C(C)(C)O)C1] | 1.88 | E | 447.3 |
| 498 | 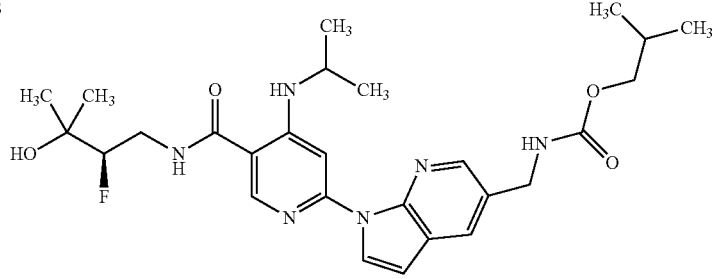 | 2.02 | E | 529.4 |
| 499 | 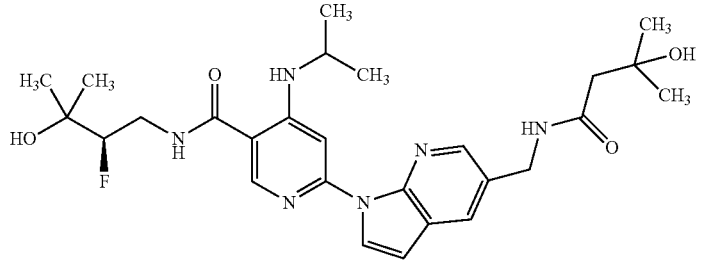 [SMILES: CC(C)Nc1cc(-n2ccc3cc(CNC(=O)CC(C)(C)O)cnc32)ncc1C(=O)NC[C@@H](F)C(C)(C)O] | 1.50 | E | 529.4 |
| 500 | 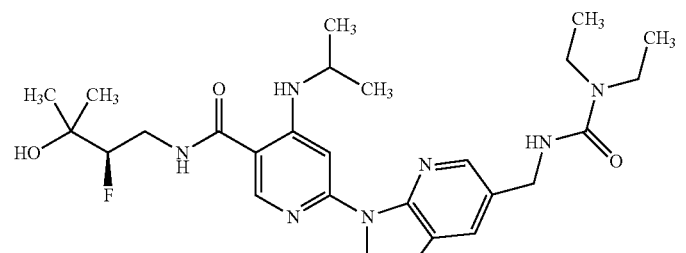 | 1.55 | E | 528.4 |

TABLE 14-continued

| Ex. No. | Structure | HPLC Rt (min) | HPLC cond. | LCMS |
|---|---|---|---|---|
| 501 | 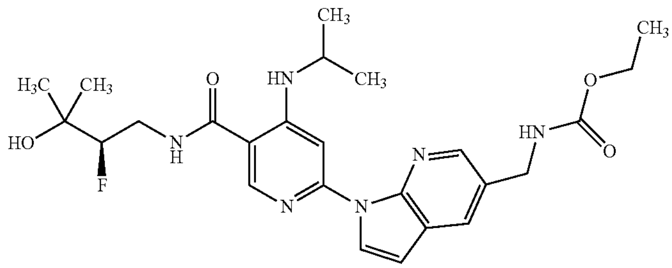 [SMILES: CCOC(=O)NCc1cnc2c(ccn2-c2cc(NC(C)C)c(C(=O)NC[C@@H](F)C(C)(C)O)cn2)c1] | 1.76 | E | 501.3 |
| 502 | 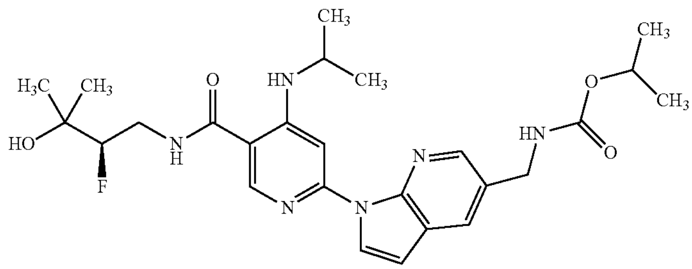 [SMILES: CC(C)Nc1cc(-n2ccc3cc(CNC(=O)OC(C)C)cnc32)ncc1C(=O)NC[C@@H](F)C(C)(C)O] | 1.74 | E | 515.3 |
| 503 | 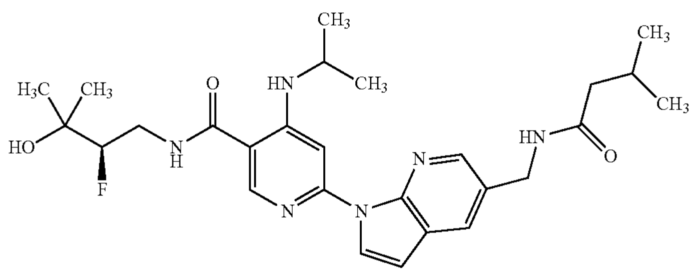 [SMILES: CC(C)CC(=O)NCc1cnc2c(ccn2-c2cc(NC(C)C)c(C(=O)NC[C@@H](F)C(C)(C)O)cn2)c1] | 1.27 | F | 513.3 |
| 504 | 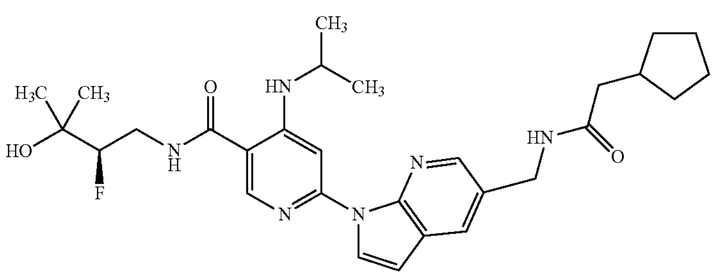 [SMILES: CC(C)Nc1cc(-n2ccc3cc(CNC(=O)CC4CCCC4)cnc32)ncc1C(=O)NC[C@@H](F)C(C)(C)O] | 1.75 | E | 539.3 |
| 505 | 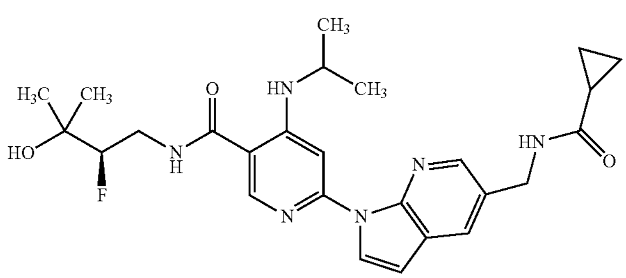 [SMILES: CC(C)Nc1cc(-n2ccc3cc(CNC(=O)C4CC4)cnc32)ncc1C(=O)NC[C@@H](F)C(C)(C)O] | 1.15 | F | 497.3 |

| Ex. No. | Structure | HPLC Rt (min) | HPLC cond. | LCMS |
|---|---|---|---|---|
| 506 | 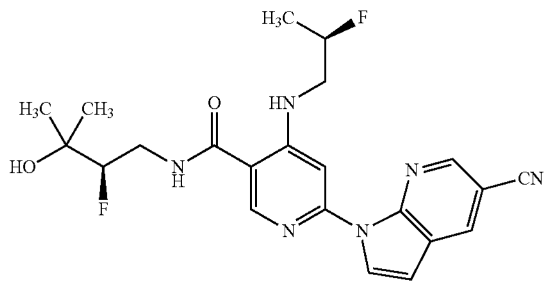 [SMILES: C[C@@H](F)CNc1cc(-n2ccc3cc(C#N)cnc32)ncc1C(=O)NC[C@@H](F)C(C)(C)O] | 1.56 | E | 443.2 |
| 507 | 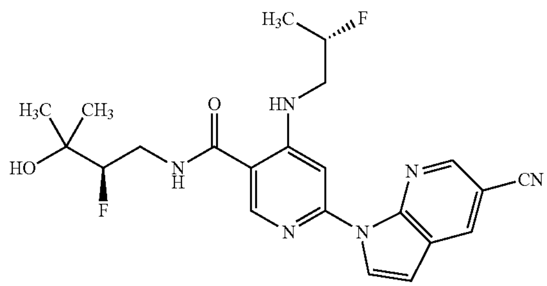 [SMILES: C[C@H](F)CNc1cc(-n2ccc3cc(C#N)cnc32)ncc1C(=O)NC[C@@H](F)C(C)(C)O] | 1.57 | E | 443.3 |
| 508 | 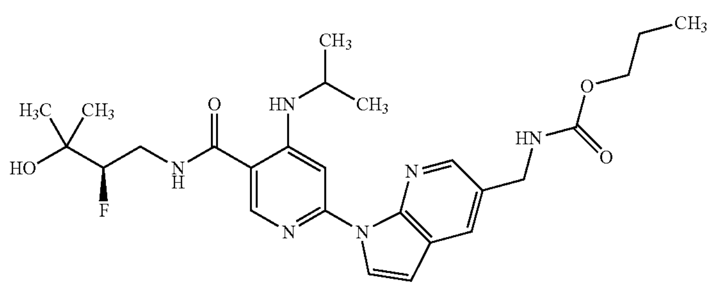 [SMILES: CCCOC(=O)NCc1cnc2c(ccn2-c2cc(NC(C)C)c(C(=O)NC[C@@H](F)C(C)(C)O)cn2)c1] | 1.89 | E | 515.4 |
| 509 | 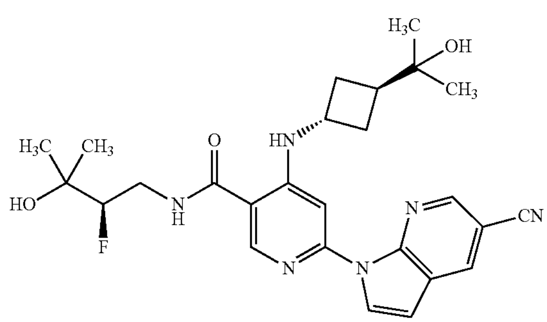 [SMILES: CC(C)(O)[C@H](F)CNC(=O)c1cnc(-n2ccc3cc(C#N)cnc32)cc1N[C@H]1C[C@H](C(C)(C)O)C1] | 1.53 | E | 495.3 |
| 510 | 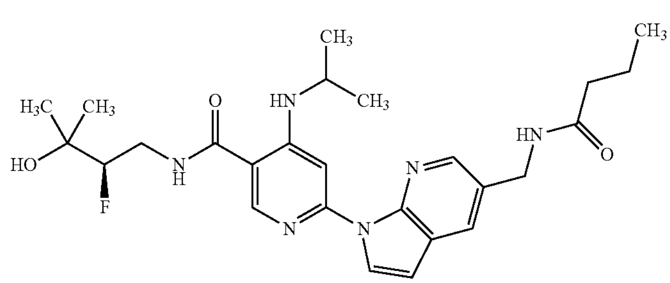 [SMILES: CCCC(=O)NCc1cnc2c(ccn2-c2cc(NC(C)C)c(C(=O)NC[C@@H](F)C(C)(C)O)cn2)c1] | 1.65 | E | 499.4 |

TABLE 14-continued

| Ex. No. | Structure | HPLC Rt (min) | HPLC cond. | LCMS |
|---|---|---|---|---|
| 511 | 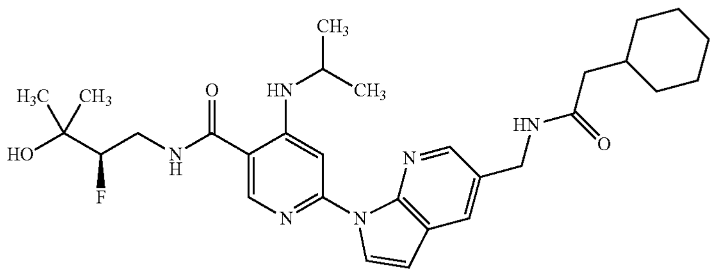 [SMILES: CC(C)Nc1cc(-n2ccc3cc(CNC(=O)CC4CCCCC4)cnc32)ncc1C(=O)NC[C@@H](F)C(C)(C)O] | 2.00 | E | 553.4 |
| 512 | 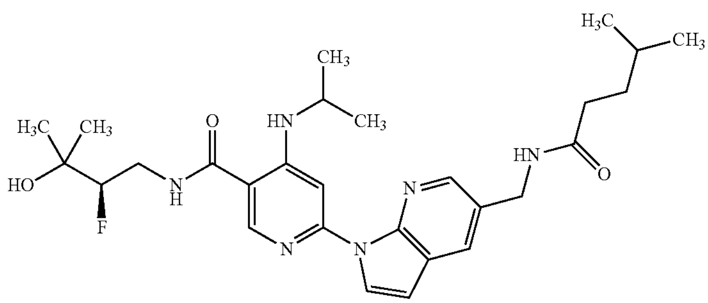 [SMILES: CC(C)CCC(=O)NCc1cnc2c(ccn2-c2cc(NC(C)C)c(C(=O)NC[C@@H](F)C(C)(C)O)cn2)c1] | 1.88 | E | 527.3 |
| 513 | 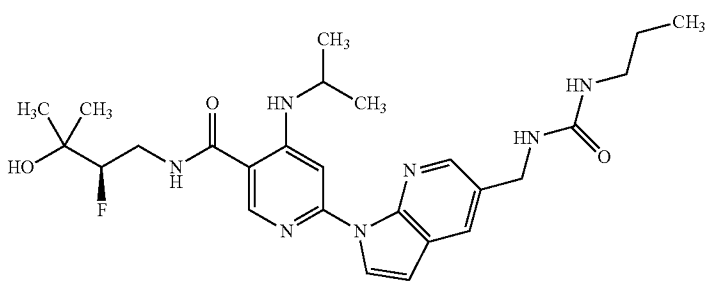 [SMILES: CCCNC(=O)NCc1cnc2c(ccn2-c2cc(NC(C)C)c(C(=O)NC[C@@H](F)C(C)(C)O)cn2)c1] | 1.60 | E | 514.3 |
| 514 | 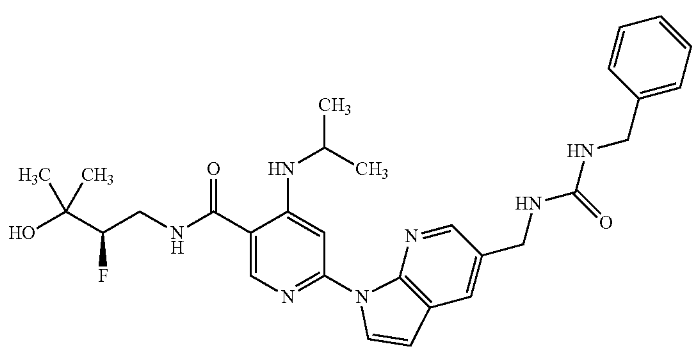 [SMILES: CC(C)Nc1cc(-n2ccc3cc(CNC(=O)NCc4ccccc4)cnc32)ncc1C(=O)NC[C@@H](F)C(C)(C)O] | 1.74 | E | 562.4 |
| 515 | 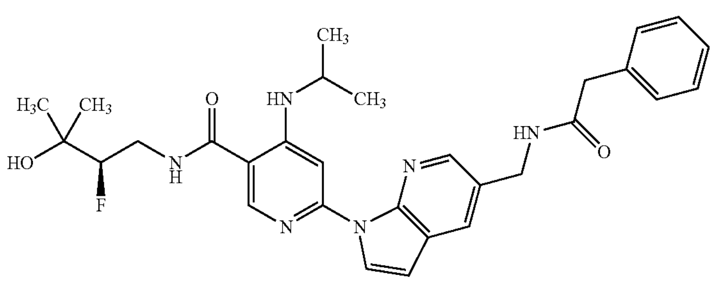 [SMILES: CC(C)Nc1cc(-n2ccc3cc(CNC(=O)Cc4ccccc4)cnc32)ncc1C(=O)NC[C@@H](F)C(C)(C)O] | 1.79 | E | 547.4 |

TABLE 14-continued
| Ex. No. | Structure | HPLC Rt (min) | HPLC cond. | LCMS |
|---|---|---|---|---|
| 516 | 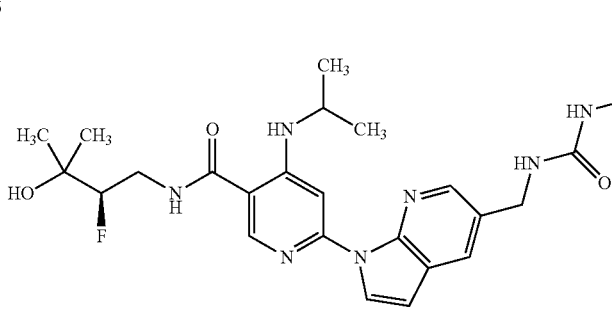 | 1.71 | E | 528.4 |
| 517 | 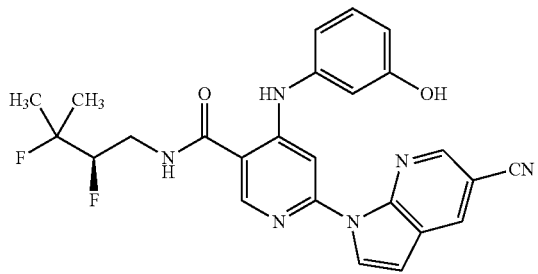 [SMILES: CC(C)(F)[C@H](F)CNC(=O)c1cnc(-n2ccc3cc(C#N)cnc32)cc1Nc1cccc(O)c1] | 1.84 | E | 477.2 |
| 518 | 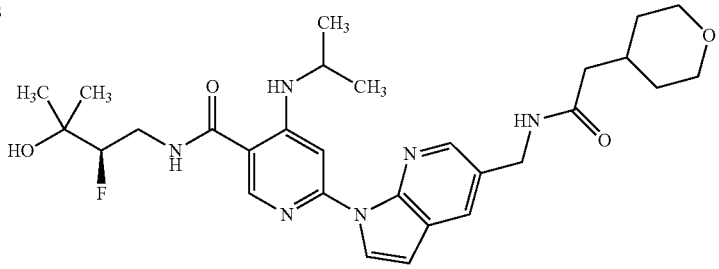 | 1.57 | E | 555.4 |
| 519 | 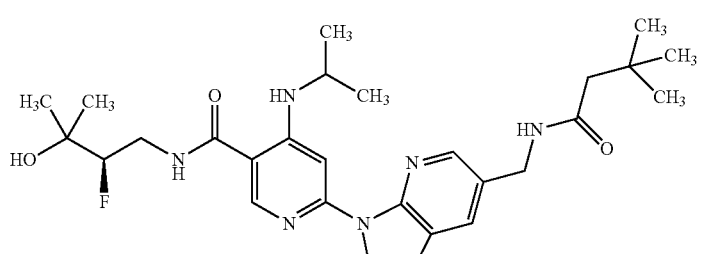 | 1.75 | E | 527.3 |
| 520 | 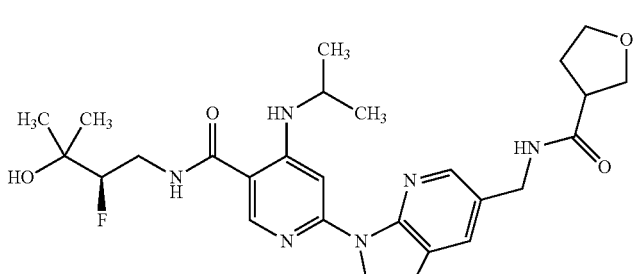 | 1.48 | E | 527.3 |

Example 521

(R)-6-(5-Cyano-1H-pyrazolo[3,4-b]pyridin-1-yl)-N-(2-fluoro-3-hydroxy-3-methylbutyl)-4-((5-(2-hydroxypropan-2-yl)thiazol-2-yl)amino)nicotinamide

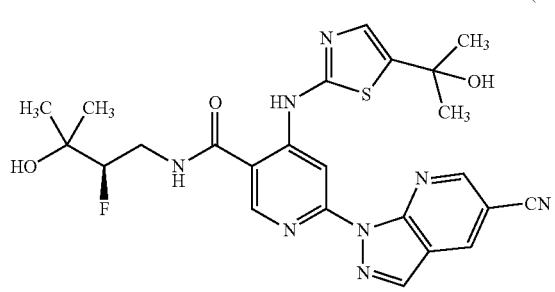
(521)

Intermediate 521A 4,6-Dichloronicotinic acid

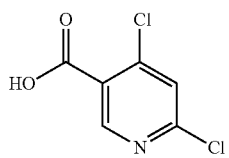
(521A)

To a solution of ethyl 4,6-dichloronicotinate (8 g, 36.4 mmol) in THF (50 mL), ethanol (25 mL) and water (25 mL) was added LiOH (2.61 g, 109 mmol). The mixture was stirred at 25° C. for 2 hours. The reaction mixture was concentrated to remove solvent. The residue was dissolved in water and acidified to neutral pH with 1.5 N HCl. The precipitated solid was filtered and washed with water (2×30 mL). The solid was dried to afford 4,6-dichloronicotinic acid (6.5 g, 83% yield). LCMS 194.1 (M+2); $^1$H NMR (400 MHz, DMSO-$d_6$) δ 8.80 (s, 1H), 7.93 (s, 1H).

Intermediate 521B (R)-4,6-Dichloro-N-(2-fluoro-3-hydroxy-3-methylbutyl) nicotinamide

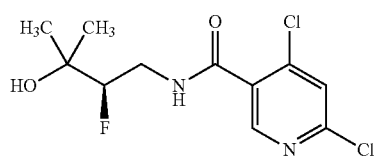
(521B)

To a solution of 4,6-dichloronicotinic acid (5 g, 26.0 mmol) in dichloromethane (30 mL) were added (R)-4-amino-3-fluoro-2-methylbutan-2-ol (3.16 g, 26 mmol) and TEA (18.15 mL, 130 mmol) at 0° C. followed by the addition of 1-propanephosphonic acid cyclic anhydride (50% in ethyl acetate) (24.86 g, 78 mmol) at the same temperature. The reaction mixture was stirred at 25° C. for 16 h. The mixture was then diluted with dichloromethane and the organic layer was washed with water and brine solution. The organic layer was dried over anhydrous $Na_2SO_4$, filtered and concentrated. The residue was purified via column chromatography (40% EtOAc/pet ether) to afford (R)-4,6-dichloro-N-(2-fluoro-3-hydroxy-3-methylbutyl)nicotinamide (3.6 g, 46% yield). $^1$H NMR (400 MHz, DMSO) δ=8.98-8.81 (m, 1H), 8.48 (s, 1H), 7.92 (s, 1H), 4.85 (s, 1H), 4.46-4.33 (m, 1H), 4.30-4.20 (m, 1H), 3.89-3.66 (m, 2H), 1.17 (dd, J=7.5, 1.5 Hz, 9H); LCMS 297.2 (M+2).

Intermediate 521C (R)-6-Chloro-N-(2-fluoro-3-hydroxy-3-methylbutyl)-4-((5-(2-hydroxypropan-2-yl)thiazol-2-yl)amino)nicotinamide

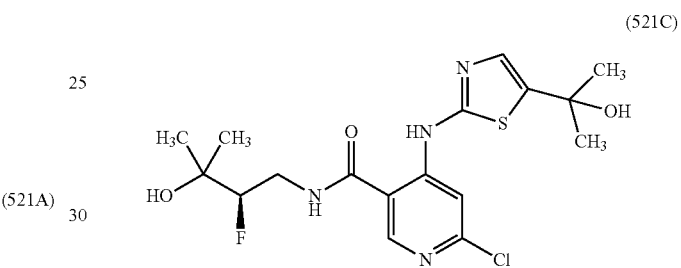
(521C)

To a solution of (R)-4,6-dichloro-N-(2-fluoro-3-hydroxy-3-methylbutyl) nicotinamide (1 g, 3.39 mmol) in DMF (15 mL) were added 2-(2-aminothiazol-5-yl) propan-2-ol (0.643 g, 4.07 mmol) and $Cs_2CO_3$ (2.208 g, 6.78 mmol). The reaction mixture was stirred at 60° C. for 2 h. The reaction mixture was then concentrated and partitioned between EtOAC and water. The layers were separated the organic layer was dried over anhydrous $Na_2SO_4$, filtered and concentrated. The crude was purified via column chromatography to afford (R)-6-chloro-N-(2-fluoro-3-hydroxy-3-methylbutyl)-4-((5-(2-hydroxypropan-2-yl)thiazol-2-yl)amino)nicotinamide (0.45 g, 31% yield). LCMS 417.0 (M+H).

Example 521

To a solution of (R)-6-chloro-N-(2-fluoro-3-hydroxy-3-methylbutyl)-4-((5-(2-hydroxypropan-2-yl)thiazol-2-yl)amino)nicotinamide (0.1 g, 0.240 mmol) in 1,4-dioxane (10 mL) were added 3a,7a-dihydro-1H-pyrazolo[3,4-b]pyridine-5-carbonitrile (0.035 g, 0.240 mmol) and Xantphos (0.056 g, 0.096 mmol). The mixture was degassed for 10 min. $K_2CO_3$ (0.133 g, 0.959 mmol) and $Pd_2(dba)_3$ (0.088 g, 0.096 mmol) were added. The mixture was degassed for 15 min and then heated at 110° C. for 16 hours. The reaction mixture was cooled and filtered through CELITE® and concentrated to remove solvent. The crude material was purified through combiflash (silica gel) and then purified by preparative HPLC to afford (R)-6-(5-cyano-1H-pyrazolo[3,4-b]pyridin-1-yl)-N-(2-fluoro-3-hydroxy-3-methylbutyl)-4-((5-(2-hydroxypropan-2-yl)thiazol-2-yl)amino) nicotinamide (8 mg, 6% yield) as a white solid. HPLC Rt 7.10, Conditions B; LCMS 525.2 (M+H); $^1$H NMR (400 MHz, DMSO) δ=12.10-11.80 (m, 1H), 9.29-9.14 (m, 1H), 9.11-9.06 (m, 1H), 9.06-9.02 (m, 1H), 8.92-8.87 (m, 1H), 8.73-8.68 (m, 1H), 7.66-7.62 (m, 1H), 7.32-7.19 (m, 1H), 7.08-6.94 (m, 1H), 5.64-5.52 (m, 1H), 4.92-4.85 (m, 1H), 4.54-4.32 (m, 1H), 3.93-3.72 (m, 1H), 3.57-3.42 (m, 1H), 1.53 (s, 6H), 1.24-1.16 (m, 6H).

The Examples in Table 15 were prepared using the general methods for Example 521 using the appropriate starting material and amine.

TABLE 15

| Ex. No. | Structure | HPLC Rt (min) | HPLC cond. | LCMS |
|---|---|---|---|---|
| 522 | 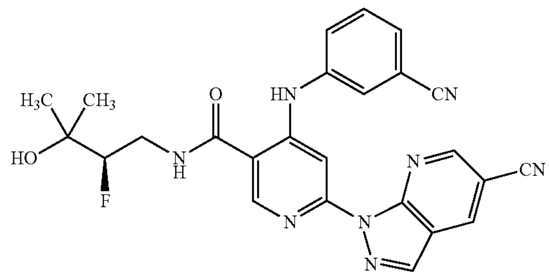 [SMILES: CC(C)(O)[C@H](F)CNC(=O)c1cnc(-n2ncc3cc(C#N)cnc32)cc1Nc1cccc(C#N)c1] | 1.5 | E | 485.3 |
| 523 | 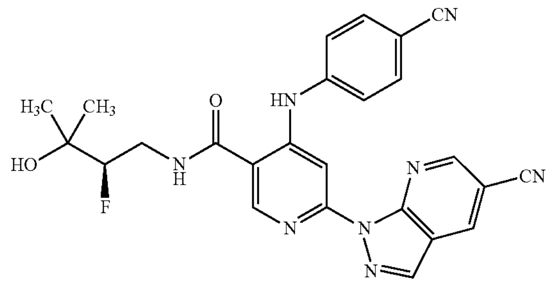 [SMILES: CC(C)(O)[C@H](F)CNC(=O)c1cnc(-n2ncc3cc(C#N)cnc32)cc1Nc1ccc(C#N)cc1] | 8.57 | A | 483.2 |
| 524 | 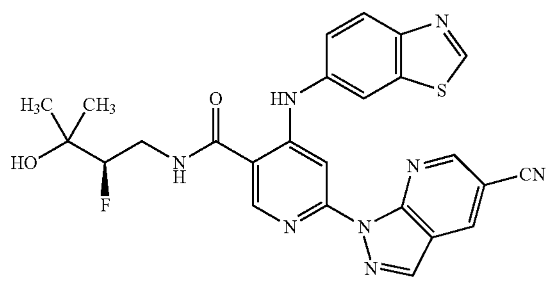 | 1.31 | E | 517.2 |
| 525 | 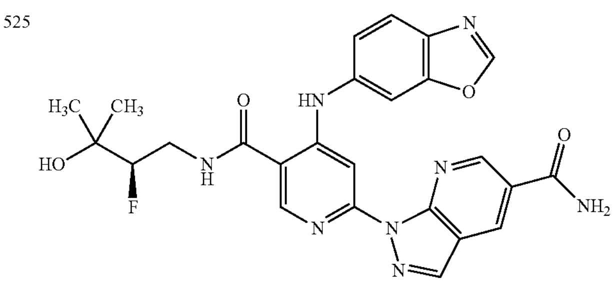 | 1.05 | E | 519.3 |
| 526 | 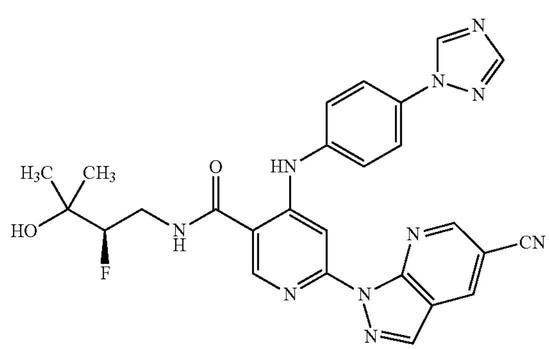 [SMILES: CC(C)(O)[C@H](F)CNC(=O)c1cnc(-n2ncc3cc(C#N)cnc32)cc1Nc1ccc(-n2cncn2)cc1] | 1.24 | E | 527.3 |

TABLE 15-continued
| Ex. No. | Structure | HPLC Rt (min) | HPLC cond. | LCMS |
|---|---|---|---|---|
| 527 | 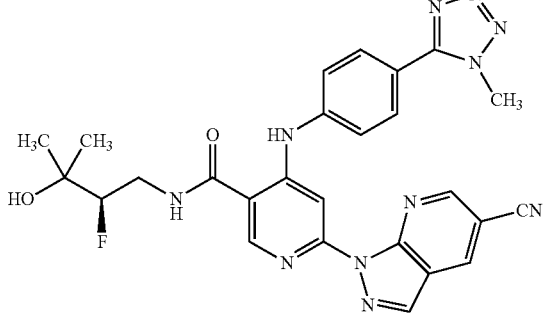 | 1.26 | E | 542.3 |
| 528 | 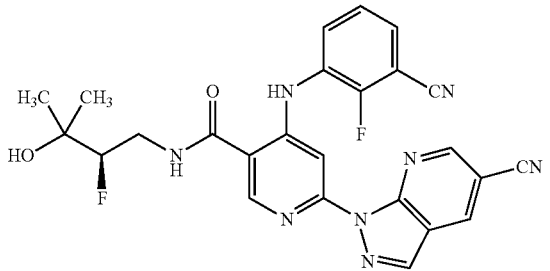 [SMILES: CC(C)(O)[C@H](F)CNC(=O)c1cnc(-n2ncc3cc(C#N)cnc32)cc1Nc1cccc(C#N)c1F] | 8.71 | A | 503.2 |
| 529 | 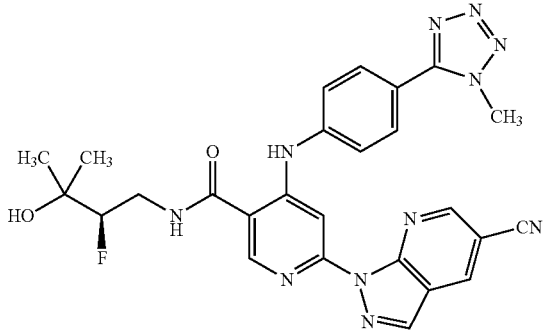 [SMILES: Cn1nnnc1-c1ccc(Nc2cc(-n3ncc4cc(C#N)cnc43)ncc2C(=O)NC[C@@H](F)C(C)(C)O)cc1] | 1.51 | E | 544.2 |
| 530 | 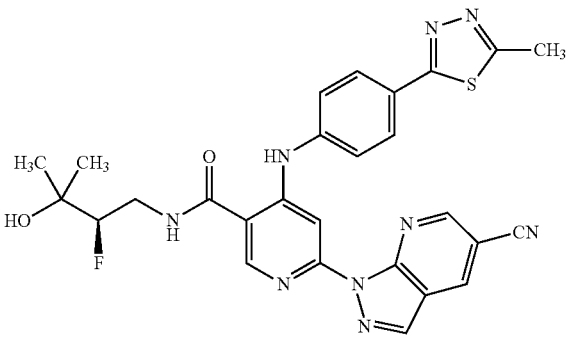 [SMILES: Cc1nnc(-c2ccc(Nc3cc(-n4ncc5cc(C#N)cnc54)ncc3C(=O)NC[C@@H](F)C(C)(C)O)cc2)s1] | 7.28 | A | 482.2 |

TABLE 15-continued

| Ex. No. | Structure | HPLC Rt (min) | HPLC cond. | LCMS |
|---|---|---|---|---|
| 531 | 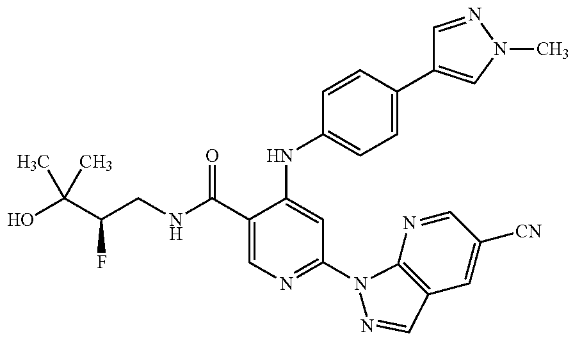 [SMILES: Cn1cc(-c2ccc(Nc3cc(-n4ncc5cc(C#N)cnc54)ncc3C(=O)NC[C@@H](F)C(C)(C)O)cc2)cn1] | 7.17 | A | 540.2 |

Example 532

6-(5-Cyano-1H-pyrazolo[3,4-b]pyridin-1-yl)-N—((R)-2-fluoro-3-hydroxy-3-methylbutyl)-4-(((R)-1-(5-fluoropyrimidin-2-yl)pyrrolidin-3-yl)amino)nicotinamide (532)

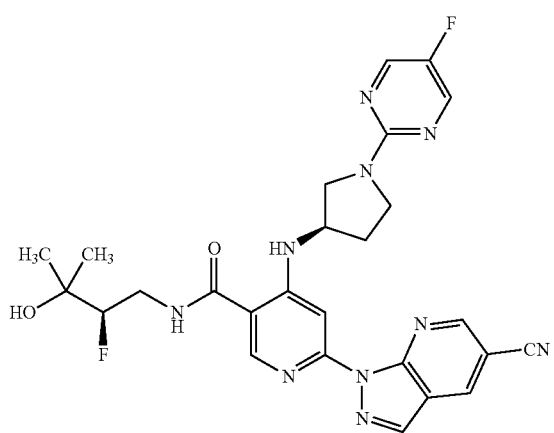

Intermediate 532A

6-Chloro-N—((R)-2-fluoro-3-hydroxy-3-methylbutyl)-4-(((R)-1-(5-fluoropyrimidin-2-yl)pyrrolidin-3-yl)amino)nicotinamide (532A)

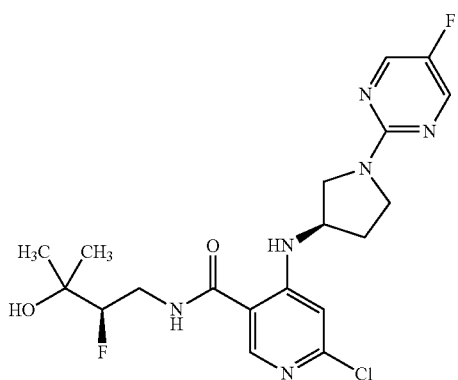

To a stirred solution of (R)-4,6-dichloro-N-(2-fluoro-3-hydroxy-3-methylbutyl) nicotinamide (300 mg, 1.02 mmol) in DMA (5 mL) were added (R)-1-(5-fluoropyrimidin-2-yl)pyrrolidin-3-amine (222 mg, 1.22 mmol) and DIPEA (0.178 mL, 1.02 mmol). The reaction mixture was heated at 130° C. for 2 hours. The mixture was then cooled and concentrated. The residue was partitioned between EtOAc and water. The layers were separated and the organic layer was dried over $Na_2SO_4$, filtered and concentrated to afford crude 6-chloro-N—((R)-2-fluoro-3-hydroxy-3-methylbutyl)-4-(((R)-1-(5-fluoropyrimidin-2-yl)pyrrolidin-3-yl)amino)nicotinamide (200 mg, 45% yield). LCMS 441.4 (M+H).

Example 532

A stirred solution of 6-chloro-N—((R)-2-fluoro-3-hydroxy-3-methylbutyl)-4-(((R)-1-(5-fluoropyrimidin-2-yl)pyrrolidin-3-yl)amino)nicotinamide (65 mg, 0.147 mmol), 1H-pyrazolo[3,4-b]pyridine-5-carbonitrile (21.25 mg, 0.147 mmol), Xantphos (85 mg, 0.147 mmol) and $Na_2CO_3$ (46.9 mg, 0.442 mmol) in 1,4-dioxane (8 mL) was degassed with nitrogen for 5 mins then $Pd_2(dba)_3$ (67.5 mg, 0.074 mmol) was added. The mixture was further degassed with nitrogen for 5 mins and then the reaction mixture was heated at 110° C. for 12 hours in a sealed tube. The mixture was cooled to room temperature, filtered and purified directly via preparative HPLC to afford 6-(5-cyano-1H-pyrazolo[3,4-b]pyridin-1-yl)-N—((R)-2-fluoro-3-hydroxy-3-methylbutyl)-4-(((R)-1-(5-fluoropyrimidin-2-yl)pyrrolidin-3-yl)amino)nicotinamide (9 mg, 11% yield). HPLC Rt 1.14 min, Conditions D; LCMS 549.2 (M+H); $^1$H NMR (400 MHz, DMSO-$d_6$) δ 9.08-9.02 (m, 2H), 8.90-8.82 (m, 2H), 8.70-8.64 (m, 2H), 8.46 (s, 2H), 7.47 (s, 1H), 4.83 (s, 1H), 4.47-4.25 (m, 2H), 3.93 (dd, J=11.5, 6.0 Hz, 1H), 3.81-3.56 (m, 3H), 3.54-3.35 (m, 2H), 2.48-2.36 (m, 1H), 2.10 (dd, J=12.3, 7.3 Hz, 1H), 1.16 (dd, J=6.3, 1.3 Hz, 6H).

The Examples in Table 16 were prepared using the general methods for Example 532 using the appropriate starting material and amine.

TABLE 16
| Ex. No. | Structure | HPLC Rt (min) | HPLC cond. | LCMS |
|---|---|---|---|---|
| 533 | 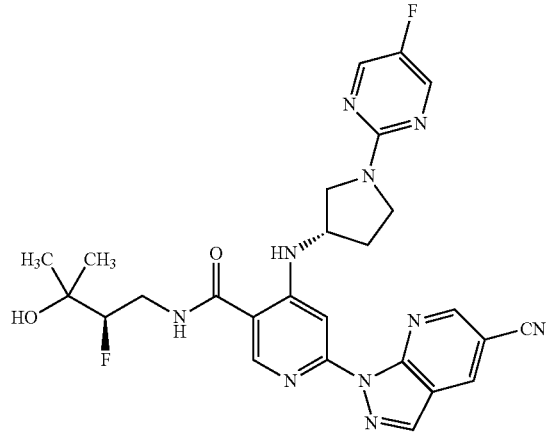 [SMILES: CC(C)(O)[C@H](F)CNC(=O)c1cnc(-n2ncc3cc(C#N)cnc32)cc1N[C@H]1CCN(c2ncc(F)cn2)C1] | 1.17 | D | 549.2 |
| 534 | 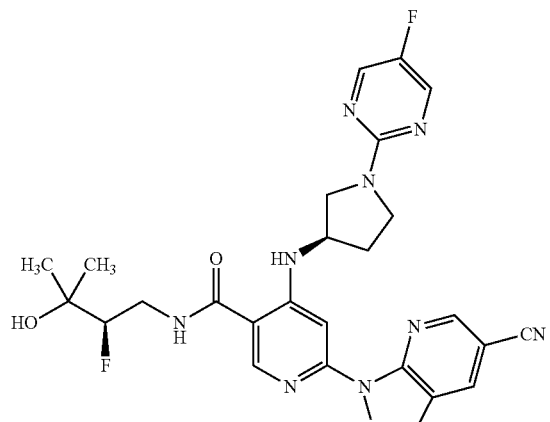 | 1.55 | D | 548.2 |
| 535 | 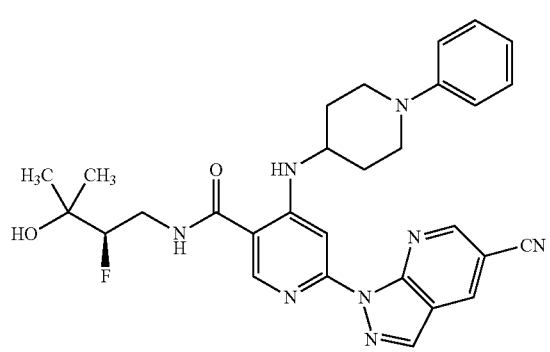 | 1.80 | E | 543.4 |

TABLE 16-continued
| Ex. No. | Structure | HPLC Rt (min) | HPLC cond. | LCMS |
|---|---|---|---|---|
| 536 | 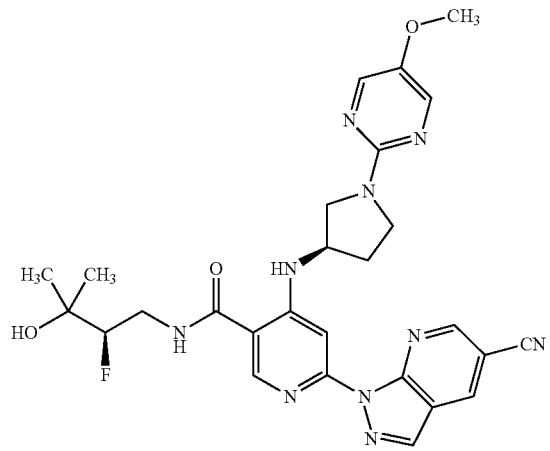 [SMILES: COc1cnc(N2CC[C@@H](Nc3cc(-n4ncc5cc(C#N)cnc54)ncc3C(=O)NC[C@@H](F)C(C)(C)O)C2)nc1] | 6.77 | B | 561.2 |
| 537 | 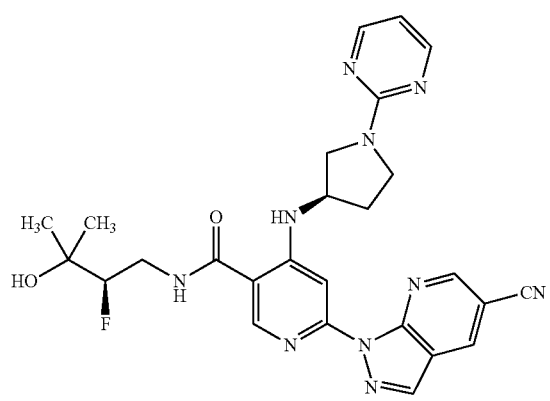 [SMILES: CC(C)(O)[C@H](F)CNC(=O)c1cnc(-n2ncc3cc(C#N)cnc32)cc1N[C@@H]1CCN(c2ncccn2)C1] | 5.82 | B | 531.3 |
| 538 | 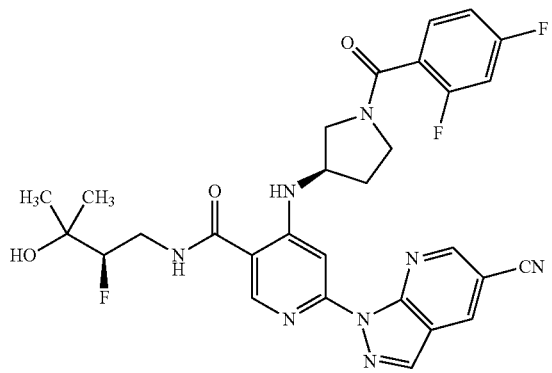 [SMILES: CC(C)(O)[C@H](F)CNC(=O)c1cnc(-n2ncc3cc(C#N)cnc32)cc1N[C@@H]1CCN(C(=O)c2ccc(F)cc2F)C1] | 1.30 | C | 593.2 |
| 539 | 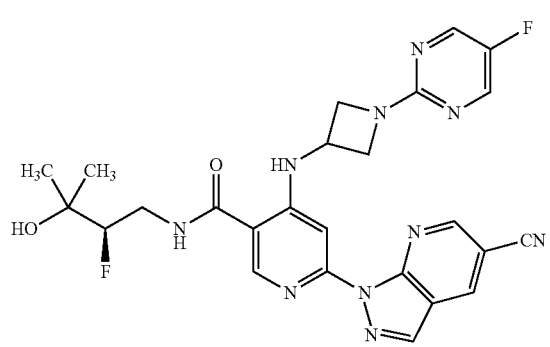 [SMILES: CC(C)(O)[C@H](F)CNC(=O)c1cnc(-n2ncc3cc(C#N)cnc32)cc1NC1CN(c2ncc(F)cn2)C1] | 1.20 | D | 535.2 |

TABLE 16-continued

| Ex. No. | Structure | HPLC Rt (min) | HPLC cond. | LCMS |
|---|---|---|---|---|
| 540 | 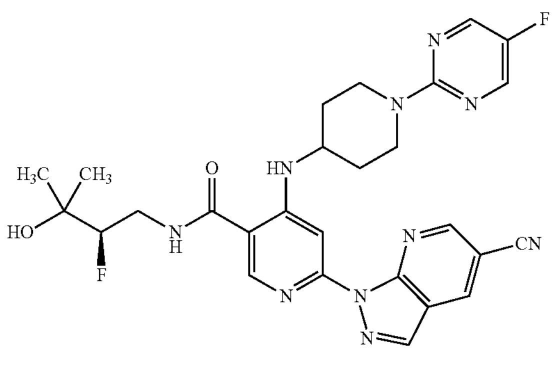 [SMILES: CC(C)(O)[C@H](F)CNC(=O)c1cnc(-n2ncc3cc(C#N)cnc32)cc1NC1CCN(c2ncc(F)cn2)CC1] | 7.64 | A | 563.2 |
| 541 | 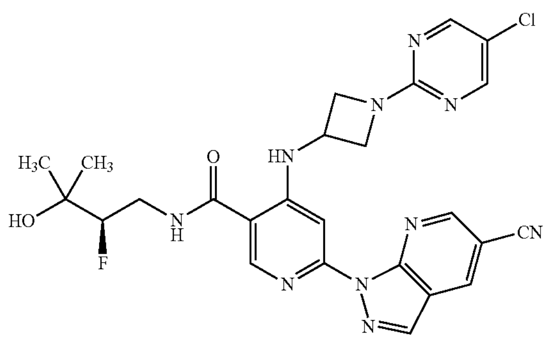 | 1.21 | D | 551.3 |
| 542 | 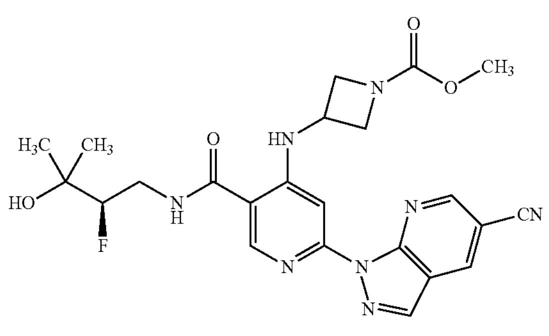 [SMILES: COC(=O)N1CC(Nc2cc(-n3ncc4cc(C#N)cnc43)ncc2C(=O)NC[C@@H](F)C(C)(C)O)C1] | 0.92 | D | 497.3 |
| 543 | 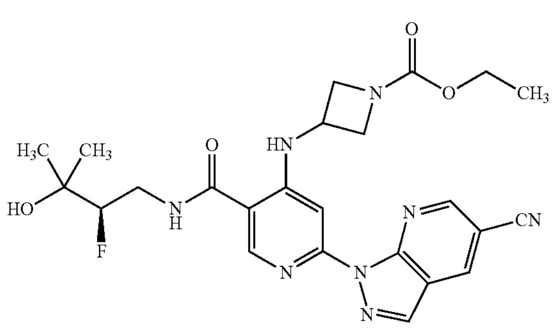 [SMILES: CCOC(=O)N1CC(Nc2cc(-n3ncc4cc(C#N)cnc43)ncc2C(=O)NC[C@@H](F)C(C)(C)O)C1] | 1.04 | D | 511.3 |

Example 544

6-(5-Cyano-1H-pyrazolo[3,4-b]pyridin-1-yl)-N—((R)-2-fluoro-3-hydroxy-3-methylbutyl)-4-(((R)-tetrahydrofuran-3-yl)amino)nicotinamide, TFA salt

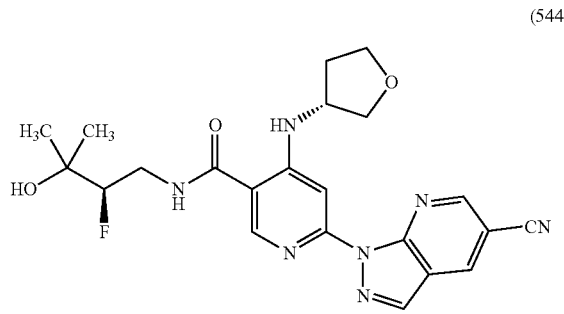 [SMILES: CC(C)(O)[C@H](F)CNC(=O)c1cnc(-n2ncc3cc(C#N)cnc32)cc1N[C@@H]1CCOC1]

(544)

Intermediate 544A

6-Chloro-N—((R)-2-fluoro-3-hydroxy-3-methylbutyl)-4-(((R)-tetrahydrofuran-3-yl)amino) nicotinamide

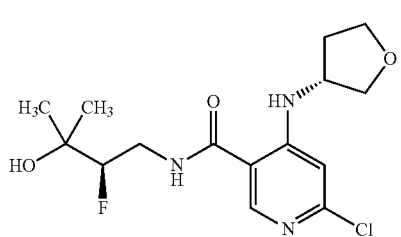

(544A)

In a vial suitable for heating, (R)-4,6-dichloro-N-(2-fluoro-3-hydroxy-3-methylbutyl)nicotinamide (150 mg, 0.51 mmol), (R)-tetrahydrofuran-3-amine, Cl (62.8 mg, 0.51 mmol) and Hunig's Base (0.266 mL, 1.53 mmol) were dissolved in DMF (5 mL) at room temperature with stirring and then heated at 120° C. for 18 h. The reaction mixture was concentrated and purified directly via preparative HPLC to afford 6-chloro-N—((R)-2-fluoro-3-hydroxy-3-methylbutyl)-4-(((R)-tetrahydrofuran-3-yl)amino) nicotinamide (127 mg, 69% yield) as a tan solid. $^1$H NMR (400 MHz, DMSO-$d_6$) δ 8.77 (t, J=5.5 Hz, 1H), 8.67 (d, J=7.0 Hz, 1H), 8.40 (s, 1H), 6.76 (s, 1H), 4.81 (s, 1H), 4.38 (dd, J=9.5, 2.0 Hz, 0.5H), 4.28-4.16 (m, 1.5H), 3.87-3.77 (m, 2H), 3.77-3.67 (m, 1.5H), 3.66-3.58 (m, 0.5H), 3.56 (dd, J=9.0, 2.9 Hz, 1H), 3.45-3.32 (m, 1H), 2.32-2.20 (m, 1H), 1.79-1.69 (m, 1H), 1.14 (dd, J=6.2, 1.1 Hz, 6H).

Example 544

In a vial suitable for heating, a mixture of 6-chloro-N—((R)-2-fluoro-3-hydroxy-3-methylbutyl)-4-(((R)-tetrahydrofuran-3-yl)amino)nicotinamide (30 mg, 0.087 mmol), 1H-pyrazolo[3,4-b]pyridine-5-carbonitrile (15.01 mg, 0.104 mmol), and potassium phosphate, tribasic (55.3 mg, 0.260 mmol) in dioxane (2 mL) was degassed with bubbling nitrogen for 5 minutes. In a separate sealed vial, a degassed, stirring mixture of Pd$_2$(dba)$_3$ (3.97 mg, 4.34 μmol) and tetramethyl t-Bu XPhos (5.00 mg, 10.41 μmol) in 5:1 toluene/dioxane (0.2 mL) was heated at 120° C. for 5 minutes. After cooling to room temperature, this solution was transferred to the vial containing the reaction mixture. The vial was sealed, and the reaction mixture was heated at 80° C. for 4 hours and then stirred at room temperature overnight. The mixture was filtered, and the filtrate was concentrated under high vacuum. The residue was purified directly via preparative HPLC to afford 6-(5-cyano-1H-pyrazolo[3,4-b]pyridin-1-yl)-N—((R)-2-fluoro-3-hydroxy-3-methylbutyl)-4-(((R)-tetrahydrofuran-3-yl)amino)nicotinamide, TFA salt (37 mg, 76% yield). HPLC Rt 1.11 min, Conditions E; LCMS 454.3 (M+H); LCMS 346.1 (M+H); $^1$H NMR (500 MHz, DMSO-$d_6$) δ 9.09 (s, 1H), 9.04 (s, 1H), 8.93 (m, 1H), 8.70 (s, 1H), 8.67 (s, 1H), 7.48 (s, 1H), 4.43 (d, J=8.1 Hz, 1H), 4.33 (d, J=8.1 Hz, 1H), 4.26 (br. s., 1H), 3.94 (dd, J=9.1, 5.4 Hz, 1H), 3.88 (q, J=7.5 Hz, 1H), 3.82-3.74 (m, 2H), 3.69 (d, J=6.4 Hz, 1H), 3.48-3.35 (m, 1H), 2.41-2.31 (m, 1H), 1.94-1.82 (m, 1H), 1.18 (d, J=7.1 Hz, 6H).

Example 545

6-(5-Cyano-1H-pyrazolo[3,4-b]pyridin-1-yl)-N—((R)-2-fluoro-3-hydroxy-3-methylbutyl)-4-(((S)-tetrahydrofuran-3-yl)amino)nicotinamide, TFA salt

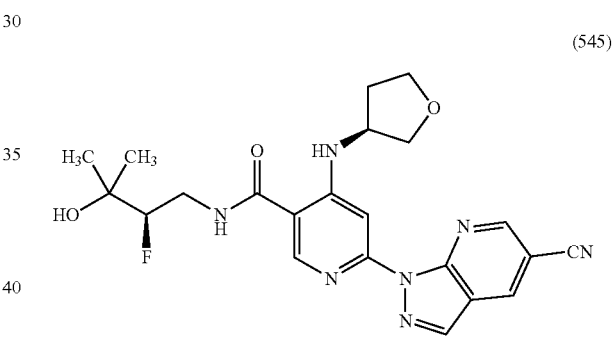

(545)

Intermediate 545A

6-Chloro-N—((R)-2-fluoro-3-hydroxy-3-methylbutyl)-4-(((S)-tetrahydrofuran-3-yl)amino)nicotinamide

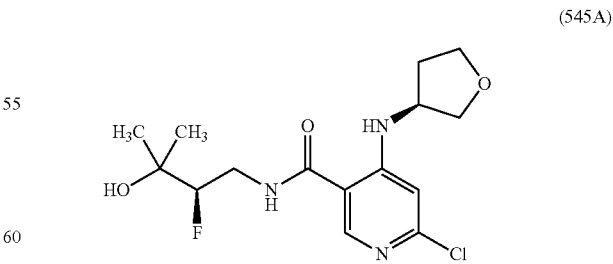

(545A)

In a vial suitable for heating, (R)-4,6-dichloro-N-(2-fluoro-3-hydroxy-3-methylbutyl)nicotinamide (150 mg, 0.508 mmol), (S)-tetrahydrofuran-3-amine, HCl (62.8 mg, 0.508 mmol) and Hunig's Base (0.266 mL, 1.525 mmol) were dissolved in DMF (5 mL) at room temperature with stirring and then heated at 120° C. overnight. The reaction mixture was cooled and the DMF removed under vacuum to afford the crude solid which was purified via column chromatography to afford 6-chloro-N—((R)-2-fluoro-3-hydroxy-3-methylbutyl)-4-(((S)-tetrahydrofuran-3-yl)amino)nicotinamide (112 mg, 61% yield) as a tan solid. LCMS 346.1 (M+H); $^1$H NMR (400 MHz, DMSO-$d_6$) δ 8.77 (t, J=5.6 Hz, 1H), 8.67 (d, J=7.0 Hz, 1H), 8.40 (s, 1H), 6.75 (s, 1H), 4.81 (s, 1H), 4.37 (dd, J=9.4, 1.9 Hz, 0.5H), 4.28-4.16 (m, 1.5H), 3.88-3.77 (m, 2H), 3.76-3.67 (m, 2H), 3.62 (dd, J=14.5, 3.3 Hz, 1H), 3.55 (dd, J=9.2, 2.9 Hz, 1H), 3.42-3.32 (m, 1H), 2.30-2.20 (m, 1H), 1.79-1.69 (m, 1H), 1.14 (dd, J=5.9, 1.1 Hz, 6H).

Example 545

In a vial suitable for heating, a mixture of 6-chloro-N—((R)-2-fluoro-3-hydroxy-3-methylbutyl)-4-(((S)-tetrahydrofuran-3-yl)amino)nicotinamide (99645-090-01) (30 mg, 0.087 mmol), 1H-pyrazolo[3,4-b]pyridine-5-carbonitrile (12.50 mg, 0.087 mmol), and potassium phosphate, tribasic (55.3 mg, 0.260 mmol) in dioxane (2 mL) was degassed with bubbling nitrogen for 5 minutes. In a separate sealed vial, a degassed, stirring mixture of $Pd_2(dba)_3$ (3.97 mg, 4.34 μmol) and tetramethyl t-Bu XPhos (5.00 mg, 10.41 μmol) in 5:1 toluene/dioxane (0.2 mL) was heated at 120° C. for 5 minutes. After cooling to room temperature, this solution was transferred to the vial containing the reaction mixture. The vial was sealed and heated at 80° C. for 4 hours and maintained at room temperature overnight. The mixture was filtered, and the filtrate was concentrated under high vacuum. The product was purified directly via preparative HPLC to afford 6-(5-cyano-1H-pyrazolo[3,4-b]pyridin-1-yl)-N—((R)-2-fluoro-3-hydroxy-3-methylbutyl)-4-(((S)-tetrahydrofuran-3-yl)amino) nicotinamide, TFA salt (49 mg, 85% yield). HPLC Rt 1.12 min, Conditions E; LCMS 454.3 (M+H); $^1$H NMR (500 MHz, DMSO-$d_6$) δ 9.10 (s, 1H), 9.04 (s, 1H), 9.01-8.91 (m, 1H), 8.71 (s, 1H), 8.66 (s, 1H), 7.52 (s, 1H), 4.42 (d, J=9.1 Hz, 1H), 4.32 (d, J=9.1 Hz, 1H), 4.26 (br. s., 1H), 3.94 (dd, J=9.1, 5.4 Hz, 1H), 3.88 (q, J=7.4 Hz, 1H), 3.82-3.74 (m, 2H), 3.73-3.65 (m, 1H), 3.48-3.35 (m, 1H), 2.41-2.32 (m, 1H), 1.89 (dd, J=7.9, 4.5 Hz, 1H), 1.18 (d, J=7.1 Hz, 7H).

The Examples in Table 17 were prepared using the general methods for Examples 544 and 545 using the appropriate starting material and amine.

TABLE 17

| Ex. No. | Structure | HPLC Rt (min) | HPLC cond. | LCMS |
|---|---|---|---|---|
| 546 | 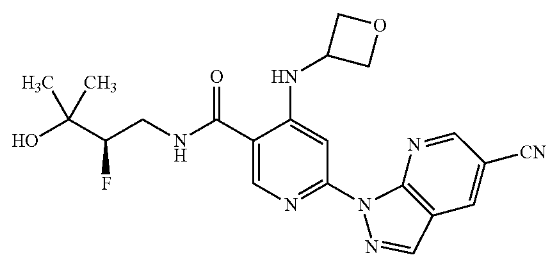 | 0.98 | E | 440.3 |
| 547 | 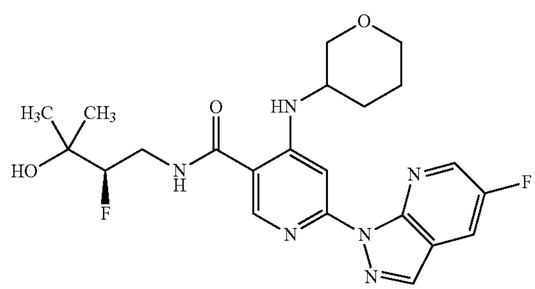 [SMILES: CC(C)(O)[C@H](F)CNC(=O)c1cnc(-n2ncc3cc(F)cnc32)cc1NC1CCCOC1] | 7.25 | B | 461.2 |
| 548 | 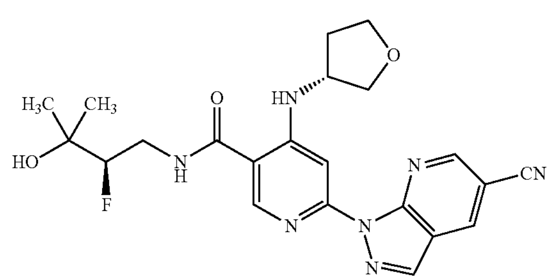 [SMILES: CC(C)(O)[C@H](F)CNC(=O)c1cnc(-n2ncc3cc(C#N)cnc32)cc1N[C@@H]1CCOC1] | 1.08 | E | 454.3 |

TABLE 17-continued

| Ex. No. | Structure | HPLC Rt (min) | HPLC cond. | LCMS |
|---|---|---|---|---|
| 549 | 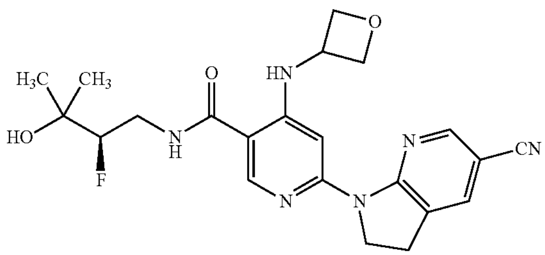 [SMILES: CC(C)(O)[C@H](F)CNC(=O)c1cnc(N2CCc3cc(C#N)cnc32)cc1NC1COC1] | 1.24 | E | 441.2 |
| 550 | 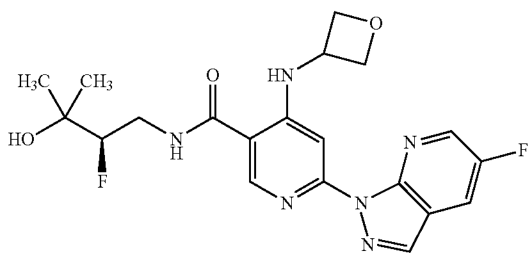 [SMILES: CC(C)(O)[C@H](F)CNC(=O)c1cnc(-n2ncc3cc(F)cnc32)cc1NC1COC1] | 0.80 | D | 433.0 |
| 551 | 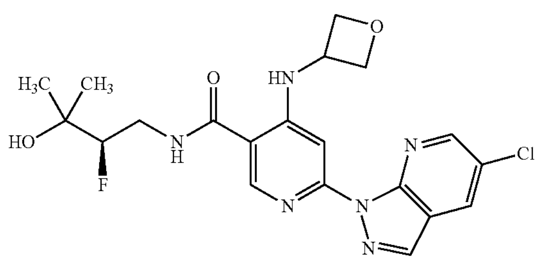 [SMILES: CC(C)(O)[C@H](F)CNC(=O)c1cnc(-n2ncc3cc(Cl)cnc32)cc1NC1COC1] | 1.17 | C | 448.8 |
| 552 | 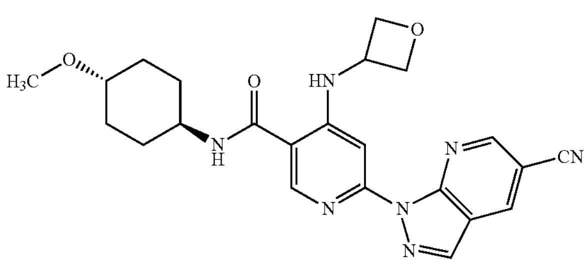 [SMILES: CO[C@H]1CC[C@H](NC(=O)c2cnc(-n3ncc4cc(C#N)cnc43)cc2NC2COC2)CC1] | .8011 | A | 448.2 |
| 553 | 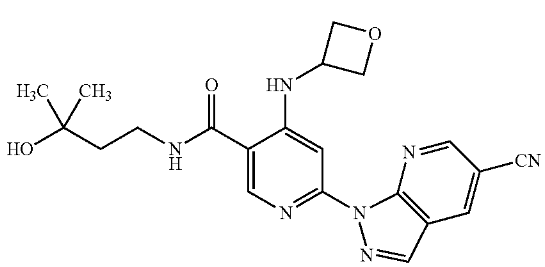 [SMILES: CC(C)(O)CCNC(=O)c1cnc(-n2ncc3cc(C#N)cnc32)cc1NC1COC1] | 10.73 | B | 422.2 |

TABLE 17-continued
| Ex. No. | Structure | HPLC Rt (min) | HPLC cond. | LCMS |
|---|---|---|---|---|
| 554 | 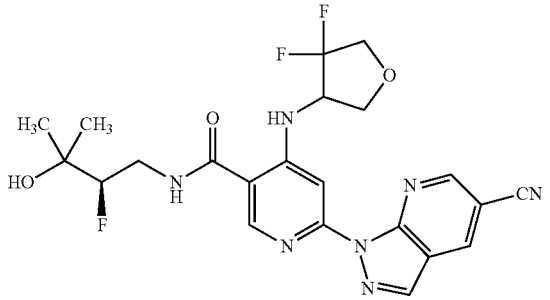 [SMILES: CC(C)(O)[C@H](F)CNC(=O)c1cnc(-n2ncc3cc(C#N)cnc32)cc1NC1COCC1(F)F] | 7.32 | A | 490.2 |
| 555 | 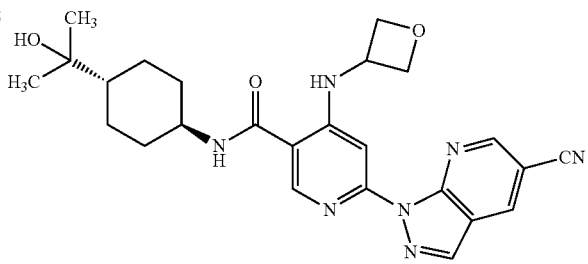 [SMILES: CC(C)(O)[C@H]1CC[C@H](NC(=O)c2cnc(-n3ncc4cc(C#N)cnc43)cc2NC2COC2)CC1] | 1.90 | G | 476.2 |
| 556 | 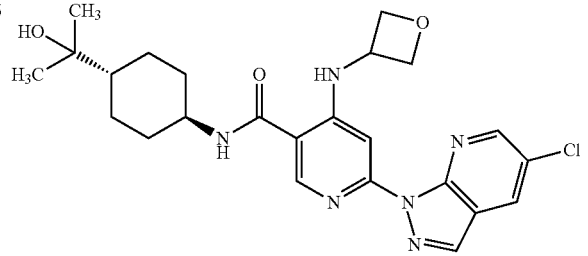 | 1.42 | A | 485.3 |
| 557 | 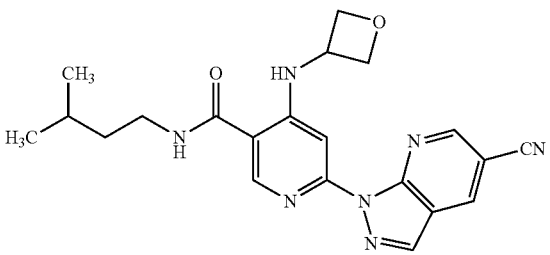 [SMILES: CC(C)CCNC(=O)c1cnc(-n2ncc3cc(C#N)cnc32)cc1NC1COC1] | 1.5 | E | 406.3 |
| 558 | 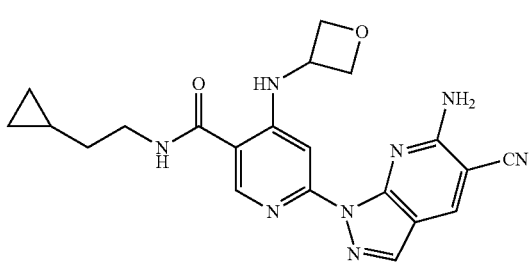 [SMILES: N#Cc1cc2cnn(-c3cc(NC4COC4)c(C(=O)NCCC4CC4)cn3)c2nc1N] | 1.28 | E | 419.3 |

TABLE 17-continued
| Ex. No. | Structure | HPLC Rt (min) | HPLC cond. | LCMS |
|---|---|---|---|---|
| 559 | 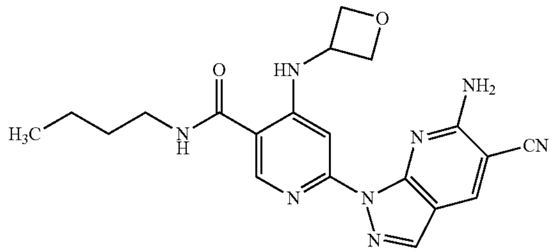 [SMILES: CCCCNC(=O)c1cnc(-n2ncc3cc(C#N)c(N)nc32)cc1NC1COC1] | 1.28 | E | 407.3 |
| 560 | 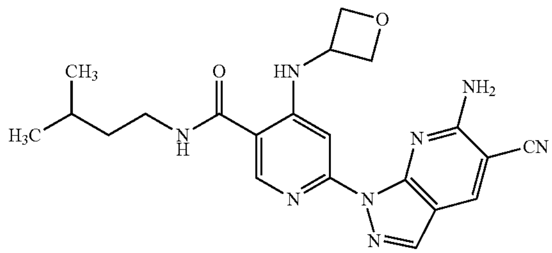 [SMILES: CC(C)CCNC(=O)c1cnc(-n2ncc3cc(C#N)c(N)nc32)cc1NC1COC1] | 1.42 | E | 421.3 |
| 561 | 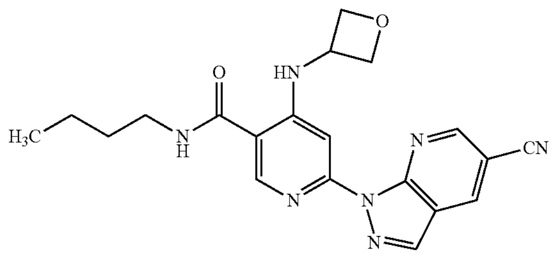 [SMILES: CCCCNC(=O)c1cnc(-n2ncc3cc(C#N)cnc32)cc1NC1COC1] | 1.34 | E | 392.2 |
| 562 | 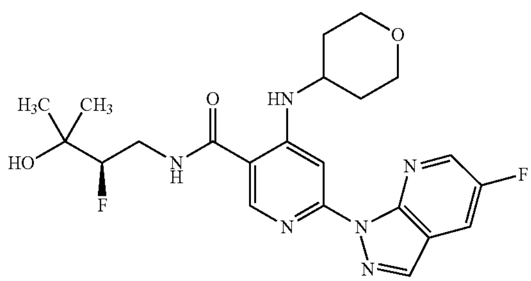 [SMILES: CC(C)(O)[C@H](F)CNC(=O)c1cnc(-n2ncc3cc(F)cnc32)cc1NC1CCOCC1] | 12.32 | B | 461.2 |
Example 563
(R)-6-(5-Cyano-1H-pyrazolo[3,4-b]pyridin-1-yl)-N-(2-fluoro-3-hydroxy-3-methylbutyl)-4-((3,3,3-trifluoropropyl)amino)nicotinamide
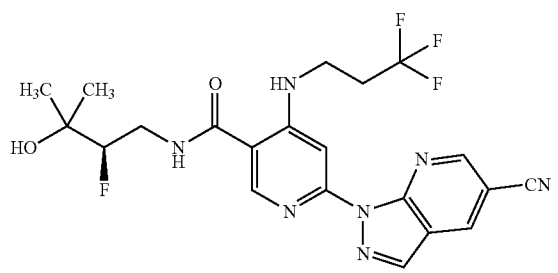
(563)
Intermediate 563A
Ethyl 6-chloro-4-((3,3,3-trifluoropropyl)amino)nicotinate
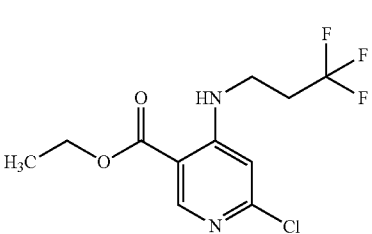
(563A)
To a solution of ethyl 4,6-dichloronicotinate (2 g, 9.09 mmol) in DMA (4 mL) were added 3,3,3-trifluoropropan-1- amine (1.028 g, 9.09 mmol) and DIPEA (1.587 mL, 9.09 mmol). The mixture was stirred at room temperature for 24 h. DMA and DIPEA were removed under vacuum and the crude material was diluted with ice cold water. The off-white solid formed was collected on a filter and dried to afford ethyl 6-chloro-4-((3,3,3-trifluoropropyl)amino)nicotinate (1.8 g, 67% yield) which was used without further purification. LCMS 297.0 (M+H).

Intermediate 563B

6-Chloro-4-((3,3,3-trifluoropropyl)amino)nicotinic acid

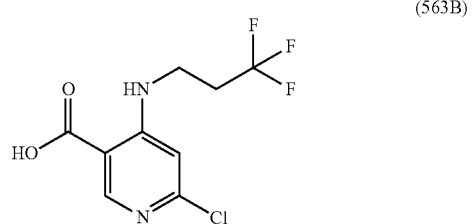 [SMILES: O=C(O)c1cnc(Cl)cc1NCCC(F)(F)F]

(563B)

To a solution of ethyl 6-chloro-4-((3,3,3-trifluoropropyl) amino)nicotinate (2 g, 6.74 mmol) in EtOH (4 mL) were added water (1 mL) and LiOH (0.484 g, 20.22 mmol). The mixture was stirred at room temperature overnight and then concentrated to remove the EtOH. The residue was acidified with 1.5N HCl and the precipitated product was filtered, washed with water and dried to afford 6-chloro-4-((3,3,3-trifluoropropyl)amino) nicotinic acid (1.5 g, 83% yield) which was used without further purification. LCMS 269.1 (M+H); $^1$H NMR (300 MHz, DMSO-$d_6$) δ 8.52 (s, 1H), 6.84 (s, 1H); 3.55 (M, 2H), 2.63 (m, 2H).

Intermediate 563C (R)-6-Chloro-N-(2-fluoro-3-hydroxy-3-methylbutyl)-4-((3,3,3-trifluoropropyl)amino)nicotinamide

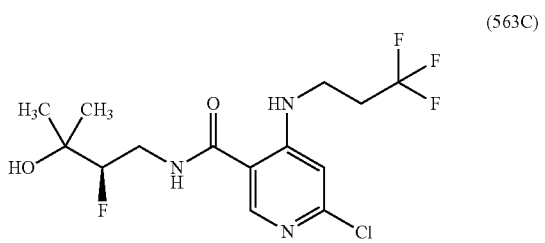 [SMILES: CC(C)(O)[C@H](F)CNC(=O)c1cnc(Cl)cc1NCCC(F)(F)F]

(563C)

To a solution of 6-chloro-4-((3,3,3-trifluoropropyl)amino) nicotinic acid (1.1 g, 4.10 mmol) in DMF (3 mL) were added HATU (1.557 g, 4.10 mmol) and DIPEA (0.715 mL, 4.10 mmol). To this stirred solution was added (R)-4-amino-3-fluoro-2-methylbutan-2-ol (0.496 g, 4.10 mmol) and the mixture was stirred at room temperature for 4 hrs. DMF was removed under vacuum and the crude mixture was diluted with water and extracted with ethyl acetate. The ethyl acetate layer was washed with water, dried and concentrated. The crude product was purified by column chromatography using 2% MeOH in chloroform to afford (R)-6-chloro-N-(2-fluoro-3-hydroxy-3-methylbutyl)-4-((3,3,3-trifluoropropyl)amino) nicotinamide (0.7 g, 46% yield) as an off-white solid. $^1$H NMR (400 MHz, DMSO-$d_6$) δ=8.82-8.72 (m, 1H), 8.63-8.54 (m, 1H), 8.39 (s, 1H), 6.78 (s, 1H), 4.82 (s, 1H), 4.44-4.22 (m, 1H), 3.79-3.59 (m, 1H), 3.50 (d, J=6.0 Hz, 2H), 3.43-3.34 (m, 1H), 2.61 (d, J=11.5 Hz, 2H), 1.16 (dd, J=4.5, 1.5 Hz, 6H).

Example 563

To solution of (R)-6-chloro-N-(2-fluoro-3-hydroxy-3-methylbutyl)-4-((3,3,3-trifluoropropyl)amino)nicotinamide (100 mg, 0.269 mmol) in dioxane (5 mL) were added 1H-pyrazolo[3,4-b]pyridine-5-carbonitrile (46.5 mg, 0.323 mmol), Xantphos (93 mg, 0.161 mmol) and $Na_2CO_3$ (86 mg, 0.807 mmol). The mixture was degassed for 10 min and $Pd_2(dba)_3$ (99 mg, 0.108 mmol) was added. The mixture was degassed again for 10 min. The reaction mixture was then heated at 100° C. in a microwave vial for 2 h. The reaction mixture was cooled and filtered through small pad of CELITE®. The filtrate was concentrated and the crude material was purified by flash column chromatography through 24 g silica gel column using (1-6%) MeOH:$CHCl_3$ as eluent. The product was further purified via preparative HPLC to afford (R)-6-(5-cyano-1H-pyrazolo[3,4-b]pyridin-1-yl)-N-(2-fluoro-3-hydroxy-3-methylbutyl)-4-((3,3,3-trifluoropropyl) amino) nicotinamide (30 mg, 21% yield). HPLC Rt 7.05 min, Conditions A; LCMS 480.2 (M+H); $^1$H NMR (400 MHz, DMSO-$d_6$) δ 9.04-9.02 (m, 2H), 8.84 (t, J=5.60 Hz, 1H), 8.71 (t, J=5.60 Hz, 1H), 8.66 (d, J=3.20 Hz, 2H), 7.40 (s, 1H), 4.85 (s, 1H), 4.38 (ddd, J=2.00, 9.20, 49.20 Hz, 1H), 3.85-3.67 (m, 1H), 3.57 (q, J=6.80 Hz, 2H), 3.50-3.39 (m, 1H), 2.74-2.66 (m, 2H), 1.19-1.15 (m, 6H).

The Examples in Table 18 were prepared using the general methods for Example 563 using the appropriate starting material and amine.

TABLE 18

| Ex. No. | Structure | HPLC Rt (min) | HPLC cond. | LCMS |
|---|---|---|---|---|
| 564 | ![structure] | 1.71 | E | 430.2 |

TABLE 18-continued

| Ex. No. | Structure | HPLC Rt (min) | HPLC cond. | LCMS |
|---|---|---|---|---|
| 565 | 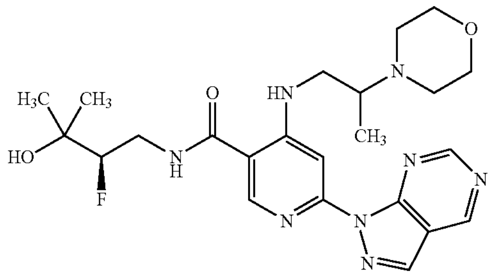 [SMILES: CC(CNc1cc(-n2ncc3cncnc32)ncc1C(=O)NC[C@@H](F)C(C)(C)O)N1CCOCC1] | 1.24 | E | 486.3 |
| 566 | 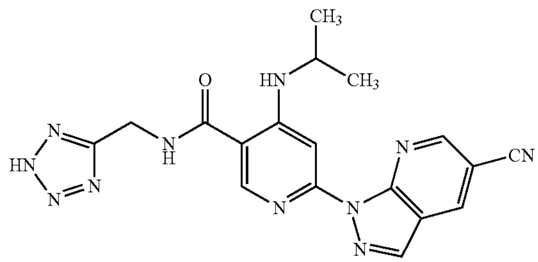 [SMILES: CC(C)Nc1cc(-n2ncc3cc(C#N)cnc32)ncc1C(=O)NCc1nn[nH]n1] | 0.92 | E | 404.2 |
| 567 | 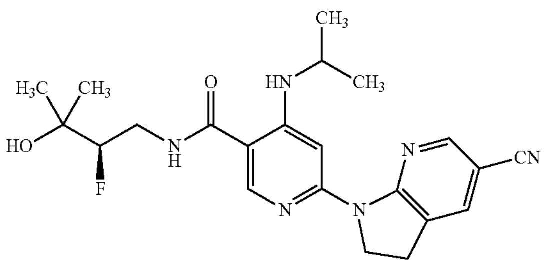 [SMILES: CC(C)Nc1cc(N2CCc3cc(C#N)cnc32)ncc1C(=O)NC[C@@H](F)C(C)(C)O] | 1.56 | E | 427.3 |
| 568 | 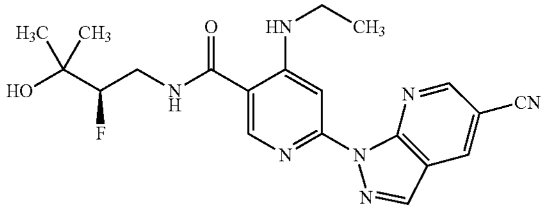 [SMILES: CCNc1cc(-n2ncc3cc(C#N)cnc32)ncc1C(=O)NC[C@@H](F)C(C)(C)O] | 1.31 | E | 412.2 |
| 569 | 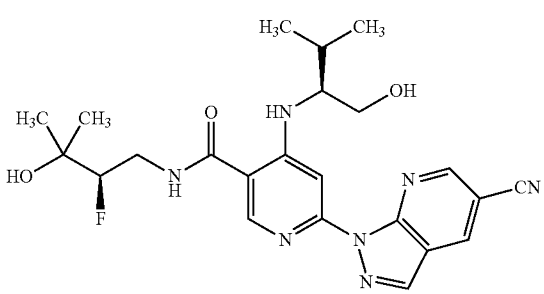 [SMILES: CC(C)[C@@H](CO)Nc1cc(-n2ncc3cc(C#N)cnc32)ncc1C(=O)NC[C@@H](F)C(C)(C)O] | 1.38 | E | 470.3 |
| 570 | 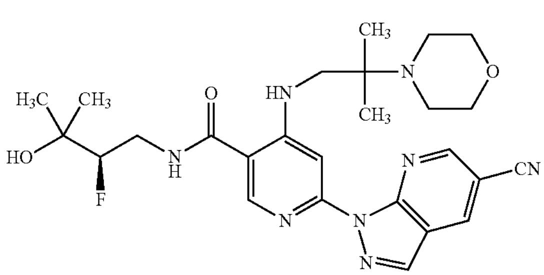 [SMILES: CC(C)(O)[C@H](F)CNC(=O)c1cnc(-n2ncc3cc(C#N)cnc32)cc1NCC(C)(C)N1CCOCC1] | 1.36 | E | 525.2 |

TABLE 18-continued

| Ex. No. | Structure | HPLC Rt (min) | HPLC cond. | LCMS |
|---|---|---|---|---|
| 571 | 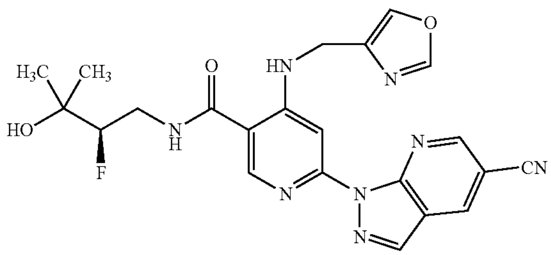 [SMILES: CC(C)(O)[C@H](F)CNC(=O)c1cnc(-n2ncc3cc(C#N)cnc32)cc1NCc1cocn1] | 11.30 | B | 465.3 |
| 572 | Diastereomer 1 | 5.23 | A | 456.3 |
| 573 | Diastereomer 2 | 5.22 | A | 456.3 |
| 574 | 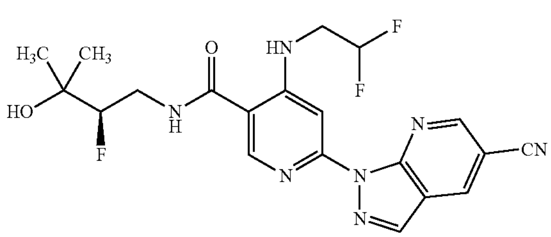 [SMILES: CC(C)(O)[C@H](F)CNC(=O)c1cnc(-n2ncc3cc(C#N)cnc32)cc1NCC(F)F] | 6.47 | A | 448.3 |
| 575 | Racemic | 5.38 | A | 474.2 |

TABLE 18-continued

| Ex. No. | Structure | HPLC Rt (min) | HPLC cond. | LCMS |
|---|---|---|---|---|
| 576 | 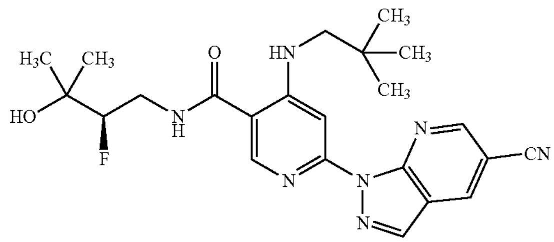 [SMILES: CC(C)(C)CNc1cc(-n2ncc3cc(C#N)cnc32)ncc1C(=O)NC[C@@H](F)C(C)(C)O] | 1.61 | A | 454.2 |
| 577 | 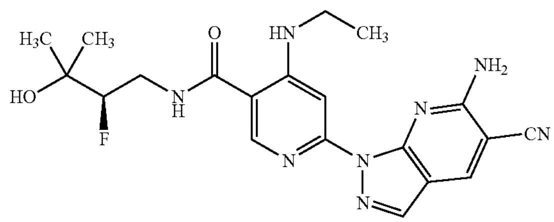 [SMILES: CCNc1cc(-n2ncc3cc(C#N)c(N)nc32)ncc1C(=O)NC[C@@H](F)C(C)(C)O] | 1.21 | E | 427.2 |
| 578 | 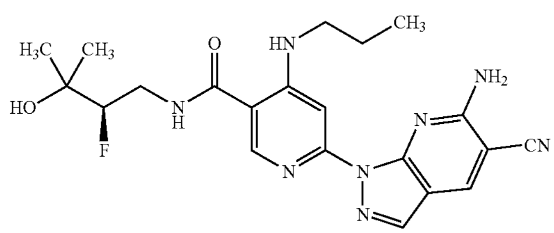 [SMILES: CCCNc1cc(-n2ncc3cc(C#N)c(N)nc32)ncc1C(=O)NC[C@@H](F)C(C)(C)O] | 1.39 | E | 441.2 |
| 579 | 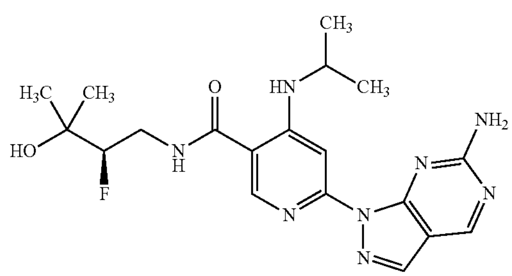 [SMILES: CC(C)Nc1cc(-n2ncc3cnc(N)nc32)ncc1C(=O)NC[C@@H](F)C(C)(C)O] | 1.16 | E | 417.2 |
| 580 | 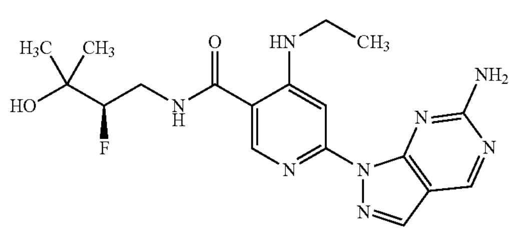 [SMILES: CCNc1cc(-n2ncc3cnc(N)nc32)ncc1C(=O)NC[C@@H](F)C(C)(C)O] | 1.04 | E | 403.2 |
| 581 | 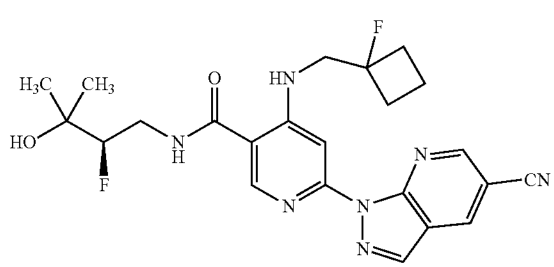 [SMILES: CC(C)(O)[C@H](F)CNC(=O)c1cnc(-n2ncc3cc(C#N)cnc32)cc1NCC1(F)CCC1] | 2.14 | G | 470.2 |

TABLE 18-continued

| Ex. No. | Structure | HPLC Rt (min) | HPLC cond. | LCMS |
|---|---|---|---|---|
| 582 | 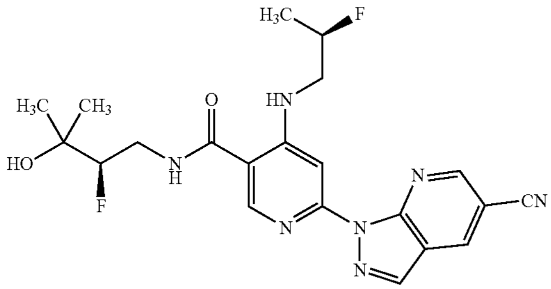 [SMILES: C[C@@H](F)CNc1cc(-n2ncc3cc(C#N)cnc32)ncc1C(=O)NC[C@@H](F)C(C)(C)O] | 1.25 | E | 444.2 |
| 583 | 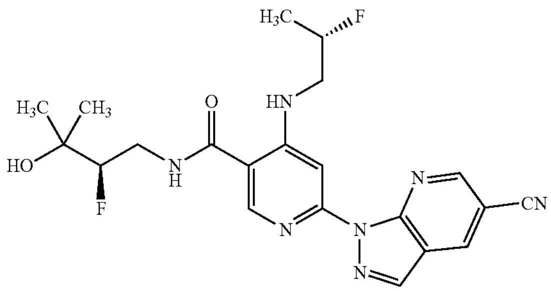 [SMILES: C[C@H](F)CNc1cc(-n2ncc3cc(C#N)cnc32)ncc1C(=O)NC[C@@H](F)C(C)(C)O] | 1.29 | E | 444.2 |
| 584 | 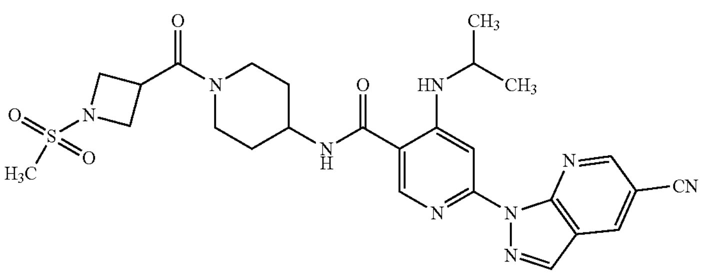 [SMILES: CC(C)Nc1cc(-n2ncc3cc(C#N)cnc32)ncc1C(=O)NC1CCN(C(=O)C2CN(S(C)(=O)=O)C2)CC1] | 2.01 | C | 566.2 |
| 585 | 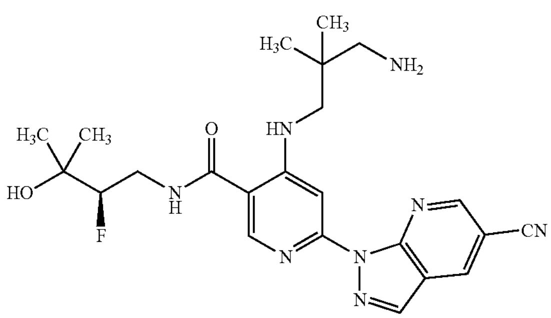 [SMILES: CC(C)(CN)CNc1cc(-n2ncc3cc(C#N)cnc32)ncc1C(=O)NC[C@@H](F)C(C)(C)O] | 1.44 | C | 469.2 |
| 586 | 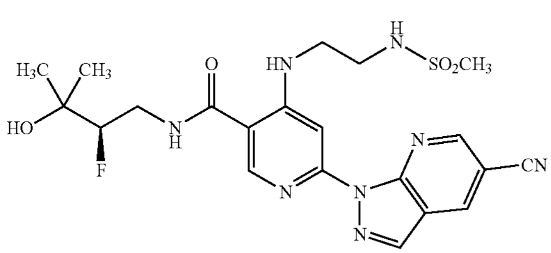 [SMILES: CC(C)(O)[C@H](F)CNC(=O)c1cnc(-n2ncc3cc(C#N)cnc32)cc1NCCNS(C)(=O)=O] | 1.52 | C | 505.2 |

TABLE 18-continued

| Ex. No. | Structure | HPLC Rt (min) | HPLC cond. | LCMS |
|---|---|---|---|---|
| 587 | 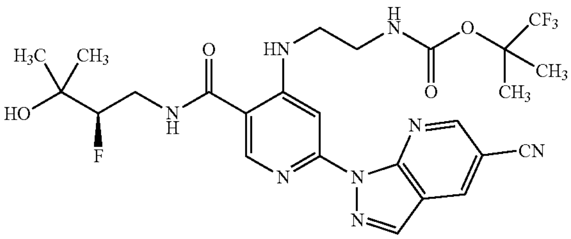 [SMILES: CC(C)(O)[C@H](F)CNC(=O)c1cnc(-n2ncc3cc(C#N)cnc32)cc1NCCNC(=O)OC(C)(C)C(F)(F)F] | 2.22 | C | 581.2 |
| 588 | 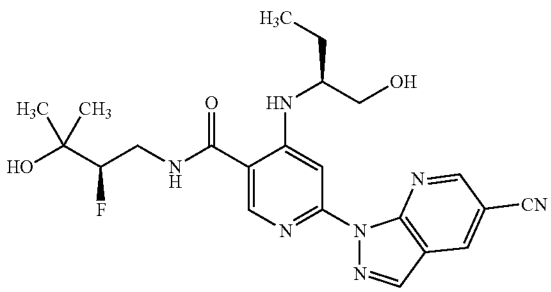 [SMILES: CC[C@@H](CO)Nc1cc(-n2ncc3cc(C#N)cnc32)ncc1C(=O)NC[C@@H](F)C(C)(C)O] | 1.12 | E | 456.2 |
| 589 | 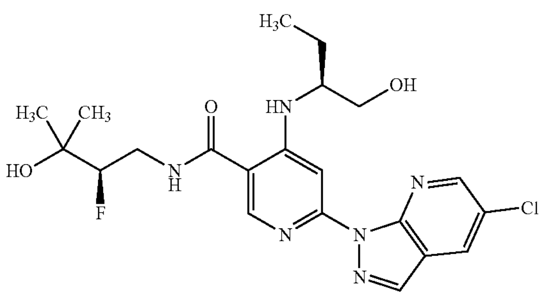 [SMILES: CC[C@@H](CO)Nc1cc(-n2ncc3cc(Cl)cnc32)ncc1C(=O)NC[C@@H](F)C(C)(C)O] | 1.33 | E | 465.2 |
| 590 | 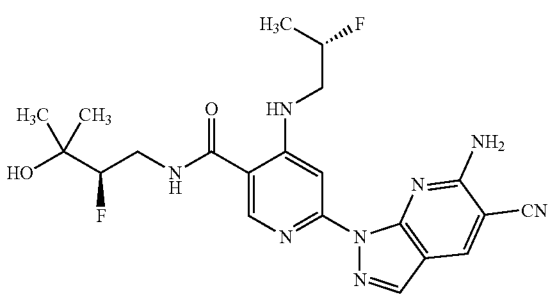 [SMILES: C[C@H](F)CNc1cc(-n2ncc3cc(C#N)c(N)nc32)ncc1C(=O)NC[C@@H](F)C(C)(C)O] | 1.21 | E | 459.2 |
| 591 | 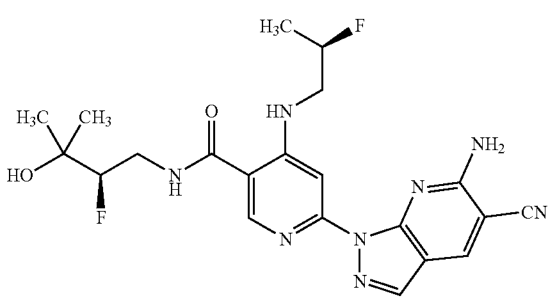 [SMILES: C[C@@H](F)CNc1cc(-n2ncc3cc(C#N)c(N)nc32)ncc1C(=O)NC[C@@H](F)C(C)(C)O] | 1.21 | E | 459.2 |

TABLE 18-continued

| Ex. No. | Structure | HPLC Rt (min) | HPLC cond. | LCMS |
|---|---|---|---|---|
| 592 | 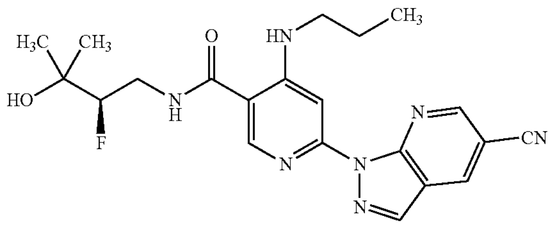 [SMILES: CCCNc1cc(-n2ncc3cc(C#N)cnc32)ncc1C(=O)NC[C@@H](F)C(C)(C)O] | 1.4 | E | 426.2 |
| 593 | 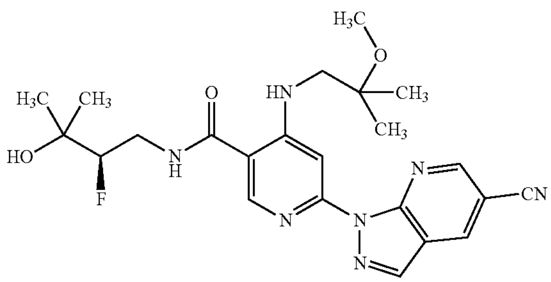 [SMILES: COC(C)(C)CNc1cc(-n2ncc3cc(C#N)cnc32)ncc1C(=O)NC[C@@H](F)C(C)(C)O] | 1.35 | C | 470.3 |
| 594 | Diastereomer 1 | 1.54 | E | 479.3 |
| 595 | 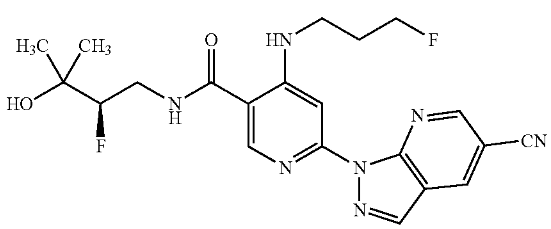 [SMILES: CC(C)(O)[C@H](F)CNC(=O)c1cnc(-n2ncc3cc(C#N)cnc32)cc1NCCCF] | 1.27 | E | 444.3 |
| 596 | Diastereomer 2 | 1.56 | E | 479.2 |

TABLE 18-continued
| Ex. No. | Structure | HPLC Rt (min) | HPLC cond. | LCMS |
|---|---|---|---|---|
| 597 | 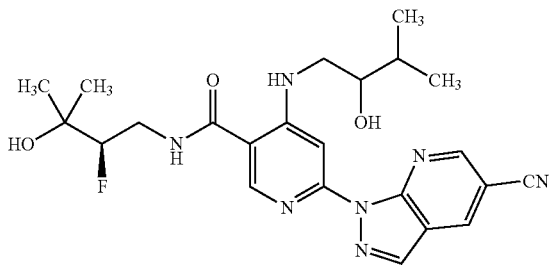 Single Diastereomer | 1.32 | E | 470.3 |
| 598 | 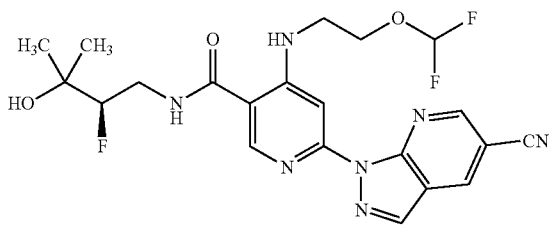 [SMILES: CC(C)(O)[C@H](F)CNC(=O)c1cnc(-n2ncc3cc(C#N)cnc32)cc1NCCOC(F)F] | 1.28 | C | 478.2 |
| 599 | 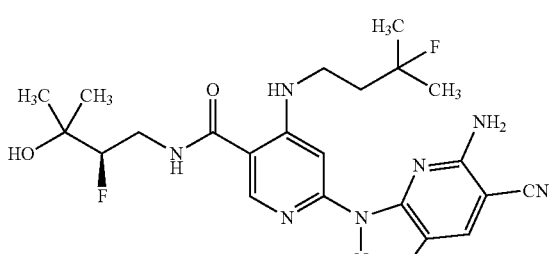 | 1.42 | E | 487.3 |
| 600 | 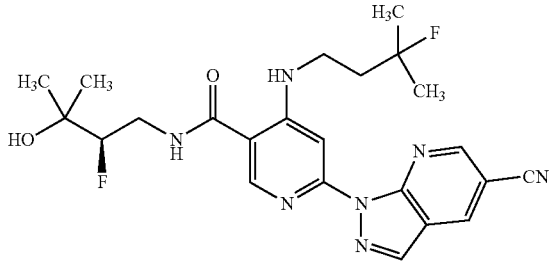 [SMILES: CC(C)(F)CCNc1cc(-n2ncc3cc(C#N)cnc32)ncc1C(=O)NC[C@@H](F)C(C)(C)O] | 1.49 | E | 472.3 |
| 601 | 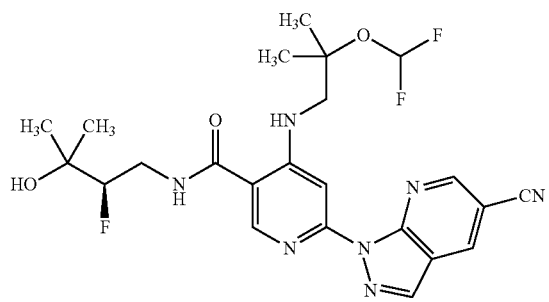 [SMILES: CC(C)(CNc1cc(-n2ncc3cc(C#N)cnc32)ncc1C(=O)NC[C@@H](F)C(C)(C)O)OC(F)F] | 1.51 | C | 506.3 |

TABLE 18-continued
| Ex. No. | Structure | HPLC Rt (min) | HPLC cond. | LCMS |
|---|---|---|---|---|
| 602 | 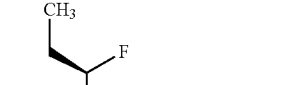 | 1.67 | C | 467.3 |
| 603 | 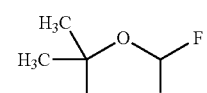 | 1.66 | C | 515.3 |
| 604 | 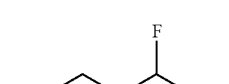 | 1.4 | E | 458.2 |
| 605 | 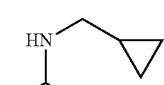 | 1.47 | E | 438.2 |

Example 606

6-(5-Cyano-1H-pyrazolo[3,4-b]pyridin-1-yl)-N—((R)-2-fluoro-3-hydroxy-3-methylbutyl)-4-(((1r,4R)-4-(2-hydroxypropan-2-yl)cyclohexyl)amino)nicotinamide (606)

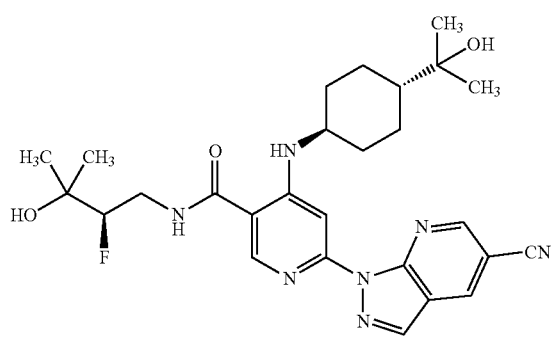

Intermediate 606A

Ethyl 6-chloro-4-(((1r,4r)-4-(2-hydroxypropan-2-yl)cyclohexyl)amino)nicotinate (606A)

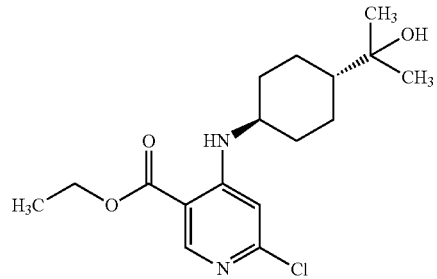

A solution of ethyl 4,6-dichloronicotinate (3 g, 13.6 mmol), 2-(4-aminocyclohexyl)propan-2-ol (2.144 g, 13.63 mmol), and DIPEA (7.14 mL, 41 mmol) in DMA (30 mL) was heated at 100° C. overnight. The reaction mixture was concentrated to remove DMA and water was added. The product was extracted with ethylacetate (3 times) and the combined extracts were washed with water and brine. The extracts were dried over anhydrous Na$_2$SO$_4$, filtered, and concentrated. This crude product was purified via column chromatography to afford ethyl 6-chloro-4-(((1r,4r)-4-(2-hydroxypropan-2-yl)cyclohexyl)amino)nicotinate (3.5 g, 75% yield). $^1$H NMR (300 MHz, DMSO-d$_6$) δ 8.53 (s, 1H), 7.98 (d, J+8.4 Hz, 1H), 6.92 (s, 1H), 4.29 (q, J=6.9 Hz, 2H), 4.08 (s, 1H), 3.40 (br s, 1H), 2.10 (br m, 2H), 1.83 (br m, 2H), 1.31 (t, J=6.9 Hz, 3H), 1.21 (m, 5H), 1.05 (s, 3H).

Intermediate 606B

6-Chloro-4-(((1r,4r)-4-(2-hydroxypropan-2-yl)cyclohexyl)amino) nicotinic acid (606B)

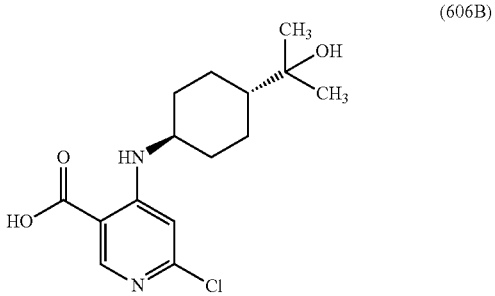 [SMILES: CC(C)(O)[C@H]1CC[C@H](Nc2cc(Cl)ncc2C(=O)O)CC1]

To a solution of ethyl 6-chloro-4-(((1r,4r)-4-(2-hydroxypropan-2-yl)cyclohexyl)amino)nicotinate (1.31 g, 3.8 mmol) in EtOH (13 mL) was added water (7 mL) and LiOH (0.27 g, 11.44 mmol). The mixture was stirred at room temperature for 2 h. The reaction mixture was concentrated and acidified with 1.5 N HCl to pH 4. The resulting solids were filtered, rinsed with water and dried to afford 6-chloro-4-(((1r,4r)-4-(2-hydroxypropan-2-yl)cyclohexyl)amino) nicotinic acid (1.0 g, 83% yield) as a white solid. LCMS 313.1 (M+H); $^1$H NMR (400 MHz, DMSO-d$_6$) δ 13.30 (br s, 1H), 8.49 (s, 1H), 8.19 (d, J=8.1 Hz, 1H), 6.68 (s, 1H), 4.08 (s, 1H), 3.44 (br s, 1H), 2.02 (m, 2H), 1.82 (M, 2H), 1.20 (m, 5H), 1.05 (s, 6H).

Intermediate 606C

6-Chloro-N—((R)-2-fluoro-3-hydroxy-3-methylbutyl)-4-(((1r,4R)-4-(2-hydroxypropan-2-yl)cyclohexyl)amino)nicotinamide (606C)

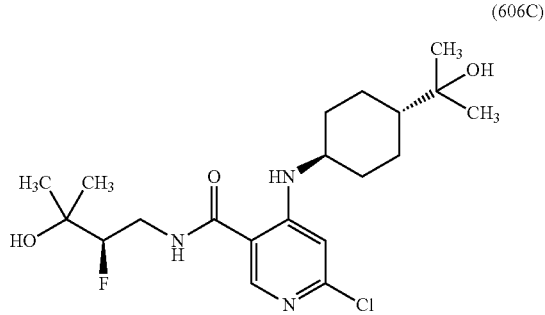 [SMILES: CC(C)(O)[C@H](F)CNC(=O)c1cnc(Cl)cc1N[C@H]1CC[C@H](C(C)(C)O)CC1]

To a stirred solution of 6-chloro-4-(((1r,4r)-4-(2-hydroxypropan-2-yl)cyclohexyl)amino)nicotinic acid (800 mg, 2.56 mmol) in DMF (8 mL) were added HATU (1.95 g, 5.1 mmol), DIPEA (1.34 mL, 7.7 mmol) and (R)-4-amino-3-fluoro-2-methylbutan-2-ol (340 mg, 2.8 mmoL). The reaction mixture was stirred at room temperature for 1 h. The mixture was concentrated, water was added, and the product was extracted with EtOAc. The organic extracts were washed with saturated aqueous sodium bicarbonate, washed with brine and collectively dried over Na$_2$SO$_4$. The solution was filtered and the filtrate concentrated to afford the crude product which was purified via column chromatography to afford 6-chloro-N—

((R)-2-fluoro-3-hydroxy-3-methylbutyl)-4-(((1r,4R)-4-(2-hydroxypropan-2-yl)cyclohexyl)amino)nicotinamide (800 mg, 75% yield) which was used in the next step. LCMS 416.1 (M+H).

Example 606

To a stirred solution of 6-chloro-N—((R)-2-fluoro-3-hydroxy-3-methylbutyl)-4-(((1S,4S)-4-(2-hydroxypropan-2-yl)cyclohexyl)amino)nicotinamide (50 mg, 0.120 mmol) in dioxane (10 mL) were added 1H-pyrazolo[3,4-b]pyridine-5-carbonitrile (17.33 mg, 0.120 mmol), Xantphos (27.8 mg, 0.048 mmol), and $Na_2CO_3$ (51.0 mg, 0.481 mmol). The mixture was degassed for 3 minutes with nitrogen. Next, $Pd_2(dba)_3$ (44.0 mg, 0.048 mmol) was added and the mixture was degassed with nitrogen for 5 min. The reaction vessel was sealed and the mixture was heated at 110° C. for 24 h. The reaction mixture was cooled to room temperature, filtered through CELITE® with 10% $MeOH/CHCl_3$ and concentrated. The residue was purified via preparative HPLC to afford 6-(5-cyano-1H-pyrazolo[3,4-b]pyridin-1-yl)-N—((R)-2-fluoro-3-hydroxy-3-methylbutyl)-4-(((1S,4S)-4-(2-hydroxypropan-2-yl)cyclohexyl)amino)nicotinamide (5 mg, 8% yield) as a pale yellow solid. HPLC Rt 1.34 min, Conditions C; LCMS 524.2 (M+H). $^1$H NMR (400 MHz, $MeOD_4$) δ 8.99 (d, J=2 Hz, 1H), 8.84 (d, J=2 Hz, 1H), 8.53 (m, 1H), 7.78 (s, 1H), 4.39 (dd, J=9.2, 2.0 Hz, 1H), 3.87 (m, 1H), 3.51 (m, 2H), 2.31 (m, 2H), 2.02 (m, 2H), 1.40 (m, 5H), 1.35 (s, 6H), 1.31 (s, 6H).

The Examples in Table 19 were prepared using the general methods for Example 606 using the appropriate starting material and amine.

TABLE 19

| Ex. No. | Structure | HPLC Rt (min) | HPLC cond. | LCMS |
|---|---|---|---|---|
| 607 | 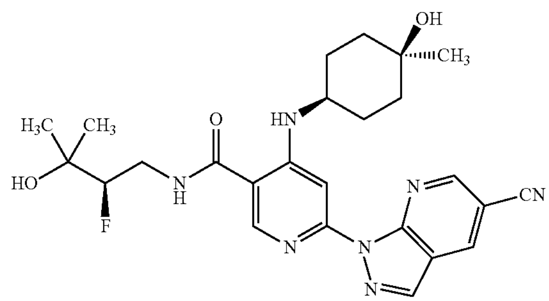 [SMILES: CC(C)(O)[C@H](F)CNC(=O)c1cnc(-n2ncc3cc(C#N)cnc32)cc1N[C@H]1CC[C@@](C)(O)CC1] | 1.29 | E | 496.4 |
| 608 | 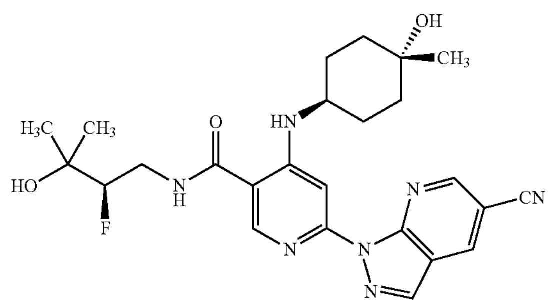 [SMILES: CC(C)(O)[C@H](F)CNC(=O)c1cnc(-n2ncc3cc(C#N)cnc32)cc1N[C@H]1CC[C@](C)(O)CC1] | 1.16 | E | 496.4 |
| 609 | Diastereomer 1 | 11.11 | B | 461.2 |

TABLE 19-continued
| Ex. No. | Structure | HPLC Rt (min) | HPLC cond. | LCMS |
|---|---|---|---|---|
| 610 | 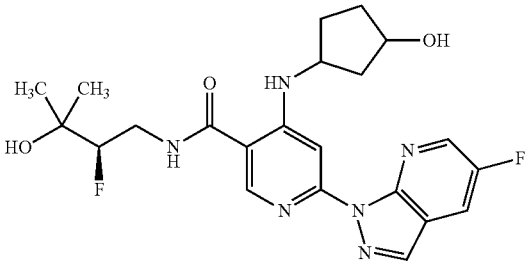 Diastereomer 2 | 11.32 | B | 461.2 |
| 611 | 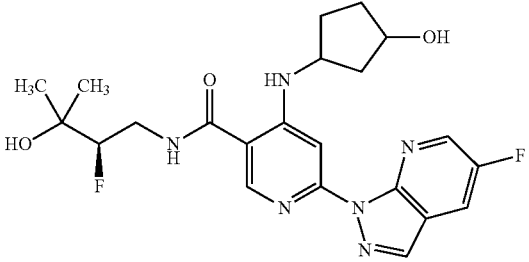 Diastereomeric Mixture | 5.53 | A | 461.2 |
| 612 | 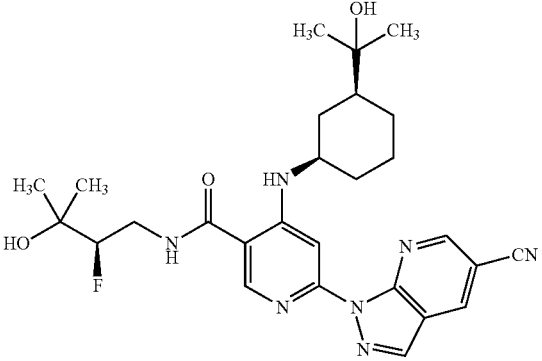 [SMILES: CC(C)(O)[C@H]1CCC[C@@H](Nc2cc(-n3ncc4cc(C#N)cnc43)ncc2C(=O)NC[C@@H](F)C(C)(C)O)C1] | 7.00 | B | 524.2 |
| 613 | 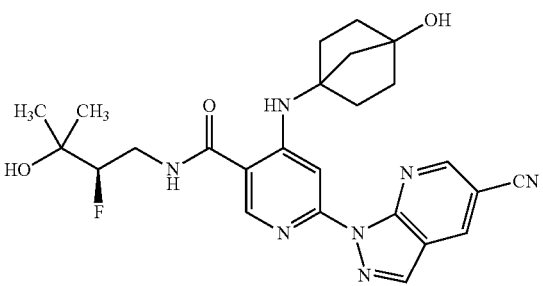 [SMILES: CC(C)(O)[C@H](F)CNC(=O)c1cnc(-n2ncc3cc(C#N)cnc32)cc1NC12CCC(O)(CC1)C2] | 1.08 | E | 494.3 |

TABLE 19-continued

| Ex. No. | Structure | HPLC Rt (min) | HPLC cond. | LCMS |
|---|---|---|---|---|
| 614 | Diastereomer 1 | 7.25 | A | 488.2 |
| 615 | Diastereomer 2 | 7.25 | A | 488.2 |
| 616 | 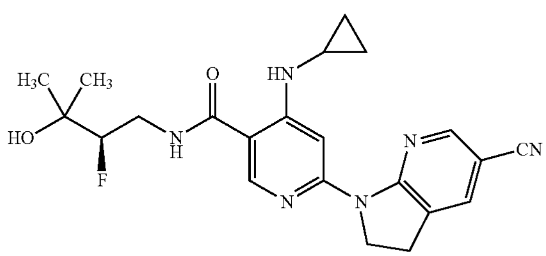 [SMILES: CC(C)(O)[C@H](F)CNC(=O)c1cnc(N2CCc3cc(C#N)cnc32)cc1NC1CC1] | 1.53 | E | 425.2 |
| 617 | 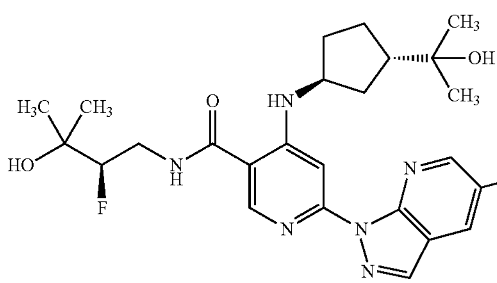 | 1.38 | E | 510.3 |
| 618 | Diastereomer 1 | 7.44 | B | 463.2 |

TABLE 19-continued

| Ex. No. | Structure | HPLC Rt (min) | HPLC cond. | LCMS |
|---|---|---|---|---|
| 619 | Diastereomer 2 | 7.45 | B | 463.2 |
| 620 | Diastereomer 3 | 7.15 | B | 463.2 |
| 621 | Diastereomer 4 | 7.16 | B | 463.2 |
| 622 | 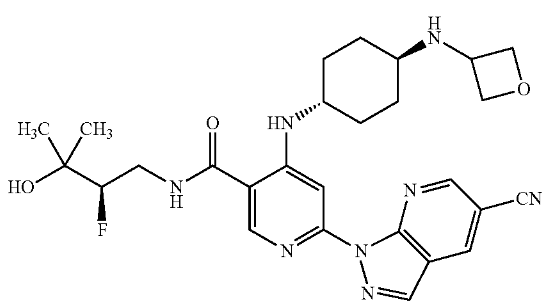 [SMILES: CC(C)(O)[C@H](F)CNC(=O)c1cnc(-n2ncc3cc(C#N)cnc32)cc1N[C@H]1CC[C@H](NC2COC2)CC1] | 0.98 | A | 537.2 |
| 623 | 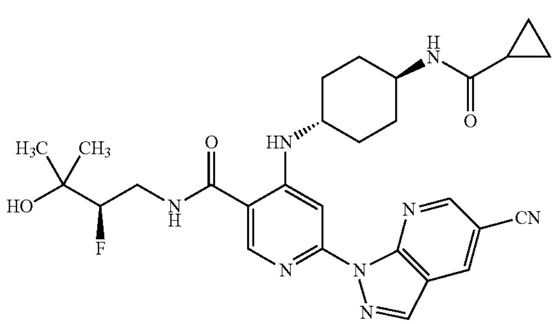 [SMILES: CC(C)(O)[C@H](F)CNC(=O)c1cnc(-n2ncc3cc(C#N)cnc32)cc1N[C@H]1CC[C@H](NC(=O)C2CC2)CC1] | 1.19 | A | 549.2 |

TABLE 19-continued
| Ex. No. | Structure | HPLC Rt (min) | HPLC cond. | LCMS |
|---|---|---|---|---|
| 624 | 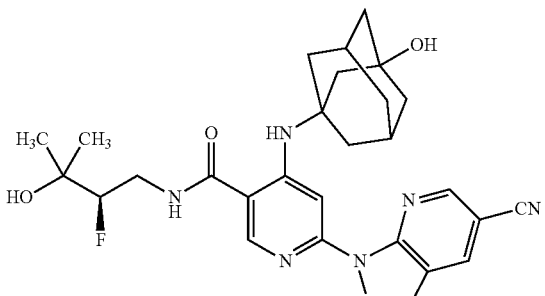 | 1.32 | E | 534.3 |
| 625 | 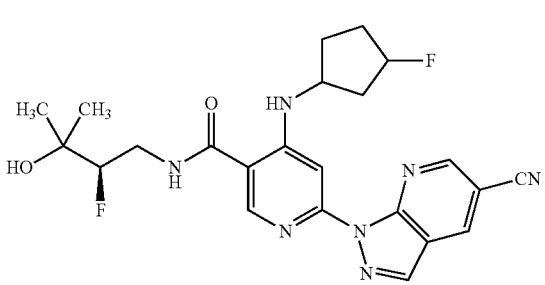 Single Diastereomer | 1.08 | D | 470.2 |
| 626 | 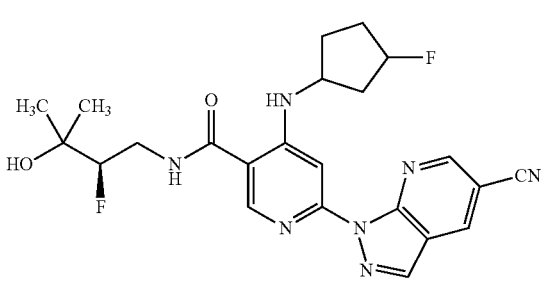 Single Diastereomer | 1.03 | D | 470.2 |
| 627 | 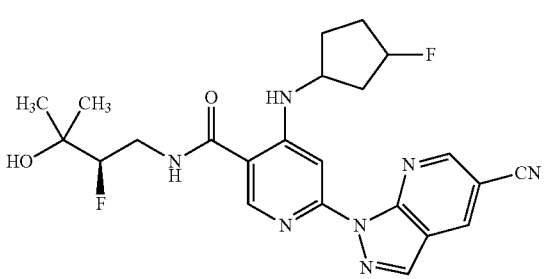 Single Diastereomer | 1.04 | D | 470.2 |
| 628 | 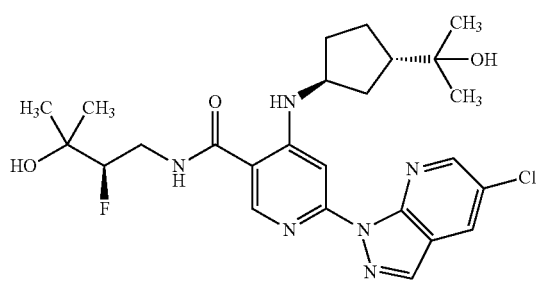 [SMILES: CC(C)(O)[C@H]1CC[C@H](Nc2cc(-n3ncc4cc(Cl)cnc43)ncc2C(=O)NC[C@@H](F)C(C)(C)O)C1] | 1.55 | E | 519.3 |

TABLE 19-continued

| Ex. No. | Structure | HPLC Rt (min) | HPLC cond. | LCMS |
|---|---|---|---|---|
| 629 | 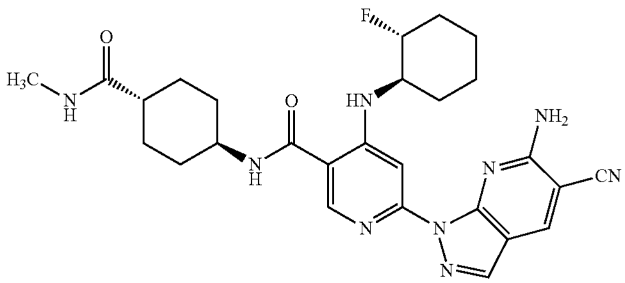 [SMILES: CNC(=O)[C@H]1CC[C@H](NC(=O)c2cnc(-n3ncc4cc(C#N)c(N)nc43)cc2N[C@@H]2CCCC[C@H]2F)CC1] | 1.41 | E | 534.3 |
| 630 | 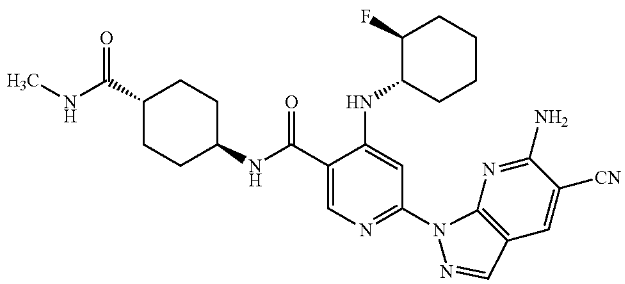 [SMILES: CNC(=O)[C@H]1CC[C@H](NC(=O)c2cnc(-n3ncc4cc(C#N)c(N)nc43)cc2N[C@H]2CCCC[C@@H]2F)CC1] | 1.41 | E | 534.3 |
| 631 | 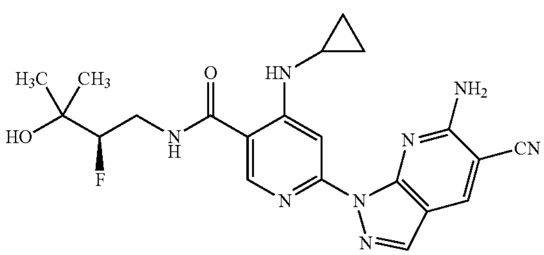 [SMILES: CC(C)(O)[C@H](F)CNC(=O)c1cnc(-n2ncc3cc(C#N)c(N)nc32)cc1NC1CC1] | 1.23 | E | 439.2 |
| 632 | 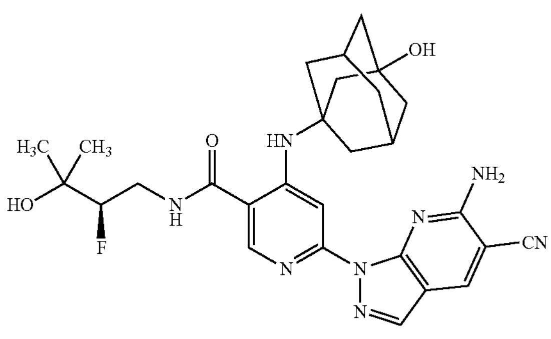 [SMILES: CC(C)(O)[C@H](F)CNC(=O)c1cnc(-n2ncc3cc(C#N)c(N)nc32)cc1NC12CC3CC(CC(O)(C3)C1)C2] | 1.36 | E | 549.3 |
| 633 | 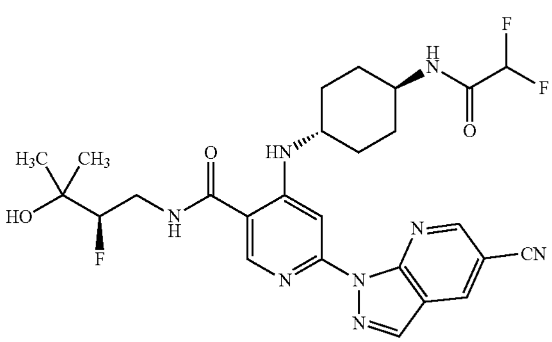 [SMILES: CC(C)(O)[C@H](F)CNC(=O)c1cnc(-n2ncc3cc(C#N)cnc32)cc1N[C@H]1CC[C@H](NC(=O)C(F)F)CC1] | 1.92 | A | 559.2 |

TABLE 19-continued

| Ex. No. | Structure | HPLC Rt (min) | HPLC cond. | LCMS |
|---|---|---|---|---|
| 634 | 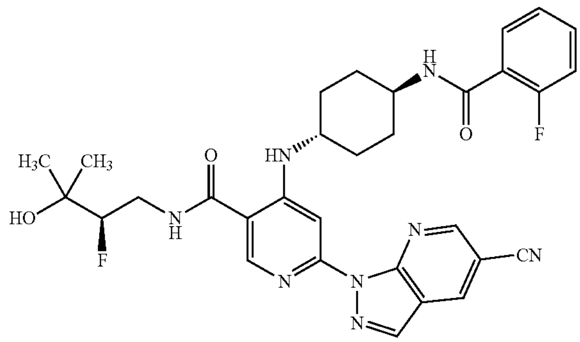 [SMILES: CC(C)(O)[C@H](F)CNC(=O)c1cnc(-n2ncc3cc(C#N)cnc32)cc1N[C@H]1CC[C@H](NC(=O)c2ccccc2F)CC1] | 2.15 | A | 603.2 |
| 635 | 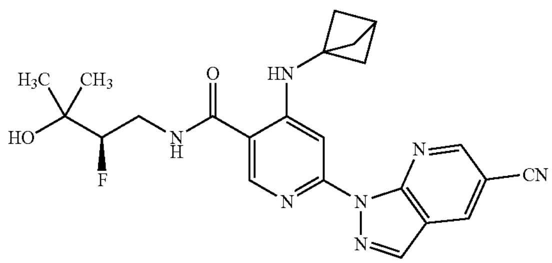 [SMILES: CC(C)(O)[C@H](F)CNC(=O)c1cnc(-n2ncc3cc(C#N)cnc32)cc1NC12CC(C1)C2] | 1.56 | E | 450.2 |
| 636 | 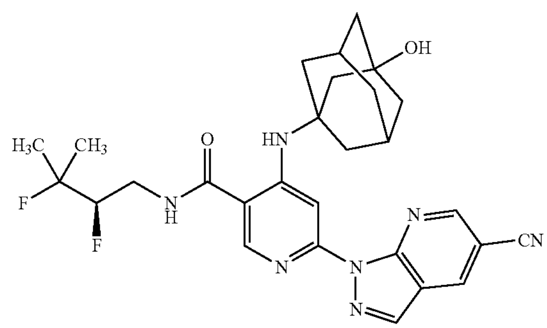 [SMILES: CC(C)(F)[C@H](F)CNC(=O)c1cnc(-n2ncc3cc(C#N)cnc32)cc1NC12CC3CC(CC(O)(C3)C1)C2] | 1.74 | E | 536.2 |
| 637 | 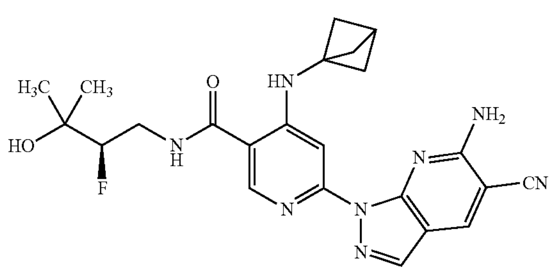 [SMILES: CC(C)(O)[C@H](F)CNC(=O)c1cnc(-n2ncc3cc(C#N)c(N)nc32)cc1NC12CC(C1)C2] | 1.56 | E | 465.3 |
| 638 | Diastereomer 2 | 10.61 | B | 468.2 |

TABLE 19-continued
| Ex. No. | Structure | HPLC Rt (min) | HPLC cond. | LCMS |
|---|---|---|---|---|
| 639 | 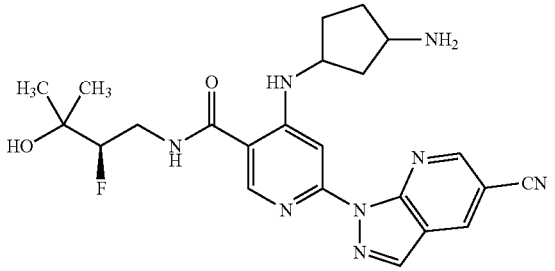  Diastereomer 3 | 10.58 | B | 468.2 |
| 640 | 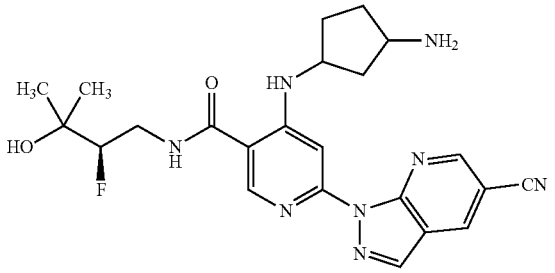  Diastereomer 4 | 5.88 | B | 468.2 |
| 641 | 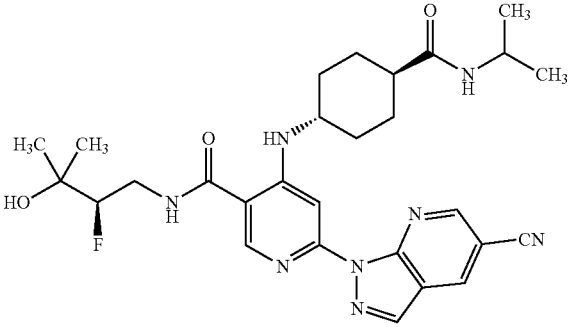 [SMILES: CC(C)NC(=O)[C@H]1CC[C@H](Nc2cc(-n3ncc4cc(C#N)cnc43)ncc2C(=O)NC[C@@H](F)C(C)(C)O)CC1] | 1.28 | A | 551.4 |
| 642 | 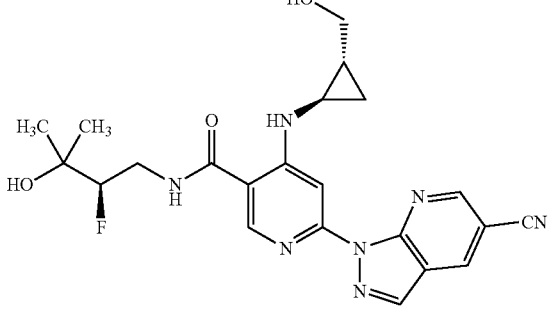  Trans Diastereomer 1 | 10.00 | B | 454.2 |

TABLE 19-continued

| Ex. No. | Structure | HPLC Rt (min) | HPLC cond. | LCMS |
|---|---|---|---|---|
| 643 | 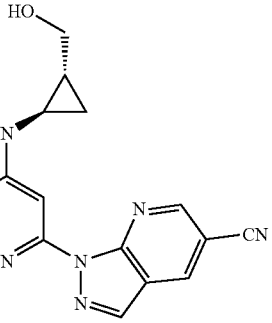 Trans Diastereomer 2 | 10.03 | B | 454.2 |
| 644 | 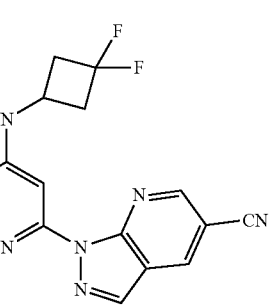 | 1.45 | E | 474.3 |
| 645 | 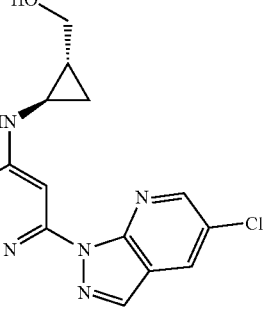 Trans Diastereomer 1 | 11.35 | B | 463.2 |
| 646 | 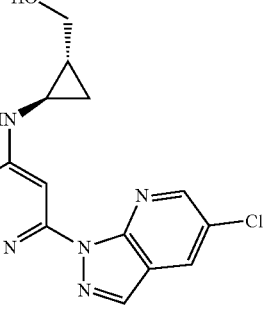 Trans Diastereomer 2 | 11.29 | B | 463.2 |

BIOLOGICAL ASSAYS

The pharmacological properties of the compounds of this invention may be confirmed by a number of biological assays. The exemplified biological assays, which follow, have been carried out with compounds of the invention.

IRAK4 Inhibition Assay

The assays were performed in U-bottom 384-well plates. The final assay volume was 30 L prepared from 15 L additions of enzyme and substrates (fluoresceinated peptide and ATP) and test compounds in assay buffer (20 mM HEPES pH 7.2, 10 mM $MgCl_2$, 0.015% Brij 35 and 4 mM DTT). The reaction was initiated by the combination of IRAK4 with substrates and test compounds. The reaction mixture was incubated at room temperature for 60 min. and terminated by adding 45 μL of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentrations of reagents in the assays are ATP, 500 μM; FL-IPTSPITTTYFFFKKK peptide 1.5 μM; IRAK4, 0.6 nM; and DMSO, 1.6%.

PBMC TLR2 Induced IL-6 Assay

Peripheral blood mononuclear cells (PBMCs) were isolated from human blood containing the anti-coagulant EDTA (2.5 mM) by centrifugation over a FICOLL® gradient. PBMCs (250000 cells/well) were cultured in assay media (RPMI with 10% heat inactivated FCS) with compounds for 30 minutes at 37° C. in a 5% $CO_2$ incubator. Following pre-treatment with compounds, cells were stimulated for 5 hours with 10 g/ml lipoteichoic acid (Invivogen, San Diego, Calif.), a TLR2 agonist. At the end of the culture, plates were centrifuged at 1800 rpm for 10 minutes to pellet the cells. Supernatants were harvested and analyzed for IL-6 levels by ELISA (BD Biosciences, San Jose, Calif.).

The table below lists the IRAK4 $IC_{50}$ values and Cell $IC_{50}$ or $EC_{50}$ values for the following Examples of this invention measured in the IRAK4 Inhibition Assay and the PBMC TLR2 Induced IL-6 Assay. The compounds of the present invention, as exemplified by the following examples, showed IRAK $IC_{50}$ inhibition values of less than 0.025 μM.

TABLE 11

IRAK4 Inhibition Data

| Ex. No. | IRAK4 $IC_{50}$ (μM) | Cell $EC_{50}$ (μM) | Cell $IC_{50}$ (μM) |
|---|---|---|---|
| 1 | 0.0033 | 0.901 | 0.873 |
| 2 | 0.0016 | 0.008 | 0.026 |
| 3 | 0.0010 | 0.011 | 0.048 |
| 4 | 0.0014 | 0.015 | 0.157 |
| 5 | 0.0023 | 0.078 | 0.095 |
| 6 | 0.0010 | 0.243 | 0.243 |
| 7 | 0.0016 | 0.477 | 0.477 |
| 8 | 0.0017 | 0.695 | 0.695 |
| 9 | 0.0015 | 0.057 | 0.043 |
| 10 | 0.0018 | 0.063 | 0.079 |
| 11 | 0.0017 | 0.050 | — |
| 12 | 0.0017 | 0.122 | — |
| 13 | 0.0120 | 0.346 | — |
| 14 | 0.0148 | 0.286 | — |
| 15 | 0.0055 | 0.171 | — |
| 16 | 0.0012 | 0.015 | — |
| 17 | 0.0012 | 0.042 | — |
| 18 | 0.0021 | 0.062 | — |
| 19 | 0.0032 | 0.252 | — |
| 20 | 0.0057 | 0.497 | — |
| 21 | 0.0023 | 0.051 | — |
| 22 | 0.0018 | 0.047 | — |
| 23 | 0.0026 | 0.110 | — |
| 24 | 0.0014 | 0.030 | — |
| 25 | 0.0015 | 0.022 | — |
| 26 | 0.0025 | 0.168 | — |
| 27 | 0.0016 | 0.044 | — |
| 28 | 0.0028 | 0.080 | — |
| 29 | 0.0037 | 0.141 | — |
| 30 | 0.0022 | 0.101 | 0.184 |
| 31 | 0.0034 | 0.367 | 1.085 |
| 32 | 0.0019 | 0.075 | 0.562 |
| 33 | 0.0071 | 0.661 | 0.403 |
| 34 | 0.0053 | 0.180 | 0.407 |
| 35 | 0.0021 | 0.117 | 0.452 |
| 36 | 0.0031 | 0.133 | — |
| 37 | 0.0118 | 1.231 | — |
| 38 | 0.0016 | 0.084 | — |
| 39 | 0.0011 | 0.151 | 0.151 |
| 40 | 0.0020 | 0.175 | 0.175 |
| 41 | 0.0019 | 0.220 | 0.220 |
| 42 | 0.0136 | 0.612 | 0.940 |
| 43 | 0.0060 | 0.316 | — |
| 44 | 0.0042 | 0.098 | — |
| 45 | 0.0232 | 0.148 | — |
| 46 | 0.0022 | 0.023 | — |
| 47 | 0.0056 | 0.173 | — |
| 48 | 0.0014 | 0.024 | — |
| 49 | 0.0032 | 0.071 | — |
| 50 | 0.0019 | 0.058 | — |
| 51 | 0.0044 | 0.065 | — |
| 52 | 0.0024 | 0.066 | — |
| 53 | 0.0019 | 0.271 | — |
| 54 | 0.0018 | 0.254 | — |
| 55 | 0.0036 | 0.513 | — |
| 56 | 0.0025 | 0.102 | — |
| 57 | 0.0015 | 0.173 | — |
| 58 | 0.0027 | 0.049 | — |
| 59 | 0.0016 | 0.153 | — |
| 60 | 0.0018 | 0.024 | — |
| 61 | 0.0013 | 0.034 | — |
| 62 | 0.0036 | 0.143 | — |
| 63 | 0.0041 | 0.012 | — |
| 64 | 0.0017 | 0.093 | — |
| 65 | 0.0015 | 0.100 | — |
| 66 | 0.0017 | 0.201 | — |
| 67 | 0.0017 | 0.102 | — |
| 68 | 0.0021 | 0.030 | — |
| 69 | 0.0013 | 0.050 | — |
| 70 | 0.0028 | 0.210 | — |
| 71 | 0.0015 | 0.028 | — |
| 72 | 0.0020 | 0.072 | — |
| 73 | 0.0131 | 0.189 | — |
| 74 | 0.0043 | — | 0.531 |
| 75 | 0.0076 | — | 0.022 |
| 76 | 0.0015 | — | 0.395 |
| 77 | 0.0026 | — | 0.161 |
| 78 | 0.0029 | — | 0.063 |
| 79 | 0.0116 | 0.436 | 0.436 |
| 80 | 0.0011 | 0.167 | 0.079 |
| 81 | 0.0142 | 0.121 | 0.565 |
| 82 | 0.0044 | 0.166 | 0.578 |
| 83 | 0.0049 | 0.443 | 0.777 |
| 84 | 0.0093 | 1.996 | 2.006 |
| 85 | 0.0133 | 0.523 | — |
| 86 | 0.0071 | 0.110 | — |
| 87 | 0.0019 | 0.063 | — |
| 88 | 0.0071 | 0.345 | — |
| 89 | 0.0033 | 0.090 | — |
| 90 | 0.0019 | 0.041 | — |
| 91 | 0.0020 | 0.032 | — |
| 92 | 0.0017 | 0.079 | — |
| 93 | 0.0084 | 0.562 | — |
| 94 | 0.0017 | 0.062 | — |
| 95 | 0.0051 | 0.408 | — |
| 96 | 0.0014 | 0.038 | — |
| 97 | 0.0049 | 0.108 | — |
| 98 | 0.0033 | 0.176 | — |
| 99 | 0.0046 | 0.223 | — |
| 100 | 0.0025 | 0.095 | — |
| 101 | 0.0078 | 0.112 | — |
| 102 | 0.0036 | 0.047 | — |
| 103 | 0.0035 | 0.125 | — |
| 104 | 0.0017 | 0.067 | — |
| 105 | 0.0039 | 0.437 | — |
| 106 | 0.0019 | 0.896 | 0.896 |
| 107 | 0.0018 | 0.057 | — |
| 108 | 0.0035 | 0.172 | — |
| 109 | 0.0010 | 0.045 | — |
| 110 | 0.0013 | 0.047 | — |

TABLE 11-continued

IRAK4 Inhibition Data

| Ex. No. | IRAK4 IC$_{50}$ (μM) | Cell EC$_{50}$ (μM) | Cell IC$_{50}$ (μM) |
|---|---|---|---|
| 111 | 0.0050 | 0.238 | — |
| 112 | 0.0044 | 0.159 | — |
| 113 | 0.0019 | 0.222 | — |
| 114 | 0.0046 | — | — |
| 115 | 0.0033 | 0.082 | — |
| 116 | 0.0062 | 0.133 | — |
| 117 | 0.0024 | 0.028 | — |
| 118 | 0.0018 | 0.018 | — |
| 119 | 0.0044 | 0.091 | — |
| 120 | 0.0051 | 0.105 | — |
| 121 | 0.0052 | 0.112 | — |
| 122 | 0.0160 | 0.501 | — |
| 123 | 0.0045 | 0.128 | — |
| 124 | 0.0048 | 0.119 | — |
| 125 | 0.0067 | 0.202 | — |
| 126 | 0.0075 | 0.150 | — |
| 127 | 0.0028 | 0.089 | — |
| 128 | 0.0089 | 0.248 | — |
| 129 | 0.0041 | 0.451 | — |
| 130 | 0.0023 | 0.099 | — |
| 131 | 0.0068 | 0.410 | — |
| 132 | 0.0047 | 0.092 | — |
| 133 | 0.0026 | 0.120 | — |
| 134 | 0.0069 | 0.282 | — |
| 135 | 0.0045 | 0.168 | — |
| 136 | 0.0031 | 0.133 | — |
| 137 | 0.0027 | 0.084 | — |
| 138 | 0.0064 | 0.152 | — |
| 139 | 0.0029 | 0.118 | — |
| 140 | 0.0083 | 0.226 | — |
| 141 | 0.0022 | 0.087 | — |
| 142 | 0.0114 | 0.354 | — |
| 143 | 0.0065 | 0.185 | — |
| 144 | 0.0062 | 0.148 | — |
| 145 | 0.0045 | 0.061 | — |
| 146 | 0.0065 | 0.267 | — |
| 147 | 0.0119 | 0.338 | — |
| 148 | 0.0014 | 0.064 | — |
| 149 | 0.0093 | 0.239 | — |
| 150 | 0.0090 | 0.593 | — |
| 151 | 0.0148 | 0.443 | — |
| 152 | 0.0056 | 0.294 | — |
| 153 | 0.0031 | 0.160 | — |
| 154 | 0.0120 | 0.584 | — |
| 155 | 0.0070 | 0.164 | — |
| 156 | 0.0095 | 0.231 | — |
| 157 | 0.0053 | 0.097 | — |
| 158 | 0.0042 | 0.127 | — |
| 159 | 0.0024 | 0.112 | — |
| 160 | 0.0058 | 0.176 | — |
| 161 | 0.0068 | 0.253 | — |
| 162 | 0.0038 | 0.129 | — |
| 163 | 0.0030 | 0.081 | — |
| 164 | 0.0035 | 0.299 | — |
| 165 | 0.0091 | 0.172 | — |
| 166 | 0.0046 | 0.192 | — |
| 167 | 0.0105 | 0.171 | — |
| 168 | 0.0131 | 0.305 | — |
| 169 | 0.0033 | 0.204 | — |
| 170 | 0.0151 | 0.423 | — |
| 171 | 0.0037 | 0.208 | 0.587 |
| 172 | 0.0025 | — | 10.000 |
| 173 | 0.0023 | 0.081 | 0.242 |
| 174 | 0.0033 | 0.182 | — |
| 175 | 0.0050 | 0.113 | — |
| 176 | 0.0064 | 0.476 | — |
| 177 | 0.0036 | 0.352 | — |
| 178 | 0.0037 | 0.100 | — |
| 179 | 0.0028 | 0.135 | — |
| 180 | 0.0053 | 0.208 | — |
| 181 | 0.0043 | 0.152 | — |
| 182 | 0.0018 | 0.074 | — |
| 183 | 0.0041 | 0.179 | — |
| 184 | 0.0055 | 0.436 | — |
| 185 | 0.0034 | 0.350 | — |
| 186 | 0.0013 | 0.044 | — |
| 187 | 0.0019 | 0.086 | — |
| 188 | 0.0017 | 0.057 | — |
| 189 | 0.0048 | 0.075 | — |
| 190 | 0.0047 | 0.120 | — |
| 191 | 0.0147 | 10.000 | — |
| 192 | 0.0026 | 0.120 | — |
| 193 | 0.0034 | — | 0.287 |
| 194 | 0.0031 | 0.160 | — |
| 195 | 0.0194 | 0.340 | 0.647 |
| 196 | 0.0104 | 0.304 | 0.328 |
| 197 | 0.0081 | 0.297 | — |
| 198 | 0.0034 | 0.134 | — |
| 199 | 0.0063 | 0.281 | — |
| 200 | 0.0028 | 0.079 | — |
| 201 | 0.0163 | 0.583 | — |
| 202 | 0.0106 | 0.131 | — |
| 203 | 0.0039 | 0.124 | — |
| 204 | 0.0049 | 0.174 | — |
| 205 | 0.0070 | 0.240 | — |
| 206 | 0.0144 | 0.086 | — |
| 207 | 0.0103 | 0.227 | — |
| 208 | 0.0160 | 0.238 | — |
| 209 | 0.0153 | 0.322 | — |
| 210 | 0.0031 | 0.206 | — |
| 211 | 0.0081 | 0.087 | — |
| 212 | 0.0124 | 0.192 | — |
| 213 | 0.0148 | 0.428 | — |
| 214 | 0.0136 | 0.209 | — |
| 215 | 0.0037 | 0.144 | — |
| 216 | 0.0045 | 0.253 | — |
| 217 | 0.0155 | 0.503 | — |
| 218 | 0.0195 | 0.111 | — |
| 219 | 0.0149 | 0.502 | 0.678 |
| 220 | 0.0065 | 0.168 | — |
| 221 | 0.0084 | 0.230 | — |
| 222 | 0.0051 | 0.305 | — |
| 223 | 0.0040 | — | 0.178 |
| 224 | 0.0067 | 0.303 | 0.159 |
| 225 | 0.0092 | 0.098 | — |
| 226 | 0.0068 | 0.248 | — |
| 227 | 0.0053 | 0.055 | — |
| 228 | 0.0069 | 0.163 | — |
| 229 | 0.0096 | 0.137 | 1.417 |
| 230 | 0.0134 | 0.410 | 0.459 |
| 231 | 0.0142 | 0.237 | 0.544 |
| 232 | 0.0023 | 0.033 | 0.211 |
| 233 | 0.0036 | 0.038 | 0.176 |
| 234 | 0.0047 | 0.128 | 1.363 |
| 235 | 0.0061 | 0.184 | — |
| 236 | 0.0116 | 0.323 | — |
| 237 | 0.0067 | 0.102 | 0.364 |
| 238 | 0.0081 | 0.357 | 1.808 |
| 239 | 0.0053 | 0.211 | 0.775 |
| 240 | 0.0157 | 0.305 | — |
| 241 | 0.0073 | 0.292 | — |
| 242 | 0.0062 | 0.089 | — |
| 243 | 0.0053 | 0.298 | 1.990 |
| 244 | 0.0063 | 0.259 | — |
| 245 | 0.0157 | 0.233 | — |
| 246 | 0.0198 | 0.353 | — |
| 247 | 0.0068 | 0.173 | — |
| 248 | 0.0036 | — | 0.554 |
| 249 | 0.0061 | — | 0.355 |
| 250 | 0.0083 | 0.497 | — |
| 251 | 0.0031 | 0.311 | — |
| 252 | 0.0036 | — | 0.197 |
| 253 | 0.0085 | — | 0.363 |
| 254 | 0.0100 | — | 0.496 |
| 255 | 0.0075 | 0.329 | — |
| 256 | 0.0147 | — | 0.148 |
| 257 | 0.0089 | 0.136 | — |
| 258 | 0.0063 | — | 0.042 |
| 259 | 0.0025 | — | 0.102 |
| 260 | 0.0033 | — | 0.159 |

TABLE 11-continued

IRAK4 Inhibition Data

| Ex. No. | IRAK4 IC$_{50}$ (μM) | Cell EC$_{50}$ (μM) | Cell IC$_{50}$ (μM) |
|---|---|---|---|
| 261 | 0.0034 | — | 0.154 |
| 262 | 0.0013 | — | 0.048 |
| 263 | 0.0135 | — | 0.401 |
| 264 | 0.0065 | — | 0.338 |
| 265 | 0.0024 | — | 0.241 |
| 266 | 0.0026 | — | 0.073 |
| 267 | 0.0045 | — | 0.516 |
| 268 | 0.0106 | — | 0.171 |
| 269 | 0.0036 | — | 0.171 |
| 270 | 0.0016 | — | 0.348 |
| 271 | 0.0159 | — | 0.176 |
| 272 | 0.0051 | — | 0.737 |
| 273 | 0.0186 | — | 0.094 |
| 274 | 0.0062 | — | 0.204 |
| 275 | 0.0080 | — | 0.115 |
| 276 | 0.0047 | — | 0.380 |
| 277 | 0.0059 | — | 0.251 |
| 278 | 0.0100 | — | 0.203 |
| 279 | 0.0065 | — | 0.247 |
| 280 | 0.0169 | — | 0.692 |
| 281 | 0.0078 | — | 0.255 |
| 282 | 0.0041 | — | 0.541 |
| 283 | 0.0028 | — | 0.135 |
| 284 | 0.0019 | — | 0.258 |
| 285 | 0.0100 | — | 0.200 |
| 286 | 0.0017 | — | 0.158 |
| 287 | 0.0082 | — | 0.489 |
| 288 | 0.0034 | — | 0.234 |
| 289 | 0.0047 | — | 0.275 |
| 290 | 0.0059 | — | 0.364 |
| 291 | 0.0035 | — | 0.349 |
| 292 | 0.0027 | — | 0.456 |
| 293 | 0.0010 | — | 0.032 |
| 294 | 0.0134 | — | 0.292 |
| 295 | 0.0019 | — | 0.240 |
| 296 | 0.0071 | — | 0.412 |
| 297 | 0.0041 | — | 0.219 |
| 298 | 0.0045 | — | 0.142 |
| 299 | 0.0063 | — | 0.252 |
| 300 | 0.0016 | — | 0.083 |
| 301 | 0.0024 | — | 0.063 |
| 302 | 0.0041 | — | 0.148 |
| 303 | 0.0035 | — | 0.176 |
| 304 | 0.0107 | — | 0.408 |
| 305 | 0.0092 | — | 0.207 |
| 306 | 0.0048 | — | 0.800 |
| 307 | 0.0020 | — | 0.127 |
| 308 | 0.0030 | — | 0.073 |
| 309 | 0.0184 | — | 0.207 |
| 310 | 0.0045 | — | 0.023 |
| 311 | 0.0047 | — | 0.347 |
| 312 | 0.0092 | — | 0.375 |
| 313 | 0.0147 | — | 0.289 |
| 314 | 0.0137 | — | 0.420 |
| 315 | 0.0107 | — | 0.267 |
| 316 | 0.0017 | — | 0.046 |
| 317 | 0.0038 | — | 0.172 |
| 318 | 0.0079 | — | 0.188 |
| 319 | 0.0065 | — | 0.191 |
| 320 | 0.0056 | — | 0.261 |
| 321 | 0.0031 | — | 0.053 |
| 322 | 0.0067 | — | 0.159 |
| 323 | 0.0173 | — | 0.612 |
| 324 | 0.0066 | — | 0.278 |
| 325 | 0.0060 | — | 0.227 |
| 326 | 0.0114 | — | 0.030 |
| 327 | 0.0111 | — | 0.181 |
| 328 | 0.0100 | — | 0.011 |
| 329 | 0.0049 | — | 0.076 |
| 330 | 0.0043 | — | 0.512 |
| 331 | 0.0062 | — | 0.057 |
| 332 | 0.0130 | — | 0.159 |
| 333 | 0.0126 | 0.524 | — |
| 334 | 0.0185 | 0.460 | — |
| 335 | 0.0033 | 0.077 | — |
| 336 | 0.0038 | 0.168 | 0.556 |
| 337 | 0.0071 | 0.572 | 0.765 |
| 338 | 0.0045 | — | 0.147 |
| 339 | 0.0040 | — | 0.332 |
| 340 | 0.0100 | 0.536 | — |
| 341 | 0.0019 | 0.161 | — |
| 342 | 0.0087 | — | 0.423 |
| 343 | 0.0035 | — | 0.428 |
| 344 | 0.0135 | — | 0.144 |
| 345 | 0.0074 | — | 0.180 |
| 346 | 0.0036 | — | 0.306 |
| 347 | 0.0013 | — | 0.146 |
| 348 | 0.0018 | — | 0.489 |
| 349 | 0.0033 | — | 0.180 |
| 350 | 0.0022 | — | 0.424 |
| 351 | 0.0023 | — | 0.027 |
| 352 | 0.0065 | — | 0.170 |
| 353 | 0.0017 | — | 0.018 |
| 354 | 0.0019 | — | 0.115 |
| 355 | 0.0024 | — | 0.122 |
| 356 | 0.0024 | — | 0.154 |
| 357 | 0.0017 | — | 0.067 |
| 358 | 0.0035 | — | 0.257 |
| 359 | 0.0013 | — | 0.084 |
| 360 | 0.0015 | — | 0.376 |
| 361 | 0.0029 | — | 0.206 |
| 362 | 0.0043 | — | 0.486 |
| 363 | 0.0032 | — | 0.459 |
| 364 | 0.0026 | — | 0.083 |
| 365 | 0.0017 | — | 0.066 |
| 366 | 0.0079 | — | 0.205 |
| 367 | 0.0013 | — | 0.041 |
| 368 | 0.0024 | — | 0.061 |
| 369 | 0.0019 | — | 0.032 |
| 370 | 0.0026 | — | 0.084 |
| 371 | 0.0021 | — | 0.045 |
| 372 | 0.0012 | — | 0.002 |
| 373 | 0.0024 | — | 0.071 |
| 374 | 0.0033 | — | 0.085 |
| 375 | 0.0018 | — | 0.156 |
| 376 | 0.0021 | — | 0.349 |
| 377 | 0.0027 | — | 0.440 |
| 378 | 0.0026 | — | 0.655 |
| 379 | 0.0025 | — | 0.188 |
| 380 | 0.0029 | — | 0.228 |
| 381 | 0.0025 | — | 0.041 |
| 382 | 0.0025 | — | 0.482 |
| 383 | 0.0014 | — | 0.113 |
| 384 | 0.0023 | — | 0.024 |
| 385 | 0.0009 | — | 0.040 |
| 386 | 0.0015 | 0.079 | 1.078 |
| 387 | 0.0033 | — | 0.198 |
| 388 | 0.0112 | — | 0.245 |
| 389 | 0.0040 | — | 0.241 |
| 390 | 0.0170 | — | 0.199 |
| 391 | 0.0062 | — | 0.241 |
| 392 | 0.0071 | — | 0.016 |
| 393 | 0.0035 | — | 0.250 |
| 394 | 0.0028 | — | 0.188 |
| 395 | 0.0022 | — | 0.085 |
| 396 | 0.0086 | — | 0.157 |
| 397 | 0.0066 | — | 0.210 |
| 398 | 0.0049 | — | 0.277 |
| 399 | 0.0013 | — | 0.024 |
| 400 | 0.0078 | — | 0.156 |
| 401 | 0.0057 | — | 0.485 |
| 402 | 0.0025 | — | 0.412 |
| 403 | 0.0025 | — | 0.147 |
| 404 | 0.0011 | — | 0.164 |
| 405 | 0.0062 | — | 0.561 |
| 406 | 0.0048 | — | 0.066 |
| 407 | 0.0031 | — | 0.287 |
| 408 | 0.0018 | — | 0.073 |
| 409 | 0.0175 | 0.463 | — |
| 410 | 0.0015 | 0.092 | — |

TABLE 11-continued

IRAK4 Inhibition Data

| Ex. No. | IRAK4 IC$_{50}$ (μM) | Cell EC$_{50}$ (μM) | Cell IC$_{50}$ (μM) |
|---|---|---|---|
| 411 | 0.0016 | 0.051 | — |
| 412 | 0.0036 | — | 0.053 |
| 413 | 0.0070 | — | 0.382 |
| 414 | 0.0100 | 0.188 | — |
| 415 | 0.0148 | 0.286 | — |
| 416 | 0.0019 | 0.058 | — |
| 417 | 0.0055 | 0.171 | — |
| 418 | 0.0044 | 0.065 | — |
| 419 | 0.0048 | 0.107 | — |
| 420 | 0.0044 | 0.186 | — |
| 421 | 0.0019 | — | 0.167 |
| 422 | 0.0023 | 0.004 | — |
| 423 | 0.0184 | 0.346 | 1.303 |
| 424 | 0.0060 | 0.338 | — |
| 425 | 0.0018 | 0.154 | — |
| 426 | 0.0016 | 0.051 | — |
| 427 | 0.0028 | 0.089 | — |
| 428 | 0.0046 | 0.361 | — |
| 429 | 0.0015 | 0.092 | — |
| 430 | 0.0021 | 0.208 | — |
| 431 | 0.0021 | 0.106 | — |
| 432 | 0.0021 | 0.080 | — |
| 433 | 0.0041 | 0.164 | 0.499 |
| 434 | 0.0016 | 0.057 | — |
| 435 | 0.0099 | 0.291 | — |
| 436 | 0.0018 | 0.165 | — |
| 437 | 0.0010 | 0.042 | — |
| 438 | 0.0025 | 0.033 | — |
| 439 | 0.0026 | 0.073 | — |
| 440 | 0.0019 | 0.072 | — |
| 441 | 0.0030 | 0.109 | — |
| 442 | 0.0015 | 0.042 | — |
| 443 | 0.0016 | 0.031 | — |
| 444 | 0.0046 | 0.186 | — |
| 445 | 0.0053 | 0.108 | — |
| 446 | 0.0039 | 0.051 | — |
| 447 | 0.0053 | 0.092 | — |
| 448 | 0.0024 | 0.175 | — |
| 449 | 0.0015 | 0.082 | 0.059 |
| 450 | 0.0028 | 0.268 | 0.438 |
| 451 | 0.0044 | 0.429 | — |
| 452 | 0.0052 | 0.700 | 0.252 |
| 453 | 0.0044 | 0.213 | 0.326 |
| 454 | 0.0059 | 0.757 | 0.289 |
| 455 | 0.0022 | 0.072 | — |
| 456 | 0.0048 | 0.241 | — |
| 457 | 0.0103 | 0.458 | 1.239 |
| 458 | 0.0071 | 0.261 | 0.260 |
| 459 | 0.0049 | 0.095 | 0.343 |
| 460 | 0.0033 | 0.088 | 0.113 |
| 461 | 0.0025 | 0.074 | 0.122 |
| 462 | 0.0029 | 0.066 | 0.398 |
| 463 | 0.0017 | 0.023 | — |
| 464 | 0.0031 | 0.257 | — |
| 465 | 0.0013 | 0.007 | 0.023 |
| 466 | 0.0139 | 0.792 | 0.130 |
| 467 | 0.0023 | 0.026 | 0.100 |
| 468 | 0.0058 | 0.128 | 1.010 |
| 469 | 0.0029 | 0.084 | 0.207 |
| 470 | 0.0080 | 0.240 | — |
| 471 | 0.0101 | 0.194 | — |
| 472 | 0.0020 | 0.070 | 0.123 |
| 473 | 0.0041 | 0.238 | 0.483 |
| 474 | 0.0012 | 0.077 | 0.315 |
| 475 | 0.0067 | 0.305 | 1.183 |
| 476 | 0.0030 | 0.198 | — |
| 477 | 0.0029 | 0.301 | 1.302 |
| 478 | 0.0047 | 0.462 | 0.805 |
| 479 | 0.0057 | 0.144 | 0.835 |
| 480 | 0.0040 | 0.170 | 0.270 |
| 481 | 0.0019 | 0.053 | 0.595 |
| 482 | 0.0174 | 0.433 | — |
| 483 | 0.0108 | 0.199 | — |
| 484 | 0.0035 | — | 0.282 |
| 485 | 0.0087 | 0.198 | 1.077 |
| 486 | 0.0012 | — | 0.177 |
| 487 | 0.0020 | 0.034 | 0.111 |
| 488 | 0.0068 | 0.208 | 0.379 |
| 489 | 0.0043 | 0.318 | 1.700 |
| 490 | 0.0043 | 0.121 | 0.225 |
| 491 | 0.0034 | 0.116 | 0.102 |
| 492 | 0.0070 | 0.250 | 0.547 |
| 493 | 0.0030 | 0.185 | 0.209 |
| 494 | 0.0030 | — | 0.289 |
| 495 | 0.0018 | — | 0.215 |
| 496 | 0.0109 | — | 0.197 |
| 497 | 0.0037 | — | 0.098 |
| 498 | 0.0057 | — | 0.248 |
| 499 | 0.0061 | — | 0.213 |
| 500 | 0.0132 | — | 0.546 |
| 501 | 0.0054 | — | 0.332 |
| 502 | 0.0048 | — | 0.366 |
| 503 | 0.0023 | — | 0.099 |
| 504 | 0.0043 | — | 0.262 |
| 505 | 0.0135 | — | 0.559 |
| 506 | 0.0015 | — | 0.065 |
| 507 | 0.0014 | — | 0.374 |
| 508 | 0.0028 | — | 0.224 |
| 509 | 0.0016 | — | 0.128 |
| 510 | 0.0032 | — | 0.250 |
| 511 | 0.0054 | — | 0.047 |
| 512 | 0.0035 | — | 0.541 |
| 513 | 0.0059 | — | 0.389 |
| 514 | 0.0082 | — | 0.047 |
| 515 | 0.0022 | — | 0.542 |
| 516 | 0.0086 | — | 0.414 |
| 517 | 0.0012 | — | 0.113 |
| 518 | 0.0140 | — | 0.094 |
| 519 | 0.0027 | — | 0.126 |
| 520 | 0.0105 | — | 0.347 |
| 521 | 0.0035 | 0.460 | — |
| 522 | 0.0026 | 0.177 | — |
| 523 | 0.0026 | 0.024 | — |
| 524 | 0.0026 | 0.132 | — |
| 525 | 0.0016 | 0.253 | — |
| 526 | 0.0037 | 0.113 | — |
| 527 | 0.0030 | 0.228 | — |
| 528 | 0.0033 | 0.091 | 0.326 |
| 529 | 0.0048 | — | 0.163 |
| 530 | 0.0114 | 0.329 | 0.163 |
| 531 | 0.0022 | — | 0.067 |
| 532 | 0.0055 | 0.127 | — |
| 533 | 0.0103 | 0.194 | — |
| 534 | 0.0015 | 0.059 | 0.824 |
| 535 | 0.0040 | 0.185 | — |
| 536 | 0.0081 | 0.189 | — |
| 537 | 0.0068 | 0.159 | — |
| 538 | 0.0096 | — | 0.698 |
| 539 | 0.0063 | 0.256 | — |
| 540 | 0.0030 | — | 0.158 |
| 541 | 0.0144 | — | 0.149 |
| 542 | 0.0073 | — | 0.973 |
| 543 | 0.0068 | — | 0.404 |
| 544 | 0.0041 | 0.239 | — |
| 545 | 0.0087 | 0.476 | — |
| 546 | 0.0037 | 0.257 | — |
| 547 | 0.0166 | 0.065 | 0.591 |
| 548 | 0.0106 | 0.708 | 0.763 |
| 549 | 0.0168 | 0.413 | 0.757 |
| 550 | 0.0103 | 0.416 | — |
| 551 | 0.0126 | — | 0.212 |
| 552 | 0.0134 | — | 0.213 |
| 553 | 0.0112 | — | 0.298 |
| 554 | 0.0055 | — | 0.370 |
| 555 | 0.0070 | — | 0.047 |
| 556 | 0.0062 | — | 0.305 |
| 557 | 0.0051 | — | 0.475 |
| 558 | 0.0061 | — | 0.615 |
| 559 | 0.0053 | — | 0.018 |
| 560 | 0.0034 | — | 0.254 |

TABLE 11-continued

IRAK4 Inhibition Data

| Ex. No. | IRAK4 IC$_{50}$ (μM) | Cell EC$_{50}$ (μM) | Cell IC$_{50}$ (μM) |
|---|---|---|---|
| 561 | 0.0078 | — | 0.321 |
| 562 | 0.0125 | 0.255 | — |
| 563 | 0.0050 | 0.159 | — |
| 564 | 0.0201 | 0.659 | — |
| 565 | 0.0157 | 0.757 | — |
| 566 | 0.0172 | 0.637 | — |
| 567 | 0.0099 | 0.164 | 0.264 |
| 568 | 0.0089 | 0.661 | 1.367 |
| 569 | 0.0130 | 0.242 | — |
| 570 | 0.0107 | 0.425 | — |
| 571 | 0.0152 | — | 0.101 |
| 572 | 0.0091 | — | 0.303 |
| 573 | 0.0088 | 0.729 | 0.270 |
| 574 | 0.0153 | — | 0.258 |
| 575 | 0.0118 | — | 0.587 |
| 576 | 0.0058 | — | 0.153 |
| 577 | 0.0032 | — | 0.175 |
| 578 | 0.0026 | — | 0.218 |
| 579 | 0.0039 | — | 0.269 |
| 580 | 0.0107 | — | 0.487 |
| 581 | 0.0084 | — | 0.227 |
| 582 | 0.0038 | — | 0.109 |
| 583 | 0.0041 | — | 0.188 |
| 584 | 0.0100 | 0.209 | 0.508 |
| 585 | 0.0085 | — | 0.147 |
| 586 | 0.0097 | — | 0.259 |
| 587 | 0.0138 | — | 0.298 |
| 588 | 0.0044 | — | 0.506 |
| 589 | 0.0041 | — | 0.361 |
| 590 | 0.0019 | — | 0.129 |
| 591 | 0.0027 | — | 0.160 |
| 592 | 0.0028 | — | 0.271 |
| 593 | 0.0196 | — | 0.408 |
| 594 | 0.0175 | — | 0.319 |
| 595 | 0.0053 | — | 0.129 |
| 596 | 0.0182 | — | 0.578 |
| 597 | 0.0156 | — | 0.307 |
| 598 | 0.0166 | — | 0.054 |
| 599 | 0.0048 | — | 0.275 |
| 600 | 0.0053 | — | 0.477 |
| 601 | 0.0142 | — | 0.490 |
| 602 | 0.0093 | — | 0.233 |
| 603 | 0.0067 | — | 0.321 |
| 604 | 0.0061 | — | 0.104 |
| 605 | 0.0075 | — | 0.165 |
| 606 | 0.0040 | 0.127 | — |
| 607 | 0.0040 | 0.332 | — |
| 608 | 0.0126 | 0.318 | — |
| 609 | 0.0227 | 0.485 | 1.441 |
| 610 | 0.0089 | 0.166 | 0.217 |
| 611 | 0.0174 | 0.536 | 1.854 |
| 612 | 0.0056 | 0.163 | 0.262 |
| 613 | 0.0028 | 0.157 | 0.130 |
| 614 | 0.0077 | 0.481 | 0.491 |
| 615 | 0.0023 | — | 0.190 |
| 616 | 0.0109 | 0.305 | 0.425 |
| 617 | 0.0028 | — | 0.485 |
| 618 | 0.0058 | 0.127 | — |
| 619 | 0.0040 | 0.119 | — |
| 620 | 0.0034 | 0.114 | — |
| 621 | 0.0040 | 0.139 | — |
| 622 | 0.0052 | — | 0.132 |
| 623 | 0.0052 | — | 0.484 |
| 624 | 0.0021 | — | 0.068 |
| 625 | 0.0022 | — | 0.210 |
| 626 | 0.0011 | — | 0.076 |
| 627 | 0.0023 | — | 0.007 |
| 628 | 0.0033 | — | 0.148 |
| 629 | 0.0033 | — | 0.135 |
| 630 | 0.0022 | — | 0.030 |
| 631 | 0.0034 | — | 0.066 |
| 632 | 0.0026 | — | 0.149 |
| 633 | 0.0033 | — | 0.257 |
| 634 | 0.0039 | — | 0.277 |
| 635 | 0.0018 | — | 0.375 |
| 636 | 0.0030 | — | 0.293 |
| 637 | 0.0015 | — | 0.165 |
| 638 | 0.0117 | — | 0.554 |
| 639 | 0.0085 | — | 0.055 |
| 640 | 0.0032 | — | 0.033 |
| 641 | 0.0064 | — | 0.718 |
| 642 | 0.0048 | — | 0.197 |
| 643 | 0.0054 | — | 0.320 |
| 644 | 0.0043 | — | 0.089 |
| 645 | 0.0069 | — | 0.154 |
| 646 | 0.0105 | — | 0.393 |

Single Crystal X-Ray Diffractometry

The single crystal x-ray diffraction data was obtained using Bruker APEX II system (Bruker-AXS, Germany) with sealed tube X-ray source (Mo target). The source is mounted on the 3-axis D8 goniometer in the standard, compact D8 safety enclosure. The data was collected on instrument with X-ray source operating at voltage (50 kV) and current (35 mA). The single crystal obtained using crystallization studies is mounted on nylon wire loop and analyzed at temperature of 296 K. The crystal was exposed to monochromatic x-ray beam. The scattered beams were analyzed using 4 K CCD detector. Indexing and processing of the measured intensity data were carried out with the APEX2 software package/program suite (APEX2 Data collection and processing user interface: APEX2 User Manual, v1.27; Bruker AXS, Inc., 5465 East Cheryl Parkway Madison, Wis. 53711 USA). The structures were solved by direct methods and refined on the basis of observed reflections using the crystallographic package SHELXTL (Bruker AXS, 5465 East Cheryl Parkway, Madison, Wis., 53711, USA).

The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w = [\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogen atoms were introduced in idealized positions with isotropic temperature factors, but no hydrogen parameters were varied.

X-Ray Powder Diffractometry

The powder diffraction data were obtained with a Bruker D8 Advance system (Bruker AXS, Germany) which was equipped with a sealed tube Cu source, operating at a tube load of 40 kV and 40 mA. The source was mounted on the 3-axis D8 goniometer in the standard, compact D8 safety enclosure. Powder samples were placed in a thin uniform layer on Silicon low background sample holders (51.5 mm, with 20 mm×0.5 mm sample cavity); the sample holder was rotated during data collection. The sample-detector distance was 280 mm. Data were collected with a step size of 0.03 degrees 2theta in the range of 2 to 32 degrees 2theta, with a sample exposure time of at least 1000 seconds. The scattered beams were analyzed using Lynx eye 1 dimensional position sensitive (PSD) detector.

What is claimed is:

1. A compound of Formula (I)

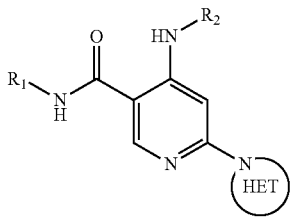

or a salt thereof, wherein:

HET is a heteroaryl selected from pyrazolyl, indolyl, pyrrolo[2,3-b]pyridinyl, pyrrolo[2,3-d]pyrimidinyl, pyrazolo[3,4-b]pyridinyl, pyrazolo[3,4-d]pyrimidinyl, 2,3-dihydro-1H-pyrrolo[2,3-b]pyridinyl, imidazo[4,5-b]pyridinyl, and purinyl, wherein said heteroaryl is substituted with $R_a$ and $R_b$;

$R_a$ is H, F, Cl, Br, —CN, —OH, $C_{1-4}$ alkyl, $C_{1-4}$ fluoroalkyl, $C_{1-4}$ hydroxyalkyl, $C_{1-4}$ alkoxy, —NH$_2$, —NH($C_{1-4}$ alkyl), —N($C_{1-4}$ alkyl)$_2$, —NH($C_{1-4}$ hydroxyalkyl), —NH($C_{1-4}$ fluoroalkyl), —NH($C_{1-6}$ hydroxy-fluoroalkyl), —C(O)NH$_2$, —CH$_2$NHC(O)($C_{1-6}$ alkyl), —CH$_2$NHC(O)($C_{1-6}$ hydroxyalkyl), —CH$_2$NHC(O)NH($C_{1-6}$ alkyl), —CH$_2$NHC(O)NHCH$_2$(phenyl), —CH$_2$NHC(O)N($C_{1-4}$ alkyl)$_2$, —CH$_2$NHC(O)O($C_{1-4}$ alkyl), —CH$_2$NHC(O)($C_{3-6}$ cycloalkyl), —CH$_2$NHC(O)(tetrahydrofuranyl), —CH$_2$NHC(O)CH$_2$($C_{3-6}$ cycloalkyl), —CH$_2$NHC(O)CH$_2$(tetrahydropyranyl), —CH$_2$NHC(O)CH$_2$(phenyl), —NHC(O)($C_{1-4}$ alkyl), pyrrolidinyl, hydroxypyrrolidinyl, or pyridazinyl;

$R_b$ is H or —NH$_2$;

$R_1$ is:

(i) $C_{1-6}$ alkyl, $C_{1-6}$ fluoroalkyl, $C_{1-6}$ hydroxyalkyl, $C_{1-8}$ hydroxy-fluoroalkyl, —($C_{1-6}$ alkylenyl)O($C_{1-4}$ alkyl), —($C_{1-6}$ alkylenyl)O($C_{1-4}$ fluoroalkyl), —($C_{1-6}$ fluoroalkylenyl)O($C_{1-4}$ alkyl), —($C_{1-6}$ fluoroalkylenyl)O($C_{1-4}$ deuteroalkyl), —($C_{1-6}$ fluoroalkylenyl)O($C_{1-4}$ fluoroalkyl), —($C_{1-4}$ fluoroalkylenyl)C($C_{3-6}$ cycloalkyl)$_2$(OH), —($C_{1-4}$ alkylenyl)NHC(O)($C_{1-4}$ alkylenyl)OC(O)($C_{1-3}$ alkyl), —($C_{1-6}$ alkylenyl)NHS(O)$_2$($C_{1-4}$ alkyl), —($C_{1-6}$ alkylenyl)P(O)($C_{1-4}$ alkoxy)$_2$, —($C_{1-6}$ fluoroalkylenyl)NH($C_{1-4}$ alkyl), —($C_{1-6}$ alkylenyl)C(O)NH($C_{1-4}$ alkyl), —($C_{1-6}$ fluoroalkylenyl)C(O)NH($C_{1-4}$ alkyl), —($C_{1-6}$ fluoroalkylenyl)C(O)NH($C_{1-4}$ hydroxyalkyl), or —($C_{1-6}$ fluoroalkylenyl)OP(O)(OH)$_2$;

(ii) —($C_{1-3}$ alkylenyl)$R_x$, —($C_{1-3}$ fluoroalkylenyl)$R_x$, —($C_{1-3}$ alkylenyl)C(O)$R_x$, —($C_{1-3}$ alkylenyl)C(O)NHR$_x$, —($C_{1-3}$ fluoroalkylenyl)C(O)$R_x$, or —CH$_2$CF=(tetrahydropyranyl), wherein $R_x$ is a cyclic group selected from $C_{3-6}$ cycloalkyl, tetrazolyl, 1,1-dioxidotetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —CH$_3$, —C(CH$_2$)$_2$OH, —OCH$_3$, —C(O)CH$_2$CN, —S(O)$_2$CH$_3$, —S(O)$_2$NH$_2$, —NHC(O)CH$_3$, —N(S(O)$_2$CH$_3$)$_2$, —CH$_2$CH$_2$(acetamidophenyl), —CH$_2$CH$_2$(methoxyphenyl), —CH$_2$CH$_2$(sulfamoylphenyl), oxetanyl, benzyl, and morpholinyl;

(iii) $C_{3-6}$ cycloalkyl or $C_{4-6}$ cycloalkenyl, each substituted with zero to 3 substituents independently selected from F, —OH, —CN, $C_{1-3}$ alkyl, $C_{1-3}$ alkoxy, —S($C_{1-3}$ alkyl), —NO$_2$, —S(O)$_2$($C_{1-3}$ alkyl), $C_{1-4}$ hydroxyalkyl, —C($C_{1-3}$ alkyl)(OH)($C_{3-6}$ cycloalkyl), —CH$_2$C(O)NH($C_{1-3}$ alkyl), —NHC(O)($C_{1-3}$ alkyl), —NHC(O)($C_{1-4}$ hydroxyalkyl), —C(O)NH($C_{1-3}$ alkyl), —C(O)NH($C_{1-3}$ deuteroalkyl), —C(O)NH($C_{3-6}$ cycloalkyl), —NHC(O)O($C_{1-3}$ alkyl), —NHS(O)$_2$($C_{1-3}$ alkyl), pyridinyl, imidazolyl, pyrazolyl, methylimidazolyl, methylpyrazolyl, and thiazolyl;

(iv) tetrahydropyranyl, piperidinyl, pyrazolyl, phenyl, pyridinyl, or pyrimidinyl, each substituted with zero to 1 substituent selected from —OH, $C_{1-3}$ alkyl, $C_{1-3}$ fluoroalkyl, $C_{1-4}$ hydroxyalkyl, $C_{1-3}$ alkoxy, —C(O)($C_{1-4}$ alkyl), —S(O)$_2$($C_{1-4}$ alkyl), —S(O)$_2$NH($C_{1-4}$ alkyl), —NH($C_{1-3}$ alkyl), —N($C_{1-3}$ alkyl)$_2$, —O($C_{1-3}$ alkylenyl)N($C_{1-3}$ alkyl)$_2$, —CH$_2$(morpholinyl), azetidinyl, oxetanyl, tetrahydropyranyl, morpholinyl, piperazinyl, piperidinyl, methylpiperazinyl, methoxypiperidinyl, pyridinyl, pyrimidinyl, methylsulfonyl azetidinyl, and —C(O)(methylsulfonyl azetidinyl); or (v) pyrrolo[2,3-c]pyridinyl, bicyclo[2.2.1]heptan-1-ol, tetrahydrobenzo[d]thiazol-2-amine, or 1,3-diazaspiro[4.5]decane-2,4-dione; and $R_2$ is:

(i) $C_{1-7}$ alkyl or $C_{2-6}$ alkenyl, each substituted with zero to three substituents independently selected from F, —OH, and —CN; —($C_{1-4}$ alkylenyl)O($C_{1-4}$ alkyl), —($C_{1-4}$ alkylenyl)O($C_{1-4}$ fluoroalkyl), —($C_{1-6}$ alkylenyl)NH$_2$, —($C_{1-6}$ alkylenyl)S(O)$_2$($C_{1-3}$ alkyl), —($C_{1-6}$ fluoroalkylenyl)NH($C_{1-3}$ alkyl), or —($C_{1-6}$ alkylenyl)NHC(O)($C_{1-4}$ fluoroalkyl);

(ii) —($C_{1-4}$ alkylenyl)$R_y$, wherein $R_y$ is $C_{3-6}$ cycloalkyl, azetidinyl, oxetanyl, oxazolyl, pyridinyl, tetrahydropyranyl, or morpholinyl, each substituted with zero to 2 substituents independently selected from F, —OH, and $C_{1-3}$ alkyl;

(iii) $C_{3-6}$ cycloalkyl, azetidinyl, oxetanyl, furanyl, tetrahydrofuranyl, pyrrolidinyl, piperidinyl, or tetrahydropyranyl, each substituted with zero to 3 substituents independently selected from F, —OH, $C_{1-3}$ alkyl, $C_{1-3}$ hydroxyalkyl, —C(O)($C_{1-3}$ alkyl), —C(O)($C_{1-3}$ fluoroalkyl), —C(O)($C_{1-3}$ cyanoalkyl), —C(O)O($C_{1-3}$ alkyl), —C(O)NH$_2$, —C(O)NH($C_{1-3}$ alkyl), —C(O)(difluorophenyl), —NH$_2$, —NH($C_{1-3}$ alkyl), —NH($C_{1-3}$ fluoroalkyl), —NH(oxetanyl), —NHC(O)($C_{1-3}$ alkyl), —NHC(O)($C_{1-3}$ fluoroalkyl), —NHC(O)($C_{3-6}$ cycloalkyl), —NHC(O)(fluorophenyl), —S(O)$_2$($C_{1-3}$ alkyl), imidazolyl, phenyl, pyrimidinyl, fluoropyrimidinyl, chloropyrimidinyl, and methoxypyrimidinyl;

(iv) adamantanyl, hydroxyadamantanyl, benzo[d]imidazolyl, benzo[d]oxazolyl, benzo[d]triazolyl, benzothiazolyl, bicyclo[1.1.1]pentanyl, or hydroxy-bicyclo[2.2.1]heptanyl; or (v) phenyl, pyrazolyl, thiazolyl, thiadiazolyl, or indazolyl, each substituted with 0 to 2 substituents independently selected from F, Cl, —OH, —CN, $C_{1-4}$ alkyl, $C_{1-4}$ hydroxyalkyl, $C_{1-4}$ fluoroalkyl, $C_{1-4}$ cyanoalkyl, $C_{1-3}$ alkoxy, $C_{3-6}$ cycloalkyl, —($C_{1-3}$ alkylenyl)O($C_{1-3}$ alkyl), —($C_{1-3}$ alkylenyl)O($C_{1-3}$ fluoroalkyl), —C(O)NH$_2$, —C(O)NH($C_{1-3}$ alkyl), —NHC(O)($C_{1-3}$ alkyl), —NHC(O)S(O)$_2$($C_{1-3}$ alkyl), —S(O)$_2$NH$_2$, —S(O)$_2$($C_{1-3}$ alkyl), pyrazolyl, methyl pyrazolyl, imidazolyl, triazolyl, methyl tetrazolyl, ethyl tetrazolyl, phenyl, pyrimidinyl, fluoropyrimidinyl, and tetrahydropyranyl.

2. The compound according to claim 1 or a salt thereof, wherein:
HET is a heteroaryl selected from:

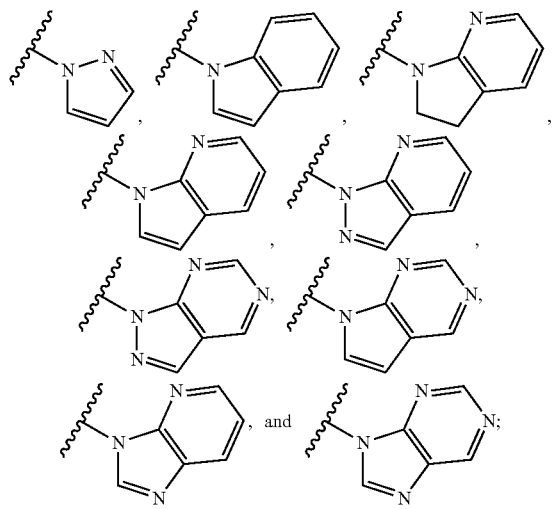

wherein each of said heteroaryl is substituted with $R_a$ and $R_b$.

3. The compound according to claim 1 or a salt thereof, wherein:
HET is a heteroaryl selected from:

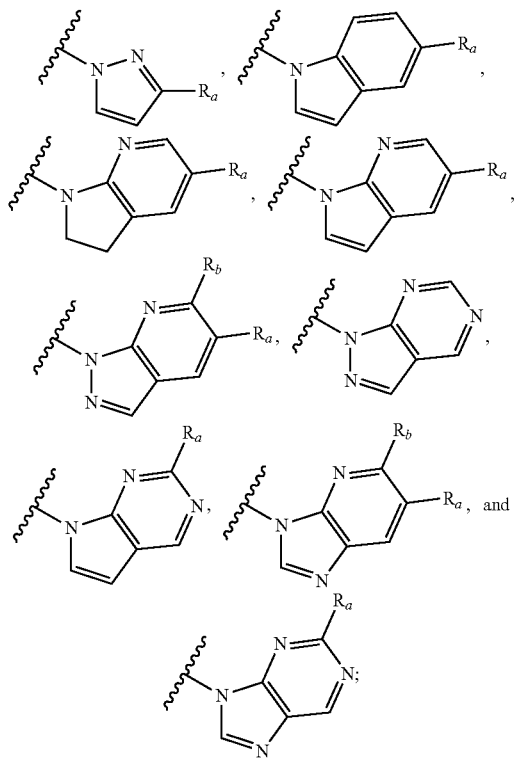

$R_a$ is H, F, Cl, Br, —CN, —OH, —CH$_3$, —CHF$_2$, —OCH$_3$, —NH$_2$, —N(CH$_3$)$_2$, —NHCH$_2$CH$_2$OH, —NHCH$_2$C(CH$_3$)$_2$OH, —NHCH$_2$CHFC(CH$_3$)$_2$OH, —C(O)NH$_2$, —CH$_2$NHC(O)CH$_2$CH$_2$CH$_3$, —CH$_2$NHC(O)CH(CH$_3$)$_2$, —CH$_2$NHC(O)CH$_2$CH(CH$_3$)$_2$, —CH$_2$NHC(O)CH$_2$C(CH$_3$)$_3$, —CH$_2$NHC(O)CH$_2$CH$_2$CH(CH$_3$)$_2$, —CH$_2$NHC(O)CH$_2$C(CH$_3$)$_2$OH, —CH$_2$NHC(O)NHCH$_2$CH$_2$CH$_3$, —CH$_2$NHC(O)NHCH$_2$CH$_2$CH$_2$CH$_3$, —CH$_2$NHC(O)NHCH$_2$(phenyl), —CH$_2$NHC(O)N(CH$_2$CH$_3$)$_2$, —CH$_2$NHC(O)OCH$_2$CH$_3$, —CH$_2$NHC(O)OCH$_2$CH(CH$_3$)$_2$, —CH$_2$NHC(O)(cyclopropyl), —CH$_2$NHC(O)(tetrahydrofuranyl), —CH$_2$NHC(O)CH$_2$(cyclopentyl), —CH$_2$NHC(O)CH$_2$(cyclohexyl), —CH$_2$NHC(O)CH$_2$(tetrahydropyranyl), —CH$_2$NHC(O)CH$_2$(phenyl), —NHC(O)CH$_3$, hydroxypyrrolidinyl, or pyridazinyl;

$R_b$ is H or —NH$_2$;

$R_1$ is:
(i) —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH$_2$CH$_2$CH(CH$_3$)$_2$, —CH$_2$CHFCH$_3$, —CH$_2$CH$_2$CF$_2$CH$_3$, —CH$_2$CHFCH(CH$_3$)$_2$, —CH$_2$CH$_2$C(CH$_3$)$_2$F, —CH$_2$CHFC(CH$_3$)$_2$F, —CH$_2$CH$_2$CH(OH)CH$_3$, —CH$_2$CH$_2$C(CH$_3$)$_2$OH, —CH$_2$CHFCH(CH$_3$)OH, —CH$_2$CHFC(CH$_3$)$_2$OH, —CH$_2$CF$_2$C(CH$_3$)$_2$OH, —CH$_2$CHFC(CH$_2$CH$_3$)$_2$OH, —CH$_2$CHFC(cyclopropyl)$_2$(OH), —CH$_2$CHFCH(OH)CH(CH$_3$)$_2$, —CH$_2$CH$_2$OCH$_2$CH$_3$, —(CH$_2$)$_3$OCH(CH$_3$)$_2$, —(CH$_2$)$_3$OC(CH$_3$)$_3$, —CH$_2$CHFCH$_2$OCH$_3$, —CH$_2$CHFC(CH$_3$)$_2$OCH$_3$, —CH$_2$CHFC(CH$_3$)$_2$OCD$_3$, —CH$_2$CHFC(CH$_3$)$_2$OCHF$_2$, —CH$_2$CHFC(CH$_3$)$_2$OCH$_2$CH$_3$, —CH$_2$CH$_2$C(O)OCH$_3$, —CH$_2$CH$_2$NHC(O)C(CH$_3$)$_2$OC(O)CH$_3$, —CH$_2$CH$_2$NHS(O)$_2$CH$_3$, —CH$_2$CH$_2$CH(CH$_3$)NHS(O)$_2$CH$_3$, —CH$_2$CH$_2$C(CH$_3$)$_2$NHS(O)$_2$CH$_3$, —CH$_2$CH$_2$P(O)(OCH$_2$CH$_3$)$_2$, —CH$_2$CHFCH(CH$_3$)NHCH(CH$_3$)$_2$, —CH$_2$CHFC(O)NHCH$_3$, —CH$_2$CH$_2$C(O)NHCH$_2$CH$_3$, —CH$_2$CHFC(O)NHCH(CH$_3$)$_2$, —CH$_2$CHFC(O)NHCH(CH$_3$)CH$_2$OH, or —CH$_2$CHFC(CH$_3$)$_2$OP(O)(OH)$_2$;

(ii) —(C$_{1-3}$ alkylenyl)R$_x$, —(C$_{1-2}$ fluoroalkylenyl)R$_x$, —(C$_{1-2}$ alkylenyl)C(O)R$_x$, —CH$_2$C(O)NHR$_x$, —CH$_2$CHFC(O)R$_x$, or —CH$_2$CF=(tetrahydropyranyl), wherein R$_x$ is a cyclic group selected from cyclopropyl, cyclopentyl, cyclohexyl, tetrazolyl, 1,1-dioxidotetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —CH$_3$, —C(CH$_2$)$_2$OH, —OCH$_3$, —C(O)CH$_2$CN, —S(O)$_2$CH$_3$, —S(O)$_2$NH$_2$, —NHC(O)CH$_3$, —N(S(O)$_2$CH$_3$)$_2$, —CH$_2$CH$_2$(acetamidophenyl), —CH$_2$CH$_2$(methoxyphenyl), —CH$_2$CH$_2$(sulfamoylphenyl), oxetanyl, benzyl, and morpholinyl;

(iii) cyclopropyl, cyclopentyl, cyclopentenyl, or cyclohexyl, each substituted with zero to 2 substituents independently selected from F, —OH, —CN, —CH$_3$, —OCH$_3$, —SCH$_3$, —NO$_2$, —S(O)$_2$CH$_3$, —C(CH$_3$)$_2$OH, —C(CH$_3$)(OH)(cyclopropyl), —CH$_2$C(O)NHCH$_3$, —NHC(O)CH(OH)CH$_3$, —C(O)NHCD$_3$, —C(O)NHCH$_3$, —C(O)NHCH$_2$CH$_3$, —C(O)NH(cyclopropyl), —NHC(O)CH$_3$, —NHC(O)OCH$_3$, —NHS(O)$_2$CH$_3$, pyridinyl, methylimidazolyl, methylpyrazolyl, and thiazolyl;

(iv) tetrahydropyranyl, piperidinyl, pyrazolyl, phenyl, pyridinyl, or pyrimidinyl, each substituted with zero to 1 substituent selected from —OH, —OCH₃, —CH₂CHF₂, —C(CH₃)₂OH, —CH₂C(CH₃)₂OH, —C(O)CH(CH₃)₂, —S(O)₂CH₃, —S(O)₂CH₂CH₃, —S(O)₂CH(CH₃)₂, —S(O)₂NHCH₃, —S(O)₂NHCH(CH₃)₂, —N(CH₃)₂, —OCH₂CH₂N(CH₃)₂, —CH₂(morpholinyl), oxetanyl, tetrahydropyranyl, morpholinyl, piperazinyl, methylpiperazinyl, methoxypiperidinyl, pyrimidinyl, methylsulfonyl azetidinyl, and —C(O)(methylsulfonyl azetidinyl); or (v) pyrrolo[2,3-c]pyridinyl, bicyclo[2.2.1]heptan-1-ol, tetrahydrobenzo[d]thiazol-2-amine, or 1,3-diazaspiro[4.5]decane-2,4-dione; and R₂ is:
(i) —CH₂CH₃, —CH₂CH₂CH₃, —CH(CH₃)₂, —C(CH₃)₃, —CH₂C(CH₃)₃, —CH(CH₃)CH₂CH₃, —CH₂CH₂CH(CH₃)₂, —CH(CH₃)CH₂CH(CH₃)₂, —CH(CH₃)CH₂OH, —CH₂CH₂CH(CH₃)OH, —CH(CH₃)CH₂CH₂OH, —CH₂C(CH₃)₂OH, —C(CH₃)₂CH₂OH, —CH(CH₃)CH(OH)CH₂CH(CH₃)₂, —CH₂CH(OH)CH(CH₃)₂, —CH(CH₂OH)CH₂CH₃, —CH(CH₂OH)CH(CH₃)₂, —CH=CHC(CH₃)₂OH, —CH₂CH₂CN, —CH₂CHF₂, —CH₂CF₃, —CH₂CHFCH₃, —CH(CH₃)CF₃, —CH₂CH₂CF₃, —CH(CH₃)CH₂F, —CH₂CH₂CH₂F, —CH₂CHFCH₂CH₃, —CH₂CH₂CHFCH₃, —CH(CH₃)CHFCH₃, —CH(CH₃)CH₂CH₂F, —CH₂CH₂C(CH₃)₂F, —CH₂CHFC(CH₃)₂OH, —CH₂CF₂C(CH₃)₂OH, —CH₂C(CH₃)FCH₂OH, —CH(CH₂F)CH₂OH, —CH₂CH₂OCHF₂, —CH₂C(CH₃)OCHF₂, —CH₂C(CH₃)₂OCHF₂, —CH₂C(CH₃)₂OCH₃, —CH₂C(CH₃)₂CH₂NH₂, —CH₂CHFC(O)NHCH(CH₃)₂, —CH₂CH₂NHS(O)₂CH₃, or —CH₂CH₂NHC(O)OC(CH₃)₂CF₃;

(ii) —CH₂(azetidinyl), —CH₂(cyclopropyl), —CH₂(fluorocyclobutyl), —CH₂(hydroxycyclobutyl), —CH₂(oxetanyl), —CH₂(methyloxetanyl), —CH₂(oxazolyl), —CH₂(methylpyridinyl), —CH₂(tetrahydropyranyl), —CH₂CH₂(methylmorpholinyl) —CH(CH₃)(cyclopropyl), —CH₂CH₂(morpholinyl), —CH₂CH(CH₃)(morpholinyl), or —CH₂C(CH₃)₂(morpholinyl);

(iii) C₃₋₆ cycloalkyl substituted with zero to 2 substituents independently selected from F, —OH, —CH₃, —CH₂OH, —C(CH₃)₂OH, —C(O)NH₂, —C(O)NHCH(CH₃)₂, —NH₂, —NHCH₂CF₃, —NH(oxetanyl), —NHC(O)CHF₂, —NHC(O)(cyclopropyl), —NHC(O)(fluorophenyl), and imidazolyl; azetidinyl substituted with —C(O)CH₃, —C(O)OCH₃, —C(O)OCH₂CH₃, —C(O)OC(CH₃)₃, —S(O)₂CH₃, fluoropyrimidinyl, or chloropyrimidinyl; tetrahydrofuranyl substituted with zero to 2 substituents independently selected from F and —OH; pyrrolidinyl substituted with zero to 1 substituent selected from —C(O)CH₃, —C(O)CH₂CF₃, —C(O)CH₂CN, —C(O)OCH₃, —S(O)₂CH₃, —C(O)(difluorophenyl), pyrimidinyl, fluoropyrimidinyl, and methoxypyrimidinyl; piperidinyl substituted with —S(O)₂CH₃, phenyl, or fluoropyrimidinyl; tetrahydropyranyl, fluorotetrahydropyranyl, or oxetanyl;

(iv) adamantanyl, hydroxyadamantanyl, benzo[d]imidazolyl, benzo[d]oxazolyl, benzo[d]triazolyl, benzothiazolyl, bicyclo[1.1.1]pentanyl, or hydroxy-bicyclo[2.2.1]heptanyl; or (v) phenyl substituted with 1 to 2 substituents independently selected from F, —OH, —CN, —CH₂OH, —C(CH₃)₂OH, —OCH₃, —C(O)NH₂, —C(O)NHCH₃, —NHC(O)CH₃, —NHC(O)S(O)₂CH₃, —S(O)₂NH₂, pyrazolyl, methyl pyrazolyl, imidazolyl, triazolyl, methyl tetrazolyl, and ethyl tetrazolyl; pyrazolyl substituted with 1 to 2 substituents independently selected from —CH₃, —CH₂CH₃, —CH₂CH₂CH₃, —CH(CH₃)₂, —CHF₂, —CH₂CHF₂, —CH₂CF₃, —CH₂CHFCH₃, —CH₂CH₂CH₂F, —CH₂C(CH₃)₂F, —CH₂CF₂CH₃, —CH₂C(CH₃)₂OH, —CH₂CH₂OCH₃, —CH₂CH(CH₃)OCHF₂, —CH₂CH₂CN, —C(O)NHCH₂CH₃, —S(O)₂CH₃, cyclopropyl, oxetanyl, phenyl, pyrimidinyl, fluoropyrimidinyl, and tetrahydropyranyl; methyl thiadiazolyl, hydroxypropyl thiazolyl, or indazolyl.

4. The compound according to claim 1 or a salt thereof, wherein:
HET is

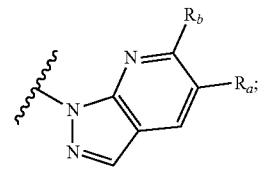

R_a is F, Cl, Br, —CN, —OH, —CH₃, —CHF₂, —OCH₃, —C(O)NH₂, or —CH₂NHC(O)CH₂CH(CH₃)₂;
R_b is H or —NH₂;
R₁ is:
(i) —CH₃, —CH₂CH₃, —CH₂CH₂CH₃, —CH(CH₃)₂, —CH₂CH₂CH₂CH₃, —CH₂CH(CH₃)₂, —C(CH₃)₃, —CH₂CH₂CH(CH₃)₂, —CH₂CHFCH₃, —CH₂CH₂CF₂CH₃, —CH₂CHFCH(CH₃)₂, —CH₂CH₂C(CH₃)₂F, —CH₂CHFC(CH₃)₂F, —CH₂CH₂CH(OH)CH₃, —CH₂CH₂C(CH₃)₂OH, —CH₂CHFC(CH₃)₂OH, —CH₂CF₂C(CH₃)₂OH, —CH₂CHFC(cyclopropyl)₂(OH), —CH₂CHFCH(OH)CH(CH₃)₂, —CH₂CH₂OCH₂CH₃, —CH₂CHFCH₂OCH₃, —CH₂CHFC(CH₃)₂OCH₃, —CH₂CHFC(CH₃)₂OCD₃, —CH₂CHFC(CH₃)₂OCH₂CH₃, —CH₂CH₂C(O)OCH₃, —CH₂CH₂NHS(O)₂CH₃, —CH₂CH₂CH(CH₃)NHS(O)₂CH₃, —CH₂CH₂C(CH₃)₂NHS(O)₂CH₃, —CH₂CH₂P(O)(OCH₃)₂, —CH₂CHFC(O)NHCH₃, —CH₂CH₂C(O)NHCH₂CH₃, —CH₂CHFC(O)NHCH(CH₃)₂, —CH₂CHFC(O)NHCH(CH₃)CH₂OH, or —CH₂CHFC(CH₃)₂OP(O)(OH)₂;

(ii) —(C₁₋₃ alkylenyl)R_x, —(C₁₋₂ fluoroalkylenyl)R_x, —(C₁₋₂ alkylenyl)C(O)R_x, —CH₂CHFC(O)R_x, or —CH₂CF=(tetrahydropyranyl), wherein R_x is a cyclic group selected from cyclopropyl, cyclopentyl, cyclohexyl, tetrazolyl, 1,1-dioxidotetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —CH₃, —C(CH₂)₂OH, —OCH₃, —C(O)CH₂CN, —S(O)₂CH₃, —S(O)₂NH₂, —NHC(O)CH₃, —N(S(O)₂CH₃)₂, oxetanyl, and benzyl;

(iii) cyclopropyl, cyclopentyl, cyclopentenyl, or cyclohexyl, each substituted with zero to 1 substituent independently selected from —CN, —CH₃, —OCH₃, —S(O)₂CH₃, —C(CH₃)₂OH, —CH₂C(O)NHCH₃, —NHC(O)CH(OH)CH₃, —C(O)NHCD₃, —C(O)NHCH₃, —NHC(O)CH₃, and —NHS(O)₂CH₃;

(iv) tetrahydropyranyl, piperidinyl, pyrazolyl, phenyl, pyridinyl, or pyrimidinyl, each substituted with a substituent selected from —OH, —OCH₃, —CH₂CHF₂, —C(CH₃)₂OH, —CH₂C(CH₃)₂OH, —C(O)CH(CH₃)₂, —S(O)₂CH₃, —S(O)₂CH₂CH₃, —S(O)₂CH(CH₃)₂, —S(O)₂NHCH₃, —S(O)₂NHCH(CH₃)₂, —N(CH₃)₂, —OCH₂CH₂N(CH₃)₂, —CH₂(morpholinyl), oxetanyl, tetrahydropyranyl, morpholinyl, piperazinyl, methylpiperazinyl, methoxypiperidinyl, pyrimidinyl, methylsulfonyl azetidinyl, and —C(O)(methylsulfonyl azetidinyl); or (v) pyrrolo[2,3-c]pyridinyl or tetrahydrobenzo[d]thiazol-2-amine; and $R_2$ is:

(i) —CH₂CH₃, —CH₂CH₂CH₃, —CH(CH₃)₂, —C(CH₃)₃, —CH₂C(CH₃)₃, —CH(CH₃)CH₂CH₃, —CH(CH₃)CH₂OH, —CH₂CH₂CH(CH₃)OH, —C(CH₃)₂CH₂OH, —CH₂CH(OH)CH(CH₃)₂, —CH(CH₂OH)CH₂CH₃, —CH(CH₂OH)CH(CH₃)₂, —CH₂CHF₂, —CH₂CF₃, —CH₂CHFCH₃, —CH(CH₃)CF₃, —CH₂CH₂CF₃, —CH(CH₃)CH₂F, —CH₂CH₂CH₂F, —CH₂CHFCH₂CH₃, —CH₂CH₂CHFCH₃, —CH(CH₃)CHFCH₃, —CH(CH₃)CH₂CH₂F, —CH₂CH₂C(CH₃)₂F, —CH₂CF₂C(CH₃)₂OH, —CH₂C(CH₃)FCH₂OH, —CH₂CH₂OCHF₂, —CH₂C(CH₃)OCHF₂, —CH₂C(CH₃)₂OCHF₂, —CH₂C(CH₃)₂OCH₃, —CH₂C(CH₃)CH₂NH₂, —CH₂CH₂NHS(O)₂CH₃, or —CH₂CH₂NHC(O)OC(CH₃)₂CF₃;

(ii) —CH₂(cyclopropyl), —CH₂(fluorocyclobutyl), —CH₂(oxazolyl), or —CH₂C(CH₃)₂(morpholinyl);

(iii) $C_{3-6}$ cycloalkyl substituted with zero to 3 substituents independently selected from F, —OH, —CH₃, —CH₂OH, —C(CH₃)₂OH, —C(O)NHCH(CH₃)₂, —NH₂, —NH(oxetanyl), —NHC(O)CHF₂, —NHC(O)(cyclopropyl), and —NHC(O)(fluorophenyl); azetidinyl substituted with —C(O)OCH₃, —C(O)OCH₂CH₃, fluoropyrimidinyl, or chloropyrimidinyl; tetrahydrofuranyl substituted with zero to 2 substituents selected from F; pyrrolidinyl substituted with —C(O)(difluorophenyl), pyrimidinyl, fluoropyrimidinyl, or methoxypyrimidinyl; piperidinyl substituted with phenyl or fluoropyrimidinyl; tetrahydropyranyl, or oxetanyl;

(iv) hydroxyadamantanyl, benzo[d]oxazolyl, benzothiazolyl, bicyclo[1.1.1]pentanyl, or hydroxy-bicyclo[2.2.1]heptanyl; or (v) phenyl substituted with 1 to 2 substituents independently selected from F, —CN, triazolyl, and methyl tetrazolyl; pyrazolyl substituted with 1 to 2 substituents independently selected from —CH₃, —CH₂CH₃, —CH₂CH₂CH₃, —CH(CH₃)₂, —CHF₂, —CH₂CHF₂, —CH₂CH₂CH₂F, —CH₂C(CH₃)₂F, —CH₂CF₂CH₃, —CH₂C(CH₃)₂OH, —CH₂CH₂OCH₃, —CH₂CH(CH₃)OCHF₂, —CH₂CH₂CN, —C(O)NHCH₂CH₃, —S(O)₂CH₃, cyclopropyl, oxetanyl, phenyl, pyrimidinyl, fluoropyrimidinyl, and tetrahydropyranyl; methyl thiadiazolyl, or hydroxypropyl thiazolyl.

5. The compound according to claim 1 or a salt thereof, wherein:

HET is

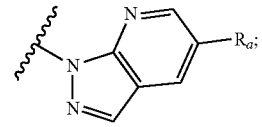

$R_a$ is F, Cl, Br, —OH, —CN, or —CH₃;
$R_1$ is —CH₂CHFCH(CH₃)OH, —CH₂CHFC(CH₃)₂OH, —CH₂CF₂C(CH₃)₂OH, —CH₂CHFC(CH₂CH₃)₂OH, or —CH₂CHFC(CH₃)₂OP(O)(OH)₂; and
$R_2$ is —CH₂CH₃, —CH₂CH₂CH₃, —CH(CH₃)₂, or —CH₂CH₂CH(CH₃)₂.

6. The compound according to claim 1 or a salt thereof, wherein:
HET is

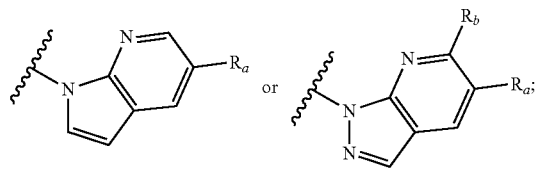

$R_a$ is Cl or —CN;
$R_b$ is H;
$R_1$ is —CH₂CH₂C(CH₃)₂OH, —CH₂CHFC(CH₃)₂OH, or —CH₂CHFC(CH₃)₂OP(O)(OH)₂; and
$R_2$ is —CH(CH₃)₂.

7. The compound according to claim 1 or a salt thereof, wherein said compound is:

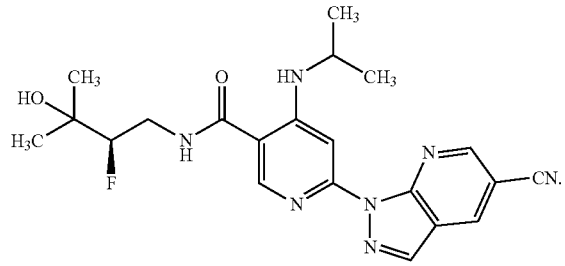 [SMILES: CC(C)Nc1cc(-n2ncc3cc(C#N)cnc32)ncc1C(=O)NC[C@@H](F)C(C)(C)O]

8. The compound according to claim 1 or a salt thereof, wherein said compound is selected from: (R)-6-(5-cyano-1H-indol-1-yl)-N-(2-fluoro-3-hydroxy-3-methylbutyl)-4-(isopropylamino)nicotinamide (1); (R)-6-(5-cyano-1H-pyrrolo[2,3-b]pyridin-1-yl)-4-(cyclopropylamino)-N-(2-fluoro-3-hydroxy-3-methylbutyl)nicotinamide (2); (R)-6-(5-cyano-1H-pyrrolo[2,3-b]pyridin-1-yl)-N-(2-fluoro-3-hydroxy-3-methylbutyl)-4-((tetrahydro-2H-pyran-4-yl)amino)nicotinamide (3); (R)-6-(5-cyano-1H-pyrrolo[2,3-b]pyridin-1-yl)-4-(ethylamino)-N-(2-fluoro-3-hydroxy-3-methylbutyl)nicotinamide (4); (R)-6-(5-cyano-1H-pyrrolo[2,3-b]pyridin-1-yl)-N-(2-fluoro-3-hydroxy-3-methylbutyl)-4-((2,2,2-trifluoroethyl)amino)nicotinamide (5); (R)-6-(5-cyano-1H-pyrrolo[2,3-b]pyridin-1-yl)-4-(cyclobutylamino)-N-(2-fluoro-3-hydroxy-3-methylbutyl)nicotinamide (6); 6-(5-cyano-1H-pyrrolo[2,3-b]pyridin-1-yl)-N—((R)-2-fluoro-3-hydroxy-3-methylbutyl)-4-((tetrahydro-2H-pyran-3-yl)amino)nicotinamide (7); 6-(5-cyano-1H-pyrrolo[2,3-b]pyridin-1-yl)-N—((S)-2-fluoro-3-hydroxy-3-methylbutyl)-4-((tetrahydro-2H-pyran-3-yl)amino)nicotinamide (8); 6-(5-cyano-1H-pyrrolo[2,3-b]

pyridin-1-yl)-N—((R)-2-fluoro-3-hydroxy-3-methylbutyl)-4-(((S)-1-hydroxypropan-2-yl)amino)nicotinamide (9); (R)-6-(5-cyano-1H-pyrrolo[2,3-b]pyridin-1-yl)-4-(cyclopentylamino)-N-(2-fluoro-3-hydroxy-3-methylbutyl) nicotinamide (10); 6-(5-cyano-1H-pyrrolo[2,3-b]pyridin-1-yl)-N-(3-hydroxy-3-methylbutyl)-4-(isopropylamino) nicotinamide (11); 6-(5-cyano-1H-pyrrolo[2,3-b]pyridin-1-yl)-N-(3-hydroxy-3-methylbutyl)-4-((tetrahydro-2H-pyran-4-yl)amino) nicotinamide (12); 4-((1s,3S)-adamantan-1-ylamino)-6-(5-cyano-1H-pyrrolo[2,3-b]pyridin-1-yl)-N—((R)-2-fluoro-3-hydroxy-3-methylbutyl)nicotinamide (13); 6-(5-cyano-1H-pyrrolo[2,3-b]pyridin-1-yl)-N-(4-hydroxybicyclo[2.2.1]heptan-1-yl)-4-(isopropylamino)nicotinamide (14); N-(3-(tert-butoxy)propyl)-6-(5-cyano-1H-pyrrolo[2,3-b]pyridin-1-yl)-4-(isopropylamino)nicotinamide (15); (R)-6-(5-cyano-1H-pyrrolo[2,3-b]pyridin-1-yl)-N-(2-fluoro-3-hydroxy-3-methylbutyl)-4-((4-hydroxybicyclo[2.2.1]heptan-1-yl)amino)nicotinamide (16); (R)-6-(5-cyano-1H-pyrrolo[2,3-b]pyridin-1-yl)-N-(2-fluoro-3-hydroxy-3-methylbutyl)-4-((1-methylcyclopropyl)amino)nicotinamide (17); (R)-6-(5-cyano-1H-pyrrolo[2,3-b]pyridin-1-yl)-N-(2-fluoro-3-hydroxy-3-methylbutyl)-4-((1-methylcyclopropyl)amino)nicotinamide (18); (R)-6-(5-cyano-1H-pyrrolo[2,3-b]pyridin-1-yl)-N-(2-fluoro-3-hydroxy-3-methylbutyl)-4-(isopentylamino) nicotinamide (19); (R)-6-(5-cyano-1H-pyrrolo[2,3-b]pyridin-1-yl)-N-(2-fluoro-3-hydroxy-3-methylbutyl)-4-(((3-methyloxetan-3-yl)methyl)amino) nicotinamide (20); 6-(5-cyano-1H-pyrrolo[2,3-b]pyridin-1-yl)-N—((R)-2-fluoro-3-hydroxy-3-methylbutyl)-4-((4-hydroxybutan-2-yl)amino)nicotinamide (21); 6-(5-cyano-1H-pyrrolo[2,3-b]pyridin-1-yl)-N—((S)-2-fluoro-3-hydroxy-3-methylbutyl)-4-((4-hydroxybutan-2-yl)amino) nicotinamide (22); (S)-6-(5-cyano-1H-pyrrolo[2,3-b]pyridin-1-yl)-N-(2-fluoro-3-hydroxy-3-methylbutyl)-4-(isopropylamino)nicotinamide (23); 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (24); diastereomer 1; 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (25); diastereomer 2; 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (26); diastereomer 3; 6-(5-cyano-1H-pyrrolo[2,3-b]pyridin-1-yl)-N—((R)-2-fluoro-3-hydroxy-3-methylbutyl)-4-((3-hydroxycyclopentyl)amino) nicotinamide (27); diastereomer 4; (R)-6-(5-cyano-1H-pyrrolo[2,3-b]pyridin-1-yl)-N-(2-fluoro-3-hydroxy-3-methylbutyl)-4-(((1-hydroxycyclobutyl)methyl)amino) nicotinamide (28); (R)-6-(5-cyano-1H-pyrrolo[2,3-b]pyridin-1-yl)-N-(2-fluoro-3-hydroxy-3-methylbutyl)-4-((oxetan-3-ylmethyl)amino) nicotinamide (29); 6-(5-cyano-1H-pyrrolo[2,3-b]pyridin-1-yl)-N—((R)-2-fluoro-3-hydroxy-3-methylbutyl)-4-(((1R,2R)-2-hydroxycyclopentyl)amino)nicotinamide (30); (R)-6-(5-chloro-1H-pyrrolo[2,3-b]pyridin-1-yl)-4-(cyclobutylamino)-N-(2-fluoro-3-hydroxy-3-methylbutyl) nicotinamide (31); (R)-6-(5-chloro-1H-pyrrolo[2,3-b]pyridin-1-yl)-N-(2-fluoro-3-hydroxy-3-methylbutyl)-4-((tetrahydro-2H-pyran-4-yl)amino) nicotinamide (32); (R)-6-(5-chloro-1H-pyrrolo[2,3-b]pyridin-1-yl)-4-(ethylamino)-N-(2-fluoro-3-hydroxy-3-methylbutyl)nicotinamide (33); (R)-6-(5-chloro-1H-pyrrolo[2,3-b]pyridin-1-yl)-4-(cyclopropylamino)-N-(2-fluoro-3-hydroxy-3-methylbutyl)nicotinamide (34); (R)-6-(5-chloro-1H-pyrrolo[2,3-b]pyridin-1-yl)-N-(2-fluoro-3-hydroxy-3-methylbutyl)-4-((2-hydroxy-2-methylpropyl)amino)nicotinamide (35); 6-(5-chloro-1H-pyrrolo[2,3-b]pyridin-1-yl)-N-(3-hydroxy-3-methylbutyl)-4-((tetrahydro-2H-pyran-4-yl)amino)nicotinamide (36); (R)-6-(5-chloro-1H-indol-1-yl)-N-(2-fluoro-3-hydroxy-3-methylbutyl)-4-(isopropylamino)nicotinamide (37); (R)-6-(5-fluoro-1H-pyrrolo[2,3-b]pyridin-1-yl)-N-(2-fluoro-3-hydroxy-3-methylbutyl)-4-(isopropylamino)nicotinamide (38); (R)—N-(2-fluoro-3-hydroxy-3-methylbutyl)-4-(isopropylamino)-6-(7H-pyrrolo[2,3-d]pyrimidin-7-yl)nicotinamide (39); (R)—N-(2-fluoro-3-hydroxy-3-methylbutyl)-6-(7H-pyrrolo[2,3-d]pyrimidin-7-yl)-4-((tetrahydro-2H-pyran-4-yl)amino)nicotinamide (40); (R)-4-(cyclopropylamino)-N-(2-fluoro-3-hydroxy-3-methylbutyl)-6-(7H-pyrrolo[2,3-d]pyrimidin-7-yl) nicotinamide (41); (R)—N-(2-fluoro-3-hydroxy-3-methylbutyl)-4-((2-hydroxy-2-methylpropyl)amino)-6-(7H-pyrrolo[2,3-d]pyrimidin-7-yl)nicotinamide (42); N-(3-hydroxy-3-methylbutyl)-6-(7H-pyrrolo[2,3-d]pyrimidin-7-yl)-4-((tetrahydro-2H-pyran-4-yl)amino)nicotinamide (43); N-(3-hydroxy-3-methylbutyl)-4-(isopropylamino)-6-(7H-pyrrolo[2,3-d]pyrimidin-7-yl)nicotinamide (44); (R)-6-(5-acetamido-1H-pyrrolo[2,3-b]pyridin-1-yl)-N-(2-fluoro-3-hydroxy-3-methylbutyl)-4-(isopropylamino)nicotinamide (45); (R)-6-(5-cyano-1H-pyrrolo[2,3-b]pyridin-1-yl)-N-(2-fluoro-3-hydroxy-3-methylbutyl)-4-((3-hydroxyphenyl) amino)nicotinamide (46); 6-(5-cyano-1H-pyrrolo[2,3-b]pyridin-1-yl)-N-(3-isopropoxypropyl)-4-(isopropylamino) nicotinamide (47); 6-(5-cyano-1H-pyrrolo[2,3-b]pyridin-1-yl)-N-((2R)-2-fluoro-3-hydroxybutyl)-4-(isopropylamino) nicotinamide (48); 6-(5-cyano-1H-pyrrolo[2,3-b]pyridin-1-yl)-N-((2S)-2-fluoro-3-hydroxybutyl)-4-(isopropylamino) nicotinamide (49); (R)-6-(5-cyano-1H-pyrrolo[2,3-b]pyridin-1-yl)-N-(2-fluoro-3-hydroxy-3-methylbutyl)-4-((3-sulfamoylphenyl)amino)nicotinamide (50); (R)-6-(5-cyano-1H-pyrrolo[2,3-b]pyridin-1-yl)-N-(2-fluoro-3-hydroxy-3-methylbutyl)-4-((3-methoxyphenyl)amino)nicotinamide (51); 6-(5-cyano-1H-pyrrolo[2,3-b]pyridin-1-yl)-N—(R)-2-fluoro-3-hydroxy-3-methylbutyl)-4-(((R)-2-fluoro-3-hydroxy-3-methylbutyl)amino)nicotinamide (52); (R)-6-(5-cyano-1H-pyrrolo[2,3-b]pyridin-1-yl)-4-((3,3-difluorocyclobutyl)amino)-N-(2-fluoro-3-hydroxy-3-methylbutyl)nicotinamide (53); (R)-4-((3-acetamidophenyl) amino)-6-(5-cyano-1H-pyrrolo[2,3-b]pyridin-1-yl)-N-(2-fluoro-3-hydroxy-3-methylbutyl) nicotinamide (54); (R)-6-(5-cyano-1H-pyrrolo[2,3-b]pyridin-1-yl)-N-(2-fluoro-3-hydroxy-3-methylbutyl)-4-((3-(methylcarbamoyl)phenyl) amino)nicotinamide (55); (R)-4-((3-carbamoylphenyl) amino)-6-(5-cyano-1H-pyrrolo[2,3-b]pyridin-1-yl)-N-(2-fluoro-3-hydroxy-3-methylbutyl)nicotinamide (56); (R)-6-(5-cyano-1H-pyrrolo[2,3-b]pyridin-1-yl)-N-(2-fluoro-3-hydroxy-3-methylbutyl)-4-((3-(methylsulfonamido)phenyl) amino) nicotinamide (57); 6-(5-cyano-1H-pyrrolo[2,3-b]pyridin-1-yl)-4-(isopropylamino)-N-(4-sulfamoylphenethyl)nicotinamide (58); (R)-6-(5-cyano-1H-pyrrolo[2,3-b]pyridin-1-yl)-N-(2-fluoro-3-hydroxy-3-methylbutyl)-4-((3-(2-hydroxypropan-2-yl)phenyl)amino) nicotinamide (59); (R)-4-((4-carbamoylphenyl)amino)-6-(5-cyano-1H-pyrrolo[2,3-b]pyridin-1-yl)-N-(2-fluoro-3-hydroxy-3-methylbutyl)nicotinamide (60); 6-(5-cyano-1H-pyrrolo[2,3-b]pyridin-1-yl)-N—((R)-2-fluoro-3-hydroxy-3-methylbutyl)-4-(((1s,4S)-4-hydroxy-4-methylcyclohexyl) amino)nicotinamide (61); 6-(5-cyano-1H-pyrrolo[2,3-b]pyridin-1-yl)-N—((R)-2-fluoro-3-hydroxy-3-methylbutyl)-4-(((trans)-4-hydroxy-4-methylcyclohexyl)amino) nicotinamide (62); 6-(5-cyano-1H-pyrrolo[2,3-b]pyridin-1-yl)-4-(isopropylamino)-N-(2-(methylsulfonamido)ethyl) nicotinamide (63); (R)-4-(benzo[d]thiazol-6-ylamino)-6-(5-cyano-1H-pyrrolo[2,3-b]pyridin-1-yl)-N-(2-fluoro-3- hydroxy-3-methylbutyl)nicotinamide (64); (R)-6-(5-cyano-1H-pyrrolo[2,3-b]pyridin-1-yl)-N-(2-fluoro-3-hydroxy-3-methylbutyl)-4-(((1-fluorocyclobutyl)methyl)amino) nicotinamide (65); (R)-6-(5-cyano-1H-pyrrolo[2,3-b]pyridin-1-yl)-4-((3-cyanophenyl)amino)-N-(2-fluoro-3-hydroxy-3-methylbutyl)nicotinamide (66); (R)-4-((4-(1H-1,2,4-triazol-1-yl)phenyl)amino)-6-(5-cyano-1H-pyrrolo[2,3-b]pyridin-1-yl)-N-(2-fluoro-3-hydroxy-3-methylbutyl) nicotinamide (67); (R)-6-(5-cyano-1H-pyrrolo[2,3-b]pyridin-1-yl)-N-(2-fluoro-3-hydroxy-3-methylbutyl)-4-((4-(1-methyl-1H-tetrazol-5-yl)phenyl)amino) nicotinamide (68); (R)-6-(5-cyano-1H-pyrrolo[2,3-b]pyridin-1-yl)-N-(2-fluoro-3-hydroxy-3-methylbutyl)-4-((4-(1-methyl-1H-tetrazol-5-yl)phenyl)amino)nicotinamide (69); 6-(5-cyano-1H-pyrrolo[2,3-b]pyridin-1-yl)-N-(2-(((1,1-dioxidotetrahydrothiophen-3-yl)amino)-2-oxoethyl)-4-(isopropylamino)nicotinamide (70); (R)-6-(5-cyano-1H-pyrrolo[2,3-b]pyridin-1-yl)-N-(2-fluoro-3-hydroxy-3-methylbutyl)-4-((3-(hydroxymethyl)phenyl)amino) nicotinamide (71); 6-(5-cyano-1H-pyrrolo[2,3-b]pyridin-1-yl)-N—((R)-2-fluoro-3-hydroxy-3-methylbutyl)-4-(((2S)-3-fluorobutan-2-yl)amino)nicotinamide (72); N-(2-amino-4,5,6,7-tetrahydrobenzo[d]thiazol-6-yl)-6-(5-cyano-1H-pyrrolo[2,3-b]pyridin-1-yl)-4-(isopropylamino)nicotinamide (73); (R)—N-(2-fluoro-3-hydroxy-3-methylbutyl)-4-(isopropylamino)-6-(1H-pyrrolo[2,3-b]pyridin-1-yl)nicotinamide (74); (R)-6-(5-cyano-1H-pyrrolo[2,3-b]pyridin-1-yl)-N-(2-fluoro-3-hydroxy-3-methylbutyl)-4-(isopropylamino)nicotinamide (75); (R)-6-(5-chloro-1H-pyrrolo[2,3-b]pyridin-1-yl)-N-(2-fluoro-3-hydroxy-3-methylbutyl)-4-(isopropylamino)nicotinamide (76); (R)-6-(5-cyano-1H-pyrrolo[2,3-b]pyridin-1-yl)-N-(2-fluoro-3-hydroxy-3-methylbutyl)-4-((2-hydroxy-2-methylpropyl)amino) nicotinamide (77); 6-(5-cyano-1H-pyrrolo[2,3-b]pyridin-1-yl)-N—((R)-2-fluoro-3-hydroxy-3-methylbutyl)-4-((1-fluoropropan-2-yl)amino) nicotinamide (78); 6-(5-cyano-1H-indol-1-yl)-4-(isopropylamino)-N-((trans)-4-(methylcarbamoyl)cyclohexyl)nicotinamide (79); 6-(5-cyano-1H-pyrrolo[2,3-b]pyridin-1-yl)-4-(isopropylamino)-N-((trans)-4-(methylcarbamoyl)cyclohexyl)nicotinamide (80); 4-(isopropylamino)-N-((trans)-4-(methylcarbamoyl)cyclohexyl)-6-(7H-pyrrolo[2,3-d]pyrimidin-7-yl)nicotinamide (81); N-((trans)-4-(methylcarbamoyl)cyclohexyl)-6-(7H-pyrrolo[2,3-d]pyrimidin-7-yl)-4-((tetrahydro-2H-pyran-4-yl)amino)nicotinamide (82); N-((trans)-4-acetamidocyclohexyl)-6-(7H-pyrrolo[2,3-d]pyrimidin-7-yl)-4-((tetrahydro-2H-pyran-4-yl)amino)nicotinamide (83); N-((trans)-4-acetamidocyclohexyl)-4-(isopropylamino)-6-(7H-pyrrolo[2,3-d]pyrimidin-7-yl)nicotinamide (84); 6-(5-cyano-1H-pyrrolo[2,3-b]pyridin-1-yl)-4-(cyclopropylamino)-N-((trans)-4-(methylcarbamoyl)cyclohexyl) nicotinamide (85); 6-(5-cyano-1H-pyrrolo[2,3-b]pyridin-1-yl)-N-((trans)-4-(methylcarbamoyl)cyclohexyl)-4-((tetrahydro-2H-pyran-4-yl)amino)nicotinamide (86); N-((trans)-4-acetamidocyclohexyl)-6-(5-cyano-1H-pyrrolo[2,3-b]pyridin-1-yl)-4-(cyclopropylamino)nicotinamide (87); N-((trans)-4-acetamidocyclohexyl)-6-(5-cyano-1H-pyrrolo[2,3-b]pyridin-1-yl)-4-((tetrahydro-2H-pyran-4-yl)amino)nicotinamide (88); 6-(5-cyano-1H-pyrrolo[2,3-b]pyridin-1-yl)-4-(((S)-1-hydroxypropan-2-yl)amino)-N-((1r,4S)-4-(methylcarbamoyl)cyclohexyl)nicotinamide (89); 6-(5-cyano-1H-pyrrolo [2,3-b]pyridin-1-yl)-4-(isopropylamino)-N-((trans)-4-(isopropylcarbamoyl)cyclohexyl) nicotinamide (90); 6-(5-cyano-1H-pyrrolo[2,3-b]pyridin-1-yl)-N-((trans)-4-(cyclopropylcarbamoyl)cyclohexyl)-4-(isopropylamino)nicotinamide (91); 6-(5-cyano-1H-pyrrolo[2,3-b]pyridin-1-yl)-N-((trans)-4-(ethylcarbamoyl) cyclohexyl)-4-(isopropylamino)nicotinamide (92); 6-(5-cyano-1H-pyrrolo[2,3-b]pyridin-1-yl)-4-((2-hydroxy-2-methylpropyl)amino)-N-((trans)-4-(methylcarbamoyl) cyclohexyl) nicotinamide (93); 6-(5-cyano-1H-pyrrolo[2,3-b]pyridin-1-yl)-4-((2-hydroxy-2-methylpropyl)amino)-N-((trans)-4-(($^2H_3$)methylcarbamoyl)cyclohexyl)nicotinamide (94); 6-(5-cyano-1H-pyrrolo[2,3-b]pyridin-1-yl)-4-(isopropylamino)-N-((trans)-4-nitrocyclohexyl)nicotinamide (95); 6-(5-cyano-1H-pyrrolo[2,3-b]pyridin-1-yl)-N-((trans)-4-(2-hydroxypropan-2-yl)cyclohexyl)-4-(isopropylamino)nicotinamide (96); methyl((trans)-4-(6-(5-cyano-1H-pyrrolo[2,3-b]pyridin-1-yl)-4-(isopropylamino) nicotinamido) cyclohexyl)carbamate (97); 6-(5-cyano-1H-pyrrolo[2,3-b]pyridin-1-yl)-N-((trans)-4-hydroxycyclohexyl)-4-(isopropylamino)nicotinamide (98); 6-(5-cyano-1H-pyrrolo[2,3-b]pyridin-1-yl)-N-((trans)-4-hydroxy-4-methylcyclohexyl)-4-(isopropylamino)nicotinamide (99); 6-(5-cyano-1H-pyrrolo[2,3-b]pyridin-1-yl)-4-(ethylamino)-N-((trans)-4-(2-hydroxypropan-2-yl)cyclohexyl)nicotinamide (100); 6-(5-cyano-1H-pyrrolo[2,3-b]pyridin-1-yl)-4-(isopropylamino)-N-((trans)-4-(methylthio)cyclohexyl) nicotinamide (101); 6-(5-cyano-1H-pyrrolo[2,3-b]pyridin-1-yl)-4-(isopropylamino)-N-((trans)-4-(methylsulfonyl) cyclohexyl)nicotinamide (102); 6-(5-cyano-1H-pyrrolo[2,3-b]pyridin-1-yl)-N-((trans)-4-(methylsulfonyl)cyclohexyl)-4-((tetrahydro-2H-pyran-4-yl)amino)nicotinamide (103); 6-(5-cyano-1H-pyrrolo[2,3-b]pyridin-1-yl)-4-(cyclopropylamino)-N-((trans)-4-(methylsulfonyl)cyclohexyl) nicotinamide (104); 4-((3-carbamoylphenyl)amino)-6-(5-cyano-1H-pyrrolo[2,3-b]pyridin-1-yl)-N-((trans)-4-(methylsulfonyl) cyclohexyl)nicotinamide (105); 6-(5-cyano-1H-pyrrolo[2,3-b]pyridin-1-yl)-N—((R)-2-fluoro-3-hydroxy-3-methylbutyl)-4-((3-fluorotetrahydro-2H-pyran-4-yl)amino) nicotinamide (106); 6-(5-cyano-1H-pyrrolo[2,3-b]pyridin-1-yl)-N—((R)-2-fluoro-3-hydroxy-3-methylbutyl)-4-((3-fluorotetrahydro-2H-pyran-4-yl)amino)nicotinamide (107); 6-(5-cyano-1H-pyrrolo[2,3-b]pyridin-1-yl)-N—((S)-2-fluoro-3-hydroxy-3-methylbutyl)-4-((3-fluorotetrahydro-2H-pyran-4-yl)amino) nicotinamide (108); 6-(5-cyano-1H-pyrrolo[2,3-b]pyridin-1-yl)-N—((R)-2-fluoro-3-hydroxy-3-methylbutyl)-4-((3-fluorocyclopentyl)amino)nicotinamide (109); 6-(5-cyano-1H-pyrrolo[2,3-b]pyridin-1-yl)-N—((S)-2-fluoro-3-hydroxy-3-methylbutyl)-4-((3-fluorocyclopentyl)amino)nicotinamide (110); 6-(5-cyano-1H-pyrrolo[2,3-b]pyridin-1-yl)-4-((3,3-difluoro-2-hydroxycyclohexyl) amino)-N—((R)-2-fluoro-3-hydroxy-3-methylbutyl) nicotinamide (111); 6-(5-cyano-1H-pyrrolo[2,3-b]pyridin-1-yl)-4-((3,3-difluoro-2-hydroxycyclohexyl)amino)-N—((R)-2-fluoro-3-hydroxy-3-methylbutyl)nicotinamide (112); N—((R)-2-fluoro-3-hydroxy-3-methylbutyl)-4-((1-fluoropropan-2-yl)amino)-6-(7H-pyrrolo[2,3-d]pyrimidin-7-yl) nicotinamide (113); 6-(5-cyano-1H-pyrazolo[3,4-b]pyridin-1-yl)-N—((R)-2-fluoro-3-hydroxy-3-methylbutyl)-4-(((R)-1-fluoropropan-2-yl)amino) nicotinamide (114); N—((R)-2-fluoro-3-hydroxy-3-methylbutyl)-4-(((R)-1-fluoropropan-2-yl)amino)-6-(7H-pyrrolo[2,3-d]pyrimidin-7-yl) nicotinamide (115); N—((R)-2-fluoro-3-hydroxy-3-methylbutyl)-4-(((S)-1-fluoropropan-2-yl)amino)-6-(7H-pyrrolo[2,3-d]pyrimidin-7-yl)nicotinamide (116); 6-(5-cyano-1H-pyrrolo[2,3-b]pyridin-1-yl)-N—((R)-2-fluoro-3-hydroxy-3-methylbutyl)-4-(((S)-1-fluoropropan-2-yl) amino)nicotinamide (117); 6-(5-cyano-1H-pyrrolo[2,3-b]pyridin-1-yl)-N—((R)-2-fluoro-3-hydroxy-3-methylbutyl)-4-(((R)-1-fluoropropan-2-yl)amino)nicotinamide (118); (S)-6-(5-cyano-1H-pyrrolo[2,3-b]pyridin-1-yl)-4-((1-fluoropropan-2-yl)amino)-N-(3-hydroxy-3-methylbutyl) nicotinamide (119); (R)-6-(5-cyano-1H-pyrrolo[2,3-b]

pyridin-1-yl)-4-((1-fluoropropan-2-yl)amino)-N-(3-hydroxy-3-methylbutyl)nicotinamide (120); 6-(5-cyano-1H-pyrazolo[3,4-b]pyridin-1-yl)-N—((R)-2-fluoro-3-hydroxy-3-methylpropan-2-yl)-4-(((S)-1-fluoropropan-2-yl)amino)nicotinamide (121); 6-(5-cyano-1H-pyrazolo[3,4-b]pyridin-1-yl)-4-(((S)-1-fluoropropan-2-yl)amino)-N-((1r,4S)-4-(methylcarbamoyl)cyclohexyl)nicotinamide (122); (R)-1-(4-(ethylamino)-5-((2-fluoro-3-hydroxy-3-methylbutyl)carbamoyl)pyridin-2-yl)-1H-pyrrolo[2,3-b]pyridine-5-carboxamide (123); (R)-1-(4-(cyclobutylamino)-5-((2-fluoro-3-hydroxy-3-methylbutyl)carbamoyl)pyridin-2-yl)-1H-pyrrolo[2,3-b]pyridine-5-carboxamide (124); 1-((2-(6-(5-cyano-1H-pyrrolo[2,3-b]pyridin-1-yl)-4-(isopropylamino) nicotinamido)ethyl)amino)-2-methyl-1-oxopropan-2-yl acetate (125); 6-(5-cyano-1H-pyrrolo[2,3-b]pyridin-1-yl)-N-(2-(2-hydroxy-2-methylpropanamido)ethyl)-4-(isopropylamino)nicotinamide (126); (R)-6-(5-cyano-1H-pyrrolo[2,3-b]pyridin-1-yl)-N-(2-fluoro-3-methoxypropyl)-4-(isopropylamino)nicotinamide (127); (R)-6-(5-cyano-1H-pyrazolo[3,4-b]pyridin-1-yl)-N-(2-fluoro-3-methoxypropyl)-4-(isopropylamino) nicotinamide (128); 6-(5-cyano-1H-pyrrolo[2,3-b]pyridin-1-yl)-N-((2R)-2-fluoro-3-(isopropylamino)butyl)-4-(isopropylamino)nicotinamide (129); 6-(5-cyano-1H-pyrrolo [2,3-b]pyridin-1-yl)-N-((2R)-2-fluoro-3-(isopropylamino)butyl)-4-(isopropylamino) nicotinamide (130); 6-(5-cyano-1H-pyrrolo[2,3-b]pyridin-1-yl)-N—((R)-2-fluoro-3-hydroxy-3-methylbutyl)-4-((1-fluoro-3-hydroxypropan-2-yl)amino)nicotinamide (131); (R)-6-(5-cyano-1H-pyrrolo[2,3-b]pyridin-1-yl)-4-(cyclopropylamino)-N-(2-fluoro-3-(methylamino)-3-oxopropyl)nicotinamide (132); (R)-6-(5-cyano-1H-pyrazolo[3,4-b]pyridin-1-yl)-N-(2-fluoro-3-hydroxy-3-methylbutyl)-4-(isopropylamino)nicotinamide (133); (R)-4-(cyclopropylamino)-N-(2-fluoro-3-hydroxy-3-methylbutyl)-6-(1H-pyrazolo[3,4-d]pyrimidin-1-yl)nicotinamide (134); (R)-6-(5-chloro-1H-pyrazolo[3,4-b]pyridin-1-yl)-N-(2-fluoro-3-hydroxy-3-methylbutyl)-4-((tetrahydro-2H-pyran-4-yl)amino) nicotinamide (135); (R)-6-(5-chloro-1H-pyrazolo[3,4-b]pyridin-1-yl)-4-(cyclopropylamino)-N-(2-fluoro-3-hydroxy-3-methylbutyl) nicotinamide (136); (R)-6-(5-chloro-1H-pyrazolo[3,4-b]pyridin-1-yl)-N-(2-fluoro-3-hydroxy-3-methylbutyl)-4-(isopropylamino)nicotinamide (137); (R)-6-(5-cyano-1H-pyrazolo[3,4-b]pyridin-1-yl)-4-(ethylamino)-N-(2-fluoro-3-hydroxy-3-methylbutyl)nicotinamide (138); (R)-6-(5-cyano-1H-pyrazolo[3,4-b]pyridin-1-yl)-4-(cyclopropylamino)-N-(2-fluoro-3-hydroxy-3-methylbutyl)nicotinamide (139); 6-(5-cyano-1H-pyrazolo[3,4-b]pyridin-1-yl)-4-(cyclopropylamino)-N-((trans)-4-(methylcarbamoyl)cyclohexyl)nicotinamide (140); (R)-6-(5-cyano-1H-pyrazolo[3,4-b]pyridin-1-yl)-N-(2-fluoro-3-hydroxy-3-methylbutyl)-4-((tetrahydro-2H-pyran-4-yl)amino)nicotinamide (141); 6-(5-cyano-1H-pyrazolo[3,4-b]pyridin-1-yl)-N—((R)-2-fluoro-3-hydroxy-3-methylbutyl)-4-((tetrahydro-2H-pyran-3-yl)amino)nicotinamide, diastereomer 1 (142); 6-(5-cyano-1H-pyrazolo[3,4-b]pyridin-1-yl)-N—((S)-2-fluoro-3-hydroxy-3-methylbutyl)-4-((tetrahydro-2H-pyran-3-yl)amino)nicotinamide, diastereomer 2 (143); (R)—N-(2-fluoro-3-hydroxy-3-methylbutyl)-4-(isopropylamino)-6-(1H-pyrazolo[3,4-d]pyrimidin-1-yl)nicotinamide (144); (R)-6-(5-cyano-1H-pyrazolo[3,4-b]pyridin-1-yl)-4-(cyclobutylamino)-N-(2-fluoro-3-hydroxy-3-methylbutyl)nicotinamide (145); 6-(5-cyano-1H-pyrazolo[3,4-b]pyridin-1-yl)-N-(3-hydroxy-3-methylbutyl)-4-(isopropylamino)nicotinamide (146); (R)-6-(5-cyano-1H-pyrazolo[3,4-b]pyridin-1-yl)-N-(2-fluoro-3-hydroxy-3-methylbutyl)-4-((2,2,2-trifluoroethyl)amino) nicotinamide (147); 6-(5-cyano-1H-pyrazolo[3,4-b]pyridin-1-yl)-N-((trans)-4-(2-hydroxypropan-2-yl)cyclohexyl)-4-(isopropylamino)nicotinamide (148); (R)—N-(3-ethyl-2-fluoro-3-hydroxypentyl)-4-(isopropylamino)-6-(1H-pyrazolo[3,4-d]pyrimidin-1-yl)nicotinamide (149); 6-(5-chloro-1H-pyrazolo[3,4-b]pyridin-1-yl)-N-((trans)-4-(2-hydroxypropan-2-yl)cyclohexyl)-4-(isopropylamino) nicotinamide (150); 6-(5-cyano-1H-pyrazolo[3,4-b]pyridin-1-yl)-N-(3-hydroxy-3-methylbutyl)-4-((tetrahydro-2H-pyran-4-yl)amino)nicotinamide (151); 6-(5-chloro-1H-pyrazolo[3,4-b]pyridin-1-yl)-4-(isopropylamino)-N-((trans)-4-(methylcarbamoyl)cyclohexyl)nicotinamide (152); (R)—N-(2-fluoro-3-hydroxy-3-methylbutyl)-6-(5-hydroxy-1H-pyrazolo[3,4-b]pyridin-1-yl)-4-(isopropylamino)nicotinamide (153); 6-(5-chloro-1H-pyrazolo[3,4-b]pyridin-1-yl)-4-(isopropylamino)-N-(2-morpholinoethyl)nicotinamide (154); (R)—N-(2-fluoro-3-hydroxy-3-methylbutyl)-4-(isopropylamino)-6-(5-methyl-1H-pyrazolo[3,4-b]pyridin-1-yl)nicotinamide (155); (R)-4-(cyclopropylamino)-6-(5-fluoro-1H-pyrazolo[3,4-b]pyridin-1-yl)-N-(2-fluoro-3-hydroxy-3-methylbutyl) nicotinamide (156); (R)-6-(5-fluoro-1H-pyrazolo[3,4-b]pyridin-1-yl)-N-(2-fluoro-3-hydroxy-3-methylbutyl)-4-(isopropylamino) nicotinamide (157); (R)-6-(5-bromo-1H-pyrazolo[3,4-b]pyridin-1-yl)-N-(2-fluoro-3-hydroxy-3-methylbutyl)-4-(isopropylamino)nicotinamide (158); 6-(5-cyano-1H-pyrazolo[3,4-b]pyridin-1-yl)-N—((R)-2-fluoro-3-hydroxy-3-methylbutyl)-4-(((trans)-4-hydroxycyclohexyl)amino)nicotinamide (159); 6-(5-cyano-1H-pyrazolo[3,4-b]pyridin-1-yl)-4-(isopropylamino)-N-((trans)-4-(methylcarbamoyl)cyclohexyl)nicotinamide (160); 6-(5-cyano-1H-pyrazolo[3,4-b]pyridin-1-yl)-4-(isopropylamino)-N-((trans)-4-(methylsulfonyl)cyclohexyl) nicotinamide (161); 6-(5-cyano-1H-pyrazolo[3,4-b]pyridin-1-yl)-4-(isopropylamino)-N-((trans)-4-(($^{2}H_{3}$)methylcarbamoyl)cyclohexyl)nicotinamide (162); (R)-6-(5-cyano-1H-pyrazolo[3,4-b]pyridin-1-yl)-N-(2-fluoro-3-hydroxy-3-methylbutyl)-4-((4-fluorocyclohexyl)amino) nicotinamide (163); N-((trans)-4-acetamidocyclohexyl)-6-(5-cyano-1H-pyrazolo[3,4-b]pyridin-1-yl)-4-(isopropylamino) nicotinamide (164); N-(2-amino-4,5,6,7-tetrahydrobenzo[d]thiazol-6-yl)-6-(5-cyano-1H-pyrazolo[3,4-b]pyridin-1-yl)-4-(isopropylamino)nicotinamide (165); 6-(5-cyano-1H-pyrazolo[3,4-b]pyridin-1-yl)-4-(isopropylamino)-N-((trans)-4-(methylsulfonamido)cyclohexyl)nicotinamide (166); 6-(5-cyano-1H-pyrazolo[3,4-b]pyridin-1-yl)-N-(2,2-difluoro-3-hydroxy-3-methylbutyl)-4-(isopropylamino)nicotinamide (167); (R)—N-(2-fluoro-3-hydroxy-3-methylbutyl)-4-(isopropylamino)-6-(3-(pyridazin-4-yl)-1H-pyrazol-1-yl)nicotinamide (168); (R)-6-(5-cyano-1H-pyrazolo[3,4-b]pyridin-1-yl)-4-((2,2-difluoro-3-hydroxy-3-methylbutyl)amino)-N-(2-fluoro-3-hydroxy-3-methylbutyl) nicotinamide (169); (R)—N-(2-fluoro-3-hydroxy-3-methylbutyl)-4-(isopropylamino)-6-(9H-purin-9-yl)nicotinamide (170); (R)-6-(2-amino-9H-purin-9-yl)-N-(2-fluoro-3-hydroxy-3-methylbutyl)-4-(isopropylamino) nicotinamide (171); (R)—N-(2-fluoro-3-hydroxy-3-methylbutyl)-6-(2-((2-hydroxyethyl)amino)-9H-purin-9-yl)-4-(isopropylamino)nicotinamide (172); 6-(5-cyano-1H-pyrrolo[2,3-b]pyridin-1-yl)-N-((1s,4s)-4-hydroxy-4-(1-methyl-1H-pyrazol-5-yl)cyclohexyl)-4-(isopropylamino)nicotinamide (173); 6-(5-cyano-1H-pyrrolo[2,3-b]pyridin-1-yl)-N-((1s,4s)-4-fluoro-4-(1-methyl-1H-pyrazol-5-yl)cyclohexyl)-4-(isopropylamino)nicotinamide (174); 6-(5-cyano-1H-pyrrolo[2,3-b]pyridin-1-yl)-N-((1s,4s)-4-hydroxy-4-(thiazol-2-yl)cyclohexyl)-4-(isopropylamino)nicotinamide (175); 6-(5-cyano-1H-pyrrolo[2,3-b]pyridin-1-yl)-N-((1s,4s)-4-hydroxy-4-(1-methyl-1H-imidazol-2-yl)cyclohexyl)-4-(isopropylamino) nicotinamide (176); 6-(5-cyano-1H-pyrrolo[2,3-b]pyridin-1-yl)-N-((1s,4s)-4-hydroxy-4-(pyridin-3-yl)cyclohexyl)-4-(isopropylamino)nicotinamide (177); 6-(5-cyano-1H-pyrrolo[2,3-b]pyridin-1-yl)-N-((1s,4s)-4-hydroxy-4-(pyridin-2-yl)cyclohexyl)-4-(isopropylamino)nicotinamide (178); 6-(5-cyano-1H-pyrrolo[2,3-b]pyridin-1-yl)-N-((1s,4s)-4-hydroxy-4-(pyridin-4-yl)cyclohexyl)-4-(isopropylamino)nicotinamide (179); 6-(5-cyano-1H-pyrrolo[2,3-b]pyridin-1-yl)-N-((1s,4s)-4-fluoro-4-(thiazol-2-yl)cyclohexyl)-4-(isopropylamino) nicotinamide (180); 6-(5-cyano-1H-pyrrolo[2,3-b]pyridin-1-yl)-N-((1s,4s)-4-fluoro-4-(1-methyl-1H-imidazol-2-yl)cyclohexyl)-4-(isopropylamino) nicotinamide (181); 6-(5-cyano-1H-pyrrolo[2,3-b]pyridin-1-yl)-N-((trans)-4-fluoro-4-(1-methyl-1H-imidazol-2-yl)cyclohexyl)-4-(isopropylamino)nicotinamide (182); 6-(5-cyano-1H-pyrrolo[2,3-b]pyridin-1-yl)-N-(2,4-dioxo-1,3-diazaspiro[4.5]decan-8-yl)-4-(isopropylamino)nicotinamide (183); (S)-6-(5-cyano-1H-pyrrolo[2,3-b]pyridin-1-yl)-4-(isopropylamino)-N-(4-(pyridin-4-yl)cyclohex-3-en-1-yl)nicotinamide (184); (R)-6-(2-(dimethylamino)-7H-pyrrolo[2,3-d]pyrimidin-7-yl)-N-(2-fluoro-3-hydroxy-3-methylbutyl)-4-(isopropylamino)nicotinamide (185); (R)-6-(2-amino-7H-pyrrolo[2,3-d]pyrimidin-7-yl)-N-(2-fluoro-3-hydroxy-3-methylbutyl)-4-(isopropylamino)nicotinamide (186); (R)—N-(2-fluoro-3-hydroxy-3-methylbutyl)-6-(2-(((2-hydroxy-2-methylpropyl)amino)-7H-pyrrolo[2,3-d]pyrimidin-7-yl)-4-(isopropylamino)nicotinamide (187); (R)—N-(2-fluoro-3-hydroxy-3-methylbutyl)-6-(2-((2-hydroxyethyl)amino)-7H-pyrrolo[2,3-d]pyrimidin-7-yl)-4-(isopropylamino) nicotinamide (188); N—((R)-2-fluoro-3-hydroxy-3-methylbutyl)-6-(2-((S)-3-hydroxypyrrolidin-1-yl)-7H-pyrrolo[2,3-d]pyrimidin-7-yl)-4-(isopropylamino) nicotinamide (189); N—((R)-2-fluoro-3-hydroxy-3-methylbutyl)-6-(2-((R)-3-hydroxypyrrolidin-1-yl)-7H-pyrrolo[2,3-d]pyrimidin-7-yl)-4-(isopropylamino) nicotinamide (190); (R)-4-(6-(5-cyano-1H-pyrazolo[3,4-b]pyridin-1-yl)-4-(isopropylamino)nicotinamido)-3-fluoro-2-methylbutan-2-yl dihydrogen phosphate (191); R)-6-(5-cyano-1H-pyrazolo[3,4-b]pyridin-1-yl)-N-(2-fluoro-3-hydroxy-3-methylbutyl)-4-(isopropylamino)nicotinamide, hydrochloride (192); (R)-4-(sec-butylamino)-6-(5-cyano-1H-pyrazolo[3,4-b]pyridin-1-yl)-N-(3-hydroxy-3-methylbutyl) nicotinamide (193); (R)—N-(2-fluoro-3-hydroxy-3-methylbutyl)-6-(5-hydroxy-1H-pyrazolo[3,4-b]pyridin-1-yl)-4-(isopropylamino)nicotinamide (194); (R)—N-(2-fluoro-3-hydroxy-3-methylbutyl)-4-(isopropylamino)-6-(5-methoxy-1H-pyrazolo[3,4-b]pyridin-1-yl)nicotinamide (195); (S)-6-(5-cyano-1H-pyrazolo[3,4-b]pyridin-1-yl)-N-(2-fluoro-3-hydroxy-3-methylbutyl)-4-(isopropylamino) nicotinamide (196); (R)-6-(5-cyano-1H-pyrazolo[3,4-b]pyridin-1-yl)-N-(2-fluoro-3-(isopropylamino)-3-oxopropyl)-4-(isopropylamino)nicotinamide (197); 6-(5-cyano-1H-pyrazolo[3,4-b]pyridin-1-yl)-4-(isopropylamino)-N-(4-methoxycyclohexyl)nicotinamide (198); N-butyl-6-(5-cyano-1H-pyrazolo[3,4-b]pyridin-1-yl)-4-(isopropylamino) nicotinamide (199); (R)-6-(5-cyano-1H-pyrazolo[3,4-b]pyridin-1-yl)-N-(2-fluoro-3-methoxy-3-methylbutyl)-4-(isopropylamino) nicotinamide (200); 6-(5-cyano-1H-pyrazolo[3,4-b]pyridin-1-yl)-4-(isopropylamino)-N-(3-morpholinopropyl)nicotinamide (201); 6-(5-cyano-1H-pyrazolo[3,4-b]pyridin-1-yl)-N—((R)-2-fluoro-3-hydroxy-3-methylbutyl)-4-(((2S)-3-fluorobutan-2-yl)amino) nicotinamide (202); 6-(5-cyano-1H-pyrazolo[3,4-b]pyridin-1-yl)-N—((R)-2-fluoro-3-hydroxy-3-methylbutyl)-4-(((2S)-3-fluorobutan-2-yl)amino)nicotinamide (203); 6-(5-cyano-1H-pyrazolo[3,4-b]pyridin-1-yl)-4-(isopropylamino)-N-(2-morpholinoethyl)nicotinamide (204); 6-(5-cyano-1H-pyrazolo[3,4-b]pyridin-1-yl)-N—((R)-2-fluoro-3-hydroxy-3-methylbutyl)-4-((4-fluorobutan-2-yl)amino)nicotinamide (205); 6-(5-cyano-1H-pyrazolo[3,4-b]pyridin-1-yl)-4-(isopropylamino)-N-(2-morpholino-2-oxoethyl) nicotinamide (206); methyl 3-(6-(5-cyano-1H-pyrazolo[3,4-b]pyridin-1-yl)-4-(isopropylamino)nicotinamido)propanoate (207); diethyl (2-(6-(5-cyano-1H-pyrazolo[3,4-b]pyridin-1-yl)-4-(isopropylamino)nicotinamido)ethyl)phosphonate (208); 6-(5-cyano-1H-pyrazolo[3,4-b]pyridin-1-yl)-N-((,1,1-dioxidotetrahydrothiophen-3-yl)methyl)-4-(isopropylamino) nicotinamide (209); (R)-6-(5-cyano-1H-pyrazolo[3,4-b]pyridin-1-yl)-N-(2-fluoro-3-trideuteromethoxy-3-methylbutyl)-4-(isopropylamino)nicotinamide (210); 6-(5-cyano-1H-pyrazolo[3,4-b]pyridin-1-yl)-N-(2-(1,1-dioxidothiomorpholino)ethyl)-4-(isopropylamino) nicotinamide (211); 6-(5-cyano-1H-pyrazolo[3,4-b]pyridin-1-yl)-N-(3-(ethylamino)-3-oxopropyl)-4-(isopropylamino) nicotinamide (212); N-(3-(1H-1,2,4-triazol-5-yl)propyl)-6-(5-cyano-1H-pyrazolo[3,4-b]pyridin-1-yl)-4-(isopropylamino) nicotinamide (213); N-((1R,4R)-4-(2-hydroxypropan-2-yl)cyclohexyl)-4-(isopropylamino)-6-(5-methyl-1H-pyrazolo[3,4-b]pyridin-1-yl)nicotinamide (214); (R)-6-(5-cyano-1H-pyrazolo[3,4-b]pyridin-1-yl)-N-(3-ethoxy-2-fluoro-3-methylbutyl)-4-(isopropylamino)nicotinamide (215); 6-(5-cyano-1H-pyrazolo[3,4-b]pyridin-1-yl)-4-(isopropylamino)-N-(6-morpholinopyridin-3-yl) nicotinamide (216); 6-(5-cyano-1H-pyrazolo[3,4-b]pyridin-1-yl)-N-(5-hydroxypyridin-2-yl)-4-(isopropylamino) nicotinamide (217); 6-(5-cyano-1H-pyrazolo[3,4-b]pyridin-1-yl)-4-(isopropylamino)-N-((1R,4R)-4-(2-(methylamino)-2-oxoethyl)cyclohexyl)nicotinamide (218); 6-(5-cyano-1H-pyrazolo[3,4-b]pyridin-1-yl)-4-(isopropylamino)-N-(2-(methylsulfonamido)ethyl)nicotinamide (219); 6-(5-cyano-1H-pyrazolo[3,4-b]pyridin-1-yl)-4-(isopropylamino)-N-(2-(tetrahydro-2H-pyran-2-yl)ethyl)nicotinamide (220); 6-(5-cyano-1H-pyrazolo[3,4-b]pyridin-1-yl)-4-(isopropylamino)-N-(5-morpholinopyridin-2-yl) nicotinamide (221); 6-(5-cyano-1H-pyrazolo[3,4-b]pyridin-1-yl)-4-(isopropylamino)-N-(4-morpholinophenyl) nicotinamide (222); 6-(5-cyano-1H-pyrazolo[3,4-b]pyridin-1-yl)-4-(isopropylamino)-N-(1H-pyrrolo[2,3-c]pyridin-5-yl)nicotinamide (223); 6-(5-cyano-1H-pyrazolo[3,4-b]pyridin-1-yl)-4-(isopropylamino)-N-(2-morpholinopyrimidin-5-yl)nicotinamide (224); 6-(5-cyano-1H-pyrazolo[3,4-b]pyridin-1-yl)-N-(5-(2-(dimethylamino)ethoxy)pyridin-2-yl)-4-(isopropylamino)nicotinamide (225); 6-(5-cyano-1H-pyrazolo[3,4-b]pyridin-1-yl)-4-(isopropylamino)-N-(4-(morpholinomethyl)phenyl)nicotinamide (226); 6-(5-cyano-1H-pyrazolo[3,4-b]pyridin-1-yl)-4-(isopropylamino)-N-(6-(piperazin-1-yl)pyridin-3-yl) nicotinamide (227); 6-(5-cyano-1H-pyrazolo[3,4-b]pyridin-1-yl)-N-(6-(dimethylamino)pyridin-3-yl)-4-(isopropylamino)nicotinamide (228); (R)-6-(5-cyano-1H-pyrazolo[3,4-b]pyridin-1-yl)-N-(2-fluoro-3-(methylamino)-3-oxopropyl)-4-(isopropylamino)nicotinamide (229); 6-(5-cyano-1H-pyrazolo[3,4-b]pyridin-1-yl)-N—((R)-2-fluoro-3-(((S)-1-hydroxypropan-2-yl)amino)-3-oxopropyl)-4-(isopropylamino) nicotinamide (230); (R)-6-(5-(difluoromethyl)-1H-pyrazolo[3,4-b]pyridin-1-yl)-N-(2-fluoro-3-hydroxy-3-methylbutyl)-4-(isopropylamino) nicotinamide (231); 6-(5-cyano-1H-pyrazolo[3,4-b]pyridin-1-yl)-N-((2R)-2-fluoro-3-hydroxy-4-methylpentyl)-4-(isopropylamino)nicotinamide (232); 6-(5-cyano-1H-pyrazolo[3,4-b]pyridin-1-yl)-N-((2R)-2-fluoro-3-hydroxy-4-methylpentyl)-4-(isopropylamino)nicotinamide (233); (R)-6-(5-cyano-1H-pyrazolo[3,4-b]pyridin-1-yl)-N-(2- fluoro-3-hydroxy-3-methylbutyl)-4-((1-hydroxy-2-methylpropan-2-yl)amino)nicotinamide (234); 6-(5-cyano-1H-pyrazolo[3,4-b]pyridin-1-yl)-N-(2-(4-hydroxytetrahydro-2H-pyran-4-yl)ethyl)-4-(isopropylamino) nicotinamide (235); 6-(5-cyano-1H-pyrazolo[3,4-b]pyridin-1-yl)-N-(5-(2-hydroxypropan-2-yl)pyridin-2-yl)-4-(isopropylamino)nicotinamide (236); 6-(5-cyano-1H-pyrazolo[3,4-b]pyridin-1-yl)-N-(2-(3-hydroxytetrahydrofuran-3-yl)ethyl)-4-(isopropylamino) nicotinamide (237); 6-(5-cyano-1H-pyrazolo[3,4-b]pyridin-1-yl)-N-(3-hydroxybutyl)-4-(isopropylamino)nicotinamide (238); 6-(5-cyano-1H-pyrazolo[3,4-b]pyridin-1-yl)-N-(3-hydroxybutyl)-4-(isopropylamino)nicotinamide (239); 6-(5-cyano-1H-pyrazolo[3,4-b]pyridin-1-yl)-4-(isopropylamino)-N-(1-(pyrimidin-2-yl)piperidin-4-yl)nicotinamide (240); 6-(5-cyano-1H-pyrazolo[3,4-b]pyridin-1-yl)-4-(isopropylamino)-N-(5-(4-methylpiperazin-1-yl)pyridin-2-yl)nicotinamide (241); 6-(5-cyano-1H-pyrazolo[3,4-b]pyridin-1-yl)-4-(isopropylamino)-N-(3-(4-methylpiperazin-1-yl)-3-oxopropyl) nicotinamide (242); 6-(5-cyano-1H-pyrazolo[3,4-b]pyridin-1-yl)-N-(2-fluoro-2-(3-hydroxyoxetan-3-yl)ethyl)-4-(isopropylamino) nicotinamide, racemic (243); 6-(5-cyano-1H-pyrazolo[3,4-b]pyridin-1-yl)-N-((1S,3S)-3-(2-hydroxypropan-2-yl) cyclopentyl)-4-(isopropylamino)nicotinamide (244); (R)-6-(5-cyano-1H-pyrazolo[3,4-b]pyridin-1-yl)-4-(isopropylamino)-N-(1-(methylsulfonyl)piperidin-3-yl) nicotinamide (245); (S)-6-(5-cyano-1H-pyrazolo[3,4-b]pyridin-1-yl)-4-(isopropylamino)-N-(1-(methylsulfonyl)piperidin-3-yl)nicotinamide (246); 6-(5-cyano-1H-pyrazolo[3,4-b]pyridin-1-yl)-4-(isopropylamino)-N-(6-(4-methoxypiperidin-1-yl)pyridin-3-yl)nicotinamide (247); 6-(5-cyano-1H-pyrazolo[3,4-b]pyridin-1-yl)-N-(2-fluoro-2-(3-hydroxyoxetan-3-yl)ethyl)-4-(isopropylamino)nicotinamide (248); 6-(5-cyano-1H-pyrazolo[3,4-b]pyridin-1-yl)-N-(2-fluoro-2-(3-hydroxyoxetan-3-yl)ethyl)-4-(isopropylamino) nicotinamide (249); 6-(5-cyano-1H-pyrazolo[3,4-b]pyridin-1-yl)-N-(2-(4-hydroxy-1-methylpiperidin-4-yl)ethyl)-4-(isopropylamino)nicotinamide (250); 6-(5-cyano-1H-pyrazolo[3,4-b]pyridin-1-yl)-4-(isopropylamino)-N-(4-sulfamoylphenethyl)nicotinamide (251); 6-(5-cyano-1H-pyrazolo[3,4-b]pyridin-1-yl)-N-(2-(1-hydroxycyclopentyl)ethyl)-4-(isopropylamino)nicotinamide (252); 6-(5-cyano-1H-pyrazolo[3,4-b]pyridin-1-yl)-N-(2-(4-hydroxy-1-(oxetan-3-yl)piperidin-4-yl)ethyl)-4-(isopropylamino) nicotinamide (253); 6-(5-cyano-1H-pyrazolo[3,4-b]pyridin-1-yl)-4-(isopropylamino)-N-(5-(4-methoxypiperidin-1-yl)pyridin-2-yl)nicotinamide (254); 6-(5-cyano-1H-pyrazolo[3,4-b]pyridin-1-yl)-N-(2-(3-hydroxypyrrolidin-3-yl)ethyl)-4-(isopropylamino)nicotinamide (255); (R)-6-(5-cyano-1H-pyrazolo[3,4-b]pyridin-1-yl)-N-(2-fluoro-3-morpholino-3-oxopropyl)-4-(isopropylamino)nicotinamide (256); (R)-6-(5-cyano-1H-pyrazolo[3,4-b]pyridin-1-yl)-N-(2-fluoro-3-(4-(methylsulfonyl)piperazin-1-yl)-3-oxopropyl)-4-(isopropylamino) nicotinamide (257); 6-(5-chloro-1H-pyrazolo[3,4-b]pyridin-1-yl)-N-(2-fluoro-2-(3-hydroxyoxetan-3-yl)ethyl)-4-(isopropylamino)nicotinamide (258); 6-(5-cyano-1H-pyrazolo[3,4-b]pyridin-1-yl)-4-(isopropylamino)-N-(2-(pyridin-4-yl)ethyl)nicotinamide (259); 6-(5-cyano-1H-pyrazolo[3,4-b]pyridin-1-yl)-N-(4-fluorophenethyl)-4-(isopropylamino)nicotinamide (260); 6-(5-cyano-1H-pyrazolo[3,4-b]pyridin-1-yl)-4-(isopropylamino)-N-(4-methoxyphenethyl)nicotinamide (261); (R)-6-(6-amino-5-cyano-1H-pyrazolo[3,4-b]pyridin-1-yl)-N-(2-fluoro-3-hydroxy-3-methylbutyl)-4-(isopropylamino) nicotinamide (262); 6-(6-amino-5-cyano-1H-pyrazolo[3,4-b]pyridin-1-yl)-N-((2-(2-hydroxypropan-2-yl)cyclopropyl)methyl)-4-(isopropylamino)nicotinamide (263); 6-(5-cyano-1H-pyrazolo[3,4-b]pyridin-1-yl)-4-(isopropylamino)-N-(3-(methylsulfonamido)butyl)nicotinamide (264); 6-(5-cyano-1H-pyrazolo[3,4-b]pyridin-1-yl)-4-(isopropylamino)-N-(3-(methylsulfonamido)butyl)nicotinamide (265); 6-(5-cyano-1H-pyrazolo[3,4-b]pyridin-1-yl)-4-(isopropylamino)-N-(2-(1-methylpiperidin-4-yl)ethyl)nicotinamide (266); N-((3-benzyl-1,2,4-oxadiazol-5-yl)methyl)-6-(5-cyano-1H-pyrazolo[3,4-b]pyridin-1-yl)-4-(isopropylamino) nicotinamide (267); 6-(5-cyano-1H-pyrazolo[3,4-b]pyridin-1-yl)-4-(isopropylamino)-N-(1-(oxetan-3-yl)-1H-pyrazol-4-yl)nicotinamide (268); 6-(5-cyano-1H-pyrazolo[3,4-b]pyridin-1-yl)-4-(isopropylamino)-N-(4-(N-(methylsulfonyl)methylsulfonamido)phenethyl)nicotinamide (269); N-(4-acetamidophenethyl)-6-(5-cyano-1H-pyrazolo[3,4-b]pyridin-1-yl)-4-(isopropylamino) nicotinamide (270); 6-(5-cyano-1H-pyrazolo[3,4-b]pyridin-1-yl)-4-(isopropylamino)-N-(1-(tetrahydro-2H-pyran-4-yl)-1H-pyrazol-4-yl)nicotinamide (271); 6-(5-cyano-1H-pyrazolo[3,4-b]pyridin-1-yl)-4-(isopropylamino)-N-(1-(isopropylsulfonyl)piperidin-4-yl)nicotinamide (272); 6-(5-cyano-1H-pyrazolo[3,4-b]pyridin-1-yl)-N-(1-isobutyrylpiperidin-4-yl)-4-(isopropylamino)nicotinamide (273); 6-(5-cyano-1H-pyrazolo[3,4-b]pyridin-1-yl)-N-((1S,4R)-4-((S)-2-hydroxypropanamido)cyclohexyl)-4-(isopropylamino)nicotinamide (274); 6-(5-cyano-1H-pyrazolo[3,4-b]pyridin-1-yl)-N-(2-(1-(2-cyanoacetyl)piperidin-4-yl)ethyl)-4-(isopropylamino)nicotinamide (275); 6-(5-cyano-1H-pyrazolo[3,4-b]pyridin-1-yl)-4-(isopropylamino)-N-(2-(pyridin-3-yl)ethyl)nicotinamide (276); 6-(5-cyano-1H-pyrazolo[3,4-b]pyridin-1-yl)-N-(2-(1,4-dihydroxy-4-methylcyclohexyl)ethyl)-4-(isopropylamino)nicotinamide (277); 6-(5-cyano-1H-pyrazolo[3,4-b]pyridin-1-yl)-4-(isopropylamino)-N-(1-(1-(methylsulfonyl) azetidine-3-carbonyl)piperidin-4-yl)nicotinamide (278); 6-(5-cyano-1H-pyrazolo[3,4-b]pyridin-1-yl)-N-(2-(4,4-difluoro-1-hydroxycyclohexyl)ethyl)-4-(isopropylamino) nicotinamide (279); (R)—N-(2-fluoro-3-hydroxy-3-methylbutyl)-4-(isopropylamino)-6-(5-((3-methylbutanamido)methyl)-1H-pyrazolo[3,4-b]pyridin-1-yl)nicotinamide (280); 6-(5-cyano-1H-pyrazolo[3,4-b]pyridin-1-yl)-4-(isopropylamino)-N-(1-(1-(methylsulfonyl) azetidin-3-yl)-1H-pyrazol-4-yl) nicotinamide (281); (R)-6-(6-amino-5-chloro-1H-pyrazolo[3,4-b]pyridin-1-yl)-N-(2-fluoro-3-hydroxy-3-methylbutyl)-4-(isopropylamino) nicotinamide (282); 4-((R)-sec-butylamino)-6-(5-cyano-1H-pyrazolo[3,4-b]pyridin-1-yl)-N—((R)-2-fluoro-3-hydroxy-3-methylbutyl) nicotinamide (283); 6-(6-amino-5-cyano-1H-pyrazolo[3,4-b]pyridin-1-yl)-4-((S)-sec-butylamino)-N—((R)-2-fluoro-3-hydroxy-3-methylbutyl)nicotinamide (284); 6-(5-cyano-1H-pyrazolo[3,4-b]pyridin-1-yl)-N-(1-(2,2-difluoroethyl)-1H-pyrazol-4-yl)-4-(isopropylamino)nicotinamide (285); (R)-4-(tert-butylamino)-6-(5-cyano-1H-pyrazolo[3,4-b]pyridin-1-yl)-N-(2-fluoro-3-hydroxy-3-methylbutyl)nicotinamide (286); 6-(5-cyano-1H-pyrazolo[3,4-b]pyridin-1-yl)-N-((1R,4R)-4-((R)-2-hydroxypropanamido)cyclohexyl)-4-(isopropylamino)nicotinamide (287); 4-(tert-butylamino)-6-(5-cyano-1H-pyrazolo[3,4-b]pyridin-1-yl)-N-(3-fluoro-3-methylbutyl)nicotinamide (288); 4-((S)-sec-butylamino)-6-(5-cyano-1H-pyrazolo[3,4-b]pyridin-1-yl)-N—((R)-2-fluoro-3-hydroxy-3-methylbutyl)nicotinamide (289); 6-(5-cyano-1H-pyrazolo[3,4-b]pyridin-1-yl)-N-(1-(ethylsulfonyl)piperidin-4-yl)-4-(isopropylamino) nicotinamide (290); 6-(5-cyano-1H-pyrazolo[3,4-b]pyridin-1-yl)-N-(2-(1-hydroxy-4-methoxycyclohexyl)ethyl)-4-(isopropylamino)nicotinamide (291); (R)-6-(5-cyano-1H-pyrazolo[3,4-b]pyridin-1-yl)-N-(2-fluoro-3-hydroxy-3- methylbutyl)-4-((1-methylcyclopropyl)amino)nicotinamide (292); (R)-6-(6-amino-5-cyano-1H-pyrazolo[3,4-b]pyridin-1-yl)-4-(tert-butylamino)-N-(2-fluoro-3-hydroxy-3-methylbutyl) nicotinamide (293); 6-(5-cyano-1H-pyrazolo[3,4-b]pyridin-1-yl)-N-(2-(dihydro-2H-pyran-4(3H)-ylidene)-2-fluoroethyl)-4-(isopropylamino)nicotinamide (294); (R)-6-(6-amino-5-cyano-1H-pyrazolo[3,4-b]pyridin-1-yl)-N-(2,3-difluoro-3-methylbutyl)-4-(isopropylamino)nicotinamide (295); 6-(5-cyano-1H-pyrazolo[3,4-b]pyridin-1-yl)-N-((3R,6S)-6-(2-hydroxypropan-2-yl)tetrahydro-2H-pyran-3-yl)-4-(isopropylamino) nicotinamide (296); 6-(5-cyano-1H-pyrazolo[3,4-b]pyridin-1-yl)-N—((R)-2-fluoro-3-hydroxy-3-methylbutyl)-4-((1,1,1-trifluoropropan-2-yl)amino) nicotinamide (297); 6-(5-cyano-1H-pyrazolo[3,4-b]pyridin-1-yl)-N-isopentyl-4-(isopropylamino)nicotinamide (298); 6-(6-amino-5-cyano-1H-pyrazolo[3,4-b]pyridin-1-yl)-N-(2-cyclopropylethyl)-4-(isopropylamino)nicotinamide (299); 6-(6-amino-5-cyano-1H-pyrazolo[3,4-b]pyridin-1-yl)-4-((R)-sec-butylamino)-N—((R)-2-fluoro-3-hydroxy-3-methylbutyl)nicotinamide (300); 6-(6-amino-5-cyano-1H-pyrazolo[3,4-b]pyridin-1-yl)-N—((R)-2-fluoro-3-hydroxy-3-methylbutyl)-4-((1,1,1-trifluoropropan-2-yl)amino) nicotinamide (301); 6-(5-cyano-1H-pyrazolo[3,4-b]pyridin-1-yl)-N-(2-cyclopropylethyl)-4-(isopropylamino) nicotinamide (302); 6-(6-amino-5-cyano-1H-pyrazolo[3,4-b]pyridin-1-yl)-N-isopentyl-4-(isopropylamino) nicotinamide (303); 6-(5-cyano-1H-pyrazolo[3,4-b]pyridin-1-yl)-N-(1-(2-hydroxy-2-methylpropyl)-1H-pyrazol-4-yl)-4-(isopropylamino)nicotinamide (304); 6-(6-amino-5-cyano-1H-pyrazolo[3,4-b]pyridin-1-yl)-4-(isopropylamino)-N-methylnicotinamide (305); 6-(5-cyano-1H-pyrazolo[3,4-b]pyridin-1-yl)-4-(isopropylamino)-N-(3-methyl-3-(methylsulfonamido)butyl)nicotinamide (306); 6-(6-amino-5-cyano-1H-pyrazolo[3,4-b]pyridin-1-yl)-N-(3-fluoro-3-methylbutyl)-4-(isopropylamino)nicotinamide (307); (R)-6-(5-cyano-1H-pyrazolo[3,4-b]pyridin-1-yl)-N-(2,3-difluoro-3-methylbutyl)-4-(isopropylamino)nicotinamide (308); 6-(5-cyano-1H-pyrazolo[3,4-b]pyridin-1-yl)-4-(isopropylamino)-N-(1-(N-isopropylsulfamoyl)piperidin-4-yl)nicotinamide (309); 6-(5-cyano-1H-pyrazolo[3,4-b]pyridin-1-yl)-4-(isopropylamino)-N-(2-(tetrahydro-2H-pyran-4-yl)ethyl)nicotinamide (310); N-(2-(1H-imidazol-4-yl)ethyl)-6-(5-cyano-1H-pyrazolo[3,4-b]pyridin-1-yl)-4-(isopropylamino) nicotinamide (311); (S)-6-(5-cyano-1H-pyrazolo[3,4-b]pyridin-1-yl)-N-(2-fluoro-3-methylbutyl)-4-(isopropylamino)nicotinamide (312); 6-(5-cyano-1H-pyrazolo[3,4-b]pyridin-1-yl)-4-(isopropylamino)-N-(1-(N-methylsulfamoyl)piperidin-4-yl)nicotinamide (313); (R)-6-(5-cyano-1H-pyrazolo[3,4-b]pyridin-1-yl)-N-(3-(difluoromethoxy)-2-fluoro-3-methylbutyl)-4-(isopropylamino)nicotinamide (314); (R)-6-(5-cyano-1H-pyrazolo[3,4-b]pyridin-1-yl)-N-(3,3-dicyclopropyl-2-fluoro-3-hydroxypropyl)-4-(isopropylamino) nicotinamide (315); 6-(5-cyano-1H-pyrazolo[3,4-b]pyridin-1-yl)-4-(isopropylamino)-N-((1R,4R)-4-(methylcarbamoyl)cyclohexyl) nicotinamide (316); N-((1R,4R)-4-acetamidocyclohexyl)-6-(6-amino-5-cyano-1H-pyrazolo[3,4-b]pyridin-1-yl)-4-(isopropylamino)nicotinamide (317); (S)-6-(5-cyano-1H-pyrazolo[3,4-b]pyridin-1-yl)-N-(2-cyclopropylethyl)-4-((1-hydroxypropan-2-yl)amino)nicotinamide (318); (S)—N-butyl-6-(5-cyano-1H-pyrazolo[3,4-b]pyridin-1-yl)-4-((1-hydroxypropan-2-yl)amino) nicotinamide (319); (S)-6-(5-cyano-1H-pyrazolo[3,4-b]pyridin-1-yl)-4-((1-hydroxypropan-2-yl)amino)-N-isopentylnicotinamide (320); (R)-6-(6-amino-5-cyano-1H-pyrazolo[3,4-b]pyridin-1-yl)-N-(2-fluoro-3-methoxy-3-methylbutyl)-4-(isopropylamino) nicotinamide (321); 6-(6-amino-5-cyano-1H-pyrazolo[3,4-b]pyridin-1-yl)-4-(isopropylamino)-N-(1-methylcyclopropyl)nicotinamide (322); (R)-6-(6-amino-5-cyano-1H-pyrazolo[3,4-b]pyridin-1-yl)-N-(1-cyclopropylethyl)-4-(isopropylamino)nicotinamide (323); 6-(6-amino-5-cyano-1H-pyrazolo[3,4-b]pyridin-1-yl)-N-cyclohexyl-4-(isopropylamino)nicotinamide (324); 6-(6-amino-5-cyano-1H-pyrazolo[3,4-b]pyridin-1-yl)-N-(1-cyanocyclopropyl)-4-(isopropylamino)nicotinamide (325); 6-(6-amino-5-cyano-1H-pyrazolo[3,4-b]pyridin-1-yl)-4-(isopropylamino)-N-propylnicotinamide (326); 6-(6-amino-5-cyano-1H-pyrazolo[3,4-b]pyridin-1-yl)-N-(cyclopent-2-en-1-yl)-4-(isopropylamino)nicotinamide (327); (R)-6-(6-amino-5-cyano-1H-pyrazolo[3,4-b]pyridin-1-yl)-N-(2-fluoropropyl)-4-(isopropylamino)nicotinamide (328); 6-(5-cyano-1H-pyrazolo[3,4-b]pyridin-1-yl)-N-(2-fluoro-2-(tetrahydro-2H-pyran-4-yl)ethyl)-4-(isopropylamino) nicotinamide (329); (R)-6-(5-chloro-1H-pyrazolo[3,4-b]pyridin-1-yl)-N-(2,3-difluoro-3-methylbutyl)-4-(isopropylamino)nicotinamide (330); 6-(5-cyano-1H-pyrazolo[3,4-b]pyridin-1-yl)-N-(2-(1-hydroxycyclopropyl)ethyl)-4-(isopropylamino) nicotinamide (331); 6-(5-cyano-1H-pyrazolo[3,4-b]pyridin-1-yl)-N-(3,3-difluorobutyl)-4-(isopropylamino)nicotinamide (332); (R)-6-(6-cyano-3H-imidazo[4,5-b]pyridin-3-yl)-N-(2-fluoro-3-hydroxy-3-methylbutyl)-4-(oxetan-3-ylamino)nicotinamide (333); N—((R)-2-fluoro-3-hydroxy-3-methylbutyl)-6-(2-(((R)-2-fluoro-3-hydroxy-3-methylbutyl)amino)-9H-purin-9-yl)-4-(isopropylamino)nicotinamide (334); (R)-6-(6-cyano-3H-imidazo[4,5-b]pyridin-3-yl)-N-(2-fluoro-3-hydroxy-3-methylbutyl)-4-(isopropylamino) nicotinamide (335); (R)-6-(6-cyano-3H-imidazo[4,5-b]pyridin-3-yl)-4-(cyclopropylamino)-N-(2-fluoro-3-hydroxy-3-methylbutyl) nicotinamide (336); (R)-6-(6-cyano-3H-imidazo[4,5-b]pyridin-3-yl)-N-(2-fluoro-3-hydroxy-3-methylbutyl)-4-(propylamino)nicotinamide (337); (R)-6-(6-cyano-3H-imidazo[4,5-b]pyridin-3-yl)-4-(cyclobutylamino)-N-(2-fluoro-3-hydroxy-3-methylbutyl)nicotinamide (338); (R)-6-(6-chloro-3H-imidazo[4,5-b]pyridin-3-yl)-N-(2-fluoro-3-hydroxy-3-methylbutyl)-4-(isopropylamino)nicotinamide (339); (R)-6-(6-chloro-3H-imidazo[4,5-b]pyridin-3-yl)-N-(2-fluoro-3-hydroxy-3-methylbutyl)-4-(oxetan-3-ylamino) nicotinamide (340); (R)-6-(5-amino-6-cyano-3H-imidazo[4,5-b]pyridin-3-yl)-N-(2-fluoro-3-hydroxy-3-methylbutyl)-4-(isopropylamino)nicotinamide (341); (R)-6-(6-cyano-3H-imidazo[4,5-b]pyridin-3-yl)-N-(2,3-difluoro-3-methylbutyl)-4-(isopropylamino)nicotinamide (342); (R)-6-(6-cyano-3H-imidazo[4,5-b]pyridin-3-yl)-N-(2-fluoro-3-hydroxy-3-methylbutyl)-4-((1-methylcyclopropyl)amino) nicotinamide (343); (R)-6-(6-cyano-3H-imidazo[4,5-b]pyridin-3-yl)-N-(2,3-difluoro-3-methylbutyl)-4-(oxetan-3-ylamino)nicotinamide (344); (R)-6-(6-cyano-3H-imidazo[4,5-b]pyridin-3-yl)-N-(2-fluoro-3-hydroxy-3-methylbutyl)-4-((tetrahydro-2H-pyran-4-yl)amino)nicotinamide (345); (R)-6-(2-amino-9H-purin-9-yl)-N-(2,3-difluoro-3-methylbutyl)-4-(isopropylamino)nicotinamide (346); (R)-6-(5-cyano-1H-pyrazolo[3,4-b]pyridin-1-yl)-4-((1-(2,2-difluoroethyl)-1H-pyrazol-4-yl)amino)-N-(2-fluoro-3-hydroxy-3-methylbutyl) nicotinamide (347); (R)-6-(5-cyano-1H-pyrazolo[3,4-b]pyridin-1-yl)-N-(2-fluoro-3-hydroxy-3-methylbutyl)-4-((1-(oxetan-3-yl)-1H-pyrazol-4-yl)amino)nicotinamide (348); (R)-6-(5-cyano-1H-pyrazolo[3,4-b]pyridin-1-yl)-N-(2-fluoro-3-hydroxy-3-methylbutyl)-4-((1-(tetrahydro-2H-pyran-4-yl)-1H-pyrazol-4-yl)amino)nicotinamide (349); (R)-6-(5-cyano-1H-pyrazolo[3,4-b]pyridin-1-yl)-N-(2-fluoro-3-hydroxy-3-methylbutyl)-4-((1-(2-hydroxy-2-methylpropyl)-1H-pyrazol-4-yl)amino)nicotinamide (350); (R)-6-(5-chloro-1H-pyrazolo[3,4-b]pyridin-1-yl)-4-((1-(2,2- difluoroethyl)-1H-pyrazol-4-yl)amino)-N-(2-fluoro-3-hydroxy-3-methylbutyl) nicotinamide (351); (R)-6-(5-chloro-1H-pyrazolo[3,4-b]pyridin-1-yl)-N-(2-fluoro-3-hydroxy-3-methylbutyl)-4-((1-(tetrahydro-2H-pyran-4-yl)-1H-pyrazol-4-yl)amino) nicotinamide (352); (R)-6-(5-cyano-1H-pyrazolo[3,4-b]pyridin-1-yl)-N-(2-fluoro-3-hydroxy-3-methylbutyl)-4-((1-(2,2,2-trifluoroethyl)-1H-pyrazol-4-yl)amino)nicotinamide (353); (R)-6-(5-chloro-1H-pyrazolo[3,4-b]pyridin-1-yl)-N-(2-fluoro-3-hydroxy-3-methylbutyl)-4-((1-(2,2,2-trifluoroethyl)-1H-pyrazol-4-yl)amino)nicotinamide (354); (R)-6-(5-cyano-1H-pyrazolo[3,4-b]pyridin-1-yl)-4-((1-ethyl-1H-pyrazol-4-yl)amino)-N-(2-fluoro-3-hydroxy-3-methylbutyl)nicotinamide (355); (R)-6-(5-cyano-1H-pyrazolo[3,4-b]pyridin-1-yl)-4-((1-(2-fluoro-2-methylpropyl)-1H-pyrazol-4-yl)amino)-N-(2-fluoro-3-hydroxy-3-methylbutyl)nicotinamide (356); (R)-6-(5-chloro-1H-pyrazolo[3,4-b]pyridin-1-yl)-4-((1-ethyl-1H-pyrazol-4-yl)amino)-N-(2-fluoro-3-hydroxy-3-methylbutyl) nicotinamide (357); (R)-6-(5-chloro-1H-pyrazolo[3,4-b]pyridin-1-yl)-N-(2-fluoro-3-hydroxy-3-methylbutyl)-4-((1-isopropyl-1H-pyrazol-4-yl)amino)nicotinamide (358); (R)-6-(6-chloro-3H-imidazo[4,5-b]pyridin-3-yl)-4-((1-(2,2-difluoroethyl)-1H-pyrazol-4-yl)amino)-N-(2-fluoro-3-hydroxy-3-methylbutyl)nicotinamide (359); (R)-6-(6-chloro-3H-imidazo[4,5-b]pyridin-3-yl)-N-(2-fluoro-3-hydroxy-3-methylbutyl)-4-((1-(2,2,2-trifluoroethyl)-1H-pyrazol-4-yl)amino)nicotinamide (360); (R)-6-(6-chloro-3H-imidazo[4,5-b]pyridin-3-yl)-4-((1-ethyl-1H-pyrazol-4-yl)amino)-N-(2-fluoro-3-hydroxy-3-methylbutyl) nicotinamide (361); (R)-6-(6-chloro-3H-imidazo[4,5-b]pyridin-3-yl)-N-(2-fluoro-3-hydroxy-3-methylbutyl)-4-((1-isopropyl-1H-pyrazol-4-yl)amino)nicotinamide (362); (R)-6-(5-cyano-1H-pyrazolo[3,4-b]pyridin-1-yl)-N-(2-fluoro-3-hydroxy-3-methylbutyl)-4-((1-(2-methoxyethyl)-1H-pyrazol-4-yl)amino)nicotinamide (363); (R)-6-(5-chloro-1H-pyrazolo[3,4-b]pyridin-1-yl)-N-(2-fluoro-3-hydroxy-3-methylbutyl)-4-((1-(2-methoxyethyl)-1H-pyrazol-4-yl)amino)nicotinamide (364); (R)-6-(5-cyano-1H-pyrazolo[3,4-b]pyridin-1-yl)-4-((1-(2,2-difluoropropyl)-1H-pyrazol-4-yl)amino)-N-(2-fluoro-3-hydroxy-3-methylbutyl) nicotinamide (365); (R)-6-(6-chloro-3H-imidazo[4,5-b]pyridin-3-yl)-N-(2-fluoro-3-hydroxy-3-methylbutyl)-4-((1-(2-methoxyethyl)-1H-pyrazol-4-yl)amino)nicotinamide (366); (R)-6-(5-chloro-1H-pyrazolo[3,4-b]pyridin-1-yl)-N-(2-fluoro-3-hydroxy-3-methylbutyl)-4-((1-(3-fluoropropyl)-1H-pyrazol-4-yl)amino) nicotinamide (367); (R)-6-(5-cyano-1H-pyrazolo[3,4-b]pyridin-1-yl)-N-(2-fluoro-3-hydroxy-3-methylbutyl)-4-((1-(3-fluoropropyl)-1H-pyrazol-4-yl)amino)nicotinamide (368); (R)-6-(5-chloro-1H-pyrazolo[3,4-b]pyridin-1-yl)-4-((1-(2,2-difluoropropyl)-1H-pyrazol-4-yl)amino)-N-(2-fluoro-3-hydroxy-3-methylbutyl)nicotinamide (369); (R)-6-(6-chloro-3H-imidazo[4,5-b]pyridin-3-yl)-N-(2-fluoro-3-hydroxy-3-methylbutyl)-4-((1-(3-fluoropropyl)-1H-pyrazol-4-yl)amino)nicotinamide (370); (R)-6-(5-cyano-1H-pyrrolo[2,3-b]pyridin-1-yl)-N-(2-fluoro-3-hydroxy-3-methylbutyl)-4-((1-(2,2,2-trifluoroethyl)-1H-pyrazol-4-yl)amino)nicotinamide (371); (R)-6-(5-cyano-1H-pyrrolo[2,3-b]pyridin-1-yl)-4-((1-ethyl-1H-pyrazol-4-yl)amino)-N-(2-fluoro-3-hydroxy-3-methylbutyl) nicotinamide (372); (R)-6-(5-cyano-1H-pyrrolo[2,3-b]pyridin-1-yl)-N-(2-fluoro-3-hydroxy-3-methylbutyl)-4-((1-(tetrahydro-2H-pyran-4-yl)-1H-pyrazol-4-yl)amino) nicotinamide (373); (R)-6-(6-chloro-3H-imidazo[4,5-b]pyridin-3-yl)-4-((1-(2-cyanoethyl)-1H-pyrazol-4-yl)amino)-N-(2-fluoro-3-hydroxy-3-methylbutyl)nicotinamide (374); (R)-6-(6-cyano-3H-imidazo[4,5-b]pyridin-3-yl)-4-((1-(2,2-difluoroethyl)-1H-pyrazol-4-yl)amino)-N-(2-fluoro-3-hydroxy-3-methylbutyl)nicotinamide (375); (R)-6-(5-cyano-1H-pyrazolo[3,4-b]pyridin-1-yl)-4-((1-(2-cyanoethyl)-1H-pyrazol-4-yl)amino)-N-(2-fluoro-3-hydroxy-3-methylbutyl)nicotinamide (376); (R)-6-(5-chloro-1H-pyrazolo[3,4-b]pyridin-1-yl)-4-((1-(2-cyanoethyl)-1H-pyrazol-4-yl)amino)-N-(2-fluoro-3-hydroxy-3-methylbutyl)nicotinamide (377); 6-(6-cyano-3H-imidazo[4,5-b]pyridin-3-yl)-N—((R)-2-fluoro-3-hydroxy-3-methylbutyl)-4-((1-(2-fluoropropyl)-1H-pyrazol-4-yl)amino)nicotinamide, racemic (378); 6-(6-cyano-3H-imidazo[4,5-b]pyridin-3-yl)-4-((1-(2-(difluoromethoxy)propyl)-1H-pyrazol-4-yl)amino)-N—((R)-2-fluoro-3-hydroxy-3-methylbutyl)nicotinamide (379); (R)-6-(5-cyano-1H-pyrazolo[3,4-b]pyridin-1-yl)-N-(2-fluoro-3-hydroxy-3-methylbutyl)-4-((1-propyl-1H-pyrazol-4-yl)amino) nicotinamide (380); (R)-6-(5-chloro-1H-pyrazolo[3,4-b]pyridin-1-yl)-N-(2-fluoro-3-hydroxy-3-methylbutyl)-4-((1-propyl-1H-pyrazol-4-yl)amino)nicotinamide (381); (R)-6-(6-chloro-3H-imidazo[4,5-b]pyridin-3-yl)-N-(2-fluoro-3-hydroxy-3-methylbutyl)-4-((1-propyl-1H-pyrazol-4-yl)amino)nicotinamide (382); (R)-6-(5-cyano-1H-pyrrolo[2,3-b]pyridin-1-yl)-N-(2-fluoro-3-hydroxy-3-methylbutyl)-4-((1-propyl-1H-pyrazol-4-yl)amino)nicotinamide (383); (R)-4-((1-(2,2-difluoroethyl)-1H-pyrazol-4-yl)amino)-6-(5-fluoro-1H-pyrazolo[3,4-b]pyridin-1-yl)-N-(2-fluoro-3-hydroxy-3-methylbutyl)nicotinamide (384); (R)-6-(5-cyano-1H-pyrazolo[3,4-b]pyridin-1-yl)-N-(2-fluoro-3-hydroxy-3-methylbutyl)-4-((1-(methylsulfonyl)-1H-pyrazol-4-yl)amino)nicotinamide (385); (R)-6-(5-cyano-1H-pyrazolo[3,4-b]pyridin-1-yl)-4-((1-(ethylcarbamoyl)-1H-pyrazol-4-yl)amino)-N-(2-fluoro-3-hydroxy-3-methylbutyl)nicotinamide (386); (R)-6-(5-cyano-1H-pyrazolo[3,4-b]pyridin-1-yl)-N-(2-fluoro-3-hydroxy-3-methylbutyl)-4-((1-methyl-1H-pyrazol-4-yl)amino)nicotinamide (387); 6-(5-cyano-1H-pyrazolo[3,4-b]pyridin-1-yl)-4-((1-(2,2-difluoroethyl)-1H-pyrazol-4-yl)amino)-N-isopropylnicotinamide (388); 6-(5-cyano-1H-pyrazolo[3,4-b]pyridin-1-yl)-4-((1-(2,2-difluoroethyl)-1H-pyrazol-4-yl)amino)-N-propylnicotinamide (389); N-(tert-butyl)-6-(5-cyano-1H-pyrazolo[3,4-b]pyridin-1-yl)-4-((1-(2,2-difluoroethyl)-1H-pyrazol-4-yl)amino)nicotinamide (390); 6-(5-cyano-1H-pyrazolo[3,4-b]pyridin-1-yl)-4-((1-(2,2-difluoroethyl)-1H-pyrazol-4-yl)amino)-N-isobutylnicotinamide (391); 6-(5-cyano-1H-pyrazolo[3,4-b]pyridin-1-yl)-4-((1-(2,2-difluoroethyl)-1H-pyrazol-4-yl)amino)-N-(2-ethoxyethyl)nicotinamide (392); 6-(5-cyano-1H-pyrazolo[3,4-b]pyridin-1-yl)-4-((1-(2,2-difluoroethyl)-1H-pyrazol-4-yl)amino)-N-ethylnicotinamide (393); (R)-6-(5-chloro-1H-pyrazolo[3,4-b]pyridin-1-yl)-4-((1-(difluoromethyl)-1H-pyrazol-4-yl)amino)-N-(2-fluoro-3-hydroxy-3-methylbutyl) nicotinamide (394); (R)-6-(5-cyano-1H-pyrazolo[3,4-b]pyridin-1-yl)-N-(2,3-difluoro-3-methylbutyl)-4-((1-(2,2-difluoroethyl)-1H-pyrazol-4-yl)amino)nicotinamide (395); 6-(5-cyano-1H-pyrazolo[3,4-b]pyridin-1-yl)-4-((1-(2,2-difluoroethyl)-1H-pyrazol-4-yl)amino)-N-((1R,4R)-4-(2-hydroxypropan-2-yl)cyclohexyl)nicotinamide (396); 6-(5-cyano-1H-pyrazolo[3,4-b]pyridin-1-yl)-N-(2,2-difluoro-3-hydroxy-3-methylbutyl)-4-((1-(2,2-difluoroethyl)-1H-pyrazol-4-yl)amino)nicotinamide (397); (R)-6-(6-chloro-3H-imidazo[4,5-b]pyridin-3-yl)-N-(2-fluoro-3-hydroxy-3-methylbutyl)-4-((1-methyl-1H-pyrazol-4-yl)amino)nicotinamide (398); (R)-6-(5-cyano-1H-pyrrolo[2,3-b]pyridin-1-yl)-N-(2-fluoro-3-hydroxy-3-methylbutyl)-4-((1-methyl-1H-pyrazol-4-yl)amino) nicotinamide (399); (R)-6-(6-chloro-3H-imidazo[4,5-b]pyridin-3-yl)-4-((1-(difluoromethyl)-1H-pyrazol-4-yl)amino)-N-(2-fluoro-3-hydroxy-3-methylbutyl) nicotinamide (400); (R)-6-(6-cyano-3H-imidazo[4,5-b]pyridin-3-yl)-4-

((1-(difluoromethyl)-1H-pyrazol-4-yl)amino)-N-(2-fluoro-3-hydroxy-3-methylbutyl) nicotinamide (401); (R)-6-(6-chloro-3H-imidazo[4,5-b]pyridin-3-yl)-N-(2,3-difluoro-3-methylbutyl)-4-((1-(2,2-difluoroethyl)-1H-pyrazol-4-yl)amino)nicotinamide (402); (R)-6-(6-cyano-3H-imidazo[4,5-b]pyridin-3-yl)-N-(2,3-difluoro-3-methylbutyl)-4-((1-(2,2-difluoroethyl)-1H-pyrazol-4-yl)amino)nicotinamide (403); (R)-6-(5-cyano-1H-pyrazolo[3,4-b]pyridin-1-yl)-4-((3-cyclopropyl-1H-pyrazol-5-yl)amino)-N-(2-fluoro-3-hydroxy-3-methylbutyl)nicotinamide (404); (R)-6-(5-cyano-1H-pyrazolo[3,4-b]pyridin-1-yl)-N-(2-fluoro-3-hydroxy-3-methylbutyl)-4-((3-methyl-1H-pyrazol-5-yl)amino)nicotinamide (405); (R)-6-(5-cyano-1H-pyrazolo[3,4-b]pyridin-1-yl)-N-(2-fluoro-3-hydroxy-3-methylbutyl)-4-((3-isopropyl-1H-pyrazol-5-yl)amino)nicotinamide (406); (R)-6-(5-cyano-1H-pyrazolo[3,4-b]pyridin-1-yl)-4-((1-(2,2-difluoroethyl)-1H-pyrazol-3-yl)amino)-N-(2-fluoro-3-hydroxy-3-methylbutyl)nicotinamide (407); (R)-6-(5-cyano-1H-pyrazolo[3,4-b]pyridin-1-yl)-N-(2-fluoro-3-hydroxy-3-methylbutyl)-4-((1-(2,2,2-trifluoroethyl)-1H-pyrazol-3-yl)amino)nicotinamide (408); (R)-6-(5-cyano-1H-pyrazolo[3,4-b]pyridin-1-yl)-N-(2-fluoro-3-hydroxy-3-methylbutyl)-4-((1-methyl-1H-pyrazol-5-yl)amino)nicotinamide (409); (R)-6-(5-cyano-1H-pyrazolo[3,4-b]pyridin-1-yl)-N-(2-fluoro-3-hydroxy-3-methylbutyl)-4-((1-(pyrimidin-2-yl)-1H-pyrazol-4-yl)amino) nicotinamide (410); (R)-6-(5-cyano-1H-pyrazolo[3,4-b]pyridin-1-yl)-N-(2-fluoro-3-hydroxy-3-methylbutyl)-4-((1-(5-fluoropyrimidin-2-yl)-1H-pyrazol-4-yl)amino) nicotinamide (411); (R)-6-(5-cyano-1H-pyrazolo[3,4-b]pyridin-1-yl)-N-(2-fluoro-3-hydroxy-3-methylbutyl)-4-((3-phenyl-1H-pyrazol-5-yl)amino)nicotinamide (412); (R)-6-(5-cyano-1H-pyrazolo[3,4-b]pyridin-1-yl)-4-((1,3-dimethyl-1H-pyrazol-5-yl)amino)-N-(2-fluoro-3-hydroxy-3-methylbutyl)nicotinamide (413); 6-(5-cyano-1H-indol-1-yl)-N-((1R,4R)-4-(2-hydroxypropan-2-yl)cyclohexyl)-4-(isopropylamino)nicotinamide (414); 6-(5-cyano-1H-pyrrolo[2,3-b]pyridin-1-yl)-N-(4-hydroxybicyclo[2.2.1]heptan-1-yl)-4-(isopropylamino)nicotinamide (415); (R)-6-(5-cyano-1H-pyrrolo[2,3-b]pyridin-1-yl)-N-(2-fluoro-3-hydroxy-3-methylbutyl)-4-((3-sulfamoylphenyl)amino)nicotinamide (416); N-(3-(tert-butoxy)propyl)-6-(5-cyano-1H-pyrrolo[2,3-b]pyridin-1-yl)-4-(isopropylamino) nicotinamide (417); (R)-6-(5-cyano-1H-pyrrolo[2,3-b]pyridin-1-yl)-N-(2-fluoro-3-hydroxy-3-methylbutyl)-4-((3-methoxyphenyl)amino)nicotinamide (418); (R,E)-6-(5-cyano-1H-pyrrolo[2,3-b]pyridin-1-yl)-N-(2-fluoro-3-hydroxy-3-methylbutyl)-4-((3-hydroxy-3-methylbut-1-en-1-yl)amino)nicotinamide (419); 6-(5-cyano-1H-pyrrolo[2,3-b]pyridin-1-yl)-N-((1R,4R)-4-fluoro-4-(1-methyl-1H-imidazol-2-yl)cyclohexyl)-4-(isopropylamino) nicotinamide (420); (R)-4-(benzo[d]oxazol-6-ylamino)-6-(5-cyano-1H-pyrrolo[2,3-b]pyridin-1-yl)-N-(2-fluoro-3-hydroxy-3-methylbutyl)nicotinamide (421); 6-(5-cyano-1H-pyrrolo[2,3-b]pyridin-1-yl)-N—((R)-2-fluoro-3-hydroxy-3-methylbutyl)-4-((3-hydroxybutyl)amino)nicotinamide (422); (R)-6-(5-cyano-1H-pyrrolo[2,3-b]pyridin-1-yl)-N-(2-fluoro-3-hydroxy-3-methylbutyl)-4-(((6-methylpyridin-3-yl)methyl)amino) nicotinamide (423); (R)-6-(5-cyano-1H-pyrrolo[2,3-b]pyridin-1-yl)-N-(2-fluoro-3-hydroxy-3-methylbutyl)-4-((1-methyl-1H-pyrazol-5-yl)amino) nicotinamide (424); (R)-6-(5-cyano-1H-pyrrolo[2,3-b]pyridin-1-yl)-N-(2-fluoro-3-hydroxy-3-methylbutyl)-4-((3,3,3-trifluoropropyl)amino)nicotinamide (425); 6-(5-cyano-1H-pyrrolo[2,3-b]pyridin-1-yl)-N—((R)-2-fluoro-3-hydroxy-3-methylbutyl)-4-((4-fluorobutan-2-yl)amino) nicotinamide (426); 6-(5-cyano-1H-pyrrolo[2,3-b]pyridin-1-yl)-N—((R)-2-fluoro-3-hydroxy-3-methylbutyl)-4-((4-fluorobutan-2-yl)amino)nicotinamide (427); 4-(cyclopropylamino)-6-(5-fluoro-1H-pyrrolo[2,3-b]pyridin-1-yl)-N-((1R,4R)-4-(2-hydroxypropan-2-yl)cyclohexyl) nicotinamide (428); 6-(5-cyano-1H-pyrrolo[2,3-b]pyridin-1-yl)-4-(cyclopropylamino)-N-((1R,4R)-4-(2-hydroxypropan-2-yl)cyclohexyl) nicotinamide (429); (R)-6-(5-cyano-1H-pyrrolo[2,3-b]pyridin-1-yl)-4-((3-cyano-2-fluorophenyl)amino)-N-(2-fluoro-3-hydroxy-3-methylbutyl)nicotinamide (430); (R)-4-((3-(1H-imidazol-2-yl)phenyl)amino)-6-(5-cyano-1H-pyrrolo[2,3-b]pyridin-1-yl)-N-(2-fluoro-3-hydroxy-3-methylbutyl)nicotinamide (431); 6-(5-fluoro-1H-pyrrolo[2,3-b]pyridin-1-yl)-4-(((S)-1-hydroxypropan-2-yl)amino)-N-((1R,4S)-4-(2-hydroxypropan-2-yl)cyclohexyl) nicotinamide (432); (R)-6-(5-cyano-1H-pyrrolo[2,3-b]pyridin-1-yl)-4-((4-(1-ethyl-1H-tetrazol-5-yl)phenyl)amino)-N-(2-fluoro-3-hydroxy-3-methylbutyl) nicotinamide (433); (R)-6-(5-cyano-1H-pyrrolo[2,3-b]pyridin-1-yl)-N-(2-fluoro-3-methoxy-3-methylbutyl)-4-(isopropylamino)nicotinamide (434); 6-(5-cyano-1H-pyrrolo[2,3-b]pyridin-1-yl)-4-(((R)-2-fluoro-3-(isopropylamino)-3-oxopropyl)amino)-N—((R)-2-fluoro-3-hydroxy-3-methylbutyl)nicotinamide (435); (R)-4-((1H-benzo[d][1,2,3]triazol-6-yl)amino)-6-(5-cyano-1H-pyrrolo[2,3-b]pyridin-1-yl)-N-(2-fluoro-3-hydroxy-3-methylbutyl)nicotinamide (436); (R)-6-(5-cyano-1H-pyrrolo[2,3-b]pyridin-1-yl)-N-(2-fluoro-3-hydroxy-3-methylbutyl)-4-(oxetan-3-ylamino)nicotinamide (437); (R)-4-((1H-indazol-5-yl)amino)-6-(5-cyano-1H-pyrrolo[2,3-b]pyridin-1-yl)-N-(2-fluoro-3-hydroxy-3-methylbutyl) nicotinamide (438); (R)-4-((1H-benzo[d]imidazol-6-yl)amino)-6-(5-cyano-1H-pyrrolo[2,3-b]pyridin-1-yl)-N-(2-fluoro-3-hydroxy-3-methylbutyl) nicotinamide (439); 6-(5-cyano-1H-pyrrolo[2,3-b]pyridin-1-yl)-N—((R)-2-fluoro-3-hydroxy-3-methylbutyl)-4-(((R)-tetrahydrofuran-3-yl)amino)nicotinamide (440); 6-(5-cyano-1H-pyrrolo[2,3-b]pyridin-1-yl)-N—((R)-2-fluoro-3-hydroxy-3-methylbutyl)-4-(((S)-tetrahydrofuran-3-yl)amino)nicotinamide (441); (R)-6-(5-cyano-1H-pyrrolo[2,3-b]pyridin-1-yl)-N-(2-fluoro-3-trideuteromethoxy-3-methylbutyl)-4-(isopropylamino) nicotinamide (442); 6-(5-cyano-1H-pyrrolo[2,3-b]pyridin-1-yl)-N—((R)-2-fluoro-3-trideuteromethoxy-3-methylbutyl)-4-((3-(hydroxymethyl)cyclohexyl)amino)nicotinamide (443); 6-(5-cyano-1H-pyrrolo[2,3-b]pyridin-1-yl)-N-(4-(1-cyclopropyl-1-hydroxyethyl)cyclohexyl)-4-(isopropylamino)nicotinamide (444); 6-(5-cyano-1H-pyrrolo[2,3-b]pyridin-1-yl)-N—((R)-2-fluoro-3-hydroxy-3-methylbutyl)-4-((3-(hydroxymethyl)cyclohexyl)amino) nicotinamide (445); 6-(5-cyano-1H-pyrrolo[2,3-b]pyridin-1-yl)-N-(4-(1-cyclopropyl-1-hydroxyethyl)cyclohexyl)-4-(isopropylamino)nicotinamide (446); 6-(5-cyano-1H-pyrrolo[2,3-b]pyridin-1-yl)-4-(isopropylamino)-N-(1-(methylsulfonyl) piperidin-4-yl)nicotinamide (447); (R)-6-(5-cyano-1H-pyrrolo[2,3-b]pyridin-1-yl)-N-(3-ethoxy-2-fluoro-3-methylbutyl)-4-(isopropylamino)nicotinamide (448); 6-(5-cyano-1H-pyrrolo[2,3-b]pyridin-1-yl)-N—((R)-2-fluoro-3-hydroxy-3-methylbutyl)-4-(((R)-1-(5-fluoropyrimidin-2-yl)pyrrolidin-3-yl)amino)nicotinamide (449); 6-(5-cyano-1H-pyrrolo[2,3-b]pyridin-1-yl)-4-(((R)-1-cyclopropylethyl)amino)-N—((R)-2-fluoro-3-hydroxy-3-methylbutyl)nicotinamide (450); 6-(5-cyano-1H-pyrrolo[2,3-b]pyridin-1-yl)-4-(((S)-1-cyclopropylethyl)amino)-N—((R)-2-fluoro-3-hydroxy-3-methylbutyl)nicotinamide (451); 6-(5-cyano-1H-pyrrolo[2,3-b]pyridin-1-yl)-4-(isopropylamino)-N-(2-(morpholine-4-sulfonamido)ethyl)nicotinamide (452); 6-(5-cyano-1H-pyrrolo[2,3-b]pyridin-1-yl)-4-(cyclopropylamino)-N-(2-(methylsulfonamido)ethyl) nicotinamide (453); 6-(5-cyano-1H-pyrrolo[2,3-b]pyridin-1-yl)-N—((R)-2-fluoro-3-hydroxy-3-methylbutyl)-4-((4- methylpentan-2-yl)amino)nicotinamide (454); 6-(5-cyano-1H-pyrrolo[2,3-b]pyridin-1-yl)-N—((R)-2-fluoro-3-hydroxy-3-methylbutyl)-4-(((3R,4S)-4-hydroxytetrahydrofuran-3-yl)amino)nicotinamide (455); 6-(5-cyano-1H-pyrrolo[2,3-b]pyridin-1-yl)-N—((R)-2-fluoro-3-hydroxy-3-methylbutyl)-4-(((3R,4S)-4-hydroxytetrahydrofuran-3-yl)amino) nicotinamide (456); (R)-tert-butyl 3-((2-(5-cyano-1H-pyrrolo[2,3-b]pyridin-1-yl)-5-((2-fluoro-3-hydroxy-3-methylbutyl)carbamoyl)pyridin-4-yl)amino)azetidine-1-carboxylate (457); 6-(5-cyano-1H-pyrrolo[2,3-b]pyridin-1-yl)-N—((R)-2-fluoro-3-hydroxy-3-methylbutyl)-4-(((3R,4S)-4-fluorotetrahydrofuran-3-yl)amino)nicotinamide (458); 6-(5-cyano-1H-pyrrolo[2,3-b]pyridin-1-yl)-N—((R)-2-fluoro-3-hydroxy-3-methylbutyl)-4-(((3R,4S)-4-fluorotetrahydrofuran-3-yl)amino) nicotinamide (459); 4-((2-(1H-imidazol-4-yl)cyclopropyl)amino)-6-(5-cyano-1H-pyrrolo[2,3-b]pyridin-1-yl)-N—((R)-2-fluoro-3-hydroxy-3-methylbutyl)nicotinamide (460); 6-(5-cyano-1H-pyrrolo[2,3-b]pyridin-1-yl)-N—((R)-2-fluoro-3-hydroxy-3-methylbutyl)-4-((3-hydroxybutyl)amino)nicotinamide (461); 6-(5-cyano-1H-pyrrolo[2,3-b]pyridin-1-yl)-N—((R)-2-fluoro-3-hydroxy-3-methylbutyl)-4-((3-hydroxybutyl)amino)nicotinamide (462); (R)-6-(5-cyano-1H-pyrrolo[2,3-b]pyridin-1-yl)-N-(2-fluoro-3-hydroxy-3-methylbutyl)-4-((1-(methylsulfonyl) piperidin-4-yl)amino)nicotinamide (463); (R)-6-(5-cyano-1H-pyrrolo[2,3-b]pyridin-1-yl)-N-(2-fluoro-3-hydroxy-3-methylbutyl)-4-((1-phenylpiperidin-4-yl)amino)nicotinamide (464); 6-(5-cyano-1H-pyrrolo[2,3-b]pyridin-1-yl)-N—((R)-2-fluoro-3-hydroxy-3-methylbutyl)-4-(((R)-1-(methylsulfonyl)pyrrolidin-3-yl)amino)nicotinamide (465); 6-(5-cyano-1H-pyrrolo[2,3-b]pyridin-1-yl)-N—((R)-2-fluoro-3-hydroxy-3-methylbutyl)-4-((R)-pyrrolidin-3-ylamino)nicotinamide (466); 6-(5-cyano-1H-pyrrolo[2,3-b]pyridin-1-yl)-4-(isopropylamino)-N-(2-(4-methylpiperazin-1-yl)-2-oxoethyl)nicotinamide (467); (R)-4-((1-acetylazetidin-3-yl)amino)-6-(5-cyano-1H-pyrrolo[2,3-b]pyridin-1-yl)-N-(2-fluoro-3-hydroxy-3-methylbutyl)nicotinamide (468); 4-(((R)-1-acetylpyrrolidin-3-yl)amino)-6-(5-cyano-1H-pyrrolo[2,3-b]pyridin-1-yl)-N—((R)-2-fluoro-3-hydroxy-3-methylbutyl) nicotinamide (469); (R)-4-((1-acetylpiperidin-4-yl)amino)-6-(5-cyano-1H-pyrrolo[2,3-b]pyridin-1-yl)-N-(2-fluoro-3-hydroxy-3-methylbutyl)nicotinamide (470); (R)-4-((4-(1H-imidazol-1-yl)phenyl)amino)-6-(5-cyano-1H-pyrrolo[2,3-b]pyridin-1-yl)-N-(2-fluoro-3-hydroxy-3-methylbutyl) nicotinamide (471); (R)-6-(5-cyano-1H-pyrrolo[2,3-b]pyridin-1-yl)-N-(2-fluoro-3-hydroxy-3-methylbutyl)-4-((1-(5-fluoropyrimidin-2-yl)azetidin-3-yl)amino)nicotinamide (472); 6-(5-cyano-1H-pyrrolo[2,3-b]pyridin-1-yl)-N—((R)-2-fluoro-3-hydroxy-3-methylbutyl)-4-(((R)-1-(3,3,3-trifluoropropanoyl)pyrrolidin-3-yl)amino)nicotinamide (473); (R)-methyl 3-((2-(5-cyano-1H-pyrrolo[2,3-b]pyridin-1-yl)-5-(((R)-2-fluoro-3-hydroxy-3-methylbutyl)carbamoyl)pyridin-4-yl)amino)pyrrolidine-1-carboxylate (474); (R)-1-(4-((azetidin-3-ylmethyl)amino)-5-((2-fluoro-3-hydroxy-3-methylbutyl)carbamoyl)pyridin-2-yl)-1H-pyrrolo[2,3-b]pyridine-5-carboxamide (475); (R)-6-(5-cyano-1H-pyrrolo[2,3-b]pyridin-1-yl)-N-(2-fluoro-3-hydroxy-3-methylbutyl)-4-((1-(methylsulfonyl)azetidin-3-yl)amino)nicotinamide (476); 6-(5-cyano-1H-pyrrolo[2,3-b]pyridin-1-yl)-4-(((R)-1-(2-cyanoacetyl)pyrrolidin-3-yl)amino)-N—((R)-2-fluoro-3-hydroxy-3-methylbutyl)nicotinamide (477); (S)-6-(5-cyano-1H-pyrrolo[2,3-b]pyridin-1-yl)-4-((1-hydroxypropan-2-yl)amino)-N-(2-(methylsulfonyl)ethyl)nicotinamide (478); 6-(5-cyano-1H-pyrrolo[2,3-b]pyridin-1-yl)-N-(2-(methylsulfonamido)ethyl)-4-((tetrahydro-2H-pyran-4-yl)amino)nicotinamide (479); (R)-6-(5-cyano-1H-pyrrolo[2,3-b]pyridin-1-yl)-N-(2-fluoro-3-hydroxy-3-methylbutyl)-4-((2-morpholinoethyl)amino)nicotinamide (480); (R)-methyl 3-((2-(5-cyano-1H-pyrrolo[2,3-b]pyridin-1-yl)-5-((2-fluoro-3-hydroxy-3-methylbutyl)carbamoyl)pyridin-4-yl)amino)azetidine-1-carboxylate (481); (R)-6-(5-cyano-1H-pyrrolo[2,3-b]pyridin-1-yl)-N-(2-fluoro-3-hydroxy-3-methylbutyl)-4-(((tetrahydro-2H-pyran-4-yl)methyl)amino)nicotinamide (482); 6-(5-cyano-1H-pyrrolo[2,3-b]pyridin-1-yl)-N—((R)-2-fluoro-3-hydroxy-3-methylbutyl)-4-((2-(3-methylmorpholino)ethyl)amino)nicotinamide (483); 6-(5-cyano-1H-pyrrolo[2,3-b]pyridin-1-yl)-4-((4,4-difluorotetrahydrofuran-3-yl)amino)-N—((R)-2-fluoro-3-hydroxy-3-methylbutyl)nicotinamide (484); 6-(5-cyano-1H-pyrrolo[2,3-b]pyridin-1-yl)-4-((4,4-difluorotetrahydrofuran-3-yl)amino)-N—((R)-2-fluoro-3-hydroxy-3-methylbutyl)nicotinamide (485); 4-(((1R,4R)-4-carbamoylcyclohexyl)amino)-6-(5-cyano-1H-pyrrolo[2,3-b]pyridin-1-yl)-N—((R)-2-fluoro-3-hydroxy-3-methylbutyl) nicotinamide (486); 6-(5-cyano-1H-pyrrolo[2,3-b]pyridin-1-yl)-N-(2-(1-hydroxycyclopentyl)ethyl)-4-(isopropylamino)nicotinamide (487); 6-(5-cyano-1H-pyrrolo[2,3-b]pyridin-1-yl)-N—((R)-2-fluoro-3-hydroxy-3-methylbutyl)-4-((3-((2,2,2-trifluoroethyl)amino)cyclopentyl)amino)nicotinamide (488); 6-(5-cyano-1H-pyrrolo [2,3-b]pyridin-1-yl)-N—((R)-2-fluoro-3-hydroxy-3-methylbutyl)-4-((3-((2,2,2-trifluoroethyl)amino)cyclopentyl)amino)nicotinamide (489); 4-((3-aminocyclopentyl)amino)-6-(5-cyano-1H-pyrrolo[2,3-b]pyridin-1-yl)-N—((R)-2-fluoro-3-hydroxy-3-methylbutyl) nicotinamide (490); 4-((3-aminocyclopentyl)amino)-6-(5-cyano-1H-pyrrolo[2,3-b]pyridin-1-yl)-N—((R)-2-fluoro-3-hydroxy-3-methylbutyl)nicotinamide (491); 4-((3-aminocyclopentyl)amino)-6-(5-cyano-1H-pyrrolo[2,3-b]pyridin-1-yl)-N—((R)-2-fluoro-3-hydroxy-3-methylbutyl) nicotinamide (492); 4-((3-aminocyclopentyl)amino)-6-(5-cyano-1H-pyrrolo[2,3-b]pyridin-1-yl)-N—((R)-2-fluoro-3-hydroxy-3-methylbutyl)nicotinamide (493); 6-(5-cyano-1H-pyrrolo[2,3-b]pyridin-1-yl)-N-(2-fluoro-2-(3-hydroxyoxetan-3-yl)ethyl)-4-(isopropylamino)nicotinamide (494); 6-(5-cyano-1H-pyrrolo[2,3-b]pyridin-1-yl)-N-(2-fluoro-2-(3-hydroxyoxetan-3-yl)ethyl)-4-(isopropylamino)nicotinamide (495); 6-(5-cyano-1H-pyrrolo[2,3-b]pyridin-1-yl)-N—((R)-2-fluoro-3-hydroxy-3-methylbutyl)-4-(((2S)-3-hydroxy-5-methylhexan-2-yl)amino) nicotinamide (496); 6-(5-cyano-1H-pyrrolo[2,3-b]pyridin-1-yl)-N-((1S,3S)-3-(2-hydroxypropan-2-yl)cyclopentyl)-4-(isopropylamino)nicotinamide (497); (R)-isobutyl ((1-(5-((2-fluoro-3-hydroxy-3-methylbutyl)carbamoyl)-4-(isopropylamino)pyridin-2-yl)-1H-pyrrolo[2,3-b]pyridin-5-yl)methyl) carbamate (498); (R)—N-(2-fluoro-3-hydroxy-3-methylbutyl)-6-(5-((3-hydroxy-3-methylbutanamido)methyl)-1H-pyrrolo[2,3-b]pyridin-1-yl)-4-(isopropylamino)nicotinamide (499); (R)-6-(5-((3,3-diethylureido)methyl)-1H-pyrrolo[2,3-b]pyridin-1-yl)-N-(2-fluoro-3-hydroxy-3-methylbutyl)-4-(isopropylamino) nicotinamide (500); (R)-ethyl ((1-(5-((2-fluoro-3-hydroxy-3-methylbutyl)carbamoyl)-4-(isopropylamino)pyridin-2-yl)-1H-pyrrolo[2,3-b]pyridin-5-yl)methyl)carbamate (501); (R)-isopropyl ((1-(5-((2-fluoro-3-hydroxy-3-methylbutyl)carbamoyl)-4-(isopropylamino)pyridin-2-yl)-1H-pyrrolo[2,3-b]pyridin-5-yl)methyl)carbamate (502); (R)—N-(2-fluoro-3-hydroxy-3-methylbutyl)-4-(isopropylamino)-6-(5-((3-methylbutanamido)methyl)-1H-pyrrolo[2,3-b]pyridin-1-yl)nicotinamide (503); (R)-6-(5-((2-cyclopentylacetamido)methyl)-1H-pyrrolo[2,3-b]pyridin-1-yl)-N-(2-fluoro-3-hydroxy-3-methylbutyl)-4-(isopropylamino)nicotinamide (504); (R)-6-(5-(cyclopropanecarboxamidomethyl)-1H-pyrrolo[2,3-b]pyridin-1-yl)-N-(2-fluoro-3-hydroxy-3-methylbutyl)-4-(isopropylamino) nicotinamide (505); 6-(5-cyano-1H-pyrrolo[2,3-b]pyridin-1-yl)-N—((R)-2-fluoro-3-hydroxy-3-methylbutyl)-4-(((R)-2-fluoropropyl)amino) nicotinamide (506); 6-(5-cyano-1H-pyrrolo[2,3-b]pyridin-1-yl)-N—((R)-2-fluoro-3-hydroxy-3-methylbutyl)-4-(((S)-2-fluoropropyl)amino)nicotinamide (507); (R)-propyl ((1-(5-((2-fluoro-3-hydroxy-3-methylbutyl)carbamoyl)-4-(isopropylamino)pyridin-2-yl)-1H-pyrrolo[2,3-b]pyridin-5-yl)methyl)carbamate (508); 6-(5-cyano-1H-pyrrolo[2,3-b]pyridin-1-yl)-N—((R)-2-fluoro-3-hydroxy-3-methylbutyl)-4-(((1R,3R)-3-(2-hydroxypropan-2-yl)cyclobutyl)amino) nicotinamide (509); (R)-6-(5-(butyramidomethyl)-1H-pyrrolo[2,3-b]pyridin-1-yl)-N-(2-fluoro-3-hydroxy-3-methylbutyl)-4-(isopropylamino)nicotinamide (510); (R)-6-(5-((2-cyclohexylacetamido)methyl)-1H-pyrrolo[2,3-b]pyridin-1-yl)-N-(2-fluoro-3-hydroxy-3-methylbutyl)-4-(isopropylamino)nicotinamide (511); (R)—N-(2-fluoro-3-hydroxy-3-methylbutyl)-4-(isopropylamino)-6-(5-((4-methylpentanamido)methyl)-1H-pyrrolo[2,3-b]pyridin-1-yl)nicotinamide (512); (R)—N-(2-fluoro-3-hydroxy-3-methylbutyl)-4-(isopropylamino)-6-(5-((3-propylureido)methyl)-1H-pyrrolo[2,3-b]pyridin-1-yl)nicotinamide (513); (R)-6-(5-((3-benzoylureido)methyl)-1H-pyrrolo[2,3-b]pyridin-1-yl)-N-(2-fluoro-3-hydroxy-3-methylbutyl)-4-(isopropylamino)nicotinamide (514); (R)—N-(2-fluoro-3-hydroxy-3-methylbutyl)-4-(isopropylamino)-6-(5-((2-phenylacetamido)methyl)-1H-pyrrolo[2,3-b]pyridin-1-yl)nicotinamide (515); (R)-6-(5-((3-butylureido)methyl)-1H-pyrrolo[2,3-b]pyridin-1-yl)-N-(2-fluoro-3-hydroxy-3-methylbutyl)-4-(isopropylamino)nicotinamide (516); (R)-6-(5-cyano-1H-pyrrolo[2,3-b]pyridin-1-yl)-N-(2,3-difluoro-3-methylbutyl)-4-((3-hydroxyphenyl)amino)nicotinamide (517); (R)—N-(2-fluoro-3-hydroxy-3-methylbutyl)-4-(isopropylamino)-6-(5-((2-(tetrahydro-2H-pyran-4-yl)acetamido)methyl)-1H-pyrrolo[2,3-b]pyridin-1-yl)nicotinamide (518); (R)-6-(5-((3,3-dimethylbutanamido)methyl)-1H-pyrrolo[2,3-b]pyridin-1-yl)-N-(2-fluoro-3-hydroxy-3-methylbutyl)-4-(isopropylamino)nicotinamide (519); N—((R)-2-fluoro-3-hydroxy-3-methylbutyl)-4-(isopropylamino)-6-(5-((tetrahydrofuran-3-carboxamido)methyl)-1H-pyrrolo[2,3-b]pyridin-1-yl)nicotinamide (520); (R)-6-(5-cyano-1H-pyrazolo[3,4-b]pyridin-1-yl)-N-(2-fluoro-3-hydroxy-3-methylbutyl)-4-((5-(2-hydroxypropan-2-yl)thiazol-2-yl)amino)nicotinamide (521); (R)-6-(5-cyano-1H-pyrazolo[3,4-b]pyridin-1-yl)-4-((3-cyanophenyl)amino)-N-(2-fluoro-3-hydroxy-3-methylbutyl)nicotinamide (522); (R)-6-(5-cyano-1H-pyrazolo[3,4-b]pyridin-1-yl)-4-((4-cyanophenyl)amino)-N-(2-fluoro-3-hydroxy-3-methylbutyl)nicotinamide (523); (R)-4-(benzo[d]thiazol-6-ylamino)-6-(5-cyano-1H-pyrazolo[3,4-b]pyridin-1-yl)-N-(2-fluoro-3-hydroxy-3-methylbutyl)nicotinamide (524); (R)-1-(4-(benzo[d]oxazol-6-ylamino)-5-((2-fluoro-3-hydroxy-3-methylbutyl)carbamoyl)pyridin-2-yl)-1H-pyrazolo[3,4-b]pyridine-5-carboxamide (525); (R)-4-((4-(1H-1,2,4-triazol-1-yl)phenyl)amino)-6-(5-cyano-1H-pyrazolo[3,4-b]pyridin-1-yl)-N-(2-fluoro-3-hydroxy-3-methylbutyl)nicotinamide (526); (R)-6-(5-cyano-1H-pyrazolo[3,4-b]pyridin-1-yl)-N-(2-fluoro-3-hydroxy-3-methylbutyl)-4-((4-(1-methyl-1H-tetrazol-5-yl)phenyl)amino)nicotinamide (527); (R)-6-(5-cyano-1H-pyrazolo[3,4-b]pyridin-1-yl)-4-((3-cyano-2-fluorophenyl)amino)-N-(2-fluoro-3-hydroxy-3-methylbutyl)nicotinamide (528); (R)-6-(5-cyano-1H-pyrazolo[3,4-b]pyridin-1-yl)-N-(2,3-difluoro-3-methylbutyl)-4-((4-(1-methyl-1H-tetrazol-5-yl)phenyl) amino) nicotinamide (529); (R)-6-(5-cyano-1H-pyrazolo[3,4-b]pyridin-1-yl)-N-(2-fluoro-3-hydroxy-3-methylbutyl)-4-((5-methyl-1,3,4-thiadiazol-2-yl)amino) nicotinamide (530); (R)-6-(5-cyano-1H-pyrazolo[3,4-b]pyridin-1-yl)-N-(2-fluoro-3-hydroxy-3-methylbutyl)-4-((4-(1-methyl-1H-pyrazol-4-yl)phenyl)amino)nicotinamide (531); 6-(5-cyano-1H-pyrazolo[3,4-b]pyridin-1-yl)-N—((R)-2-fluoro-3-hydroxy-3-methylbutyl)-4-(((R)-1-(5-fluoropyrimidin-2-yl)pyrrolidin-3-yl)amino)nicotinamide (532); 6-(5-cyano-1H-pyrazolo[3,4-b]pyridin-1-yl)-N—((R)-2-fluoro-3-hydroxy-3-methylbutyl)-4-(((S)-1-(5-fluoropyrimidin-2-yl)pyrrolidin-3-yl)amino)nicotinamide (533); 6-(5-cyano-1H-pyrazolo[3,4-b]pyridin-1-yl)-N—((R)-2-fluoro-3-hydroxy-3-methylbutyl)-4-(((R)-1-(5-fluoropyrimidin-2-yl)pyrrolidin-3-yl)amino)nicotinamide (534); (R)-6-(5-cyano-1H-pyrazolo[3,4-b]pyridin-1-yl)-N-(2-fluoro-3-hydroxy-3-methylbutyl)-4-((1-phenylpiperidin-4-yl)amino) nicotinamide (535); 6-(5-cyano-1H-pyrazolo[3,4-b]pyridin-1-yl)-N—((R)-2-fluoro-3-hydroxy-3-methylbutyl)-4-(((R)-1-(5-methoxypyrimidin-2-yl)pyrrolidin-3-yl)amino) nicotinamide (536); 6-(5-cyano-1H-pyrazolo[3,4-b]pyridin-1-yl)-N—((R)-2-fluoro-3-hydroxy-3-methylbutyl)-4-(((R)-1-(pyrimidin-2-yl)pyrrolidin-3-yl)amino)nicotinamide (537); 6-(5-cyano-1H-pyrazolo[3,4-b]pyridin-1-yl)-4-(((R)-1-(2,4-difluorobenzoyl)pyrrolidin-3-yl)amino)-N—((R)-2-fluoro-3-hydroxy-3-methylbutyl) nicotinamide (538); (R)-6-(5-cyano-1H-pyrazolo[3,4-b]pyridin-1-yl)-N-(2-fluoro-3-hydroxy-3-methylbutyl)-4-((1-(5-fluoropyrimidin-2-yl)azetidin-3-yl)amino)nicotinamide (539); (R)-6-(5-cyano-1H-pyrazolo[3,4-b]pyridin-1-yl)-N-(2-fluoro-3-hydroxy-3-methylbutyl)-4-((1-(5-fluoropyrimidin-2-yl)piperidin-4-yl)amino)nicotinamide (540); (R)-4-((1-(5-chloropyrimidin-2-yl)azetidin-3-yl)amino)-6-(5-cyano-1H-pyrazolo[3,4-b]pyridin-1-yl)-N-(2-fluoro-3-hydroxy-3-methylbutyl) nicotinamide (541); (R)-methyl 3-((2-(5-cyano-1H-pyrazolo[3,4-b]pyridin-1-yl)-5-((2-fluoro-3-hydroxy-3-methylbutyl)carbamoyl)pyridin-4-yl)amino)azetidine-1-carboxylate (542); (R)-ethyl 3-((2-(5-cyano-1H-pyrazolo[3,4-b]pyridin-1-yl)-5-((2-fluoro-3-hydroxy-3-methylbutyl)carbamoyl)pyridin-4-yl)amino)azetidine-1-carboxylate (543); 6-(5-cyano-1H-pyrazolo[3,4-b]pyridin-1-yl)-N—((R)-2-fluoro-3-hydroxy-3-methylbutyl)-4-(((R)-tetrahydrofuran-3-yl)amino)nicotinamide, TFA salt (544); 6-(5-cyano-1H-pyrazolo[3,4-b]pyridin-1-yl)-N—((R)-2-fluoro-3-hydroxy-3-methylbutyl)-4-(((S)-tetrahydrofuran-3-yl)amino) nicotinamide, TFA salt (545); (R)-6-(5-cyano-1H-pyrazolo[3,4-b]pyridin-1-yl)-N-(2-fluoro-3-hydroxy-3-methylbutyl)-4-(oxetan-3-ylamino)nicotinamide (546); 6-(5-fluoro-1H-pyrazolo[3,4-b]pyridin-1-yl)-N—((R)-2-fluoro-3-hydroxy-3-methylbutyl)-4-((tetrahydro-2H-pyran-3-yl) amino)nicotinamide (547); 6-(6-cyano-3H-imidazo[4,5-b]pyridin-3-yl)-N—((R)-2-fluoro-3-hydroxy-3-methylbutyl)-4-(((R)-tetrahydrofuran-3-yl)amino)nicotinamide (548); (R)-6-(5-cyano-2,3-dihydro-1H-pyrrolo[2,3-b]pyridin-1-yl)-N-(2-fluoro-3-hydroxy-3-methylbutyl)-4-(oxetan-3-ylamino)nicotinamide (549); (R)-6-(5-fluoro-1H-pyrazolo[3,4-b]pyridin-1-yl)-N-(2-fluoro-3-hydroxy-3-methylbutyl)-4-(oxetan-3-ylamino)nicotinamide (550); (R)-6-(5-chloro-1H-pyrazolo[3,4-b]pyridin-1-yl)-N-(2-fluoro-3-hydroxy-3-methylbutyl)-4-(oxetan-3-ylamino)nicotinamide (551); 6-(5-cyano-1H-pyrazolo[3,4-b]pyridin-1-yl)-N-((1R,4R)-4-methoxycyclohexyl)-4-(oxetan-3-ylamino)nicotinamide (552); 6-(5-cyano-1H-pyrazolo[3,4-b]pyridin-1-yl)-N-(3-hydroxy-3-methylbutyl)-4-(oxetan-3-ylamino) nicotinamide (553); 6-(5-cyano-1H-pyrazolo[3,4-b]pyridin-1-yl)-4-((4,4-difluorotetrahydrofuran-3-yl)amino)-N—((R)-2-fluoro-3-hydroxy-3-methylbutyl)nicotinamide (554); 6-(5-cyano-1H-pyrazolo[3,4-b]pyridin-1-yl)-N-((1R,4R)-4-(2-hydroxypropan-2-yl)cyclohexyl)-4-(oxetan-3-ylamino) nicotinamide (555); 6-(5-chloro-1H-pyrazolo[3,4-b]pyridin- 1-yl)-N-((1R,4R)-4-(2-hydroxypropan-2-yl)cyclohexyl)-4-(oxetan-3-ylamino)nicotinamide (556); 6-(5-cyano-1H-pyrazolo[3,4-b]pyridin-1-yl)-N-isopentyl-4-(oxetan-3-ylamino)nicotinamide (557); 6-(6-amino-5-cyano-1H-pyrazolo[3,4-b]pyridin-1-yl)-N-(2-cyclopropylethyl)-4-(oxetan-3-ylamino) nicotinamide (558); 6-(6-amino-5-cyano-1H-pyrazolo[3,4-b]pyridin-1-yl)-N-butyl-4-(oxetan-3-ylamino)nicotinamide (559); 6-(6-amino-5-cyano-1H-pyrazolo[3,4-b]pyridin-1-yl)-N-isopentyl-4-(oxetan-3-ylamino)nicotinamide (560); N-butyl-6-(5-cyano-1H-pyrazolo[3,4-b]pyridin-1-yl)-4-(oxetan-3-ylamino) nicotinamide (561); (R)-6-(5-fluoro-1H-pyrazolo[3,4-b]pyridin-1-yl)-N-(2-fluoro-3-hydroxy-3-methylbutyl)-4-((tetrahydro-2H-pyran-4-yl)amino)nicotinamide (562); (R)-6-(5-cyano-1H-pyrazolo[3,4-b]pyridin-1-yl)-N-(2-fluoro-3-hydroxy-3-methylbutyl)-4-((3,3,3-trifluoropropyl)amino) nicotinamide (563); 6-(5-cyano-1H-pyrazolo[3,4-b]pyridin-1-yl)-4-(isopropylamino)-N-(5-methoxypyrazine-2-yl) nicotinamide (564); N-((R)-2-fluoro-3-hydroxy-3-methylbutyl)-4-((2-morpholinopropyl)amino)-6-(7H-pyrrolo[2,3-d]pyrimidin-7-yl)nicotinamide (565); N-((2H-tetrazol-5-yl)methyl)-6-(5-cyano-1H-pyrazolo[3,4-b]pyridin-1-yl)-4-(isopropylamino)nicotinamide (566); (R)-6-(5-cyano-2,3-dihydro-1H-pyrrolo[2,3-b]pyridin-1-yl)-N-(2-fluoro-3-hydroxy-3-methylbutyl)-4-(isopropylamino) nicotinamide (567); (R)-6-(6-cyano-3H-imidazo[4,5-b]pyridin-3-yl)-4-(ethylamino)-N-(2-fluoro-3-hydroxy-3-methylbutyl)nicotinamide (568); 6-(5-cyano-1H-pyrazolo[3,4-b]pyridin-1-yl)-N—((R)-2-fluoro-3-hydroxy-3-methylbutyl)-4-(((S)-1-hydroxy-3-methylbutan-2-yl)amino) nicotinamide (569); (R)-6-(5-cyano-1H-pyrazolo[3,4-b]pyridin-1-yl)-N-(2-fluoro-3-hydroxy-3-methylbutyl)-4-((2-methyl-2-morpholinopropyl)amino)nicotinamide (570); (R)-6-(5-cyano-1H-pyrazolo[3,4-b]pyridin-1-yl)-N-(2-fluoro-3-hydroxy-3-methylbutyl)-4-((oxazol-4-ylmethyl)amino) nicotinamide (571); 6-(5-cyano-1H-pyrazolo[3,4-b]pyridin-1-yl)-N—(R)-2-fluoro-3-hydroxy-3-methylbutyl)-4-(((R)-3-hydroxybutyl)amino) nicotinamide (572); 6-(5-cyano-1H-pyrazolo[3,4-b]pyridin-1-yl)-N—((R)-2-fluoro-3-hydroxy-3-methylbutyl)-4-(((R)-3-hydroxybutyl)amino) nicotinamide (573); (R)-6-(5-cyano-1H-pyrazolo[3,4-b]pyridin-1-yl)-4-((2,2-difluoroethyl)amino)-N-(2-fluoro-3-hydroxy-3-methylbutyl)nicotinamide (574); 6-(5-cyano-1H-pyrazolo[3,4-b]pyridin-1-yl)-4-((2-fluoro-3-hydroxy-2-methylpropyl)amino)-N—((R)-2-fluoro-3-hydroxy-3-methylbutyl)nicotinamide (575); (R)-6-(5-cyano-1H-pyrazolo[3,4-b]pyridin-1-yl)-N-(2-fluoro-3-hydroxy-3-methylbutyl)-4-(neopentylamino)nicotinamide (576); (R)-6-(6-amino-5-cyano-1H-pyrazolo[3,4-b]pyridin-1-yl)-4-(ethylamino)-N-(2-fluoro-3-hydroxy-3-methylbutyl) nicotinamide (577); (R)-6-(6-amino-5-cyano-1H-pyrazolo[3,4-b]pyridin-1-yl)-N-(2-fluoro-3-hydroxy-3-methylbutyl)-4-(propylamino)nicotinamide (578); (R)-6-(6-amino-1H-pyrazolo[3,4-d]pyrimidin-1-yl)-N-(2-fluoro-3-hydroxy-3-methylbutyl)-4-(isopropylamino)nicotinamide (579); (R)-6-(6-amino-1H-pyrazolo[3,4-d]pyrimidin-1-yl)-4-(ethylamino)-N-(2-fluoro-3-hydroxy-3-methylbutyl)nicotinamide (580); (R)-6-(5-cyano-1H-pyrazolo[3,4-b]pyridin-1-yl)-N-(2-fluoro-3-hydroxy-3-methylbutyl)-4-(((1-fluorocyclobutyl)methyl)amino)nicotinamide (581); 6-(5-cyano-1H-pyrazolo[3,4-b]pyridin-1-yl)-N—((R)-2-fluoro-3-hydroxy-3-methylbutyl)-4-(((R)-2-fluoropropyl)amino) nicotinamide (582); 6-(5-cyano-1H-pyrazolo[3,4-b]pyridin-1-yl)-N—((R)-2-fluoro-3-hydroxy-3-methylbutyl)-4-(((S)-2-fluoropropyl)amino)nicotinamide (583); 6-(5-cyano-1H-pyrazolo[3,4-b]pyridin-1-yl)-4-(isopropylamino)-N-(1-(1-(methylsulfonyl)azetidine-3-carbonyl)piperidin-4-yl) nicotinamide (584); (R)-4-((3-amino-2,2-dimethylpropyl)amino)-6-(5-cyano-1H-pyrazolo[3,4-b]pyridin-1-yl)-N-(2-fluoro-3-hydroxy-3-methylbutyl)nicotinamide (585); (R)-6-(5-cyano-1H-pyrazolo[3,4-b]pyridin-1-yl)-N-(2-fluoro-3-hydroxy-3-methylbutyl)-4-((2-(methylsulfonamido)ethyl) amino)nicotinamide (586); (R)-1,1,1-trifluoro-2-methylpropan-2-yl (2-((2-(5-cyano-1H-pyrazolo[3,4-b]pyridin-1-yl)-5-((2-fluoro-3-hydroxy-3-methylbutyl) carbamoyl)pyridin-4-yl)amino)ethyl) carbamate (587); 6-(5-cyano-1H-pyrazolo[3,4-b]pyridin-1-yl)-N—((R)-2-fluoro-3-hydroxy-3-methylbutyl)-4-(((S)-1-hydroxybutan-2-yl) amino)nicotinamide (588); 6-(5-chloro-1H-pyrazolo[3,4-b]pyridin-1-yl)-N—((R)-2-fluoro-3-hydroxy-3-methylbutyl)-4-(((S)-1-hydroxybutan-2-yl)amino)nicotinamide (589); 6-(6-amino-5-cyano-1H-pyrazolo[3,4-b]pyridin-1-yl)-N—((R)-2-fluoro-3-hydroxy-3-methylbutyl)-4-(((S)-2-fluoropropyl)amino)nicotinamide (590); 6-(6-amino-5-cyano-1H-pyrazolo[3,4-b]pyridin-1-yl)-N—((R)-2-fluoro-3-hydroxy-3-methylbutyl)-4-(((R)-2-fluoropropyl)amino)nicotinamide (591); (R)-6-(5-cyano-1H-pyrazolo[3,4-b]pyridin-1-yl)-N-(2-fluoro-3-hydroxy-3-methylbutyl)-4-(propylamino)nicotinamide (592); (R)-6-(5-cyano-1H-pyrazolo[3,4-b]pyridin-1-yl)-N-(2-fluoro-3-hydroxy-3-methylbutyl)-4-((2-methoxy-2-methylpropyl)amino)nicotinamide (593); 6-(5-chloro-1H-pyrazolo[3,4-b]pyridin-1-yl)-N—((R)-2-fluoro-3-hydroxy-3-methylbutyl)-4-((2-hydroxy-3-methylbutyl)amino) nicotinamide (594); (R)-6-(5-cyano-1H-pyrazolo[3,4-b]pyridin-1-yl)-N-(2-fluoro-3-hydroxy-3-methylbutyl)-4-((3-fluoropropyl)amino)nicotinamide (595); 6-(5-chloro-1H-pyrazolo[3,4-b]pyridin-1-yl)-N—((R)-2-fluoro-3-hydroxy-3-methylbutyl)-4-((2-hydroxy-3-methylbutyl)amino) nicotinamide (596); 6-(5-cyano-1H-pyrazolo[3,4-b]pyridin-1-yl)-N—((R)-2-fluoro-3-hydroxy-3-methylbutyl)-4-((2-hydroxy-3-methylbutyl)amino)nicotinamide (597); (R)-6-(5-cyano-1H-pyrazolo[3,4-b]pyridin-1-yl)-4-((2-(difluoromethoxy)ethyl)amino)-N-(2-fluoro-3-hydroxy-3-methylbutyl)nicotinamide (598); (R)-6-(6-amino-5-cyano-1H-pyrazolo[3,4-b]pyridin-1-yl)-N-(2-fluoro-3-hydroxy-3-methylbutyl)-4-((3-fluoro-3-methylbutyl)amino) nicotinamide (599); (R)-6-(5-cyano-1H-pyrazolo[3,4-b]pyridin-1-yl)-N-(2-fluoro-3-hydroxy-3-methylbutyl)-4-((3-fluoro-3-methylbutyl)amino)nicotinamide (600); (R)-6-(5-cyano-1H-pyrazolo[3,4-b]pyridin-1-yl)-4-((2-(difluoromethoxy)-2-methylpropyl)amino)-N-(2-fluoro-3-hydroxy-3-methylbutyl)nicotinamide (601); 6-(5-chloro-1H-pyrazolo[3,4-b]pyridin-1-yl)-N—((R)-2-fluoro-3-hydroxy-3-methylbutyl)-4-(((R)-2-fluorobutyl)amino) nicotinamide (602); (R)-6-(5-chloro-1H-pyrazolo[3,4-b]pyridin-1-yl)-4-((2-(difluoromethoxy)-2-methylpropyl) amino)-N-(2-fluoro-3-hydroxy-3-methylbutyl)nicotinamide (603); 6-(5-cyano-1H-pyrazolo[3,4-b]pyridin-1-yl)-N—((R)-2-fluoro-3-hydroxy-3-methylbutyl)-4-((3-fluorobutyl) amino)nicotinamide (604); (R)-6-(5-cyano-1H-pyrazolo[3,4-b]pyridin-1-yl)-4-((cyclopropylmethyl)amino)-N-(2-fluoro-3-hydroxy-3-methylbutyl)nicotinamide (605); 6-(5-cyano-1H-pyrazolo[3,4-b]pyridin-1-yl)-N—((R)-2-fluoro-3-hydroxy-3-methylbutyl)-4-(((1R,4R)-4-(2-hydroxypropan-2-yl)cyclohexyl)amino)nicotinamide (606); 6-(5-cyano-1H-pyrazolo[3,4-b]pyridin-1-yl)-N—((R)-2-fluoro-3-hydroxy-3-methylbutyl)-4-(((1s,4S)-4-hydroxy-4-methylcyclohexyl)amino)nicotinamide (607); 6-(5-cyano-1H-pyrazolo[3,4-b]pyridin-1-yl)-N—((R)-2-fluoro-3-hydroxy-3-methylbutyl)-4-(((1R,4R)-4-hydroxy-4-methylcyclohexyl)amino) nicotinamide (608); 6-(5-fluoro-1H-pyrazolo[3,4-b]pyridin-1-yl)-N—((R)-2-fluoro-3-hydroxy-3-methylbutyl)-4-((3-hydroxycyclopentyl)amino) nicotinamide (609); 6-(5-fluoro-1H-pyrazolo[3,4-b]pyridin- 1-yl)-N—((R)-2-fluoro-3-hydroxy-3-methylbutyl)-4-((3-hydroxycyclopentyl)amino)nicotinamide (610); 6-(5-fluoro-1H-pyrazolo[3,4-b]pyridin-1-yl)-N—((R)-2-fluoro-3-hydroxy-3-methylbutyl)-4-((3-hydroxycyclopentyl)amino) nicotinamide (611); 6-(5-cyano-1H-pyrazolo[3,4-b]pyridin-1-yl)-N—((R)-2-fluoro-3-hydroxy-3-methylbutyl)-4-(((1R,3S)-3-(2-hydroxypropan-2-yl)cyclohexyl)amino) nicotinamide (612); (R)-6-(5-cyano-1H-pyrazolo[3,4-b]pyridin-1-yl)-N-(2-fluoro-3-hydroxy-3-methylbutyl)-4-((4-hydroxybicyclo[2.2.1]heptan-1-yl)amino)nicotinamide (613); 6-(5-cyano-1H-pyrazolo[3,4-b]pyridin-1-yl)-4-((3,3-difluorocyclopentyl)amino)-N—((R)-2-fluoro-3-hydroxy-3-methylbutyl)nicotinamide (614); 6-(5-cyano-1H-pyrazolo[3,4-b]pyridin-1-yl)-4-((3,3-difluorocyclopentyl)amino)-N—((R)-2-fluoro-3-hydroxy-3-methylbutyl)nicotinamide (615); (R)-6-(5-cyano-2,3-dihydro-1H-pyrrolo[2,3-b]pyridin-1-yl)-4-(cyclopropylamino)-N-(2-fluoro-3-hydroxy-3-methylbutyl)nicotinamide (616); 6-(5-cyano-1H-pyrazolo[3,4-b]pyridin-1-yl)-N—((R)-2-fluoro-3-hydroxy-3-methylbutyl)-4-(((1S,3S)-3-(2-hydroxypropan-2-yl)cyclopentyl)amino)nicotinamide (617); 6-(5-fluoro-1H-pyrazolo[3,4-b]pyridin-1-yl)-N—((R)-2-fluoro-3-hydroxy-3-methylbutyl)-4-((3-fluorocyclopentyl)amino)nicotinamide (618); 6-(5-fluoro-1H-pyrazolo[3,4-b]pyridin-1-yl)-N—((R)-2-fluoro-3-hydroxy-3-methylbutyl)-4-((3-fluorocyclopentyl)amino) nicotinamide (619); 6-(5-fluoro-1H-pyrazolo[3,4-b]pyridin-1-yl)-N—((R)-2-fluoro-3-hydroxy-3-methylbutyl)-4-((3-fluorocyclopentyl)amino) nicotinamide (620); 6-(5-fluoro-1H-pyrazolo[3,4-b]pyridin-1-yl)-N—((R)-2-fluoro-3-hydroxy-3-methylbutyl)-4-((3-fluorocyclopentyl)amino)nicotinamide (621); 6-(5-cyano-1H-pyrazolo[3,4-b]pyridin-1-yl)-N—((R)-2-fluoro-3-hydroxy-3-methylbutyl)-4-(((1R,4R)-4-(oxetan-3-ylamino)cyclohexyl)amino)nicotinamide (622); 6-(5-cyano-1H-pyrazolo[3,4-b]pyridin-1-yl)-4-(((1R,4R)-4-(cyclopropanecarboxamido)cyclohexyl)amino)-N—((R)-2-fluoro-3-hydroxy-3-methylbutyl)nicotinamide (623); 6-(5-cyano-1H-pyrazolo[3,4-b]pyridin-1-yl)-N—((R)-2-fluoro-3-hydroxy-3-methylbutyl)-4-(((1R,5S)-3-hydroxyadamantan-1-yl)amino) nicotinamide (624); 6-(5-cyano-1H-pyrazolo[3,4-b]pyridin-1-yl)-N—((R)-2-fluoro-3-hydroxy-3-methylbutyl)-4-((3-fluorocyclopentyl)amino)nicotinamide (625); 6-(5-cyano-1H-pyrazolo[3,4-b]pyridin-1-yl)-N—((R)-2-fluoro-3-hydroxy-3-methylbutyl)-4-((3-fluorocyclopentyl)amino)nicotinamide (626); 6-(5-cyano-1H-pyrazolo[3,4-b]pyridin-1-yl)-N—((R)-2-fluoro-3-hydroxy-3-methylbutyl)-4-((3-fluorocyclopentyl)amino)nicotinamide (627); 6-(5-chloro-1H-pyrazolo[3,4-b]pyridin-1-yl)-N—((R)-2-fluoro-3-hydroxy-3-methylbutyl)-4-(((1S,3S)-3-(2-hydroxypropan-2-yl)cyclopentyl)amino) nicotinamide (628); 6-(6-amino-5-cyano-1H-pyrazolo[3,4-b]pyridin-1-yl)-4-(((1R,2R)-2-fluorocyclohexyl)amino)-N-((1R,4R)-4-(methylcarbamoyl)cyclohexyl)nicotinamide (629); 6-(6-amino-5-cyano-1H-pyrazolo[3,4-b]pyridin-1-yl)-4-(((1S,2S)-2-fluorocyclohexyl)amino)-N-((1R,4S)-4-(methylcarbamoyl)cyclohexyl)nicotinamide (630); (R)-6-(6-amino-5-cyano-1H-pyrazolo[3,4-b]pyridin-1-yl)-4-(cyclopropylamino)-N-(2-fluoro-3-hydroxy-3-methylbutyl)nicotinamide (631); 6-(6-amino-5-cyano-1H-pyrazolo[3,4-b]pyridin-1-yl)-N—((R)-2-fluoro-3-hydroxy-3-methylbutyl)-4-(((1R,5S)-3-hydroxyadamantan-1-yl)amino)nicotinamide (632); 6-(5-cyano-1H-pyrazolo[3,4-b]pyridin-1-yl)-4-(((1R,4R)-4-(2,2-difluoroacetamido)cyclohexyl)amino)-N—((R)-2-fluoro-3-hydroxy-3-methylbutyl)nicotinamide (633); 6-(5-cyano-1H-pyrazolo[3,4-b]pyridin-1-yl)-N—((R)-2-fluoro-3-hydroxy-3-methylbutyl)-4-(((1R,4R)-4-(2-fluorobenzamido)cyclohexyl)amino)nicotinamide (634); (R)-4-(bicyclo[1.1.1]pentan-2-ylamino)-6-(5-cyano-1H-pyrazolo[3,4-b]pyridin-1-yl)-N-(2-fluoro-3-hydroxy-3-methylbutyl) nicotinamide (635); 6-(5-cyano-1H-pyrazolo[3,4-b]pyridin-1-yl)-N—((R)-2,3-difluoro-3-methylbutyl)-4-(((1R,5S)-3-hydroxyadamantan-1-yl)amino)nicotinamide (636); (R)-6-(6-amino-5-cyano-1H-pyrazolo[3,4-b]pyridin-1-yl)-4-(bicyclo[1.1.1]pentan-1-ylamino)-N-(2-fluoro-3-hydroxy-3-methylbutyl) nicotinamide (637); 4-((3-aminocyclopentyl)amino)-6-(5-cyano-1H-pyrazolo[3,4-b]pyridin-1-yl)-N—((R)-2-fluoro-3-hydroxy-3-methylbutyl) nicotinamide (638); 4-((3-aminocyclopentyl)amino)-6-(5-cyano-1H-pyrazolo[3,4-b]pyridin-1-yl)-N—((R)-2-fluoro-3-hydroxy-3-methylbutyl) nicotinamide (639); 4-((3-aminocyclopentyl)amino)-6-(5-cyano-1H-pyrazolo[3,4-b]pyridin-1-yl)-N—((R)-2-fluoro-3-hydroxy-3-methylbutyl)nicotinamide (640); 6-(5-cyano-1H-pyrazolo[3,4-b]pyridin-1-yl)-N—((R)-2-fluoro-3-hydroxy-3-methylbutyl)-4-(((1R,4R)-4-(isopropylcarbamoyl)cyclohexyl)amino)nicotinamide (641); 6-(5-cyano-1H-pyrazolo[3,4-b]pyridin-1-yl)-N—((R)-2-fluoro-3-hydroxy-3-methylbutyl)-4-(((1R,2R)-2-(hydroxymethyl)cyclopropyl)amino)nicotinamide (642); 6-(5-cyano-1H-pyrazolo[3,4-b]pyridin-1-yl)-N—((R)-2-fluoro-3-hydroxy-3-methylbutyl)-4-(((1R,2R)-2-(hydroxymethyl)cyclopropyl)amino) nicotinamide (643); (R)-6-(5-cyano-1H-pyrazolo[3,4-b]pyridin-1-yl)-4-((3,3-difluorocyclobutyl)amino)-N-(2-fluoro-3-hydroxy-3-methylbutyl)nicotinamide (644); 6-(5-chloro-1H-pyrazolo[3,4-b]pyridin-1-yl)-N—((R)-2-fluoro-3-hydroxy-3-methylbutyl)-4-(((1R,2R)-2-(hydroxymethyl)cyclopropyl)amino)nicotinamide (645); and 6-(5-chloro-1H-pyrazolo[3,4-b]pyridin-1-yl)-N—((R)-2-fluoro-3-hydroxy-3-methylbutyl)-4-(((1R,2R)-2-(hydroxymethyl)cyclopropyl)amino)nicotinamide (646).

9. A pharmaceutical composition comprising one or more compounds according to claim 1 and a pharmaceutically acceptable carrier or diluent.

* * * * *

UNITED STATES PATENT AND TRADEMARK OFFICE
CERTIFICATE OF CORRECTION

PATENT NO. : 9,169,252 B2  
APPLICATION NO. : 14/588470  
DATED : October 27, 2015  
INVENTOR(S) : Joseph B. Santella et al.

It is certified that error appears in the above-identified patent and that said Letters Patent is hereby corrected as shown below:

In the Claims:

Claim 3, col. 395, line 43, delete "to 2" and insert -- to 3 --, therefor.

Claim 8, col. 404, line 59, delete "((1 s,4s)-" and insert -- ((1s,4s)- --, therefor.

Claim 8, col. 404, lines 66-67, delete "((1 s,4s)-" and insert -- ((1s,4s)- --, therefor.

Claim 8, col. 405, line 7, delete "((1 s,4s)-" and insert -- ((1s,4s)- --, therefor.

Claim 8, col. 405, line 12, delete "((1 s,4s)-" and insert -- ((1s,4s)- --, therefor.

Claim 8, col. 422, line 3, delete "(((1 S,2S)-" and insert -- (((1S,2S)- --, therefor.

Signed and Sealed this  
Ninth Day of August, 2016

Michelle K. Lee  
*Director of the United States Patent and Trademark Office*